(12) United States Patent
Artman, III et al.

(10) Patent No.: US 8,431,584 B2
(45) Date of Patent: Apr. 30, 2013

(54) HETEROBICYCLIC CARBOXAMIDES AS INHIBITORS FOR KINASES

(75) Inventors: Gerald David Artman, III, Cambridge, MA (US); Jason Matthew Elliott, Cambridge, MA (US); Nan Ji, Cambridge, MA (US); Donglei Liu, Cambridge, MA (US); Fupeng Ma, Cambridge, MA (US); Nello Mainolfi, Cambridge, MA (US); Erik Meredith, Cambridge, MA (US); Karl Miranda, Cambridge, MA (US); James J. Powers, Cambridge, MA (US); Chang Rao, Cambridge, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/488,760

(22) Filed: Jun. 5, 2012

(65) Prior Publication Data

US 2012/0245187 A1    Sep. 27, 2012

Related U.S. Application Data

(63) Continuation of application No. 12/632,396, filed on Dec. 7, 2009, now Pat. No. 8,242,125.

(60) Provisional application No. 61/201,243, filed on Dec. 9, 2008, provisional application No. 61/233,341, filed on Aug. 12, 2009.

(51) Int. Cl.
*C07D 487/04* (2006.01)
*C07D 487/08* (2006.01)
*A61K 31/404* (2006.01)

(52) U.S. Cl.
USPC ........................................ 514/264.1; 544/279

(58) Field of Classification Search .................. 544/279; 514/264.1
See application file for complete search history.

(56) References Cited

U.S. PATENT DOCUMENTS

| 7,253,286 B2 | 8/2007 | Funahashi et al. |
| 2006/0004029 A1 | 1/2006 | Tsuruoka et al. |

FOREIGN PATENT DOCUMENTS

| WO | 01/58899 A1 | 8/2001 |
| WO | 03/040102 A1 | 5/2003 |
| WO | 03/099771 A2 | 12/2003 |
| WO | 2004/020434 A1 | 3/2004 |
| WO | 2004/043379 A2 | 5/2004 |
| WO | 2005/021512 A1 | 3/2005 |
| WO | 2006/034833 A1 | 4/2006 |
| WO | 2006/059234 A2 | 6/2006 |
| WO | 2006/091671 A1 | 8/2006 |
| WO | 2007/031265 A2 | 3/2007 |
| WO | 2007/116029 A2 | 10/2007 |
| WO | 2009/023179 A2 | 2/2009 |
| WO | 2009/036066 A1 | 3/2009 |
| WO | 2009/057811 A2 | 5/2009 |

*Primary Examiner* — Bruck Kifle
(74) *Attorney, Agent, or Firm* — John B. Alexander

(57) ABSTRACT

The invention relates to novel organic compounds of formula (I)

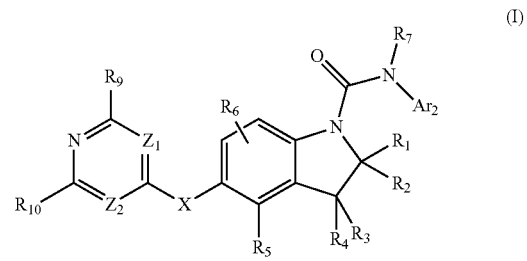

and their use in the treatment of the animal or human body, to pharmaceutical compositions comprising a compound of formula I and to the use of a compound of formula I for the preparation of pharmaceutical compositions for use in the treatment of protein kinase dependent diseases, especially of proliferative diseases, such as in the treatment of tumor diseases and ocular neovascular diseases.

6 Claims, No Drawings

HETEROBICYCLIC CARBOXAMIDES AS INHIBITORS FOR KINASES

This application is a continuation of U.S. application Ser. No. 12/632,396 filed Dec. 7, 2009 now U.S. Pat. No. 8,242,125, which claims benefit under 35 U.S.C. §119(e) of U.S. Provisional Application No. 61/201,243, filed Dec. 9, 2008, and U.S. Provisional Application No. 61/233,341, filed Aug. 12, 2009, the contents of which are incorporated herein by reference in their entirety.

The invention relates to bicyclic heterocyclyl compounds substituted at both rings of formula I and their use in the treatment of the animal or human body, to pharmaceutical compositions comprising a compound of formula I and to the use of a compound of formula I for the preparation of pharmaceutical compositions for use in the treatment of protein kinase dependent diseases, especially of proliferative diseases, such as in particular tumour diseases and ocular neovascularization diseases.

Protein kinases (PKs) are enzymes which catalyze the phosphorylation of specific serine, threonine or tyrosine residues in cellular proteins. These post-translational modifications of substrate proteins act as molecular switch regulating cell proliferation, activation and/or differentiation. Aberrant or excessive wild-type or mutated PK activity has been observed in many disease states including benign and malignant proliferative disorders. In many cases, it has been possible to treat diseases, such as proliferative disorders, by making use of PK inhibitors.

In view of the large number of protein kinases and the multitude of proliferative and other PK-related diseases, there is an ever-existing need to provide compounds that are useful as PK inhibitors and thus in the treatment of these PK related diseases.

It has now been found that the compounds of formula I show inhibition of a number of protein kinases. The compounds of formula I, described below in more detail, especially show inhibition of one or more of the following protein kinases: EphB4, c-Abl, Bcr-Abl, c-Kit, Raf kinases such as especially B-Raf, the rearranged during transfection (RET) proto-oncogene, Platelet-derived Growth Factor Receptors (PDGF-Rs), Lck, Hck and most especially the Vascular Endothelial Growth Factor Receptors (VEGF-Rs) such as in particular VEGF-R2. The compounds of formula I further also inhibit mutants of said kinases. In view of these activities, the compounds of formula I can be used for the treatment of diseases related to especially aberrant or excessive activity of such types of kinases, especially those mentioned.

The invention relates to compounds of the formula I,

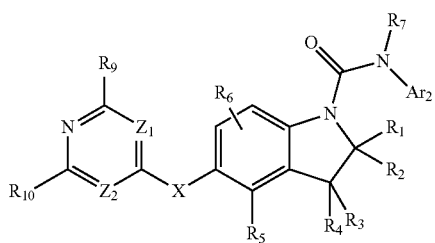

I or a salt thereof wherein
$R_1$ is hydrogen or $C_1$-$C_6$alkyl;
$R_2$ is hydrogen or $C_1$-$C_6$alkyl;
$R_3$ is hydrogen or $C_1$-$C_6$alkyl;
$R_4$ is hydrogen or $C_1$-$C_6$alkyl; or
$R_2$ and $R_4$, taken in combination form a bond;
$R_5$ is hydrogen, $C_1$-$C_6$alkyl, or halogen;
$R_6$ represents 0, 1 or 2 residues independently selected at each occurrence from halogen or $C_1$-$C_6$alkyl;
$R_7$ is hydrogen or $C_1$-$C_6$alkyl;
X is O or S;
$Z_1$ and $Z_2$ are independently selected from the group consisting of N and $CR_8$;
$R_8$ and $R_{10}$ are independently selected from the group consisting of hydrogen and $C_1$-$C_6$alkyl;
$R_9$ is selected from the group consisting of $(CR_{11}R_{12})_n$$NR_{13}R_{14}$, $(CR_{11}R_{12})_n$heterocycle, $(CR_{11}R_{12})_n$$OR_{15}$, $(CR_{11}R_{12})_n$C(O)E$R_{13}$, and $(CR_{11}R_{12})_n$S(O)$_m$$R_{17}$; or
$R_8$ and $R_9$, taken in combination, together with the atoms to which they are attached, form a saturated 4-7 membered heterocyclic ring having 1 or 2 ring heteroatoms selected from N, O or S, which heterocyclic ring is substituted with 0, 1, or 2 residues independently selected from the group consisting of oxo, $C_1$-$C_6$alkyl, $C_1$-$C_6$haloalkyl, $C_1$-$C_6$alkoxy, $C_1$-$C_6$haloalkoxy, halogen, hydroxyl, amino, hydroxy$C_1$-$C_6$alkyl, amino$C_1$-$C_6$alkyl, mono- and di-$C_1$-$C_6$alkylamino$C_1$-$C_6$alkyl, $C_3$-$C_7$cycloalkyl$C_1$-$C_4$alkyl, heterocycle$C_1$-$C_4$alkyl, $C_1$-$C_6$alkanoyl, mono- and di-$C_1$-$C_6$alkylamino, aminocarbonyl, mono- and di-$C_1$-$C_6$alkylaminocarbonyl, mono- and di-$C_1$-$C_4$alkylamino$C_1$-$C_4$alkanoyl, $C_1$-$C_6$alkoxycarbonyl, $C_1$-$C_6$alkylsulfonyl, aminosulfonyl, and mono- and di-$C_1$-$C_6$alkylaminosulfonyl;
$Ar_2$ is selected from the group consisting of phenyl, naphthyl, a monocyclic or bicyclic heteroaryl, and bicyclic or tricyclic heterocycle wherein each heteroaryl or heterocycle residue has 1, 2, 3 or 4 ring heteroatoms selected from N, O or S and wherein the phenyl, naphthyl, heteroaryl or heterocycle group is unsubstituted or substituted by 1, 2, or 3 groups independently selected from $C_1$-$C_8$alkyl, $C_1$-$C_8$haloalkyl, hydroxy$C_1$-$C_6$alkyl, $C_1$-$C_8$alkoxy, $C_1$-$C_8$haloalkoxy, halogen, hydroxy, amino, amino$C_1$-$C_6$alkyl, mono- and di-$C_1$-$C_6$alkylamino$C_1$-$C_6$alkyl, mono- and di-$C_1$-$C_6$alkylamino, $CO_2$$C_1$-$C_6$alkyl, phenyl$C_0$-$C_4$alkyl, $C_3$-$C_7$cycloalkyl$C_0$-$C_4$alkyl, spirocyclic $C_3$-$C_7$cycloalkyl, aminosulfonyl, and mono- and di-$C_1$-$C_6$alkylaminosulfonyl;
m is 0, 1, or 2;
n is 0, 1, 2, or 3;
E is absent, O or $NR_{18}$;
$R_{11}$, $R_{12}$ and $R_{18}$ are the same or different and are independently selected at each occurrence from the group consisting of hydrogen and $C_1$-$C_4$alkyl; and
$R_{13}$, $R_{14}$, $R_{15}$, $R_{16}$ and $R_{17}$ are independently selected at each occurrence from the group consisting of hydrogen, $C_1$-$C_6$alkyl, $C_1$-$C_6$alkanoyl, $C_3$-$C_6$cycloalkyl, phenyl and heterocycle, each of which is substituted with 0, 1 or 2 residues independently selected from $C_1$-$C_4$alkyl, $C_1$-$C_4$alkoxy, halogen, hydroxyl, amino, and mono- and di-$C_1$-$C_6$alkylamino.

The present invention also relates to a method of treating a kinase dependent and/or proliferative disease comprising administering a compound of the formula I to a warm-blooded animal, especially a human, and the use of a compound of the formula I, especially for treating a kinase dependent disease or disorder. The present invention also relates to pharmaceutical preparations comprising a compound of the formula I, especially for the treatment of a kinase dependent disease or disorder, a process for the manufacture of a compound of the formula I, and novel starting materials and intermediates for their manufacture. The present invention also relates to the use of a compound of formula I in the manufacture of a pharmaceutical preparation for the treatment of a kinase dependent disease.

The general terms used hereinbefore and hereinafter preferably have, within this disclosure, the following meanings, unless otherwise indicated (where preferred embodiments can be defined by replacing one or more up to all general expressions or symbols with (a) more specific or more preferred definition(s) given herein):

Certain compounds of Formula I provided herein are compounds according to Formula II:

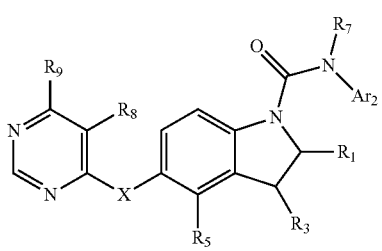

II or a salt thereof wherein
$R_1$ is hydrogen or $C_1$-$C_6$alkyl;
$R_3$ is hydrogen or $C_1$-$C_6$alkyl;
$R_5$ is hydrogen or halogen;
$R_7$ is hydrogen or $C_1$-$C_6$alkyl;
X is O or S;
$R_8$ is selected from the group consisting of hydrogen and $C_1$-$C_4$alkyl;
$R_9$ is selected from the group consisting of $(CR_{11}R_{12})_n$ $NR_{13}R_{14}$, $(CR_{11}R_{22})_n$heterocycle, $(CR_{11}R_{22})_n OR_{15}$, $(CR_{11}R_{22})_n C(O)ER_{13}$, and $(CR_{11}R_{12})_n S(O)_m R_{17}$; or
$R_8$ and $R_9$, taken in combination with the atoms to which they are attached form a saturated 4-7 membered heterocyclic ring having 1 or 2 ring heteroatoms selected from N, O or S, which heterocyclic ring is substituted with 0, 1, or 2 residues independently selected from the group consisting of $C_1$-$C_6$alkyl, $C_1$-$C_6$haloalkyl, halogen, hydroxy$C_1$-$C_6$alkyl, amino$C_1$-$C_6$alkyl, $C_3$-$C_7$cycloalkyl$C_1$-$C_4$alkyl, heterocycle$C_1$-$C_4$alkyl, $C_1$-$C_6$alkanoyl, mono- and di-$C_1$-$C_6$alkylaminocarbonyl, mono- and di-$C_1$-$C_4$alkylamino$C_1$-$C_4$alkanoyl, $C_1$-$C_6$alkoxycarbonyl, and $C_1$-$C_6$alkylsulfonyl.
$Ar_2$ is phenyl, naphthyl, 5 or 6 membered monocyclic heteroaryl, wherein each heteroaryl has 1, 2, or 3 ring heteroatoms selected from N, O or S and wherein the phenyl, naphthyl, or heteroaryl group is unsubstituted or substituted by 1, 2, or 3 groups independently selected from the group consisting of $C_1$-$C_6$alkyl, $C_1$-$C_6$haloalkyl, halo, hydroxyl, $CO_2R$, phenyl, and $C_3$-$C_7$cycloalkyl;
m is 0, 1, or 2;
n is 0, 1, 2, or 3;
E is O or $NR_{18}$;
$R_{11}$, $R_{12}$ and $R_{18}$ are the same or different and are independently selected at each occurrence from the group consisting of hydrogen and $C_1$-$C_4$alkyl; and
$R_{13}$, $R_{14}$, $R_{15}$, $R_{16}$ and $R_{17}$ are independently selected at each occurrence from the group consisting of hydrogen, $C_1$-$C_6$alkyl, $C_3$-$C_6$cycloalkyl, phenyl and heterocycle, each of which is substituted with 0, 1 or 2 residues independently selected from hydroxyl, amino, and mono- and di-$C_1$-$C_6$alkylamino.

Certain other compounds of Formula I provided herein are compounds according to Formula III:

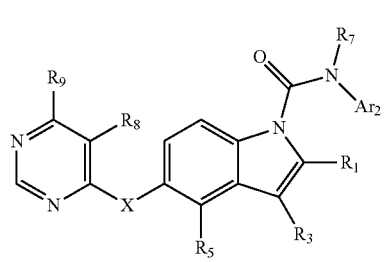

III or a salt thereof wherein
$R_1$ is hydrogen or $C_1$-$C_6$alkyl;
$R_3$ is hydrogen or $C_1$-$C_6$alkyl;
$R_5$ is hydrogen or halogen;
$R_7$ is hydrogen or $C_1$-$C_6$alkyl;
X is O or S;
$R_8$ is selected from the group consisting of hydrogen and $C_1$-$C_4$alkyl;
$R_9$ is selected from the group consisting of $(CR_{11}R_{12})_n$ $NR_{13}R_{14}$, $(CR_{11}R_{12})_n$heterocycle, $(CR_{11}R_{12})_n OR_{15}$, $(CR_{11}R_{12})_n C(O)ER_{13}$, and $(CR_{11}R_{12})_n S(O)_m R_{17}$; or
$R_8$ and $R_9$, taken in combination together with the atoms to which they are attached form a saturated 4-7 membered heterocyclic ring having 1 or 2 ring heteroatoms selected from N, O or S, which heterocyclic ring is substituted with 0, 1, or 2 residues independently selected from the group consisting of $C_1$-$C_6$alkyl, $C_1$-$C_6$haloalkyl, halogen, hydroxy$C_1$-$C_6$alkyl, amino$C_1$-$C_6$alkyl, $C_3$-$C_7$cycloalkyl$C_1$-$C_4$alkyl, heterocycle$C_1$-$C_4$alkyl, $C_1$-$C_6$alkanoyl, mono- and di-$C_1$-$C_6$alkylaminocarbonyl, mono- and di-$C_1$-$C_4$alkylamino$C_1$-$C_4$alkanoyl, $C_1$-$C_6$alkoxycarbonyl, and $C_1$-$C_6$alkylsulfonyl.
$Ar_2$ is phenyl, naphthyl, 5 or 6 membered monocyclic heteroaryl, wherein each heteroaryl has 1, 2, or 3 ring heteroatoms selected from N, O or S and wherein the phenyl, naphthyl, or heteroaryl group is unsubstituted or substituted by 1, 2, or 3 groups independently selected from the group consisting of $C_1$-$C_6$alkyl, $C_1$-$C_6$haloalkyl, halo, hydroxyl, $CO_2R$, phenyl, and $C_3$-$C_7$cycloalkyl;
m is 0, 1, or 2;
n is 0, 1, 2, or 3;
E is O or $NR_{18}$;
$R_{11}$, $R_{12}$ and $R_{18}$ are the same or different and are independently selected at each occurrence from the group consisting of hydrogen and $C_1$-$C_4$alkyl; and
$R_{13}$, $R_{14}$, $R_{15}$, $R_{16}$ and $R_{17}$ are independently selected at each occurrence from the group consisting of hydrogen, $C_1$-$C_6$alkyl, $C_3$-$C_6$cycloalkyl, phenyl and heterocycle, each of which is substituted with 0, 1 or 2 residues independently selected from hydroxyl, amino, and mono- and di-$C_1$-$C_6$alkylamino.

In certain embodiments, compounds of formula I, II, and/or III include those compounds in which $R_1$ and $R_3$ are hydrogen. In certain other compounds of formula I, II, and/or III, $R_1$ is hydrogen or $C_1$-$C_4$alkyl (e.g., methyl or ethyl), $R_3$ is hydrogen and either (1) $R_2$ and $R_4$ are hydrogen or (2) $R_2$ and $R_4$, taken in combination form a bond.

In certain embodiments $R_5$ is selected from hydrogen, methyl, methoxy, fluoro, or chloro. In certain other embodiments $R_5$ is selected from hydrogen or fluoro. In certain compounds of formula I, $R_1$ is methyl or ethyl and $R_5$ is fluoro.

In certain other embodiments, $R_6$ is absent.

In certain compounds of Formula I, II, or III, $R_7$ is hydrogen or methyl. In yet other embodiments, $R_7$ is hydrogen.

In yet other embodiments, X is oxygen.

Certain compounds of formula I, II, and/or III include those in which $R_1$ is hydrogen or $C_1$-$C_4$alkyl (e.g., methyl or ethyl), $R_3$ is hydrogen, $R_5$ is hydrogen or fluoro, $R_6$ is absent, X is oxygen and either (1) $R_2$ and $R_4$ are hydrogen or (2) $R_2$ and $R_4$, taken in combination form a bond.

In certain embodiments, $R_8$ is hydrogen. In other embodiments $R_{10}$ is hydrogen. In yet other embodiments, $R_8$ and $R_{10}$ are hydrogen.

In certain embodiments, $R_{10}$ is hydrogen and $R_8$ and $R_9$, taken in combination, form a saturated 5 or 6 membered heterocyclic ring having 1 ring nitrogen atoms, which heterocyclic ring is substituted with 0, 1, or 2 residues independently selected from the group consisting of $C_1$-$C_4$alkyl, $C_1$-$C_4$haloalkyl, hydroxy$C_1$-$C_4$alkyl, amino$C_1$-$C_4$alkyl, heterocycle$C_1$-$C_4$alkyl, $C_1$-$C_4$alkanoyl, mono- and di-$C_1$-$C_4$alkylaminocarbonyl, mono- and di-$C_1$-$C_4$alkylamino$C_1$-$C_4$alkanoyl, mono- and di-$C_1$-$C_4$alkylaminocarbonyl$C_1$-$C_4$alkyl, aminocarbonyl$C_1$-$C_4$alkyl, $C_1$-$C_4$alkoxycarbonyl, and $C_1$-$C_4$alkylsulfonyl.

Certain compounds of Formula I, II, or III, in which $R_8$ and $R_9$ form a ring include those in which the fragment:

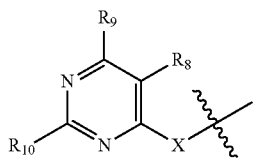

is selected from a residue of the formula:

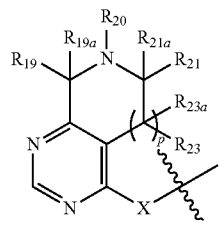

and salts thereof, wherein
p is 0 or 1;
$R_{19}$, $R_{19a}$, $R_{20}$, $R_{21}$, $R_{21a}$, $R_{23}$, and $R_{23a}$ are independently selected from the group consisting of hydrogen, oxo, hydroxyl, $C_1$-$C_4$alkyl, $C_1$-$C_4$haloalkyl, hydroxy$C_1$-$C_4$alkyl, HOC(O)CH$_2$, NH$_2$C(O)CH$_2$, mono- and di-$C_1$-$C_4$alkylNHMeC(O)CH$_2$, $C_1$-$C_4$alkanoyl, mono- and di-$C_1$-$C_4$alkyl$C_1$-$C_4$alkanoyl, $C_1$-$C_4$sulfonyl, or $R_{19}$ and $R_{19a}$ taken in combination or $R_{21}$ and $R_{21a}$ taken in combination or $R_{23}$ and $R_{23a}$ taken in combination form a three to seven membered spiro cyclic ring. In certain other compounds, $R_{19a}$, $R_{21a}$, $R_{23}$, and $R_{23a}$, are hydrogen, two of variables $R_{19}$, $R_{20}$ or $R_{21}$ are hydrogen and other is selected from the group consisting of hydrogen, methyl, ethyl, or hydroxyethyl.

Certain embodiments provide compounds of Formula I or III represented by the Formula IV:

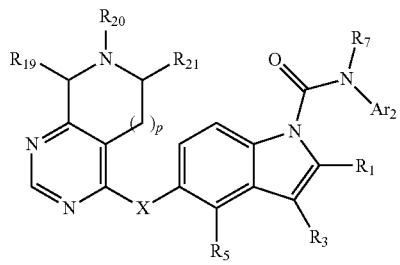

and salts thereof, wherein
p is 0 or 1;
$R_{19}$, $R_{20}$, and $R_{21}$ are independently selected from the group consisting of hydrogen, $C_1$-$C_4$alkyl, hydroxy$C_1$-$C_4$alkyl, NH$_2$C(O)CH$_2$, and NHMeC(O)CH$_2$.

Certain compounds of Formula IV include those compounds in which two of variables $R_{19}$, $R_{20}$ or $R_{21}$ are hydrogen and other is selected from the group consisting of hydrogen, methyl, ethyl, or hydroxyethyl. Certain other compounds of formula IV include those in which p is 0, $R_{19}$ and $R_{21}$ are hydrogen and $R_{20}$ is selected from hydrogen, methyl, and ethyl.

Certain embodiments provide compounds of Formula I or III represented by the Formula V:

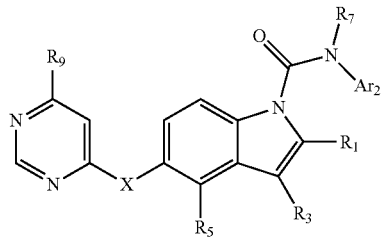

and salts thereof, wherein
$R_9$ is selected from the group consisting of CH$_2$NR$_{13}$R$_{14}$, CH$_2$OR$_{15}$, CH$_2$C(O)ER$_{13}$, and CH$_2$S(O)$_2$ER$_{17}$; or
E is absent, O or NR$_{18}$;
$R_{18}$ is hydrogen, methyl or ethyl; and
$R_{13}$, $R_{14}$, $R_{15}$, $R_{16}$ and $R_{17}$ are independently selected at each occurrence from the group consisting of hydrogen, $C_1$-$C_4$alkyl, and hydroxy$C_1$-$C_4$alkyl.

In certain compounds of Formula I, II, III, or V, $R_9$ is selected from the group consisting of (CH$_2$)$_n$NHR$_{13}$, (CR$_{11}$R$_{12}$)$_n$heterocycle, (CR$_{11}$R$_{12}$)$_n$OR$_{15}$, (CH$_2$)$_n$S(O)$_m$R$_{17}$ and (CH$_2$)$_n$S(O)$_m$N(R$_{18}$)$_2$;
n is 1 or 2;
$R_{13}$ is hydrogen, $C_1$-$C_4$alkyl, hydroxy$C_1$-$C_4$alkyl, or $C_3$-$C_6$cycloalkyl;
$R_{15}$ is hydrogen or $C_1$-$C_4$alkyl;
$R_{17}$ is $C_1$-$C_4$alkyl;
$R_{18}$ is independently selected at each occurrence from the group consisting of hydrogen, methyl or ethyl.

In certain other compounds of Formula I or III, or a salt thereof, wherein
$R_1$ is hydrogen, methyl or ethyl;
$R_3$ is hydrogen;

R₅ is hydrogen, fluoro or chloro;

X is O or S;

R₈ is selected from the group consisting of hydrogen and $C_1$-$C_4$alkyl;

R₉ is selected from the group consisting of $CH_2NR_{13}R_{14}$, $CH_2$heterocycle, $CH_2OR_{15}$, $CH_2C(O)ER_{13}$, and $CH_2S(O)_2ER_{17}$; or R₈ and R₉, taken in combination form a saturated 4-7 membered heterocyclic ring having one ring nitrogen atom, which heterocyclic ring is substituted with 0, 1, or 2 residues independently selected from the group consisting of $C_1$-$C_6$alkyl, $C_1$-$C_6$haloalkyl, halogen, $C_1$-$C_6$alkanoyl, and $C_1$-$C_6$alkylsulfonyl;

Ar₂ is phenyl, 5 membered monocyclic heteroaryl, wherein each heteroaryl has one ring nitrogen and 0 or 1 additional ring heteroatoms selected from N, O or S and wherein the phenyl or heteroaryl group is unsubstituted or substituted by 1, 2, or 3 groups independently selected from the group consisting of $C_1$-$C_6$alkyl, $C_1$-$C_6$haloalkyl, halo, hydroxyl, $CO_2R$, phenyl, and $C_3$-$C_7$cycloalkyl;

m is 0, 1, or 2;

n is 0, 1, 2, or 3;

E is O or $NR_{18}$;

R₁₈ is selected from the group consisting of hydrogen and $C_1$-$C_4$alkyl; and

R₁₃, R₁₄, R₁₅, R₁₆ and R₁₇ are independently selected at each occurrence from the group consisting of hydrogen, $C_1$-$C_6$alkyl, $C_3$-$C_6$cycloalkyl, phenyl and heterocycle, each of which is substituted with 0, 1 or 2 residues independently selected from hydroxyl, amino, and mono- and di-$C_1$-$C_6$alkylamino.

In certain compounds of Formula I, II, III, IV, or V, or salts thereof, Ar₂ is phenyl which is unsubstituted or substituted with 1 or 2 groups independently selected from halogen, $C_1$-$C_4$alkyl, $C_1$-$C_4$alkoxy, $C_1$-$C_4$haloalkyl, and $C_1$-$C_4$haloalkoxy. In other compounds of Formula I, II, III, IV, or V, or salts thereof, Ar₂ is a five membered heteroaryl having 1 ring nitrogen atom and 0 or 1 additional ring heteroatoms selected from N and O and wherein said heteroaryl group is unsubstituted or substituted with 1 or 2 groups independently selected from the group consisting of $C_1$-$C_4$alkyl, $C_1$-$C_4$haloalkyl, $C_1$-$C_4$alkoxy, $C_1$-$C_4$haloalkoxy, halogen, amino, amino$C_1$-$C_4$alkyl, mono- and di-$C_1$-$C_4$alkylamino$C_1$-$C_4$alkyl, mono- and di-$C_1$-$C_4$alkylamino, hydroxyl, $CO_2C_1$-$C_4$alkyl, phenyl$C_0$-$C_4$alkyl, $C_3$-$C_6$cycloalkyl$C_0$-$C_2$alkyl, aminosulfonyl, and mono- and di-$C_1$-$C_4$alkylaminosulfonyl. In certain other compounds of Formula I, II, III, IV, or V, or salts thereof, Ar₂ is a bicyclic heterocycle having a ring nitrogen atom and 0 or 1 additional ring heteroatoms selected from N and O which is saturated, partially unsaturated, or partially aromatic (e.g., a heteroaryl or phenyl ring fused to a heterocyclic or carbocyclic ring such that the bicyclic heterocycle comprises at least one ring heteroatom in at least one ring) and wherein the bicyclic heterocycle is unsubstituted or substituted by 1 or 2 groups independently selected from the group consisting of $C_1$-$C_4$alkyl, $C_1$-$C_4$haloalkyl, $C_1$-$C_4$alkoxy, $C_1$-$C_4$haloalkoxy, halogen, amino, amino$C_1$-$C_4$alkyl, mono- and di-$C_4$-$C_4$alkylamino$C_1$-$C_4$alkyl, mono- and di-$C_1$-$C_4$alkylamino, hydroxyl, $CO_2C_1$-$C_4$alkyl, phenyl$C_0$-$C_4$alkyl, $C_3$-$C_6$cycloalkyl$C_0$-$C_2$alkyl, aminosulfonyl, and mono- and di-$C_1$-$C_4$alkylaminosulfonyl. In certain compounds in which Ar₂ is a five membered heteroaryl or a bicyclic heterocycle, Ar₂ is unsubstituted or substituted with a $C_1$-$C_4$alkyl or a hydroxy$C_1$-$C_4$alkyl.

In certain compounds of Formula I, II, III, IV, or V, or salts thereof, Ar₂ is a group of the formula:

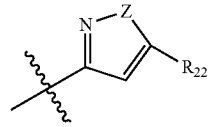

wherein

R₂₂ is selected from $C_1$-$C_4$alkyl, $C_3$-$C_6$cycloalkyl, $C_3$-$C_6$cycloalkyl$C_1$-$C_4$alkyl, $C_1$-$C_4$haloalkyl, hydroxy$C_1$-$C_4$alkyl, phenyl, 5 and 6 membered heterocycle; and Z is O, NH or $N(C_1$-$C_4$alkyl). In certain compounds R₂₂ is selected from $C_1$-$C_4$alkyl, $C_3$-$C_6$cycloalkyl, 1-methyl-$C_3$-$C_6$cycloalkyl, $C_{1-2}$haloalkyl, and hydroxy$C_1$-$C_4$alkyl; and Z is O or NH. In still other compounds R₂₂ is selected from isopropyl, tert-butyl, cyclopropyl, cyclobutyl, 1-methyl-cyclopropyl, 1-trifluoromethyl-cyclopropyl, 1-ethyl-cyclopropyl, 1-methylcyclobutyl, 1-methylcyclobutyl, hydroxyl-tert-butyl, and trifluoromethyl; and Z is O. In certain compound where Z is N, the compounds may exist as one or both of the 1H or 2H pyrazole tautomer, e.g.,

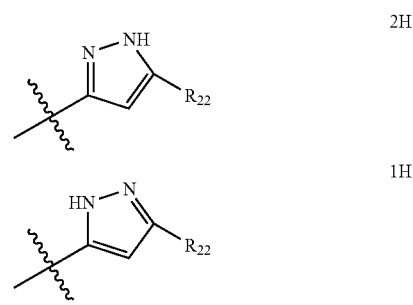

Certain compounds of Formula I include the exemplified compounds prepared herein. Certain compounds of Formula I include compounds selected from the group consisting of:

5-(7-Ethyl-5,6,7,8-tetrahydro-pyrido[3,4-d]pyrimidin-4-yloxy)-indole-1-carboxylic acid (3-trifluoromethyl-phenyl)-amide;

5-(6-Methylaminomethyl-pyrimidin-4-yloxy)-indole-1-carboxylic acid (4-fluoro-3-trifluoromethyl-phenyl)-amide;

6-Tetrazol-2-ylmethyl-pyrimidin-4-yloxy)-indole-1-carboxylic acid (4-fluoro-3-trifluoromethyl-phenyl)-amide;

5-(6-Cyclopropylaminomethyl-pyrimidin-4-yloxy)-indole-1-carboxylic acid (4-fluoro-3-trifluoromethyl-phenyl)-amide;

5-(5,6,7,8-Tetrahydro-pyrido[3,4-d]pyrimidin-4-yloxy)-indole-1-carboxylic acid (3-trifluoromethyl-phenyl)-amide;

N-(4-Fluoro-3-(trifluoromethyl)phenyl)-5-(6-(methylsulfonylmethyl)pyrimidin-4-yloxy)-1H-indole-1-carboxamide;

N-(4-Methoxy-3-(trifluoromethyl)phenyl)-5-(6-(methylamino)methyl)pyrimidin-4-yloxy)-1H-indole-1-carboxamide;

5-(7-Methanesulfonyl-5,6,7,8-tetrahydro-pyrido[3,4-a]pyrimidin-4-yloxy)-indole-1-carboxylic acid (3-trifluoromethyl-phenyl)-amide;

5-(6,7-Dihydro-5H-pyrrolo[3,4-d]pyrimidin-4-yloxy)-indole-1-carboxylic acid (5-tert-butyl-isoxazol-3-yl)-amide;

5-[6-(2-Hydroxy-ethyl)-6,7-dihydro-5H-pyrrolo[3,4-d]pyrimidin-4-yloxy]-indole-1-carboxylic acid (3-trifluoromethyl-phenyl)-amide;

5-(6,7-Dihydro-5H-pyrrolo[3,4-d]pyrimidin-4-yloxy)-indole-1-carboxylic acid (3-trifluoromethyl phenyl)-amide;

5-(5,6,7,8-Tetrahydro-pyrido[3,4-d]pyrimidin-4-yloxy)-indole-1-carboxylic acid (4-fluoro-3-trifluoromethyl-phenyl)-amide;

5-(5,6,7,8-Tetrahydro-pyrido[3,4-a]pyrimidin-4-yloxy)-indole-1-carboxylic acid (5-tert-butyl-isoxazol-3-yl)-amide;

(−)-(S)-5-(6-Methyl-5,6,7,8-tetrahydro-pyrido[3,4-d]pyrimidin-4-yloxy)-indole-1-carboxylic acid (3-trifluoromethyl-phenyl)-amide;

(+)-(R)-5-(6-Methyl-5,6,7,8-tetrahydro-pyrido[3,4-a]pyrimidin-4-yloxy)-indole-1-carboxylic acid (3-trifluoromethyl-phenyl)-amide;

4-Fluoro-5-(5,6,7,8-tetrahydro-pyrido[3,4-d]pyrimidin-4-yloxy)-indole-1-carboxylic acid (3-trifluoromethyl-phenyl)-amide;

5-(6-Methylaminomethyl-pyrimidin-4-yloxy)-indole-1-carboxylic acid (5-tert-butyl-2H-pyrazol-3-yl)-amide;

5-(6,7-Dihydro-5H-pyrrolo[3,4-d]pyrimidin-4-yloxy)-indole-1-carboxylic acid (2-fluoro-3-trifluoromethyl-phenyl)-amide;

5-(6,7-Dihydro-5H-pyrrolo[3,4-d]pyrimidin-4-yloxy)-indole-1-carboxylic acid (5-cyclopropyl-isoxazol-3-yl)-amide;

5-(6,7-Dihydro-5H-pyrrolo[3,4-d]pyrimidin-4-yloxy)-indole-1-carboxylic acid (5-isobutyl-isoxazol-3-yl)-amide;

5-(6,7-Dihydro-5H-pyrrolo[3,4-d]pyrimidin-4-yloxy)-indole-1-carboxylic acid [5-(1-methyl-cyclopropyl)-isoxazol-3-yl]-amide;

5-(5,6,7,8-Tetrahydro-pyrido[3,4-a]pyrimidin-4-yloxy)-indole-1-carboxylic acid (5-tert-butyl-2H-pyrazol-3-yl)-amide;

5-(6-Methyl-6,7-dihydro-5H-pyrrolo[3,4-d]pyrimidin-4-yloxy)-indole-1-carboxylic acid (3-trifluoromethyl-phenyl)-amide;

5-(5,6,7,8-Tetrahydro-pyrido[3,4-d]pyrimidin-4-yloxy)-indole-1-carboxylic acid (3-fluoro-5-trifluoromethyl-phenyl)-amide;

6,7-Dihydro-5H-pyrrolo[3,4-d]pyrimidin-4-yloxy)-indole-1-carboxylic acid (3-tert-butyl-isoxazol-5-yl)-amide;

(−)-5-Methyl-6,7-dihydro-5H-pyrrolo[3,4-d]pyrimidin-4-yloxy)-indole-1-carboxylic acid (5-tert-butyl-isoxazol-3-yl)-amide;

(+)-5-Methyl-6,7-dihydro-5H-pyrrolo[3,4-a]pyrimidin-4-yloxy)-indole-1-carboxylic acid (5-tert-butyl-isoxazol-3-yl)-amide;

4-Fluoro-2-methyl-5-(6-((methylamino)methyl)pyrimidin-4-yloxy)-N-(3(trifluoromethyl)-phenyl)-1H-indole-1-carboxamide;

5-(5,6,7,8-Tetrahydro-pyrido[3,4-a]pyrimidin-4-yloxy)-indole-1-carboxylic acid [5-(1-methyl-cyclopropyl)-2H-pyrazol-3-yl]-amide;

4-Fluoro-5-(6-methylaminomethyl-pyrimidin-4-yloxy)-indole-1-carboxylic acid (5-trifluoromethyl-1H-pyrazol-3-yl)-amide;

(+)-5-((S)-6-Methyl-5,6,7,8-tetrahydro-pyrido[3,4-d]pyrimidin-4-yloxy)-indole-1-carboxylic acid (5-tert-butyl-isoxazol-3-yl)-amide;

(−)-5-((R)-6-Methyl-5,6,7,8-tetrahydro-pyrido[3,4-d]pyrimidin-4-yloxy)-indole-1-carboxylic acid (5-tert-butyl-isoxazol-3-yl)-amide;

5-(6,7-Dihydro-5H-pyrrolo[3,4 d]pyrimidin-4-yloxy)-indole-1-carboxylic acid [5-(1-methyl-cyclopropyl)-2H-pyrazol-3-yl]-amide;

5-(2-(2-Morpholinoethyl)pyrimidin-4-yloxy)-N-(3-(trifluoromethyl)phenyl)-1H-indole-1-carboxamide;

5-(6,7-Dihydro-5H-pyrrolo[3,4-d]pyrimidin-4-yloxy)-indole-1-carboxylic acid (5-isopropyl-isoxazol-3-yl)-amide;

5-(5,6,7,8-Tetrahydro-pyrido[4,3-d]pyrimidin-4-yloxy)-indole-1-carboxylic acid (3-trifluoromethyl-phenyl)-amide;

5-[6-((1R, 4S)-5-Acetyl-2,5-diaza-bicyclo[2.2.1]hept-2-ylmethyl)-pyrimidin-4-yloxy]-indole-1-carboxylic acid (3-trifluoromethyl-phenyl)-amide;

5-(6-Methanesulfonylmethyl-pyrimidin-4-yloxy)-indole-1-carboxylic acid (2-fluoro-3-trifluoromethyl-phenyl)-amide;

5-[2-(5-oxo-4,5-dihydro-[1,3,4]oxadiazol-2-yl)-pyridin-4-yloxy]-indole-1-carboxylic acid (3-trifluoromethyl-phenyl)-amide;

5-[7-(3-Diethylamino-propionyl)-5,6,7,8-tetrahydro-pyrido[3,4-d]pyrimidin-4-yloxy]-indole-1-carboxylic acid (3-trifluoromethyl-phenyl)-amide;

5-(2-Cyclopropylcarbamoyl-pyridin-4-yloxy)-indole-1-carboxylic acid (3-trifluoromethyl-phenyl)-amide;

6-(5-Methyl-tetrazol-2-ylmethyl)-pyrimidin-4-yloxy]-indole-1-carboxylic acid (4-fluoro-3-trifluoromethyl-phenyl)-amide;

5-((S)-6-Methyl-5,6,7,8-tetrahydro-pyrido[3,4-d]pyrimidin-4-yloxy)-indole-1-carboxylic acid [5-(1-methyl-cyclopropyl)-2H-pyrazol-3-yl]-amide;

5-((R)-6-Methyl-5,6,7,8-tetrahydro-pyrido[3,4-d]pyrimidin-4-yloxy)-indole-1-carboxylic acid [5-(1-methyl-cyclopropyl)-2H-pyrazol-3-yl]-amide;

5-(6,7-Dihydro-5H-pyrrolo[3,4-d]pyrimidin-4-yloxy)-indole-1-carboxylic acid [5-(4-fluoro-phenyl)-isoxazol-3-yl]-amide;

5-[6-(4-Methanesulfonylamino-piperidin-1-ylmethyl)-pyrimidin-4-yloxy]-indole-1-carboxylic acid (3-trifluoromethyl-phenyl)-amide;

5-[7-(2-Hydroxy-ethyl)-5,6,7,8-tetrahydro-pyrido[3,4-d]pyrimidin-4-yloxy]-indole-1-carboxylic acid (3-trifluoromethyl-phenyl)-amide;

5-(2-Methylcarbamoyl-pyridin-4-yloxy)-indole-1-carboxylic acid (3-trifluoromethyl-phenyl)-amide;

5-(5,6,7,8-Tetrahydro-pyrido[3,4-a]pyrimidin-4-yloxy)-indole-1-carboxylic acid [5-(2-hydroxy-1,1-dimethyl-ethyl)-2H-pyrazol-3-yl]-amide;

5-(5,6,7,8-Tetrahydro-pyrido[3,4-a]pyrimidin-4-yloxy)-indole-1-carboxylic acid (5-trifluoromethyl-pyridin-3-yl)-amide;

5-(6,7-Dihydro-5H-pyrrolo[3,4-d]pyrimidin-4-yloxy)-indole-1-carboxylic acid (1-methyl-1H-indol-4-yl)-amide;

5-(6-Morpholin-4-ylmethyl-pyrimidin-4-yloxy)-2,3-dihydro-indole-1-carboxylic acid (3-trifluoromethyl-phenyl)-amide hydrochloride;

5-(6,7-Dihydro-5H-pyrrolo[3,4-d]pyrimidin-4-yloxy)-2-methyl-indole-1-carboxylic acid (5-tert-butyl-isoxazol-3-yl)-amide;

5-(2-Hydroxymethyl-pyridin-4-yloxy)-indole-1-carboxylic acid (3-trifluoromethylphenyl)-amide;

5-(6-Isobutyl-pyrimidin-4-yloxy)-indole-1-carboxylic acid (3-trifluoromethyl-phenyl)-amide;

5-(5,6,7,8-Tetrahydro-pyrido[3,4-d]pyrimidin-4-yloxy)-indole-1-carboxylic acid (5-phenyl-2H-pyrazol-3-yl)-amide;

2-Methyl-5-(5,6,7,8-tetrahydro-pyrido[3,4-d]pyrimidin-4-yloxy)-indole-1-carboxylic acid (3-trifluoromethyl-phenyl)-amide;

4-Fluoro-5-((S)-6-methyl-5,6,7,8-tetrahydro-pyrido[3,4-d]pyrimidin-4-yloxy)-indole-1-carboxylic acid [5-(1-methyl-cyclopropyl)-2H-pyrazol-3-yl]-amide;

4-Fluoro-5-((R)-6-methyl-5,6,7,8-tetrahydro-pyrido[3,4-d]pyrimidin-4-yloxy)-indole-1-carboxylic acid [5-(1-methyl-cyclopropyl)-2H-pyrazol-3-yl]-amide;

5-(6-Pyrrolidin-1-ylmethyl-pyrimidin-4-yloxy)-indole-1-carboxylic acid (3-trifluoromethyl-phenyl)-amide;

5-(2-Cyclopropylaminomethyl-pyridin-4-yloxy)-indole-1-carboxylic acid (3-trifluoromethyl-phenyl)-amide;

(−)-5-((S)-7-Acetyl-6-methyl-5,6,7,8-tetrahydro-pyrido[3,4-d]pyrimidin-4-yloxy)-indole-1-carboxylic acid (5-cyclopropyl-isoxazol-3-yl)-amide;

4-Fluoro-5-(2-methanesulfonylmethyl-pyrimidin-4-yloxy)-2-methyl-indole-1-carboxylic acid (3-trifluoromethyl-phenyl)-amide;

5-(6-Methylaminomethyl-pyrimidin-4-yloxy)-indole-1-carboxylic acid (5-cyclopropyl-1-methyl-1H-pyrazol-3-yl)-amide; and a tautomer thereof and/or a pharmaceutically acceptable salt thereof.

In a preferred embodiment the present invention relates to a compound selected from the group consisting of 5-(7-Ethyl-5,6,7,8-tetrahydro-pyrido[3,4-d]pyrimidin-4-yloxy)-indole-1-carboxylic acid (3-trifluoromethyl-phenyl)-amide;

5-(6-Methylaminomethyl-pyrimidin-4-yloxy)-indole-1-carboxylic acid (4-fluoro-3-trifluoromethyl-phenyl)-amide;

6-Tetrazol-2-ylmethyl-pyrimidin-4-yloxy)-indole-1-carboxylic acid (4-fluoro-3-trifluoromethyl-phenyl)-amide;

5-(5,6,7,8-Tetrahydro-pyrido[3,4-d]pyrimidin-4-yloxy)-indole-1-carboxylic acid (3-trifluoromethyl-phenyl)-amide;

N-(4-Fluoro-3-(trifluoromethyl)phenyl)-5-(6-(methylsulfonylmethyl)pyrimidin-4-yloxy)-1H-indole-1-carboxamide;

5-(7-Methanesulfonyl-5,6,7,8-tetrahydro-pyrido[3,4-a]pyrimidin-4-yloxy)-indole-1-carboxylic acid (3-trifluoromethyl-phenyl)-amide;

5-(6,7-Dihydro-5H-pyrrolo[3,4-d]pyrimidin-4-yloxy)-indole-1-carboxylic acid (5-tert-butyl-isoxazol-3-yl)-amide;

5-[6-(2-Hydroxy-ethyl)-6,7-dihydro-5H-pyrrolo[3,4-d]pyrimidin-4-yloxy]-indole-1-carboxylic acid (3-trifluoromethyl-phenyl)-amide;

5-(6,7-Dihydro-5H-pyrrolo[3,4-d]pyrimidin-4-yloxy)-indole-1-carboxylic acid (3-trifluoromethyl phenyl)-amide;

5-(5,6,7,8-Tetrahydro-pyrido[3,4-a]pyrimidin-4-yloxy)-indole-1-carboxylic acid (5-tert-butyl-isoxazol-3-yl)-amide;

(−)-(S)-5-(6-Methyl-5,6,7,8-tetrahydro-pyrido[3,4-a]pyrimidin-4-yloxy)-indole-1-carboxylic acid (3-trifluoromethyl-phenyl)-amide;

(+)-(R)-5-(6-Methyl-5,6,7,8-tetrahydro-pyrido[3,4-a]pyrimidin-4-yloxy)-indole-1-carboxylic acid (3-trifluoromethyl-phenyl)-amide;

4-Fluoro-5-(5,6,7,8-tetrahydro-pyrido[3,4-d]pyrimidin-4-yloxy)-indole-1-carboxylic acid (3-trifluoromethyl-phenyl)-amide;

5-(6,7-Dihydro-5H-pyrrolo[3,4-d]pyrimidin-4-yloxy)-indole-1-carboxylic acid (2-fluoro-3-trifluoromethyl-phenyl)-amide;

5-(6,7-Dihydro-5H-pyrrolo[3,4-d]pyrimidin-4-yloxy)-indole-1-carboxylic acid (5-cyclopropyl-isoxazol-3-yl)-amide;

5-(6,7-Dihydro-5H-pyrrolo[3,4-d]pyrimidin-4-yloxy)-indole-1-carboxylic acid [5-(1-methyl-cyclopropyl)-isoxazol-3-yl]-amide;

5-(5,6,7,8-Tetrahydro-pyrido[3,4-a]pyrimidin-4-yloxy)-indole-1-carboxylic acid [5-(1-methyl-cyclopropyl)-2H-pyrazol-3-yl]-amide;

(+)-5-((S)-6-Methyl-5,6,7,8-tetrahydro-pyrido[3,4-d]pyrimidin-4-yloxy)-indole-1-carboxylic acid (5-tert-butyl-isoxazol-3-yl)-amide;

5-(6,7-Dihydro-5H-pyrrolo[3,4-d]pyrimidin-4-yloxy)-indole-1-carboxylic acid (5-isopropyl-isoxazol-3-yl)-amide;

5-[7-(3-Diethylamino-propionyl)-5,6,7,8-tetrahydro-pyrido[3,4-d]pyrimidin-4-yloxy]-indole-1-carboxylic acid (3-trifluoromethyl-phenyl)-amide;

5-((S)-6-Methyl-5,6,7,8-tetrahydro-pyrido[3,4-d]pyrimidin-4-yloxy)-indole-1-carboxylic acid [5-(1-methyl-cyclopropyl)-2H-pyrazol-3-yl]-amide;

5-((R)-6-Methyl-5,6,7,8-tetrahydro-pyrido[3,4-d]pyrimidin-4-yloxy)-indole-1-carboxylic acid [5-(1-methyl-cyclopropyl)-2H-pyrazol-3-yl]-amide;

5-((S)-6-Methyl-5,6,7,8-tetrahydro-pyrido[3,4-d]pyrimidin-4-yloxy)-indole-1-carboxylic acid (5-cyclopropyl-isoxazol-3-yl)-amide;

5-(6-Methylaminomethyl-pyrimidin-4-yloxy)-indole-1-carboxylic acid (5-isopropyl-1H-pyrazol-3-yl)-amide;

5-(6-Methylaminomethyl-pyrimidin-4-yloxy)-indole-1-carboxylic acid (5-cyclopropyl-1H-pyrazol-3-yl)-amide;

5-(6-Methylaminomethyl-pyrimidin-4-yloxy)-indole-1-carboxylic acid (5-cyclopropyl-1-methyl-1H-pyrazol-3-yl)-amide;

5-(6-Methylaminomethyl-pyrimidin-4-yloxy)-indole-1-carboxylic acid [5-(1-methyl cyclopropyl)-isoxazol-3-yl]-amide;

5-((S)-7-Acetyl-6-methyl-5,6,7,8-tetrahydro-pyrido[3,4-d]pyrimidin-4-yloxy)-indole-1-carboxylic acid [5-(1 trifluoromethyl-cyclopropyl)-isoxazol-3-yl]-amide;

5-[(S)-6-Methyl-7-(3-methyl-butyryl)-5,6,7,8-tetrahydro-pyrido[3,4-d]pyrimidin-4-yloxy]-indole-1-carboxylic acid [5-(1-trifluoromethyl-cyclopropyl)-isoxazol-3-yl]-amide;

5-((S)-7-Cyclopropylmethyl-6-methyl-5,6,7,8-tetrahydro-pyrido[3,4-d]pyrimidin-4-yloxy)-indole-1-carboxylic acid [5-(1-trifluoromethyl-cyclopropyl)-isoxazol-3-yl]-amide;

5-((S)-7-Ethyl-6-methyl-5,6,7,8-tetrahydro-pyrido[3,4-d]pyrimidin-4-yloxy)-indole-1-carboxylic acid [5-(1-trifluoromethyl-cyclopropyl)-isoxazol-3-yl]-amide;

5-((S)-7-Cyclopropanecarbonyl-6-methyl-5,6,7,8-tetrahydro-pyrido[3,4-d]pyrimidin-4-yloxy)-indole-1-carboxylic acid (5-cyclopropyl-isoxazol-3-yl)-amide;

5-((S)-6,7-Dimethyl-5,6,7,8-tetrahydro-pyrido[3,4-d]pyrimidin-4-yloxy)-indole-1-carboxylic acid (5-cyclopropyl-isoxazol-3-yl)-amide;

5-((S)-7-Ethyl-6-methyl-5,6,7,8-tetrahydro-pyrido[3,4-d]pyrimidin-4-yloxy)-indole-1-carboxylic acid (4,4-dimethyl-5,6-dihydro-4H-pyrrolo[1,2-b]pyrazol-2-yl)-amide;

(−)-5-((S)-7-Acetyl-6-methyl-5,6,7,8-tetrahydro-pyrido[3,4-d]pyrimidin-4-yloxy)-indole-1-carboxylic acid (5-cyclopropyl-isoxazol-3-yl)-amide;

4-Methyl-5-((S)-6-methyl-5,6,7,8-tetrahydro-pyrido[3,4-d]pyrimidin-4-yloxy)-indole-1-carboxylic acid (5-cyclopropyl-isoxazol-3-yl)-amide;

5-((S)-6-Methyl-5,6,7,8-tetrahydro-pyrido[3,4-d]pyrimidin-4-yloxy)-indole-1-carboxylic acid [5-(1-trifluoromethyl-cyclopropyl)-isoxazol-3-yl]-amide;

5-((S)-6-Methyl-5,6,7,8-tetrahydro-pyrido[3,4-d]pyrimidin-4-yloxy)-indole-1-carboxylic acid (1-tert-butyl-1H-pyrazol-3-yl)-amide;

5-(6,7-Dihydro-5H-pyrrolo[3,4-d]pyrimidin-4-yloxy)-4-methyl-indole-1-carboxylic acid (5-cyclopropyl-isoxazol-3-yl)-amide;

5-(6,7-Dihydro-5H-pyrrolo[3,4-d]pyrimidin-4-yloxy)-indole-1-carboxylic acid [5-(1 trifluoromethyl-cyclopropyl)-isoxazol-3-yl]-amide;

5-(6,7,8,9-Tetrahydro-5H-pyrimido[4,5-c]azepin-4-yloxy)-indole-1-carboxylic acid [5-(1-trifluoromethyl-cyclopropyl)-isoxazol-3-yl]-amide;

5-(6,7-Dihydro-5H-pyrrolo[3,4-d]pyrimidin-4-yloxy)-indole-1-carboxylic acid [4-methyl-5-(1-methyl-cyclopropyl)-isoxazol-3-yl]-amide;

5-((S)-7-Acetyl-6-methyl-5,6,7,8-tetrahydro-pyrido[3,4-d]pyrimidin-4-yloxy)-4-methyl-indole-1-carboxylic acid (5-cyclopropyl-isoxazol-3-yl)-amide;

4-Methyl-5-((S)-6-methyl-5,6,7,8-tetrahydro-pyrido[3,4-d]pyrimidin-4-yloxy)-indole-1-carboxylic acid (5-cyclopropyl-isoxazol-3-yl)-amide;

5-(6-Methylaminomethyl-pyrimidin-4-yloxy)-indole-1-carboxylic acid (1-tert-butyl-1H-pyrazol-3-yl)-amide;

5-(6-Methylaminomethyl-pyrimidin-4-yloxy)-indole-1-carboxylic acid (1-methyl-5-trifluoromethyl-1H-pyrazol-3-yl)-amide;

5-((S)-7-Acetyl-6-methyl-5,6,7,8-tetrahydro-pyrido[3,4-d]pyrimidin-4-yloxy)-indole-1-carboxylic acid (1-tert-butyl-1H-pyrazol-3-yl)-amide;

5-((S)-7-Butyryl-6-methyl-5,6,7,8-tetrahydro-pyrido[3,4-d]pyrimidin-4-yloxy)-indole-1-carboxylic acid (5-cyclopropyl-isoxazol-3-yl)-amide;

5-((S)-6-Methyl-7-propionyl-5,6,7,8-tetrahydro-pyrido[3,4-d]pyrimidin-4-yloxy)-indole-1-carboxylic acid (5-cyclopropyl-isoxazol-3-yl)-amide;

4-[1-(5-Cyclopropyl-isoxazol-3-ylcarbamoyl)-1H-indol-5-yloxy]-5,6,7,8-tetrahydro-pyrido[3,4-d]pyrimidine-6-carboxylic acid methylamide;

N-(1-methyl-5-(trifluoromethyl)-1H-pyrazol-3-yl)-5-(2-((methylamino)methyl)pyridin-4-yloxy)-1H-indole-1-carboxamide;

5-(6-Methylaminomethyl-pyrimidin-4-yloxy)-indole-1-carboxylic acid (1,5-dicyclopropyl-1H-pyrazol-3-yl)-amide;

5-(6-Methylaminomethyl-pyrimidin-4 yloxy)-indole-1-carboxylic acid (5-cyclopropyl-1-ethyl-1H-pyrazol-3-yl)-amide;

4-Methyl-5-((S)-6-methyl-5,6,7,8-tetrahydro-pyrido[3,4-d]pyrimidin-4-yloxy)-indole-1-carboxylic acid (1-methyl-5-trifluoromethyl-1H-pyrazol-3-yl)-amide; and tautomer thereof and/or a pharmaceutically acceptable salt thereof.

For purposes of interpreting this specification, the following definitions will apply and whenever appropriate, terms used in the singular will also include the plural and vice versa.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "haloalkyl" refers to an alkyl as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Preferably, the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

The term "aryl" refers to monocyclic or bicyclic aromatic hydrocarbon groups having 6-20 carbon atoms in the ring portion. Preferably, the aryl is a ($C_6$-$C_{10}$) aryl. Non-limiting examples include phenyl, biphenyl, naphthyl or tetrahydronaphthyl, each of which may optionally be substituted by 1-4 substituents, such as alkyl, trifluoromethyl, cycloalkyl, halogen, hydroxy, alkoxy, acyl, alkyl-C(O)—O—, aryl-O—, heteroaryl-O—, amino, thiol, alkyl-S—, aryl-S—, nitro, cyano, carboxy, alkyl-O—C(O)—, carbamoyl, alkyl-S(O)—, sulfonyl, sulfonamido, heterocyclyl and the like.

Furthermore, the term "aryl" as used herein, refers to an aromatic substituent which can be a single aromatic ring, or multiple aromatic rings that are fused together, linked covalently, or linked to a common group such as a methylene or ethylene moiety. The common linking group also can be a carbonyl as in benzophenone or oxygen as in diphenylether or nitrogen as in diphenylamine.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-7, more preferably about 1-4 carbons.

As used herein, the term "alkanoyl" refers to a group R—C(O)— of from 1 to 10 carbon atoms of a straight, branched, or cyclic configuration or a combination thereof, attached to the parent structure through carbonyl functionality. R in the alkanoyl residue is hydrogen, alkyl, cycloalkyl, or cycloalkyl-alkyl.

As used herein, the term "carbamoyl" refers to $H_2NC$(O)—, alkyl-NHC(O)—, (alkyl)$_2$NC(O)—, aryl-NHC(O)—, alkyl(aryl)-NC(O)—, heteroaryl-NHC(O)—, alkyl(heteroaryl)-NC(O)—, aryl-alkyl-NHC(O)—, and alkyl(aryl-alkyl)-NC(O)—.

As used herein, the term "sulfonyl" refers to R—$SO_2$—, wherein R is hydrogen, alkyl, aryl, heteroaryl, aryl-alkyl, heteroaryl-alkyl, alkoxy, aryloxy, cycloalkyl, or heterocyclyl.

As used herein, the term "sulfonamido" refers to alkyl-S(O)$_2$—NH—, aryl-S(O)$_2$—NH—, aryl-alkyl-S(O)$_2$—NH—, heteroaryl-S(O)$_2$—NH—, heteroaryl-alkyl-S(O)$_2$—NH—, alkyl-S(O)$_2$—N(alkyl)-, aryl-S(O)$_2$—N(alkyl)-, aryl-alkyl-S(O)$_2$—N(alkyl)-, heteroaryl-S(O)$_2$—N(alkyl)-, and heteroaryl-alkyl-S(O)$_2$—N(alkyl)-.

As used herein, the term "heterocyclyl" or "heterocyclo" refers to an optionally substituted, saturated or unsaturated non-aromatic ring or ring system, e.g., which is a 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. The heterocyclic group can be attached at a heteroatom or a carbon atom. The heterocyclyl can include fused or bridged rings as well as spiro-cyclic rings. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, and thiomorpholine.

The term "heterocyclyl" further refers to heterocyclic groups as defined herein substituted with 1, 2 or 3 substituents selected from the groups consisting of the following:

(a) alkyl;
(b) hydroxy (or protected hydroxy);
(c) halo;
(d) oxo, i.e., =O;
(e) amino, alkylamino or dialkylamino;
(f) alkoxy;
(g) cycloalkyl;
(h) carboxyl;
(i) heterocyclooxy, wherein heterocyclooxy denotes a heterocyclic group bonded through an oxygen bridge;
(j) alkyl-O—C(O)—;
(k) mercapto;
(l) nitro;
(m) cyano;
(n) sulfamoyl or sulfonamido;
(o) aryl;
(p) alkyl-C(O)—O—;
(q) aryl-C(O)—O—;
(r) aryl-S—;
(s) aryloxy;
(t) alkyl-S—;
formyl, i.e., HC(O)—;
carbamoyl;
(w) aryl-alkyl—; and
(x) aryl substituted with alkyl, cycloalkyl, alkoxy, hydroxy, amino, alkyl-C(O)—NH—, alkylamino, dialkylamino or halogen.

As used herein, the term "cycloalkyl" refers to saturated or unsaturated monocyclic, bicyclic or tricyclic hydrocarbon groups of 3-12 carbon atoms, preferably 3-9, or 3-7 carbon atoms, each of which can be optionally substituted by one, or two, or three, or more substituents, such as alkyl, halo, oxo, hydroxy, alkoxy, alkyl-C(O)—, acylamino, carbamoyl, alkyl-NH—, (alkyl)$_2$N—, thiol, alkyl-S—, nitro, cyano, carboxy, alkyl-O—C(O)—, sulfonyl, sulfonamido, sulfamoyl, and heterocyclyl. Exemplary monocyclic hydrocarbon groups include, but are not limited to, cyclopropyl, cyclobutyl, cyclopentyl, cyclopentenyl, cyclohexyl and cyclohexenyl. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, and bicyclo[2.2.2]octyl. Exemplary tricyclic hydrocarbon groups include adamantyl.

As used herein, the term "sulfamoyl" refers to H$_2$NS(O)$_2$—, alkyl-NHS(O)$_2$—, (alkyl)$_2$NS(O)$_2$—, aryl-NHS(O)$_2$—, alkyl(aryl)-NS(O)$_2$—, (aryl)$_2$NS(O)$_2$—, heteroaryl-NHS(O)$_2$—, (aryl-alkyl)-NHS(O)$_2$—, and (heteroaryl-alkyl)-NHS(O)$_2$—.

As used herein, the term "aryloxy" refers to both an —O-aryl and an —O-heteroaryl group, wherein aryl and heteroaryl are defined herein.

As used herein, the term "heteroaryl" refers to a 5-14 membered monocyclic- or bicyclic- or polycyclic-aromatic ring system, having 1 to 8 heteroatoms selected from N, O or S. Preferably, the heteroaryl is a 5-10 or 5-7 membered ring system. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinoliyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4-aH carbazolyl, 1-, 2-, 3-, 4-, 5-, 6-, 7-, or 8-carbazolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenanthrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

A heteroaryl group may be mono-, bi-, i-, or polycyclic, preferably mono-, bi-, or tricyclic, more preferably mono- or bicyclic.

As used herein, the term "halogen" or "halo" refers to fluoro, chloro, bromo, and iodo.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)- isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the term "pharmaceutically acceptable salts" refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto. Pharmaceutically acceptable acid addition salts can be formed with inorganic acids and organic acids, e.g., acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Inorganic acids from which salts can be derived include, for example, hydrochloric acid, hydrobromic acid, sulfuric acid, nitric acid and phosphoric acid. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, and aluminum; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, and basic ion exchange resins, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

The present invention includes all pharmaceutically acceptable isotopically-labeled compounds of the invention, i.e. compounds of formula (I), wherein (1) one or more atoms are replaced by atoms having the same atomic number, but an atomic mass or mass number different from the atomic mass or mass number usually found in nature, and/or (2) the isotopic ratio of one or more atoms is different from the naturally occurring ratio.

Examples of isotopes suitable for inclusion in the compounds of the invention comprises isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labeled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. In certain compounds of Formula I, residues $R_9$ or the ring formed by the combination of $R_8$ and $R_9$ may comprise one or more deuterium atoms to improve metabolic stability of the compound in vivo.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula I that contain groups capable of acting as donors and/or acceptors for hydrogen bonds may be capable of forming co-crystals with suitable co-crystal formers. These co-crystals may be prepared from compounds of formula I by known co-crystal forming procedures. Such procedures include grinding, heating, co-subliming, co-melting, or contacting in solution compounds of formula I with the co-crystal former under crystallization conditions and isolating co-crystals thereby formed. Suitable co-crystal formers include those described in WO 2004/078163. Hence the invention further provides co-crystals comprising a compound of formula I.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by VEGF or a receptor thereof, or (ii) associated with VEGF activity or the activity of a VEGF receptor, or (iii) characterized by abnormal activity of VEGF or a receptor thereof; or (2) reducing or inhibiting the activity of VEGF or a receptor thereof; or (3) reducing or inhibiting the expression of VEGF or a receptor thereof. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of VEGF or a receptor thereof; or at least partially reducing or inhibiting the expression of VEGF or a receptor thereof. The meaning of the term "a therapeutically effective amount" as illustrated in the above embodiment for VEGF or a receptor thereof applies by the same means to any other relevant proteins/peptides/enzymes, such as Ret, PDGFR alpha, and ckit.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "inhibition" or "inhibiting" refers to the reduction or suppression of a given condition, symptom, or disorder, or disease, or a significant decrease in the baseline activity of a biological activity or process.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50 enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the □-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization.

In another aspect, the present invention provides a pharmaceutical composition comprising a compound of the present invention and a carrier, e.g., a pharmaceutically acceptable carrier. The pharmaceutical composition can be formulated for particular routes of administration such as oral administration, ophthalmic administration (e.g., topical administration, intravitreal injection, implant (including intravitreal, transscleral, sub-Tenon, and the like, depot or the like), and parenteral administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers etc.

Typically, the pharmaceutical compositions are tablets and gelatin capsules comprising the active ingredient together with
 a) diluents, e.g., lactose, dextrose, sucrose, mannitol, sorbitol, cellulose and/or glycine;
 b) lubricants, e.g., silica, talcum, stearic acid, its magnesium or calcium salt and/or polyethyleneglycol; for tablets also
 c) binders, e.g., magnesium aluminum silicate, starch paste, gelatin, tragacanth, methylcellulose, sodium carboxymethylcellulose and/or polyvinylpyrrolidone; if desired
 d) disintegrants, e.g., starches, agar, alginic acid or its sodium salt, or effervescent mixtures; and/or
 e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Certain injectable compisitions include ocular implants and ocular depot formulations which are suitable for intraocular, periocular, subconjunctival and/or sub-tenon administration. Typicaly injectable compositions comprise a compound of formula (I) in combination with a biocompatible or biodegradable polymeric material.

Suitable compositions for transdermal application include an effective amount of a compound of the invention with carrier. Carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for ocular application, e.g., for the treatment of ocular disease, e.g., for prophylactic or therapeutic use in the treatment of macular degeneration, diabetic retinopathy, rubeosis iridis, neovascularization of the cornea, sclera, retina or other ocular tissue and the like. They are thus particularly suited for use in topical formulations well-known in the art. Such may contain solubilizers, stabilizers, tonicity enhancing agents, buffers and preservatives.

Certain suitable topical eye drop formulations comprise an aqueous solution or aqueous suspension of a compound of Formula I, optionally further comprising one or more preservatives, tonicity agents, and/or lubricants.

As used herein a topical application may also pertain to an inhalation or to an intranasal application. They are conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of formula I in free form or in pharmaceutically acceptable salt form, exhibit valuable pharmacological properties, e.g. VEGF receptor modulating properties, e.g. as indicated in in vitro and in vivo tests as provided in the next sections and are therefore indicated for therapy.

Based on the property of the compounds of formula I as potent VEGF receptor inhibitors, the compounds of formula I are especially suitable for the treatment of diseases associated with deregulated angiogenesis, especially diseases caused by ocular neovascularisation, especially retinopathies such as diabetic retinopathy or age-related macular degeneration, rubeosis iridis, psoriasis, Von Hippel Lindau disease, hemangioblastoma, angioma, mesangial cell proliferative disorders such as chronic or acute renal diseases, e.g. diabetic nephropathy, malignant nephrosclerosis, thrombotic microangiopathy syndromes or transplant rejection, or especially inflammatory renal disease, such as glomerulonephritis, especially mesangioproliferative glomerulonephritis, haemolytic-uraemic syndrome, diabetic nephropathy, hypertensive nephrosclerosis, atheroma, arterial restenosis, autoimmune diseases, acute inflammation, fibrotic disorders (e.g. hepatic cirrhosis), diabetes, endometriosis, chronic asthma, arterial or post-transplantational atherosclerosis, neurodegenerative disorders, and especially neoplastic diseases (especially solid tumours but also leukemias), such as especially breast cancer, adenocarcinoma, colorectal cancer, lung cancer (especially non-small-cell lung cancer), renal cancer, liver cancer, pancreatic cancer, ovarian cancer or cancer of the prostate as well as myeloma, especially multiple myeloma, myelodysplastic syndrome, AML (acute myeloid leukemia), AMM (agnogenic myeloid metaplasia), mesothelioma, glioma and glioblastoma. A compound of formula I is especially suited also to preventing the metastatic spread of tumours and the growth of micrometastases.

Thus, as a further embodiment, the present invention provides the use of a compound of formula (I) or subformulae thereof, e.g., compounds of Formula II or III, in therapy. In a further embodiment, the therapy is selected from a disease which is ameliorated by inhibition of VEGF receptor activity. In another embodiment, the disease is selected from the aforementioned list, suitably ocular diseases, more suitably wet and dry age-related macular degeneration, geographic atrophy, central serous retinopathy, cystoid macular edema, diabetic retinopathy, proliferative diabetic retinopathy, diabetic macular edema, rubeosis iridis, Retinopathy of prematurity, Central and branch retinal vein occlusions, Inflammatory/infectious retinal neovascularization/edema (e.g. posterior uveitis, sarcoid, toxoplasmosis, histoplasmosis, Vogt-Koyanagi-Harada Disease, chronic uveitis, tuberculsosis, syphyllis, punctate and multifocal inner choroidopathy), retinoblastoma, melanoma, ocular tumors, retinal detachment, myopic neovascularization, angiod streaks, Eales disease, ischemic retinopathy (Retinal artery occlusion, Takayasu's, carotid artery occlusion), choroidal rupture, contact lens wear, dry eye, blepharitis, corneal dystrophies, Trauma and previous surgery to the cornea (corneal grafts, LASIK, LASEK), corneal infections (bacterial, viral, parasitic, herpetic), corneal burns (chemical, alkali, acid), corneal graft rejection, Immunological corneal disease (pemhigoid, stevens-Johnsons syndrome), and degenerative corneal diseases.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

In other embodiments, a pharmaceutical composition is provided which comprises at least one compound according to any one of Formulae I, II, III, IV, V, or VI, or a subformulae thereof and at least one carrier.

In other embodiments, a combination, in particular a pharmaceutical combination, is provided which comprises a therapeutically effective amount of the compound according to any one of Formulae I, II, III, IV, V or VI, or a subformulae thereof and one or more therapeutically active agents.

A compound of the formula I may also be used to advantage in combination with other antiproliferative agents. Such antiproliferative agents include, but are not limited to aromatase inhibitors; antiestrogens; topoisomerase I inhibitors; topoisomerase II inhibitors; microtubule active agents; alkylating agents; historic deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further antiangiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; agents used in the treatment of hematologic malignancies; compounds which target, decrease or inhibit the activity of Flt-3; Hsp90 inhibitors; temozolomide (ILMODAL®); and leucovorin.

A compound of the formula I may also be used to advantage in combination with other ophthalmic therapeutics including but not limited to Macugen, VEGF trap, photodynamic therapy, anecortave Acetate, Steroids, non-steroidal anti-inflammatory (e.g. Naproxen, ibuprofen, diclofenac) Cox-1 and Cox-2 inhibitors, cyclosporine, dexamethasone, mtor (mammalian target of rapamycin) inhibitors such as rapamycin, everolimus, and the like, PKC (protein kinase C) beta inhibitors, Tumor necrosis alpha inhibitors, interleukin one beta inhibitors, platelet derived growth factor beta and alpha and receptors inhibitors, Lucentis, Avastin, VEGF antibodies, PLGF antibodies, siRNA against VEGF family (A-E, PLGF, neuropilin)/VEGF receptors, complement inhibitors targeting classical, alternative and lectin pathways, IL-10 inhibitors, C5aR inhibitors, C3aR inhibitors, and inhibitors of sphingosine phosphate and receptors.

The compound of the present invention may be administered either simultaneously with, or before or after, at least one other therapeutic agent. The compound of the present invention may be administered separately, by the same or different route of administration, or together in the same pharmaceutical composition.

In one embodiment, the other therapeutic agent is selected from:

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Aminoglutethimide can be administered, e.g., in the form as it is marketed, e.g. under the trademark ORIMETEN. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active agent" relates to microtubule stabilizing, microtubule destabilizing agents and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating agent" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g. under the trademark HOLOXAN.

The term "histone deacetylase inhibitors" or "HDAC inhibitors" relates to compounds which inhibit the histone deacetylase and which possess antiproliferative activity. This includes compounds disclosed in WO 02/22577, especially N-hydroxy-3-[4-[[(2-hydroxyethyl)[2-(1H-indol-3-yl) ethyl]-amino]methyl]phenyl]-2E-2-propenamide, N-hydroxy-3-[4-[[[2-(2-methyl-1H-indol-3-yl)-ethyl]-amino] methyl]phenyl]-2E-2-propenamide and pharmaceutically acceptable salts thereof. It further especially includes Suberoylanilide hydroxamic acid (SAHA).

The term "antineoplastic antimetabolite" includes, but is not limited to, 5-fluorouracil (5-FU); capecitabine; gemcitabine; DNA de-methylating agents, such as 5-azacytidine and decitabine; methotrexate; edatrexate; and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR. Also included is the monoclonal antibody trastuzumab which can be administered, e.g., in the form as it is marketed, e.g. under the trademark HERCEPTIN.

The term "platin compound" as used herein includes, but is not limited to, carboplatin, cis-platin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity and further anti-angiogenic compounds" as used herein includes, but is not limited to: protein tyrosine kinase and/or serine and/or threonine kinase inhibitors or lipid kinase inhibitors, e.g.:
a) compounds targeting, decreasing or inhibiting the activity of the fibroblast growth factor-receptors (FGF-Rs);
b) compounds targeting, decreasing or inhibiting the activity of the insulin-like growth factor I receptor (IGF-IR), especially compounds which inhibit the IGF-IR, such as those compounds disclosed in WO 02/092599;
c) compounds targeting, decreasing or inhibiting the activity of the Trk receptor tyrosine kinase family;
d) compounds targeting, decreasing or inhibiting the activity of the Axl receptor tyrosine kinase family;
e) compounds targeting, decreasing or inhibiting the activity of the c-Met receptor;
f) compounds targeting, decreasing or inhibiting the activity of members of the protein kinase C (PKC) and Raf family of serine/threonine kinases, members of the MEK, SRC, JAK, FAK, PDK and Ras/MAPK family members, or PI(3) kinase family, or of the PI(3)-kinase-related kinase family, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; ilmofosine; RO 318220 and RO 320432; GO 6976; Isis 3521; LY333531/LY379196; isochinoline compounds such as those disclosed in WO 00/09495; FTIs; PD184352 or QAN697 (a PI3K inhibitor);
g) compounds targeting, decreasing or inhibiting the activity of a protein-tyrosine kinase, such as imatinib mesylate (GLIVEC/GLEEVEC) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); and
h) compounds targeting, decreasing or inhibiting the activity of the epidermal growth factor family of receptor tyrosine kinases (EGF-R, ErbB2, ErbB3, ErbB4 as homo- or heterodimers), such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (HERCEPTIN), cetuximab, Iressa, erlotinib (Tarceva™), CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541.

Further anti-angiogenic compounds include compounds having another mechanism for their activity, e.g. unrelated to protein or lipid kinase inhibition e.g. thalidomide (THALOMID) and TNP-470.

Compounds which target, decrease or inhibit the activity of a protein or lipid phosphatase are e.g. inhibitors of phosphatase 1, phosphatase 2A, PTEN or CDC25, e.g. okadaic acid or a derivative thereof.

Compounds which induce cell differentiation processes are e.g. retinoic acid, α- γ- or δ-tocopherol or α- γ- or δ-tocotrienol.

The term "cyclooxygenase inhibitor" as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA™. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "heparanase inhibitor" as used herein refers to compounds which target, decrease or inhibit heparin sulphate degradation. The term includes, but is not limited to, PI-88.

The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor", e.g. L-744832, DK8G557 or R115777 (Zamestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. PS-341 and MLN 341.

The term "matrix metalloproteinase inhibitor" or ("MMP inhibitor") as used herein includes, but is not limited to collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "agents used in the treatment of hematologic malignancies" as used herein includes, but is not limited to FMS-like tyrosine kinase inhibitors e.g. compounds targeting, decreasing or inhibiting the activity of Flt-3; interferon, 1-b-D-arabinofuransylcytosine (ara-c) and bisulfan; and ALK inhibitors e.g. compounds which target, decrease or inhibit anaplastic lymphoma kinase.

The term "compounds which target, decrease or inhibit the activity of Flt-3" are especially compounds, proteins or antibodies which inhibit Flt-3, e.g. PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteasome pathway. Compounds targeting, decreasing or inhibiting the intrinsic ATPase activity of HSP90 are especially compounds, proteins or antibodies which inhibit the ATPase activity of HSP90 e.g., 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to trastuzumab (Herceptin™), Trastuzumab-DM1, ranibizumab (Lucentis®) bevacizumab (Avastin™), rituximab (Rituxan®), PRO64553 (anti-CD40) and 2C4 Antibody. By antibodies is meant e.g. intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of formula I can be used in combination with standard leukemia therapies, especially in combination with therapies used for the treatment of AML. In particular, compounds of formula I can be administered in combination with e.g. farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The structure of the active agents identified by code nos., generic or trade names may be taken from the actual edition of the standard compendium "The Merck Index" or from databases, e.g. Patents International (e.g. IMS World Publications).

The above-mentioned compounds, which can be used in combination with a compound of the formula I, can be prepared and administered as described in the art such as in the documents cited above.

A compound of the formula I may also be used to advantage in combination with known therapeutic processes, e.g., the administration of hormones or especially radiation.

A compound of formula I may in particular be used as a radiosensitizer, especially for the treatment of tumors which exhibit poor sensitivity to radiotherapy.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by VEGF or a VEGF receptor activity. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) in the manufacture of a medicament for treating a disease or condition mediated by VEGF or a VEGF receptor activity, wherein the medicament is prepared for administration with another therapeutic agent. The invention also provides the use of a another therapeutic agent in the manufacture of medicament for treating a disease or condition mediated by VEGF or a VEGF receptor activity], wherein the medicament is prepared for administration with a compound of formula (I).

The invention also provides a compound of formula (I) for use in a method of treating a disease or condition mediated by VEGF or a VEGF receptor activity, wherein the compound of formula (I) is prepared for administration with another therapeutic agent. The invention also provides another therapeutic agent for use in a method of treating a disease or condition mediated by VEGF or a VEGF receptor activity, wherein the other therapeutic agent is prepared for administration with a compound of formula (I). The invention also provides a compound of formula (I) for use in a method of treating a disease or condition mediated by VEGF or a VEGF receptor activity, wherein the compound of formula (I) is administered with another therapeutic agent. The invention also provides another therapeutic agent for use in a method of treating a disease or condition mediated by VEGF or a VEGF receptor activity, wherein the other therapeutic agent is administered with a compound of formula (I).

The invention also provides the use of a compound of formula (I) in the manufacture of a medicament for treating a disease or condition mediated by VEGF or a A a VEGF receptor, wherein the patient has previously (e.g. within 24 hours) been treated with another therapeutic agent. The invention also provides the use of another therapeutic agent in the manufacture of a medicament for treating a disease or condition mediated by VEGF or the receptor thereof, wherein the patient has previously (e.g. within 24 hours) been treated with a compound of formula (I).

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Based on the property of the compounds of formula I as potent VEGF receptor inhibitors, the compounds of formula I are especially suitable for the treatment of diseases associated with deregulated angiogenesis, especially diseases caused by ocular neovascularisation, especially retinopathies such as diabetic retinopathy or age-related macula degeneration, psoriasis, Von Hippel Lindau disease, hemangioblastoma, angioma, mesangial cell proliferative disorders such as chronic or acute renal diseases, e.g. diabetic nephropathy, malignant nephrosclerosis, thrombotic microangiopathy syndromes or transplant rejection, or especially inflammatory renal disease, such as glomerulonephritis, especially mesangioproliferative glomerulonephritis, haemolytic-uraemic syndrome, diabetic nephropathy, hypertensive nephrosclerosis, atheroma, arterial restenosis, autoimmune diseases, acute inflammation, including rheumatoid arthritis, fibrotic disorders (e.g. hepatic cirrhosis), diabetes, endometriosis, chronic asthma, arterial or post-transplantational atherosclerosis, neurodegenerative disorders, e.g. multiple sclerosis, and especially neoplastic diseases such as cancer (especially solid tumours but also leukemias), such as especially breast cancer, adenocarcinoma, colorectal cancer, lung cancer (especially non-small-cell lung cancer), renal cancer, liver cancer, pancreatic cancer, ovarian cancer or cancer of the prostate as well as myeloma, especially multiple myeloma, myelodysplastic syndrome, AIVIL (acute myeloid leukemia), AMM (agnogenic myeloid metaplasia), mesothelioma, glioma and glioblastoma. A compound of formula I is especially suited also to preventing the metastatic spread of tumours and the growth of micrometastases. The compounds of the formula I, due to their activity as kinases, are also useful as in treatment in connection with transplantation.

The following Examples serve to illustrate the invention without limiting the scope thereof.

General Synthetic Aspects

Typically, the compounds of formula (I) can be prepared according to the Schemes provided infra.

Scheme 1

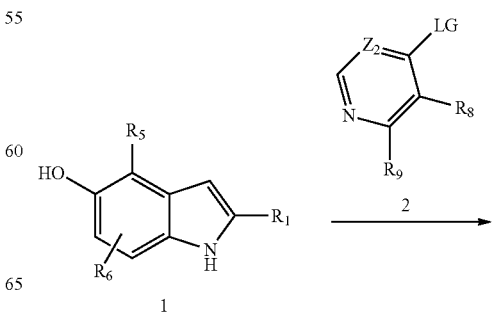

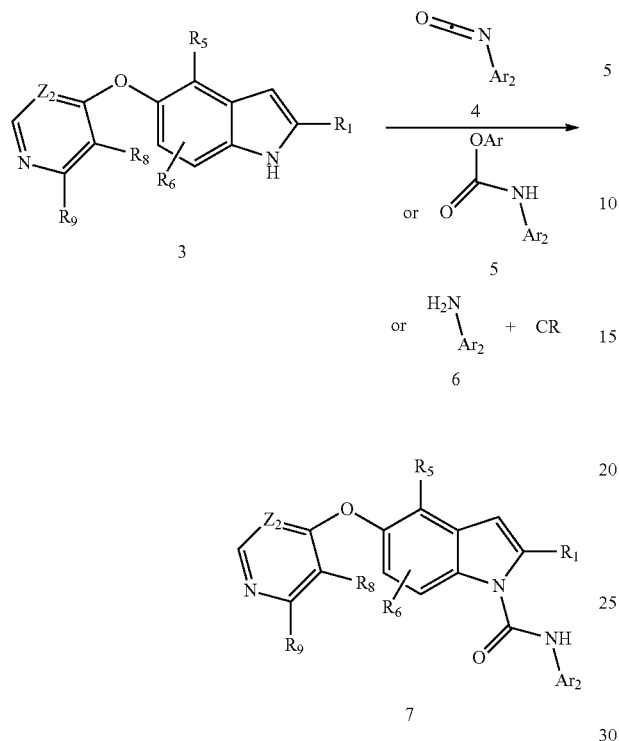

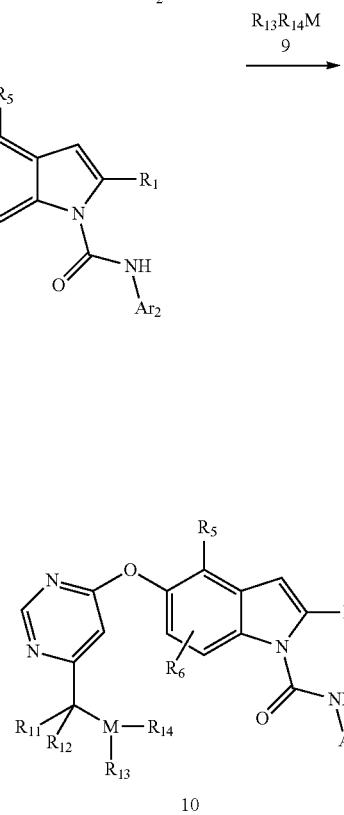

Compounds such as 7 (wherein $R_1$ is H or alkyl, $R_8$ and $R_9$ are substituted alkyl, H or taken together to be heterocyclic, $Ar_2$ is substituted phenyl, heteroaryl, or heterocyclyl, $R_5$ and $R_6$ are H or halo, $Z_2$ is N or CH) can be prepared by the general method outlined in scheme 1. Coupling of hydroxyl indole 1 to the functionalized pyrimidine or pyridine 2 (wherein LG is halo or the like or an activated alcohol) is accomplished by treatment of with a suitable base (such as DBU) in a solvent (such as acetonitrile) either at rt or with heating preferably at a temperature between rt and reflux to provide 3. Formation of urea 7 can be achieved by several methods such as, treatment of 3 with a suitable base (such as NaH or LiTMP) in a solvent (such as DMF or THF) preferably at 0° C. up to rt followed by the addition of an isocyanate 4 or an activated carbamate 5 (wherein $Ar_2$ is phenyl or substituted phenyl). Alternatively, 7 can be prepared by pre activation of either 3 or 6 with a coupling reagent (CR) such as CDI or the like followed by coupling to the other component facilitated by a suitable base (such as $Et_3N$, NaH).

Scheme 2

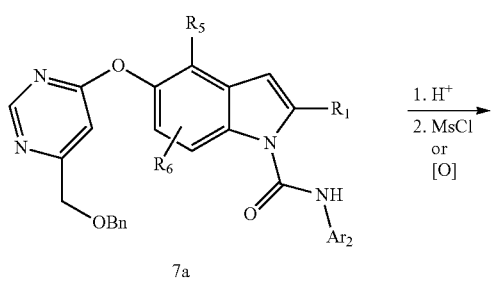

Compounds such as 10 (wherein $R_1$, $Ar_2$, and $R_5$ and $R_6$ are as described above, $R_{11}$ and $R_{12}$ are H or alkyl, and $R_{13}$ and $R_{14}$ are H, alkyl, substituted alkyl, aryl, heteroaryl, heterocyclyl or taken together to be heterocyclyl or hetereoaryl and M is N or $—S(O_2)—$) are prepared by the general method depicted in Scheme 2. Compound 8 is formed by deprotection of 7a upon treatment with an acid (TFA, MsOH or the like) followed by conversion of the resulting alcohol to a suitable LG (mesylate, halo or the like). Carbonyl 8a can be prepared by oxidation (with DMP or the like) of the previous alcohol to give the aldehyde ($R_2$=H) or a sequence of oxidation to the aldehyde followed by the addition of an alkyl organometallic reagent (such as an alkyl grignard) followed by a second oxidation to provide the corresponding keto-compound 8a ($R_2$=alkyl). Treatment of nucleophile 9 with a suitable base ($Et_3N$, NaH or the like) and 8 between 0° C. and reflux in a suitable solvent provides 10. Alternatively, 10 can be prepared by reaction with 9 under reductive amination conditions ($Na(AcO)_3BH$ or the like) with carbonyl 8a.

Scheme 3

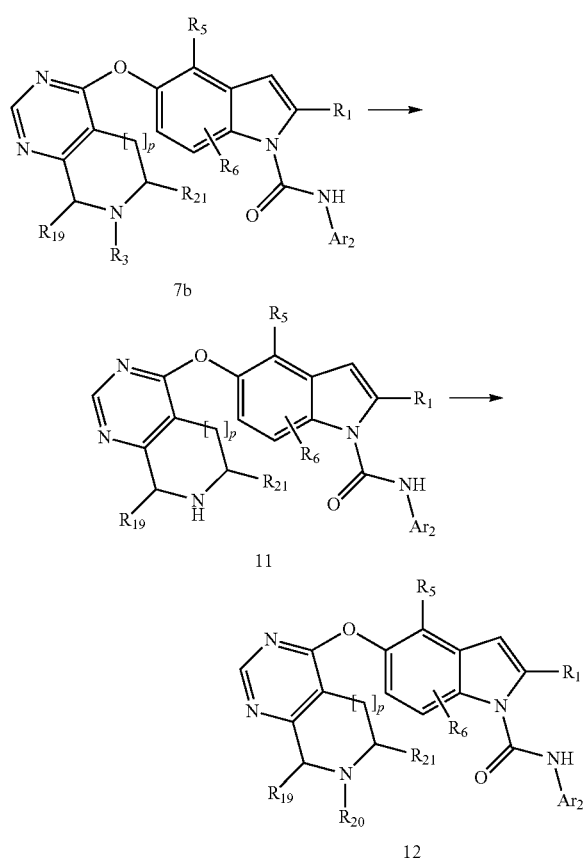

Compounds such as 12 (wherein $R_1$, $Ar_2$, and $R_5$ and $R_6$ are as described above, $R_{19}$ and $R_{21}$ are H, or alkyl, $R_{20}$ is alkyl, acyl, or sulfonyl and p is 0 or 1) are prepared by the general method depicted in Scheme 3. Compound II is formed by deprotection of 7b (wherein $R_3$ is a suitable nitrogen protecting group such as tert-butyl carbamate) upon treatment with an acid (TFA or the like). The free amine in 11 is then alkylated, acylated or sulfonlyated to give compound 12.

Scheme 4

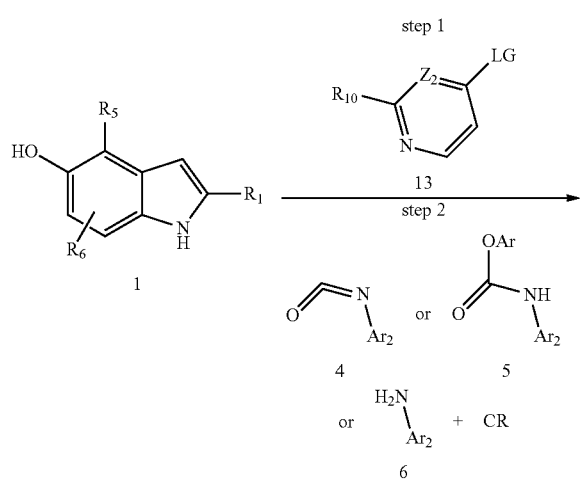

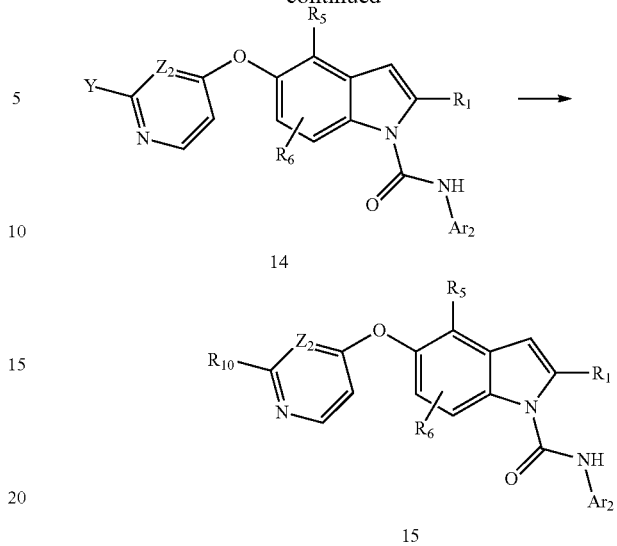

Compounds of type 15 (wherein $R_1$, $Ar_2$, and $R_5$ and $R_6$ are defined as described above and $R_{10}$ is alkyl, substituted alky, carboxylic amide, ester or acid) are generally prepared as described in Scheme 4. Coupling of hydroxyl indole 1 to the functionalized pyrimidine or pyridine 13 (wherein LG is halo, the like or an activated alcohol and Y is halo, alkyl or carboxyl) is accomplished by treatment of with a suitable base (such as DBU, NaH, NaOH or the like) in a suitable solvent either at rt or with heating preferably at a temperature between it and reflux followed by subsequent urea formation, generally as described in Scheme 1, to give 14. Further modification of Y (such as reduction, amidation, hydrolysis, and organometallic coupling) in compound 14 provides compounds of type 15.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known per se.

With the groups of preferred compounds of formula I mentioned hereinafter, definitions of substituents from the general definitions mentioned hereinbefore may reasonably be used, for example, to replace one or more up to all more general definitions with more specific definitions or especially with definitions characterized as being preferred.

Compounds of formula I are prepared analogously to methods that, for other compounds, are in principle known in the art, but are novel when applied in the manufacture of the compounds of the present invention, and are especially prepared according to the methods described hereinbelow under 'Examples' or by analogous methods.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3$^{rd}$ edition, John Wiley and Sons, Inc., 1999. Corresponding protecting groups can be introduced, used and removed at appropriate stages at any stage in the manufacture of a compound of the formula I.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Intermediates and final products can be worked up and/or purified according to standard methods, e.g. using chromatographic methods, distribution methods, (re-) crystallization, and the like.

ABBREVIATIONS

ACN acetonitrile
app apparent
aq aqueous
atm atmosphere
ATP adenosine 5'-triphosphate
BOC tertiary butyl carboxy
BOP (benzotriazol-1-yloxy)tris(dimethylamino)phosphonium hexafluorophosphate
br broad
BSA bovine serum albumin
d doublet
DBU 1,8-diazabicyclo[5.4.0]undec-7-ene
DCE 1,2-dichloroethane
dd doublet of doublets
DCM dichloromethane
DIEA diisopropylethylamine
DMAP 4,4-dimethylaminopyridine
DME 1,4-dimethoxyethane
DMF N,N-dimethylformamide
DMP Dess-Martin reagent; 1,1,1-Triacetoxy-1,1-dihydro-1,2-benziodoxol-3(1H)-one
DMSO dimethylsulfoxide
DTT dithiothreitol
EDTA ethylenediamine tetraacetic acid
ESI electrospray ionization
EtOAc ethyl acetate
FCC flash column chromatography
g grams
h hour(s)
HATU 2-(1H-7-azabenzotriazol-1-yl)-1,1,3,3-tetramethyl uronium hexafluorophosphate methanaminium
HBTU 1-[bis(dimethylamino)methylene]-1H-benzotriazolium hexafluorophosphate(1-)3-oxide
HOBt 1-hydroxy-7-azabenzotriazole
HPLC high pressure liquid chromatography
IR infrared spectroscopy
LCMS liquid chromatography and mass spectrometry
LTMP lithium 2,2',6,6'-tetramethylpiperidine
M molar
m multiplet
MeOH methanol
min minutes
mL milliliter(s)
mmol millimoles
MS mass spectrometry
MsOH methanesulfonic acid
MW microwave
m/z mass to charge ratio
N normal
NMR nuclear magnetic resonance
Pd/C palladium on carbon
ppm parts per million
PyBOP benzotriazol-1-yloxytripyrrolidinophosphonium hexafluorophosphate
rac racemic
rt room temperature
$R_t$ retention time
s singlet
sat saturated
SFC Supercritical Fluid Chromatography
t triplet
TBSCl tert-butyldimethylsilyl chloride
TFA trifluoroacetic acid
THF tetrahydrofuran

EXAMPLE 1

2-Methyl-1H-indol-5-ol

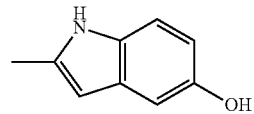

To a precooled (0° C.) solution of 5-methoxy-2-methyl-1H-indole (5.0 g, 31.0 mmol) in 100 mL DCM is added BBr$_3$ (1 M solution, 46.5 mL) under a dry nitrogen atmosphere. The solution is then allowed to slowly warm to room temperature over a 2 h period. The solution is then poured into water, neutralized to pH 7 with sat aq sodium bicarbonate solution and extracted with EtOAc. The extract is washed by brine, dried over sodium sulfate, and concentrated to give 2-methyl-1H-indol-5-ol. MS (ESI) m/z 148.2 (M+1).

EXAMPLE 2

6-Fluoro-1H-indol-5-ol

2-A.
1-Benzyloxy-2-fluoro-3-methyl-4-nitro-benzene

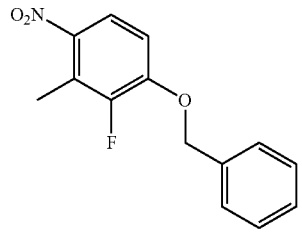 [SMILES: Cc1c([N+](=O)[O-])ccc(OCc2ccccc2)c1F]

To a suspension of potassium carbonate (19.2 g, 138 mmol) and benzyl alcohol (22 mL) is added 1,2-difluoro-3-methyl-4-nitrobenzene (12 g, 69 mmol, ref. WO2007121416) and the mixture is heated to 180° C. for 2 h. The reaction mixture is then diluted with EtOAc and washed with water. The organic layer is concentrated and the residue is separated with FCC (EtOAc/heptane from 0 to 20%) to give 1-benzyloxy-2-fluoro-3-methyl-4-nitrobenzene. ¹H NMR (400 MHz, MeOD) δ ppm 7.87 (dd, J=9.35, 2.02 Hz, 1 H), 7.44-7.47 (m, 2 H), 7.32-7.41 (m, 3 H), 7.17 (t, J=8.72 Hz, 1 H), 5.26 (s, 2 H), 2.49 (d, J=2.78 Hz, 3 H).

2-B. 4-Fluoro-1H-indol-5-ol

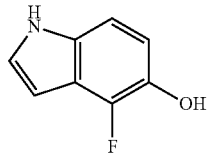 [SMILES: Oc1ccc2[nH]ccc2c1F]

1-Benzyloxy-2-fluoro-3-methyl-4-nitrobenzene (5 g, 19 mmol) is dissolved N,N-dimethylformamide dimethyl acetal (15 mL) and heated in a microwave reactor at 180° C. in a sealed vial for 1 hour. The solution is then concentrated under reduced pressure. The resulting residue is dissolved in THF and Pd/C (1.0 g, 10%, 0.95 mmol) is added. The mixture is stirred under a hydrogen atmosphere at room temperature for 16 h before being filtered through a pad of Celite® and concentrated. The residue is separated by FCC (EtOAc/heptane from 0 to 40%) to give 4-fluoro-1H-indol-5-ol (1.5 g, 52% yield). MS (ESI) m/z 152.1 (M+1); ¹H NMR (400 MHz, DMSO-d₆) δ ppm 11.02 (br. s., 1 H), 8.79 (s, 1 H), 7.26 (t, J=2.78 Hz, 1 H), 7.00 (d, J=8.59 Hz, 1 H), 6.75 (t, J=8.46 Hz, 1 H), 6.34 (m, 1 H).

2-C. 6-Fluoro-1H-indol-5-ol

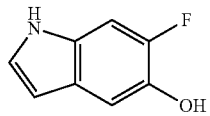 [SMILES: Oc1cc2cc[nH]c2cc1F]

6-Fluoro-1H-indol-5-ol is synthesized according to ref WO2003064413. MS (ESI) m/z 152.1 (M+1).

EXAMPLE 3

5-[2-(tert-Butyl-dimethyl-silanyloxy)-1,1-dimethyl-ethyl]-2H-pyrazol-3-ylamine

3-A. 3-(tert-Butyl-dimethyl-silanyloxy)-2,2-dimethyl-propionic acid methyl ester

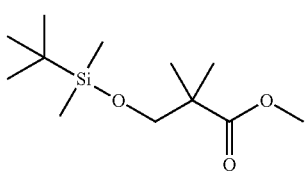 [SMILES: COC(=O)C(C)(C)CO[Si](C)(C)C(C)(C)C]

3-Hydroxy-2,2-dimethyl-propionic acid methyl ester (5 g, 37.8 mmol), imidazole (3.86 g, 56.8 mmol), and 4-pyrrolidinopyridine (193 mg, 1.32 mmol) are combined in DCM (400 mL) before tert-butyldimethylsilyl chloride (6.84 g, 45.4 mmol) is added. The mixture is then stirred at rt for 4 h. The mixture is then partitioned between DCM and saturated aqueous NaHCO₃. The organic layer separated, dried over anhydrous Na₂SO₄, and concentrated in vacuo. The residue is then separated via FCC (heptanes to EtOAc/heptanes 5:95) to give the product as an oil (6.4 g, 69%). ¹H NMR (400 MHz, CDCl₃) δ ppm 3.63 (s, 3 H) 3.54 (s, 2 H) 1.13 (s, 6 H) 0.85 (s, 9 H), 0.00 (s, 6 H).

3-B. 5-(tert-Butyl-dimethyl-silanyloxy)-4,4-dimethyl-3-oxo-pentanenitrile

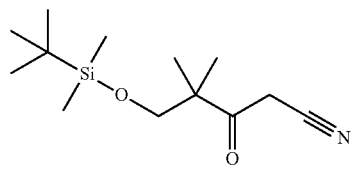 [SMILES: CC(C)(CO[Si](C)(C)C(C)(C)C)C(=O)CC#N]

A solution of n-butyllithium (17.9 mL, 28.6 mmol, 1.6 M in heptane) is added to a precooled (−78° C.) solution of diisopropylamine (4.26 mL, 29.9 mmol) and THF (45 mL). After 30 min a combination of 3-(tert-butyl-dimethyl-silanyloxy)-2,2-dimethyl-propionic acid methyl ester (3.2 g, 12.9 mmol) and acetonitrile (1.35 mL, 26 mmol) is added. The content of the flask are allowed to warm to rt and the pH is then adjusted to 8 by the addition of 4 N HCl. The mixture is then partitioned between DCM and saturated aqueous NaHCO₃. The organic layer is separated and dried over anhydrous Na₂SO₄, filtered, and concentrated to provide the title compound. MS (ESI) m/z 256.1 (M+1).

3-C. 5-[2-(tert-Butyl-dimethyl-silanyloxy)-1,1-dimethyl-ethyl]-2H-pyrazol-3-ylamine

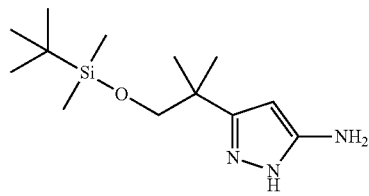 [SMILES: CC(C)(CO[Si](C)(C)C(C)(C)C)c1cc(N)[nH]n1]

A solution of 5-(tert-butyl-dimethyl-silanyloxy)-4,4-dimethyl-3-oxo-pentanenitrile (3.32 g, 12.9 mmol), hydrazine (0.62 g, 19.5 mmol), and MeOH (50 mL) is heated at 70° C. for 6 h. The solution is then concentrated in vacuo and the residue is separated via FCC (50-100% EtOAc/heptanes) to obtain the title compound. MS (ESI) m/z 270.3 (M+1).

EXAMPLE 4

4-Methyl-tetrahydro-pyran-4-carboxylic acid methyl ester

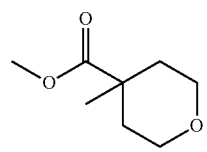

To a solution of diisopropylamine (10.2 ml, 72.8 mmol) in THF (400 ml) at −78° C., n-BuLi (25.2 ml, 1.6 M in heptane) is added. The reaction is removed from the bath and stirred for 10 min. It is then cooled to −78° C. again and methyl tetrahydro-2H-pyran-4-carboxylate (6.48 ml, 48.6 mmol) is added. After 30 min, iodomethane (6.07 ml, 97 mmol) is added and the reaction allowed to reach rt. The reaction is then quenched with 1 N HCl (200 mL) and extracted with EtOAc. The organic layer is dried and evaporated to give 4-methyl-tetrahydro-pyran-4-carboxylic acid methyl ester. MS (ESI) m/z 159.3 (M+1).

EXAMPLE 5

3-(1-Methyl-cyclopropyl)-5-phenoxycarbonylamino-pyrazole-1-carboxylic acid tert-butyl ester 5-A. 3-(1-Methyl-cyclopropyl)-3-oxo-propionitrile

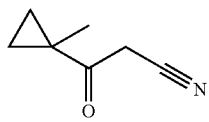

A solution of n-butyllithium (18.1 mL, 28.9 mmol, 1.6 M in heptane) is added to a precooled (−78° C.) solution of diisopropylamine (4.31 mL, 30.2 mmol) and THF (60 mL). After 30 min a combination of 1-methyl-cyclopropanecarboxylic acid methyl ester (1.5 g, 13.1 mmol) and acetonitrile (1.37 mL, 26.3 mmol) is added. The reaction is allowed to warm to room temperature and the pH is adjusted 8 by the addition of AcOH. The mixture is then concentrated to provide the title compound. MS (ESI) m/z 173.9 (M+1).

5-B. 5-(1-Methyl-cyclopropyl)-2H-pyrazol-3-ylamine

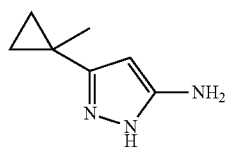

A solution of 3-(1-methyl-cyclopropyl)-3-oxo-propionitrile (1.0 g, 8.1 mmol), hydrazine (0.52 g, 16.2 mmol) and MeOH (40 mL) is heated at 70° C. for 6 h. The solution is then concentrated in vacuo and purified via semi-prep HPLC (X-Bridge C18; 10-100% ACN/H$_2$O with 0.1% NH$_4$OH) to provide the title compound. Alternatively the crude residue can be used in the next step as is without further purification. MS (ESI) m/z 137.9 (M+1).

5-C. 5-Amino-3-(1-methyl-cyclopropyl)-pyrazole-1-carboxylic acid tert-butyl ester BOC protection carried out as described in reference *Tetrahedron Letters* 2003, 44, 4491.

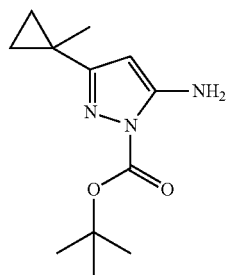 [SMILES: CC(C)(C)OC(=O)n1nc(C2(C)CC2)cc1N]

MS (ESI) m/z 238.0 (M+1).

5-D. 3-(1-Methyl-cyclopropyl)-5-phenoxycarbonylamino-pyrazole-1-carboxylic acid tert-butyl ester

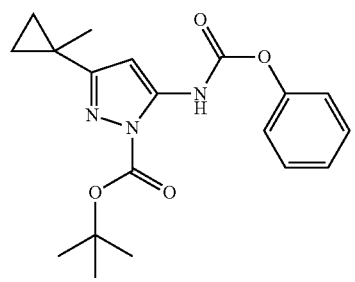 [SMILES: CC(C)(C)OC(=O)n1nc(C2(C)CC2)cc1NC(=O)Oc1ccccc1]

To a solution of 5-amino-3-(1-methyl-cyclopropyl)-pyrazole-1-carboxylic acid tert-butyl ester (3.90 g, 16.4 mmol) and phenyl chloroformate (3.11 mL, 24.6 mmol) in DCM (150 mL) is added 2,6-lutidine (5.74 mL, 49.3 mmol). After 18 h the solution is diluted with DCM (100 mL) and washed with 1 M HCl (250 mL). The organic layer is then dried (Na$_2$SO$_4$), filtered, and concentrated to provide the title compound. MS (ESI) m/z 358.0 (M+1).

The following compounds are prepared with similar method.

| | Structure/Chemical Name | MS (ESI) m/z (M − 1) |
|---|---|---|
| 5-E | 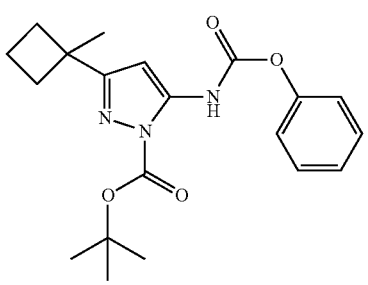<br>3-(1-Methyl-cyclobutyl)-5-phenoxycarbonylamino-pyrazole-1-carboxylic acid tert-butyl ester | 370.1 |

| | Structure/Chemical Name | MS (ESI) m/z (M − 1) |
|---|---|---|
| 5-F | 3-Isopropyl-5-phenoxycarbonylamino-pyrazole-1-carboxylic acid tert-butyl ester | 344.3 |
| 5-G | 3-(4-Methyl-tetrahydro-pyran-4-yl)-5-phenoxycarbonylamino pyrazole-1-carboxylic acid tert-butyl ester | 400.2 |
| 5-H | 3-Cyclopropyl-5-phenoxycarbonylamino-pyrazole-1-carboxylic acid tert-butyl ester | 342.2 |
| 5-I | (1-Isopropyl-1H-pyrazol-3-yl)-carbamic acid phenyl ester | 246.2 |
| 5-J | (1-Isopropyl-5-methyl-1H-pyrazol-3-yl)-carbamic acid phenyl ester | 260.2 |
| 5-K | (1,5-Dimethyl-1H-pyrazol-3-yl)-carbamic acid phenyl ester | 232.2 |
| 5-L | (1-tert-Butyl-1H-pyrazol-3-yl)-carbamic acid phenyl ester | 260.2 |
| 5-M | (1-Isopropyl-5-methyl-1H-pyrazol-3-yl)-carbamic acid phenyl ester | 260.19 |
| 5-N | (5-Cyclopropyl-1-methyl-1H-pyrazol-3-yl)-carbamic acid phenyl ester | 258.2 |
| 5-O | (1-Methyl-5-trifluoromethyl-1H-pyrazol-3-yl)-carbamic acid phenyl ester | 286.2 |
| 5-P | [5-Methyl-1-(2,2,2-trifluoro-ethyl)-1H-pyrazol-3-yl]-carbamic acid phenyl ester | 300.1 |

| | Structure/Chemical Name | MS (ESI) m/z (M − 1) |
|---|---|---|
| 5-Q | 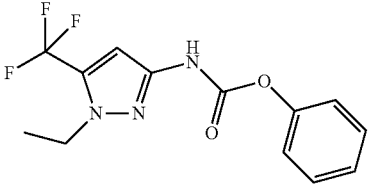<br>(1-Ethyl-5-trifluoromethyl-1H-pyrazol-3-yl)-carbamic acid phenyl ester | 300.1 |
| 5-R | 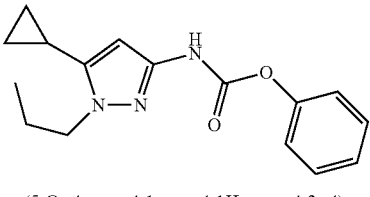<br>(5-Cyclopropyl-1-propyl-1H-pyrazol-3-yl)-carbamic acid phenyl ester | 286.3 |
| 5-S | 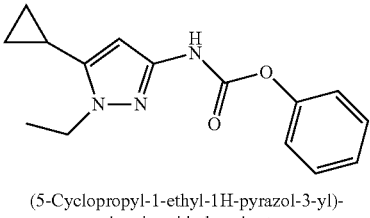<br>(5-Cyclopropyl-1-ethyl-1H-pyrazol-3-yl)-carbamic acid phenyl ester | 272.2 |

EXAMPLE 6

6-A. 3-Isopropyl-isoxazol-5-ylamine

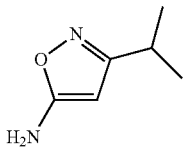

A solution of hydroxylamine sulfate (1.72 g, 20.9 mmol) in water (4 mL) is added to a solution of 5-methyl-3-oxo-hexanenitrile (2.38 g, 19.0 mmol) and sodium hydroxide (0.837 g, 20.9 mmol) in water (10 mL) at rt. After the mixture has been adjusted to pH 8.20 with 5% NaOH, it is heated to 100° C. for 1.5 h. At this point, concentrated hydrochloric acid (1.73 mL, 17.1 mmol) is added to the reaction mixture followed by heating at 100° C. for 15 min. After cooling, the pH is adjusted to 11 with 30% NaOH and the mixture extracted with EtOAc (3×). The organic extracts are dried over $Na_2SO_4$ and concentrated to give 5-isopropyl-isoxazol-3-ylamine. MS (ESI) m/z 127.2 (M+1).

The following compounds are prepared with similar method.

| | Structure/Chemical Name | MS (ESI) m/z (M + 1) |
|---|---|---|
| 6-B | 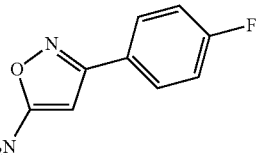<br>3-(4-Fluoro-phenyl)-isoxazol-5-ylamine | 179.3 |
| 6-C | 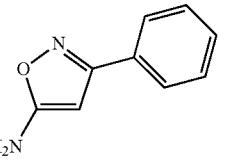<br>3-Phenyl-isoxazol-5-ylamine | 161.2 |
| 6-D | 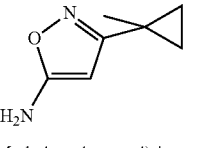<br>3-(1-Methyl-cyclopropyl)-isoxazol-5-ylamine | 139.2 |
| 6-E | 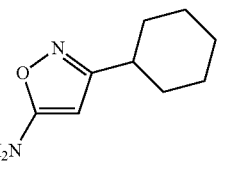<br>3-Cyclohexyl-isoxazol-5-ylamine | 167.5 |
| 6-F | 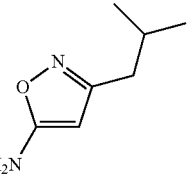<br>3-Isobutyl-isoxazol-5-ylamine | 141.5 (M − 1) |
| 6-G | 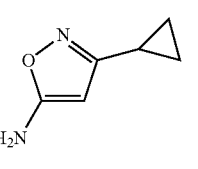<br>3-Cyclopropyl-isoxazol-5-ylamine | 123.2 (M − 1) |
| 6-H | 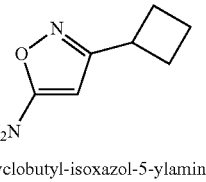<br>3-Cyclobutyl-isoxazol-5-ylamine | 139.2 |

EXAMPLE 7

7-A. 5-Isopropyl-isoxazol-3-ylamine

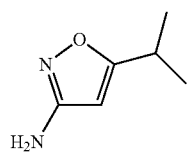

To a mixture of 4-methyl-3-oxopentanenitrile (11 g, 99 mmol) and water (200 mL) is added NaOH (4.95 g, 124 mmol). Once the NaOH pellets are completely dissolved, hydroxylamine sulfate (8.93 g, 109 mmol) is added and after 5 min the pH is measured (pH 7-8). The reaction is warmed to 40° C. and stirred for 72 h. At this point HCl (13.0 mL, 158 mmol, 37%) is added in one portion and the reaction warmed to 50° C. for 2.5 h. The reaction is removed from the oil bath and allowed to cool to rt. At this point a solution of NaOH (30% in $H_2O$) is added to give a solution of pH 11. EtOAc is then added and the layers separated. The water layer is extracted with EtOAc (3×) until no more product appears in the LCMS of the water layer. The combined organics are dried ($Na_2SO_4$) and evaporated to give 5-isopropyl-isoxazol-3-ylamine. MS (ESI) m/z 127.2 (M+1).

The following compounds are prepared with similar method.

| | Structure/Chemical Name | MS (ESI) m/z (M + 1) |
|---|---|---|
| 6-I | 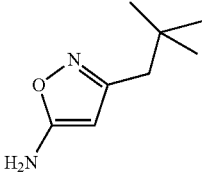3-(2,2-Dimethyl-propyl)-isoxazol-5-ylamine | 155.5 |
| 7-B | 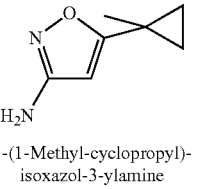5-(1-Methyl-cyclopropyl)-isoxazol-3-ylamine | 151.2 (M − 1) |
| 7-C | 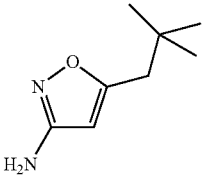5-(2,2-Dimethyl-propyl)-isoxazol-3-ylamine | 155.5 |
| 7-D | 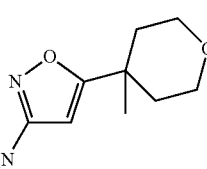5-(4-Methyl-tetrahydro-pyran-4-yl)-isoxazol-3-ylamine | 183.2 |
| 7-E | 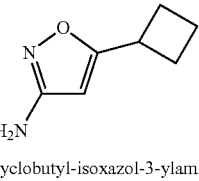5-Cyclobutyl-isoxazol-3-ylamine | 139.2 |
| 7-F | 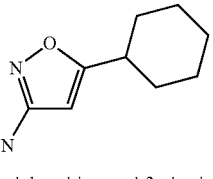5-Cyclohexyl-isoxazol-3-ylamine | 167.5 |
| 7-G | 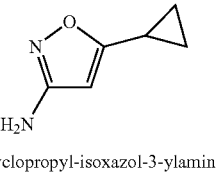5-Cyclopropyl-isoxazol-3-ylamine | 125.2 |
| 7-H | 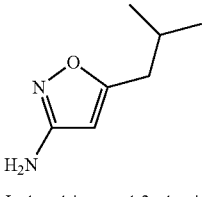5-Isobutyl-isoxazol-3-ylamine | 141.5 (M − 1) |
| 7-I | 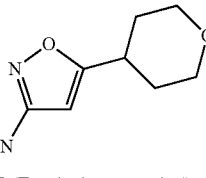5-(Tetrahydro-pyran-4-yl)-isoxazol-3-ylamine | 1 |

-continued

| | Structure/Chemical Name | MS (ESI) m/z (M + 1) |
|---|---|---|
| 7-J | 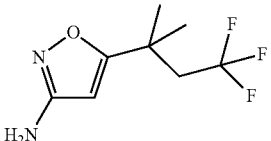<br>5-(3,3,3-Trifluoro-1,1-dimethyl-propyl)-isoxazol-3-ylamine | 209.1 |

EXAMPLE 8

8-A. 5-Phenyl-isoxazol-3-ylamine

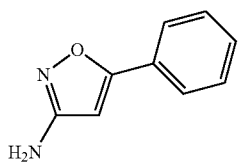 [SMILES: Nc1cc(-c2ccccc2)on1]

Hydroxylamine sulfate (2.5 g, 30.3 mmol) is added to a stirred solution of 3-oxo-3-phenylpropanenitrile (4 g, 27.6 mmol) and NaOH (1.27 g, 31.7 mmol) in $H_2O$ (25 mL)/EtOH (25 mL). The mixture is stirred at rt and then heated to 80° C. for 22 h. At this point, conc. HCl (3.39 ml, 41.3 mmol) is added and the mixture heated at 80° C. for an additional 2 h. It is then basified to pH 10 and extracted with EtOAc to give 5-phenyl-isoxazol-3-ylamine. MS (ESI) m/z 161.2 (M+1).

The following compound are prepared with similar method.

8-B. 5-(4-Fluoro-phenyl)-isoxazol-3-ylamine

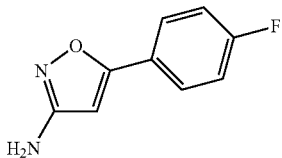

MS (ESI) m/z 179.3 (M+1).

EXAMPLE 9

3-(tert-Butyl-dimethyl-silanyloxymethyl)-5-trifluoromethyl-phenylamine

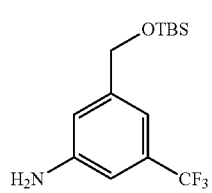

To a solution of 3-Amino-5-trifluoromethyl-benzoic acid (2.0 g, 9.76 mmol) in THF (40 mL) at 0° C. is added $LiAlH_4$ in THF (1 M, 39 mL). The mixture is warmed to reflux and stirred for 62 h. The mixture is then cooled to 0° C. and NaF (2.2 g) is added followed by $H_2O$ (3.8 mL). The slurry is stirred for 10 minutes and then allowed to warm to rt and stir an additional 40 min. The mixture is filtered and the solid is rinsed with EtOAc and MeOH. The filtrate is concentrated and the crude residue is mixed with imidazole (2.66 g, 39 mmol) and DCM (30 mL) at 0° C. TBSCl (3.5 g, 23.4 mmol) is added and the mixture is stirred at rt for 5 h. The reaction mixture is then diluted with EtOAc, washed with saturated aqueous $NaHCO_3$, brine, and dried over $Na_2SO_4$. Concentration provides the title compound that is carried on to next step without further purification. MS (ESI) m/z 306.1 (M+1).

EXAMPLE 10

5-Trifluoromethyl-pyridin-3-ylamine

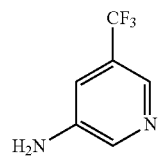

A mixture of 2-chloro-5-nitro-3-trifluoromethyl-pyridine (30 mg, 0.13 mmol), 10% Pd/C (3 mg, 10% w/w), and MeOH (5 mL) is stirred under 1 atm of hydrogen for 3 h. The mixture is then filtered over Celite® and concentrated in vacuo to give the title compound as an oil. MS (ESI) m/z 162.9 (M+1).

EXAMPLE 11

3-Amino-N-isopropyl-5-(trifluoromethyl)benzamide

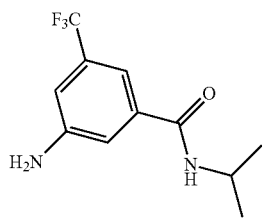 [SMILES: CC(C)NC(=O)c1cc(N)cc(C(F)(F)F)c1]

To a solution of 3-amino-5-(trifluoromethyl)benzoic acid (0.25 g, 1.22 mmol) in DMF (3 mL) is added HOBt (0.494 g, 3.66 mmol) followed by HATU (0.695 g, 1.83 mmol), propan-2-amine (0.311 mL, 3.66 mmol) and DIEA (0.96 mL, 5.48 mmol). After stirring at it overnight the solution is concentrated and the residue is dissolved in EtOAc, washed with sat aq $NaHCO_3$, brine, and dried over $Na_2SO_4$. Following concentration the residue is carried on to next step without further purification. MS (ESI) m/z 247.1 (M+1).

EXAMPLE 12

3-Amino-5-trifluoromethyl-benzonitrile

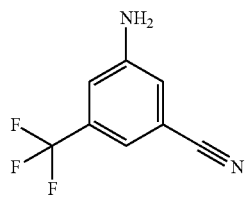 [SMILES: N#Cc1cc(N)cc(C(F)(F)F)c1]

To a solution of 3-nitro-5-(trifluoromethyl)benzonitrile (500 mg, 2.31 mmol) and acetic acid (6.62 mL, 116 mmol) in EtOH (10 mL) and water (10 mL) is added tin (II) chloride (2.61 g, 11.6 mmol) and the reaction mixture is heated at 80° C. for 6 h. The solvent is removed in vacuo and then the residue is portioned between DCM and 4 N HCl solution. The organic layer separated and then dried over anhydrous $Na_2SO_4$, filtered and concentrated. The residue is then separated via FCC (10-100% EtOAc/heptane) to give the compound as a yellow oil (213 mg, 49%). MS (ESI) m/z 185.3 (M+1).

EXAMPLE 13

13-A. (5-Trifluoromethyl-pyridin-3-yl)-carbamic acid phenyl ester

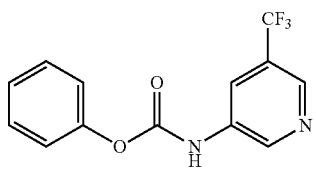 [SMILES: O=C(Nc1cncc(C(F)(F)F)c1)Oc1ccccc1]

Example 7-A, 5-trifluoromethyl-pyridin-3-ylamine, (385 mg, 2.37 mmol) is taken up in THF (25 mL) and pyridine (0.38 mL, 4.75 mmol) at 0° C. before phenyl chloroformate (558 mg, 3.56 mmol) is added. After 2 h, the reaction is diluted with DCM (50 mL) and washed with water (50 mL). The organic layer is separated, dried over anhydrous $Na_2SO_4$, filtered and concentrated. The residue is then separated via FCC (EtOAc/heptanes 1:9 to EtOAc/heptanes 1:1) to give the title compound. MS (ESI) m/z 283.0 (M+1).

The following compounds are prepared with similar method.

| | Structure/Chemical Name | MS (ESI) m/z (M + 1) |
|---|---|---|
| 13-B | Phenyl 3-(isopropylcarbamoyl)-5-(trifluoromethyl)phenylcarbamate | 367.1 |
| 13-C | Phenyl 3-((tert-butyldimethylsilyloxy)methyl)-5-(trifluoromethyl)phenylcarbamate | 426.1 |
| 13-D | (5-Isopropyl-isoxazol-3-yl)-carbamic acid phenyl ester | 247.3 |
| 13-E | (5-tert-Butyl-isoxazol-3-yl)-carbamic acid phenyl ester | 261.2 |
| 13-F | (3-Cyano-5-trifluoromethyl-phenyl)-carbamic acid phenyl ester | 305.0 |

| | Structure/Chemical Name | MS (ESI) m/z (M + 1) |
|---|---|---|
| 13-G | 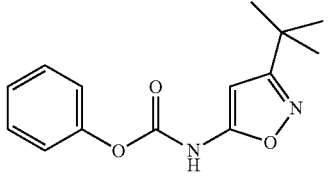<br>(3-tert-Butyl-isoxazol-5-yl)-carbamic acid phenyl ester | 261.2 |
| 13-H | 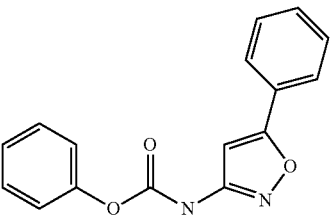<br>(5-Phenyl-isoxazol-3-yl)-carbamic acid phenyl ester | 281.2 |
| 13-I | 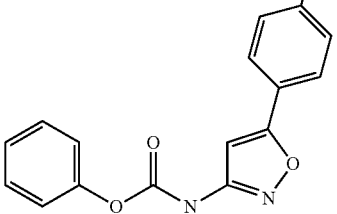<br>[5-(4-Fluoro-phenyl)-isoxazol-3-yl]-carbamic acid phenyl ester | 299.1 |
| 13-J | 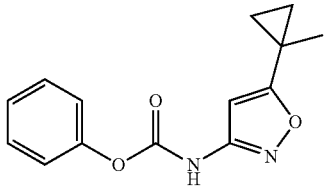<br>[5-(1-Methyl-cyclopropyl)-isoxazol-3-yl]-carbamic acid phenyl ester | 259.2 |
| 13-K | 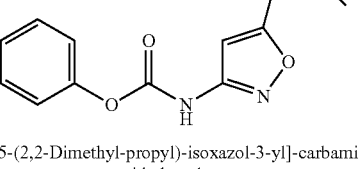<br>[5-(2,2-Dimethyl-propyl)-isoxazol-3-yl]-carbamic acid phenyl ester | 275.2 |
| 13-L | 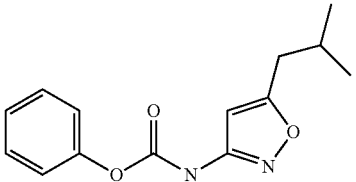<br>(5-Isobutyl-isoxazol-3-yl)-carbamic acid phenyl ester | 261.3 |
| 13-M | 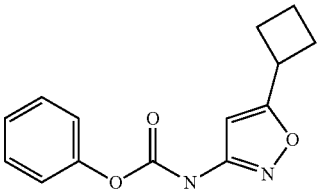<br>(5-Cyclobutyl-isoxazol-3-yl)-carbamic acid phenyl ester | 259.2 |
| 13-N | 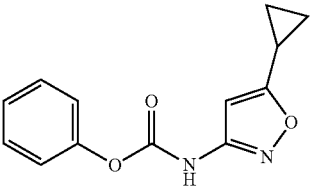<br>(5-Cyclopropyl-isoxazol-3-yl)-carbamic acid phenyl ester | 245.2 |
| 13-O | 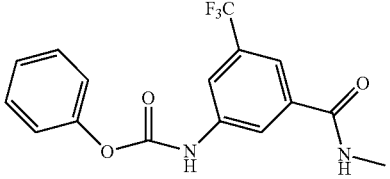<br>Phenyl 3-(methylcarbamoyl)-5-(trifluoromethyl)phenylcarbamate | 339.1 |
| 13-P | 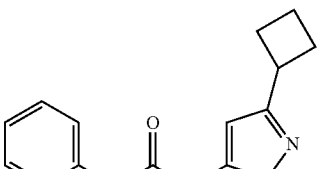<br>(3-Cyclobutyl-isoxazol-5-yl)-carbamic acid phenyl ester | 259.2 |
| 13-Q | 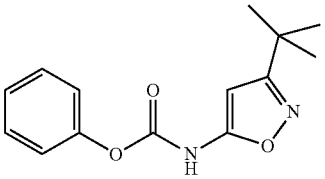<br>(3-tert-Butyl-isoxazol-5-yl)-carbamic acid phenyl ester | 261.2 |

| | Structure/Chemical Name | MS (ESI) m/z (M + 1) |
|---|---|---|
| 13-R | 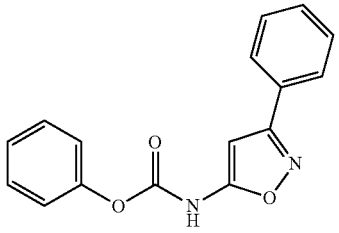<br>(3-Phenyl-isoxazol-5-yl)-carbamic acid phenyl ester | 281.2 |
| 13-S | 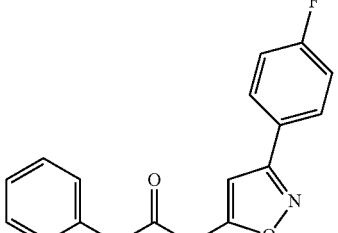<br>[3-(4-Fluoro-phenyl)-isoxazol-5-yl]-carbamic acid phenyl ester | 299.1 |
| 13-T | 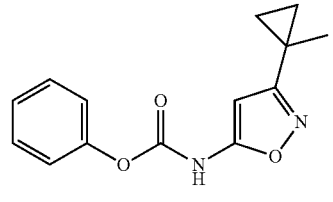<br>[3-(1-Methyl-cyclopropyl)-isoxazol-5-yl]-carbamic acid phenyl ester | 259.2 |
| 13-U | 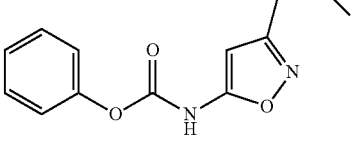<br>[3-(2,2-Dimethyl-propyl)-isoxazol-5-yl]-carbamic acid phenyl ester | 275.2 |
| 13-V | 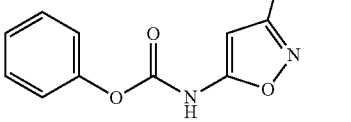<br>(3-Isobutyl-isoxazol-5-yl)-carbamic acid phenyl ester | 261.3 |
| 13-W | 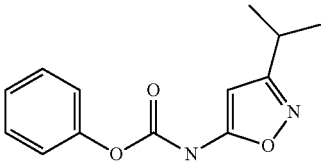<br>(3-Isopropyl-isoxazol-5-yl)-carbamic acid phenyl ester | 247.3 |
| 13-X | 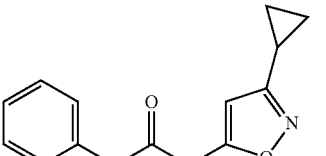<br>(3-Cyclopropyl-isoxazol-5-yl)-carbamic acid phenyl ester | 245.2 |
| 13-Y | 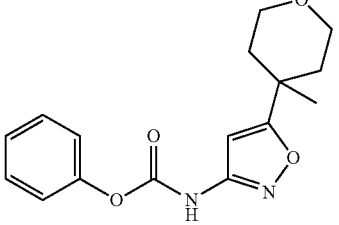<br>[5-(4-Methyl-tetrahydro-pyran-4-yl)-isoxazol-3-yl]-carbamic acid phenyl ester | 303.2 |
| 13-Z | 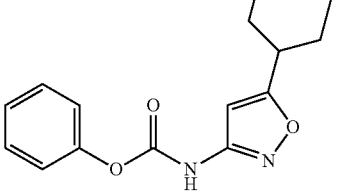<br>(5-Cyclohexyl-isoxazol-3-yl)-carbamic acid phenyl ester | 287.2 |
| 13-AA | 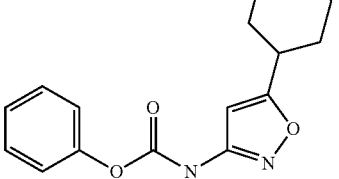<br>[5-(Tetrahydro-pyran-4-yl)-isoxazol-3-yl]-carbamic acid phenyl ester | 289.2 |

| | Structure/Chemical Name | MS (ESI) m/z (M + 1) |
|---|---|---|
| 13-AB | 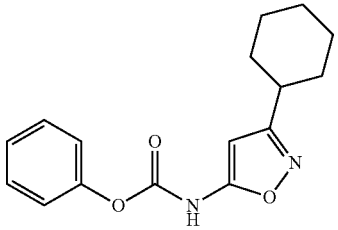 (3-Cyclohexyl-isoxazol-5-yl)-carbamic acid phenyl ester | 287.2 |
| 13-AC | 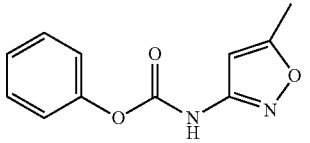 (5-Methyl-isoxazol-3-yl)-carbamic acid phenyl ester | 219.2 |
| 13-AD | 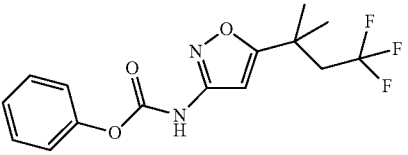 (5-(3,3,3-Trifluoro-1,1-dimethyl-propyl))-isoxazol-3-yl-carbamic acid phenyl ester | 329.0 |

EXAMPLE 14

14-A. 5-(6-Benzyloxymethyl-pyrimidin-4-yloxy)-1H-indole

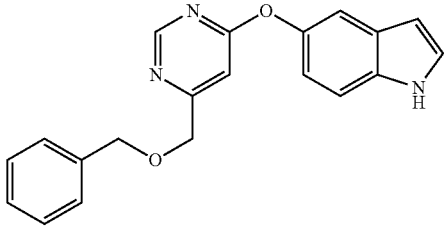 [SMILES: c1ccc(COCc2cc(Oc3ccc4[nH]ccc4c3)ncn2)cc1]

To a solution of 5-hydroxy indole (1.33 g, 10 mmol) and 4-benzyloxymethyl-6-chloro-pyrimidine (2.35 g, 10 mmol) in acetonitrile (20 mL) is added DBU. After 16 h at rt the solution is concentrated under reduced pressure. The residue is purified by FCC (EtOAc/Heptane from 0% to 40%) to give 546-benzyloxymethyl-pyrimidin-4-yloxy)-1H-indole. MS (ESI) m/z 447.0 (M+1).

The following compounds are prepared with similar method.

14-B. 5-(6-Benzyloxymethyl-pyrimidin-4-yloxy)-4-fluoro-2-methyl-1H-indole

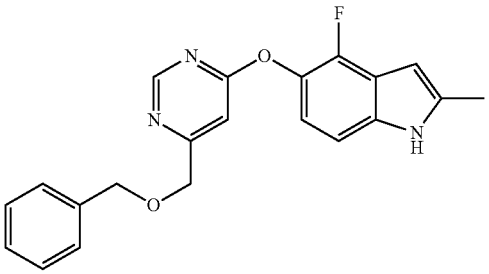 [SMILES: Cc1cc2c(F)c(Oc3cc(COCc4ccccc4)ncn3)ccc2[nH]1]

MS (ESI) m/z 364.0 (M+1)

14-C. 5-(6-Benzyloxymethyl-pyrimidin-4-yloxy)-4-fluoro-1H-indole

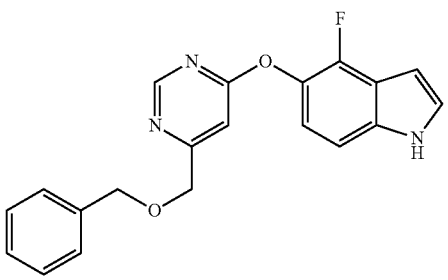 [SMILES: Fc1c(Oc2cc(COCc3ccccc3)ncn2)ccc2[nH]ccc12]

MS (ESI) m/z 350.2 (M+1)

EXAMPLE 15

15-A. 5-(6-Benzyloxymethyl-pyrimidin-4-yloxy)-indole-1-carboxylic acid (4-fluoro-3-trifluoromethyl-phenyl)-amide

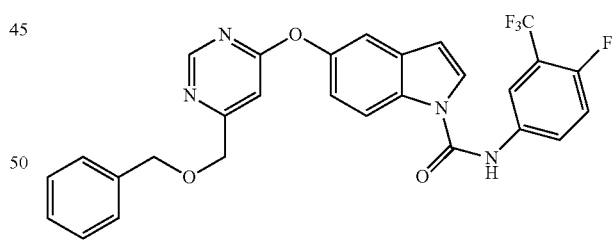

To a solution of 2,2,6,6-tetramethyl-piperidine (1.07 g, 7.6 mmol) in THF (40 mL) at −78° C. is added n-butyllithium (2.5 M in hexane, 2.9 mL) followed by 5-(6-benzyloxymethyl-pyrimidin-4-yloxy)-1H-indole (2.4 g, 7.3 mmol) while keeping the temperature below −70° C. The reaction is stirred for 10 min before 1-fluoro-4-isocyanato-2-trifluoromethyl-benzene (1.56 g, 7.6 mmol) is added and then the solution is allowed to slowly warm to rt and stir for an additional 16 h. The solvent is then removed under reduced pressure and the residue partitioned between EtOAc and water. The organic layer is separated, dried and concentrated. The residue is then separated via FCC (EtOAc/heptane from 0% to 100%) to give the title compound. MS (ESI) m/z 537.0 (M+1).

The following compounds are prepared with similar method.

| | Structure/Chemical Name | MS (ESI) m/z (M + 1) |
|---|---|---|
| 15-B | 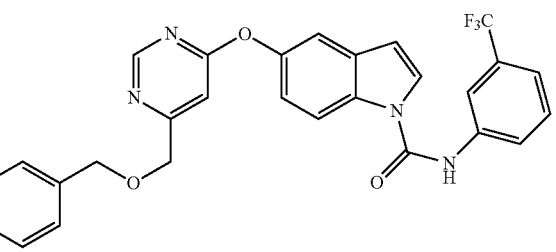<br>5-(6-Benzyloxymethyl-pyrimidin-4-yloxy)-indole-1-carboxylic acid (3-trifluoromethyl-phenyl)-amide | 519.2 |
| 15-C | 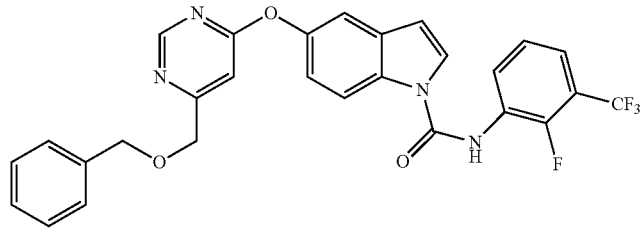<br>5-(6-Benzyloxymethyl-pyrimidin-4-yloxy)-indole-1-carboxylic acid (2-fluoro-3-trifluoromethyl-phenyl)-amide | 537.0 |
| 15-D | 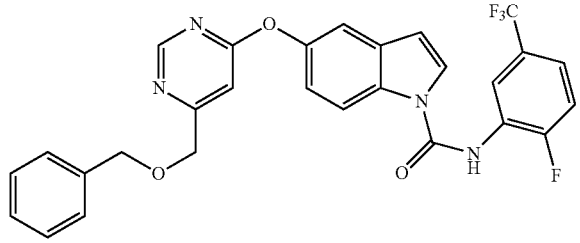<br>5-(6-Benzyloxymethyl-pyrimidin-4-yloxy)-indole-1-carboxylic acid (2-fluoro-5-trifluoromethyl-phenyl)-amide | 537.0 |
| 15-E | 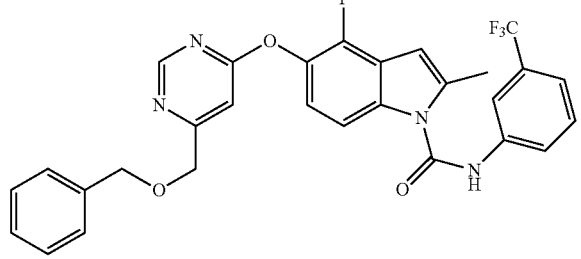<br>5-(6-Benzyloxymethyl-pyrimidin-4-yloxy)-4-fluoro-2-methyl-indole-1-carboxylic acid (3-trifluoromethyl-phenyl)-amide | 551.0 |

| | Structure/Chemical Name | MS (ESI) m/z (M + 1) |
|---|---|---|
| 15-F | 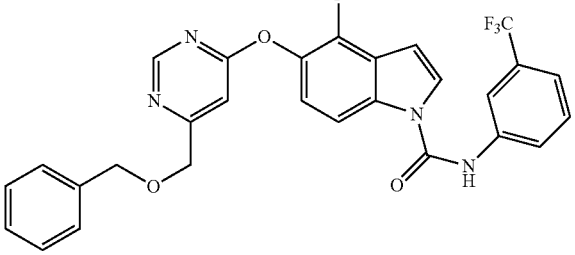<br>5-(6-Benzyloxymethyl-pyrimidin-4-yloxy)-4-fluoro-indole-1-carboxylic acid (3-trifluoromethyl-phenyl)-amide | 537.0 |

EXAMPLE 16

16-A. 5-(6-Hydroxymethyl-pyrimidin-4-yloxy)-indole-1-carboxylic acid (4-fluoro-3-trifluoromethyl-phenyl)-amide

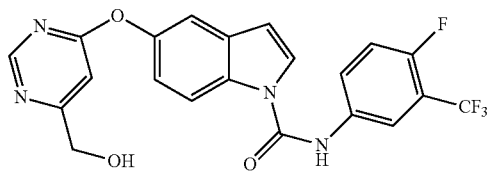 [SMILES: O=C(Nc1ccc(F)c(C(F)(F)F)c1)n1ccc2cc(Oc3cc(CO)ncn3)ccc21]

A solution of 5-(6-benzyloxymethyl-pyrimidin-4-yloxy)-indole-1-carboxylic acid (4-fluoro-3-trifluoromethyl-phenyl)-amide (2.0 g, 3.7 mmol) in TFA (20 mL) is heated at 60° C. for 24 h before being allowed to cool to rt. The solution is then poured onto 100 g crushed ice. The oily product is removed and then separated by FCC (EtOAc/Heptane from 0% to 100%) to provide the title compound. MS (ESI) m/z 447.0 (M+1); $^1$H NMR (400 MHz, DMSO-$d_6$) δ ppm 10.40 (s, 1 H), 8.65 (d, J=1.01 Hz, 1 H), 8.29 (d, J=9.09 Hz, 1 H), 8.09-8.12 (m, 2H), 8.99-8.04 (m, 1 H), 7.58 (t, J=9.60 Hz, 1 H), 7.51 (d, J=2.53 Hz, 1 H), 7.16 (dd, J=8.84, 2.53 Hz, 1 H), 6.99 (d, J=1.01 Hz, 1 H), 6.82 (d, J=3.79 Hz, 1 H), 5.61 (t, J=5.05 Hz, 1 H), 4.52 (d, J=5.05 Hz, 2 H).

The following compounds are prepared with similar method.

| | Structure/Chemical Name | $^1$H NMR (400 MHz) | MS (ESI) m/z (M + 1) |
|---|---|---|---|
| 16-B | 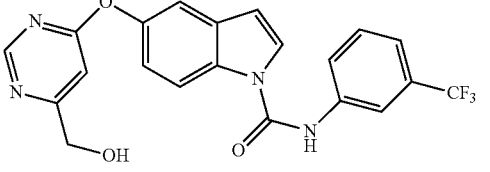<br>5-(6-Hydroxymethyl-pyrimidin-4-yloxy)-indole-1-carboxylic acid (3-trifluoromethyl-phenyl)-amide | (MeOD) δ ppm 8.61 (d, J = 1.01 Hz, 1H), 8.37 (d, J = 8.84 Hz, 1H), 8.07 (s, 1H), 7.96 (d, J = 3.79 Hz, 1H), 7.90 (dd, J = 7.96, 1.39 Hz, 1H), 7.58 (t, J = 7.96 Hz, 1H), 7.45 (s, 1H), 7.43 (d, J = 2.27 Hz, 1H), 7.13 (dd, J = 8.97, 2.40 Hz, 1H), 7.08 (d, J = 1.01 Hz, 1H), 6.76 (d, J = 3.79 Hz, 1H), 4.63 (s, 2H). | 429.1 |
| 16-C | 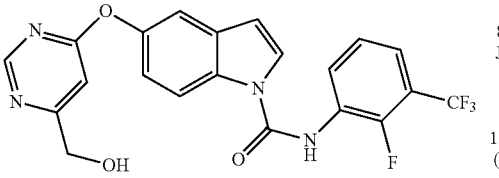<br>5-(6-Hydroxymethyl-pyrimidin-4-yloxy)-indole-1-carboxylic acid (2-fluoro-3-trifluoromethyl-phenyl)-amide | (DMSO-$d_6$) δ ppm 10.28 (s, 1H), 8.65 (d, J = 1.01 Hz, 1H), 8.27 (d, J = 8.84 Hz, 1H), 8.11 (d, J = 3.79 Hz, 1H), 7.92-7.96 (m, 1H), 7.68-7.73 (m, 1H), 7.47-7.52 (m, 2H), 7.16 (dd, J = 8.97, 2.40 Hz, 1H), 6.98 (d, J = 1.01 Hz, 1H), 6.83 (d, J = 3.79 Hz, 1H), 5.60-5.62 (m, 1H), 4.52 (d, J = 5.81 Hz, 2H). | 466.9 |

| Structure/Chemical Name | ¹H NMR (400 MHz) | MS (ESI) m/z (M + 1) |
|---|---|---|
| 16-D 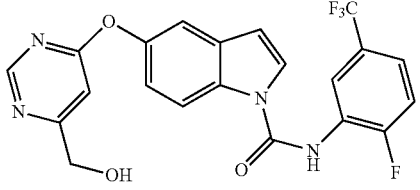<br>5-(6-Hydroxymethyl-pyrimidin-4-yloxy)-indole-1-carboxylic acid (2-fluoro-5-trifluoromethyl-phenyl)-amide | (DMSO-$d_6$) δ ppm 10.27 (s, 1H), 8.65 (d, J = 1.01 Hz, 1H), 8.27 (d, J = 8.84 Hz, 1H), 8.10 (d, J = 3.79 Hz, 1H), 8.05 (dd, J = 6.95, 2.15 Hz, 1H), 7.72 (d, J = 4.04 Hz, 1H), 7.62 (t, J = 9.35 Hz, 1H), 7.51 (d, J = 2.27 Hz, 1H), 7.16 (dd, J = 8.97, 2.40 Hz, 1H), 6.98 (d, J = 1.01 Hz, 1H), 6.82 (d, J = 3.79 Hz, 1H), 5.61 (t, J = 5.68 Hz, 1H), 4.52 (d, J = 5.31 Hz, 2H). | 446.9 |
| 16-E 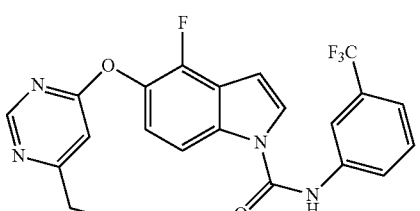<br>4-Fluoro-5-(6-hydroxymethyl-pyrimidin-4-yloxy)-indole-1-carboxylic acid (3-trifluoromethyl-phenyl)-amide | (DMSO-$d_6$) δ ppm 10.49 (s, 1H) 8.65 (s, 1H), 8.08-8.19 (m, 3H), 7.97 (d, J = 8.59 Hz, 1H) 7.66 (t, J = 8.08 Hz, 1H) 7.52 (d, J = 7.83 Hz, 1H), 7.27-7.34 (m, 1H) 7.17 (s, 1H) 6.94 (d, J = 3.54 Hz, 1H), 5.68 (br. S, 1H) 4.57 (s, 2H). | 447.0 |

EXAMPLE 17

17-A. 4-Fluoro-5-(6-hydroxymethyl-pyrimidin-4-yloxy)-2-methyl-indole-1-carboxylic acid (3-trifluoromethyl-phenyl)-amide

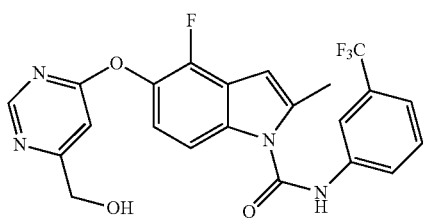 [SMILES: Cc1cc2c(F)c(Oc3cc(CO)ncn3)ccc2n1C(=O)Nc1cccc(C(F)(F)F)c1]

A solution of 5-(6-benzyloxymethyl-pyrimidin-4-yloxy)-4-fluoro-2-methyl-indole-1-carboxylic acid (3-trifluoromethyl-phenyl)-amide (2.0 g, 3.6 mmol) and MsOH (15 mL) is heated at 100° C. for 8 min before being poured into saturated aqueous NaHCO₃. The aqueous phase is extracted with EtOAc. The organic phase is washed with brine, dried over anhydrous Na₂SO₄, and purified via FCC (EtOAc/heptanes 2:8 to EtOAc) to give the title compound. MS (ESI) m/z 461.1 (M+1); ¹H NMR (400 MHz, DMSO-$d_6$) δ ppm 11.00 (s, 1 H) 8.61-8.65 (m, 1 H) 8.12 (s, 1 H) 7.91 (s, 1 H) 7.66 (t, J=7.71 Hz, 1 H) 7.52 (d, J=8.84 Hz, 1 H) 7.12-7.22 (m, 2 H) 6.84 (br. S., 1 H) 6.63 (s, 1 H) 5.66 (t, J=5.94 Hz, 1 H) 4.56 (d, J=5.56 Hz, 2 H) 2.59 (s, 3 H).

The following compound is prepared by a similar method.

17-B. [6-(4-Fluoro-2-methyl-1H-indol-5-yloxy)-pyrimidin-4-yl]-methanol

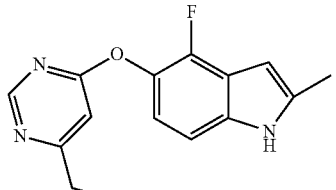

MS (ESI) m/z 274.2 (M+1).

EXAMPLE 18

18-A. 5-(6-Methanesulfonylmethyl-pyrimidin-4-yloxy)-indole-1-carboxylic acid (4-fluoro-3-trifluoromethyl-phenyl)-amide

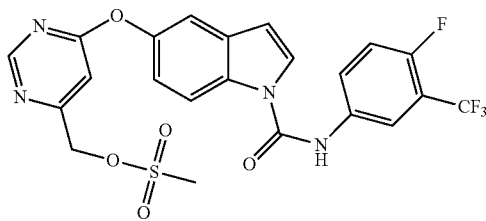 [SMILES: CS(=O)(=O)OCc1cc(Oc2ccc3c(ccn3C(=O)Nc3ccc(F)c(C(F)(F)F)c3)c2)ncn1]

To a solution of 5-(6-hydroxymethyl-pyrimidin-4-yloxy)-indole-1-carboxylic acid (4-fluoro-3-trifluoromethyl-phenyl)-amide (260 mg, 0.6 mmol), methanesulfonic anhydride (240 mg, 1.4 mmol), and THF (15 mL) is added pyridine (0.2 mL). The mixture is stirred at rt for 0.5 h before being filtered. The filtrate is used in the next step without purification. MS (ESI) m/z 525.0 (M+1).

The following compounds are prepared with similar method.

| Structure/Chemical Name | MS (ESI) m/z (M + 1) |
|---|---|
| 18-B 5-(6-Methanesulfonylmethyl-pyrimidin-4-yloxy)-indole-1-carboxylic acid (3-trifluoromethyl-phenyl)-amide | 507.0 |
| 18-C 5-(6-Methanesulfonylmethyl-pyrimidin-4-yloxy)-indole-1-carboxylic acid (2-fluoro-3-trifluoromethyl-phenyl)-amide | 524.8 |
| 18-D 5-(6-Methanesulfonylmethyl-pyrimidin-4-yloxy)-indole-1-carboxylic acid (2-fluoro-5-trifluoromethyl-phenyl)-amide | 524.8 |
| 18-E Methanesulfonic acid 6-[4-fluoro-2-methyl-1-(3-trifluoromethyl-phenylcarbamoyl)-1H-indol-5-yloxy]-pyrimidin-4-ylmethyl ester | 538.8 |
| 18-F Methanesulfonic acid 6-(4-fluoro-2-methyl-1H-indol-5-yloxy)-pyrimidin-4-ylmethyl ester | 352.0 |
| 18-G Methanesulfonic acid 6-[4-fluoro-1-(3-trifluoromethyl-phenylcarbamoyl)-1H-indol-5-yloxy]-pyrimidin-4-ylmethyl ester | 525.0 |

EXAMPLE 19

19-A. 5-(6-Methylaminomethyl-pyrimidin-4-yloxy)-indole-1-carboxylic acid (4-fluoro-3-trifluoromethyl-phenyl)-amide

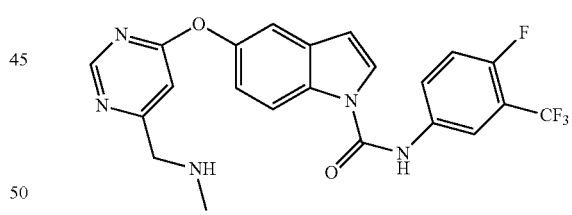

To a solution of 5-(6-methanesulfonylmethyl-pyrimidin-4-yloxy)-indole-1-carboxylic acid (4-fluoro-3-trifluoromethyl-phenyl)-amide, Example 18A, (180 mg, 0.35 mmol) is added methyl amine (1 mL, 2.0 M in methanol). The mixture is stirred at room temperature for 16 h, then concentrated under reduced pressure. The residue is diluted with EtOAc and washed with water and brine. The organic layer is removed, dried, and concentrated. The residue is then separated by FCC (MeOH with 1% NH₄OH/DCM from 0% to 10%) to give the title compound. MS (ESI) m/z 460.1 (M+1); $^1$H NMR (400 MHz, MeOD) δ ppm 8.65 (d, J=1.01 Hz, 1 H), 8.35 (d, J=8.84 Hz, 1 H), 8.04 (dd, J=6.19, 2.65 Hz, 1 H), 7.90-7.94 (m, 2 H), 7.41 (d, J=2.27 Hz, 1 H), 7.35 (t, J=9.60 Hz, 1 H), 7.11 (dd, J=8.97, 2.40 Hz, 1 H), 7.00 (s, 1 H), 6.74 (d, J=3.79 Hz, 1 H), 3.82 (s, 2 H), 2.43 (s, 3 H).

The following compounds are prepared with similar method starting from compounds of Example 18A-G.

| | Structure/Chemical Name | ¹H NMR (400 MHz) | MS (ESI) m/z (M + 1) |
|---|---|---|---|
| 19-B | 5-(6-Methylaminomethyl-pyrimidin-4-yloxy)-indole-1-carboxylic acid (3-trifluoromethyl-phenyl)-amide | (MeOD) δ ppm 8.64 (s, 1H), 8.34 (d, J = 9.09 Hz, 1H), 8.05 (s, 1H), 7.93 (d, J = 3.79 Hz, 1H), 7.89 (d, J = 8.08 Hz, 1H), 7.56 (t, J = 7.96 Hz, 1H), 7.40-7.46 (m, 2H), 7.10 (dd, J = 8.97, 2.40 Hz, 1H), 6.99 (s, 1H), 6.73 (d, J = 3.79 Hz, 1H), 3.77 (s, 2H), 2.40 (s, 3H). | 442.1 |
| 19-C | 5-[6-(Isopropylamino-methyl)-pyrimidin-4-yloxy]-indole-1-carboxylic acid (4-fluoro-3-trifluoromethyl-phenyl)-amide | (MeOD) δ ppm 8.65 (d, J = 1.01 Hz, 1H), 8.36 (d, J = 8.84 Hz, 1H), 8.05 (dd, J = 6.19, 2.91 Hz, 1H), 7.91-7.95 (m, 2H), 7.42 (d, J = 2.27 Hz, 1H), 7.36 (t, J = 9.60 Hz, 1H), 7.12 (d, J = 8.84, 2.53 Hz, 1H), 7.03 (s, 1H), 6.75 (d, J = 3.79 Hz, 1H), 3.85 (s, 2H), 2.83 (m, 1H), 1.10 (d, J = 6.32 Hz, 6H). | 488.0 |
| 19-D | 5-{6-[(2-Methoxy-ethylamino)-methyl]-pyrimidin-4-yloxy}-indole-1-carboxylic acid (4-fluoro-3-trifluoromethyl-phenyl)-amide | (MeOD) δ ppm 8.64 (d, J = 1.01 Hz, 1H), 8.35 (d, J = 9.09 Hz, 1H), 8.04 (dd, J = 6.32, 2.78 Hz, 1H), 7.92 (d, J = 3.79 Hz, 1H), 7.90-7.94 (m, 1H), 7.41 (d, J = 2.27 Hz, 1H), 7.35 (t, J = 9.60 Hz, 1H), 7.11 (dd, J = 8.97, 2.40 Hz, 1H), 7.02 (d, J = 1.01 Hz, 1H), 6.74 (d, J = 3.79 Hz, 1H), 3.85 (s, 2H), 3.47-3.51 (m, 2H), 3.32 (s, 3H), 2.76-2.79 (m, 2H). | 504.0 |
| 19-E | 5-(6-Morpholin-4-ylmethyl-pyrimidin-4-yloxy)-indole-1-carboxylic acid (3-trifluoromethyl-phenyl)-amide | (MeOD) δ ppm 8.62 (d, J = 1.01 Hz, 1H), 8.34 (d, J = 8.84 Hz, 1H), 8.05 (s, 1H), 7.93 (d, J = 3.54 Hz, 1H), 7.89 (d, J = 8.08 Hz, 1H), 7.56 (t, J = 8.21 Hz, 1H), 7.40-7.45 (m, 2H), 7.09 (s, 1H), 7.02 (s, 1H), 6.73 (d, J = 3.79 Hz, 1H), 3.65 (br. S., 1H), 3.67 (d, m, 4H), 3.58 (s, 2H), 2.50 (d, m, 4H). | 498.0 |
| 19-F | 5-(6-Dimethylaminomethyl-pyrimidin-4-yloxy)-indole-1-carboxylic acid (3-trifluoromethyl-phenyl)-amide | (MeOD) δ ppm 8.64 (s, 1H), 8.35 (d, J = 8.84 Hz, 1H), 8.06 (s, 1H), 7.94 (d, J = 3.54 Hz, 1H), 7.90 (d, J = 8.08 Hz, 1H), 7.57 (t, J = 7.96 Hz, 1H), 7.42 (d, J = 2.53 Hz, 2H), 7.11 (dd, J = 8.84, 2.27 Hz, 1H), 7.03 (s, 1H), 6.74 (d, J = 3.54 Hz, 1H), 3.55 (s, 2H), 2.29 (s, 6H). | 456.1 |

| | Structure/Chemical Name | ¹H NMR (400 MHz) | MS (ESI) m/z (M + 1) |
|---|---|---|---|
| 19-G | 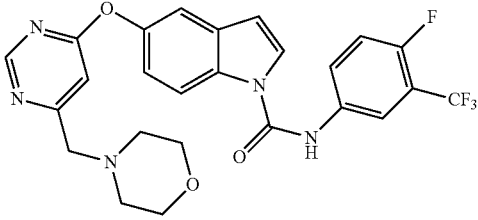<br>5-(6-Morpholin-4-ylmethyl-pyrimidin-4-yloxy)-indole-1-carboxylic acid (4-fluoro-3-trifluoromethyl-phenyl)-amide | (MeOD) δ ppm 8.63 (d, J = 1.01 Hz, 1H), 8.36 (d, J = 8.84 Hz, 1H), 8.05 (dd, J = 6.32, 2.78 Hz, 1H), 7.94 (d, J = 3.79 Hz, 1H), 7.91-7.95 (m, 1H), 7.43 (d, J = 2.27 Hz, 1H), 7.36 (t, J = 9.47 Hz, 1H), 7.10-7.14 (m, 2H), 6.75 (d, J = 3.79 Hz, 1H), 3.68 (m, 4H), 3.61 (s, 2H), 2.52 (m, 4H). | 516.0 |
| 19-H | 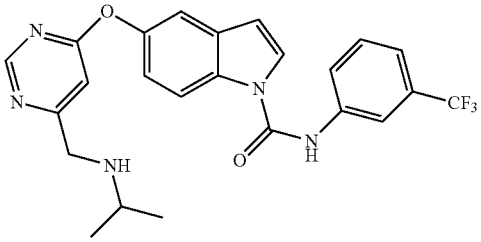<br>5-[6-(Isopropylamino-methyl)-pyrimidin-4-yloxy]-indole-1-carboxylic acid (3-trifluoromethyl-phenyl)-amide | (MeOD) δ ppm 8.64 (s, 1H), 8.35 (d, J = 9.09 Hz, 1H), 8.06 (s, 1H), 7.94 (d, J = 3.54 Hz, 1H), 7.89 (d, J = 8.08 Hz, 1H), 7.56 (t, J = 8.08 Hz, 1H), 7.40-7.46 (m, 2H), 7.10 (dd, J = 8.84, 2.27 Hz, 1H), 7.02 (s, 1H), 6.74 (d, J = 3.79 Hz, 1H), 3.82 (s, 2H), 2.81 (quin, J = 6.25 Hz, 1H), 1.09 (d, J = 6.32 Hz, 6H). | 470.1 |
| 19-I | 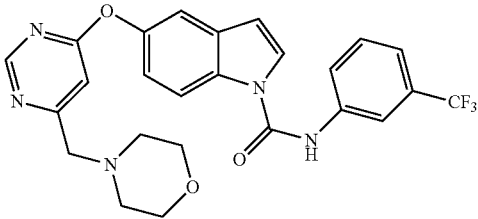<br>5-(6-Morpholin-4-ylmethyl-pyrimidin-4-yloxy)-indole-1-carboxylic acid (3-trifluoromethyl-phenyl)-amide | (MeOD) δ ppm 8.62 (d, J = 1.01 Hz, 1H), 8.34 (d, J = 8.84 Hz, 1H), 8.05 (s, 1H), 7.93 (d, J = 3.54 Hz, 1H), 7.89 (d, J = 8.08 Hz, 1H), 7.56 (t, J = 8.21 Hz, 1H), 7.40-7.45 (m, 2H), 7.09 (s, 1H), 6.73 (d, J = 3.79 Hz, 1H), 3.65 (br. S., 1H), 3.67 (d, m, 4H), 3.58 (s, 2H), 2.50 (d, m, 4H). | 498.0 |
| 19-J | 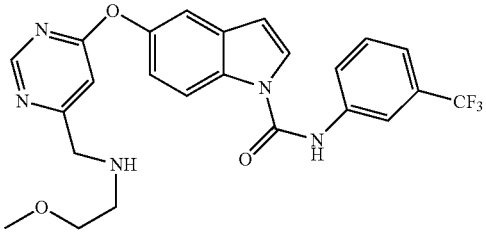<br>5-{6-[(2-Methoxy-ethylamino)-methyl]-pyrimidin-4-yloxy}-indole-1-carboxylic acid (3-trifluoromethyl-phenyl)-amide | (MeOD) δ ppm 8.63 (d, J = 1.01 Hz, 1H), 8.34 (d, J = 8.84 Hz, 1H), 8.05 (s, 1H,) 7.93 (d, J = 3.79 Hz, 1H), 7.89 (d, J = 8.34 Hz, 1H), 7.56 (t, J = 8.08 Hz, 1H), 7.40-7.45 (m, 2H), 7.10 (dd, J = 8.97, 2.40 Hz, 1H), 7.01 (s, 1H), 6.73 (d, J = 3.79 Hz, 1H), 3.84 (s, 2H), 3.47-3.50 (m, 2H), 3.31 (s, 3H), 2.75-2.79 (m, 2H). | 486.0 |
| 19-K | 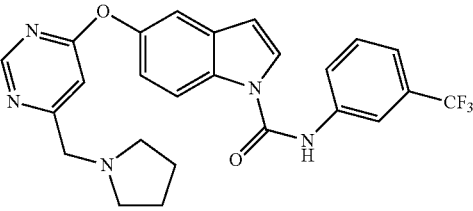<br>5-(6-Pyrrolidin-1-ylmethyl-pyrimidin-4-yloxy)-indole-1-carboxylic acid (3-trifluoromethyl-phenyl)-amide | (MeOD) δ ppm 8.64 (d, J = 1.01 Hz, 1H), 8.36 (d, J = 8.84 Hz, 1H), 8.06 (s, 1H), 7.95 (d, J = 3.79 Hz, 1H), 7.90 (d, J = 8.34 Hz, 1H), 7.57 (t, J = 7.96 Hz, 1H), 7.43 (d, J = 2.27 Hz, 2H), 7.12 (dd, J = 8.84, 2.27 Hz, 1H), 7.05 (s, 1H), 6.75 (d, J = 3.79 Hz, 1H), 3.74 (s, 2H), 2.61 (m, 4H), 1.81 (m, 4H). | 482.0 |

| | Structure/Chemical Name | ¹H NMR (400 MHz) | MS (ESI) m/z (M + 1) |
|---|---|---|---|
| 19-L | 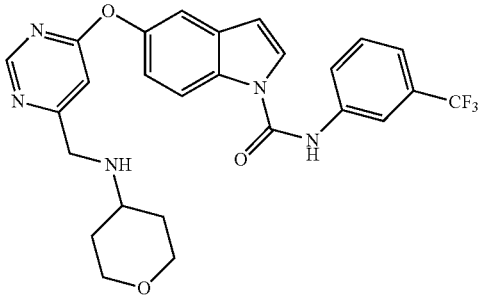<br>5-{6-[(Tetrahydro-pyran-4-ylamino)-methyl]-pyrimidin-4-yloxy}-indole-1-carboxylic acid (3-trifluoromethyl-phenyl)-amide | (MeOD) δ ppm 8.64 (d, J = 1.01 Hz, 1H), 8.35 (d, J = 8.84 Hz, 1H), 8.06 (s, 1H), 7.94 (d, J = 3.79 Hz, 1H), 7.89 (d, J = 8.08 Hz, 1H), 7.56 (t, J = 7.96 Hz, 1H), 7.40-7.45 (m, 2H), 7.10 (dd, J = 8.97, 2.40 Hz, 1H), 7.03 (s, 1H), 6.74 (d, J = 3.79 Hz, 1H), 3.92 (ddd, J = 11.87, 4.04, 2.02 Hz, 2H), 3.86 (s, 2H), 3.38 (td, J = 11.75, 2.02 Hz, 2H), 2.69 (tt, J = 10.74, 4.04 Hz, 1H), 1.83 (ddd, J = 12.63, 4.04, 2.02 Hz, 2H), 1.35-1.45 (m, 2H). | 512.0 |
| 19-M | 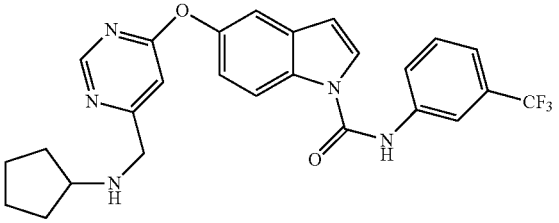<br>5-(6-Cyclopentylaminomethyl-pyrimidin-4-yloxy)-indole-1-carboxylic acid (3-trifluoromethyl-phenyl)-amide | (MeOD) δ ppm 8.64 (s, 1H), 8.35 (d, J = 8.84 Hz, 1H), 8.06 (s, 1H), 7.94 (d, J = 3.54 Hz, 1H), 7.89 (d, J = 6.57 Hz, 1H), 7.57 (t, J = 8.21 Hz, 1H), 7.41-7.46 (m, 2H), 7.11 (dd, J = 8.97, 2.40 Hz, 1H), 7.02 (s, 1H), 6.74 (d, J = 3.79 Hz, 1H), 3.81 (s, 2H), 3.08 (quin, J = 6.88 Hz, 1H), 1.81-1.91 (m, 2H), 1.65-1.76 (m, 2H), 1.50-1.60 (m, 2H), 1.32-1.44 (m, 2H). | 496.1 |
| 19-N | 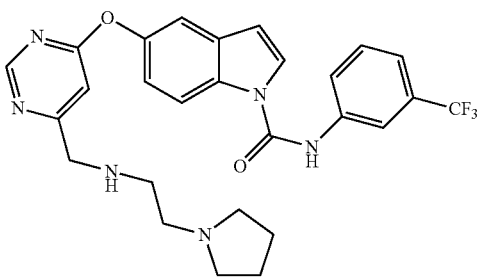<br>5-{6-[(2-Pyrrolidin-1-yl-ethylamino)-methyl]-pyrimidin-4-yloxy}-indole-1-carboxylic acid (3-trifluoromethyl-phenyl)-amide | (MeOD) δ ppm 8.65 (d, J = 1.01 Hz, 1H), 8.37 (d, J = 8.84 Hz, 1H), 8.06 (s, 1H), 7.95 (d, J = 3.79 Hz, 1H), 7.91 (d, J = 2.02 Hz, 1H), 7.58 (t, J = 7.96 Hz, 1H), 7.46 (s, 1H), 7.43 (d, J = 2.27 Hz, 1H), 7.12 (dd, J = 8.97, 2.40 Hz, 1H), 7.02 (s, 1H), 6.75 (d, J = 3.79 Hz, 1H), 3.85 (s, 2H), 2.73-2.77 (m, 2H), 2.61-2.65 (m, 2H), 2.54 (m, 4H), 1.79 (m, 4H). | 525.1 |
| 19-O | 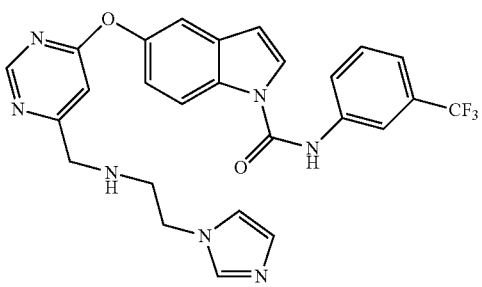<br>5-{6-[(2-Imidazol-1-yl-ethylamino)-methyl]-pyrimidin-4-yloxy}-indole-1-carboxylic acid (3-trifluoromethyl-phenyl)-amide | (MeOD) δ ppm 8.62 (d, J = 1.01 Hz, 1H), 8.36 (d, J = 9.09 Hz, 1H), 8.06 (s, 1H), 7.95 (d, J = 3.79 Hz, 1H), 7.90 (d, J = 8.08 Hz, 1H), 7.56 (s, 1H), 7.58 (t, J = 8.08 Hz, 1H), 7.41-7.46 (m, 2H), 7.11 (t, J = 1.39 Hz, 1H), 7.11 (dd, J = 8.97, 2.40 Hz, 1H), 6.92-6.95 (m, 2H), 6.75 (d, J = 3.79 Hz, 1H), 4.12 (t, J = 6.19 Hz, 2H), 3.82 (s, 2H), 2.97 (t, J = 6.19 Hz, 2H). | 522.0 |

| | Structure/Chemical Name | ¹H NMR (400 MHz) | MS (ESI) m/z (M + 1) |
|---|---|---|---|
| 19-P | 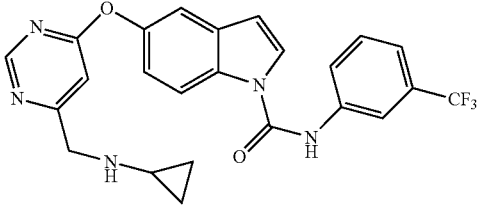<br>5-(6-Cyclopropylaminomethyl-pyrimidin-4-yloxy)-indole-1-carboxylic acid (3-trifluoromethyl-phenyl)-amide | (MeOD) δ ppm 8.64 (d, J = 1.01 Hz, 1H), 8.34 (d, J = 9.09 Hz, 1H), 8.05 (s, 1H), 7.93 (d, J = 3.79 Hz, 1H), 7.89 (d, J = 8.08 Hz, 1H), 7.56 (t, J = 7.96 Hz, 1H), 7.39-7.45 (m, 2H), 7.09 (dd, J = 8.84, 2.27 Hz, 1H), 7.00 (d, J = 1.01 Hz, 1H), 6.73 (d, J = 3.54 Hz, 1H), 3.87 (s, 2H), 2.13-2.19 (m, 1H), 0.35-0.48 (m, 4H). | 468.0 |
| 19-Q | 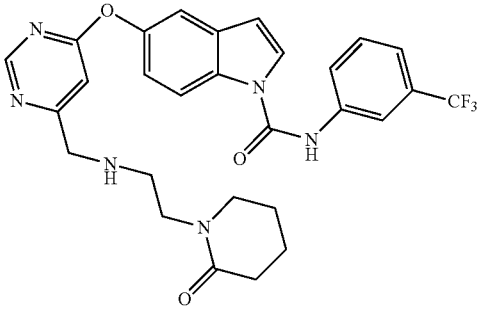<br>5-(6-{[2-(2-Oxo-piperidin-1-yl)-ethylamino]-methyl}-pyrimidin-4-yloxy)-indole-1-carboxylic acid (3-trifluoromethyl-phenyl)-amide | (MeOD) δ ppm 8.67 (s, 1H), 8.37 (d, J = 8.84 Hz, 1H), 8.07 (s, 1H), 7.96 (d, J = 3.79 Hz, 1H), 7.90 (d, J = 8.34 Hz, 1H), 7.58 (t, J = 8.08 Hz, 1H), 7.43 (d, J = 2.53 Hz, 1H), 7.46 (s, 1H), 7.12 (dd, J = 8.97, 2.40 Hz, 1H), 7.02 (s, 1H), 6.76 (d, J = 3.79 Hz, 1H), 3.95 (s, 2H), 3.53 (t, J = 6.32 Hz, 2H), 3.35 (t, J = 5.81 Hz, 2H), 2.89 (t, J = 6.32 Hz, 2H), 2.32 (t, J = 6.06 Hz, 2H), 1.74-1.82 (m, 4H). | 553.1 |
| 19-R | 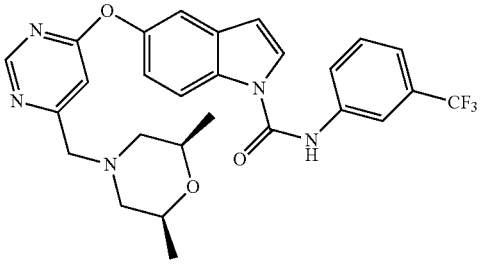<br>5-[6-((2R,6S)-2,6-Dimethyl-morpholin-4-ylmethyl)-pyrimidin-4-yloxy]-indole-1-carboxylic acid (3-trifluoromethyl-phenyl)-amide | (CD₂Cl₂) δ ppm 8.66 (s, 1H), 8.29 (d, J = 8.84 Hz, 1H), 7.96 (s, 1H), 7.80 (s, 1H), 7.66 (d, J = 3.54 Hz, 1H), 7.60 (t, J = 7.96 Hz, 2H), 7.49-7.52 (m, 1H), 7.45 (d, J = 2.02 Hz, 1H), 7.18 (dd, J = 8.84, 2.27 Hz, 1H), 7.14 (br. S., 1H), 6.79 (d, J = 3.03 Hz, 1H), 3.71 (br. S., 2H), 3.60 (br. S., 2H), 2.74 (br. S., 2H), 1.91 (br. S., 2H), 1.15 (d, J = 6.32 Hz, 6H). | 526.0 |
| 19-S | 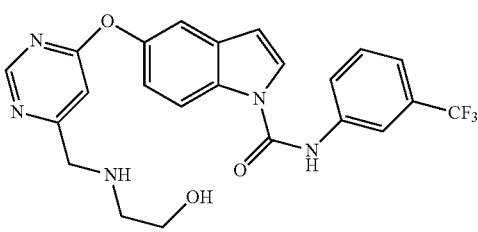<br>5-{6-[(2-Hydroxy-ethylamino)-methyl]-pyrimidin-4-yloxy}-indole-1-carboxylic acid (3-trifluoromethyl-phenyl)-amide | (DMSO-d₆) δ ppm 10.39 (br. S., 1H), 8.65 (d, J = 1.01 Hz, 1H), 8.29 (d, J = 8.84 Hz, 1H), 8.13 (d, J = 3.54 Hz, 1H), 8.10 (s, 1H), 7.98 (d, J = 8.34 Hz, 1H), 7.65 (t, J = 8.08 Hz, 1H), 7.51 (s, 1H), 7.49 (d, J = 2.53 Hz, 1H), 7.15 (dd, J = 8.97, 2.40 Hz, 1H), 7.10 (s, 1H), 6.81 (d, J = 3.79 Hz, 1H), 4.50 (t, J = 5.31 Hz, 1H), 3.79 (s, 2H), 3.46 (q, J = 5.73 Hz, 2H), 2.60 (t, J = 5.68 Hz, 2H). | 472.0 |

| | Structure/Chemical Name | ¹H NMR (400 MHz) | MS (ESI) m/z (M + 1) |
|---|---|---|---|
| 19-T | 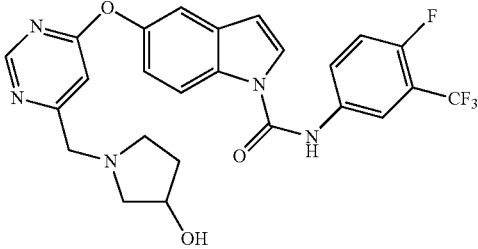<br>6-(3-Hydroxy-pyrrolidin-1-ylmethyl)-pyrimidin-4-yloxy]-indole-1-carboxylic acid (4-fluoro-3-trifluoromethyl-phenyl)-amide | (MeOD) δ ppm 8.65 (d, J = 1.01 Hz, 1H) 8.37 (s, 1H) 8.07 (s, 1H) 7.95 (d, J = 3.79 Hz, 2H) 7.45 (d, J = 2.02 Hz, 1H) 7.38 (d, J =19.70 Hz, 1H) 7.14 (dd, J = 9.09, 2.53 Hz, 1H) 7.12 (s, 1H) 6.78 (d, J = 3.79 Hz, 1H) 4.37 (d, J = 7.83 Hz, 1H) 3.78 (d, J = 4.29 Hz, 2H) 3.50 (dt, J = 3.28, 1.64 Hz, 1H) 3.15 (dt, J = 3.28, 1.64 Hz, 1H) 2.84 (d, J = 16.17 Hz, 2H) 2.60 (s, 2H) | 516.9 |
| 19-U | 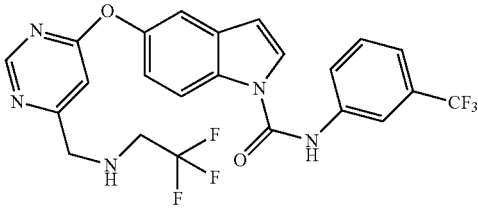<br>5-{6-[(2,2,2-Trifluoro-ethylamino)-methyl]-pyrimidin-4-yloxy}-indole-1-carboxylic acid (3-trifluoromethyl-phenyl)-amide | (CD₂Cl₂) δ ppm 8.70 (s, 1H), 8.29 (d, J = 8.84 Hz, 1H), 7.96 (s, 1H), 7.80 (s, 1H), 7.66 (d, J = 3.79 Hz, 1H), 7.60 (s, 1H), 7.49-7.55 (m, 2H), 7.45 (d, J = 2.53 Hz, 1H), 7.19 (dd, J = 9.09, 2.27 Hz, 1H), 6.99 (s, 1H), 6.80 (d, J = 3.54 Hz, 1H), 4.00 (s, 2H), 3.27-3.34 (m, 2H). | 509.9 |
| 19-V | 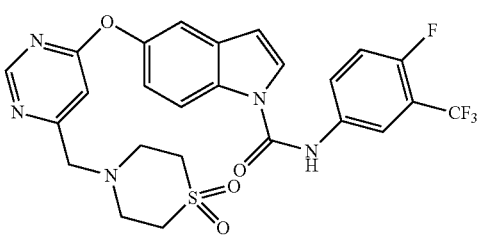<br>6-(1,1-Dioxo-1lambda*6*-thiomorpholin-4-ylmethyl)-pyrimidin-4-yloxy]-indole-1-carboxylic acid (4-fluoro-3-trifluoromethyl-phenyl)-amide | (MeOD) δ ppm 8.66 (s, 1H), 8.37 (d, J = 9.09 Hz, 1H) 8.06 (d, J = 6.06 Hz, 1H) 7.95 (br. S., 2H) 7.44 (s, 1H) 7.37 (t, J = 9.47 Hz, 1H) 7.12 (d, J = 1.77 Hz, 1H) 7.14 (s, 1H) 6.77 (br. S., 1H) 3.33 (m. S., 6H) 3.24 (m, 4H) | 563.1 |
| 19-W | 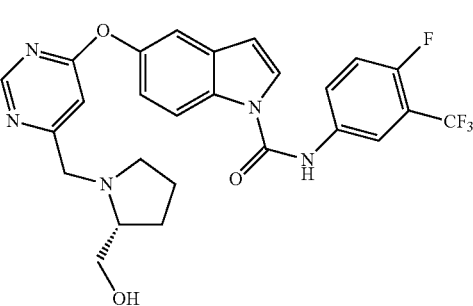<br>6-((S)-2-Hydroxymethyl-pyrrolidin-1-ylmethyl)-pyrimidin-4-yloxy]-indole-1-carboxylic acid (4-fluoro-3-trifluoromethyl-phenyl)-amide | (MeOD) δ ppm 8.65 (br. S., 1H) 8.38 (br. S., 1H) 8.07 (br. S., 1H) 7.95 (br. S., 2H) 7.41 (s, 2H) 7.14 (br. S., 2H) 6.78 (s, 1H) 4.19 (d, J = 16.0 Hz, 1H) 3.55 (d, J = 16.0 Hz, 1H) 3.54 (m, 3H) 3.04 (m, 1H) 2.76 (m, 1H) 2.36 (m, 1H) 1.96 (m, 1H) 1.77 (m, 2H) | 530.9 |

-continued

| | Structure/Chemical Name | ¹H NMR (400 MHz) | MS (ESI) m/z (M + 1) |
|---|---|---|---|
| 19-X | 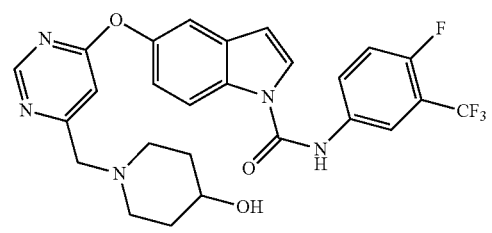<br>[6-(4-Hydroxy-piperidin-1-ylmethyl)-pyrimidin-4-yloxy]-indole-1-carboxylic acid (4-fluoro-3-trifluoromethyl-phenyl)-amide | (MeOD) δ ppm 8.63 (s, 1H) 8.36 (d, J = 8.84 Hz, 1H) 8.05 (d, J = 6.32 Hz, 1H) 7.93 (d, J = 3.79 Hz, 2H) 7.36 (t, J = 9.47 Hz, 1H) 7.43 (d, J = 2.27 Hz, 1H) 7.12 (dd, J = 8.84, 2.27 Hz, 1H) 7.08 (s, 1H) 6.75 (d, J = 3.54 Hz, 1H) 3.59 (m, 3H) 2.79 (m, 2H) 2.25 (m, 2H) 1.82 (m, 2H) 1.54 (m, 2H) | 530.9 |
| 19-Y | 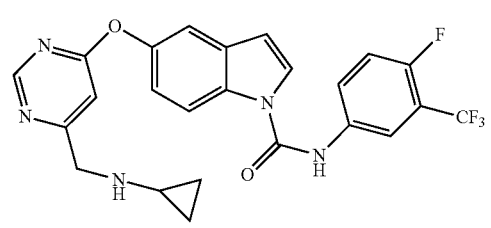<br>5-(6-Cyclopropylaminomethyl-pyrimidin-4-yloxy)-indole-1-carboxylic acid (4-fluoro-3-trifluoromethyl-phenyl)-amide | (MeOD) δ ppm 8.65 (d, J = 1.01 Hz, 1H), 8.35 (d, J = 9.09 Hz, 1H), 8.05 (dd, J = 6.32, 2.78 Hz, 1H), 7.93 (d, J = 3.79 Hz, 1H), 7.91-7.95 (m, 1H), 7.42 (d, J = 2.27 Hz, 1H), 7.36 (t, J = 9.73 Hz, 1H), 7.11 (dd, J = 8.97, 2.40 Hz, 1H), 7.02 (s, 1H), 6.75 (d, J = 3.79 Hz, 1H), 3.88 (s, 2H), 2.15-2.20 (m, 1H), 0.35-0.49 (m, 4H). | 485.9 |
| 19-Z | 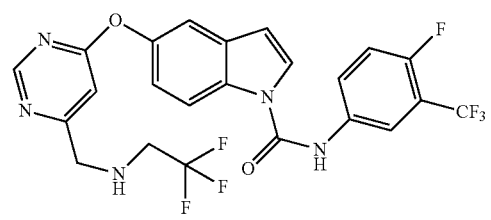<br>5-{6-[(2,2,2-Trifluoro-ethylamino)-methyl]-pyrimidin-4-yloxy}-indole-1-carboxylic acid (4-fluoro-3-trifluoromethyl-phenyl)-amide | (Aceton-d₆) δ ppm 9.60 (s, 1H), 8.63 (s, 1H), 8.40 (d, J = 9.09 Hz, 1H), 8.18 (dd, J = 6.32, 2.78 Hz, 1H), 8.05 (d, J = 3.79 Hz, 1H), 8.04-8.11 (m, 1H), 7.45-7.51 (m, 2H), 7.18 (dd, = 8.97, 2.40 Hz, 1H), 7.12 (s, 1H), 6.79 (d, J = 3.54 Hz, 1H), 4.00-4.03 (m, 2H), 3.36-3.45 (m, 2H). | 527.9 |
| 19-AA | 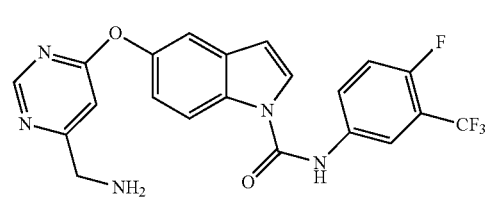<br>6-Aminomethyl-pyrimidin-4-yloxy)-indole-1-carboxylic acid (4-fluoro-3-trifluoromethyl-phenyl)-amide | (MeOD) δ ppm 8.62 (s, 1H) 8.33 (d, J = 9.09 Hz, 1H) 8.03 (dd, J = 6.19, 2.65 Hz, 1H) 7.91 (br. S., 1H) 7.90 (d, J = 3.79 Hz, 1H) 7.39 (d, J = 2.27 Hz, 1H) 7.33 (t, J = 9.60 Hz, 1H) 7.08 (dd, J = 8.97, 2.40 Hz, 1H) 7.00 (s, 1H) 6.72 (d, J = 3.54 Hz, 1H) 3.84 (s, 2H) | 446.9 |
| 19-AB | 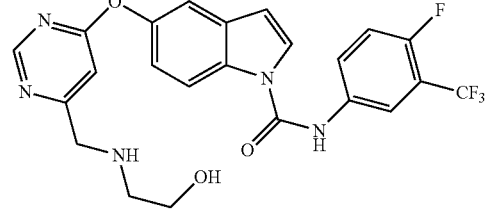<br>6-[(2-Hydroxy-ethylamino)-methyl]-pyrimidin-4-yloxy}-indole-1-carboxylic acid (4-fluoro-3-trifluoromethyl-phenyl)-amide | (MeOD) δ ppm 8.65 (d, J = 1.01 Hz, 1H) 8.36 (d, J = 8.84 Hz, 1H) 8.05 (dd, J = 6.32, 2.78 Hz, 1H) 7.93 (d, J = 4.04 Hz, 1H) 7.85-7.95 (m, 1H) 7.42 (d, J = 2.02 Hz, 1H) 7.31-7.44 (m, 1H) 7.12 (dd, J = 8.97, 2.40 Hz, 1H) 7.04 (d, J = 1.01 Hz, 1H) 6.75 (d, J = 3.79 Hz, 1H) 3.87 (s, 2H) 3.65 (d, J = 5.56 Hz, 1H) 3.67 (s, 1H) 2.74 (s, 2H) 2.76 (d, J = 5.56 Hz, 1H) | 490.9 |

| | Structure/Chemical Name | $^1$H NMR (400 MHz) | MS (ESI) m/z (M + 1) |
|---|---|---|---|
| 19-AC | 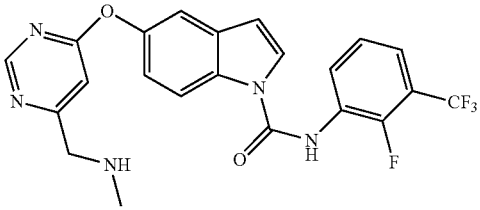<br>5-(6-Methylaminomethyl-pyrimidin-4-yloxy)-indole-1-carboxylic acid (2-fluoro-3-trifluoromethyl-phenyl)-amide | (DMSO-d$_6$) δ ppm 8.66 (d, J = 1.01 Hz, 1H), 8.29 (d, J = 8.84 Hz, 1H), 8.10 (d, J = 3.79 Hz, 1H), 7.96-7.98 (m, 1H), 7.67 (t, J = 6.69 Hz, 1H), 7.45-7.50 (m, 2H), 7.14 (dd, J = 8.97, 2.40 Hz, 1H), 7.04 (s, 1H), 6.80 (d, J = 3.79 Hz, 1H), 3.73 (s, 2H), 2.30 (s, 3H). | 459.9 |
| 19-AD | 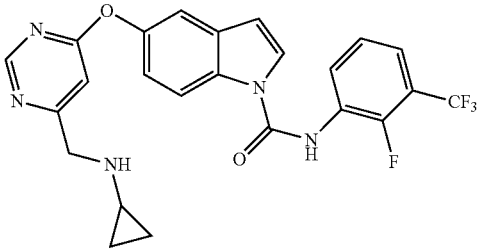<br>5-(6-Cyclopropylaminomethyl-pyrimidin-4-yloxy)-indole-1-carboxylic acid (2-fluoro-3-trifluoromethyl-phenyl)-amide | (DMSO-d$_6$) δ ppm 10.27 (br. S., 1H), 8.65 (d, J = 1.01 Hz, 1H), 8.26 (d, J = 9.09 Hz, 1H), 8.10 (d, J = 3.79 Hz, 1H), 7.94 (t, J = 7.07 Hz, 1H), 7.70 (t, J = 7.20 Hz, 1H), 7.47-7.52 (m, 2H), 7.14 (dd, J = 8.84, 2.53 Hz, 1H), 7.07 (d, J = 1.01 Hz, 1H), 6.82 (d, J = 4.29 Hz, 1H), 3.80 (s, 2H), 2.10 (ddd, J = 6.69, 3.28, 3.16 Hz, 1H), 0.34-0.38 (m, 2H), 0.23-0.27 (m, 2H) | 485.9 |
| 19-AE | 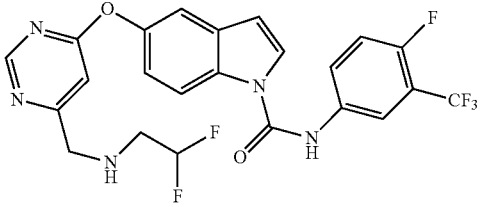<br>5-{6-[(2,2-Difluoro-ethylamino)-methyl]-pyrimidin-4-yloxy}-indole-1-carboxylic acid (4-fluoro-3-trifluoromethyl-phenyl)-amide | (DMSO-d$_6$) δ ppm 10.35 (br. S., 1H), 8.66 (d, J = 1.0 Hz, 1H), 8.29 (d, J = 8.8 Hz, 1H), 8.07-8.14 (m, 2H), 7.97-8.05 (m, 1H), 7.51-7.62 (m, 1H), 7.49 (d, J = 2.3 Hz, 1H), 7.15 (dd, J = 9.0, 2.4 Hz, 1H), 7.09 (d, J = 1.0 Hz, 1H), 6.78-6.82 (m, 1H), 5.85-6.19 (m, 1H), 3.81-3.88 (m, 2H), 2.85-3.01 (m, 2H), 2.70-2.84 (m, 1H) | 510.0 |
| 19-AF | 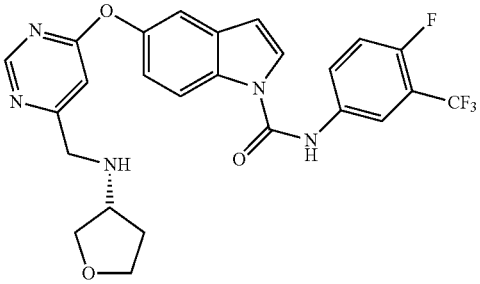<br>5-(6-{[I-(Tetrahydro-furan-3-yl)amino]-methyl}-pyrimidin-4-yloxy)-indole-1-carboxylic acid (4-fluoro-3-trifluoromethyl-phenyl)-amide | (DMSO-d$_6$) δ ppm 10.39 (s, 1H), 8.65 (d, J = 1.0 Hz, 1H), 8.29 (d, J = 8.8 Hz, 1H), 8.06-8.14 (m, 2H), 7.96-8.05 (m, 1H), 7.57 (t, J = 9.7 Hz, 1H), 7.48 (d, J = 2.5 Hz, 1H), 7.14 (dd, J = 9.0, 2.4 Hz, 1H), 7.10 (s, 1H), 6.81 (d, J = 3.3 Hz, 1H), 3.58-3.83 (m, 6H), 3.43 (dd, J = 8.7, 4.2 Hz, 1H), 1.86-2.00 (m, 1H), 1.61-1.73 (m, 1H) | 516.1 |
| 19-AG | 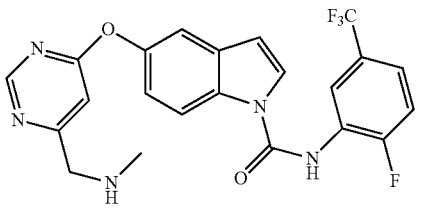<br>5-(6-Methylaminomethyl-pyrimidin-4-yloxy)-indole-1-carboxylic acid (2-fluoro-5-trifluoromethyl-phenyl)-amide | (MeOD) δ ppm 8.65 (s, 1H), 8.33 (d, J = 9.09 Hz, 1H), 8.17 (dd, J = 6.95, 1.89 Hz, 1H), 7.92 (d, J = 3.79 Hz, 1H), 7.60 (ddd, J = 8.08, 4.29, 2.27 Hz, 1H), 7.43 (d, J = 2.02 Hz, 1H), 7.44 (t, J = 9.47 Hz, 1H), 7.12 (dd, J = 8.84, 2.27 Hz, 1H), 7.00 (s, 1H), 6.77 (d, J = 3.79 Hz, 1H), 3.80 (s, 2H), 2.42 (s, 3H). | 459.9 |

| | Structure/Chemical Name | ¹H NMR (400 MHz) | MS (ESI) m/z (M + 1) |
|---|---|---|---|
| 19-AH | 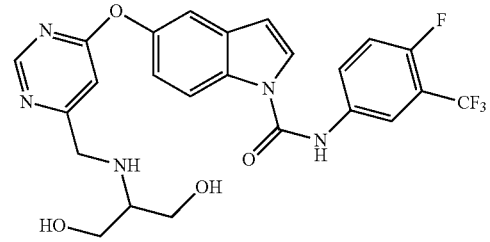{6-[(2-Hydroxy-1-hydroxymethyl-ethylamino)-methyl]-pyrimidin-4-yloxy}-indole-1-carboxylic acid (4-fluoro-3-trifluoromethyl-phenyl)-amide | (MeOD) δ ppm 8.65 (d, J = 1.01 Hz, 1H) 8.36 (d, J = 9.09 Hz, 1H) 7.93 (d, J = 3.54 Hz, 1H) 7.42 (d, J = 2.02 Hz, 2H) 7.34-7.39 (m, 1H) 7.11 (s, 1H) 7.13 (d, J = 2.53 Hz, 2H) 6.76 (d, J = 3.54 Hz, 1H) 3.99 (s, 2H) 3.63 (d, J = 5.31 Hz, 2H) 3.57 (d, J = 5.81 Hz, 2H) 2.77 (m, 1H) | 520.9 |
| 19-AI | 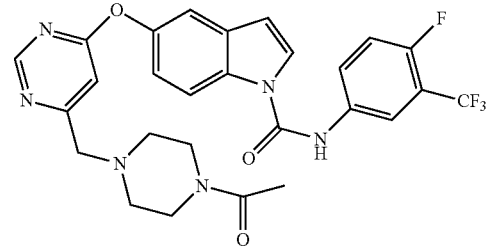5-[6-(4-Acetyl-piperazin-1-ylmethyl)-pyrimidin-4-yloxy]-indole-1-carboxylic acid (4-fluoro-3-trifluoromethyl-phenyl)-amide | (DMSO-d₆) δ ppm 10.39 (br. S., 1H), 8.67 (d, J = 1.0 Hz, 1H), 8.29 (d, J = 8.8 Hz, 1H), 8.08-8.14 (m, 2H), 7.95-8.04 (m, 1H), 7.57 (t, J = 9.9 Hz, 1H), 7.50 (d, J = 2.5 Hz, 1H), 7.16 (dd, J = 9.0, 2.4 Hz, 1H), 7.10 (s, 1H), 6.81 (d, J = 3.5 Hz, 1H), 3.62 (s, 2H), 3.44 (q, J = 4.3 Hz, 4H), 2.47 (d, J = 4.8 Hz, 2H), 2.40 (t, J = 4.9 Hz, 2H), 1.98 (s, 3H) | 557.2 |
| 19-AJ | 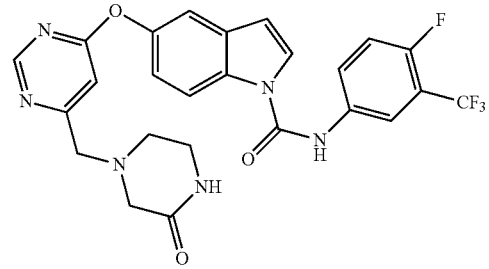5-[6-(3-Oxo-piperazin-1-ylmethyl)-pyrimidin-4-yloxy]-indole-1-carboxylic acid (4-fluoro-3-trifluoromethyl-phenyl)-amide | (DMSO-d₆) δ ppm 10.39 (s, 1H), 8.68 (s, 1H), 8.28 (d, J = 8.8 Hz, 1H), 8.07-8.14 (m, 2H), 7.95-8.06 (m, 1H), 7.76 (s, 1H), 7.57 (t, J = 9.9 Hz, 1H), 7.50 (d, J = 2.3 Hz, 1H), 7.16 (dd, J = 9.0, 2.4 Hz, 1H), 7.06 (s, 1H), 6.80 (d, J = 3.8 Hz, 1H), 3.66 (s, 2H), 3.16 (t, J = 4.3 Hz, 2H), 3.05 (s, 2H), 2.64 (t, J = 5.4 Hz, 2H) | 529.1 |
| 19-AK | 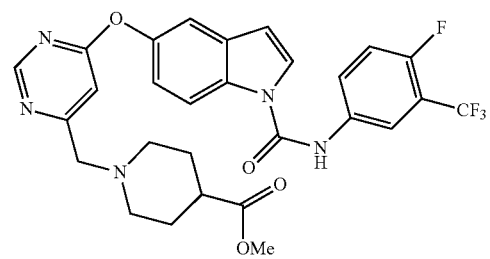1-{6-[1-(4-Fluoro-3-trifluoromethyl-phenylcarbamoyl)-1H-indol-5-yloxy]-pyrimidin-4-ylmethyl}-piperidine-4-carboxylic acid methyl ester | (DMSO-d₆) δ ppm 10.36-10.43 (m, 1H), 8.65 (d, J = 1.0 Hz, 1H), 8.28 (d, J = 9.1 Hz, 1H), 8.09-8.13 (m, 2H), 7.97-8.04 (m, 1H), 7.57 (t, J = 9.7 Hz, 1H), 7.50 (d, J = 2.5 Hz, 1H), 7.15 (dd, J = 9.0, 2.4 Hz, 1H), 7.04 (d, J = 0.8 Hz, 1H), 6.80 (d, J = 3.5 Hz, 1H), 3.60 (s, 3H), 3.56 (s, 2H), 2.75-2.83 (m, 2H), 2.30-2.37 (m, 1H), 2.09-2.18 (m, 2H), 1.76-1.85 (m, 2H), 1.51-1.63 (m, 2H) | 572.2 |

| | Structure/Chemical Name | ¹H NMR (400 MHz) | MS (ESI) m/z (M + 1) |
|---|---|---|---|
| 19-AL | 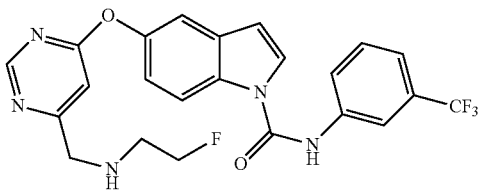<br>5-{6-[(2-Fluoro-ethylamino)-methyl]-pyrimidin-4-yloxy}-indole-1-carboxylic acid (3-trifluoromethyl-phenyl)-amide | (DMSO-d₆) δ ppm 10.34-10.45 (m, 1H), 8.67 (s, 1H), 8.29 (d, J = 9.1 Hz, 1H), 8.13 (d, J = 3.8 Hz, 1H), 8.10 (s, 1H), 7.98 (d, J = 7.8 Hz, 1H), 7.65 (t, J = 8.1 Hz, 1H), 7.47-7.53 (m, 2H), 7.09-7.18 (m, 2H), 6.81 (d, J = 3.8 Hz, 1H), 4.54 (t, J = 4.8 Hz, 1H), 4.40-4.47 (m, 1H), 3.83 (s, 2H), 2.76-2.92 (m, 2H) | 474.0 |
| 19-AM | 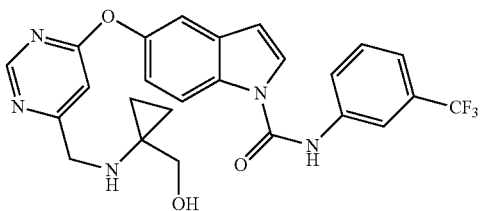<br>5-{6-[(1-Hydroxymethyl-cyclopropylamino)-methyl]-pyrimidin-4-yloxy}-indole-1-carboxylic acid (3-trifluoromethyl-phenyl)-amide | (DMSO-d₆) δ ppm 10.39 (s, 1H), 8.62 (d, J = 1.0 Hz, 1H), 8.28 (d, J = 9.1 Hz, 1H), 8.13 (d, J = 3.5 Hz, 1H), 8.10 (d, J = 1.3 Hz, 1H), 7.98 (d, J = 8.1 Hz, 1H), 7.65 (t, J = 8.1 Hz, 1H), 7.46-7.53 (m, 2H), 7.13 (dd, J = 9.0, 2.4 Hz, 1H), 7.08 (d, J = 0.8 Hz, 1H), 6.80 (d, J = 3.8 Hz, 1H), 4.59 (t, J = 5.7 Hz, 1H), 3.86 (s, 2H), 3.34-3.40 (m, 2H), 0.39-0.50 (m, 4H) | 498.1 |
| 19-AN | 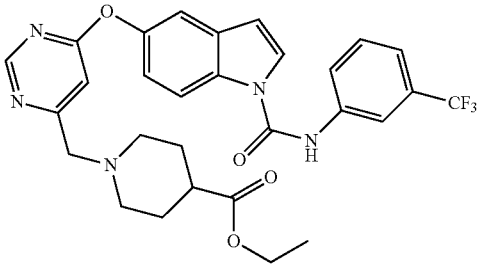<br>1-{6-[1-(3-Trifluoromethyl-phenylcarbamoyl)-1H-indol-5-yloxy]-pyrimidin-4-ylmethyl}-piperidine-4-carboxylic acid ethyl ester | (DMSO-d₆) δ ppm 10.40 (s, 1H), 8.66 (d, J = 1.0 Hz, 1H), 8.29 (d, J = 9.0 Hz, 1H), 8.13 (d, J = 3.7 Hz, 1H), 8.10 (s, 1H), 7.97 (d, J = 7.8 Hz, 1H), 7.65 (t, J = 8.0 Hz, 1H), 7.46-7.53 (m, 2H), 7.16 (dd, J = 9.0, 2.4 Hz, 1H), 7.04 (s, 1H), 6.80 (d, J = 3.7 Hz, 1H), 4.05 (q, J = 7.1 Hz, 2H), 3.56 (s, 2H), 2.79 (d, J = 11.6 Hz, 2H), 2.24-2.32 (m, 1H), 2.12 (t, J = 12.1 Hz, 2H), 1.74-1.86 (m, 2H), 1.48-1.63 (m, 2H), 1.16 (t, J = 7.1 Hz, 3H) | 568.1 |
| 19-AO | 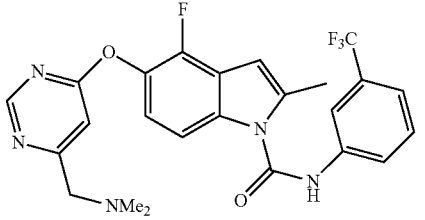<br>5-(6-((Dimethylamino)methyl)-pyrimidin-4-yloxy)-4-fluoro-2-methyl-N-(3-(trifluoromethyl)-phenyl)-1H-indole-1-carboxamide | (DMSO-d₆) δ ppm 10.99 (br. S., 1H) 8.65 (s, 1H) 8.12 (s, 1H) 7.91 (br. M, 1H) 7.66 (t, J = 7.6 Hz, 1H) 7.52 (m, 2H) 7.14 (m, 2H) 6.63 (s, 1H) 3.54 (s, 2H) 2.58 (s, 3H) 2.23 (s, 6H) | 487.9 |
| 19-AP | 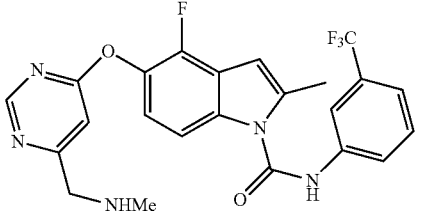<br>4-Fluoro-2-methyl-5-(6-((methylamino)methyl)pyrimidin-4yloxy)-N-(3(trifluoromethyl)-phenyl)-1H-indole-1-carboxamide | (DMSO-d₆) δ ppm 10.99 (br. S, 1H) 8.64 (s, 1H) 8.12 (s, 1H) 7.90 (m, 1H) 7.66 (t, J = 7.6 Hz, 1H) 7.51 (m, 2H) 7.15-7.18 (m, 2H) 6.62 (s, 1H) 3.74 (s, 2H) 2.58 (s, 3H) 2.32 (s, 3H) | 473.9 |

| | Structure/Chemical Name | ¹H NMR (400 MHz) | MS (ESI) m/z (M + 1) |
|---|---|---|---|
| 19-AQ | 5-(6-((Cyclopropylamino)-methyl)pyrimidin-4-yloxy)-4-fluoro-2-methyl-N-(3-(trifluoromethyl)phenyl)-1H-indole-1-carboxamide | (MeOD) δ ppm 8.61 (d, J = 1.01 Hz, 1H) 8.07 (s, 1H) 7.87 (d, J = 8.84 Hz, 1H) 7.55-7.62 (m, 1H), 7.45-7.51 (m, 2H) 7.14 (s, 1H) 7.07 (dd, J = 8.72, 7.45 Hz, 1H) 6.53 (s, 1H) 3.92 (s, 2H) 2.61 (d, 3H) 2.19 (m, 1H) 0.37-0.51 (m, 4H) | 500.2 |
| 19-AR | 4-Fluoro-2-methyl-5-[6-(3-oxo-piperazin-1-ylmethyl)-pyrimidin-4-yloxy]-indole-1-carboxylic acid (3-trifluoromethyl-phenyl)-amide | (DMSO-d₆) δ ppm 10.99 (s, 1H) 8.69 (s, 1H) 8.12 (s, 1H) 7.92 (d, J = 8.84 Hz, 1H) 7.86 (br. S, 1H) 7.66 (t, J = 7.96 Hz, 1H) 7.52 (d, J = 8.84 Hz, 1H) 7.24 (s, 1H) 7.17 (t, J = 8.21 Hz, 1H) 6.62 (s, 1H) 3.81 (br. S., 2H) 3.23 (br. S., 2H) 3.17 (s, 2H) 2.77 (br. S., 2H) 2.59 (s, 3H) | 538.8 |
| 19-AS | 5-[6-(4-Acetyl-piperazin-1-ylmethyl)-pyrimidin-4-yloxy]-4-fluoro-2-methyl-indole-1-carboxylic acid (3-trifluoromethyl-phenyl)-amide | (DMSO-d₆) δ ppm 10.98 (s, 1H) 8.65 (d, J = 1.01 Hz, 1H) 8.12 (s, 1H) 7.90 (d, J = 8.7 Hz,, 1H) 7.66, (t, J = 8.2 Hz, 1H), 7.53 (m, 2H) 7.25 (s, 1H) 7.15 (m, 1H) 6.62 (s, 1H) 3.48-3.55 (br. M, 8H) 2.58 (s, 3H) 2.40 (m, 2H) 2.00 (s, 3H) | 570.9 |
| 19-AT | 5-(6-{[(1H-Imidazol-2-ylmethyl)-amino]-methyl}-pyrimidin-4-yloxy)-indole-1-carboxylic acid (4-fluoro-3-trifluoromethyl-phenyl)-amide | (DMSO-d₆) δ ppm 10.44 (s, 1H), 8.68 (d, J = 1.0 Hz, 1H), 8.29 (d, J = 9.1 Hz, 1H), 8.09-8.17 (m, 2H), 7.98-8.06 (m, 1H), 7.58 (t, J = 9.9 Hz, 1H), 7.49 (d, J = 2.5 Hz, 1H), 7.10-7.20 (m, 4H), 6.81 (d, J = 3.8 Hz, 1H), 3.94 (s, 2H), 3.91 (s, 2H). | 526.1 |

| Structure/Chemical Name | ¹H NMR (400 MHz) | MS (ESI) m/z (M + 1) |
|---|---|---|
| 19-AU 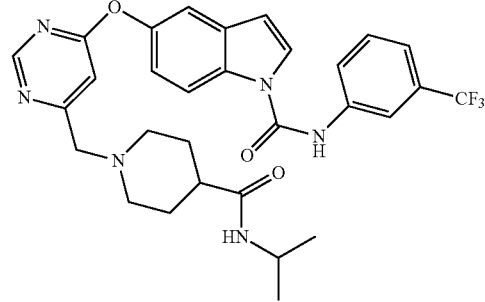<br>5-[6-(4-Isopropylcarbamoyl-piperidin-1-ylmethyl)-pyrimidin-4-yloxy]-indole-1-carboxylic acid (3-trifluoromethyl-phenyl)-amide | (DMSO-$d_6$) δ ppm 10.39 (s, 1H), 8.65 (d, J = 1.0 Hz, 1H), 8.29 (d, J = 9.1 Hz, 1H), 8.13 (d, J = 3.8 Hz, 1H), 8.10 (s, 1H), 7.97 (d, J = 8.1 Hz, 1H), 7.64 (t, J = 8.1 Hz, 1H), 7.55 (d, J = 7.8 Hz, 1H), 7.47-7.52 (m, 2H), 7.13-7.18 (m, 1H), 7.04 (d, J = 0.8 Hz, 1H), 6.80 (d, J = 3.8 Hz, 1H), 3.71-3.88 (m, 1H), 3.55 (s, 2H), 2.85 (d, J = 11.6 Hz, 2H), 1.95-2.12 (m, 3H), 1.48-1.70 (m, 4H), 1.01 (d, J = 6.6 Hz, 6H) | 581.3 |
| 19-AV 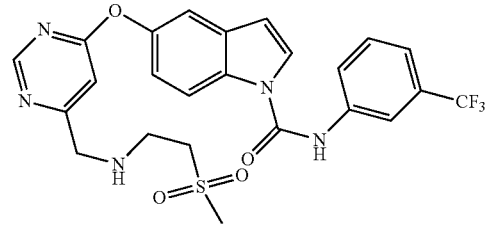<br>5-{6-[(2-Methanesulfonyl-ethylamino)-methyl]-pyrimidin-4-yloxy}-indole-1-carboxylic acid (3-trifluoromethyl-phenyl)-amide | (DMSO-$d_6$) δ ppm 10.30-10.43 (m, 1H), 8.67 (s, 1H), 8.29 (d, J = 8.8 Hz, 1H), 8.13 (d, J = 3.8 Hz, 1H), 8.10 (s, 1H), 7.98 (d, J = 8.8 Hz, 1H), 7.65 (t, J = 8.1 Hz, 1H), 7.47-7.54 (m, 2H), 7.15 (dd, J = 8.8, 2.3 Hz, 1H), 7.08 (s, 1H), 6.81 (d, J = 3.8 Hz, 1H), 3.80 (s, 2H), 3.22-3.28 (m, 2H), 2.99 (s, 3H), 2.95 (t, J = 6.7 Hz, 2H) | 534.0 |
| 19-AW 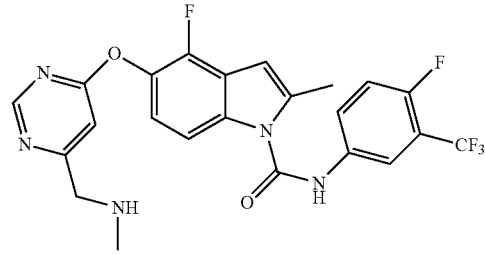<br>4-Fluoro-2-methyl-5-(6-methylaminomethyl-pyrimidin-4-yloxy)-indole-1-carboxylic acid (4-fluoro-3-trifluoromethyl-phenyl)-amide | (DMSO-$d_6$) δ ppm 10.96 (br. S, 1H) 8.64 (d, J = 1.01 Hz, 1H) 8.13 (dd, J = 6.57, 2.53 Hz, 1H) 7.96 (dd, J = 4.67, 3.41 Hz, 1H) 7.59 (t, J = 9.73 Hz, 1H) 7.53 (d, J = 8.84 Hz, 1H) 7.19 (s, 1H) 7.16 (dd, J = 8.84, 7.58 Hz, 1H) 6.62 (s, 1H) 3.75 (s, 2H) 2.58 (s, 3H) 2.32 (s, 3H). | 492.1 |

| Structure/Chemical Name | ¹H NMR (400 MHz) | MS (ESI) m/z (M + 1) |
|---|---|---|
| 19-AX 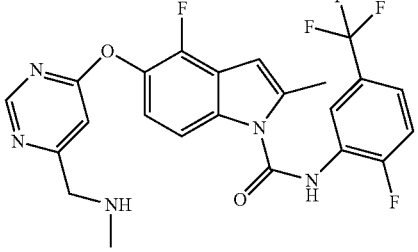<br>4-Fluoro-2-methyl-5-(6-methylaminomethyl-pyrimidin-4-yloxy)-indole-1-carboxylic acid (2-fluoro-5-trifluoromethyl-phenyl)-amide | (MeOD) δ ppm 8.63 (s, 1H) 8.40 (dd, J = 7.07, 2.02 Hz, 1H) 7.62 (s, 2H) 7.47 (d, J = 10.11 Hz, 1H) 7.11-7.13 (m, 1H) 7.09 (d, J = 1.26 Hz, 1H) 6.55 (s, 1H) 3.84 (s, 2H) 2.65 (s, 3H) 2.44 (s, 3H) | 492.4 |
| 19-AY 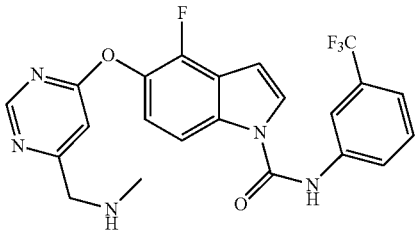<br>4-Fluoro-5-(6-methylaminomethyl-pyrimidin-4-yloxy)-indole-1-carboxylic acid (3-trifluoromethyl-phenyl)-amide | (DMSO-d₆) δ ppm 8.67 (s, 1H) 8.16 (d, J = 8.84 Hz, 1H) 8.07 (s, 1H) 7.97 (d, J = 3.79 Hz, 1H) 7.90 (d, J = 8.34 Hz, 1H) 7.58 (t, J = 7.96 Hz, 1H) 7.46 (d, J = 7.83 Hz, 1H) 7.14-7.30 (m, 2H) 6.84 (d, J = 3.79 Hz, 1H) 4.03 (s, 2H) 2.58 (s, 3H). | 460.0 |
| 19-AZ 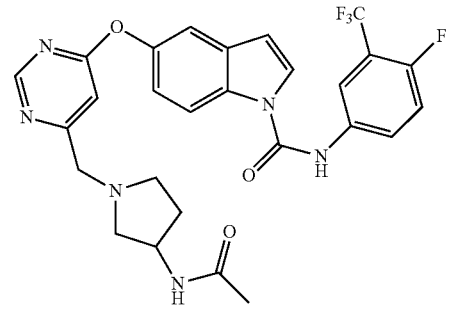<br>5-(6-((3-acetamidopyrrolidin-1-yl)methyl)pyrimidin-4-yloxy)-N-(4-fluoro-3-(trifluoromethyl)phenyl)-1H-indole-1-carboxamide | (DMSO-d₆) δ ppm 10.39 (s, 1H), 8.65 (s, 1H), 8.28 (d, J = 9.1 Hz, 1H), 8.08-8.14 (m, 2H), 7.95-8.05 (m, 2H), 7.57 (t, J = 9.9 Hz, 1H), 7.49 (d, J = 2.5 Hz, 1H), 7.15 (dd, J = 9.0, 2.4 Hz, 1H), 7.10 (s, 1H), 6.80 (d, J = 3.5 Hz, 1H), 4.09-4.22 (m, 1H), 3.62-3.77 (m, 2H), 2.67-2.77 (m, 2H), 2.39-2.48 (m, 2H), 2.02-2.16 (m, 1H), 1.77 (s, 3H), 1.50-1.64 (m, 1H) | 557.2 |

EXAMPLE 20

20-A. 5-(6-Methoxymethyl-pyrimidin-4-yloxy)-indole-1-carboxylic acid (3-trifluoromethyl-phenyl)-amide

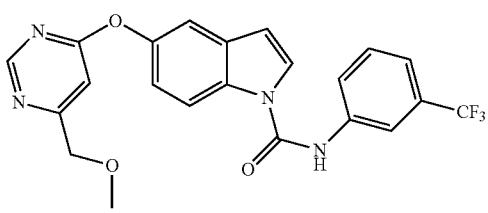 [SMILES: COCc1cc(Oc2ccc3c(ccn3C(=O)Nc3cccc(C(F)(F)F)c3)c2)ncn1]

To a solution of 5-(6-methanesulfonylmethyl-pyrimidin-4-yloxy)-indole-1-carboxylic acid (3-trifluoromethyl-phenyl)-amide (230 mg, 0.46 mmol) is added 1 mL methanol followed by sodium hydride (100 mg, 60% in mineral oil) is added portions over 5 min. The mixture is stirred at rt for 0.5 h and then poured into water, extracted with EtOAc. The extract is dried, filtered, and concentrated under reduced pressure. The residue is purified by FCC (MeOH with 1% NH₄OH/DCM from 0% to 5%) to give the title compound.

MS (ESI) m/z 443.0 (M+1); ¹H NMR (400 MHz, MeOD) δ ppm 8.63 (s, 1 H), 8.36 (d, J=8.84 Hz, 1 H), 8.06 (s, 1 H), 7.95 (d, J=3.79 Hz, 1 H), 7.90 (d, J=8.08 Hz, 1 H), 7.58 (t, J=7.83 Hz, 1 H), 7.43 (d, J=2.27 Hz, 2 H), 7.12 (dd, J=8.97, 2.40 Hz, 1 H), 7.00 (d, J=1.01 Hz, 1 H), 6.76 (d, J=3.79 Hz, 1 H), 4.50 (s, 2 H) 3.46 (s, 3 H).

The following compounds are prepared with similar method.

| | Structure/Chemical Name | ¹H NMR (400 MHz) | MS (ESI) m/z (M + 1) |
|---|---|---|---|
| 20-B | 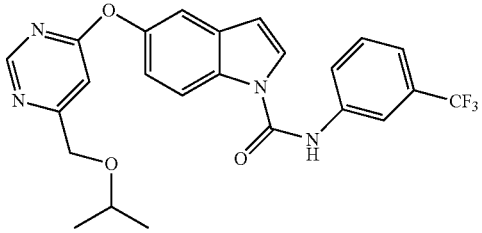<br>5-(6-Isopropoxymethyl-pyrimidin-4-yloxy)-indole-1-carboxylic acid (3-trifluoromethyl-phenyl)-amide | (MeOD) δ ppm 8.61 (d, J = 1.01 Hz, 1H), 8.36 (d, J = 8.84 Hz, 1H), 8.06 (s, 1H), 7.95 (d, J = 3.54 Hz, 1H), 7.90 (d, J = 8.34 Hz, 1H), 7.57 (t, J = 7.96 Hz, 1H), 7.42 (d, J = 2.27 Hz, 2H), 7.12 (dd, J = 8.97, 2.40 Hz, 1H), 7.04 (s, 1H), 6.75 (d, J = 3.79 Hz, 1H), 4.55 (s, 2H), 3.73 (quin, J = 6.06 Hz, 1H), 1.20 (d, J = 6.06 Hz, 6H). | 471.1 |
| 20-C | 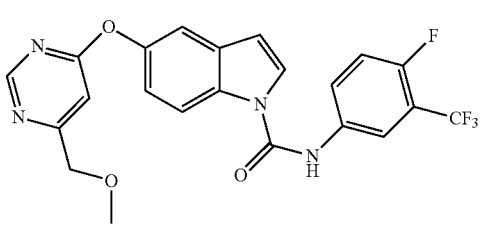<br>5-(6-Methoxymethyl-pyrimidin-4-yloxy)-indole-1-carboxylic acid (4-fluoro-3-trifluoromethyl-phenyl)-amide | (DMSO-$d_6$) δ ppm 10.40 (s, 1H), 8.69 (d, J = 1.01 Hz, 1H), 8.29 (d, J = 8.84 Hz, 1H), 8.10-8.12 (m, 2H), 7.98-8.03 (m, 1H), 7.55-7.58 (m, 1H), 7.51 (d, J = 2.27 Hz, 1H), 7.16 (dd, J = 8.97, 2.40 Hz, 1H), 6.94 (d, J = 1.01 Hz, 1H), 6.82 (d, J = 3.79 Hz, 1H), 4.48 (s, 2H), 3.39 (s, 3H). | 460.9 |
| 20-D | 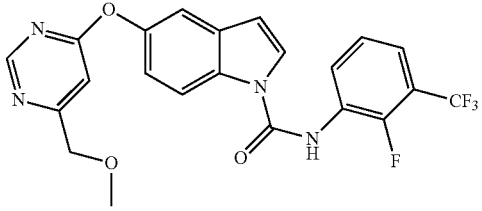<br>5-(6-Methoxymethyl-pyrimidin-4-yloxy)-indole-1-carboxylic acid (2-fluoro-3-trifluoromethyl-phenyl)-amide | (DMSO-$d_6$) δ ppm 10.28 (s, 1H), 8.69 (d, J = 1.01 Hz, 1H), 8.27 (d, J = 9.09 Hz, 1H), 8.11 (d, J = 3.79 Hz, 1H), 7.94 (m, 1H), 7.71 (t, J = 7.20 Hz, 1H), 7.47-7.52 (m, 2H), 7.16 (dd, J = 8.97, 2.40 Hz, 1H), 6.93 (d, J = 1.01 Hz, 1H), 6.82 (d, J = 3.79 Hz, 1H), 4.48 (s, 2H), 3.39 (s, 3H). | 460.9 |

EXAMPLE 21

5-[6-(Acetylamino-methyl)-pyrimidin-4-yloxy]-indole-1-carboxylic acid (3-trifluoromethyl-phenyl)-amide

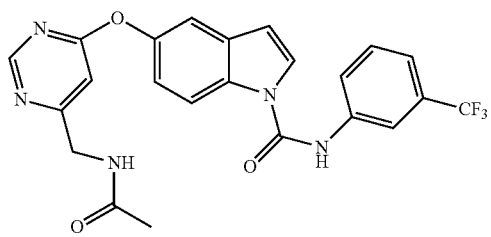 [SMILES: CC(=O)NCc1cc(Oc2ccc3c(ccn3C(=O)Nc3cccc(C(F)(F)F)c3)c2)ncn1]

To a solution of 5-(6-aminomethyl-pyrimidin-4-yloxy)-indole-1-carboxylic acid (3-trifluoromethyl-phenyl)-amide (50 mg, 0.12 mmol) and THF (5 mL) is added acetyl chloride (50 mg) and triethylamine (50 mg). The solution is stirred at rt for 10 min before being partitioned between EtOAc and water. The organic layer is washed further with brine. The organic layer is then dried ($Na_2SO_4$), filtered, and concentrated under reduced pressure to give the title compound. MS (ESI) m/z 470.0 (M+1); ¹H NMR (400 MHz, MeOD) δ ppm 8.61 (d, J=1.01 Hz, 1 H), 8.34 (d, J=9.09 Hz, 1 H), 8.05 (s, 1 H), 7.93 (d, J=3.54 Hz, 1 H), 7.89 (d, J=7.83 Hz, 1 H), 7.56 (t, J=7.96 Hz, 1 H), 7.39-7.45 (m, 2 H), 7.09 (dd, J=8.97, 2.40 Hz, 1 H), 6.88 (s, 1 H), 6.73 (d, J=3.79 Hz, 1 H), 4.40 (s, 2 H) 2.01 (s, 3 H).

EXAMPLE 22

5-[6-(3,3-Dimethyl-ureidomethyl)-pyrimidin-4-yloxy]-indole-1-carboxylic acid (3-trifluoromethyl-phenyl)-amide

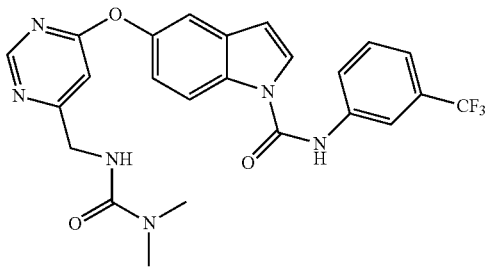 [SMILES: CN(C)C(=O)NCc1cc(Oc2ccc3c(ccn3C(=O)Nc3cccc(C(F)(F)F)c3)c2)ncn1]

To a solution of 5-(6-aminomethyl-pyrimidin-4-yloxy)-indole-1-carboxylic acid (3-trifluoromethyl-phenyl)-amide (50 mg, 0.12 mmol), THF (5 mL), and dimethylcarbamyl chloride (50 mg) is added triethylamine (50 mg). After 10 min the solution is partitioned between EtOAc and water. The organic layer is separated and washed further with brine, dried over $Na_2SO_4$, filtered, and concentrated under reduced pressure to give the title compound.

MS (ESI) m/z 499.0 (M+1); $^1$H NMR (400 MHz, MeOD) δ ppm 8.60 (s, 1 H), 8.34 (d, J=9.09 Hz, 1 H), 8.06 (s, 1 H), 7.86-7.95 (m, 2 H), 7.56 (t, J=7.96 Hz, 1 H), 7.38-7.46 (m, 2 H), 7.09 (dd, J=9.09, 2.27 Hz, 1 H), 6.83 (d, J=1.01 Hz, 1 H), 6.73 (d, J=3.79 Hz, 1 H), 4.36 (s, 2 H), 2.89 (s, 6 H).

EXAMPLE 23

5-[6-(Methanesulfonylamino-methyl)-pyrimidin-4-yloxy]-indole-1-carboxylic acid (3-trifluoromethyl-phenyl)-amide

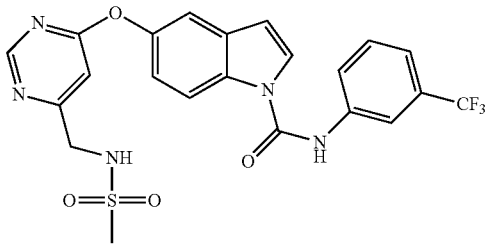 [SMILES: CS(=O)(=O)NCc1cc(Oc2ccc3c(ccn3C(=O)Nc3cccc(C(F)(F)F)c3)c2)ncn1]

To a solution of 5-(6-aminomethyl-pyrimidin-4-yloxy)-indole-1-carboxylic acid (3-trifluoromethyl-phenyl)-amide (100 mg, 0.23 mmol) and THF (5 mL) is added methanesulfonic anhydride (87 mg, 0.5 mmol) and pyridine (0.2 mL). After 0.5 h the solution is partitioned between EtOAc and water. The organic layer is washed further with brine, dried over sodium sulfate, and concentrated under reduced pressure. The residue is separated by FCC (EtOAc/heptane from 10 to 100%) to give the title compound.

MS (ESI) m/z 505.8 (M+1); $^1$H NMR (400 MHz, MeOD) δ ppm 8.64 (d, J=1.01 Hz, 1 H), 8.36 (d, J=9.09 Hz, 1 H), 8.06 (s, 1 H), 7.95 (d, J=3.79 Hz, 1 H), 7.90 (d, J=8.34 Hz, 1 H), 7.58 (t, J=8.08 Hz, 1 H), 7.43 (d, J=2.53 Hz, 1 H), 7.45 (s, 1 H), 7.12 (dd, J=8.97, 2.40 Hz, 1 H), 7.10 (d, J=1.01 Hz, 1 H), 6.75 (d, J=3.79 Hz, 1 H), 4.34 (s, 2 H), 2.99 (s, 3 H).

EXAMPLE 24

24-A. 5-(2-Chloro-pyrimidin-4-yloxy)-indole-1-carboxylic acid (3-trifluoromethyl-phenyl)-amide

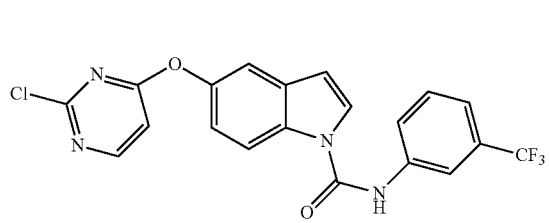 [SMILES: O=C(Nc1cccc(C(F)(F)F)c1)n1ccc2cc(Oc3ccnc(Cl)n3)ccc21]

To a precooled (–78° C.) solution of 2,2,6,6-tetramethylpiperidine (0.79 mL, 4.71 mmol) in THF (10 mL) is added n-butyllithium (1.76 mL, 2.5 M). After 10 min a solution of 5-(2-Chloro-pyrimidin-4-yloxy)-1H-indole, prepared as in WO2006/034833, (0.771 g, 3.32 mmol) in THF (10 mL) is added. After an additional 15 min 3-(trifluoromethyl)-phenyl isocyanate (0.88 mL, 6.28 mmol) is added. The solution is then allowed to warm gradually to rt. After 1 h the solution is concentrated and the residue taken up in EtOAc and washed with brine. The title compound is isolated via flash chromatography (10-30% EtOAc/heptane).

MS (ESI) m/z 433.0 & 434.9 (M+1).

24-B. 5-(2-Methyl-pyrimidin-4-yloxy)-indole-1-carboxylic acid (3-trifluoromethyl-phenyl)-amide

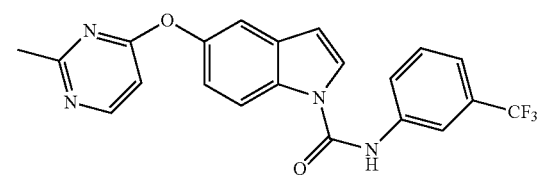 [SMILES: Cc1nccc(Oc2ccc3c(ccn3C(=O)Nc3cccc(C(F)(F)F)c3)c2)n1]

To a solution of 5-(2-Chloro-pyrimidin-4-yloxy)-indole-1-carboxylic acid (3-trifluoromethyl-phenyl)-amide (Example 24-A, 0.150 g, 0.347 mmol), Pd(tBu$_3$P)$_2$ (0.009 g, 0.017 mmol) and THF (5 mL) is added MeZnCl (0.35 mL, 2.0 M THF) under an argon atmosphere The solution is then heated to reflux for 2 h. After cooling to rt the THF is removed in vacuo and the residue is separated by flash chromatography (30-75% EtOAc/heptane) followed by additional separation via semi-prep HPLC to give the title compound MS (ESI) m/z 413.1 (M+1);

$^1$H NMR (400 MHz, DMSO-d$_6$) δ ppm 10.38 (s, 1 H), 8.54 (d, J=5.6 Hz, 1 H), 8.29 (d, J=8.8 Hz, 1 H), 8.13 (d, J=3.8 Hz, 1 H), 8.10 (s, 1 H), 7.97 (d, J=7.8 Hz, 1 H), 7.65 (t, J=8.0 Hz, 1 H), 7.51 (s, 1 H), 7.48 (d, J=2.3 Hz, 1 H), 7.14 (dd, J=9.0, 2.4 Hz, 1 H), 6.84 (d, J=5.8 Hz, 1 H), 6.81 (d, J=3.5 Hz, 1 H), 2.43 (s, 3 H).

The following compounds are prepared with similar method.

| | Structure/Chemical Name | ¹H NMR (400 MHz) | MS (ESI) m/z (M + 1) |
|---|---|---|---|
| 24-C | 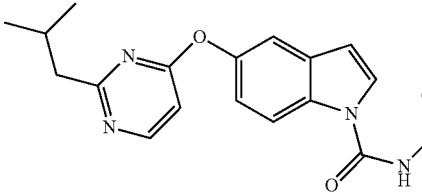<br>5-(2-Isobutyl-pyrimidin-4-yloxy)-indole-1-carboxylic acid (3-trifluoromethyl-phenyl)-amide | (DMSO-d₆) δ ppm 10.4 (s, 1H), 8.57 (d, J = 5.8 Hz, 1H), 8.29 (d, J = 9.1 Hz, 1H), 8.13 (d, J = 3.5 Hz, 1H), 8.10 (s, 1H), 7.97 (d, J = 8.6 Hz, 1H), 7.65 (t, J = 8.0 Hz, 1H), 7.47-7.54 (m, 1H), 7.48 (d, J = 2.5 Hz, 1H), 7.14 (dd, J = 9.0, 2.4 Hz, 1H), 6.83 (d, J = 5.8 Hz, 1H), 6.80 (d, J = 3.8 Hz, 1H), 2.56 (d, J = 7.1 Hz, 2H), 2.00-2.13 (m, 1H), 0.84 (d, J = 6.8 Hz, 6H) | 455.1 |
| 24-D | 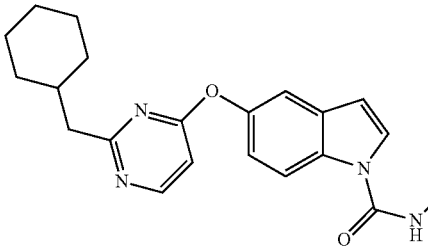<br>5-(2-Cyclohexylmethyl-pyrimidin-4-yloxy)-indole-1-carboxylic acid (3-trifluoromethyl-phenyl)-amide | (DMSO-d₆) δ ppm 10.38 (s, 1H), 8.56 (d, J = 5.8 Hz, 1H), 8.28 (d, J = 8.8 Hz, 1H), 8.13 (d, J = 3.5 Hz, 1H), 8.10 (s, 1H), 7.98 (d, J = 8.1 Hz, 1H), 7.50 (d, J = 7.8 Hz, 1H), 7.48 (d, J = 2.3 Hz, 1H), 7.14 (dd, J = 9.0, 2.4 Hz, 1H), 6.82 (d, J = 5.8 Hz, 1H), 6.80 (d, J = 3.5 Hz, 1H), 2.57 (d, J = 7.3 Hz, 2H), 1.70-1.83 (m, 1H), 1.52-1.65 (m, 6H), 1.08-1.19 (m, 2H), 0.86-0.98 (m, 2H) | 495.2 |
| 24-E | 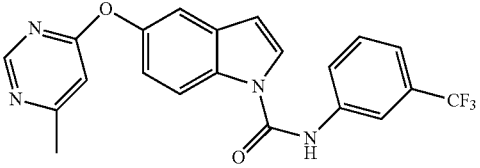<br>5-(6-Methyl-pyrimidin-4-yloxy)-indole-1-carboxylic acid (3-trifluoromethyl-phenyl)-amide | (CDCl₃) δ ppm 8.69 (d, J = 0.8 Hz, 1H), 8.23 (d, J = 8.8 Hz, 1H), 7.86 (s, 1H), 7.78 (d, J = 8.1 Hz, 1H), 7.60 (d, J = 3.8 Hz, 1H), 7.50-7.58 (m, 2H), 7.44-7.49 (m, 1H), 7.41 (d, J = 2.3 Hz, 1H), 7.16 (dd, J = 8.9, 2.3 Hz, 1H), 6.76 (s, 1H), 6.72 (d, J = 3.4 Hz, 1H), 2.52 (s, 3H) | 413.1 |
| 24-F | 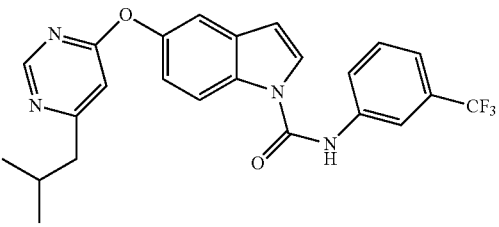<br>5-(6-Isobutyl-pyrimidin-4-yloxy)-indole-1-carboxylic acid (3-trifluoromethyl-phenyl)-amide | (DMSO-d₆) δ ppm 10.38 (s, 1H), 8.64 (d, J = 1.0 Hz, 1H), 8.28 (d, J = 9.0 Hz, 1H), 8.13 (d, J = 3.7 Hz, 1H), 8.10 (s, 1H), 7.97 (d, J = 8.6 Hz, 1H), 7.65 (t, J = 8.0 Hz, 1H), 7.47-7.53 (m, 2H), 7.14 (dd, J = 9.0, 2.4 Hz, 1H), 6.94 (d, J = 0.9 Hz, 1H), 6.80 (d, J = 3.4 Hz, 1H), 2.57 (d, J = 7.1 Hz, 2H), 2.00-2.18 (m, 1H), 0.90 (d, J = 6.7 Hz, 6H) | 455.1 |

EXAMPLE 25

5-(2-Hydroxymethyl-pyridin-4-yloxy)-indole-1-carboxylic acid (3-trifluoromethylphenyl)-amide

25-A. 4-Chloro-pyridine-2-carboxylic acid tert-butyl ester

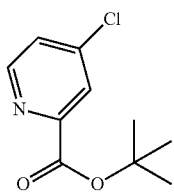

4-Chloro-pyridine-2-carbonyl chloride•hydrochloride (ref. *Org. Proc. Res. Dev.* 2002, 6, 777) (17.0 g, 81.3 mmol) is taken up in THF (200 mL) and sodium tert-butoxide (23.4 g, 243.5 mmol) is added in portions. After 1.5 h the mixture is diluted with water (500 mL) and extracted with EtOAc (2×500 mL). The combined organic layers are dried (Na$_2$SO$_4$), filtered and then concentrated. The residue is then separated via FCC (10-30% EtOAc/heptane) to give the title compound. MS (ESI) m/z 213.9 & 215.9 (M+1)

25-B. 4-(1H-Indol-5-yloxy)-pyridine-2-carboxylic acid tert-butyl ester

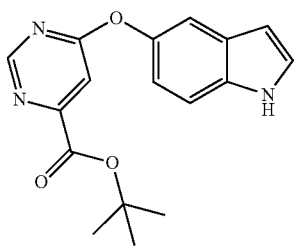 [SMILES: CC(C)(C)OC(=O)c1cc(Oc2ccc3[nH]ccc3c2)ncn1]

5-Hydroxyindole (100 mg, 0.72 mmol), 4-Chloro-pyridine-2-carboxylic acid tert-butyl ester (160 mg, 0.72 mmol) and cesium carbonate (245 mg, 0.72 mmol) are combined in DMSO (1.5 mL) and heated at 105° C. for 3 h in a sealed tube. The reaction is cooled to rt and partitioned between EtOAc and brine. The organic layer is removed, dried over anhydrous Na$_2$SO$_4$, filtered, and concentrated. The residue is separated via FCC (EtOAc/heptanes 2:8 to EtOAc) to give the title compound. MS (ESI) m/z 311.1 (M+1); $^1$H NMR (400 MHz, DMSO-d$_6$) δ ppm 11.29 (br. S., 1 H), 8.50 (d, J=5.8 Hz, 1 H), 7.50 (d, J=8.6 Hz, 1 H), 7.46 (t, J=2.8 Hz, 1 H), 7.37 (m, 2 H), 7.07 (dd, J=5.6, 2.5 Hz, 1 H), 6.91 (dd, J=8.6, 2.3 Hz, 1 H), 6.47 (t, J=2.1 Hz, 1 H), 1.51 (s, 9 H).

25-C. 4-[1-(3-Trifluoromethyl-phenylcarbamoyl)-1H-indol-5-yloxy]-pyridine-2-carboxylic acid tert-butyl ester

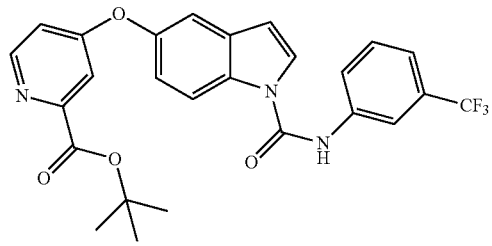 [SMILES: CC(C)(C)OC(=O)c1cc(Oc2ccc3c(ccn3C(=O)Nc3cccc(C(F)(F)F)c3)c2)ccn1]

A solution of n-butyllithium (0.75 mL, 1.20 mmol, 1.6M in hexanes) is added to a precooled (−78° C.) solution of 2,2,6,6-tetramethylpiperidine (0.22 mL, 1.30 mmol) and THF (5 mL). After 15 min a THF solution (2 mL) of 4-(1H-indol-5-yloxy)-pyridine-2-carboxylic acid tert-butyl ester (310 mg, 1.00 mmol) is added. After an additional 0.5 h 3-trifluoromethylphenyl isocyanate (0.27 mL, 2.00 mmol) is added. Reaction is then allowed to warm to rt and stir for 3 h. At that point the reaction is partitioned between EtOAc and pH 7 buffer solution. Organic removed and dried over anhydrous Na$_2$SO$_4$. Following concentration the residue is separated via FCC (EtOAc/heptanes 1:9 to EtOAc/heptanes 7:3) to give the title compound. MS (ESI) m/z 498.2 (M+1); $^1$H NMR (400 MHz, CD$_2$Cl$_2$) δ ppm 8.41-8.47 (m, 1 H), 8.37 (s, 1 H), 8.34 (d, J=9.1 Hz, 1 H), 7.97 (s, 1 H), 7.85 (d, J=8.3 Hz, 1 H), 7.73 (d, J=3.5 Hz, 1 H), 7.63 (d, 1 H), 7.57 (t, J=8.1 Hz, 1 H), 7.46-7.51 (m, 1 H), 7.38 (d, 1 H), 7.13 (dd, J=9.0, 2.4 Hz, 1 H), 6.92 (dd, J=5.6, 2.5 Hz, 1 H), 6.69 (d, J=3.8 Hz, 1 H), 1.60 (s, 9 H).

25-D. 5-(2-Hydroxymethyl-pyridin-4-yloxy)-indole-1-carboxylic acid (3-trifluoromethylphenyl)-amide

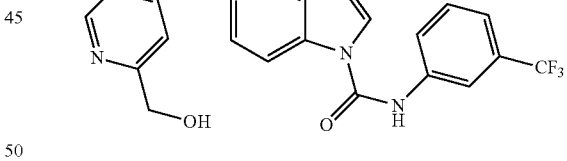

Dissolve 4-[1-(3-trifluoromethyl-phenylcarbamoyl)-1H-indol-5-yloxy]-pyridine-2-carboxylic acid tert-butyl ester (400 mg, 0.80 mmol) in THF (10 mL) at 0° C. before adding lithium aluminum hydride (2.4 mL, 2.40 mmol, 1.0M ether solution). The reaction is allowed to warm to room temperature for 3 h before quenching it and extracting between EtOAc and saturated aqueous NH$_4$Cl. Organic is dried over anhydrous Na$_2$SO$_4$ and purified via FCC (EtOAc/heptanes 3:7 to EtOAc) to give the title compound as a white solid (182 mg, 53%). MS (ESI) m/z 428.1 (M+1); $^1$H NMR (400 MHz, DMSO-d$_6$) δ ppm 10.39 (s, 1 H), 8.29-8.37 (m, 2 H), 8.15 (d, J=3.8 Hz, 1 H), 8.09 (s, 1 H), 7.98 (d, J=8.5 Hz, 1 H), 7.65 (t, J=8.0 Hz, 1 H), 7.50 (d, J=7.7 Hz, 1 H), 7.47 (d, J=2.4 Hz, 1 H), 7.13 (dd, J=8.9, 2.5 Hz, 1 H), 6.92 (d, J=2.4 Hz, 1 H), 6.77-6.85 (m, 2 H), 5.35 (t, J=5.8 Hz, 1 H), 4.49 (d, J=5.8 Hz, 2 H).

EXAMPLE 26

26-A. Methanesulfonic acid 4-[1-(3-trifluoromethyl-phenylcarbamoyl)-1H-indol-5-yloxy]pyridin-2-ylmethyl ester

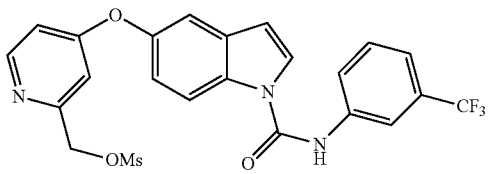 [SMILES: CS(=O)(=O)OCc1cc(Oc2ccc3c(ccn3C(=O)Nc3cccc(C(F)(F)F)c3)c2)ccn1]

Methansulfonyl chloride (0.2 mL, 2.46 mmol) is added to a solution of 5-(2-hydroxymethyl-pyridin-4-yloxy)-indole-1-carboxylic acid (3-trifluoromethylphenyl)-amide, Example 25-D, (700 mg, 1.64 mmol) and triethylamine (0.7 mL, 4.92 mmol) in DCM (50 mL) at rt. After 1 h the reaction is partitioned between DCM and saturated aqueous $NaHCO_3$. Organic layer is removed, dried over anhydrous $Na_2SO_4$, concentrated and then separated via FCC (EtOAc/heptanes 2:4 to EtOAc/heptanes 9:1) to give the title compound. MS (ESI) m/z 506.0 (M+1).

26-B. 5-[2-(Isopropylamino-methyl)-pyridin-4-yloxy]-indole-1-carboxylic acid (3-trifluoromethyl-phenyl)-amide

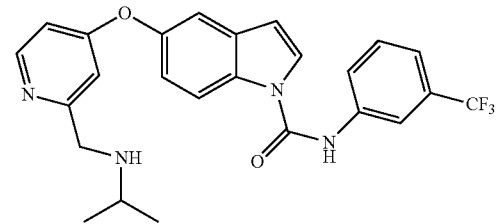 [SMILES: CC(C)NCc1cc(Oc2ccc3c(ccn3C(=O)Nc3cccc(C(F)(F)F)c3)c2)ccn1]

A solution of methanesulfonic acid 4-[1-(3-trifluoromethyl-phenylcarbamoyl)-1H-indol-5-yloxy]pyridine-2-ylmethyl ester (150 mg, 0.30 mmol) and isopropyl amine (5 mL) is stirred at It for 2 h. The reaction is concentrated under reduced pressure and the residue separated via semi-prep HPLC (C18; 10-100% I/$H_2O$ with 0.1% $NH_4OH$) to give 5-[2-(isopropylamino-methyl)-pyridin-4-yloxy]-indole-1-carboxylic acid (3-trifluoromethyl-phenyl)-amide. MS (ESI) m/z 469.2 (M+1); $^1$H NMR (400 MHz, MeOD) δ ppm 8.25-8.37 (m, 2 H), 7.97 (s, 1 H), 7.88 (d, J=3.8 Hz, 1 H), 7.80 (d, J=8.1 Hz, 1 H), 7.48 (t, J=8.0 Hz, 1 H), 7.36 (d, J=7.6 Hz, 1 H), 7.30 (d, J=2.3 Hz, 1 H), 7.00 (dd, J=9.0, 2.4 Hz, 1 H), 6.90 (d, J=2.3 Hz, 1 H), 6.81 (dd, J=5.8, 2.3 Hz, 1 H), 6.66 (d, J=3.8 Hz, 1 H), 4.01 (s, 2 H), 3.09-3.18 (m, 1 H), 1.18 (d, J=6.6 Hz, 6 H).

The following compounds are prepared with similar method.

| | Structure/Chemical Name | $^1$H NMR (400 MHz) | MS (ESI) m/z (M + 1) |
|---|---|---|---|
| 26-C | 5-(2-Cyclopropylaminomethyl-pyridin-4-yloxy)-indole-1-carboxylic acid (3-trifluoromethyl-phenyl)-amide | (MeOD) δ ppm 8.23-8.33 (m, 2 H), 7.97 (s, 1H), 7.87 (d, J = 3.8 Hz, 1H), 7.80 (d, J = 8.3 Hz, 1H), 7.48 (t, J = 8.1 Hz, 1H), 7.35 (d, J = 7.8 Hz, 1H), 7.30 (d, J = 2.3 Hz, 1H), 7.00 (dd, J = 9.0, 2.4 Hz, 1 H), 6.90 (d, J = 2.3 Hz, 1H), 6.78 (dd, J = 5.8, 2.3 Hz, 1H), 6.66 (d, J = 3.5 Hz, 1H), 3.99 (s, 2H), 2.28-2.38 (m, 1H), 0.44-0.59 (m, 4H). | 467.2 |
| 26-D | 5-(2-Methylaminomethyl-pyridin-4-yloxy)-indole-1-carboxylic acid (3-trifluoromethyl-phenyl)-amide | (MeOD) δ ppm 8.24-8.33 (m, 2 H), 7.97 (s, 1H), 7.87 (d, J = 3.8 Hz, 1H), 7.81 (d, J = 8.1 Hz, 1H), 7.48 (t, J = 8.0 Hz, 1H), 7.35 (d, J = 7.8 Hz, 1H), 7.30 (d, J = 2.3 Hz, 1H), 7.00 (dd, J = 9.0, 2.4 Hz, 1 H), 6.89 (d, J = 2.3 Hz, 1H), 6.75 (dd, J = 5.8, 2.3 Hz, 1H), 6.66 (d, J = 3.8 Hz, 1H), 3.73 (s, 2H), 2.33 (s, 3H). | 441.2 |

| | Structure/Chemical Name | ¹H NMR (400 MHz) | MS (ESI) m/z (M + 1) |
|---|---|---|---|
| 26-E | 5-(2-Morpholin-4-ylmethyl-pyridin-4-yloxy)-indole-1-carboxylic acid (3-trifluoromethyl-phenyl)-amide | (MeOD) δ ppm 8.28 (d, J = 8.8 Hz, 1H), 8.21 (d, J = 5.8 Hz, 1H), 7.97 (s, 1H), 7.87 (d, J = 3.8 Hz, 1 H), 7.81 (d, J = 8.1 Hz, 1H), 7.48 (t, J = 8.1 Hz, 1H), 7.35 (d, J = 7.3 Hz, 1H), 7.29 (d, J = 2.3 Hz, 1H), 6.95-7.03 (m, 2H), 6.75 (dd, J = 5.8, 2.5 Hz, 1H), 6.66 (d, J = 3.8 Hz, 1H), 3.52-3.58 (m, 4 H), 3.47 (s, 2H), 2.31-2.41 (m, 4H). | 497.3 |
| 26-F | 5-{2-[(Tetrahydro-pyran-4-ylamino)-methyl]-pyridin-4-yloxy}-indole-1-carboxylic acid (3-trifluoromethyl-phenyl)-amide | (MeOD) δ ppm 8.22-8.23 (m, 2 H), 7.97 (s, 1H), 7.87 (d, J = 3.5 Hz, 1H), 7.80 (d, J = 8.1 Hz, 1H), 7.48 (t, J = 8.0 Hz, 1H), 7.35 (d, J = 8.6 Hz, 1H), 7.29 (d, J = 2.3 Hz, 1H), 7.00 (dd, J = 9.0, 2.4 Hz, 1 H), 6.91 (d, J = 2.3 Hz, 1H), 6.76 (dd, J = 5.8, 2.5 Hz, 1H), 6.66 (d, J = 3.5 Hz, 1H), 3.78-3.88 (m, 4 H), 3.24-3.32 (m, 2H), 2.59-2.74 (m, 1H), 1.68-1.82 (m, 2 H), 1.26-1.41 (m, 2H). | 511.2 |
| 26-G | 5-{2-[(2-Hydroxy-ethylamino)-methyl]-pyridin-4-yloxy}-indole-1-carboxylic acid (3-trifluoromethyl-phenyl)-amide | (MeOD) δ ppm 8.21-8.33 (m, 2 H), 7.97 (s, 1H), 7.87 (d, J = 3.8 Hz, 1H), 7.81 (d, J = 8.1 Hz, 1H), 7.49 (t, J = 8.1 Hz, 1H), 7.35 (d, J = 7.8 Hz, 1H), 7.30 (d, J = 2.3 Hz, 1H), 7.00 (dd, J = 9.0, 2.4 Hz, 1 H), 6.92 (d, J = 2.5 Hz, 1H), 6.74 (dd, J = 5.8, 2.5 Hz, 1H), 6.66 (d, J = 3.8 Hz, 1H), 3.75 (s, 2H), 3.55 (t, J = 5.6 Hz, 2H), 2.63 (t, J = 5.6 Hz, 2H). | 471.3 |
| 26-H | 5-(2-Methylaminomethyl-pyridin-4-yloxy)-indole-1-carboxylic acid (4-fluoro-3-trifluoromethyl-phenyl)-amide | (MeOD) δ ppm 8.16-8.32 (m, 2 H), 7.95 (dd, J = 6.3, 2.8 Hz, 1H), 7.77-7.87 (m, 2H), 7.18-7.32 (m, 2H), 6.99 (dd, J = 8.8, 2.3 Hz, 1H), 6.89 (d, J = 2.3 Hz, 1H), 6.73 (dd, J = 5.8, 2.3 Hz, 1H), 6.65 (d, J = 3.5 Hz, 1H), 3.67 (s, 2 H), 2.29 (s, 3H). | 459.1 |

EXAMPLE 27

27-A. 6-Tetrazol-2-ylmethyl-pyrimidin-4-yloxy)-indole-1-carboxylic acid (4-fluoro-3-trifluoromethyl-phenyl)-amide

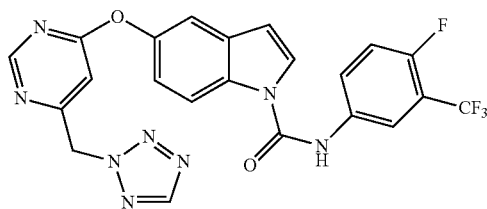 [SMILES: O=C(Nc1ccc(F)c(C(F)(F)F)c1)n1ccc2cc(Oc3cc(Cn4ncnn4)ncn3)ccc21]

To a solution of 1H-tetrazole (48 mg, 0.68 mmol) in DMF (3 mL), NaH (27 mg, 0.68 mmol) is added at 0° C. After 30 min, methanesulfonic acid 6-[1-(4-fluoro-3-trifluoromethyl-phenylcarbamoyl)-1H-indol 5-yloxy]-pyrimidin-4-ylmethyl ester (300 mg, 0.57 mmol) is added and the reaction is allowed to reach rt and then stir overnight. A saturated solution of ammonium chloride is added (2 mL) followed by EtOAc (4 mL). The layers are separated and the aqueous layer is extracted further with EtOAc (3×). The combined organics are evaporated and dried to give the crude product. The residue is purified using silica gel column chromatography FCC (gradient elution: 100% DCM to 98% DCM 2% MeOH) to give the titled compound. MS (ESI) m/z 499.1 (M+1);

$^1$H NMR (400 MHz, MeOD) δ ppm 8.78 (s, 1 H) 8.63 (d, J=1.01 Hz, 1 H) 8.35 (d, J=9.09 Hz, 1 H) 8.05 (dd, J=6.06, 2.53 Hz, 1 H) 7.93 (d, J=3.79 Hz, 2 H) 7.42 (d, J=2.27 Hz, 1 H) 7.36 (t, J=9.60 Hz, 1 H) 7.11 (dd, J=9.09, 2.53 Hz, 1 H) 6.88 (s, 1 H) 6.75 (d, J=3.79 Hz, 1 H) 6.03 (s, 2 H).

The following compounds are prepared with similar method.

| | Structure/Chemical Name | $^1$H NMR (400 MHz) | MS (ESI) m/z (M + 1) |
|---|---|---|---|
| 27-B | 6-Tetrazol-1-ylmethyl-pyrimidin-4-yloxy)-indole-1-carboxylic acid (4-fluoro-3-trifluoromethyl-phenyl)-amide | (MeOD) δ ppm 9.33 (s, 1H) 8.62 (d, J = 1.01 Hz, 1H) 8.34 (d, J = 8.84 Hz, 1H) 8.04 (dd, J = 6.32, 2.78 Hz, 1H) 7.92 (d, J = 3.79 Hz, 2H) 7.41 (d, J = 2.27 Hz, 1H) 7.35 (t, J = 9.60 Hz, 1H) 7.10 (dd, J = 8.97, 2.40 Hz, 1H) 6.97 (s, 1H) 6.74 (d, J = 3.79 Hz, 1H) 5.82 (s, 2H) | 499.1 |
| 27-C | 6-(2,4-Dimethyl-imidazol-1-ylmethyl)-pyrimidin-4-yloxy]-indole-1-carboxylic acid (4-fluoro-3-trifluoromethyl-phenyl)-amide | (MeOD) δ ppm 8.53 (d, J = 1.01 Hz, 1H) 8.22 (d, J = 9.09 Hz, 1H) 7.94 (dd, J = 6.19, 2.65 Hz, 1H) 7.79-7.84 (m, 2H) 7.22-7.28 (m, 2H) 6.96 (dd, J = 8.84, 2.27 Hz, 1H) 6.61 (m, 2H) 6.34 (s, 1H) 5.04 (s, 2H) 2.17 (s, 3H) 1.91 (s, 3H) | 525.9 |
| 27-D | 5-(6-[1,2,4]Triazol-1-ylmethyl-pyrimidin-4-yloxy)-indole-1-carboxylic acid (4-fluoro-3-trifluoromethyl-phenyl)-amide | (DMSO-d$_6$) δ ppm 10.39 (s, 1H), 8.58-8.77 (m, 2H), 8.23-8.32 (m, 1H), 8.07-8.15 (m, 2H), 7.96-8.05 (m, 2H), 7.57 (t, J = 9.7 Hz, 1H), 7.49 (d, J = 2.3 Hz, 1H), 7.14 (dd, J = 9.0, 2.4 Hz, 1H), 6.87 (d, J = 1.0 Hz, 1H), 6.80 (d, J = 3.5 Hz, 1H), 5.56 (s, 2H) | 498.0 |

| | Structure/Chemical Name | $^1$H NMR (400 MHz) | MS (ESI) m/z (M + 1) |
|---|---|---|---|
| 27-E | 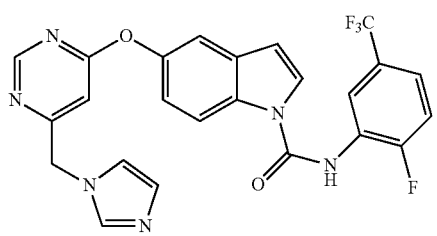<br>5-(6-Pyrazol-1-ylmethyl-pyrimidin-4-yloxy)-indole-1-carboxylic acid (2-fluoro-5-trifluoromethyl-phenyl)-amide | (MeOD) δ ppm 8.64 (d, J = 1.01 Hz, 1H), 8.30 (d, J = 8.84 Hz, 1H), 8.17 (dd, J = 7.07, 2.02 Hz, 1H), 7.91 (d, J = 3.54 Hz, 1H), 7.80 (d, J = 2.53 Hz, 1H), 7.56 (d, J = 1.77 Hz, 1H), 7.56-7.62 (m, 1H), 7.44 (t, J = 9.35 Hz, 1H), 7.37 (d, J = 2.27 Hz, 1H), 7.07 (dd, J = 8.97, 2.40 Hz, 1H), 6.75 (d, J = 3.79 Hz, 1H), 6.37 (t, J = 2.15 Hz, 1H), 6.39 (s, 1H), 5.45 (s, 2H). | 496.9 |
| 27-F | 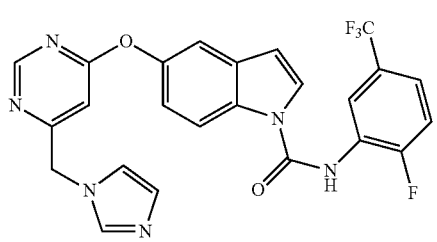<br>5-(6-Imidazol-1-ylmethyl-pyrimidin-4-yloxy)-indole-1-carboxylic acid (2-fluoro-5-trifluoromethyl-phenyl)-amide | (MeOD) δ ppm 8.66 (s, 1H), 8.31 (d, J = 9.09 Hz, 1H), 8.17 (dd, J = 6.95, 2.15 Hz, 1H), 7.92 (d, J = 3.79 Hz, 1H), 7.80 (s, 1H), 7.60 (m, 1H), 7.40 (d, J = 2.53 Hz, 1H), 7.45 (t, J = 9.35 Hz, 1H), 7.20-7.21 (m, 1H), 7.09 (dd, J = 9.09, 2.27 Hz, 1H), 7.02 (s, 1H), 6.75 (d, J = 3.79 Hz, 1H), 6.63 (s, 1H), 5.33 (s, 2H). | 496.9 |
| 27-G | 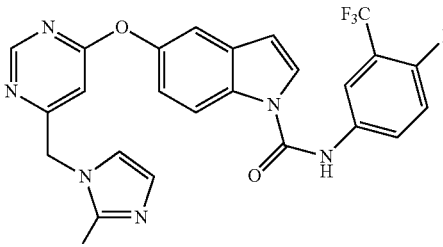<br>5-[6-(2-Amino-imidazol-1-ylmethyl)-pyrimidin-4-yloxy]-indole-1-carboxylic acid (4-fluoro-3-trifluoromethyl-phenyl)-amide | (DMSO-d$_6$) δ ppm 10.39 (br. S., 1H), 8.70 (d, J = 1.0 Hz, 1H), 8.27 (d, J = 8.8 Hz, 1H), 8.08-8.14 (m, 2H), 7.95-8.04 (m, 1H), 7.57 (t, J = 9.7 Hz, 1H), 7.47 (d, J = 2.5 Hz, 1H), 7.12 (dd, J = 9.0, 2.4 Hz, 1H), 6.79 (d, J = 3.5 Hz, 1H), 6.66 (d, J = 1.3 Hz, 1H), 6.50 (d, J = 0.8 Hz, 1H), 6.44 (d, J = 1.5 Hz, 1H), 5.37-5.46 (m, 2H), 5.05 (s, 2H) | 512.0 |
| 27-H | 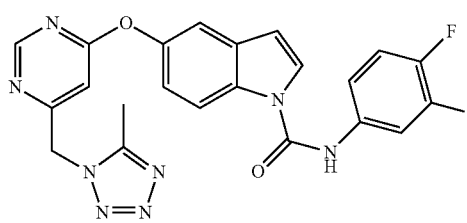<br>6-(5-Methyl-tetrazol-1-ylmethyl)-pyrimidin-4-yloxy]-indole-1-carboxylic acid (4-fluoro-3-trifluoromethyl-phenyl)-amide | (Acetone-d$_6$) δ ppm 10.66 (s, 1H) 9.19 (s, 1H) 8.98 (d, J = 9.09 Hz, 1H) 8.80 (dd, J = 6.32, 2.53 Hz, 1H) 8.76 (d, J = 3.79 Hz, 1H) 8.68 (dd, J = 8.84, 3.79 Hz, 1H) 8.03 (d, J = 2.27 Hz, 1H) 7.99 (t, J = 9.73 Hz, 1H) 7.73 (dd, J = 8.97, 2.40 Hz, 1H) 7.63 (s, 1H) 7.30 (d, J = 3.79 Hz, 1H) 6.37 (s, 2H) 3.20 (s, 3H). | 513.9 |

-continued

| | Structure/Chemical Name | ¹H NMR (400 MHz) | MS (ESI) m/z (M + 1) |
|---|---|---|---|
| 27-I | 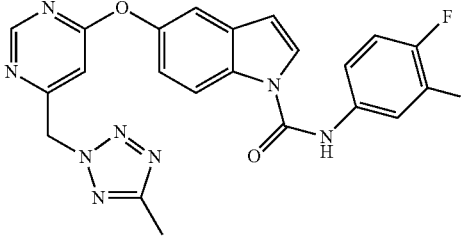<br>6-(5-Methyl-tetrazol-2-ylmethyl)-pyrimidin-4-yloxy]-indole-1-carboxylic acid (4-fluoro-3-trifluoromethyl-phenyl)-amide | (Acetone-$d_6$) δ ppm 10.67 (s, 1H) 9.24 (s, 1H) 9.01 (d, J = 9.09 Hz, 1H) 8.83 (dd, J = 6.32, 2.53 Hz, 1H) 8.78 (d, J = 3.79 Hz, 1H) 8.72 (dd, J = 8.08, 3.79 Hz, 1H) 8.01-8.07 (m, 1H) 8.06 (d, J = 2.02 Hz, 1H) 7.76 (dd, J = 8.97, 2.40 Hz, 1H) 7.51 (s, 1H) 7.34 (d, J = 3.54 Hz, 1H) 6.57 (s, 2H) 3.09 (s, 3H). | 513.9 |
| 27-J | 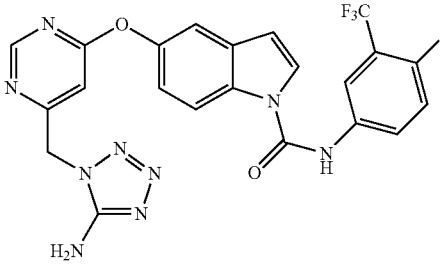<br>5-[6-(5-Amino-tetrazol-1-ylmethyl)-pyrimidin-4-yloxy]-indole-1-carboxylic acid (4-fluoro-3-trifluoromethyl-phenyl)-amide | (DMSO-$d_6$) δ ppm 10.38 (br. S., 1H), 8.70 (d, J = 1.0 Hz, 1H), 8.29 (d, J = 9.1 Hz, 1H), 8.06-8.17 (m, 2H), 7.96-8.05 (m, 1H), 8.57 (t, J = 9.9 Hz, 1H), 7.50 (d, J = 2.5 Hz, 1H), 7.15 (dd, J = 9.0, 2.4 Hz, 1H), 6.77-6.88 (m, 4H), 5.50 (s, 2H) | 514.0 |
| 27-K | 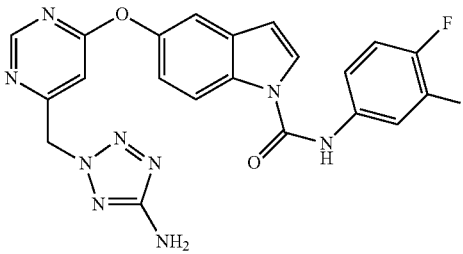<br>5-[6-(5-Amino-tetrazol-2-ylmethyl)-pyrimidin-4-yloxy]-indole-1-carboxylic acid (4-fluoro-3-trifluoromethyl-phenyl)-amide | (DMSO-$d_6$) δ ppm 10.40 (s, 1H), 8.70 (d, J = 1.0 Hz, 1H), 8.28 (d, J = 9.1 Hz, 1H), 8.11 (d, J = 3.8 Hz, 2H), 7.95-8.06 (m, 1H), 7.57 (t, J = 9.9 Hz, 1H), 7.51 (d, J = 2.3 Hz, 1H), 7.16 (dd, J = 9.0, 2.4 Hz, 1H), 7.00 (s, 1H), 6.81 (d, J = 3.3 Hz, 1H), 6.08 (d, J = 5.3 Hz, 1H), 5.76 (s, 2H) | 514.0 |
| 27-L | 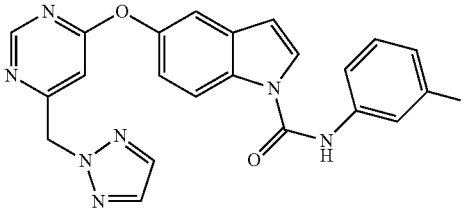<br>5-(6-[1,2,3]Triazol-2-ylmethyl-pyrimidin-4-yloxy)-indole-1-carboxylic acid (3-trifluoromethyl-phenyl)-amide | (DMSO-$d_6$) δ ppm 8.69 (d, 1H), 8.28 (d, J = 8.8 Hz, 1H), 8.13 (d, J = 3.8 Hz, 1H), 8.08-8.11 (m, 1H), 7.95-8.00 (m, 1H), 7.88 (s, 2H), 7.65 (t, J = 8.0 Hz, 1H), 7.47-7.54 (m, 2H), 7.14 (dd, J = 9.0, 2.4 Hz, 1H), 6.80 (d, J = 3.5 Hz, 1H), 6.70 (d, J = 0.8 Hz, 1H), 5.80 (s, 2H) | 480.0 |

| | Structure/Chemical Name | ¹H NMR (400 MHz) | MS (ESI) m/z (M + 1) |
|---|---|---|---|
| 27-M | 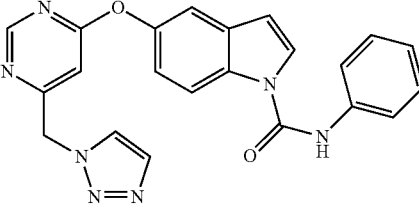<br>5-(6-[1,2,3]Triazol-1-ylmethyl-pyrimidin-4-yloxy)-indole-1-carboxylic acid (3-trifluoromethyl-phenyl)-amide | (DMSO-d₆) δ ppm 10.39 (s, 1H), 8.70 (d, J = 1.0 Hz, 1H), 8.28 (d, J = 9.1 Hz, 1H), 8.25 (d, J = 0.8 Hz, 1H), 8.13 (d, J = 3.8 Hz, 1H), 8.08-8.11 (m, 1H), 7.95-8.01 (m, 1H), 7.80 (d, J = 1.0 Hz, 1H), 7.65 (t, J = 8.0 Hz, 1H), 7.47-7.53 (m, 2H), 7.15 (dd, J = 9.0, 2.4 Hz, 1H), 6.87 (d, J = 0.8 Hz, 1H), 6.81 (d, J = 3.5 Hz, 1H), 5.77 (s, 2H) | 480.0 |
| 27-N | 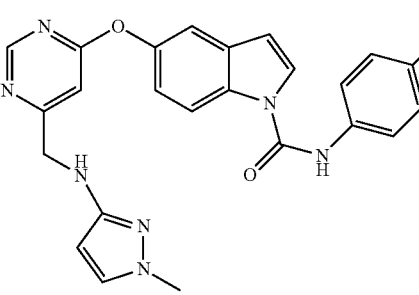<br>6-[(1-Methyl-1H-pyrazol-3-ylamino)-methyl]-pyrimidin-4-yloxy}-indole-1-carboxylic acid (4-fluoro-3-trifluoromethyl-phenyl)-amide | (MeOD) δ ppm 8.62 (d, J = 1.01 Hz, 1H) 8.32 (d, J = 9.09 Hz, 1H), 8.05 (dd, J = 6.19, 2.65 Hz, 1H), 7.90-7.95 (m, 2H) 7.34-7.39 (m, 2H) 7.22 (d, J = 2.53 Hz, 1H) 7.05 (dd, J = 8.97, 2.40 Hz, 1H) 6.94 (s, 1 H) 6.73 (d, J = 3.79 Hz, 1H) 5.46 (d, J = 2.27 Hz, 1H) 4.37 (s, 2H) 3.63 (s, 3H) | 526.9 |

EXAMPLE 28

28-A. 4-[1-(3-Trifluoromethyl-phenylcarbamoyl)-1H-indol-5-yloxy]-pyridine-2-carboxylic acid

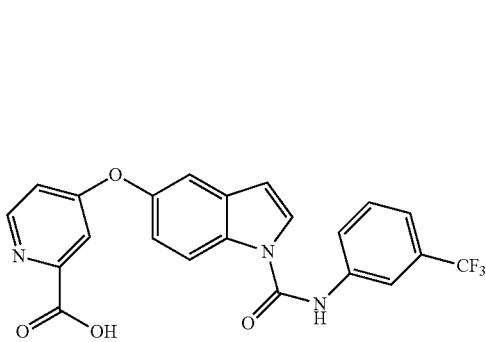 [SMILES: O=C(O)c1cc(Oc2ccc3c(ccn3C(=O)Nc3cccc(C(F)(F)F)c3)c2)ccn1]

A solution of 4-[1-(3-trifluoromethyl-phenylcarbamoyl)-1H-indol-5-yloxy]-pyridine-2-carboxylic acid tert-butyl ester (1 g, 2.01 mmol) and TFA (20 mL) is stirred at rt for 2 h. The reaction is concentrated in vacuo and used without further purification in the next step. MS (ESI) m/z 442.0 (M+1).

28-B. 5-(2-Methylcarbamoyl-pyridin-4-yloxy)-indole-1-carboxylic acid (3-trifluoromethyl-phenyl)-amide

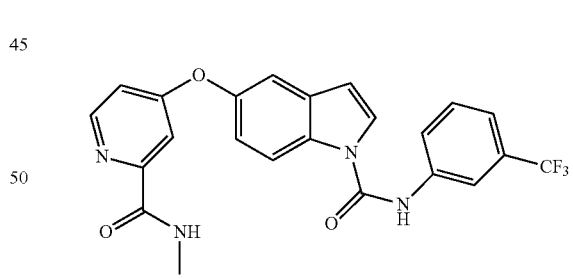

A mixture of 4-[1-(3-trifluoromethyl-phenylcarbamoyl)-1H-indol-5-yloxy]-pyridine-2-carboxylic acid (150 mg, 0.27 mmol), DCM (3 mL), and triethylamine (0.11 mL, 0.81 mmol) is stirred at 0° C. and oxalyl chloride (0.27 mL, 0.54 mmol, 2.0 M DCM solution) is added. After 30 min, excess methylamine (2.0M DCM solution) is added. After an additional 30 min, the reaction is partitioned between DCM and saturated aqueous NaHCO₃.

Organic layer is removed and dried over anhydrous Na₂SO₄. Following concentration the residue is separated via semi-prep HPLC (C18; 10-100% I/H₂O with 0.1% NH₄OH) to give the title compound.

MS (ESI) m/z 455.2 (M+1); ¹H NMR (400 MHz, MeOD) δ ppm 8.36 (d, J=5.6 Hz, 1 H), 8.29 (d, J=8.8 Hz, 1 H), 7.97 (s, 1 H), 7.87 (d, J=3.8 Hz, 1 H), 7.81 (d, J=8.3 Hz, 1 H), 7.47-7.52 (m, 1 H), 7.45 (d, J=2.5 Hz, 1 H), 7.35 (d, J=7.8 Hz, 1 H), 7.31 (d, J=2.3 Hz, 1 H), 7.01 (dd, J=9.0, 2.4 Hz, 1H), 6.96 (dd, J=5.6, 2.5 Hz, 1H), 6.66 (d, J=3.8 Hz, 1 H), 2.83 (s, 3 H).

The following compounds are prepared with similar method.

| | Structure/Chemical Name | ¹H NMR (400 MHz) | MS (ESI) m/z (M + 1) |
|---|---|---|---|
| 28-C | 5-[2-(1-Methyl-1H-pyrazol-3-ylcarbamoyl)-pyridin-4-yloxy]-indole-1-carboxylic acid (3-trifluoromethyl-phenyl)-amide. | (MeOD) δ ppm 8.42 (d, J = 5.6 Hz, 1H), 8.31 (d, J = 9.1 Hz, 1H), 7.97 (s, 1H), 7.87 (d, J = 3.8 Hz, 1H), 7.81 (d, J = 8.3 Hz, 1H), 7.56 (d, J = 2.3 Hz, 1H), 7.48 (t, J = 8.1 Hz, 1H), 7.40 (d, J = 2.3 Hz, 1H), 7.30-7.38 (m, 2H), 6.98-7.06 (m, 2H), 6.67 (d, J = 3.8 Hz, 1H), 6.55 (d, J = 2.5 Hz, 1H), 3.73 (s, 3H). | 521.1 |
| 28-D | 5-[2-(2-Pyrrolidin-1-yl-ethylcarbamoyl)-pyridin-4-yloxy]-indole-1-carboxylic acid (3-trifluoromethyl-phenyl)-amide. | (MeOD) δ ppm 8.36 (d, J = 5.6 Hz, 1H), 8.29 (d, J = 9.1 Hz, 1H), 7.97 (s, 1H), 7.86 (d, J = 3.8 Hz, 1H), 7.81 (d, J = 8.1 Hz, 1H), 7.43-7.52 (m, 2H), 7.27-7.38 (m, 2H), 6.93-7.04 (m, 2H), 6.66 (d, J = 3.5 Hz, 1 H), 3.46 (t, J = 6.7 Hz, 2H), 2.64 (t, J = 6.7 Hz, 2H), 2.54 (br. s., 4H), 1.64-1.77 (m, 4 H). | 538.2 |
| 28-E | 5-(2-Carbamoyl-pyridin-4-yloxyl)-indole-1-carboxylic acid (3-trifluoromethyl-phenyl)-amide | (DMSO-d₆) δ ppm 10.42 (s, 1H), 8.51 (d, J = 5.6 Hz, 1H), 8.35 (d, J = 8.8 Hz, 1H), 8.17 (d, J = 3.8 Hz, 1H), 8.10 (s, 2H), 7.98 (d, J = 8.3 Hz, 1H), 7.59-7.73 (m, 2H), 7.45-7.58 (m, 2H), 7.38 (d, J = 2.5 Hz, 1 H), 7.11-7.25 (m, 2H), 6.83 (d, J = 3.5 Hz, 1H). | 44 |

| | Structure/Chemical Name | ¹H NMR (400 MHz) | MS (ESI) m/z (M + 1) |
|---|---|---|---|
| 28-F | 5-(2-Cyclopropylcarbamoyl-pyridin-4-yloxy)-indole-1-carboxylic acid (3-trifluoromethyl-phenyl)-amide | (DMSO-d₆) δ ppm 10.42 (s, 1H), 8.72 (d, J = 5.1 Hz, 1H), 8.49 (d, J = 5.6 Hz, 1H), 8.34 (d, J = 8.8 Hz, 1H), 8.17 (d, J = 3.8 Hz, 1H), 8.10 (s, 1H), 7.98 (d, J = 8.1 Hz, 1H), 7.65 (t, J = 8.0 Hz, 1H), 7.45-7.54 (m, 2 H), 7.37 (d, J = 2.5 Hz, 1H), 7.12-7.23 (m, 2H), 6.83 (d, J = 3.5 Hz, 1H), 2.79-2.90 (m, 1H), 0.66 (d, J = 9.3 Hz, 4H) | 481.0 |
| 28-G | 5-(2-Isopropylcarbamoyl-pyridin-4-yloxy)-indole-1-carboxylic acid (3-trifluoromethyl-phenyl)-amide | (DMSO-d₆) δ ppm 10.44 (br. S., 1H), 8.41-8.54 (m, 3H), 8.16 (d, J = 3.8 Hz, 1H), 8.07 (s, 1H), 7.87 (br. S., 1H), 7.54 (br. S., 1H), 7.46 (br. S., 1H), 7.26-7.41 (m, 2 H), 7.17 (dd, J = 6.2, 1.6 Hz, 1H), 7.06-7.14 (m, 1H), 6.71 (br. S., 1H), 4.00-4.11 (m, 1H), 1.16 (d, J = 6.6 Hz, 6H) | 483.1 |
| 28-H | 5-[2-(2-Methoxy-ethylcarbamoyl)-pyridin-4-yloxy]-indole-1-carboxylic acid (3-trifluoromethyl-phenyl)-amide | (DMSO-d₆) δ ppm 10.49 (s, 1H), 8.63-8.71 (m, 1H), 8.52 (d, J = 5.8 Hz, 1H), 8.41 (d, J = 9.1 Hz, 1H), 8.21 (d, J = 3.8 Hz, 1H), 8.10 (s, 1H), 7.95 (d, J = 8.3 Hz, 1H), 7.60 (t, J = 8.0 Hz, 1H), 7.50 (d, J = 2.3 Hz, 1H), 7.43 (d, J = 7.8 Hz, 1H), 7.39 (d, J = 2.5 Hz, 1H), 7.19 (dd, J = 5.7, 2.7 Hz, 1H), 7.14 (dd, J = 8.8, 2.5 Hz, 1H), 6.77 (d, J = 3.5 Hz, 1H), 3.40-3.46 (m, 4H), 3.28-3.38 (m, 3 H). | 499.1 |
| 28-I | 5-(2-Cyclobutylcarbamoyl-pyridin-4-yloxy)-indole-1-carboxylic acid (3-trifluoromethyl-phenyl)-amide | (DMSO-d₆) δ ppm 10.50 (s, 1H), 8.90 (d, J = 8.3 Hz, 1H), 8.52 (d, J = 5.6 Hz, 1H), 8.40 (d, J = 8.8 Hz, 1H), 8.21 (d, J = 3.5 Hz, 1H), 8.11 (s, 1H), 7.96 (d, J = 8.3 Hz, 1H), 7.61 (t, J = 8.0 Hz, 1H), 7.49 (d, J = 2.3 Hz, 1H), 7.44 (d, J = 7.6 Hz, 1H), 7.37 (d, J = 2.5 Hz, 1H), 7.10-7.21 (m, 2H), 6.78 (d, J = 3.5 Hz, 1H), 4.32-4.45 (m, 1H), 2.09-2.21 (m, 4H), 1.59-1.71 (m, 2H). | 495.1 |

| Structure/Chemical Name | ¹H NMR (400 MHz) | MS (ESI) m/z (M + 1) |
|---|---|---|
| 28-J<br><br>5-[2-(3-Methoxy-propylcarbamoyl)-pyridin-4-yloxy]-indole-1-carboxylic acid (3-trifluoromethyl-phenyl)-amide | (DMSO-d$_6$) δ ppm 10.46 (br. S., 1H), 8.80 (t, J = 6.1 Hz, 1H), 8.51 (d, J = 5.6 Hz, 1H), 8.38 (d, J = 9.1 Hz, 1H), 8.18 (d, J = 3.3 Hz, 1H), 8.10 (s, 1H), 7.96 (d, J = 7.8 Hz, 1H), 7.62 (t, J = 8.0 Hz, 1H), 7.51 (d, J = 2.3 Hz, 1H), 7.46 (d, J = 7.1 Hz, 1H), 7.38 (d, J = 2.5 Hz, 1H), 3.26-3.37 (m, 6H), 3.22 (s, 3H). | 513.1 |
| 28-K<br><br>4-Fluoro-5-[2-(methoxy-methyl-carbamoyl)-pyridin-4-yloxy]-2-methyl-indole-1-carboxylic acid (3-trifluoromethyl-phenyl)-amide | (ACETONITRILE-d$_3$) δ ppm 8.84 (s, 1H) 8.49 (d, J = 6.06 Hz, 1H) 8.08 (s, 1H) 7.87 (s, 1H) 7.63-7.68 (m, 2H) 7.54-7.58 (m, 1H) 7.14 (dd, J = 8.97, 7.71 Hz, 1 H) 7.01-7.07 (m, 2H) 6.61 (s, 1H) 3.70 (s, 3H) 3.28-3.34 (m, 3H) 2.66 (s, 3H) | 516.9 |
| 28-L<br><br>4-Fluoro-2-methyl-5-(2-methylcarbamoyl-pyridin-4-yloxy)-indole-1-carboxylic acid (3-trifluoromethyl-phenyl)-amide | (ACETONITRILE-d$_3$) δ ppm 8.83 (br. S, 1H) 8.36 (d, J = 5.81 Hz, 1H) 7.97 (s, 2H) 7.77 (d, J = 8.34 Hz, 1H) 7.53 (d, J = 8.08 Hz, 2H) 7.44 (d, J = 7.58 Hz, 1H) 7.38 (d, J = 2.53 1H) 6.93-7.07 (m, 2H) 6.48 (s, 1 H) 2.79 (m, 3H) 2.54 (s, 3H) | 486.9 |

EXAMPLE 29

4-Fluoro-5-(2-hydroxymethyl-pyridin-4-yloxy)-2-methyl-indole-1-carboxylic acid (3-trifluoromethyl-phenyl)-amide

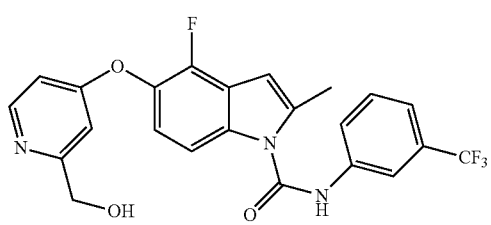 [SMILES: Cc1cc2c(F)c(Oc3ccnc(CO)c3)ccc2n1C(=O)Nc1cccc(C(F)(F)F)c1]

Example 28-K (960 mg, 1.86 mmol) is dissolved in MeOH (30 ml) and cooled to 0° C. with stirring under nitrogen. At this time, NaBH$_4$ (392 mg, 10.4 mmol) is added and the reaction is stirred at 0° C. The reaction is allowed to warm to rt and stirred for 1.5 h. The reaction is stopped and concentrated under reduced pressure. The resulting foam is taken up into EtOAc and 0.5N NaOH is added. The biphasic solution is vigorously shaken and the layers allowed to separate. The aqueous layer is washed a second time with EtOAc and the combined organics are dried over Na$_2$SO$_4$, filtered and concentrated in vacuo. The resulting crude oil is separated by FCC. MS (ESI) m/z 459.9 (M+1); ¹H NMR (400 MHz, CHLOROFORM-d) δ ppm 8.39 (d, J=6.06 Hz, 1 H), 7.90 (s, 1H), 7.79 (d, J=7.83 Hz, 1 H), 7.66 (s, 1H), 7.56 (t, J=7.96 Hz, 1 H), 7.45-7.53 (m, 2 H), 7.04 (dd, J=8.84, 7.33 Hz, 1 H), 6.84 (dd, J=5.94, 2.40 Hz, 1 H), 6.78 (d, J=2.27 Hz, 1 H), 6.54 (s, 1 H), 4.67 (s, 2 H), 2.67 (s, 3 H).

EXAMPLE 30

5-(2-((Dimethylamino)methyl)pyridin-4-yloxy)-4-fluoro-2-methyl-N-(3-(trifluoromethyl)phenyl)-1H-indole-1-carboxamide

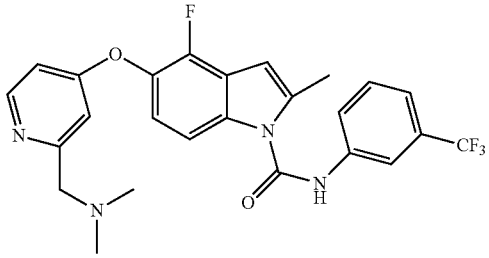 [SMILES: Cc1cc2c(F)c(Oc3ccnc(CN(C)C)c3)ccc2n1C(=O)Nc1cccc(C(F)(F)F)c1]

In a 100 mL round-bottomed flask is added Example 29 (865 mg, 1.88 mmol) in DCM (20 mL) to give a suspension. The reaction vessel is cooled to 0° C. using an ice/water bath. MsCl (300 µl, 3.85 mmol) and DIPEA (600 µl, 3.44 mmol) are added via syringe. The reaction mixture quickly becomes homogenous and is warmed to rt with stirring. After 2 h, the reaction is stopped and concentrated in vacuo. The resulting brown oil is absorbed onto a prepacked 12 g silica gel cartridge. The product is eluted using a 0-100% EtOAc/heptane gradient to give (4-(4-Fluoro-2-methyl-1-(3-(trifluoromethyl)phenylcarbamoyl)-1H-indol-5-yloxy)pyridine-2-yl)methyl methanesulfonate [MS (ESI) m/z 538.9 (M+1)] along with a minor product that is identified as 5-(2-(chloromethyl)pyridine-4-yloxy)-4-fluoro-2-methyl-N-(3-(trifluoromethyl)phenyl)-1H-indole-1-carboxamide. MS (ESI) m/z 479.9 (M+1).

In a 1-DRAM vial the above mixture (140 mg, 0.260 mmol) is taken up in DCM (1.5 mL) to give a orange solution. Dimethylamine in MeOH (2.0 M, 0.4 mL, 0.800 mmol) is added and the reaction is stirred at rt. After standing overnight the reaction mixture is loaded onto a 12-g silica gel prepacked solid load cartridge. The residual solvent is removed via high pressure air blowing through the plug. The desired product is eluted using a 0-10% MeOH/DCM gradient from the silica gel cartridge to give 5-(2-((dimethylamino)methyl)pyridine-4-yloxy)-4-fluoro-2-methyl-N-(3-(trifluoromethyl)phenyl)-1H-indole-1-carboxamide. MS (ESI) m/z 486.9 (M+1); $^1$H NMR (400 MHz, DMSO-d$_6$) δ ppm 11.01 (s, 1 H), 8.37 (d, J=4.55 Hz, 1 H), 8.11 (s, 1 H), 7.91 (d, J=7.33 Hz, 1 H), 7.67 (t, J=7.96 Hz, 1 H), 7.55 (d, J=8.59 Hz, 2 H), 7.17 (d, J=7.83 Hz, 1 H), 6.79-6.94 (m, 2 H), 6.66 (s, 1 H), 3.46 (s, 2 H), 2.59 (s, 3 H), 2.13 (s, 6 H).

EXAMPLE 31

31-A. 4-Oxo-4,5,6,8-tetrahydro-3H-pyrido[3,4-d]pyrimidine-7-carboxylic acid tert-butyl ester

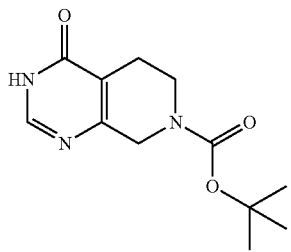 [SMILES: CC(C)(C)OC(=O)N1CCc2c(nc[nH]c2=O)C1]

7-Benzyl-5,6,7,8-tetrahydro-3H-pyrido[3,4-d]pyrimidin-4-one (ref. *Org. Proc. Res. Dev.* 2005, 9, 80) (36.9 g, 153 mmol) and BOC anhydride (40.1 g, 184 mmol) are taken up in MeOH (600 mL). The vessel is purged with argon and palladium on carbon (10% w/w; wet) (5.0 g) is added. The contents are then stirred under a hydrogen atmosphere (1 atm) for 18 h. At that time the suspension is filtered over Celite® and the resulting solution is concentrated to give the title compound. MS (ESI) m/z 252.0 (M+1).

31-B. 4-Chloro-5,8-dihydro-6H-pyrido[3,4-d]pyrimidine-7-carboxylic acid tert-butyl ester

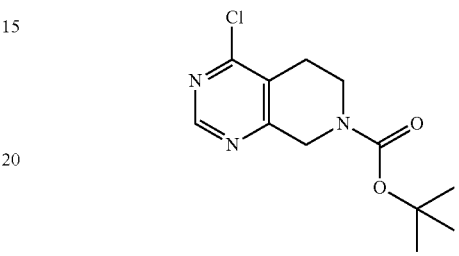

Triphenylphosphine (17.3 g, 66.1 mmol) is added to a solution of 4-oxo-4,5,6,8-tetrahydro-3H-pyrido[3,4-d]pyrimidine-7-carboxylic acid tert-butyl ester (8.30 g, 33.0 mmol), CCl$_4$ (9.6 mL, 99 mmol), and 1,2-dichloroethane (250 mL). The solution is heated at 70° C. for 2.5 h. The solution is concentrated in vacuo to about 50 mL. The contents of the flask are then filtered over a silica gel plug eluting with 60% EtOAc/heptane. The residue following concentration is then further separated via flash chromatography (10-30% EtOAc/heptane) to give the title compound.

MS (ESI) m/z 270.0 & 272.0 (M+1); $^1$H NMR (400 MHz, CDCl$_3$) δ ppm 8.79 (s, 1 H), 4.65 (s, 2 H), 3.74 (t, J=5.8 Hz, 2 H), 2.87 (t, J=5.8 Hz, 2 H), 1.49 (s, 9 H).

31-C. 4-(1H-Indol-5-yloxy)-5,8-dihydro-6H-pyrido[3,4-d]pyrimidine-7-carboxylic acid tert-butyl ester

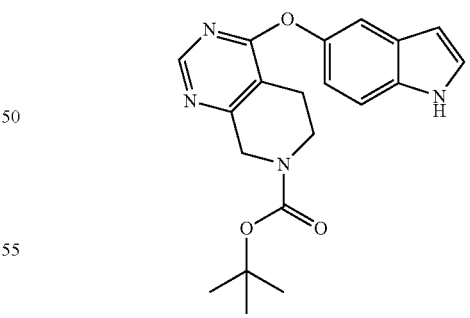

To a solution of 4-Chloro-5,8-dihydro-6H-pyrido[3,4-d]pyrimidine-7-carboxylic acid tert-butyl ester (5.46 g, 20.2 mmol), 5-hydroxyindole (3.50 g, 26.3 mmol) and CH$_3$CN (100 mL) is added DBU (4.0 mL, 26.3 mmol). The mixture is then heated at 50° C. for 4 h. At that time the solvent is removed in vacuo and the residue separated via FCC (10-50% EtOAc/heptane) to give the title compound. MS (ESI) m/z 367.1 (M+1).

The following compounds are prepared with similar method.

31-D. 4-(4-Fluoro-2-methyl-1H-indol-5-yloxy)-5,8-dihydro-6H-pyrido[3,4-d]pyrimidine-7-carboxylic acid tert-butyl ester

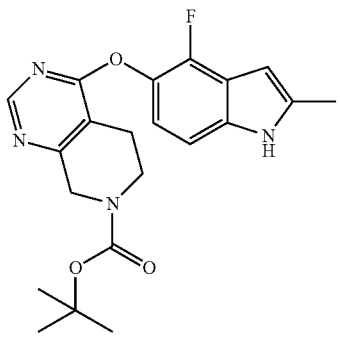 [SMILES: Cc1cc2c(F)c(Oc3ncnc4c3CCN(C(=O)OC(C)(C)C)C4)ccc2[nH]1]

MS (ESI) m/z 399.0 (M+1)

31-E. 4-(4-Fluoro-1H-indl-5-yloxy)-5,8-dihydro-6H-pyrido[3,4-d]pyrimidine-7-carboxylic acid tert-butyl ester

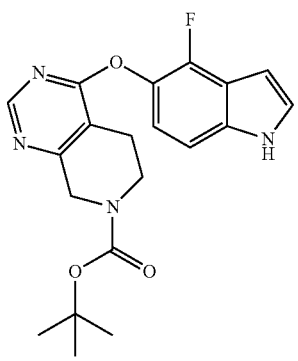 [SMILES: CC(C)(C)OC(=O)N1CCc2c(ncnc2Oc2ccc3[nH]ccc3c2F)C1]

MS (ESI) m/z 385.1 (M+1)

31-F. 4-(6-Fluoro-1H-indol-5-yloxy)-5,8-dihydro-6H-pyrido[3,4-d]pyrimidine-7-carboxylic acid tert-butyl ester

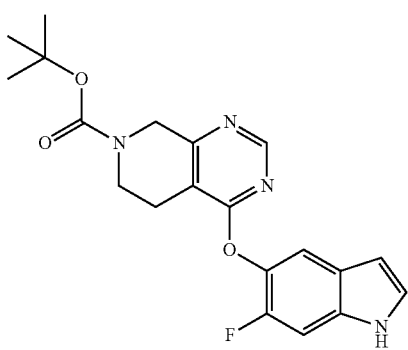 [SMILES: CC(C)(C)OC(=O)N1CCc2c(ncnc2Oc2cc3cc[nH]c3cc2F)C1]

MS (ESI) m/z 385.0 (M+1)

EXAMPLE 32

4-(2-Methyl-1H-indol-5-yloxy)-5,8-dihydro-6H-pyrido[3,4-d]pyrimidine-7-carboxylic acid tert-butyl ester

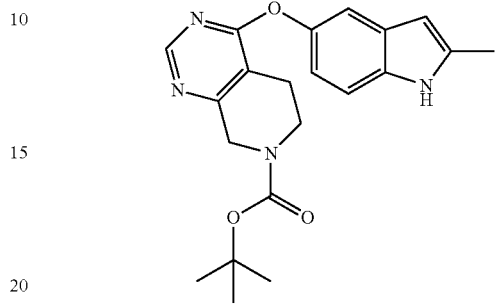

To a stirring solution of 4-oxo-4,5,6,8-tetrahydro-3H-pyrido[3,4-d]pyrimidine-7-carboxylic acid tert-butyl ester, Example 31-A, (300 mg, 1.2 mmol) in I (5 mL) is added PyBOP (800 mg, 1.55 mmol) and DBU (0.2 mL, 1.43 mmol). After 20 min 2-methyl-1H-indol-5-ol (211 mg, 1.43 mmol) is added. The mixture is then stirred at room temperature for 16 h. At that point the reaction is concentrated under reduced pressure and the residue is dissolved in EtOAc and washed by water and brine. The organic layer is dried over sodium sulfate, concentrated under reduced pressure. The residue is purified by FCC (EtOAc/heptane from 0% to 40%) to give the title compound. MS (ESI) m/z 381.0 (M+1).

EXAMPLE 33

33-A. 4-[1-(2-Fluoro-5-trifluoromethyl-phenylcarbamoyl)-1H-indol-5-yloxy]-5,8-dihydro-6H-pyrido[3,4-d]pyrimidine-7-carboxylic acid tert-butyl ester

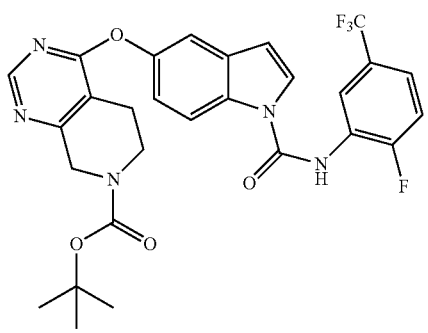 [SMILES: CC(C)(C)OC(=O)N1CCc2c(ncnc2Oc2ccc3c(ccn3C(=O)Nc3cc(C(F)(F)F)ccc3F)c2)C1]

Sodium hydride (0.025 g, 0.614 mmol, 60% in mineral oil) is added to a solution of 4-(1H-Indol-5-yloxy)-5,8-dihydro-6H-pyrido[3,4-c]pyrimidine-7-carboxylic acid tert-butyl ester, Example 31-C, (0.150 g, 0.409 mmol) and THF (5 mL) at 0° C. After 20 min 2-fluoro-5-(trifluoromethyl)phenyl isocyanate (0.168 g, 0.819 mmol) is added. After an additional 1 h the contents of the flask are poured into saturated aqueous NaHCO₃ (25 mL) and extracted with EtOAc (3×25 mL). The combined organic layers are then dried (Na₂SO₄), filtered and concentrated. The crude residue is then separated via FCC (20-50% EtOAc/heptane) to provide the title compound. MS (ESI) m/z 572.1 (M+1).

33-B. 5-(5,6,7,8-Tetrahydro-pyrido[3,4-d]pyrimidin-4-yloxy)-indole-1-carboxylic acid (2-fluoro-5-trifluoromethyl-phenyl)-amide

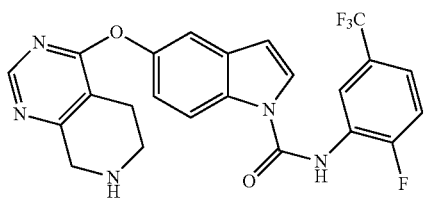 [SMILES: O=C(Nc1cc(C(F)(F)F)ccc1F)n1ccc2cc(Oc3ncnc4c3CCNC4)ccc21]

TFA (1 mL, 13.0 mmol) is added to a solution of 4-[1-(2-fluoro-5-trifluoromethyl-phenylcarbamoyl)-1H-indol-5-yloxy]-5,8-dihydro-6H-pyrido[3,4-d]pyrimidine-7-carboxylic acid tert-butyl ester (0.125 g, 0.219 mmol) and DCM (2.5 mL). After 1 h the solution is concentrated in vacuo. The residue is taken up in MeOH and neutralized to pH 7 by the addition of $NH_4OH$ and the solution is separated via semi-prep HPLC (C18; 10-100% I/$H_2O$ with 0.1% $NH_4OH$) to give 5-(5,6,7,8-Tetrahydro-pyrido[3,4-d]pyrimidin-4-yloxy)-indole-1-carboxylic acid (2-fluoro-5-trifluoromethyl-phenyl)-amide. MS (ESI) m/z 472.1 (M+1); $^1$H NMR (400 MHz, DMSO-$d_6$) δ ppm 8.40 (s, 1 H), 8.25 (d, J=8.8 Hz, 1 H), 8.07 (d, J=3.8 Hz, 1 H), 8.03-8.07 (m, 1 H), 7.67-7.75 (m, 1 H), 7.56-7.64 (m, 1 H), 7.45 (d, J=2.5 Hz, 1 H), 7.11 (dd, J=9.0, 2.4 Hz, 1 H), 6.79 (d, J=3.5 Hz, 1 H), 3.83 (s, 2 H), 3.04 (t, J=5.8 Hz, 2 H), 2.73 (t, J=5.6 Hz, 2 H).

The following compounds are prepared with similar method.

| | Structure/Chemical Name | $^1$H NMR (400 MHz) | MS (ESI) m/z (M + 1) |
|---|---|---|---|
| 33-C | 5-(5,6,7,8-Tetrahydro-pyrido[3,4-d]pyrimidin-4-yloxy)-indole-1-carboxylic acid (3-trifluoromethyl-phenyl)-amide | (DMSO-$d_6$) δ ppm 10.43 (s, 1H), 8.54 (s, 1H), 8.30 (d, J = 8.8 Hz, 1H), 8.15 (d, J = 3.5 Hz, 1H), 8.11 (s, 1H), 7.98 (d, J = 8.3 Hz, 1H), 7.65 (t, J = 8.0 Hz, 1H), 7.44-7.53 (m, 2H), 7.14 (dd, J = 9.0, 2.4 Hz, 1H), 6.81 (d, J = 3.8 Hz, 1H), 4.26 (s, 2H), 3.45 (t, J = 5.9 Hz, 2H), 3.00 (t, J = 5.8 Hz, 2H) | 454.0 |
| 33-D | 5-(5,6,7,8-Tetrahydro-pyrido[3,4-d]pyrimidin-4-yloxy)-indole-1-carboxylic acid (4-fluoro-3-trifluoromethyl-phenyl)-amide | (DMSO-$d_6$) δ ppm 10.38 (br. S., 1H), 8.43 (s, 1H), 8.26 (d, J = 8.8 Hz, 1H), 8.06-8.16 (m, 2H), 7.95-8.05 (m, 1 H), 7.57 (t, J = 9.7 Hz, 1H), 7.46 (d, J = 2.3 Hz, 1H), 7.12 (dd, J = 9.0, 2.4 Hz, 1H), 6.80 (d, J = 3.3 Hz, 1H), 3.93 (s, 2 H), 3.14 (t, J = 5.9 Hz, 2H), 2.79 (t, J = 5.7 Hz, 2H) | 472.0 |
| 33-E | 4-Fluoro-5-(5,6,7,8-tetrahydro-pyrido[3,4-d]pyrimidin-4-yloxy)-indole-1-carboxylic acid (3-trifluoromethyl-phenyl)-amide | (MeOD) δ ppm 8.38 (s, 1H), 8.13 (d, J = 9.09 Hz, 1H), 8.06 (s, 1H), 7.89 (d, J = 8.34 Hz, 1H), 7.94 (d, J = 3.79 Hz, 1 H), 7.58 (t, J = 7.96 Hz, 1H), 7.45 (d, J = 7.83 Hz, 1H), 7.19 (m, 1H), 6.82 (d, J = 3.79 Hz, 1H), 3.96 (s, 2H), 3.19 (t, J = 5.94 Hz, 2H), 2.91 (t, J = 5.68 Hz, 2 H). | 471.9 |

-continued

| | Structure/Chemical Name | ¹H NMR (400 MHz) | MS (ESI) m/z (M + 1) |
|---|---|---|---|
| 33-F | 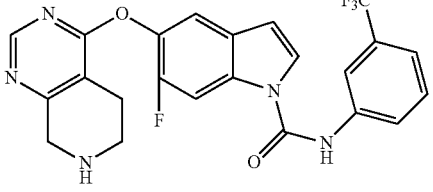<br>6-Fluoro-5-(5,6,7,8-tetrahydro-pyrido[3,4-d]pyrimidin-4-yloxy)-indole-1-carboxylic acid (3-trifluoromethyl-phenyl)-amide | (MeOD) δ ppm 8.39 (s, 1H), 8.19 (d, J = 11.62 Hz, 1H), 8.05 (s, 1H), 7.95 (d, J = 3.54 Hz, 1H), 7.90 (d, J = 8.34 Hz, 1 H), 7.58 (t, J = 7.96 Hz, 1H), 7.45 (d, J = 7.83 Hz, 1H), 7.50 (d, J = 7.58 Hz, 1 H), 6.75 (d, J = 3.79 Hz, 1H), 3.96 (s, 2 H), 3.19 (t, J = 5.94 Hz, 2H), 2.91 (t, J = 5.56 Hz, 2H). | 471.9 |
| 33-G | 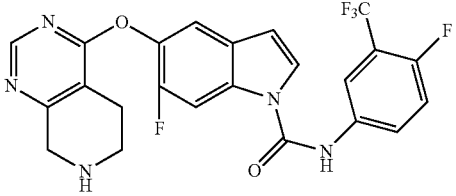<br>6-Fluoro-5-(5,6,7,8-tetrahydro-pyrido[3,4-d]pyrimidin-4-yloxy)-indole-1-carboxylic acid (4-fluoro-3-trifluoromethyl-phenyl)-amide | (MeOD) δ ppm 8.38 (s, 1H), 8.18 (d, J = 11.37 Hz, 1H), 8.04 (dd, J = 6.19, 2.65 Hz, 1H), 7.92 (d, J = 3.79 Hz, 1H), 7.95 (br. S., 1H), 7.50 (d, J = 7.58 Hz, 1H), 7.33-7.37 (m, 1H), 6.75 (d, J = 3.79 Hz, 1H), 3.96 (s, 2H), 3.19 (t, J = 5.94 Hz, 2 H), 2.91 (t, J = 5.56 Hz, 2H). | 489.9 |
| 33-H | 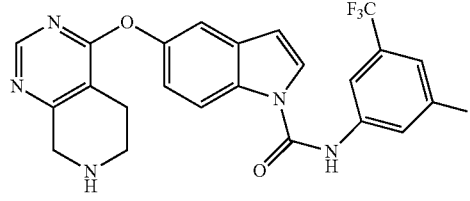<br>5-(5,6,7,8-Tetrahydro-pyrido[3,4-d]pyrimidin-4-yloxy)-indole-1-carboxylic acid (3-fluoro-5-trifluoromethyl-phenyl)-amide | (DMSO-d₆) δ ppm 10.53 (br. S., 1H), 8.40 (s, 1H), 8.26 (d, J = 8.8 Hz, 1H), 8.09 (d, J = 3.8 Hz, 1H), 7.83-7.94 (m, 2 H), 7.46 (d, J = 2.5 Hz, 1H), 7.39-7.45 (m, 1H), 7.13 (dd, J = 9.0, 2.4 Hz, 1H), 6.81 (d, J = 3.8 Hz, 1H), 3.82 (s, 2H), 3.04 (t, J = 5.8 Hz, 2H), 2.73 (t, J = 5.7 Hz, 2H) | 472.0 |
| 33-I | 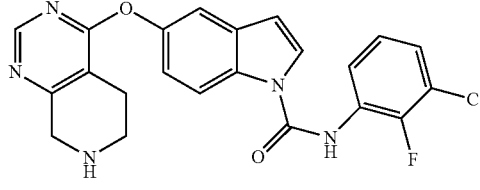<br>5-(5,6,7,8-Tetrahydro-pyrido[3,4-d]pyrimidin-4-yloxy)-indole-1-carboxylic acid (2-fluoro-3-trifluoromethyl-phenyl)-amide | (DMSO-d₆) δ ppm 10.22 (br. S., 1H), 8.40 (s, 1H), 8.24 (d, J = 8.8 Hz, 1H), 8.08 (d, J = 3.5 Hz, 1H), 7.89-8.00 (m, 1 H), 7.64-7.74 (m, 1H), 7.36-7.53 (m, 2H), 7.12 (dd, J = 9.0, 2.4 Hz, 1H), 6.80 (d, J = 3.5 Hz, 1H), 3.83 (s, 2H), 3.04 (t, J = 5.8 Hz, 2H), 2.73 (t, J = 5.6 Hz, 2H). | 472.0 |
| 33-J | 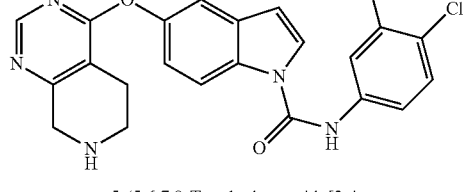<br>5-(5,6,7,8-Tetrahydro-pyrido[3,4-d]pyrimidin-4-yloxy)-indole-1-carboxylic acid (4-chloro-3-trifluoromethyl-phenyl)-amide | (DMSO-d₆) δ ppm 10.43 (br. S., 1H), 8.40 (s, 1H), 8.26 (d, J = 9.1 Hz, 1H), 8.22 (d, J = 2.8 Hz, 1H), 8.09 (d, J = 3.8 Hz, 1H), 8.00 (d, 1H), 7.75 (d, J = 8.8 Hz, 1H), 7.44-7.48 (m, 1H), 7.08-7.16 (m, 1H), 6.79 (d, J = 3.5 Hz, 1H), 3.82 (s, 2H), 3.03 (t, J = 5.8 Hz, 2H), 2.72 (t, J = 5.6 Hz, 2H) | 488.0 |

| | Structure/Chemical Name | $^1$H NMR (400 MHz) | MS (ESI) m/z (M + 1) |
|---|---|---|---|
| 33-K | 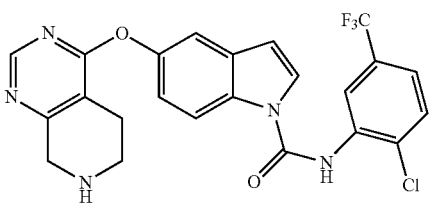<br>5-(5,6,7,8-Tetrahydro-pyrido[3,4-d]pyrimidin-4-yloxy)-indole-1-carboxylic acid (2-chloro-5-trifluoromethyl-phenyl)-amide | (DMSO-d$_6$) δ ppm 8.40 (s, 1H), 8.28 (d, J = 8.8 Hz, 1H), 8.09 (d, J = 3.5 Hz, 2 H), 7.84 (d, J = 8.6 Hz, 1H), 7.68 (d, J = 7.8 Hz, 1H), 7.45 (d, J = 2.5 Hz, 1H), 7.10 (dd, J = 9.0, 2.4 Hz, 1H), 6.78 (d, J = 3.5 Hz, 1H), 3.84 (s, 2H), 3.05 (t, J = 5.8 Hz, 2H), 2.74 (t, J = 5.7 Hz, 2H). | 488.0 |
| 33-L | 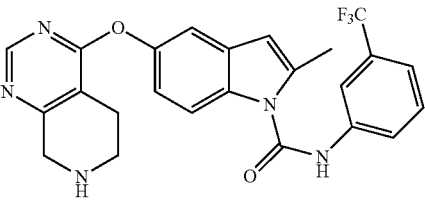<br>2-Methyl-5-(5,6,7,8-tetrahydro-pyrido[3,4-d]pyrimidin-4-yloxy)-indole-1-carboxylic acid (3-trifluoromethyl-phenyl)-amide | (MeOD) δ ppm 8.36 (s, 1H), 8.07 (s, 1 H), 7.86 (s, 1H), 7.68 (d, J = 8.84 Hz, 1 H), 7.59 (s, 1H), 7.46 (d, J = 8.59 Hz, 1 H), 7.72 (d, J = 1.77 Hz, 1H), 6.99 (dd, J = 9.09, 2.27 Hz, 1H), 6.44 (s, 1H), 3.94 (s, 2H), 3.17 (t, J = 5.94 Hz, 2H), 2.85-2.89 (m, 2H), 2.61 (s, 3H). | 467.9 |
| 33-M | 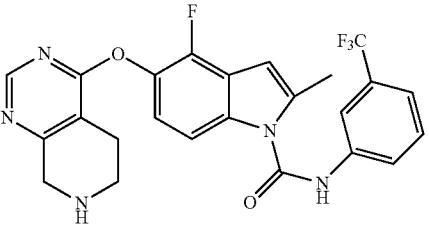<br>4-Fluoro-2-methyl-5-(5,6,7,8-tetrahydro-pyrido[3,4-d]pyrimidin-4-yloxy)-indole-1-carboxylic acid (3-trifluoromethyl-phenyl)-amide | (DMSO-d$_6$) δ ppm 10.99 (s, 1H) 8.57 (s, 1H) 8.12 (s, 1H), 7.92 (d, J = 6.57 Hz, 1 H) 7.64-7.69 (m, 1H) 7.53 (d, J = 8.84 Hz, 2H) 7.15 (dd, J = 8.84, 7.83 Hz, 1H) 6.62 (s, 1H) 4.33 (s, 2H) 3.51 (t, J = 6.06 Hz, 2H) 3.05 (s, 2H) 2.59 (s, 3H) 1.75 (s, 1H) | 485.8 |
| 33-N | 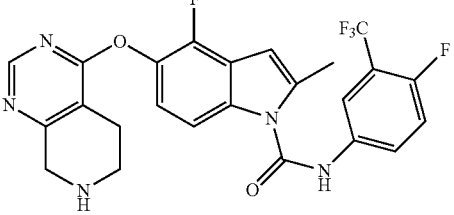<br>4-Fluoro-2-methyl-5-(5,6,7,8-tetrahydro-pyrido[3,4-d]pyrimidin-4-yloxy)-indole-1-carboxylic acid (4-fluoro-3-trifluoromethyl-phenyl)-amide | (MeOD) δ ppm 8.37 (s, 1H) 8.07 (dd, J = 6.32, 2.78 Hz, 1H) 7.90 (br. S., 1H) 7.49 (d, J = 8.84 Hz, 1H) 7.39 (t, J = 9.60 Hz, 1H) 7.07 (dd, J = 8.72, 7.45 Hz, 1H) 6.52 (s, 1H) 3.96 (s, 2H) 3.19 (t, J = 5.94 Hz, 2H) 2.90 (t, J = 5.43 Hz, 2H) 2.61 (s, 3H) | 503.1 |

EXAMPLE 34

5-(7-Acetyl-5,6,7,8-tetrahydro-pyrido[3,4-d]pyrimidin-4-yloxy)-indole-1-carboxylic acid (3-trifluoromethyl-phenyl)-amide

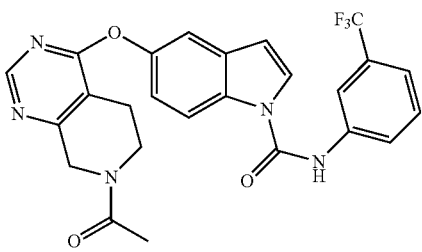 [SMILES: CC(=O)N1CCc2c(ncnc2Oc2ccc3c(ccn3C(=O)Nc3cccc(C(F)(F)F)c3)c2)C1]

To a solution of Example 33-C (0.150 g, 0.331 mmol), Et$_3$N (0.14 mL, 0.792 mmol) and DCM (5 mL) is added acetic anhydride (0.05 mL, 0.496 mmol). After 0.5 h the solution is concentrated and then separated via semi-prep HPLC (10-90% I/H$_2$O with 0.1% NH$_4$OH) to give the title compound. MS (ESI) m/z 496.0 (M+1); $^1$H NMR (400 MHz, DMSO-d$_6$) δ ppm 10.38 (s, 1 H), 8.45-8.53 (m, 1 H), 8.27 (d, J=9.1 Hz, 1 H), 8.12 (d, J=3.8 Hz, 1 H), 8.10 (s, 1 H), 7.97 (d, J=8.8 Hz, 1 H), 7.65 (t, J=8.1 Hz, 1 H), 7.50 (d, J=7.8 Hz, 1 H), 7.47 (d, J=2.3 Hz, 1 H), 7.14 (dd, J=9.0, 2.4 Hz, 1 H), 6.80 (d, J=3.5 Hz, 1H), 4.63 (s, 2 H), 3.81 (t, J=5.9 Hz, 2 H), 2.93 (t, J=5.7 Hz, 2 H), 2.16 (s, 3 H).

EXAMPLE 35

5-(7-Methanesulfonyl-5,6,7,8-tetrahydro-pyrido[3,4-d]pyrimidin-4-yloxy)-indole-1-carboxylic acid (3-trifluoromethyl-phenyl)-amide

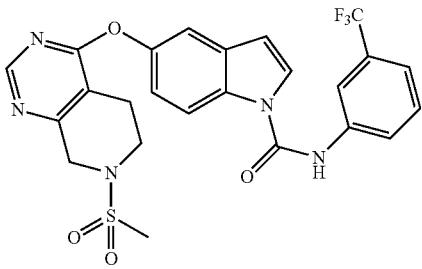 [SMILES: CS(=O)(=O)N1CCc2c(ncnc2Oc2ccc3c(ccn3C(=O)Nc3cccc(C(F)(F)F)c3)c2)C1]

To a solution of Example 33-C (0.150 g, 0.331 mmol), Et$_3$N (0.14 mL, 0.792 mmol) and DCM (5 mL) is added methanesulfonyl chloride (0.04 mL, 0.496 mmol). After 0.5 h the solution is concentrated and then separated via semi-prep HPLC (10-90% I/H$_2$O with 0.1% NH$_4$OH) to give the title compound. MS (ESI) m/z 532.0 (M+1); $^1$H NMR (400 MHz, DMSO-d$_6$) δ ppm 10.39 (s, 1 H), 8.51 (s, 1 H), 8.28 (d, J=9.1 Hz, 1 H), 8.13 (d, J=3.8 Hz, 1 H), 8.10 (s, 1 H), 7.97 (d, J=8.6 Hz, 1 H), 7.65 (t, J=8.1 Hz, 1 H), 7.51 (s, 1 H), 7.49 (d, J=2.3 Hz, 1 H), 7.15 (dd, J=9.0, 2.4 Hz, 1 H), 6.81 (d, J=3.3 Hz, 1 H), 4.39 (s, 2 H), 3.58 (t, J=5.9 Hz, 2 H), 3.06 (s, 3 H), 2.97 (t, J=5.7 Hz, 2 H).

EXAMPLE 36

4-[1-(3-Trifluoromethyl-phenylcarbamoyl)-1H-indol-5-yloxy]-5,8-dihydro-6H-pyrido[3,4-d]pyrimidine-7-carboxylic acid ethyl ester

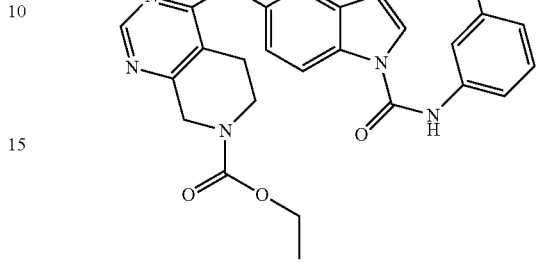

To a solution of Example 33-C (0.200 g, 0.441 mmol), pyridine (0.11 mL, 1.32 mmol) and DCM (5 mL) is added ethyl chloroformate (0.06 mL, 0.661 mmol). After 0.5 h the solution is concentrated and then separated via semi-prep HPLC (10-90% I/H$_2$O with 0.1% NH$_4$OH) to give the title compound. MS (ESI) m/z 526.1 (M+1); $^1$H NMR (400 MHz, DMSO-d$_6$) δ ppm 10.38 (s, 1 H), 8.49 (s, 1 H), 8.27 (d, J=8.8 Hz, 1 H), 8.12 (d, J=3.8 Hz, 1 H), 8.10 (s, 1 H), 7.97 (d, J=8.3 Hz, 1 H), 7.65 (t, J=8.1 Hz, 1 H), 7.50 (d, J=7.8 Hz, 1 H), 7.47 (d, J=2.3 Hz, 1 H), 7.14 (dd, J=8.8, 2.3 Hz, 1 H), 6.80 (d, J=3.5 Hz, 1 H), 4.57 (br. S., 2 H), 4.12 (q, J=7.1 Hz, 2 H), 3.76 (t, J=5.4 Hz, 2 H), 2.86 (t, J=5.6 Hz, 2 H), 1.24 (t, J=7.1 Hz, 3 H).

EXAMPLE 37

37-A. 5-(7-Ethyl-5,6,7,8-tetrahydro-pyrido[3,4-d]pyrimidin-4-yloxy)-indole-1-carboxylic acid (3-trifluoromethyl-phenyl)-amide

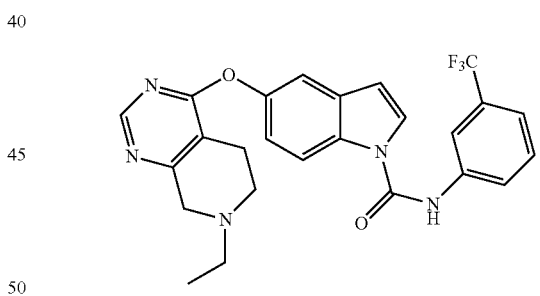

To a solution of the TFA salt of Example 33-C (0.720 g, 1.59 mmol), acetaldehyde (0.18 mL, 3.18 mmol), Et$_3$N (0.44 mL, 3.18 mmol) and DCE (10 mL) is added sodium triacetoxyborohydride (0.673 g, 0.3.18 mmol). After 1 h the suspension is poured into brine (50 mL) and extracted with DCM (3×50 mL). The combined organic layers are then dried (Na$_2$SO$_4$) filtered and concentrated. The reside is the separated via semi-prep HPLC (10-90% I/H$_2$O with 0.1% NH$_4$OH) to give the title compound. MS (ESI) m/z 482.2 (M+1); $^1$H NMR (400 MHz, DMSO-d$_6$) δ ppm 10.38 (br. S., 1 H), 8.42 (s, 1 H), 8.28 (d, J=9.1 Hz, 1 H), 8.11 (d, J=3.8 Hz, 1 H), 8.10 (s, 1 H), 7.96 (d, J=9.1 Hz, 1 H), 7.63 (t, J=8.0 Hz, 1 H), 7.48 (d, J=7.8 Hz, 1 H), 7.46 (d, J=2.5 Hz, 1 H), 7.13 (dd, J=9.0, 2.4 Hz, 1 H), 6.78 (d, J=3.8 Hz, 1 H), 3.57 (s, 2 H), 2.74-2.87 (m, 4 H), 2.59 (q, J=7.2 Hz, 2 H), 1.12 (t, J=7.2 Hz, 3 H).

The following compounds are prepared with similar method.

| | Structure/Chemical Name | $^1$H NMR (400 MHz) | MS (ESI) m/z (M + 1) |
|---|---|---|---|
| 37-B | 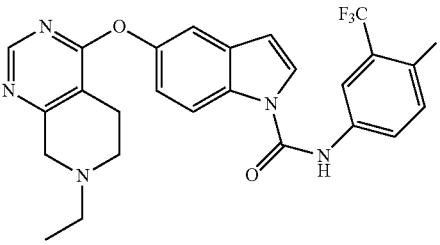<br>5-(7-Ethyl-5,6,7,8-tetrahydro-pyrido[3,4-d]pyrimidin-4-yloxy)-indole-1-carboxylic acid (4-fluoro-3-trifluoromethyl-phenyl)-amide | (MeOD) δ ppm 8.39 (s, 1H), 8.33 (d, J = 9.1 Hz, 1H), 8.04 (dd, J = 6.3, 2.8 Hz, 1H), 7.89-7.95 (m, 2H), 7.40 (d, J = 2.3 Hz, 1H), 7.36 (t, J = 9.6 Hz, 1H), 7.10 (dd, J = 9.0, 2.4 Hz, 1H), 6.74 (d, J = 3.0 Hz, 1H), 3.68 (s, 2H), 2.94-3.00 (m, 2H), 2.87-2.92 (m, 2H), 2.71 (q, J = 7.2 Hz, 2H), 1.24 (t, J = 7.2 Hz, 3H). | 500.1 |
| 37-C | 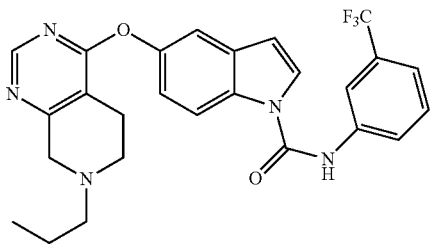<br>5-(7-Propyl-5,6,7,8-tetrahydro-pyrido[3,4-d]pyrimidin-4-yloxy)-indole-1-carboxylic acid (3-trifluoromethyl-phenyl)-amide | (MeOD) δ ppm 8.53 (s, 1H), 8.36 (d, J = 9.1 Hz, 1H), 8.07 (s, 1H), 7.96 (d, J = 3.8 Hz, 1H), 7.90 (d, J = 8.1 Hz, 1H), 7.58 (t, J = 8.0 Hz, 1H), 7.40-7.48 (m, 2H), 7.13 (dd, J = 9.0, 2.4 Hz, 1H), 6.75 (d, J = 3.8 Hz, 1H), 4.46 (br. S., 2H), 3.70 (br. S., 2H), 3.24 (t, J = 5.7 Hz, 2 H), 1.85-1.97 (m, 2H), 1.29 (s, 2H), 1.10 (t, J = 7.5 Hz, 3H). | 496.1 |
| 37-D | 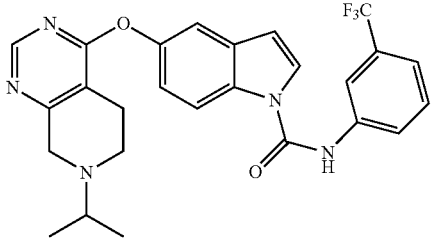<br>5-(7-Isopropyl-5,6,7,8-tetrahydro-pyrido[3,4-d]pyrimidin-4-yloxy)-indole-1-carboxylic acid (3-trifluoromethyl-phenyl)-amide | (MeOD) δ ppm 8.53 (s, 1H), 8.36 (d, J = 9.1 Hz, 1H), 8.07 (s, 1H), 7.96 (d, J = 3.8 Hz, 1H), 7.89 (d, J = 8.8 Hz, 1H), 7.58 (t, J = 8.0 Hz, 1H), 7.38-7.47 (m, 2H), 7.12 (dd, J = 9.1, 2.3 Hz, 1H), 6.75 (d, J = 3.8 Hz, 1H), 4.45 (br. S., 2H), 3.77-3.87 (m, 1H), 3.67 (br. S., 2H), 3.25 (br. S., 2H), 1.50 (d, J = 6.6 Hz, 6H). | 496.1 |
| 37-E | 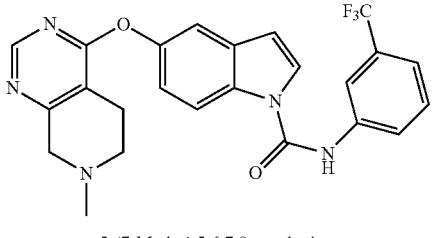<br>5-(7-Methyl-5,6,7,8-tetrahydro-pyrido[3,4-d]pyrimidin-4-yloxy)-indole-1-carboxylic acid (3-trifluoromethyl-phenyl)-amide | (MeOD) δ ppm 8.39 (s, 1H), 8.33 (d, J = 9.1 Hz, 1H), 8.06 (s, 1H), 7.93 (d, J = 3.5 Hz, 1H), 7.90 (d, J = 9.9 Hz, 1H), 7.57 (t, J = 8.0 Hz, 1H), 7.44 (d, J = 7.1 Hz, 1H), 7.40 (d, J = 2.3 Hz, 1H), 7.11 (dd, J = 9.0, 2.4 Hz, 1H), 6.74 (d, J = 3.5 Hz, 1H), 3.64 (s, 2H), 2.98 (t, J = 5.8 Hz, 2H), 2.83-2.90 (m, 2H), 2.54 (s, 3H). | 468.0 |

| Structure/Chemical Name | ¹H NMR (400 MHz) | MS (ESI) m/z (M + 1) |
|---|---|---|
| 37-F ![structure] 5-(7-Ethyl-5,6,7,8-tetrahydro-pyrido[3,4-d]pyrimidin-4-yloxy)-4-fluoro-2-methyl-indole-1-carboxylic acid (3-trifluoromethyl-phenyl)-amide | (MeOD) δ ppm 8.38 (s, 1H) 8.07 (s, 1H) 7.87 (d, J = 8.08 Hz, 1H) 7.59 (t, J = 8.08 Hz, 1 H) 7.48 (m, 2H) 7.06 (dd, J = 8.72, 7.45 Hz, 1 H) 6.51 (s, 1H) 3.68 (s, 2H) 2.97 (d, J = 5.81 Hz, 2H) 2.91 (d, J = 5.31 Hz, 2H) 2.70 (q, J = 7.07 Hz, 2H) 2.61 (s, 3H) 1.23 (t, J = 7.33 Hz, 3H) | 513.2 |

EXAMPLE 38

38-A. 5-[6-(4-Amino-piperidin-1-ylmethyl)-pyrimidin-4-yloxy]-indole-1-carboxylic acid-(3-trifluoromethyl-phenyl)-amide

38-B. 5-[6-(4-Acetylamino-piperidin-1-ylmethyl)-pyrimidin-4-yloxy]-indole-1-carboxylic acid (3-trifluoromethyl-phenyl)-amide

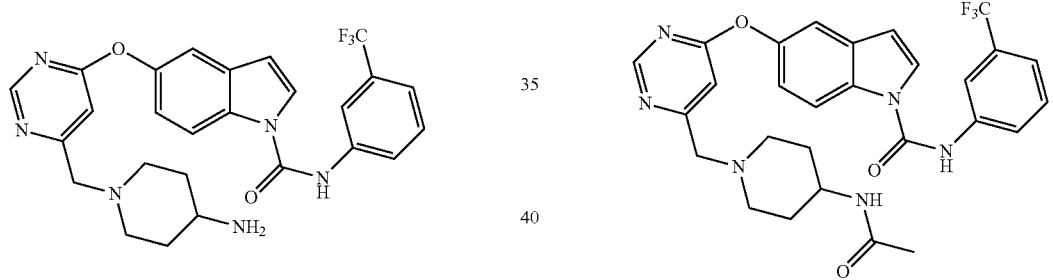

To a solution of methanesulfonic acid 6-[1-(3-trifluoromethyl-phenylcarbamoyl)-1H-indol-5-yloxy]-pyrimidin-4-ylmethyl ester, Example 18-B, (0.6 g, 1.19 mmol) in THF (8 mL) and DMF (8 mL) is added tert-butyl piperidin-4-ylcarbamate (0.713 g, 3.56 mmol) followed by DIEA (0.62 mL, 3.56 mmol) and sodium iodide (0.534 g, 3.56 mmol). The solution is stirred at it for 2.5 h. before being partitioned between EtOAc and sat aq NaHCO₃. The layers are separated and the organic layer is washed further with brine and then dried over Na₂SO₄, filtered and concentrated. After concentration the residue is separated by FCC (20-80% EtOAc/heptane). The product is then treated with 50% TFA in DCM at it for 1 h. After concentration, the residue is purified by semi-prep HPLC (20-55% CAN/H₂O with 0.1% NH₄OH) to provide the title compound. MS (ESI) m/z 511.1 (M+1); ¹H NMR (400 MHz, DMSO-d₆) δ ppm 8.66 (s, 1 H), 8.29 (d, J=9.0 Hz, 1 H), 8.16 (d, J=3.7 Hz, 1 H), 8.11 (s, 1H), 7.98 (d, J=8.2 Hz, 1 H), 7.65 (t, J=8.0 Hz, 1 H), 7.46-7.54 (m, 2 H), 7.16 (dd, J=8.9, 2.3 Hz, 1 H), 7.03 (s, 1 H), 6.80 (d, J=3.7 Hz, 1 H), 3.57 (s, 2 H), 2.74-2.90 (m, 3 H), 2.11 (t, J=10.8 Hz, 2 H), 1.78 (d, J=12.4 Hz, 2 H), 1.31-1.51 (m, 2 H).

To a solution of 5-[6-(4-amino-piperidin-1-ylmethyl)-pyrimidin-4-yloxy]-indole-1-carboxylic acid-(3-trifluoromethyl-phenyl)-amide (0.159 g, 0.312 mmol) in THF (2 mL) and DCM (2 mL) at 0° C. is added DIEA (0.163 mL, 0.935 mmol) and acetyl chloride (29 uL, 0.405 mmol). The reaction is stirred at 0° C. for 2.5 h before being partitioned between EtOAc and sat aq NaHCO₃. The layers are separated and the organic layer is washed further with brine and then dried over Na₂SO₄. After concentration the residue is taken up in THF (8 mL) and MeOH (8 mL) and treated with K₂CO₃ at rt for 0.5 h. The mixture is then filtered and concentrated. The residue is then separated by semi-prep HPLC (20-50% I/H₂O with 0.1% NH₄OH) to provide the title compound.

MS (ESI) m/z 553.2 (M+1); ¹H NMR (400 MHz, DMSO-d₆) δ ppm 8.66 (d, J=1.0 Hz, 1 H), 8.49-8.61 (m, 1 H), 8.12 (d, J=3.5 Hz, 1 H), 8.04 (s, 1 H), 7.69-7.83 (m, 2 H), 7.37-7.51 (m, 2 H), 7.14-7.26 (m, 1 H), 7.04 (d, J=9.1 Hz, 1 H), 6.96 (s, 1 H), 6.55-6.63 (m, 1 H), 3.44-3.59 (m, 3 H), 2.72-2.82 (m, 2 H), 2.06-2.18 (m, 2 H), 1.76 (s, 3 H), 1.63-1.73 (m, 2 H), 1.27-1.42 (m, 2 H), 1.24 (s, 1 H).

The following compounds are prepared with similar method.

38-C. 5-{6-[4-(Cyclopropanecarbonyl-amino)-piperidin-1-ylmethyl]-pyrimidin-4-yloxy}-indole-1-carboxylic acid (3-trifluoromethyl-phenyl)-amide

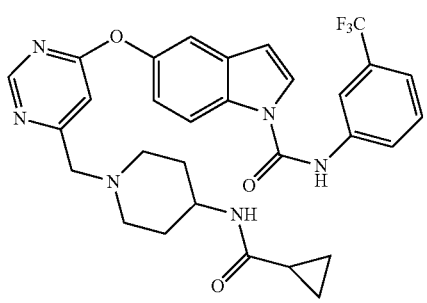 [SMILES: O=C(NC1CCN(Cc2cc(Oc3ccc4c(ccn4C(=O)Nc4cccc(C(F)(F)F)c4)c3)ncn2)CC1)C1CC1]

MS (ESI) m/z 579.1 (M+1); ¹H NMR (400 MHz, DMSO-d₆) δ ppm 8.66 (s, 1 H), 8.29 (d, J=8.8 Hz, 1H), 8.14 (d, J=3.5 Hz, 1 H), 8.10 (s, 1 H), 7.96 (t, J=8.6 Hz, 2 H), 7.65 (t, J=8.0 Hz, 1 H), 7.47-7.53 (m, 2 H), 7.17 (dd, J=9.0, 2.4 Hz, 1 H), 7.04 (s, 1 H), 6.81 (d, J=3.5 Hz, 1 H), 3.48-3.62 (m, 3 H), 2.80 (d, J=11.1 Hz, 2 H), 2.14 (t, J=10.7 Hz, 2 H), 1.72 (d, J=12.4 Hz, 2 H), 1.47-1.57 (m, 1H), 1.33-1.48 (m, 2 H), 0.55-0.68 (m, 4 H).

EXAMPLE 39

5-[6-(4-Methanesulfonylamino-piperidin-1-ylmethyl)-pyrimidin-4-yloxy]-indole-1-carboxylic acid (3-trifluoromethyl-phenyl)-amide

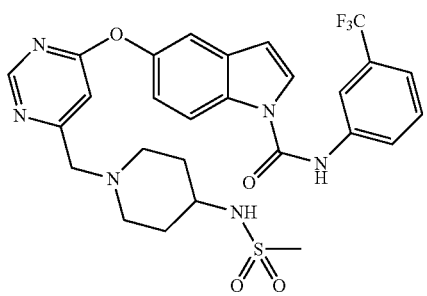 [SMILES: CS(=O)(=O)NC1CCN(Cc2cc(Oc3ccc4c(ccn4C(=O)Nc4cccc(C(F)(F)F)c4)c3)ncn2)CC1]

Prepared in similar manner as described for Example 35. MS (ESI) m/z 589.1 (M+1); ¹H NMR (400 MHz, DMSO-d₆) δ ppm 8.66 (d, J=1.0 Hz, 1 H), 8.33-8.58 (m, 1 H), 8.12 (d, J=3.8 Hz, 1 H), 8.05 (s, 1 H), 7.74-7.93 (m, 1 H), 7.36-7.60 (m, 2 H), 7.01-7.13 (m, 2 H), 6.99 (s, 1 H), 6.56-6.74 (m, 1 H), 3.54 (s, 2 H), 3.04-3.21 (m, 1 H), 2.90 (s, 3 H), 2.72-2.84 (m, 2 H), 2.06-2.20 (m, 2 H), 1.74-1.87 (m, 2 H), 1.36-1.54 (m, 2 H).

EXAMPLE 40

5-[7-(3-Diethylamino-propionyl)-5,6,7,8-tetrahydro-pyrido[3,4-d]pyrimidin-4-yloxy]-indole-1-carboxylic acid (3-trifluoromethyl-phenyl)-amide

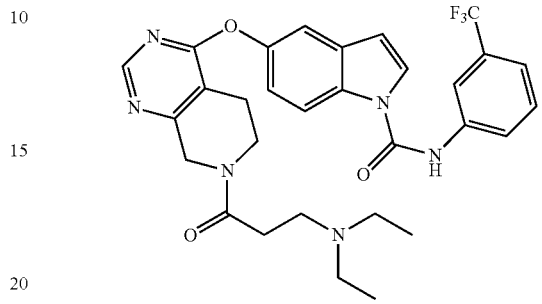

To a solution of 5-(5,6,7,8-tetrahydro-pyrido[3,4-a]pyrimidin-4-yloxy)-indole-1-carboxylic acid (3-trifluoromethyl-phenyl)-amide, Example 31-C, (120 mg, 0.26 mmol), HATU (198 mg, 0.52 mmol), DIEA (0.2 mL, 1.30 mmol) and DMF (5 mL) is added 3-diethylamino-propionic acid hydrochloride (47 mg, 0.26 mmol). After stirring at rt for 2 h the contents of the flask are partitioned between DCM and 10% aqueous LiCl. Organic layer is removed, dried over anhydrous Na₂SO₄ and concentrated in vacuo. The residue is then separated via semi-prep HPLC (C18; 10-100% I/H₂O with 0.1% NH₄OH) to give the title compound. MS (ESI) m/z 581.2 (M+1); ¹H NMR (400 MHz, MeOD) δ ppm 8.40-8.48 (m, 1 H), 8.33 (d, J=8.8 Hz, 1 H), 8.06 (s, 1 H), 7.94 (d, J=3.5 Hz, 1 H), 7.89 (d, J=8.6 Hz, 1 H), 7.57 (t, J=8.1 Hz, 1 H), 7.36-7.47 (m, 2 H), 7.10 (dd, J=9.0, 2.1 Hz, 1 H), 6.74 (d, J=3.8 Hz, 1 H), 4.71-4.79 (m, 2 H), 3.85-4.05 (m, 2 H), 3.20 (d, J=5.8 Hz, 2 H), 2.84-3.08 (m, 8 H), 1.23 (q, J=7.1 Hz, 6 H).

EXAMPLE 41

41-A. {4-[1-(3-Trifluoromethyl-phenylcarbamoyl)-1H-indol-5-yloxy]-5,8-dihydro-6H-pyrido[3,4d]pyrimidin-7-yl}-acetic acid tert-butyl ester

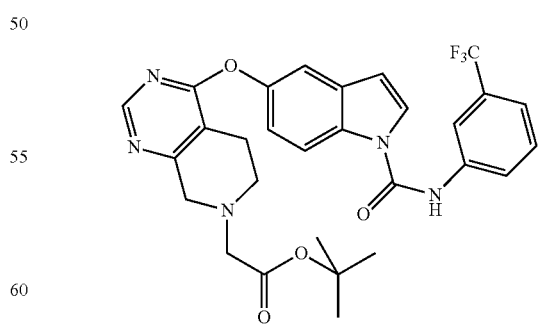

A solution of 5-(5,6,7,8-tetrahydro-pyrido[3,4-a]pyrimidin-4-yloxy)-indole-1-carboxylic acid (3-trifluoromethyl-phenyl)-amide, Example 33-C, (250 mg, 0.55 mmol), bromo tert-butylacetate (204 μL, 1.38 mmol), TEA (384 μL, 2.76 mmol) and ACN (5 mL) is stirred at room temperature. Following completion of the reaction the contents of the flask are partitioned between DCM and brine. Organic layer is dried over anhydrous Na₂SO₄, concentrated, and the residue is separated via FCC (50-100% EtOAc/heptane) to give the title compound. MS (ESI) m/z 568.1 (M+1).

41-B. {4-[1-(3-Trifluoromethyl-phenylcarbamoyl)-1H-indol-5-yloxy]-5,8-dihydro-6H-pyrido[3,4-d]pyrimidin-7-yl}-acetic acid

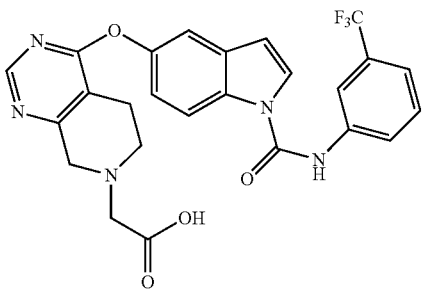 [SMILES: O=C(O)CN1CCc2c(ncnc2Oc2ccc3c(ccn3C(=O)Nc3cccc(C(F)(F)F)c3)c2)C1]

A solution of {4-[1-(3-trifluoromethyl-phenylcarbamoyl)-1H-indol-5-yloxy]-5,8-dihydro-6H-pyrido[3,4-d]pyrimidin-7-yl}-acetic acid tert-butyl ester (250 mg, 0.44 mmol), DCM (5 mL), and TFA (5 mL) is stirred at rt for 1 h. The solution is concentrated in vacuo and separated via semi-prep HPLC (C18; 10-100% I/H₂O with 0.1% NH₄OH) to give the title compound. MS (ESI) m/z 512.0 (M+1); ¹H NMR (400 MHz, MeOD) δ ppm 8.41 (s, 1 H), 8.33 (d, J=9.1 Hz, 1 H), 8.06 (s, 1 H), 7.93 (d, J=3.5 Hz, 1 H), 7.89 (s, 1 H), 7.57 (t, J=8.1 Hz, 1 H), 7.38-7.47 (m, 2 H), 7.12 (dd, J=9.0, 2.4 Hz, 1 H), 6.74 (d, J=3.5 Hz, 1 H), 4.08 (s, 2 H), 3.56 (s, 2 H), 3.26 (t, J=6.1 Hz, 2 H), 3.07 (t, J=5.7 Hz, 2 H).

41-C. 5-(7-Methylcarbamoylmethyl-5,6,7,8-tetrahydro-pyrido[3,4-d]pyrimidin-4-yloxy)-indole-1-carboxylic acid (3-trifluoromethyl-phenyl)-amide

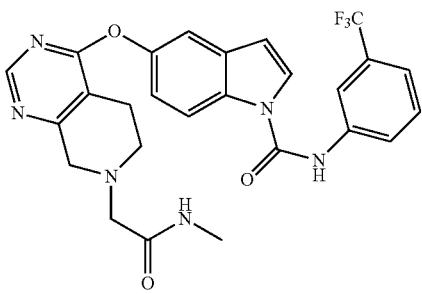 [SMILES: CNC(=O)CN1CCc2c(ncnc2Oc2ccc3c(ccn3C(=O)Nc3cccc(C(F)(F)F)c3)c2)C1]

A combination of {4-[1-(3-trifluoromethyl-phenylcarbamoyl)-1H-indol-5-yloxy]-5,8-dihydro-6H-pyrido[3,4-d]pyrimidin-7-yl}-acetic acid (246 mg, 0.48 mmol), HATU (366 mg, 0.56 mmol), DIEA (0.4 mL, 2.41 mmol) methylamine (201 µL, 0.48 mmol, 2.0 M THF solution) and DMF (10 mL) is stirred in a sealed tube at rt for 2 h. Reaction is partitioned between DCM and 10% aqueous LiCl. Organic layer is then dried over anhydrous Na₂SO₄, concentrated, and the residue separated via semi-prep HPLC (C18; 10-100% I/H₂O with 0.1% TFA). The pooled fractions are diluted with saturated aqueous NaHCO₃ and extracted with EtOAc. Drying of the organic layer over Na₂SO₄, followed by filtration and concentration provided the title compound. MS (ESI) m/z 525.0 (M+1); ¹H NMR (400 MHz, MeOD) δ ppm 8.38 (s, 1 H), 8.33 (d, J=8.8 Hz, 1 H), 8.06 (s, 1 H), 7.94 (d, J=3.5 Hz, 1 H), 7.91 (s, 1 H), 7.57 (t, J=8.0 Hz, 1 H), 7.44 (d, J=7.8 Hz, 1 H), 7.40 (d, J=2.3 Hz, 1 H), 7.10 (dd, J=8.8, 2.3 Hz, 1 H), 6.74 (d, J=3.5 Hz, 1 H), 3.75 (s, 2 H), 3.00 (d, J=5.3 Hz, 2 H), 2.90-2.96 (m, 2 H), 2.80 (s, 3 H).

EXAMPLE 42

42-A. 4-Oxo-3,5,7,8-tetrahydro-4H-pyrido[4,3-d]pyrimidine-6-carboxylic acid tert-butyl ester

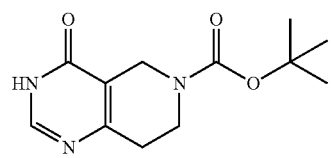 [SMILES: CC(C)(C)OC(=O)N1CCc2nc[nH]c(=O)c2C1]

6-Benzyl-5,6,7,8-tetrahydro-3H-pyrido[4,3-d]pyrimidin-4-one (36.9 g, 153 mmol) and BOC anhydride (40.1 g, 184 mmol) are taken up in MeOH (600 mL). The vessel is purged with argon and palladium on carbon (10% w/w; wet) (5.0 g) is added. The contents are then stirred under a hydrogen atmosphere (1 atm) for 18 h. At that time the suspension is filtered over Celite® and the solution concentrated to give the title compound. MS (ESI) m/z 252.0 (M+1).

42-B. 4-Chloro-7,8-dihydro-5H-pyrido[4,3-d]pyrimidine-6-carboxylic acid tert-butyl ester

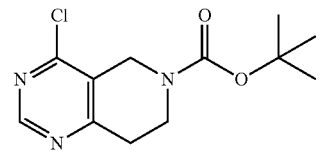 [SMILES: CC(C)(C)OC(=O)N1CCc2ncnc(Cl)c2C1]

Triphenylphosphine (12.8 g, 48.7 mmol) is added to a solution of Example 42-A (6.08 g, 24.1 mmol), CCl₄ (7.0 mL, 72.3 mmol), and 1,2-dichloroethane (250 mL). The solution is then warmed to 70° C. After 2.5 h the solution is concentrated in vacuo to about 50 mL. The residue is then separated via FCC (10-30% EtOAc/heptane) to give the title compound. MS (ESI) m/z 270.0 & 271.9 (M+1).

42-C. 4-(1H-Indol-5-yloxy)-7,8-dihydro-5H-pyrido[4,3-d]pyrimidine-6-carboxylic acid tert-butyl ester

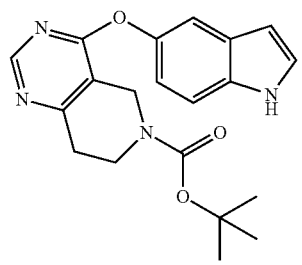 [SMILES: CC(C)(C)OC(=O)N1CCc2ncnc(Oc3ccc4[nH]ccc4c3)c2C1]

To a solution of Example 42-B (0.250 g, 0.926 mmol), 5-hydroxyindole (0.160 g, 1.20 mmol) and CH₃CN (5 mL) is added DBU (0.18 mL, 1.20 mmol). The mixture is then warmed to 50° C. for 3 h. At that time the solvent is removed in vacuo and the residue separated via FCC (10-50% EtOAc/heptane) to give the title compound. MS (ESI) m/z 367.1 (M+1).

42-D. 4-[1-(3-Trifluoromethyl-phenylcarbamoyl)-1H-indol-5-yloxy]-7,8-dihydro-5H-pyrido[4,3-d]pyrimidine-6-carboxylic acid tert-butyl ester

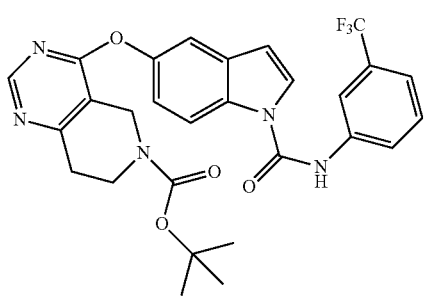 [SMILES: CC(C)(C)OC(=O)N1CCc2ncnc(Oc3ccc4c(ccn4C(=O)Nc4cccc(C(F)(F)F)c4)c3)c2C1]

Sodium hydride (0.030 g, 0.749 mmol, 60% in mineral oil) is added to a solution of Example 42-C (0.183 g, 0.499 mmol) and THF (5 mL) at 0° C. After 15 min 3-(trifluoromethyl)-phenyl isocyanate (0.14 mL, 0.0.998 mmol) is added. After an additional 1.5 h the contents of the flask are poured into pH 7 buffer (50 mL) and extracted with DCM (2×25 mL). The combined organic layers are then dried (Na₂SO₄), filtered and concentrated. The crude residue is then separated via FCC (20-50% EtOAc/heptane). MS (ESI) m/z 554.0 (M+1).

42-E. 5-(5,6,7,8-Tetrahydro-pyrido[4,3-d]pyrimidin-4-yloxy)-indole-1-carboxylic acid (3-trifluoromethyl-phenyl)-amide

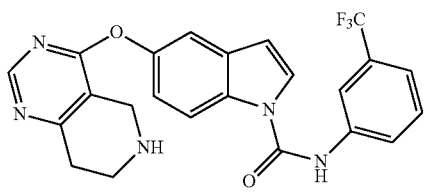 [SMILES: O=C(Nc1cccc(C(F)(F)F)c1)n1ccc2cc(Oc3ncnc4c3CNCC4)ccc21]

TFA (1 mL) is added to a solution of Example 42-D (0.136 g, 0.245 mmol) and DCM (5 mL). After 1 h the solution is concentrated in vacuo. The residue is taken up in MeOH and neutralized to pH 7 by the addition of NH₄OH and then separated via semi-prep HPLC (10-90% I/H₂O with 0.1% NH₄OH) to give the title compound. MS (ESI) m/z 454.0 (M+1); ¹H NMR (400 MHz, DMSO-d₆) δ ppm 10.38 (s, 1 H), 8.46 (s, 1 H), 8.27 (d, J=9.1 Hz, 1 H), 8.12 (d, J=3.8 Hz, 1 H), 8.10 (s, 1 H), 7.97 (d, J=8.1 Hz, 1H), 7.65 (t, J=8.0 Hz, 1 H), 7.50 (d, J=7.3 Hz, 1 H), 7.46 (s, 1 H), 7.12 (dd, J=9.0, 2.4 Hz, 1 H), 6.80 (d, J=3.5 Hz, 1 H), 3.92-4.09 (m, 2 H), 3.17 (t, J=5.7 Hz, 2 H), 2.81 (t, J=5.7 Hz, 2 H).

EXAMPLE 43

43-A. 5-(6-Methyl-5,6,7,8-tetrahydro-pyrido[4,3-d]pyrimidin-4-yloxy)-indole-1-carboxylic acid (3-trifluoromethyl-phenyl)-amide

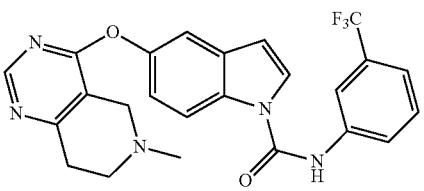 [SMILES: CN1CCc2ncnc(Oc3ccc4c(ccn4C(=O)Nc4cccc(C(F)(F)F)c4)c3)c2C1]

5-(5,6,7,8-Tetrahydro-pyrido[4,3-d]pyrimidin-4-yloxy)-indole-1-carboxylic acid (3-trifluoromethyl-phenyl)-amide (Example 42-E, 125 mg, 0.28 mmol), paraformaldehyde (16.6 mg, 0.55 mmol), NaBH(OAc)₃ (117 mg, 0.55 mmol) and acetic acid (32 uL, 0.55 mmol) are dissolved in 1,2-DCE (7.5 mL) and heated at 60° C. for 4 h. The reaction mixture is then partitioned between DCM and saturated aqueous NaHCO₃. The organic layer is then dried over anhydrous Na₂SO₄ and concentrated in vacuo. The crude residue is separated via FCC (MeOH/EtOAc 1:9 to MeOH/EtOAc 2:8) to give the title compound. MS (ESI) m/z 468.0 (M+1); ¹H NMR (400 MHz, MeOD) δ ppm 8.41 (s, 1 H), 8.33 (d, J=8.8 Hz, 1 H), 8.06 (s, 1 H), 7.93 (d, J=3.5 Hz, 1 H), 7.90 (d, J=9.3 Hz, 1 H), 7.57 (t, J=8.0 Hz, 1 H), 7.44 (d, J=7.6 Hz, 1 H), 7.41 (d, J=2.3 Hz, 1 H), 7.11 (dd, J=9.0, 2.4 Hz, 1 H), 6.74 (d, J=3.8 Hz, 1 H), 3.74 (s, 2 H), 2.96-3.04 (m, 2 H), 2.87-2.94 (m, 2 H), 2.57 (s, 3 H).

The following compounds are prepared with similar method.

43-B. 5-(6-Ethyl-5,6,7,8-tetrahydro-pyrido[4,3-d]pyrimidin-4-yloxy)-indole-1-carboxylic acid (3-trifluoromethyl-phenyl)-amide

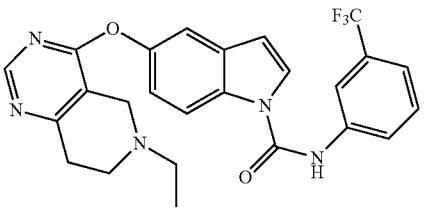 [SMILES: CCN1CCc2ncnc(Oc3ccc4c(ccn4C(=O)Nc4cccc(C(F)(F)F)c4)c3)c2C1]

A mixture of 5-(5,6,7,8-tetrahydro-pyrido[4,3-a]pyrimidin-4-yloxy)-indole-1-carboxylic acid (3-trifluoromethyl-phenyl)-amide (Example 42-E, 125 mg, 0.28 mmol), acetaldehyde (31 μL, 0.55 mmol), NaBH(OAc)₃ (117 mg, 0.55 mmol) and TEA (77 uL, 0.55 mmol) in 1,2-DCE at rt for 4 h. The mixture is then partitioned between DCM and saturated aqueous NaHCO₃. The organic layer is dried over anhydrous Na₂SO₄ and concentrated in vacuo. The crude residue is then separated via FCC (MeOH/EtOAc 1:9 to MeOH/EtOAc 2:8) to give the title compound (74 mg, 55%). MS (ESI) m/z 482.1 (M+1); ¹H NMR (400 MHz, MeOD) δ ppm 8.57 (s, 1 H), 8.36 (d, J=9.1 Hz, 1 H), 8.07 (s, 1 H), 7.97 (d, J=3.8 Hz, 1 H), 7.89

(d, J=8.5 Hz, 1 H), 7.58 (t, J=8.1 Hz, 1 H), 7.42-7.48 (m, 2 H), 7.13 (dd, J=9.0, 2.4 Hz, 1 H), 6.76 (d, J=3.8 Hz, 1 H), 3.43-3.54 (m, 3 H), 3.26 (br. S., 3 H), 1.51 (t, J=7.3 Hz, 3 H).

EXAMPLE 44

44-A. 4-Oxo-3,4,5,7-tetrahydro-pyrrolo[3,4-d]pyrimidine-6-carboxylic acid tert-butyl ester

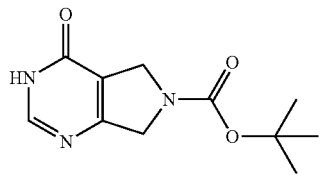

To a solution of 4-oxo-pyrrolidine-1,3-dicarboxylic acid 1-tert-butyl ester 3-ethyl ester (2 g, 7.8 mmol) in EtOH (78 mL), fomamidine hydrochloride (1.87 g, 25.5 mmol) is added, followed by NaOEt (8.7 mL, 27.2 mmol). The reaction is heated at 90° C. for 2 h. The reaction mixture is then evaporated and a saturated solution of ammonium chloride (20 mL) is added followed by DCM (80 mL). The layers are separated and the aqueous layer is extracted further with DCM (50 mL×3). The organics are combined, dried and evaporated to give the crude product. The title compound is purified using silica gel FCC (gradient elution 100% DCM to 94% DCM/6% MeOH). MS (ESI) m/z 238.2 (M+1).

44-B. 4-(1H-Indol-5-yloxy)-5,7-dihydro-pyrrolo[3,4-d]pyrimidine-6-carboxylic acid tert-butyl ester

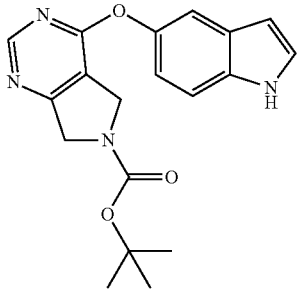 [SMILES: CC(C)(C)OC(=O)N1Cc2ncnc(Oc3ccc4[nH]ccc4c3)c2C1]

To a solution of 4-oxo-3,4,5,7-tetrahydro-pyrrolo[3,4-d]pyrimidine-6-carboxylic acid tert-butyl ester (74 mg, 0.31 mmol) in acetonitrile (3 mL), BOP (179 mg, 0.405 mmol) is added followed by DBU (0.094 mL, 0.624 mmol). After 20 min 5-hydroxyindole (83 mg, 0.624 mmol) is added. The reaction is left stirring at rt for 3 h. The reaction mixture is evaporated and the crude product is purified using silica gel FCC (gradient elution 100% heptane to 60% heptane/40% ethyl acetate) to give the title compound. MS (ESI) m/z 353.1 (M+1).

The following compounds are prepared with similar method.

44-C. 4-(4-Fluoro-2-methyl-1H-indol-5-yloxy)-5,7-dihydro-pyrrolo[3,4-d]pyrimidine-6-carboxylic acid tert-butyl ester

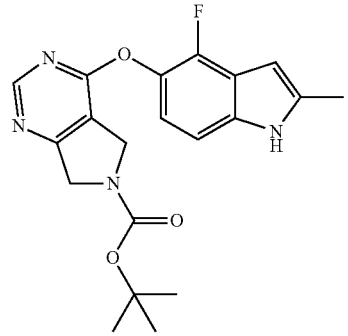 [SMILES: Cc1cc2c(F)c(Oc3ncnc4c3CN(C(=O)OC(C)(C)C)C4)ccc2[nH]1]

MS (ESI) m/z 385.9 (M+1).

44-D. 4-(4-Fluoro-1H-indol-5-yloxy)-5,7-dihydro-pyrrolo[3,4-d]pyrimidine-6-carboxylic acid tert-butyl ester

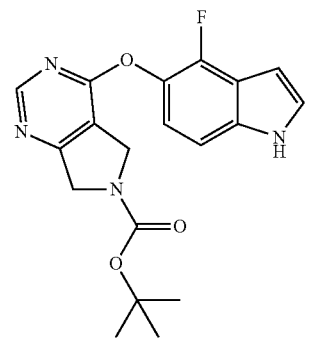 [SMILES: CC(C)(C)OC(=O)N1Cc2ncnc(Oc3ccc4[nH]ccc4c3F)c2C1]

Method carried out as above (Example 44-B) using PyBOP in place of BOP. MS (ESI) m/z 369.1 (M−1).

44-E. 4-(2-Methyl-1H-indol-5-yloxy)-5,7-dihydro-pyrrolo[3,4-d]pyrimidine-6-carboxylic acid tert-butyl ester

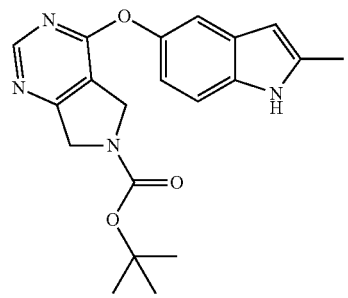 [SMILES: Cc1cc2cc(Oc3ncnc4c3CN(C(=O)OC(C)(C)C)C4)ccc2[nH]1]

Method carried out as above (Example 44-B) using PyBOP in place of BOP. MS (ESI) m/z 365.1 (M−1).

EXAMPLE 45

45-A. 4-[1-(3-Trifluoromethyl-phenylcarbamoyl)-1H-indol-5-yloxy]-5,7-dihydro pyrrolo[3,4-d]pyrimidine-6-carboxylic acid tert-butyl ester

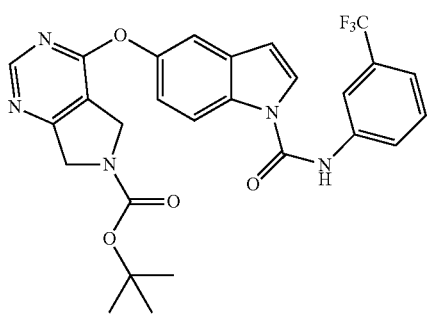 [SMILES: CC(C)(C)OC(=O)N1Cc2ncnc(Oc3ccc4c(ccn4C(=O)Nc4cccc(C(F)(F)F)c4)c3)c2C1]

To a solution of 4-(1H-indol-5-yloxy)-5,7-dihydro-pyrrolo[3,4-d]pyrimidine-6-carboxylic acid tert-butyl ester (3.59 g, 10.2 mmol) in THF (100 mL) at 0° C., NaH (0.611 g, 15.3 mmol) is added. After 10 min, 1-isocyanato-3-trifluoromethyl-benzene (2.93 mL, 20.4 mmol) is added and the reaction is allowed to reach room temperature. After 2.5 h, a saturated solution of $NH_4Cl$ in water (50 mL) is added. The mixture is extracted with EtOAc (×3), and the combined organic extracts are dried and evaporated to give the crude 4-[1-(3-trifluoromethyl-phenylcarbamoyl)-1H-indol-5-yloxy]-5,7-dihydro pyrrolo[3,4-d]pyrimidine-6-carboxylic acid tert-butyl ester. MS (ESI) m/z 540.9 (M+1).

45-B. 5-(6,7-Dihydro-5H-pyrrolo[3,4-d]pyrimidin-4-yloxy)-indole-1-carboxylic acid (3-trifluoromethyl phenyl)-amide

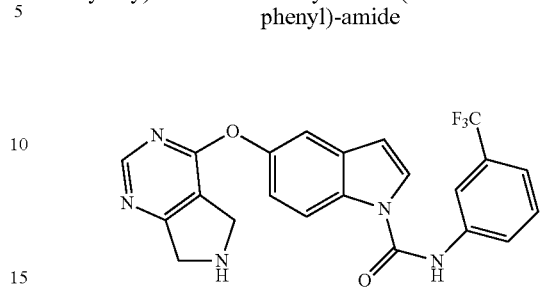

To a solution of 4-[1-(3-trifluoromethyl-phenylcarbamoyl)-1H-indol-5-yloxy]-5,7-dihydro pyrrolo[3,4-d]pyrimidine-6-carboxylic acid tert-butyl ester in DCM (20 mL), TFA (20 mL, 260 mmol) is added at 0° C. The reaction is allowed to reach room temperature and stirred for an additional 1 h. TFA/DCM are evaporated and then the product is taken up in EtOAc (100 mL) and washed with dilute $NH_4OH$ in $H_2O$ (20 mL). The organic layer is separated and the water layer is extracted further with EtOAc (2×). The combined organics are dried and evaporated. The crude residue is separated via FCC (eluted with DCM/MeOH/$NH_4OH$ (100:0:0 to 93:6:1)) to give 5-(6,7-dihydro-5H-pyrrolo[3,4-d]pyrimidin-4-yloxy)-indole-1-carboxylic acid (3-trifluoromethyl phenyl)-amide. MS (ESI) m/z 440.9 (M+1); $^1$H NMR (400 MHz, MeOD) δ ppm 8.55 (s, 1 H) 8.33 (d, J=8.84 Hz, 1 H) 8.06 (br. S., 1 H) 7.89 (d, J=8.34 Hz, 1 H) 7.94 (d, J=3.54 Hz, 1 H) 7.57 (t, J=7.96 Hz, 1H) 7.41-7.46 (m, 2 H) 7.13 (dd, J=9.09, 2.27 Hz, 1 H) 6.74 (d, J=3.03 Hz, 1 H) 4.26 (d, J=12.13 Hz, 4 H).

The following compounds are prepared with similar method.

| | Structure/Chemical Name | $^1$H NMR (400 MHz) | MS (ESI) m/z (M + 1) |
|---|---|---|---|
| 45-C | ![structure]<br>6,7-Dihydro-5H-pyrrolo[3,4-d]pyrimidin-4-yloxy)-4-fluoro-2-methyl-indole-1-carboxylic acid (4-fluoro-3-trifluoromethyl-phenyl)-amide | (MeOD) δ ppm 8.55 (s, 1H) 8.08 (dd, J = 6.32, 2.78 Hz, 1H) 7.91 (dt, J = 9.03, 3.44 Hz, 1H) 7.49 (d, J = 8.84 Hz, 1H) 7.37 (t, J = 9.60 Hz, 1H) 7.08 (dd, J = 8.84, 7.33 Hz, 1 H), 6.50 (s, 1H) 4.48 (br. S., 2H) 4.37 (br. S., 2H) 2.60 (d, J = 1.01 Hz, 3H). | 490.9 |
| 45-D | ![structure]<br>6,7-Dihydro-5H-pyrrolo[3,4-d]pyrimidin-4-yloxy)-indole-1-carboxylic acid (4-fluoro-3-trifluoromethyl-phenyl)-amide | (MeOD) δ ppm 8.52 (s, 1H) 8.32 (d, J = 9.09 Hz, 1H) 8.04 (dd, J = 6.19, 2.15 Hz, 1H) 7.91 (d, J = 3.54 Hz, 2H) 7.42 (d, J = 2.02 Hz, 1H) 7.34 (t, J = 9.60 Hz, 1H) 7.11 (dd, J = 8.97, 2.15 Hz, 1H) 6.72 (d, J = 3.54 Hz, 1 H) 4.18 (d, J = 8.84 Hz, 4H). | 458.9 |

| | Structure/Chemical Name | $^1$H NMR (400 MHz) | MS (ESI) m/z (M + 1) |
|---|---|---|---|
| 45-E | 6,7-Dihydro-5H-pyrrolo[3,4-d]pyrimidin-4-yloxy)-4-fluoro-2-methyl-indole-1-carboxylic acid (3-trifluoromethyl-phenyl)-amide | (MeOD) δ ppm 8.57 (s, 1H) 8.09 (s, 1H) 7.87 (d, J = 8.08 Hz, 1H) 7.59 (t, J = 7.96 Hz, 1H) 7.45-7.51 (m, 2H) 7.10 (dd, J = 8.72, 7.45 Hz, 1H) 6.52 (s, 1H) 4.53 (br. S., 2H) 4.41 (br. S., 2H) 2.61 (s, 3H). | 472.0 |
| 45-F | 5-(6,7-Dihydro-5H-pyrrolo-[3,4-d]pyrimidin-4-yloxy)-indole-1-carboxylic acid (3-fluoro-trifluoromethyl-phenyl)-amide | (DMSO-d$_6$) δ ppm 8.56 (s, 1H) 8.27 (d, J = 8.84 Hz, 1H) 8.10 (d, J = 3.54 Hz, 1H) 7.88-7.93 (m, 2H) 7.49 (d, J = 2.02 Hz, 1 H) 7.41-7.45 (m, 1H) 7.14-7.18 (m, 1H) 6.81 (br. S., 1H) 4.08 (s, 4H). | 458.9 |
| 45-G | 5-(6,7-Dihydro-5H-pyrrolo[3,4-d]pyrimidin-4-yloxy)-indole-1-carboxylic acid (2-fluoro-3-trifluoromethyl-phenyl)-amide | (DMSO-d$_6$) δ ppm 8.56 (s, 1H) 8.24 (d, J = 9.09 Hz, 1H) 8.09 (d, J = 3.54 Hz, 1H) 7.89-8.01 (m, 1H) 7.66-7.73 (m, 1H) 7.45-7.58 (m, 2H) 7.15 (dd, J = 8.97, 2.40 Hz, 1H) 6.81 (d, J = 3.03 Hz, 1H) 4.11 (d, J = 13.89 Hz, 4H). | 458.9 |
| 45-H | 5-(6,7-Dihydro-5H-pyrrolo[3,4-d]pyrimidin-4-yloxy)-indole-1-carboxylic acid (2-fluoro-5-trifluoromethyl-phenyl)-amide | (MeOD) δ ppm 8.53 (s, 1H) 8.30 (d, J = 8.84 Hz, 1H) 8.15-8.20 (m, 1H) 7.88-7.92 (m, 1H) 7.58 (ddd, J = 6.13, 3.98, 2.27 Hz, 1H) 7.39-7.46 (m, 2H) 7.12 (dd, J = 9.09, 2.02 Hz, 1H) 6.74 (d, J = 3.79 Hz, 1 H) 4.19 (d, J = 9.35 Hz, 4H). | 458.9 |
| 45-I | 5-(6,7-Dihydro-5H-pyrrolo[3,4-d]pyrimidin-4-yloxy)-indole-1-carboxylic acid (2-chloro-5-trifluoromethyl-phenyl)-amide | (MeOD) δ ppm 8.53 (s, 1H) 8.30 (d, J = 8.84 Hz, 1H) 8.15-8.20 (m, 1H) 7.88-7.92 (m, 1H) 7.58 (ddd, J = 6.13, 3.98, 2.27 Hz, 1 H) 7.39-7.46 (m, 2H) 7.12 (dd, J = 9.09, 2.02 Hz, 1H) 6.74 (d, J = 3.79 Hz, 1H) 4.19 (d, J = 9.35 Hz, 4H). | 475.9 |

| | Structure/Chemical Name | $^1$H NMR (400 MHz) | MS (ESI) m/z (M + 1) |
|---|---|---|---|
| 45-J | 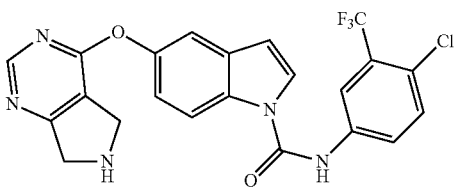<br>5-(6,7-Dihydro-5H-pyrrolo[3,4-d]pyrimidin-4-yloxy)-indole-1-carboxylic acid (4-chloro-3-trifluoromethyl-phenyl)-amide | (MeOD) δ ppm 8.53 (s, 1H) 8.30 (d, J = 8.84 Hz, 1H) 8.15-8.20 (m, 1H) 7.88-7.92 (m, 1H) 7.58 (ddd, J = 6.13, 3.98, 2.27 Hz, 1 H) 7.39-7.46 (m, 2H) 7.12 (dd, J = 9.09, 2.02 Hz, 1H) 6.74 (d, J = 3.79 Hz, 1H) 4.19 (d, J = 9.35 Hz, 4H). | 475.9 |
| 45-K | 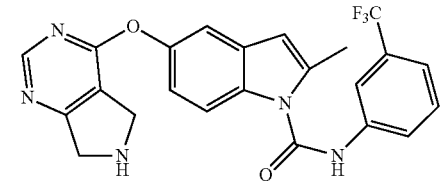 [SMILES: O=C(Nc1cccc(C(F)(F)F)c1)n1ccc2cc(Oc3ncnc4c3CNC4)ccc21]<br>5-(6,7-Dihydro-5H-pyrrolo[3,4-d]pyrimidin-4-yloxy)-2-methyl-indole-1-carboxylic acid (3-trifluoromethyl-phenyl)-amide | (MeOD) δ ppm 8.52 (s, 1H), 8.07 (s, 1H), 7.87 (d, J = 7.83 Hz, 1H), 7.69 (d, J = 8.59 Hz, 1H), 7.59 (t, J = 7.71 Hz, 1H), 7.46 (d, J = 8.08 Hz, 1H), 7.30 (d, J = 2.02 Hz, 1H), 7.02 (dd, J = 8.84, 2.27 Hz, 1H), 6.44 (s, 1 H) 4.18 (br. S., 4H), 2.61 (s, 3H). | 453.9 |
| 45-L | 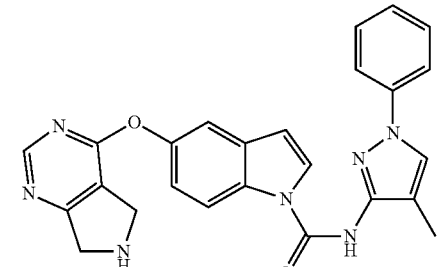<br>5-(6,7-Dihydro-5H-pyrrolo[3,4-d]pyrimidin-4-yloxy)-indole-1-carboxylic acid (5-methyl-1-phenyl-1H-pyrazol-4-yl)-amide | (MeOD) δ ppm 8.56 (s, 1H) 8.33 (d, J = 8.84 Hz, 1H) 7.93 (d, J = 3.54 Hz, 1H) 7.78 (s, 1 H) 7.43-7.59 (m, 6H) 7.12 (dd, J = 8.84, 2.27 Hz, 1H) 6.75 (d, J = 3.54 Hz, 1H) 4.30 (d, J = 12.38 Hz, 4H) 2.31 (s, 3H). | 453.0 |
| 45-M | 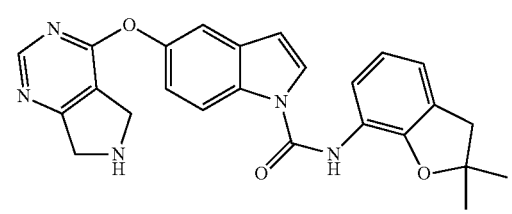<br>5-(6,7-Dihydro-5H-pyrrolo[3,4-d]pyrimidin-4-yloxy)-indole-1-carboxylic acid (2,2-dimethyl-2,3-dihydro-benzofuran-7-yl)-amide. | (DMSO-d$_6$) δ ppm 9.67 (s, 1H) 8.56 (s, 1 H) 8.24 (d, J = 8.84 Hz, 1H) 8.09 (d, J = 3.79 Hz, 1H) 7.47 (d, J = 2.53 Hz, 1H) 7.17 (d, J = 7.58 Hz, 1H) 7.12 (dd, J = 5.81, 3.03 Hz, 1 H) 7.10 (s, 1H) 6.84 (t, J = 7.71 Hz, 1H) 6.75 (d, J = 3.79 Hz, 1H) 4.09 (d, J = 9.35 Hz, 2H) 4.06-4.12 (m, 2H) 3.08 (s, 2H) 1.44 (s, 6H) | 442.1 |

| Structure/Chemical Name | ¹H NMR (400 MHz) | MS (ESI) m/z (M + 1) |
|---|---|---|
| 45-N 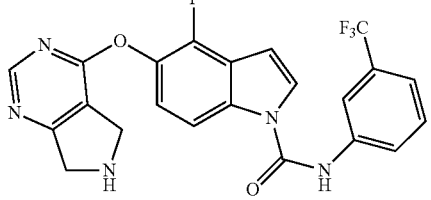<br>6,7-Dihydro-5H-pyrrolo[3,4-d]pyrimidin-4-yloxy)-4-fluoro-indole-1-carboxylic acid (3-trifluoromethyl-phenyl)-amide | (MeOD) δ ppm 8.53 (s, 1H) 8.14 (d, J = 9.09 Hz, 1H) 8.06 (s, 1H) 7.95 (d, J = 3.79 Hz, 1 H) 7.90 (d, J = 7.58 Hz, 1H) 7.58 (t, J = 8.08 Hz, 1H) 7.45 (d, J = 7.58 Hz, 1H) 7.21 (dd, J = 8.84, 7.58 Hz, 1H) 6.83 (d, J = 3.79 Hz, 1 H) 4.33 (s, 2H) 4.21 (t, J = 1.64 Hz, 2H) | 458.1 |
| 45-O 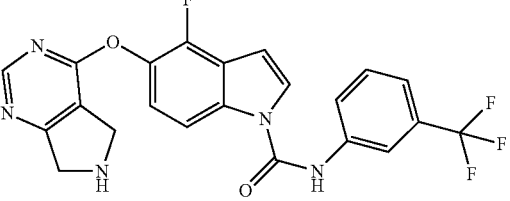<br>6,7-Dihydro-5H-pyrrolo[3,4-d]pyrimidin-4-yloxy)-4-fluoro-indole-1-carboxylic acid (2-fluoro-3-trifluoromethyl-phenyl)-amide | (DMSO-d₆) δ ppm 8.57 (s, 1H) 8.13 (d, J = 3.79 Hz, 1H) 8.08 (d, J = 8.84 Hz, 1H) 7.95 (t, J = 7.58 Hz, 1H) 7.71 (t, J = 7.33 Hz, 1H) 7.49 (t, J = 8.08 Hz, 1H) 7.31 (d, J = 7.83 Hz, 1H) 6.93 (d, J = 3.54 Hz, 1H) 4.23 (s, 2 H) 4.10-4.13 (m, 2H) | 476.1 |

EXAMPLE 46

46-A. 5-(6,7-Dihydro-5H-pyrrolo[3,4-d]pyrimidin-4-yloxy)-indole-1-carboxylic acid (3-methoxy-5 trifluoromethyl-phenyl)-amide

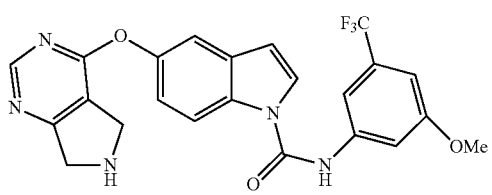 [SMILES: COc1cc(NC(=O)n2ccc3cc(Oc4ncnc5c4CNC5)ccc32)cc(C(F)(F)F)c1]

To a solution of 4-(1H-indol-5-yloxy)-5,7-dihydro-pyrrolo[3,4-d]pyrimidine-6-carboxylic acid tert-butyl ester (158 mg, 0.44 mmol) in DMF (4 mL), CDI (145 mg, 0.89 mmol) is added in one portion, followed by TEA (0.37 mL, 2.7 mmol). After 3 h at rt, 3-methoxy-5-trifluoromethyl-phenylamine (514 mg, 2.7 mmol) and DMAP (5.5 mg, 0.04 mmol) are added and the reaction is left stirring for 40 h. Ethyl acetate (2 mL) is added followed by the addition of 1 N HCl solution (3 mL). The organics are extracted with EtOAc (×3) and concentrated. The crude mixture is dissolved in CH₂Cl₂ (10 mL) and cooled to 0° C. and TFA (10 mL, 130 mmol) is added. The reaction is allowed to reach it over 2 h. The reaction mixture is evaporated, redissolved in EtOAc and few drops of NH₄OH are added to freebase the amine. The solvent is removed and the residue separated by FCC (DCM/MeOH/NH₄OH (100: 0:0 to 93:6:1)) to give 5-(6,7-dihydro-5H-pyrrolo[3,4-d]pyrimidin-4-yloxy)-indole-1-carboxylic acid (3-methoxy-5 trifluoromethyl-phenyl)-amide. MS (ESI) m/z 471.0 (M+1); ¹H NMR (400 MHz, MeOD) δ ppm 8.50-8.56 (m, 1 H) 7.93 (d, J=3.54 Hz, 1 H) 7.59 (d, J=19.71 Hz, 2 H) 7.42 (d, J=2.27 Hz, 1 H) 7.12 (dd, J=8.97, 2.40 Hz, 1 H) 6.96 (s, 1 H) 6.73 (d, J=3.79 Hz, 1 H) 6.52 (s, 1 H) 4.19 (d, J=8.34 Hz, 4 H) 3.76 (s, 3 H)

The following compounds are prepared with similar method.

46-B. 5-(6,7-Dihydro-5H-pyrrolo[3,4-d]pyrimidin-4-yloxy)-indole-1-carboxylic acid (5-trifluoromethyl-2H-pyrazol-3-yl)-amide

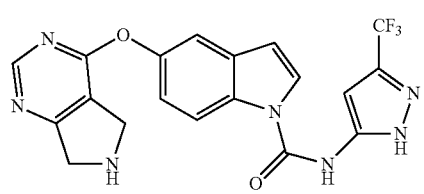 [SMILES: O=C(Nc1cc(C(F)(F)F)n[nH]1)n1ccc2cc(Oc3ncnc4c3CNC4)ccc21]

MS (ESI) m/z 431.9 (M+1) ¹H NMR (400 MHz, MeOD) δ ppm 8.44 (s, 1 H) 8.32 (d, J=9.09 Hz, 1H) 7.78 (d, J=3.54 Hz, 1 H) 7.33 (s, 1 H) 7.05 (d, J=7.33 Hz, 1 H) 6.66 (d, J=3.54 Hz, 1 H) 6.43 (br. S., 1 H) 5.35 (s, 1 H) 4.12 (d, J=13.14 Hz, 4 H).

46-C. 5-(6,7-Dihydro-5H-pyrrolo[3,4-d]pyrimidin-4-yloxy)-indole-1-carboxylic acid (5-tert-butyl-2H-pyrazol-3-yl)-amide

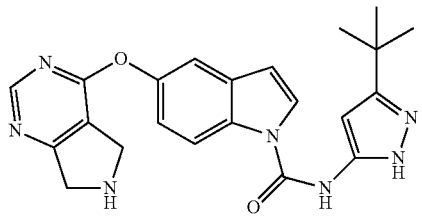 [SMILES: CC(C)(C)c1cc(NC(=O)n2ccc3cc(Oc4ncnc5c4CNC5)ccc32)[nH]n1]

MS (ESI) m/z 418.1 (M+1) ¹H NMR. (400 MHz, MeOD) δ ppm 8.51 (s, 1 H) 8.31 (d, J=9.09 Hz, 1H) 7.87 (d, J=3.54 Hz, 1 H) 7.40 (d, J=2.53 Hz, 1 H) 7.10 (dd, J=8.97, 2.40 Hz, 1 H) 6.69 (d, J=3.54 Hz, 1 H) 6.38 (s, 1 H) 4.17 (d, J=7.07 Hz, 4 H) 1.36 (s, 9 H).

EXAMPLE 47

47-A. (±)-2-Benzylamino-propionic acid ethyl ester

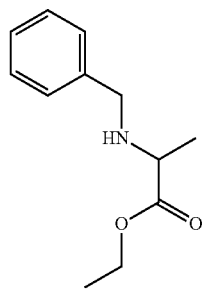

Ethyl alanine hydrochloride (5.5 g, 36.8 mmol), benzaldehyde (7.9 mL, 77.8 mmol), TEA (10.8 mL, 77.8 mmol) and NaBH(Oac)₃ (16.5 g, 77.8 mmol) are taken up in 1,2-DCE (200 mL) and stirred at rt for 4 h. The reaction is then partitioned between DCM and saturated aqueous NaHCO₃. The organic layer is removed, dried over anhydrous Na₂SO₄, and concentrated in vacuo. The crude residue is used without further purification. MS (ESI) m/z 208.2 (M+1).

47-B. (±)-4-[Benzyl-(1-ethoxycarbonyl-ethyl)-amino]-butyric acid methyl ester

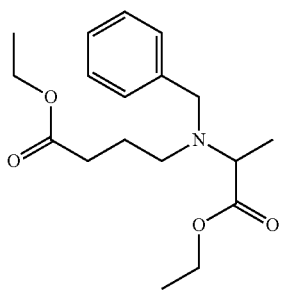 [SMILES: CCOC(=O)CCCN(Cc1ccccc1)C(C)C(=O)OCC]

2-Benzylamino-propionic acid ethyl ester (1.4 g, 6.7 mmol), methyl oxo-butanoate (1.7 g, 13.5 mmol), LEA (1.9 mL, 13.5 mmol) and NaBH(Oac)₃ (2.9 g, 13.5 mmol) are taken up in 1,2-DCE (35 mL) and stirred at rt for 4 h. The reaction is partitioned between DCM and saturated aqueous NaHCO₃. The organic layer is removed, dried over anhydrous Na₂SO₄, and concentrated in vacuo. The crude residue is used without further purification. MS (ESI) m/z 308.3 (M+1).

47-C. (±)-1-Benzyl-2-methyl-3-oxo-piperidine-4-carboxylic acid methyl ester

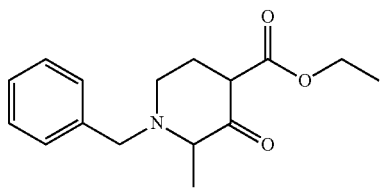 [SMILES: CCOC(=O)C1CCN(Cc2ccccc2)C(C)C1=O]

A mixture of 4-[benzyl-(1-ethoxycarbonyl-ethyl)-amino]-butyric acid methyl ester (1.5 g, 4.9 mmol), potassium tert-butoxide (906 mg, 8.9 mmol) and toluene (100 mL) is stirred at rt for 3 h. The mixture is then partitioned between DCM and saturated aqueous NH₄Cl. The organic layer is removed, dried over anhydrous Na₂SO₄, and concentrated. The crude residue is used without further purification. MS (ESI) m/z 262.2 (M+1).

47-D. (±)-7-Benzyl-8-methyl-5,6,7,8-tetrahydro-3H-pyrido[3,4-d]pyrimidin-4-one

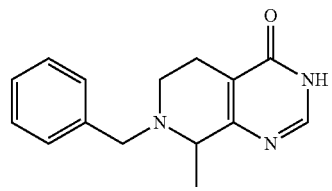 [SMILES: CC1c2nc[nH]c(=O)c2CCN1Cc1ccccc1]

A mixture of 1-benzyl-2-methyl-3-oxo-piperidine-4-carboxylic acid methyl ester (1.0 g, 3.9 mmol), formamidine hydrochloride (930 mg, 11.6 mmol), and EtOH (6 mL) is treated with NaOEt solution (5.5 mL, 13.57 mmol, 21% w/w in EtOH) and the reaction is stirred at 90° C. for 2 h. Reaction is concentrated in vacuo after adjusting to pH 6. Residue is via semi-prep HPLC (C18; 10-100% I/H₂O with 0.1% NH₄OH) to give the title compound. MS (ESI) m/z 256.0 (M+1).

47-E. (±)-8-Methyl-4-oxo-4,5,6,7-tetrahydro-3H-pyrido[3,4-d]pyrimidine-7-carboxylic acid tert-butyl ester

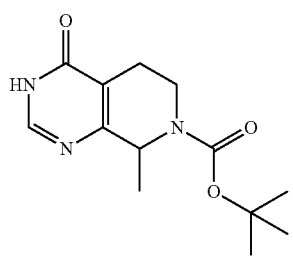

7-Benzyl-8-methyl-5,6,7,8-tetrahydro-3H-pyrido[3,4-a]pyrimidin-4-one (359 mg, 1.41 mmol) and BOC-anhydride (368 mg, 1.69 mmol) are taken up in MeOH (20 mL) and THF (20 mL). To this solution is added 10% Pd/C (75 mg, 20% w/w) and the mixture is stirred under a hydrogen atmosphere (1 atm) for 3 h. The mixture is filtered through a Celite® pad and the filtrate is concentrated to give the title compound which is used without further purification. MS (ESI) m/z 266.1 (M+H).

47-F. (±)-4-Chloro-8-methyl-5,8-dihydro-6H-pyrido[3,4-d]pyrimidine-7-carboxylic acid tert-butyl ester

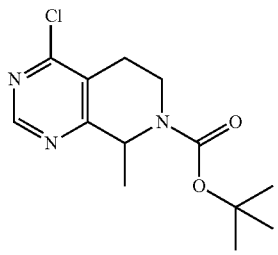 [SMILES: CC1c2ncnc(Cl)c2CCN1C(=O)OC(C)(C)C]

A combination of 8-methyl-4-oxo-4,5,6,8-tetrahydro-3H-pyrido[3,4-d]pyrimidine-7-carboxylic acid tert-butyl ester (374 mg, 1.41 mmol), triphenylphosphine (739 mg, 2.82 mmol) and carbon tetrachloride (409 uL, 4.23 mmol) and 1,2-DCE (10 mL) are heated at 70° C. for 6 h. The solution is then concentrated in vacuo and the residue separated via FCC (5-60% EtOAc/heptane). MS (ESI) m/z 284.2 (M+H).

47-G. (±)-4-(1H-Indol-5-yloxy)-8-methyl-5,8-dihydro-6H-pyrido[3,4-d]pyrimidine-7-carboxylic acid tert-butyl ester

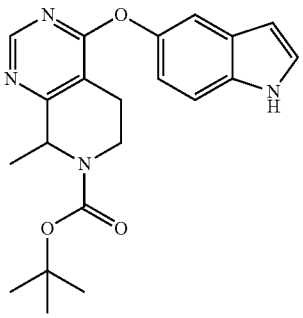 [SMILES: CC1c2ncnc(Oc3ccc4[nH]ccc4c3)c2CCN1C(=O)OC(C)(C)C]

To a solution of 4-chloro-8-methyl-5,8-dihydro-6H-pyrido[3,4-d]pyrimidine-7-carboxylic acid tert-butyl ester (228 mg, 0.80 mmol), 5-hydroxyindole (139 mg, 1.05 mmol) and MeCN (5 mL) is added DBU (0.15 mL, 1.05 mmol). The resulting mixture is heated at 80° C. for 4 h. The reaction is then concentrated in vacuo and the residue separated via FCC (5-60% EtOAc/heptane). MS (ESI) m/z 381.1 (M+H).

47-H. (±)-8-Methyl-4-[1-(3-trifluoromethyl-phenyl-carbamoyl)-1H-indol-5-yloxy]-5,8-dihydro-6H-pyrido[3,4-d]pyrimidine-7-carboxylic acid tert-butyl ester

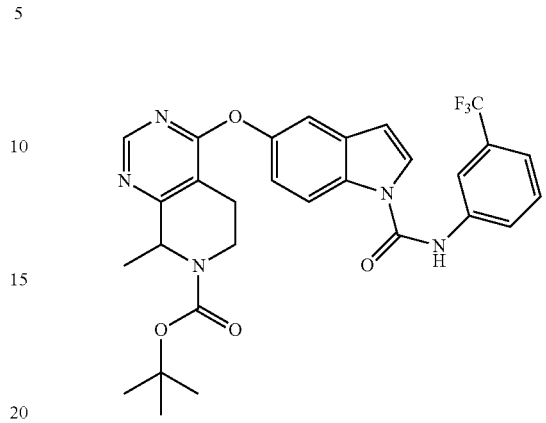

A solution of 4-(1H-indol-5-yloxy)-8-methyl-5,8-dihydro-6H-pyrido[3,4-a]pyrimidine-7-carboxylic acid tert-butyl ester (224 mg, 0.50 mmol) and THF (8 mL) is cooled to 0° C. To this is added NaH (35 mg, 0.88 mmol, 60% in mineral oil) followed by 3-trifluoromethylisocyanate (164 uL, 1.18 mmol) and the mixture is allowed to warm to room temperature. After completion of the reaction as seen by LCMS the mixture is partitioned between DCM and pH 7 buffer solution. The organic layer is separated, dried over anhydrous $Na_2SO_4$, and concentrated. The crude residue is purified via FCC (5-60% EtOAc/heptane) to give the title compound. MS (ESI) m/z 568.1 (M+1).

47-I. (±)-5-(8-Methyl-5,6,7,8-tetrahydro-pyrido[3,4-d]pyrimidin-4-yloxy)-indole-1-carboxylic acid (3-trifluoromethyl-phenyl)-amide

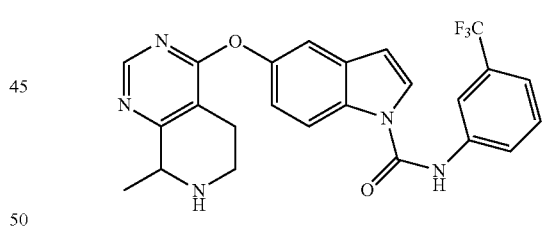

A solution of 8-methyl-4-[1-(3-trifluoromethyl-phenyl-carbamoyl)-1H-indol-5-yloxy]-5,8-dihydro-6H-pyrido[3,4-a]pyrimidine-7-carboxylic acid tert-butyl ester (217 mg, 0.38 mmol), DCM (5 mL), and TFA (5 mL) is stirred at rt for 2 h. At that point the solution is concentrated in vacuo and the residue is separated via semi-prep HPLC (C18; 10-100% I/$H_2O$ with 0.1% $NH_4OH$) to give the title compound. MS (ESI) m/z 468.1 (M+1); $^1$H NMR (400 MHz, DMSO-$d_6$) δ ppm 10.39 (s, 1 H), 8.51 (s, 1 H), 8.28 (d, J=9.1 Hz, 1 H), 8.06-8.15 (m, 2 H), 7.97 (d, J=8.6 Hz, 1 H), 7.65 (t, J=8.0 Hz, 1H), 7.43-7.53 (m, 2 H), 7.13 (dd, J=9.0, 2.4 Hz, 1 H), 6.80 (d, J=3.5 Hz, 1 H), 4.19 (q, J=6.6 Hz, 1 H), 3.34-3.42 (m, 1 H), 3.08-3.20 (m, 1 H), 2.88 (t, J=5.7 Hz, 2 H), 1.49 (d, J=7.1 Hz, 3 H).

EXAMPLE 48

48-A. 4-[1-(3-Trifluoromethoxy-phenylcarbamoyl)-1H-indol-5-yloxy]-5,8-dihydro-6H-pyrido[3,4-d]pyrimidine-7-carboxylic acid tert-butyl ester

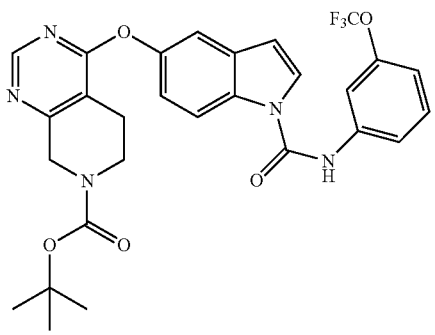 [SMILES: CC1c2ncnc(Oc3ccc4c(ccn4C(=O)Nc4cccc(C(F)(F)F)c4)c3)c2CCN1C(=O)OC(C)(C)C]

A solution of 4-(1H-indol-5-yloxy)-5,8-dihydro-6H-pyrido[3,4-d]pyrimidine-7-carboxylic acid tert-butyl ester (Example 31-C, 300 mg, 0.82 mmol), CDI (265 mg, 1.64 mmol), TEA (342 uL, 2.46 mmol), and DCM (5 mL) is stirred at rt for 1 h before 3-trifluoromethoxy aniline (435 mg, 2.46 mmol) is added. After an additional 24 h, the reaction is concentrated in vacuo and purified via FCC (5-90% EtOAc/heptane) to give the title compound. MS (ESI) m/z 564.1 (M+1).

48-B. 5-(5,6,7,8-Tetrahydro-pyrido[3,4-d]pyrimidin-4-yloxy)-indole-1-carboxylic acid (3-trifluoromethoxy-phenyl)-amide

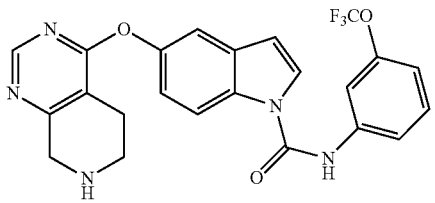 [SMILES: O=C(Nc1cccc(OC(F)(F)F)c1)n1ccc2cc(Oc3ncnc4c3CCNC4)ccc21]

A solution of 4-[1-(3-trifluoromethoxy-phenylcarbamoyl)-1H-indol-5-yloxy]-5,8-dihydro-6H-pyrido[3,4-d]pyrimidine-7-carboxylic acid tert-butyl ester (212 mg, 0.37 mmol), DCM (5 mL), and TFA (5 mL) is stirred at rt for 2 h. The solution is then concentrated in vacuo and purified via semi-prep HPLC (C18; 10-100% I/H$_2$O with 0.1% NH$_4$OH) to give the title compound. MS (ESI) m/z 470.0 (M+1); $^1$H NMR (400 MHz, MeOD) δ ppm 8.41 (s, 1 H), 8.33 (d, J=9.1 Hz, 1 H), 7.93 (d, J=3.8 Hz, 1 H), 7.74 (s, 1 H), 7.62 (dd, J=8.2, 1.1 Hz, 1 H), 7.46 (t, J=8.2 Hz, 1 H), 7.40 (d, J=2.3 Hz, 1 H), 7.00-7.15 (m, 2 H), 6.73 (d, J=3.8 Hz, 1 H), 4.05 (s, 2 H), 3.31-3.29 (obs. M, 2 H), 2.96 (t, J=5.7 Hz, 2 H).

EXAMPLE 49

49-A. 4-(1-{5-[2-(tert-Butyl-dimethyl-silanyloxy)-1,1-dimethyl-ethyl]-2H-pyrazol-3-ylcarbamoyl}-1H-indol-5-yloxy)-5,8-dihydro-6H-pyrido[3,4-d]pyrimidine-7-carboxylic acid tert-butyl ester

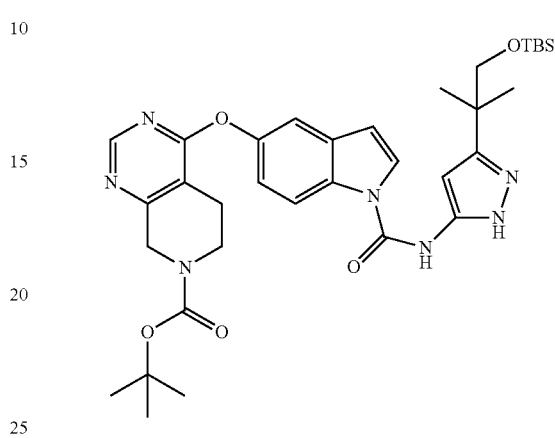

A solution of 4-(1H-indol-5-yloxy)-5,8-dihydro-6H-pyrido[3,4-d]pyrimidine-7-carboxylic acid tert-butyl ester (Example 31-C, 200 mg, 0.55 mmol), CDI (177 mg, 1.10 mmol), TEA (0.23 mL, 1.64 mmol), and DMF (5 mL) is stirred at rt for 1 h before 5-[2-(tert-butyl-dimethyl-silanyloxy)-1,1-dimethyl-ethyl]-2H-pyrazol-3-ylamine (441 mg, 1.64 mmol) and 4-pyrrolidinopyridine (4 mg, 27 umol) are added. After 24 h, the solution is concentrated in vacuo and the residue is separated via FCC (5-90% EtOAc/heptane) to give the title compound. MS (ESI) m/z 662.3 (M+1).

49-B. 5-(5,6,7,8-Tetrahydro-pyrido[3,4-d]pyrimidin-4-yloxy)-indole-1-carboxylic acid [5-(2-hydroxy-1,1-dimethyl-ethyl)-2H-pyrazol-3-yl]-amide

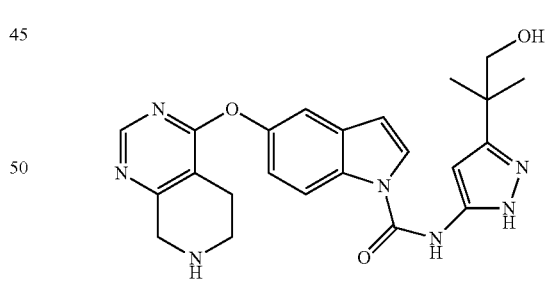

A solution of 4-O-{5-[2-(tert-butyl-dimethyl-silanyloxy)-1,1-dimethyl-ethyl]-2H-pyrazol-3-ylcarbamoyl}-1H-indol-5-yloxy)-5,8-dihydro-6H-pyrido[3,4-d]pyrimidine-7-carboxylic acid tert-butyl ester (252 mg, 0.38 mmol), DCM (2 mL), and TFA (2 mL) is stirred at rt for 2 h. At that point the solution is concentrated in vacuo and the residue separated via semi-prep HPLC (C18; 10-100% I/H$_2$O with 0.1% NH$_4$OH) to give the title compound. MS (ESI) m/z 448.1 (M+1); $^1$H NMR (400 MHz, MeOD) δ ppm 1.33 (s, 6 H) 2.92 (t, J=5.43 Hz, 2 H) 3.25 (t, J=5.94 Hz, 2 H) 3.30 (s, 2 H) 3.57 (s, 2 H) 4.02 (s, 2 H) 6.40 (s, 1 H) 6.70 (d, J=3.54 Hz, 1 H) 7.07

(dd, J=8.97, 2.15 Hz, 1 H) 7.38 (s, 1 H) 7.88 (d, J=3.79 Hz, 1 H) 8.31 (d, J=9.09 Hz, 1 H) 8.39 (s, 1 H).

EXAMPLE 50

50-A. 4-(1-Phenyl-ethylamino)-pentanoic acid ethyl ester

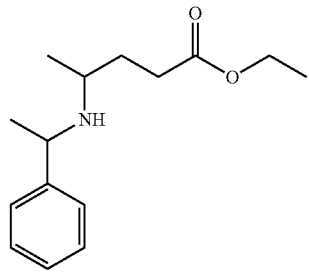 [SMILES: CCOC(=O)CCC(C)NC(C)c1ccccc1]

Racemic 1-phenylethylamine (10 g, 83 mmol), ethyl levulinate (11.76 mL, 83 mmol), NaBH(Oac)$_3$ (35 g, 165 mmol) and 1,2-DCE (200 mL) are stirred at rt for 4 h. The mixture is then partitioned between DCM and saturated aqueous NaHCO$_3$. The organic layer is removed, dried over anhydrous Na$_2$SO$_4$, and concentrated in vacuo. The crude residue is used without further purification. MS (ESI) m/z 250.2 (M+1).

50-B. 4-[Ethoxycarbonylmethyl-(1-phenyl-ethyl)-amino]-pentanoic acid ethyl ester

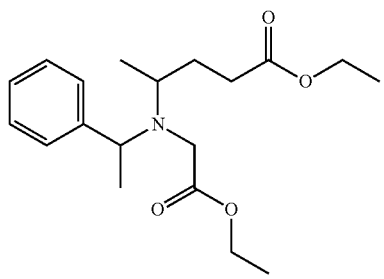 [SMILES: CCOC(=O)CCC(C)N(CC(=O)OCC)C(C)c1ccccc1]

A combination of 4-(1-phenyl-ethylamino)-pentanoic acid ethyl ester (20.5 g, 82 mmol), ethyl glyoxylate (33 mL, 165 mmol, 50% toluene solution), NaBH(Oac)$_3$ (34.9 g, 165 mmol), and 1,2-DCE (200 mL) are stirred at rt for 4 h. The mixture is then partitioned between DCM and saturated aqueous NaHCO$_3$. The organic layer is removed, dried over anhydrous Na$_2$SO$_4$, and concentrated in vacuo. The crude residue is used without further purification. MS (ESI) m/z 336.4 (M+1).

50-C. 2-Methyl-5-oxo-1-(1-phenyl-ethyl)-piperidine-4-carboxylic acid ethyl ester

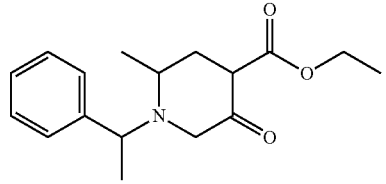 [SMILES: CCOC(=O)C1CC(C)N(C(C)c2ccccc2)CC1=O]

A mixture of 4-[ethoxycarbonylmethyl-(1-phenyl-ethyl)-amino]-pentanoic acid ethyl ester (13 g, 39 mmol), KtOBu (10.9 g, 97 mmol), and toluene (300 mL) is stirred at rt for 3 h. The mixture is then partitioned between DCM and saturated aqueous NH$_4$Cl. The organic layer is removed, dried over anhydrous Na$_2$SO$_4$, and concentrated in vacuo. The crude residue is separated via FCC (5-30% EtOAc/heptane) to give the title compound. MS (ESI) m/z 290.3 (M+1).

50-D. 6-Methyl-7-(1-phenyl-ethyl)-5,6,7,8-tetrahydro-3H-pyrido[3,4-d]pyrimidin-4-one

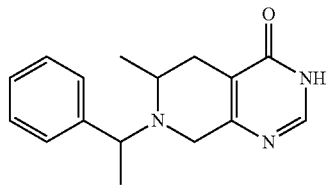 [SMILES: CC1Cc2c(nc[nH]c2=O)CN1C(C)c1ccccc1]

A combination of 2-methyl-5-oxo-1-(1-phenyl-ethyl)-piperidine-4-carboxylic acid ethyl ester, (7.4 g, 25.6 mmol), formamidine acetate (7.98 g, 77 mmol), and EtOH (60 mL) is treated with NaOEt solution (36.7 mL, 90 mmol, 21% w/w EtOH solution) and then heated at 90° C. for 4 h. At that point the pH is adjusted to 6 and the mixture is concentrated in vacuo. The residue is partitioned between DCM and saturated aqueous NH$_4$Cl. The organic layer is removed, dried over anhydrous Na$_2$SO$_4$, and concentrated in vacuo. The crude residue is separated via FCC (1-10% MeOH/DCM) to give the title compound. MS (ESI) m/z 270.1 (M+1).

50-E. (±)-6-Methyl-4-oxo-4,5,6,8-tetrahydro-3H-pyrido[3,4-d]pyrimidine-7-carboxylic acid tert-butyl ester

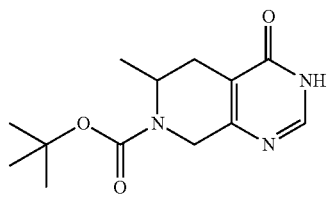 [SMILES: CC1Cc2c(nc[nH]c2=O)CN1C(=O)OC(C)(C)C]

To a mixture of 6-methyl-7-(1-phenyl-ethyl)-5,6,7,8-tetrahydro-3H-pyrido[3,4-d]pyrimidin-4-one, (6.8 g, 25.2 mmol), ammonium formate (7.96 g, 126 mmol), BOC-anhydride (8.27 g, 37.9 mmol), MeOH (250 mL), and THF (167 mL) is added 10% Pd/C (1.36 g, 20% w/w) and the reaction is heated at reflux for 3 h. The mixture is then filtered through a Celite® pad and the filterate is concentrated. The residue is purified via FCC (1-10% MeOH/DCM) to give the title compound. MS (ESI) m/z 266.1 (M+H).

50-F. (±)-4-Chloro-6-methyl-5,8-dihydro-6H-pyrido[3,4-d]pyrimidine-7-carboxylic acid tert-butyl ester

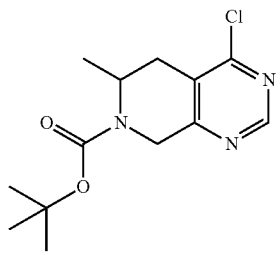 [SMILES: CC1Cc2c(Cl)ncnc2CN1C(=O)OC(C)(C)C]

A solution of (±)-6-methyl-4-oxo-4,5,6,8-tetrahydro-3H-pyrido[3,4-d]pyrimidine-7-carboxylic acid tert-butyl ester, (7.5 g, 28.3 mmol), triphenylphosphine (14.8 g, 56.5 mmol) and carbon tetrachloride (8.2 mL, 85 mmol) in 1,2-DCE (100 mL) is heated at 80° C. for 6 h. At that time the solution is concentrated in vacuo and the residue is separated via FCC (5-60% EtOAc/heptane) to give the title compound. MS (ESI) m/z 284.1 (M+H).

50-G. (±)-4-(1H-Indol-5-yloxy)-6-methyl-5,8-dihydro-6H-pyrido[3,4-d]pyrimidine-7-carboxylic acid tert-butyl ester

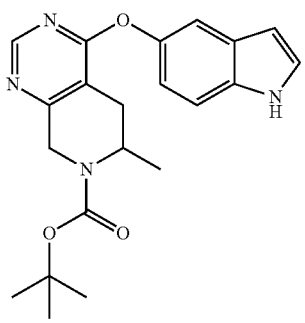 [SMILES: CC1Cc2c(ncnc2Oc2ccc3[nH]ccc3c2)CN1C(=O)OC(C)(C)C]

A solution of (±)-4-chloro-6-methyl-5,8-dihydro-6H-pyrido[3,4-a]pyrimidine-7-carboxylic acid tert-butyl ester (220 mg, 0.77 mmol), 5-hydroxy indole (155 mg, 1.16 mmol) and MeCN (10 mL) is treated with DBU (0.2 mL, 1.16 mmol) and heated at 80° C. for 4 h. The volume is reduced in vacuo and the residue is separated via FCC (5-90% EtOAc/heptane) to give the title compound. MS (ESI) m/z 381.3 (M+H).

The following compounds are prepared with similar method.

50-H. (±)-4-(4-Fluoro-1H-Indol-5-yloxy)-6-methyl-5,8-dihydro-6H-pyrido[3,4-d]pyrimidine-7-carboxylic acid tert-butyl ester

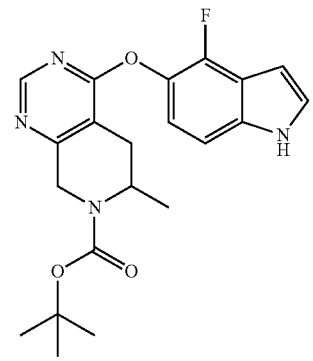 [SMILES: CC1Cc2c(ncnc2Oc2ccc3[nH]ccc3c2F)CN1C(=O)OC(C)(C)C]

MS (ESI) m/z 399.1 (M+H).

EXAMPLE 51

51-A. (±)-4-[1-(5-tert-Butyl-2H-pyrazol-3-ylcarbamoyl)-1H-indol-5-yloxy]-6-methyl-5,8-dihydro-6H-pyrido[3,4-d]pyrimidine-7-carboxylic acid tert-butyl ester

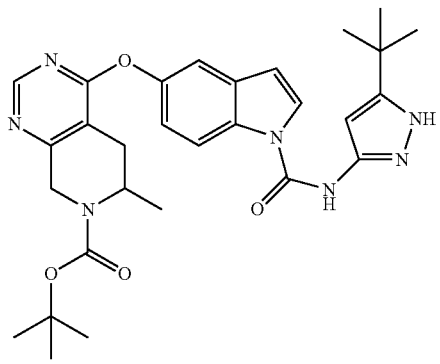 [SMILES: CC1Cc2c(ncnc2Oc2ccc3c(ccn3C(=O)Nc3cc(C(C)(C)C)[nH]n3)c2)CN1C(=O)OC(C)(C)C]

A solution of 4-(1H-indol-5-yloxy)-6-methyl-5,8-dihydro-6H-pyrido[3,4-d]pyrimidine-7-carboxylic acid tert-butyl ester (210 mg, 0.55 mmol), CDI (179 mg, 1.10 mmol), TEA (230 uL, 1.65 mmol), and DMF (5 mL) is stirred at rt 1 h before 5-tert-butyl-2H-pyrazol-3-ylamine (77 mg, 0.55 mmol) and 4-pyrrolidinopyridine (16.4 mg, 0.11 mmol) are added. After 24 h, the reaction is concentrated in vacuo and the purified via FCC (5-90% EtOAc/heptane) to give the title compound. MS (ESI) m/z 546.3 (M+1).

51-B. (±)-5-(6-Methyl-5,6,7,8-tetrahydro-pyrido[3,4-d]pyrimidin-4-yloxy)-indole-1-carboxylic acid (5-tert-butyl-2H-pyrazol-3-yl)-amide

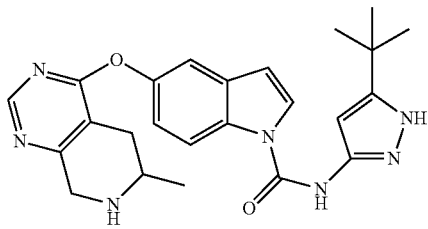 [SMILES: CC1Cc2c(ncnc2Oc2ccc3c(ccn3C(=O)Nc3cc(C(C)(C)C)[nH]n3)c2)CN1]

A solution of 4-[1-(5-tert-butyl-2H-pyrazol-3-ylcarbamoyl)-1H-indol-5-yloxy]-6-methyl-5,8-dihydro-6H-pyrido[3,4-d]pyrimidine-7-carboxylic acid tert-butyl ester (300 mg, 0.55 mmol), DCM (5 mL), and TFA (5 mL) is stirred at it for 2 h. At that point the solution is concentrated and the residue separated via semi-prep HPLC (C18; 10-100% I/H$_2$O with 0.1% NH$_4$OH) to give the title compound. MS (ESI) m/z 446.2 (M+1); $^1$H NMR (400 MHz, MeOD) δ ppm 8.37 (s, 1 H), 8.32 (d, J=8.8 Hz, 1H), 7.88 (d, J=3.5 Hz, 1 H), 7.38 (d, J=2.3 Hz, 1 H), 7.08 (dd, J=9.1, 2.3 Hz, 1 H), 6.71 (d, J=3.8 Hz, 1 H), 6.38 (br. S., 1 H), 6.06 (br. S., 1 H), 4.00 (d, J=6.1 Hz, 2 H), 3.05-3.15 (m, 1 H), 3.00 (dd, J=17.2, 3.5 Hz, 1 H), 2.47 (dd, J=17.2, 10.4 Hz, 1 H), 1.36 (s, 9 H), 1.34 (d, J=6.3 Hz, 3 H).

The following compounds are prepared with similar method.

| | Structure/Chemical Name | $^1$H NMR (400 MHz) | MS (ESI) m/z (M + 1) |
|---|---|---|---|
| 51-C | 5-(5,6,7,8-Tetrahydro-pyrido[3,4-d]pyrimidin-4-yloxy)-indole-1-carboxylic acid (5-tert-butyl-2H-pyrazol-3-yl)-amide. | (MeOD) δ ppm 8.37 (s, 1H), 8.32 (d, J = 8.8 Hz, 1H) 7.88 (d, J = 3.5 Hz, 1H), 7.38 (d, J = 2.3 Hz, 1H) 7.08 (dd, J = 9.1, 2.3 Hz, 1H), 6.71 (d, J = 3.8 Hz, 1H), 6.37 (s, 1H), 3.96 (s, 2H), 3.19 (t, J = 5.9 Hz, 2 H), 2.89 (t, J = 5.7 Hz, 2H), 1.36 (s, 9H). | 432.1 |
| 51-D | 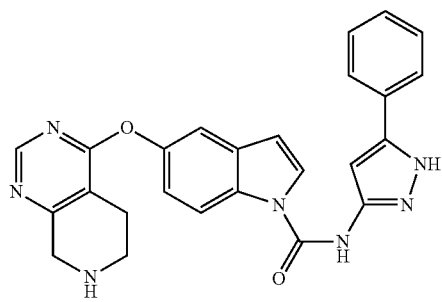 5-(5,6,7,8-Tetrahydro-pyrido[3,4-d]pyrimidin-4-yloxy)-indole-1-carboxylic acid (5-phenyl-2H-pyrazol-3-yl)-amide | (MeOD) δ 8.32-8.40 (m, 2H), 7.92 (d, J = 3.8 Hz, 1H), 7.73 (d, J = 7.6 Hz, 2 H), 7.46 (t, J = 7.6 Hz, 2H), 7.34-7.41 (m, 2H), 7.10 (dd, J = 9.0, 2.4 Hz, 1H), 6.89 (br. S., 1H), 6.73 (d, J = 3.5 Hz, 1H), 3.94 (s, 2H), 3.18 (t, J = 5.9 Hz, 2H), 2.88 (t, J = 5.8 Hz, 2H). | 452.1 |

| Structure/Chemical Name | $^1$H NMR (400 MHz) | MS (ESI) m/z (M + 1) |
|---|---|---|
| 51-E 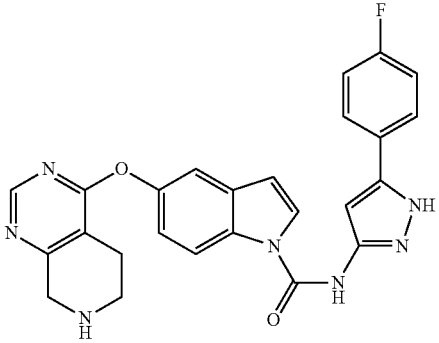 5-(5,6,7,8-Tetrahydro-pyrido[3,4-d]pyrimidin-4-yloxy)-indole-1-carboxylic acid [5-(4-fluoro-phenyl)-2H-pyrazol-3-yl]-amide | (MeOD) δ ppm 8.31-8.40 (m, 2H), 7.91 (d, J = 3.5 Hz, 1H), 7.75 (dd, J = 8.6, 5.3 Hz, 2H), 7.40 (d, J = 2.3 Hz, 1H), 7.20 (t, J = 8.8 Hz, 2H), 7.10 (dd, J = 9.1, 2.3 Hz, 1H), 6.86 (br. S., 1H), 6.73 (d, J = 3.8 Hz, 1H), 3.94 (s, 2H), 3.18 (t, J = 5.8 Hz, 2 H), 2.88 (t, J = 5.7 Hz, 2H). | 470.1 |
| 51-F 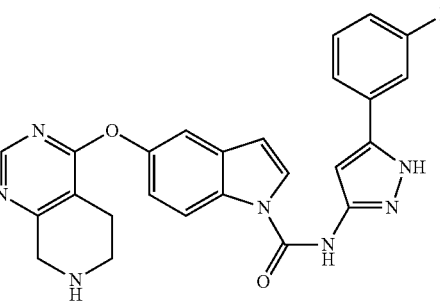 5-(5,6,7,8-Tetrahydro-pyrido[3,4-d]pyrimidin-4-yloxy)-indole-1-carboxylic acid [5-(3-fluoro-phenyl)-2H-pyrazol-3-yl]-amide | (DMSO-d$_6$) δ ppm 13.10 (d, J = 2.5 Hz, 1 H), 10.77 (br. S., 1H), 8.40 (s, 1H), 8.33 (d, J = 9.1 Hz, 1H), 8.20 (br. S., 1H), 7.65 (d, J = 7.8 Hz, 2H), 7.52 (q, J = 7.6 Hz, 1 H), 7.43 (d, J = 2.3 Hz, 1H), 7.20 (d, J = 16.2 Hz, 1H), 7.11 (dd, J = 9.1, 2.3 Hz, 2H), 6.74 (d, J = 3.3 Hz, 1H), 3.82 (s, 2 H), 3.04 (t, J = 5.7 Hz, 2H), 2.73 (t, J = 5.3 Hz, 2H). | 470.2 |
| 51-G 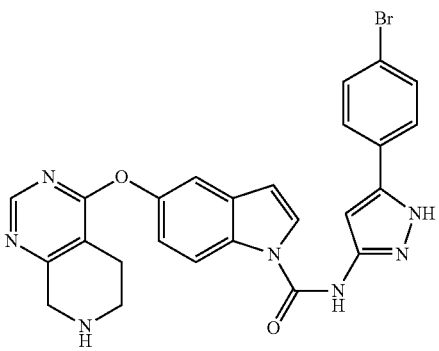 5-(5,6,7,8-Tetrahydro-pyrido[3,4-d]pyrimidin-4-yloxy)-indole-1-carboxylic acid [5-(4-bromo-phenyl)-2H-pyrazol-3-yl]-amide | (DMSO-d$_6$) δ ppm 13.09 (br. S., 1H), 10.76 (br. S., 1H), 8.40 (s, 1H), 8.33 (d, J = 8.8 Hz, 1H), 8.20 (d, J = 3.0 Hz, 1H), 7.72-7.79 (m, 2H), 7.63-7.70 (m, 2H), 7.43 (d, J = 2.3 Hz, 1H), 7.11 (dd, J = 9.0, 2.4 Hz, 1H), 6.99 (br. S., 1H), 6.74 (d, J = 3.8 Hz, 1H), 3.83 (s, 2H), 3.04 (t, J = 5.8 Hz, 2H), 2.73 (t, J = 5.6 Hz, 2H). | 531.9 |

| | Structure/Chemical Name | $^1$H NMR (400 MHz) | MS (ESI) m/z (M + 1) |
|---|---|---|---|
| 51-H | 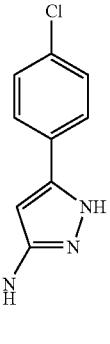<br>5-(5,6,7,8-Tetrahydro-pyrido[3,4-d]pyrimidin-4-yloxy)-indole-1-carboxylic acid [5-(4-chloro-phenyl)-2H-pyrazol-3-yl]-amide | (MeOD) δ ppm 8.32-8.40 (m, 2H), 7.92 (d, J = 3.7 Hz, 1H), 7.73 (d, J = 8.1 Hz, 2H), 7.47 (d, J = 8.3 Hz, 2H), 7.40 (d, J = 2.1 Hz, 1H), 7.11 (dd, J = 9.0, 2.3 Hz, 1H), 6.96 (br. S., 1H), 6.74 (d, J = 3.5 Hz, 1H), 3.95 (s, 2H), 3.19 (t, J = 5.9 Hz, 2H), 2.89 (t, J = 5.7 Hz, 2H). | 486.1 |
| 51-I | 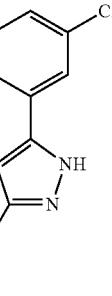<br>5-(5,6,7,8-Tetrahydro-pyrido[3,4-d]pyrimidin-4-yloxy)-indole-1-carboxylic acid [5-(3-chloro-phenyl)-2H-pyrazol-3-yl]-amide | (DMSO-d$_6$) δ ppm 13.12 (br. S., 1H), 10.77 (br. S., 1H), 8.40 (s, 1H), 8.33 (d, J = 8.8 Hz, 1H), 8.20 (br. S., 1H), 7.89 (s, 1H), 7.77 (d, J = 7.8 Hz, 1H), 7.38-7.58 (m, 3H), 7.11 (dd, J = 9.0, 2.4 Hz, 2H), 6.73 (d, J = 3.5 Hz, 1H), 3.82 (s, 2H), 3.03 (t, J = 5.8 Hz, 2H), 2.72 (t, J = 5.7 Hz, 2H). | 486.1 |
| 51-J | 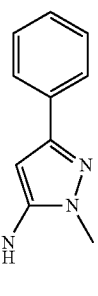<br>5-(5,6,7,8-Tetrahydro-pyrido[3,4-d]pyrimidin-4-yloxy)-indole-1-carboxylic acid (2-methyl-5-phenyl-2H-pyrazol-3-yl)-amide | (DMSO-d$_6$) δ ppm 8.42 (s, 1H), 8.29 (d, J = 8.8 Hz, 1H), 8.10 (d, J = 3.5 Hz, 1H), 7.81 (d, J = 7.1 Hz, 2H), 7.38-7.48 (m, 3H), 7.31 (t, J = 7.3 Hz, 1H), 7.12 (dd, J = 9.0, 2.4 Hz, 1H), 6.80 (d, J = 3.5 Hz, 1H), 6.77 (s, 1H), 3.88 (s, 2H), 3.81 (s, 3H), 3.09 (t, J = 5.8 Hz, 2H), 2.76 (br. S., 2H). | 466.1 |
| 51-K | 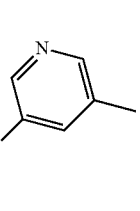<br>5-(5,6,7,8-Tetrahydro-pyrido[3,4-d]pyrimidin-4-yloxy)-indole-1-carboxylic acid (5-methyl-pyridin-3-yl)-amide | (MeOD) δ ppm 8.64 (d, J = 2.0 Hz, 1H), 8.37 (s, 1H), 8.33 (d, J = 8.8 Hz, 1H), 8.18 (d, J = 1.0 Hz, 1H), 8.03 (s, 1H), 7.92 (d, J = 3.5 Hz, 1H), 7.40 (d, J = 2.3 Hz, 1H), 7.10 (dd, J = 9.1, 2.3 Hz, 1H), 6.74 (d, J = 3.0 Hz, 1H), 3.95 (s, 2H), 3.18 (t, J = 5.9 Hz, 2H), 2.88 (t, J = 5.8 Hz, 2H), 2.41 (s, 3H). | 401.1 |

| Structure/Chemical Name | $^1$H NMR (400 MHz) | MS (ESI) m/z (M + 1) |
|---|---|---|
| 51-L  5-{[5-(5,6,7,8-Tetrahydro-pyrido[3,4-d]pyrimidin-4-yloxy)-indole-1-carbonyl]-amino}-1H-pyrazole-3-carboxylic acid ethyl ester | (DMSO-d$_6$) δ ppm 13.65 (br. S., 1H), 8.40 (s, 1H), 8.31 (d, J = 8.8 Hz, 1H), 8.17 (d, J = 3.8 Hz, 1H), 7.42 (d, J = 2.3 Hz, 1 H), 7.11 (dd, J = 9.0, 2.4 Hz, 1H), 7.00 (br. S., 1H), 6.73 (d, J = 3.5 Hz, 1H), 4.33 (q, J = 7.2 Hz, 2H), 3.83 (s, 2H), 3.04 (t, J = 5.8 Hz, 2H), 2.73 (t, J = 5.4 Hz, 2H), 1.33 (t, J = 7.1 Hz, 3H). | 448.1 |
| 51-M  M-1: (+)-5-(6-Methyl-5,6,7,8-tetrahydro-pyrido[3,4-d]pyrimidin-4-yloxy)-indole-1-carboxylic acid (5-trifluoromethyl-1H-pyrazol-3-yl)-amide  M-2: (−)-5-(6-Methyl-5,6,7,8-tetrahydro-pyrido[3,4-d]pyrimidin-4-yloxy)-indole-1-carboxylic acid (5-trifluoromethyl-1H-pyrazol-3-yl)-amide | Enantiomers separated by chiral HPLC (Ia column, 2:8 hptane/EtOH)  M-1: (MeOD) δ ppm 8.32-8.47 (m, 2H), 7.88 (d, J = 3.8 Hz, 1 H), 7.39 (d, J = 2.3 Hz, 1H) 7.10 (dd, J = 9.1, 2.3 Hz, 1H), 6.74 (d, J = 3.8 Hz, 1 H), 6.51 (s, 1H), 3.87-4.07 (m, 2H), 3.05-3.17 (m, 1H), 3.00 (dd, J = 16.9, 3.8 Hz, 1H), 2.39-2.56 (m, 1H), 1.34 (d, J = 6.3 Hz, 3H); Chiral HPLC Rt = 20.6 min  M-2: (MeOD) δ ppm 8.29-8.47 (m, 2H), 7.88 (d, J = 3.8 Hz, 1 H), 7.39 (d, J = 2.3 Hz, 1H), 7.10 (dd, J = 9.1, 2.3 Hz, 1H), 6.73 (d, J = 3.5 Hz, 1 H), 6.51 (s, 1H), 3.92-4.05 (m, 2H), 3.05-3.18 (m, 1H), 3.00 (dd, J = 17.3, 3.7 Hz, 1H), 2.40-2.58 (m, 1H), 1.34 (d, J = 6.3 Hz, 3H); Chiral HPLC Rt = 29.7 min. | 458.0 |

EXAMPLE 52

52-A. (±)-6-Methyl-4-[1-(3-trifluoromethyl-phenyl-carbamoyl)-1H-indol-5-yloxy]-5,8-dihydro-6H-pyrido[3,4-d]pyrimidine-7-carboxylic acid tert-butyl ester A solution of 4-(1H-indol-5-yloxy)-6-methyl-5,8-dihydro-6H-pyrido[3,4-d]pyrimidine-7-carboxylic acid tert-butyl ester (150 mg, 0.39 mmol) and THF (5 mL) is cooled to 0° C. To this is added NaH (23.6 mg, 0.59 mmol, 60% in mineral oil) followed by 3-trifluoromethylisocyanate (0.11 mL, 0.79 mmol) and the reaction is allowed to warm to room temperature. After the reaction is complete as seen by LCMS the mixture is partitioned between DCM and pH 7 buffer solution. The organic layer is removed, dried over anhydrous Na$_2$SO$_4$, and concentrated. The crude residue is separated via FCC (5-90% EtOAc/heptane) to give the title compound. MS (ESI) m/z 568.3 (M+1).

52-B. 52-B-1: (−)-(S)-5-(6-Methyl-5,6,7,8-tetrahydro-pyrido[3,4-d]pyrimidin-4-yloxy)-indole-1-carboxylic acid (3-trifluoromethyl-phenyl)-amide and 52-B-2: (+)-I-5-(6-Methyl-5,6,7,8-tetrahydro-pyrido[3,4-d]pyrimidin-4-yloxy)-indole-1-carboxylic acid (3-trifluoromethyl-phenyl)-amide A solution of 6-methyl-4-[1-(3-trifluoromethyl-phenyl-carbamoyl)-1H-indol-5-yloxy]-5,8-dihydro-6H-pyrido[3,4- d]pyrimidine-7-carboxylic acid tert-butyl ester (74 mg, 0.13 mmol), DCM (5 mL), and TFA (5 mL) is stirred at rt for 2 h. At that point the solution is concentrated in vacuo and the residue is separated via semi-prep HPLC (C18; 10-100% I/H$_2$O with 0.1% NH$_4$OH) to give the racemic title compound. The racemate is then separated via chiral liquid chromatography (Chiralpak AD-column; heptane/EtOH 1:1) to give the two corresponding enantiomers B-1 and B-2.

52-B-1: The compound with R$_t$ 5.5 min is assigned as the (+)-(S)-enantiomer; MS (ESI) m/z 468.3 (M+1); $^1$H NMR (400 MHz, MeOD) δ ppm 8.37 (s, 1 H) 8.32 (d, J=8.84 Hz, 1 H) 8.05 (s, 1 H) 7.92 (d, J=3.79 Hz, 1 H) 7.89 (d, J=8.59 Hz, 1 H) 7.56 (t, J=7.96 Hz, 1 H) 7.43 (d, J=7.58 Hz, 1 H) 7.38 (d, J=1.77 Hz, 1 H) 7.08 (dd, J=8.97, 1.89 Hz, 1 H) 6.72 (d, J=3.54 Hz, 1 H) 3.92-4.08 (m, 2 H) 3.04-3.15 (m, 1 H) 2.98 (dd, J=17.18, 3.28 Hz, 1 H) 2.46 (dd, J=16.93, 10.61 Hz, 1 H) 1.33 (d, J=6.32 Hz, 3 H).

52-B-2: The compound with R$_t$ 6.7 min is assigned as the (−)-I enantiomer; MS (ESI) m/z 468.2 (M+1); $^1$H NMR (400 MHz, MeOD) δ ppm 8.37 (s, 1 H) 8.32 (d, J=8.84 Hz, 1 H) 8.05 (s, 1 H) 7.92 (d, J=3.79 Hz, 1 H) 7.89 (d, J=8.59 Hz, 1 H) 7.56 (t, J=7.96 Hz, 1 H) 7.44 (d, J=7.83 Hz, 1 H) 7.39 (d, J=2.27 Hz, 1 H) 7.09 (dd, J=8.97, 2.40 Hz, 1 H) 6.73 (d, J=3.79 Hz, 1 H) 3.89-4.09 (m, 2 H) 3.05-3.16 (m, 1 H) 2.99 (dd, J=17.18, 379 Hz, 1 H) 2.47 (dd, J=17.18, 10.36 Hz, 1 H) 1.34 (d, J=6.57 Hz, 3 H).

The following compounds are prepared with similar method.

52-C. (±)-4-Fluoro-5-(6-methyl-5,6,7,8-tetrahydro-pyrido[3,4-d]pyrimidin-4-yloxy)-indole-1-carboxylic acid (3-trifluoromethyl-phenyl)-amide

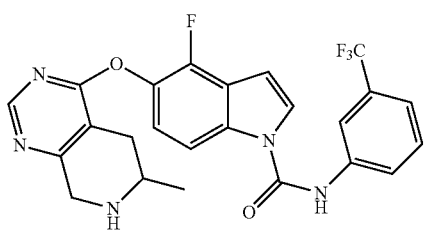 [SMILES: CC1Cc2c(ncnc2Oc2ccc3c(ccn3C(=O)Nc3cccc(C(F)(F)F)c3)c2F)CN1]

MS (ESI) m/z 486.1 (M+1); $^1$H NMR (400 MHz, MeOD) δ ppm 8.58 (s, 1 H), 8.31 (d, J=8.84 Hz, 1H), 8.25 (s, 1 H), 8.01-8.17 (m, 2 H), 7.76 (t, J=7.96 Hz, 1 H), 7.63 (d, J=7.58 Hz, 1 H), 7.37 (t, J=8.59 Hz, 1 H), 7.00 (d, J=3.79 Hz, 1 H), 4.20 (d, J=5.05 Hz, 2 H), 3.29 (ddd, J=10.48, 6.32, 4.17 Hz, 1 H), 3.20 (dd, J=17.18, 3.79 Hz, 1 H), 2.69 (dd, J=17.18, 10.36 Hz, 1 H), 1.53 (d, J=6.32 Hz, 3 H).

EXAMPLE 53

53-A. 53-A-1: (S)-2-Methyl-5-oxo-1-((S)-1-phenyl-ethyl)-piperidine-4-carboxylic acid ethyl ester and 53-A-2: (R)-2-Methyl-5-oxo-1-((S)-1-phenyl-ethyl)-piperidine-4-carboxylic acid ethyl ester

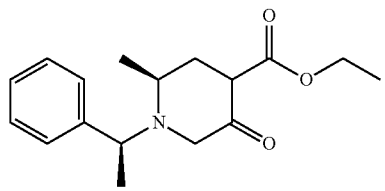

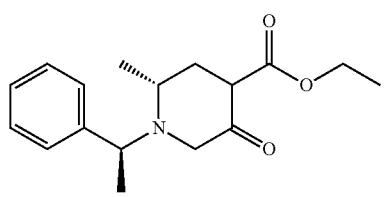

Prepared with similar method as Example 50C substituting chiral (−)-(S)-1-phenylethylamine for racemic 1-phenylethylamine in Example 50A. The diastereomers A-1 and A-2 are separated via FCC (2.5% EtOAc/heptane).

53-A-1: MS (ESI) m/z 290.2 (M+1); $^1$H NMR (400 MHz, CDCl$_3$) δ ppm 11.81 (s, 1 H), 7.18-7.37 (m, 5 H), 4.16-4.27 (m, 2 H), 3.70 (q, J=6.6 Hz, 1 H), 3.27-3.38 (m, 1 H), 2.82-3.13 (m, 2 H), 2.53 (dd, J=15.5, 5.2 Hz, 1 H), 2.10 (dd, J=15.5, 3.7 Hz, 1 H), 1.33 (d, J=6.6 Hz, 3 H), 1.30 (t, J=7.1 Hz, 3 H), 1.05 (d, J=6.6 Hz, 3 H).

53-A-2: MS (ESI) m/z 290.2 (M+1); $^1$H NMR (400 MHz, CDCl$_3$) δ ppm 11.94 (s, 1 H), 7.19-7.36 (m, 5 H), 4.13-4.29 (m, 2 H), 3.63 (q, J=6.6 Hz, 1 H), 3.09-3.52 (m, 2 H), 2.94-3.05 (m, 1 H), 2.34-2.47 (m, 1 H), 1.94 (d, J=15.4 Hz, 1 H), 1.34 (d, J=6.6 Hz, 3 H), 1.28 (t, J=7.2 Hz, 3 H), 0.90 (d, J=6.8 Hz, 3 H).

53-B. 53-B-1: (S)-4-(1H-Indol-5-yloxy)-6-methyl-5,8-dihydro-6H-pyrido[3,4-d]pyrimidine-7-carboxylic acid tert-butyl ester and 53-B-2: (R)-4-(1H-Indol-5-yloxy)-6-methyl-5,8-dihydro-6H-pyrido[3,4-d]pyrimidine-7-carboxylic acid tert-butyl ester

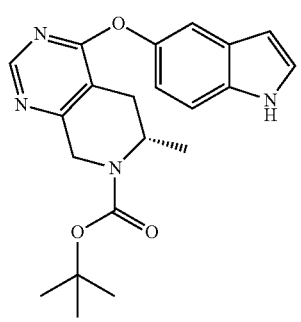

169
-continued

53-B-2

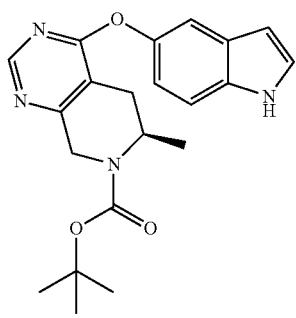

Enantiomers 53-B-1 and 53-B-2 are prepared respectively from Example 53-A-1 and Example 53-A-2 as described for Example 50-G. 53-B-1: MS (ESI) m/z 381.1 (M+1). 53-B-2: MS (ESI) m/z 381.1 (M+1).

The following compounds are prepared with similar method.

53-C. 53-C-1: (S)-4-(4-Fluoro-1H-Indol-5-yloxy)-6-methyl-5,8-dihydro-6H-pyrido[3,4-d]pyrimidine-7-carboxylic acid tert-butyl ester and 53-C-2: l-4-(4-Fluoro-1H-Indol-5-yloxy)-6-methyl-5,8-dihydro-6H-pyrido[3,4-d]pyrimidine-7-carboxylic acid tert-butyl ester

53-C-1

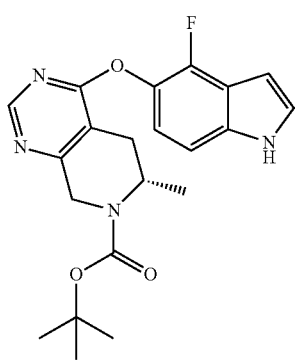

53-C-2

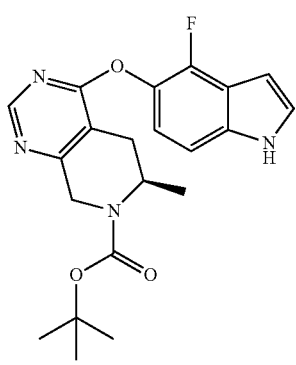

Enantiomers 53-C-1 and 53-C-2 are prepared respectively from Example 53-A-1 and Example 53-A-2 as described for Example 50-H. 53-C-1: MS (ESI) m/z 399.1 (M+1).

53-C-2: MS (ESI) m/z 397.2 (M−1).

170
EXAMPLE 54

54-A. (S)-4-{1-[2-tert-Butoxycarbonyl-5-(1-methyl-cyclopropyl)-2H-pyrazol-3-ylcarbamoyl]-1H-indol-5-yloxy}-6-methyl-5,8-dihydro-6H-pyrido[3,4-d]pyrimidine-7-carboxylic acid tert-butyl ester

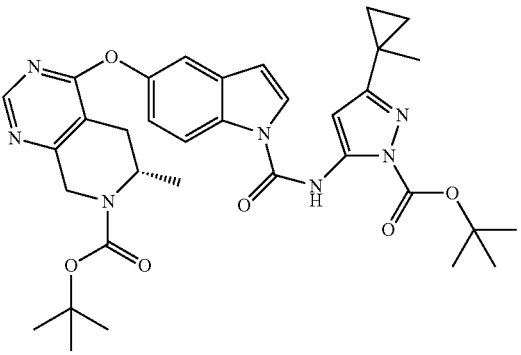 [SMILES: C[C@H]1Cc2c(ncnc2Oc2ccc3c(ccn3C(=O)Nc3cc(C4(C)CC4)nn3C(=O)OC(C)(C)C)c2)CN1C(=O)OC(C)(C)C]

Sodium hydride (0.024 g, 0.990 mmol; 60% in oil) is added to a solution of (S)-4-(1H-Indol-5-yloxy)-6-methyl-5,8-dihydro-6H-pyrido[3,4-d]pyrimidine-7-carboxylic acid tert-butyl ester, Example 53-B-1, (0.126 g, 0.330 mmol) and DMF (7.5 mL) at it. After 5 min 3-(1-Methyl-cyclopropyl)-5-phenoxycarbonylamino-pyrazole-1-carboxylic acid tert-butyl ester, Example 5-D, (0.178 g, 0.495 mmol) is then added. After 1 h the mixture is quenched by the addition of saturated aqueous NH$_4$Cl and then concentrated. The residue is separated directly via FCC (20-70% EtOAc/heptane). MS (ESI) m/z 644.2 (M+1).

54-B. 5-((S)-6-Methyl-5,6,7,8-tetrahydro-pyrido[3,4-d]pyrimidin-4-yloxy)-indole-1-carboxylic acid [5-(1-methyl-cyclopropyl)-2H-pyrazol-3-yl]-amide A solution of (S)-4-{1-[2-tert-Butoxycarbonyl-5-(1-methyl-cyclopropyl)-2H-pyrazol-3-ylcarbamoyl]-1H-indol-5-yloxy}-6-methyl-5,8-dihydro-6H-pyrido[3,4-d]pyrimidine-7-carboxylic acid tert-butyl ester (0.212 g, 0.330 mmol), DCM (5 mL), and TFA (2 mL) is stirred at rt for 1 h. The solution is concentrated in vacuo, taken up in MeOH and neutralized by the addition of several drops of aqueous NH$_4$OH. The residue is then separated via semi-prep HPLC (C18; 10-100% l/H$_2$O with 0.1% NH$_4$OH) to give the title compound. MS (ESI) m/z 444.1 (M+1); $^1$H NMR (400 MHz, DMSO-d$_6$) δ ppm 12.13 (br. S., 1 H), 10.55 (s, 1 H), 8.40 (s, 1 H), 8.29 (d, J=8.8 Hz, 1 H), 8.16 (d, J=3.5 Hz, 1 H), 7.40 (d, J=2.3 Hz, 1 H), 7.08 (dd, J=9.1, 2.3 Hz, 1 H), 6.70 (d, J=3.8 Hz, 1 H), 6.30 (s, 1 H), 3.76-3.98 (m, 2 H), 2.92-3.05 (m, 1 H), 2.85 (dd, J=16.5, 3.4 Hz, 1 H), 2.27-2.40 (m, 1 H), 1.41 (s, 3 H), 1.22 (d, J=6.3 Hz, 3 H), 0.89-0.97 (m, 2 H), 0.73-0.82 (m, 2 H).

The following compounds are prepared with similar method.

| | Structure/Chemical Name | ¹H NMR (400 MHz) | MS (ESI) m/z (M + 1) |
|---|---|---|---|
| 54-C | 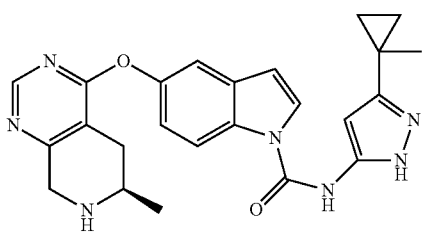<br>5-(I-6-Methyl-5,6,7,8-tetrahydro-pyrido[3,4-d]pyrimidin-4-yloxy)-indole-1-carboxylic acid [5-(1-methyl-cyclopropyl)-2H-pyrazol-3-yl]-amide. | (MeOD) δ ppm 8.51 (s, 1H), 8.34 (d, J = 9.0 Hz, 1H), 7.90 (d, J = 3.8 Hz, 1H), 7.41 (d, J = 2.1 Hz, 1H), 7.10 (dd, J = 9.0, 2.3 Hz, 1 H), 6.72 (d, J = 3.7 Hz, 1H), 6.28 (s, 1H), 3.73-3.88 (m, 1H), 2.86 (dd, J = 17.9, 10.7 Hz, 1H), 1.59 (d, J = 6.4 Hz, 3H), 1.46 (s, 3 H), 0.92-1.03 (m, 2H), 0.75-0.88 (m, 2 H). | 444.1 |
| 54-D | 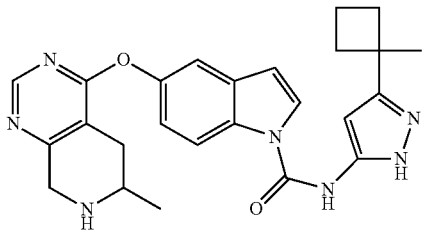<br>(±)-5-(6-Methyl-5,6,7,8-tetrahydro-pyrido[3,4-d]pyrimidin-4-yloxy)-indole-1-carboxylic acid [5-(1-methyl-cyclobutyl)-2H-pyrazol-3-yl]-amide. | (MeOD) δ ppm 8.52 (s, 1H), 8.35 (d, J = 9.0 Hz, 1H), 7.91 (d, J = 3.7 Hz, 1H), 7.41 (d, J = 2.3 Hz, 1H), 7.10 (dd, J = 9.0, 2.4 Hz, 1 H), 6.73 (d, J = 3.7 Hz, 1H), 6.39 (s, 1H), 3.72-3.86 (m, 1H), 2.86 (dd, J = 17.8, 11.0 Hz, 1H), 2.36-2.52 (m, 3H), 2.03-2.17 (m, 4H), 1.90-2.02 (m, 2H), 1.53-1.62 (m, 6H). | 485.1 |
| 54-E | 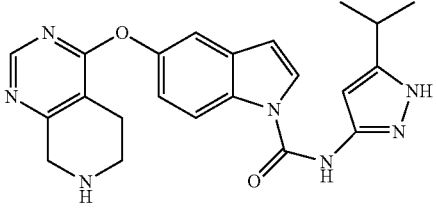<br>5-(5,6,7,8-Tetrahydro-pyrido[3,4-d]pyrimidin-4-yloxy)-indole-1-carboxylic acid (5-isopropyl-1H-pyrazol-3-yl)-amide. | (DMSO-d₆) δ ppm 12.21 (br. S., 1H), 10.56 (s, 1H), 8.39 (s, 1H), 8.29 (d, J = 9.1 Hz, 1 H), 8.16 (d, J = 3.5 Hz, 1H), 7.41 (d, J = 2.3 Hz, 1H), 7.08 (dd, J = 9.1, 2.3 Hz, 1H), 6.70 (d, J = 3.5 Hz, 1H), 6.34 (s, 1H), 3.81 (s, 2 H), 2.87-3.07 (m, 3H), 2.72 (t, J = 5.6 Hz, 2 H), 1.25 (d, J = 6.8 Hz, 6H). | 418.2 |
| 54-F | 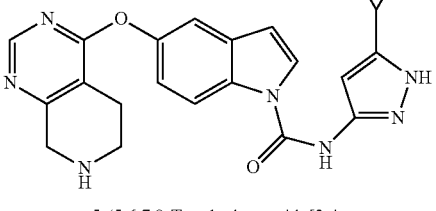<br>5-(5,6,7,8-Tetrahydro-pyrido[3,4-d]pyrimidin-4-yloxy)-indole-1-carboxylic acid (5-cyclopropyl-1H-pyrazol-3-yl)-amide. | (DMSO-d₆) δ ppm 12.23 (br. S., 1H), 10.54 (br. S., 1H), 8.39 (s, 1H), 8.28 (d, J = 9.1 Hz, 1H), 8.15 (d, J = 3.3 Hz, 1H), 7.40 (d, J = 2.3 Hz, 1H), 7.08 (dd, J = 9.0, 2.4 Hz, 1 H), 6.69 (d, J = 3.8 Hz, 1H), 6.22 (br. S., 1 H), 3.81 (s, 2H), 3.03 (t, J = 5.8 Hz, 2H), 2.72 (t, J = 5.6 Hz, 2H), 1.82-2.00 (m, 1H), 0.90-1.01 (m, 2H), 0.65-0.76 (m, 2H). | 416.2 |

-continued

| | Structure/Chemical Name | ¹H NMR (400 MHz) | MS (ESI) m/z (M + 1) |
|---|---|---|---|
| 54-G | (±)-4-Fluoro-5-(6-methyl-5,6,7,8-tetrahydro-pyrido[3,4-d]pyrimidin-4-yloxy)-indole-1-carboxylic acid [5-(1-methyl-cyclopropyl)-2H-pyrazol-3-yl]-amide | (MeOD) δ ppm 8.39 (s, 1H), 8.12 (d, J = 8.84 Hz, 1H), 7.89 (d, J = 3.79 Hz, 1H), 7.17 (dd, J = 8.84, 7.58 Hz, 1H), 6.80 (d, J = 3.28 Hz, 1H), 6.30 (br. S., 1H), 4.02 (d, J = 6.32 Hz, 2H), 3.13 (ddd, J = 10.23, 6.44, 3.79 Hz, 1H), 3.03 (dd, J = 17.18, 3.28 Hz, 1 H), 2.55 (dd, J = 17.18, 10.36 Hz, 1H), 1.46 (s, 3H), 1.35 (d, J = 6.32 Hz, 3H), 0.91-1.04 (m, 2H), 0.74-0.88 (m, 2H). | 462.1 |
| 54-H | 4-Fluoro-5-((S)-6-methyl-5,6,7,8-tetrahydro-pyrido[3,4-d]pyrimidin-4-yloxy)-indole-1-carboxylic acid [5-(1-methyl-cyclopropyl)-2H-pyrazol-3-yl]-amide. | (MeOD) δ ppm 8.39 (s, 1H), 8.12 (d, J = 8.84 Hz, 1H), 7.89 (d, J = 3.79 Hz, 1H), 7.17 (dd, J = 8.84, 7.58 Hz, 1H), 6.80 (d, J = 3.28 Hz, 1H), 6.30 (br. S., 1H), 4.02 (d, J = 6.32 Hz, 2H), 3.13 (ddd, J = 10.23, 6.44, 3.79 Hz, 1H), 3.03 (dd, J = 17.18, 3.28 Hz, 1 H), 2.55 (dd, J = 17.18, 10.36 Hz, 1H), 1.46 (s, 3H), 1.35 (d, J = 6.32 Hz, 3H), 0.91-1.04 (m, 2H), 0.74-0.88 (m, 2H). | 462.1 |
| 54-I | 4-Fluoro-5-((R)-6-methyl-5,6,7,8-tetrahydro-pyrido[3,4-d]pyrimidin-4-yloxy)-indole-1-carboxylic acid [5-(1-methyl-cyclopropyl)-2H-pyrazol-3-yl]-amide. | (MeOD) δ ppm 8.39 (s, 1H), 8.12 (d, J = 8.84 Hz, 1H), 7.89 (d, J = 3.79 Hz, 1H), 7.17 (dd, J = 8.84, 7.58 Hz, 1H), 6.80 (d, J = 3.28 Hz, 1H), 6.30 (br. S., 1H), 4.02 (d, J = 6.32 Hz, 2H), 3.13 (ddd, J = 10.23, 6.44, 3.79 Hz, 1H), 3.03 (dd, J = 17.18, 3.28 Hz, 1 H), 2.55 (dd, J = 17.18, 10.36 Hz, 1H), 1.46 (s, 3H), 1.35 (d, J = 6.32 Hz, 3H), 0.91-1.04 (m, 2H), 0.74-0.88 (m, 2H). | 462.1 |
| 54-J | 4-Fluoro-5-(5,6,7,8-tetrahydro-pyrido[3,4-d]pyrimidin-4-yloxy)-indole-1-carboxylic acid [5-(1-methyl-cyclopropyl)-2H-pyrazol-3-yl]-amide. | MeOD) δ ppm 8.38 (s, 1H), 8.12 (d, J = 8.84 Hz, 1H), 7.88 (d, J = 3.79 Hz, 1H), 7.17 (dd, J = 8.84, 7.58 Hz, 1H), 6.80 (d, J = 3.79 Hz, 1H), 6.31 (br. S., 1H), 3.96 (s, 2 H), 3.19 (t, J = 5.94 Hz, 2H), 2.91 (t, J = 5.68 Hz, 2H), 1.46 (s, 3H) 0.92-1.03 (m, 2H), 0.76-0.86 (m, 2H). | 448.1 |

| | Structure/Chemical Name | ¹H NMR (400 MHz) | MS (ESI) m/z (M + 1) |
|---|---|---|---|
| 54-K | 5-(6,7-dihydro-5H-pyrrolo[3,4-d]pyrimidin-4-yloxy)-4-fluoro-indole-1-carboxylic acid [5-(1-methyl-cyclopropyl)-1H-pyrazol-3-yl]-amide. | (DMSO-d₆) δ ppm 12.17 (br. S., 1H), 10.71 (br. S., 1H), 8.56 (s, 1H), 8.20 (d, J = 3.54 Hz, 1H), 8.12 (d, J = 8.84 Hz, 1H), 7.27 (d, J = 7.83 Hz, 1H), 6.84 (d, J = 3.79 Hz, 1H), 6.29 (s, 1H), 4.21 (s, 2H), 4.10 (s, 2H), 1.41 (s, 3H), 0.85-1.01 (m, 2H), 0.70-0.85 (m, 2H). | 434.1 |
| 54-L | 5-(6,7-dihydro-5H-pyrrolo[3,4-d]pyrimidin-4-yloxy)-indole-1-carboxylic acid [5-(4-methyl-tetrahydro-pyran-4-yl)-2H-pyrazol-3-yl]-amide. | (DMSO-d₆) δ ppm 12.27 (br. S., 1H) 10.62 (s, 1H) 8.55 (s, 1H) 8.30 (d, J = 8.84 Hz, 1 H) 8.18 (d, J = 3.54 Hz, 1H) 7.45 (d, J = 2.27 Hz, 1H) 7.11 (dd, J = 8.84, 2.27 Hz, 1H) 6.71 (d, J = 3.54 Hz, 1H) 6.39 (s, 1H) 3.96-4.26 (m, 4H) 3.60-3.78 (m, 2H) 3.46 (ddd, J = 11.49, 8.46, 2.78 Hz, 2H) 2.01 (m, 2 H) 1.63 (m, 2H) 1.29 (s, 3H) | 460.2 |
| 54-M | 5-(6,7-dihydro-5H-pyrrolo[3,4-d]pyrimidin-4-yloxy)-indole-1-carboxylic acid (5-cyclopropyl-2H-pyrazol-3-yl)-amide. | (DMSO-d₆) δ ppm 12.24 (br. S., 1H) 10.56 (s, 1H) 8.55 (s, 1H) 8.29 (d, J = 9.09 Hz, 1 H) 8.17 (d, J = 3.54 Hz, 1H) 7.44 (d, J = 2.27 Hz, 1H) 7.12 (d, J = 9.09 Hz, 1H) 6.70 (d, J = 3.54 Hz, 1H) 6.22 (s, 1H) 4.07-4.13 (m, 4H) 1.91 (dd, J = 13.39, 3.54 Hz, 1H) 0.95 (dd, J = 8.34, 2.27 Hz, 2H) 0.70-0.74 (m, 2H) | 402.1 |
| 54-N | 5-(6,7-dihydro-5H-pyrrolo[3,4-d]pyrimidin-4-yloxy)-indole-1-carboxylic acid (5-isopropyl-2H-pyrazol-3-yl)-amide. | (DMSO-d₆) δ ppm 12.22 (br. S., 1H) 10.58 (s, 1H) 8.55 (s, 1H) 8.30 (d, J = 9.09 Hz, 1 H) 8.18 (d, J = 3.79 Hz, 1H) 7.44 (d, J = 2.27 Hz, 1H) 7.11 (dd, J = 8.59, 2.53 Hz, 1H) 6.71 (d, J = 3.79 Hz, 1H) 6.34 (s, 1H) 4.07-4.12 (m, 2H) 4.09 (d, J = 14.15 Hz, 2H) 2.95 (d, J = 7.07 Hz, 1H) 1.25 (d, J = 6.82 Hz, 6H). | 404.1 |

| | Structure/Chemical Name | ¹H NMR (400 MHz) | MS (ESI) m/z (M + 1) |
|---|---|---|---|
| 54-O | 5-(6,7-dihydro-5H-pyrrolo[3,4-d]pyrimidin-4-yloxy)-indole-1-carboxylic acid [5-(1-methyl-cyclopropyl)-2H-pyrazol-3-yl]-amide | (DMSO-d₆) δ ppm 12.13 (s, 1H) 10.57 (s, 1 H) 8.55 (s, 1H) 8.29 (d, J = 9.09 Hz, 1H) 8.17 (d, J = 3.79 Hz, 1H) 7.44 (d, J = 2.27 Hz, 1H) 7.11 (dd, J = 9.09, 2.53 Hz, 1H) 6.71 (d, J = 3.54 Hz, 1H) 6.29 (s, 1H) 4.09 (d, J = 12.63 Hz, 4H) 1.41 (s, 3H) 0.91-0.93 (m, 2H) 0.74-0.78 (m, 2H) | 416.2 |
| 54-P | 5-(6,7-dihydro-5H-pyrrolo[3,4-d]pyrimidin-4-yloxy)-indole-1-carboxylic acid [5-(1-methyl-cyclobutyl)-2H-pyrazol-3-yl]-amide | (DMSO-d₆) δ ppm 10.11 (s, 1H) 8.54 (s, 1 H) 8.43 (d, J = 9.09 Hz, 1H) 8.19 (d, J = 3.79 Hz, 1H) 7.51 (d, J = 2.53 Hz, 2H) 7.22 (dd, J = 8.97, 2.40 Hz, 1H) 6.76-6.90 (m, 2H) 4.21 (t, J = 2.15 Hz, 2H) 4.14 (t, J = 2.27 Hz, 2H) 3.48 (s, 2H) 2.78-2.82 (m, 2H) 1.41-1.52 (m, 5H) | 430.3 |
| 54-Q | 5-(5,6,7,8-Tetrahydro-pyrido[3,4-d]pyrimidin-4-yloxy)-indole-1-carboxylic acid [5-(1-methyl-cyclopropyl)-2H-pyrazol-3-yl]-amide | (DMSO-d₆) δ ppm 12.13 (br. S., 1H), 10.55 (s, 1H), 8.40 (s, 1H), 8.29 (d, J = 8.8 Hz, 1 H), 8.16 (d, J = 3.8 Hz, 1H), 7.41 (d, J = 2.3 Hz, 1H), 7.08 (dd, J = 9.0, 2.4 Hz, 1H), 6.70 (d, J = 3.5 Hz, 1H), 6.29 (s, 1H), 3.84 (s, 2 H), 3.05 (t, J = 5.8 Hz, 2H), 2.69-2.78 (m, 2 H), 1.41 (s, 3H), 1.25 (br. S., 2H), 0.89-0.97 (m, 2H) | 430.2 |
| 54-R | 5-((S)-6-Methyl-5,6,7,8-tetrahydro-pyrido[3,4-d]pyrimidin-4-yloxy)-indole-1-carboxylic acid (5-isopropyl-1H-pyrazol-3-yl)-amide | (DMSO-d₆) δ ppm 10.56 (s, 1H), 8.40 (s, 1 H), 8.29 (d, J = 9.1 Hz, 1H), 8.16 (d, J = 3.8 Hz, 1H), 7.40 (d, J = 2.3 Hz, 1H), 7.08 (dd, J = 9.0, 2.4 Hz, 1H), 6.70 (d, J = 3.5 Hz, 1H), 6.34 (br. S., 1H), 3.79-3.98 (m, 2H), 2.89-3.04 (m, 2H), 2.85 (dd, J = 16.8, 3.4 Hz, 1 H), 2.27-2.39 (m, 1H), 1.17-1.30 (m, 9 H) | 432.2 |

| | Structure/Chemical Name | ¹H NMR (400 MHz) | MS (ESI) m/z (M + 1) |
|---|---|---|---|
| 54-S | 5-(R)-6-Methyl-5,6,7,8-tetrahydro-pyrido[3,4-d]pyrimidin-4-yloxy)-indole-1-carboxylic acid (5-isopropyl-1H-pyrazol-3-yl)-amide | (DMSO-d₆) δ ppm 10.56 (s, 1H), 8.40 (s, 1 H), 8.29 (d, J = 9.1 Hz, 1H), 8.16 (d, J = 3.5 Hz, 1H), 7.40 (d, J = 2.5 Hz, 1H), 7.08 (dd, J = 9.0, 2.4 Hz, 1H), 6.70 (d, J = 3.8 Hz, 1H), 6.34 (s, 1H), 3.77-3.98 (m, 2H), 2.90-3.03 (m, 2H), 2.85 (dd, J = 16.9, 3.5 Hz, 1 H), 2.27-2.39 (m, 1H), 1.16-1.33 (m, 9 H) | 432.2 |
| 54-T | 5-(5,6,7,8-Tetrahydro-pyrido[3,4-d]pyrimidin-4-yloxy)-indole-1-carboxylic acid [5-(1-trifluoromethyl-cyclopropyl)-1H-pyrazol-3-yl]-amide | (DMSO-d₆) δ ppm 12.79 (br. S., 1H), 10.72 (br. S., 1H), 8.40 (s, 1H), 8.29 (d, J = 9.0 Hz, 1H), 8.16 (br. S., 1H), 7.42 (d, J = 1.8 Hz, 1 H), 7.10 (d, J = 10.9 Hz, 1H), 6.60-6.77 (m, 2H), 3.84 (br. S., 2H), 3.06 (br. S., 2H), 2.74 (br. S., 2H), 1.39 (br. S., 2H), 1.29 (br. S., 2H) | 484.1 |
| 54-U | 5-(6,7-Dihydro-5H-pyrrolo[3,4-d]pyrimidin-4-yloxy)-indole-1-carboxylic acid (1-tert-butyl-1H-pyrazol-3-yl)-amide | (MeOD) δ ppm 8.53 (s, 1H) 8.33 (d, J = 8.84 Hz, 1H) 7.90 (d, J = 3.79 Hz, 1H) 7.67 (d, J = 2.53 Hz, 1H) 7.42 (d, J = 2.27 Hz, 1H) 7.11 (dd, J = 8.97, 2.40 Hz, 1H) 6.71 (d, J = 3.79 Hz, 1H) 6.55 (d, J = 2.27 Hz, 1H) 4.19 (d, J = 7.83 Hz, 4H) 1.59 (s, 9H) | 418.1 |
| 54-V | 5-((S)-6-Methyl-5,6,7,8-tetrahydro-pyrido[3,4-d]pyrimidin-4-yloxy)-indole-1-carboxylic acid (1-tert-butyl-1H-pyrazol-3-yl)-amide | (DMSO-d₆) δ ppm 8.40 (s, 1H) 8.30 (d, J = 9.09 Hz, 1H) 8.20 (d, J = 3.79 Hz, 1H) 7.78 (d, J = 2.27 Hz, 1H) 7.40 (d, J = 2.53 Hz, 1H) 7.08 (dd, J = 8.97, 2.40 Hz, 1H) 6.70 (d, J = 3.79 Hz, 1H) 6.52 (d, J = 2.53 Hz, 1H) 3.87 (d, J = 6.82 Hz, 2H) 2.96 (ddd, J = 10.36, 6.06, 4.29 Hz, 1H) 2.85 (dd, J = 16.80, 3.92 Hz, 1H) 2.33 (dd, J = 16.42, 9.60 Hz, 1H) 1.54 (s, 9H) 1.21 (d, J = 6.32 Hz, 3H) | 446.1 |
| 54-W | 5-(5,6,7,8-Tetrahydro-pyrido[3,4-d]pyrimidin-4-yloxy)-indole-1-carboxylic acid (1,5-dimethyl-1H-pyrazol-3-yl)-amide | (DMSO-d₆) δ ppm 10.57 (s, 1H) 8.39 (s, 1 H) 8.28 (d, J = 8.84 Hz, 1H) 8.15 (d, J = 3.79 Hz, 1H) 7.41 (d, J = 2.27 Hz, 1H) 7.08 (dd, J = 8.97, 2.40 Hz, 1H) 6.70 (d, J = 3.79 Hz, 1 H) 6.34 (s, 1H) 3.81 (s, 2H) 3.68 (s, 3H) 3.03 (t, J = 5.81 Hz, 2H) 2.72 (t, J = 5.68 Hz, 2H) 2.27 (s, 3H) | 404.0 |

| | Structure/Chemical Name | ¹H NMR (400 MHz) | MS (ESI) m/z (M + 1) |
|---|---|---|---|
| 54-X | 5-(5,6,7,8-Tetrahydro-pyrido[3,4-d]pyrimidin-4-yloxy)-indole-1-carboxylic acid (1-tert-butyl-1H-pyrazol-3-yl)-amide | (DMSO-d₆) δ ppm 10.70 (s, 1H) 8.39 (s, 1 H) 8.30 (d, J = 8.97 Hz, 1H) 8.20 (d, J = 3.54 Hz, 1H) 7.78 (d, J = 2.27 Hz, 1H) 7.41 (d, J = 2.53 Hz, 1H) 7.08 (dd, J = 8.97, 2.40 Hz, 1 H) 6.70 (d, J = 3.03 Hz, 1H) 6.52 (d, J = 2.53 Hz, 1H) 3.81 (s, 2H) 3.03 (t, J = 5.94 Hz, 2 H) 2.72 (t, J = 5.68 Hz, 2H) 1.54 (s, 9H) | 432.0 |
| 54-Y | 5-(6,7-Dihydro-5H-pyrrolo[3,4-d]pyrimidin-4-yloxy)-indole-1-carboxylic acid (1-isopropyl-5-methyl-1H-pyrazol-3-yl)-amide | (MeOD) δ ppm 8.53 (s, 1H) 8.32 (d, J = 8.84 Hz, 1H) 7.88 (d, J = 3.79 Hz, 1H), 7.42 (d, J = 2.53 Hz, 1H) 7.11 (dd, J = 8.97, 2.40 Hz, 1 H) 6.71 (d, J = 3.54 Hz, 1H) 6.32 (s, 1H) 4.51 (qd, J = 6.61, 6.44 Hz, 1H) 4.19 (d, J = 6.06 Hz, 4H) 2.32 (s, 3H) 1.44 (d, J = 6.82 Hz, 6H) | 418.0 |
| 54-Z | 5-(5,6,7,8-Tetrahydro-pyrido[3,4-d]pyrimidin-4-yloxy)-indole-1-carboxylic acid (1-isopropyl-5-methyl-1H-pyrazol-3-yl)-amide | (DMSO-d₆) δ ppm 10.62 (s, 1 H) 8.39 (s, 1 H) 8.29 (d, J = 8.84 Hz, 1H) 8.19 (d, J = 3.79 Hz, 1H) 7.40 (d, J = 2.78 Hz, 1H) 7.08 (dd, J = 8.97, 2.40 Hz, 1H) 6.69 (d, J = 3.03 Hz, 1H) 6.33 (s, 1H) 4.48 (quin, J = 6.57 Hz, 1 H) 3.81 (s, 2H) 3.02 (t, J = 5.81 Hz, 2H) 2.72 (t, J = 5.56 Hz, 2H) 2.29 (s, 3H) 1.38 (d, J = 6.57 Hz, 6H) | 432.0 |
| 54-AA | 5-(5,6,7,8-Tetrahydro-pyrido[3,4-d]pyrimidin-4-yloxy)-indole-1-carboxylic acid (1-isopropyl-1H-pyrazol-3-yl)-amide | (DMSO-d₆) δ ppm 10.72 (s, 1H) 8.39 (s, 1 H) 8.30 (d, J = 8.84 Hz, 1H) 8.19 (d, J = 3.79 Hz, 1H) 7.73 (d, J = 2.27 Hz, 1H) 7.41 (d, J = 2.27 Hz, 1H) 7.08 (dd, J = 8.97, 2.40 Hz, 1 H) 6.70 (d, J = 3.79 Hz, 1H) 6.51 (d, J = 2.27 Hz, 1H) 4.45 (dt, J = 13.33, 6.60 Hz, 1H) 3.81 (s, 2H) 3.03 (t, J = 5.81 Hz, 2H) 2.72 (t, J = 5.68 Hz, 2H) 1.44 (d, J = 6.57 Hz, 6H) | 418.0 |
| 54-AB | 5-(6,7-Dihydro-5H-pyrrolo[3,4-d]pyrimidin-4-yloxy)-indole-1-carboxylic acid (1,5-dimethyl-1H-pyrazol-3-yl)-amide | (DMSO-d₆) δ ppm 10.58 (d, J = 1.26 Hz, 1 H) 8.55 (s, 1H) 8.30 (d, J = 8.59 Hz, 1H) 8.16 (d, J = 3.54 Hz, 1H) 7.44 (d, J = 2.27 Hz, 1H) 7.11 (dd, J = 8.97, 2.40 Hz, 1H) 6.70 (d, J = 4.04 Hz, 1H) 6.34 (s, 1H) 4.06-4.11 (m, 4H) 3.68 (s, 3H) 2.27 (s, 3H) | 390.0 |

| Structure/Chemical Name | $^1$H NMR (400 MHz) | MS (ESI) m/z (M + 1) |
|---|---|---|
| 54-AC <br> 5-(6,7-dihydro-5H-pyrrolo[3,4-d]pyrimidin-4-yloxy)-indole-1-carboxylic acid (1-isopropyl-1H-pyrazol-3-yl)-amide | (MeOD) δ ppm 8.53 (s, 1H) 8.33 (d, J = 8.84 Hz, 1H) 7.90 (d, J = 3.54 Hz, 1H) 7.60 (d, J = 2.27 Hz, 1H) 7.42 (d, J = 2.27 Hz, 1H) 7.12 (dd, J = 8.97, 2.40 Hz, 1H) 6.71 (d, J = 3.54 Hz, 1H) 6.53 (d, J = 2.53 Hz, 1H) 4.46 (dt, J = 13.39, 6.69 Hz, 1H) 4.19 (d, J = 6.82 Hz, 4H) 1.50 (d, J = 6.82 Hz, 6H) | 401 |
| 54-AD <br> 5-(6,7-dihydro-5H-pyrido[3,4-d]pyrimidin-4-yloxy)-indole-1-carboxylic acid [5-(1-trifluoromethyl-cyclopropyl)-1H-pyrazol-3-yl]-amide | (MeOD) δ ppm 12.80 (br. S., 1H) 10.74 (s, 1H) 8.55 (s, 1H) 8.30 (d, J = 8.84 Hz, 1H) 8.18 (d, J = 3.28 Hz, 1H) 7.45 (s, 1H) 7.13 (s, 1H) 6.72 (d, J = 3.28 Hz, 1H) 6.67 (s, 1 H) 4.08 (d, J = 1.52 Hz, 2H) 4.06-4.13 (m, 2H) 1.40 (br. S., 2H) 1.30 (br. S., 2H) | 470.9 |

EXAMPLE 55

55-A. 4-[1-(5-Trifluoromethyl-pyridin-3-ylcarbamoyl)-1H-indol-5-yloxy]-5,8-dihydro-6H-pyrido[3,4-d]pyrimidine-7-carboxylic acid tert-butyl ester

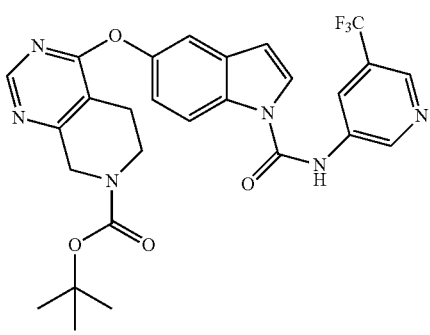 [SMILES: CC(C)(C)OC(=O)N1CCc2c(ncnc2Oc2ccc3c(ccn3C(=O)Nc3cncc(C(F)(F)F)c3)c2)C1]

A solution of 4-(1H-indol-5-yloxy)-5,8-dihydro-6H-pyrido[3,4-d]pyrimidine-7-carboxylic acid tert-butyl ester (92 mg, 0.25 mmol) and THF (5 mL) is treated with NaH (20 mg, 0.50 mmol, 60% mineral oil) and then Example 13-A (304 mg, 0.75 mmol) is added. After 24 h, the reaction is concentrated in vacuo and partitioned between DCM and water. The organic layer is removed, dried, and concentrated. The crude residue is separated via FCC (5-90% EtOAc/heptane) to give the title compound. MS (ESI) m/z 555.1 (M+1).

55-B. 5-(5,6,7,8-Tetrahydro-pyrido[3,4-d]pyrimidin-4-yloxy)-indole-1-carboxylic acid (5-trifluoromethyl-pyridin-3-yl)-amide

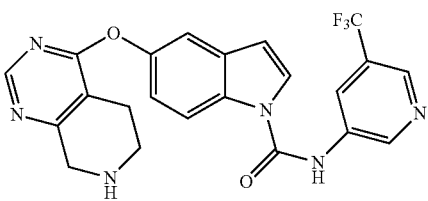 [SMILES: O=C(Nc1cncc(C(F)(F)F)c1)n1ccc2cc(Oc3ncnc4c3CCNC4)ccc21]

A solution of 4-[1-(5-trifluoromethyl-pyridin-3-ylcarbamoyl)-1H-indol-5-yloxy]-5,8-dihydro-6H-pyrido[3,4-d]pyrimidine-7-carboxylic acid tert-butyl ester (47 mg, 85 umol), DCM (2 mL), and TEA (2 mL) is stirred at rt for 2 h. The solution is then concentrated and the residue is separated via semi-prep HPLC (C18; 10-100% I/H$_2$O with 0.1% NH$_4$OH) to give the title compound. MS (ESI) m/z 455.1 (M+1); $^1$H NMR (400 MHz, DMSO-d$_6$) δ ppm 10.54 (s, 1 H), 9.11 (d, J=2.3 Hz, 1 H), 8.72 (s, 1 H), 8.50 (t, J=2.0 Hz, 1 H), 8.40 (s, 1 H), 8.30 (d, J=8.8 Hz, 1 H), 8.11 (d, J=3.8 Hz, 1 H), 7.46 (d, J=2.3 Hz, 1 H), 7.13 (dd, J=9.0, 2.4 Hz, 1 H), 6.81 (d, J=3.5 Hz, 1 H), 3.82 (s, 2 H), 3.04 (t, J=5.8 Hz, 2 H), 2.73 (t, J=5.6 Hz, 2 H).

The following compounds are prepared with similar method.

55-C. (±)-5-(6-Methyl-5,6,7,8-tetrahydro-pyrido[3,4-d]pyrimidin-4-yloxy)-indole-1-carboxylic acid (5-trifluoromethyl-pyridin-3-yl)-amide

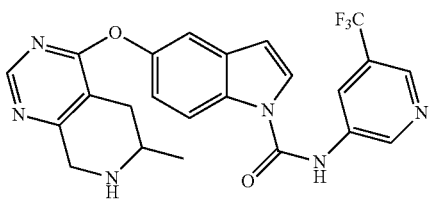 [SMILES: CC1Cc2c(ncnc2Oc2ccc3c(ccn3C(=O)Nc3cncc(C(F)(F)F)c3)c2)CN1]

MS (ESI) m/z 469.0 (M+1); $^1$H NMR (400 MHz, MeOD) δ ppm 9.07 (d, J=2.3 Hz, 1 H), 8.64 (s, 1 H), 8.57 (s, 1 H), 8.32-8.42 (m, 2 H), 7.95 (d, J=3.5 Hz, 1 H), 7.41 (d, J=2.5 Hz, 1 H), 7.12 (dd, J=9.1, 2.3 Hz, 1 H), 6.77 (d, J=3.8 Hz, 1 H), 4.05 (d, J=7.6 Hz, 2 H), 3.18 (ddd, J=10.5, 6.3, 4.2 Hz, 1 H), 3.04 (dd, J=17.4, 3.8 Hz, 1 H), 2.52 (dd, J=17.4, 10.4 Hz, 1 H), 1.37 (d, J=6.3 Hz, 3 H).

EXAMPLE 56

56-A. 4-[1-(5-tert-Butyl-isoxazol-3-ylcarbamoyl)-1H-indol-5-yloxy]-5,8-dihydro-6H-pyrido[3,4-d]pyrimidine-7-carboxylic acid tert-butyl ester

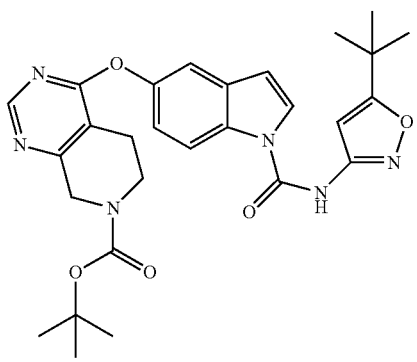 [SMILES: CC(C)(C)OC(=O)N1CCc2c(ncnc2Oc2ccc3c(ccn3C(=O)Nc3cc(C(C)(C)C)on3)c2)C1]

To a solution of 4-(1H-indol-5-yloxy)-5,8-dihydro-6H-pyrido[3,4-d]pyrimidine-7-carboxylic acid tert-butyl ester, Example 31-C, (1.1 g, 3.00 mmol) in THF (50 ml), NaH (0.360 g, 9.01 mmol) is added under nitrogen at 0° C. and the resulting mixture is stirred for 1 h. Then a solution of (5-tert-butyl-isoxazol-3-yl)-carbamic acid phenyl ester (1.56 g, 6.00 mmol) in THF is added. The resulting mixture is stirred at 0° C. for 1 h. The mixture is allowed to warm to rt and stir overnight. The mixture is then quenched with sat aq ammonium chloride solution and then extracted with EtOAc (2×). The combined organic layers are washed with brine, dried over anhydrous sodium sulfate, filtered, and condensed. The residue is then separated by FCC (0-70% EtOAc/Heptane) to provide the title compound. MS (ESI) m/z 533.1 (M+1).

56-B. 5-(5,6,7,8-Tetrahydro-pyrido[3,4-d]pyrimidin-4-yloxy)-indole-1-carboxylic acid (5-tert-butyl-isoxazol-3-yl)-amide

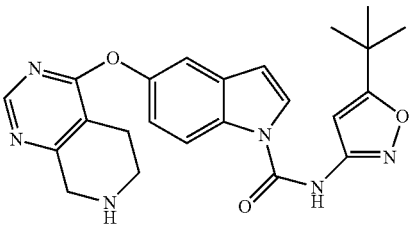 [SMILES: CC(C)(C)c1cc(NC(=O)n2ccc3cc(Oc4ncnc5c4CCNC5)ccc32)no1]

4-[1-(5-Tert-Butyl-isoxazol-3-ylcarbamoyl)-1H-indol-5-yloxy]-5,8-dihydro-6H-pyrido[3,4-d]pyrimidine-7-carboxylic acid tert-butyl ester (1.4 g) is stirred in the mixture of DCM (200 ml) and TFA (2 ml) overnight. After removal of solvents, the residue is neutralized with sat aqueous sodium bicarbonate and extracted with EtOAc (3×). Combined organic layers are washed with water, brine, dried with $Na_2SO_4$, filtered, and condensed. The residue is then separated by FCC (0-10%, 2 M $NH_3$ in MeOH/DCM) to provide the title compound. MS (ESI) m/z 432.9 (M+1);

$^1$H NMR (400 MHz, MeOD) δ ppm 8.37 (s, 1 H) 8.33 (d, J=8.84 Hz, 1 H) 7.88 (d, J=3.79 Hz, 1 H) 7.38 (d, J=2.02 Hz, 1 H) 7.10 (dd, J=8.84, 2.27 Hz, 1 H) 6.72 (d, J=3.79 Hz, 1 H) 6.65 (s, 1 H) 3.94 (s, 2 H) 3.17 (t, J=5.94 Hz, 2 H) 2.87 (t, J=5.68 Hz, 2 H) 1.38 (s, 9 H).

The following compounds are prepared with similar method.

| | Structure/Chemical Name | $^1$H NMR (400 MHz) | MS (ESI) m/z (M + 1) |
|---|---|---|---|
| 56-C | 4-Fluoro-2-methyl-5-(5,6,7,8-tetrahydro-pyrido[3,4-d]pyrimidin-4-yloxy)-indole-1-carboxylic acid (5-tert-butyl-isoxazol-3-yl)-amide. | (MeOD) δ ppm 8.35 (br. S., 1H) 7.48 (d, J = 8.84 Hz, 1H) 7.04 (t, J = 6.69 Hz, 1H) 6.66 (s, 1H) 6.49 (br. S., 1H) 3.93 (br. S., 2H) 3.15 (br. S., 2H) 2.87 (br. S., 2H) 2.58 (br. S., 3H) 1.38 (s, 9H). | 464.9 |

| | Structure/Chemical Name | $^1$H NMR (400 MHz) | MS (ESI) m/z (M + 1) |
|---|---|---|---|
| 56-D | 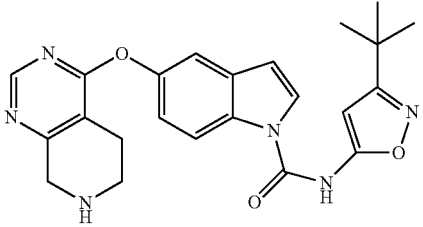<br>5-(6,7-dihydro-5H-pyrido[3,4-d]pyrimidin-4-yloxy)-indole-1-carboxylic acid (5-trifluoromethyl-oxazol-2-yl)-amide. | (MeOD) δ ppm 8.35-8.39 (m, 2H) 7.90 (d, J = 3.79 Hz, 1H) 7.38 (d, J = 2.27 Hz, 1H) 7.09 (s, 1H) 6.71 (d, J = 3.79 Hz, 1H) 6.37 (s, 1H) 4.00 (s, 2H) 3.21-3.25 (m, 2H) 2.91 (s, 2H) 1.36 (s, 9H). | 433.0 |
| 56-E | 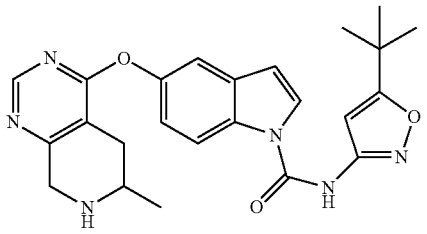<br>(±)-5-(6-Methyl-5,6,7,8-tetrahydro-pyrido[3,4-d]pyrimidin-4-yloxy)-indole-1-carboxylic acid (5-tert-butyl-isoxazol-3-yl)-amide | (MeOD) δ ppm 8.37 (s, 1H), 8.34 (d, J = 8.8 Hz, 1H), 7.90 (d, J = 3.8 Hz, 1H), 7.39 (d, J = 2.3 Hz, 1H), 7.10 (dd, J = 9.0, 2.4 Hz, 1H), 6.73 (d, J = 3.8 Hz, 1H), 6.65 (s, 1H), 3.90-4.08 (m, 2H), 3.05-3.16 (m, 1H), 3.00 (dd, J = 17.1, 3.7 Hz, 1H), 2.48 (dd, J = 17.1, 10.7 Hz, 1H), 1.39 (s, 9H), 1.34 (d, J = 6.3 Hz, 3H). | 447.1 |
| 56-F | 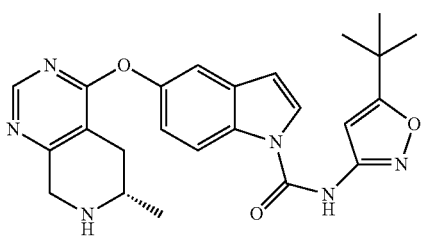<br>(+)-5-((S)-6-Methyl-5,6,7,8-tetrahydro-pyrido[3,4-d]pyrimidin-4-yloxy)-indole-1-carboxylic acid (5-tert-butyl-isoxazol-3-yl)-amide. | (DMSO-d$_6$) δ ppm 8.40 (s, 1H) 8.29 (d, J = 9.09 Hz, 1H) 8.15 (d, J = 3.28 Hz, 1H) 7.43 (d, J = 1.26 Hz, 1H) 7.11 (dd, J = 8.72, 1.39 Hz, 1H) 6.75 (d, J = 3.03 Hz, 1H) 6.68 (s, 1H) 3.79-3.98 (m, 2H) 2.91-3.05 (m, 1H) 2.85 (d, J = 16.17 Hz, 1H) 2.34 (dd, J = 16.17, 9.60 Hz, 1 H) 1.34 (s, 9H) 1.21 (d, J = 6.32 Hz, 3H). R$_t$ 8.92 min (Chiralpak IA column-MeCN/EtOH 4:6) | 447.2 |
| 56-G | 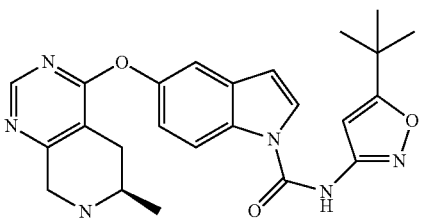<br>(−)-5-((R)-6-Methyl-5,6,7,8-tetrahydro-pyrido[3,4-d]pyrimidin-4-yloxy)-indole-1-carboxylic acid (5-tert-butyl-isoxazol-3-yl)-amide. | (DMSO-d$_6$) δ ppm 8.40 (s, 1H) 8.29 (d, J = 9.09 Hz, 1H) 8.15 (d, J = 3.79 Hz, 1H) 7.43 (d, J = 2.27 Hz, 1H) 7.11 (dd, J = 8.97, 2.40 Hz, 1H) 6.75 (d, J = 3.79 Hz, 1H) 6.68 (s, 1H) 3.81-3.95 (m, 2H) 2.90-3.02 (m, 1H) 2.85 (dd, J = 17.05, 3.66 Hz, 1H) 2.34 (dd, J = 16.67, 9.85 Hz, 1H) 1.34 (s, 9H) 1.21 (d, J = 6.32 Hz, 3H). R$_t$ 11.77 min (Chiralpak IA column-MeCN/EtOH 4:6) | 447.1 |

| | Structure/Chemical Name | ¹H NMR (400 MHz) | MS (ESI) m/z (M + 1) |
|---|---|---|---|
| 56-H | 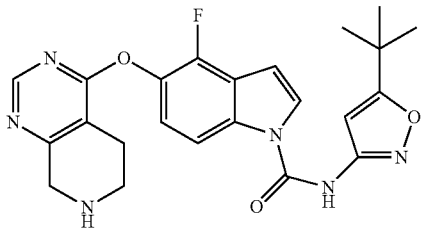<br>4-Fluoro-5-(5,6,7,8-tetrahydro-pyrido[3,4-d]pyrimidin-4-yloxy)-indole-1-carboxylic acid (5-tert-butyl-isoxazol-3-yl)-amide. | (DMSO-d₆) δ ppm 8.41 (s, 1H), 8.18 (d, J = 3.8 Hz, 1H), 8.12 (d, J = 9.1 Hz, 1H), 7.21-7.32 (m, 1H), 6.87 (d, J = 3.8 Hz, 1H), 6.67 (s, 1H), 3.85 (s, 2H), 3.06 (t, J = 5.8 Hz, 2H), 2.76 (t, J = 5.7 Hz, 2H), 1.34 (s, 9H). | 451.1 |
| 56-I | 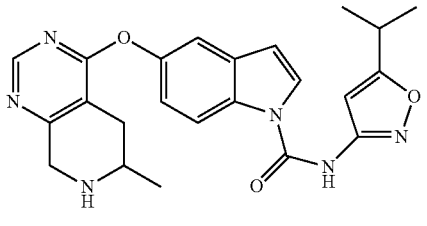<br>(±)-5-(6-Methyl-5,6,7,8-tetrahydro-pyrido[3,4-d]pyrimidin-4-yloxy)-indole-1-carboxylic acid (5-isopropyl-isoxazol-3-yl)-amide. | (DMSO-d₆) δ ppm 8.40 (s, 1H), 8.29 (d, J = 9.1 Hz, 1H), 8.15 (d, J = 3.5 Hz, 1H), 7.43 (d, J = 2.5 Hz, 1H), 7.11 (dd, J = 9.0, 2.4 Hz, 1H), 6.75 (d, J = 3.5 Hz, 1H), 6.69 (d, J = 0.8 Hz, 1 H), 3.79-3.96 (m, 2H), 3.04-3.18 (m, 1H), 2.90-3.03 (m, 1H), 2.85 (dd, J = 16.8, 3.4 Hz, 1H), 2.33 (dd, J = 16.7, 10.4 Hz, 1H), 1.29 (d, J = 6.8 Hz, 6H), 1.21 (d, J = 6.3 Hz, 3H). | 433.1 |
| 56-J | 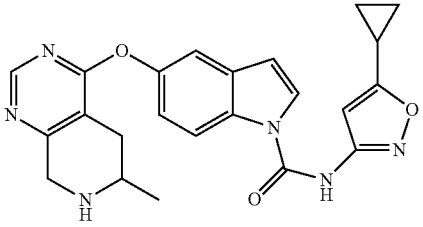<br>(±)-5-(6-Methyl-5,6,7,8-tetrahydro-pyrido[3,4-d]pyrimidin-4-yloxy)-indole-1-carboxylic acid (5-cyclopropyl-isoxazol-3-yl)-amide. | (DMSO-d₆) δ ppm 8.40 (s, 1H), 8.28 (d, J = 9.1 Hz, 1H), 8.14 (d, J = 3.5 Hz, 1H), 7.42 (d, J = 2.3 Hz, 1H), 7.11 (dd, J = 8.8, 2.3 Hz, 1H), 6.74 (d, J = 3.8 Hz, 1H), 6.65 (s, 1H), 3.80-3.95 (m, 2H), 2.90-3.03 (m, 1H), 2.84 (dd, J = 16.9, 3.5 Hz, 1H), 2.33 (dd, J = 16.7, 10.4 Hz, 1H), 2.12-2.21 (m, 1H), 1.21 (d, J = 6.1 Hz, 3 H), 1.03-1.12 (m, 2H), 0.91-0.97 (m, 2H). | 431.0 |
| 56-K | 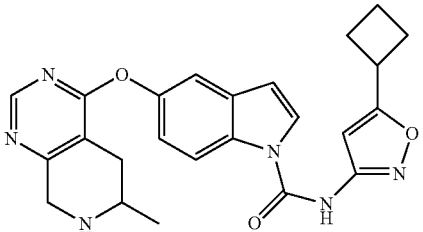<br>(±)-5-(6-Methyl-5,6,7,8-tetrahydro-pyrido[3,4-d]pyrimidin-4-yloxy)-indole-1-carboxylic acid (5-cyclobutyl-isoxazol-3-yl)-amide. | (DMSO-d₆) δ ppm 8.40 (s, 1H), 8.29 (d, J = 8.8 Hz, 1H), 8.16 (d, J = 3.8 Hz, 1H), 7.43 (d, J = 2.5 Hz, 1H), 7.11 (dd, J = 8.8, 2.3 Hz, 1H), 6.72-6.78 (m, 2H), 3.81-3.95 (m, 2H), 3.64-3.76 (m, 1H), 2.90-3.03 (m, 1H), 2.85 (dd, J = 16.5, 3.4 Hz, 1H), 2.31-2.41 (m, 3H), 2.18-2.31 (m, 2H), 1.98-2.12 (m, 1H), 1.87-1.98 (m, 1H), 1.18-1.24 (m, 3H). | 445.1 |

|  | Structure/Chemical Name | ¹H NMR (400 MHz) | MS (ESI) m/z (M + 1) |
|---|---|---|---|
| 56-L | 5-(5,6,7,8-Tetrahydro-pyrido[3,4-d]pyrimidin-4-yloxy)-indole-1-carboxylic acid (5-cyclobutyl-isoxazol-3-yl)-amide. | (DMSO-d₆) δ ppm 8.39 (s, 1H), 8.30 (d, J = 8.8 Hz, 1H), 8.15 (d, J = 3.8 Hz, 1H), 7.43 (d, J = 2.5 Hz, 1H), 7.11 (dd, J = 9.0, 2.4 Hz, 1H), 6.71-6.78 (m, 2H), 3.82 (s, 2H), 3.63-3.75 (m, 1H), 3.03 (t, J = 5.8 Hz, 2H), 2.72 (t, J = 5.7 Hz, 2H), 2.30-2.43 (m, 2H), 2.17-2.31 (m, 2H), 1.99-2.11 (m, 1H), 1.86-1.99 (m, 1 H). | 431.3 |
| 56-M | 5-(5,6,7,8-Tetrahydro-pyrido[3,4-d]pyrimidin-4-yloxy)-indole-1-carboxylic acid (5-cyclopropyl-isoxazol-3-yl)-amide. | (DMSO-d₆) δ ppm 8.39 (s, 1H), 8.28 (d, J = 8.8 Hz, 1H), 8.14 (d, J = 3.8 Hz, 1H), 7.43 (d, J = 2.3 Hz, 1H), 7.11 (dd, J = 9.0, 2.4 Hz, 1H), 6.74 (d, J = 3.5 Hz, 1H), 6.65 (s, 1H), 3.82 (s, 2 H), 3.03 (t, J = 5.8 Hz, 2H), 2.72 (t, J = 5.7 Hz, 2 H), 2.12-2.22 (m, 1H), 1.04-1.13 (m, 2H), 0.89-0.98 (m, 2H). | 417.2 |
| 56-N | 5-(5,6,7,8-Tetrahydro-pyrido[3,4-d]pyrimidin-4-yloxy)-indole-1-carboxylic acid (5-isopropyl-isoxazol-3-yl)-amide. | (DMSO-d₆) δ ppm 8.40 (s, 1H), 8.29 (d, J = 8.8 Hz, 1H), 8.16 (d, J = 3.5 Hz, 1H), 7.43 (d, J = 2.3 Hz, 1H), 7.11 (dd, J = 9.0, 2.4 Hz, 1H), 6.75 (d, J = 3.8 Hz, 1H), 6.69 (d, J = 0.8 Hz, 1 H), 3.82 (s, 2H), 3.06-3.16 (m, 1H), 3.03 (t, J = 5.8 Hz, 2H), 2.72 (t, J = 5.6 Hz, 2H), 1.29 (d, J = 7.1 Hz, 6H). | 419. |
| 56-O | 5-(5,6,7,8-Tetrahydro-pyrido[3,4-d]pyrimidin-4-yloxy)-indole-1-carboxylic acid [5-(1-methyl-cyclopropyl)-isoxazol-3-yl]-amide. | (DMSO-d₆) δ ppm 8.40 (s, 1H), 8.29 (d, J = 8.8 Hz, 1H), 8.15 (d, J = 3.5 Hz, 1H), 7.43 (d, J = 2.5 Hz, 1H), 7.12 (dd, J = 9.0, 2.4 Hz, 1H), 6.75 (d, J = 3.8 Hz, 1H), 6.67 (s, 1H), 3.82 (s, 2 H), 3.03 (t, J = 5.8 Hz, 2H), 2.72 (t, J = 5.7 Hz, 2 H), 1.46 (s, 3H), 1.12-1.18 (m, 2H), 0.90-0.97 (m, 2H). | 431.2 |

-continued

| | Structure/Chemical Name | $^1$H NMR (400 MHz) | MS (ESI) m/z (M + 1) |
|---|---|---|---|
| 56-P | 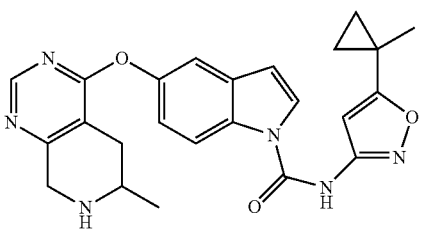<br>(±)-5-(6-Methyl-5,6,7,8-tetrahydro-pyrido[3,4-d]pyrimidin-4-yloxy)-indole-1-carboxylic acid [5-(1-methyl-cyclopropyl)-isoxazol-3-yl]-amide. | (DMSO-d$_6$) δ ppm 8.40 (s, 1H), 8.28 (d, J = 8.8 Hz, 1H), 8.15 (d, J = 3.8 Hz, 1H), 7.43 (d, J = 2.3 Hz, 1H), 7.11 (dd, J = 9.0, 2.4 Hz, 1H), 6.75 (d, J = 3.5 Hz, 1H), 6.66 (s, 1H), 3.80-3.95 (m, 2H), 2.91-3.03 (m, 1H), 2.85 (dd, J = 16.9, 3.5 Hz, 1H), 2.34 (dd, J = 16.8, 10.2 Hz, 1H), 1.46 (s, 3H), 1.21 (d, J = 6.3 Hz, 3H), 1.12-1.17 (m, 2H), 0.91-0.96 (m, 2H). | 445.3 |
| 56-Q | 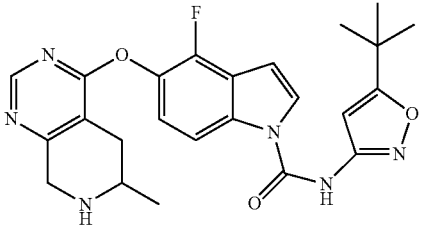<br>(±)-4-Fluoro-5-(6-methyl-5,6,7,8-tetrahydro-pyrido[3,4-d]pyrimidin-4-yloxy)-indole-1-carboxylic acid (5-tert-butyl-isoxazol-3-yl)-amide. | (DMSO-d$_6$) δ ppm 8.42 (s, 1H), 8.19 (d, J = 3.79 Hz, 1H), 8.12 (d, J = 8.84 Hz, 1H), 7.27 (d, J = 7.58 Hz, 1H), 6.87 (d, J = 3.79 Hz, 1H), 6.67 (s, 1H), 3.90 (d, J = 7.07 Hz, 2H), 3.00 (ddd, J = 10.23, 6.44, 3.79 Hz, 1H), 2.86 (dd, J = 17.18, 3.28 Hz, 1H), 2.40 (dd, J = 17.18, 10.36 Hz, 1H), 1.34 (s, 9H), 1.22 (d, J = 6.32 Hz, 3H). | 465.1 |
| 56-R | 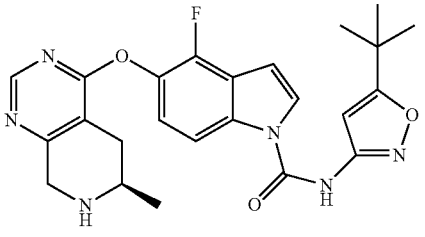<br>4-Fluoro-5-((R)-6-methyl-5,6,7,8-tetrahydro-pyrido[3,4-d]pyrimidin-4-yloxy)-indole-1-carboxylic acid (5-tert-butyl-isoxazol-3-yl)-amide | (DMSO-d$_6$) δ ppm 8.42 (s, 1H), 8.19 (d, J = 3.79 Hz, 1H), 8.12 (d, J = 8.84 Hz, 1H), 7.27 (d, J = 7.58 Hz, 1H), 6.87 (d, J = 3.79 Hz, 1H), 6.67 (s, 1H), 3.90 (d, J = 7.07 Hz, 2H), 3.00 (ddd, J = 10.23, 6.44, 3.79 Hz, 1H), 2.86 (dd, J = 17.18, 3.28 Hz, 1H), 2.40 (dd, J = 17.18, 10.36 Hz, 1H), 1.34 (s, 9H), 1.22 (d, J = 6.32 Hz, 3H). | 465.1 |
| 56-S | 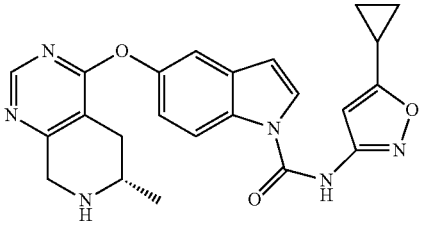<br>5-((S)-6-Methyl-5,6,7,8-tetrahydro-pyrido[3,4-d]pyrimidin-4-yloxy)-indole-1-carboxylic acid (5-cyclopropyl-isoxazol-3-yl)-amide | (DMSO-d$_6$) δ ppm 8.40 (s, 1H), 8.27 (d, J = 9.1 Hz, 1H), 8.15 (d, J = 3.8 Hz, 1H), 7.43 (d, J = 2.3 Hz, 1H), 7.11 (dd, J = 9.0, 2.4 Hz, 1H), 6.74 (d, J = 3.3 Hz, 1H), 6.65 (s, 1H), 3.79-3.95 (m, 2H), 2.90-3.01 (m, 1H), 2.85 (dd, J = 16.9, 3.5 Hz, 1H), 2.34 (dd, J = 16.8, 10.2 Hz, 1H), 2.12-2.23 (m, 1H), 1.21 (d, J = 6.3 Hz, 3H), 1.05-1.12 (m, 2H), 0.91-0.97 (m, 2H) | 431.2 |

-continued

| | Structure/Chemical Name | $^1$H NMR (400 MHz) | MS (ESI) m/z (M + 1) |
|---|---|---|---|
| 56-T | 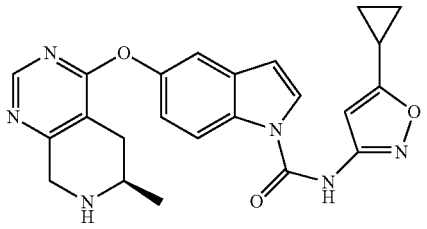<br>5-((R)-6-Methyl-5,6,7,8-tetrahydro-pyrido[3,4-d]pyrimidin-4-yloxy)-indole-1-carboxylic acid (5-cyclopropyl-isoxazol-3-yl)-amide | (DMSO-d$_6$) δ ppm 8.40 (s, 1H), 8.27 (d, J = 8.8 Hz, 1H), 8.15 (d, J = 3.8 Hz, 1H), 7.43 (d, J = 2.4 Hz, 1H), 7.11 (dd, J = 9.0, 2.3 Hz, 1H), 6.75 (d, J = 3.8 Hz, 1H), 6.65 (s, 1H), 3.78-3.95 (m, 2H), 2.91-3.04 (m, 1H), 2.80-2.90 (m, 1H), 2.27-2.40 (m, 1H), 2.12-2.22 (m, 1H), 1.21 (d, J = 6.3 Hz, 3H), 1.04-1.12 (m, 2H), 0.90-0.98 (m, 2H) | 431.0 |
| 56-U | 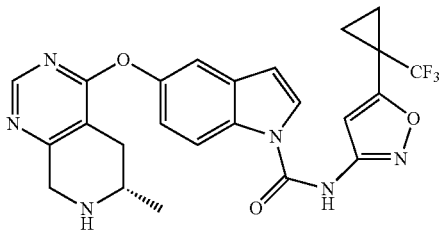<br>5-((S)-6-Methyl-5,6,7,8-tetrahydro-pyrido[3,4-d]pyrimidin-4-yloxy)-indole-1-carboxylic acid [5-(1-trifluoromethyl-cyclopropyl)-isoxazol-3-yl]-amide | (DMSO-d$_6$) δ ppm 8.41 (s, 1H), 8.29 (d, J = 8.8 Hz, 1H), 8.15 (d, J = 3.8 Hz, 1H), 7.43 (d, J = 2.3 Hz, 1H), 7.12 (dd, J = 9.0, 2.4 Hz, 1H), 7.04 (s, 1H), 6.75 (d, J = 3.5 Hz, 1H), 3.77-3.96 (m, 2H), 2.95-3.05 (m, 1H), 2.86 (dd, J = 17.1, 3.4 Hz, 1H), 2.32 (dd, J = 3.9, 1.9 Hz, 1H), 1.50-1.60 (m, 4H), 1.22 (d, J = 6.3 Hz, 3H) | 499.1 |
| 56-V | 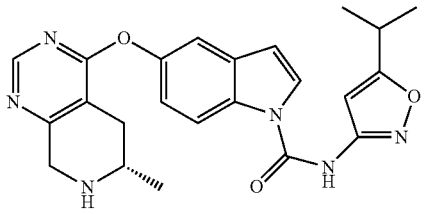<br>5-((S)-6-Methyl-5,6,7,8-tetrahydro-pyrido[3,4-d]pyrimidin-4-yloxy)-indole-1-carboxylic acid (5-isopropyl-isoxazol-3-yl)-amide | (DMSO-d$_6$) δ ppm 1.21 (d, J = 6.3 Hz, 3H), 1.29 (d, J = 6.8 Hz, 6H), 2.27-2.40 (m, 1H), 2.85 (dd, J = 16.9, 3.5 Hz, 1H), 2.92-3.02 (m, 1H), 3.05-3.18 (m, 1H), 3.80-3.95 (m, 2H), 6.69 (s, 1H), 6.75 (d, J = 3.8 Hz, 1H), 7.12 (dd, J = 9.0, 2.4 Hz, 1H), 7.43 (d, J = 2.3 Hz, 1H), 8.16 (d, J = 3.8 Hz, 1H), 8.28 (d, J = 8.8 Hz, 1H), 8.40 (s, 1H) | 433.2 |
| 56-W | 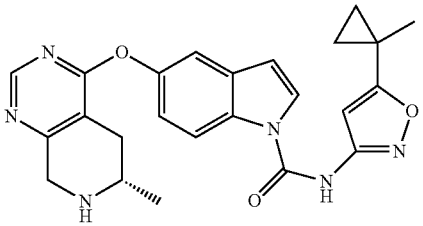<br>5-((S)-6-Methyl-5,6,7,8-tetrahydro-pyrido[3,4-d]pyrimidin-4-yloxy)-indole-1-carboxylic acid [5-(1-methyl-cyclopropyl)-isoxazol-3-yl]-amide. | (DMSO-d$_6$) δ ppm 0.90-0.97 (m, 2H), 1.11-1.18 (m, 2H), 1.21 (d, J = 6.3 Hz, 3H), 1.46 (s, 3H), 2.34 (dd, J = 16.8, 10.2 Hz, 1H), 2.85 (dd, J = 16.9, 3.5 Hz, 1H), 2.90-3.03 (m, 1H), 3.79-3.96 (m, 2H), 6.67 (s, 1H), 6.75 (d, J = 3.8 Hz, 1H), 7.11 (dd, J = 9.0, 2.4 Hz, 1H), 7.43 (d, J = 2.4 Hz, 1H), 8.16 (d, J = 3.7 Hz, 1H), 8.28 (d, J = 9.0 Hz, 1H), 8.40 (s, 1H) | 445.2 |

| Structure/Chemical Name | ¹H NMR (400 MHz) | MS (ESI) m/z (M + 1) |
|---|---|---|
| 56-X 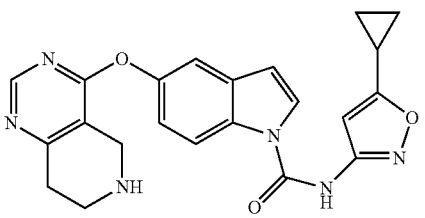<br>5-(5,6,7,8-Tetrahydro-pyrido[4,3-d]pyrimidin-4-yloxy)-indole-1-carboxylic acid (5-cyclopropyl-isoxazol-3-yl)-amide | (DMSO-d$_6$) δ ppm 8.41 (s, 1H), 8.27 (d, J = 9.1 Hz, 1H), 8.15 (d, J = 3.8 Hz, 1H), 7.43 (d, J = 2.5 Hz, 1H), 7.11 (dd, J = 9.0, 2.4 Hz, 1H), 6.74 (d, J = 3.8 Hz, 1H), 6.65 (s, 1H), 3.92 (s, 2H), 3.06 (t, J = 5.7 Hz, 2H), 2.74 (t, J = 5.7 Hz, 2H), 2.12-2.22 (m, 1H), 1.04-1.13 (m, 2H), 0.90-0.98 (m, 2H). | 417.1 |
| 56-Y 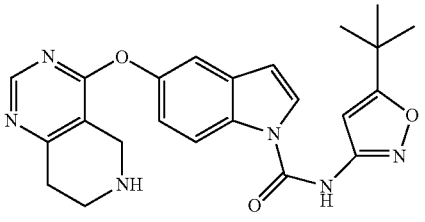<br>5-(5,6,7,8-Tetrahydro-pyrido[4,3-d]pyrimidin-4-yloxy)-indole-1-carboxylic acid (5-tert-butyl-isoxazol-3-yl)-amide | (DMSO-d$_6$) δ ppm 8.44 (s, 1H), 8.29 (d, J = 9.1 Hz, 1H), 8.16 (d, J = 3.8 Hz, 1H), 7.44 (d, J = 2.5 Hz, 1H), 7.12 (dd, J = 9.0, 2.4 Hz, 1H), 6.76 (d, J = 3.8 Hz, 1H), 6.68 (s, 1H), 4.00 (s, 2H), 3.14 (app t, J = 5.7 Hz, 2H), 2.79 (app t, J = 5.7 Hz, 2H), 1.34 (s, 9H) | 433.1 |
| 56-X 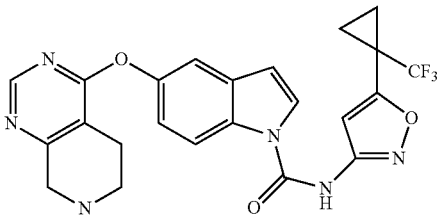<br>5-(5,6,7,8-Tetrahydro-pyrido[3,4-d]pyrimidin-4-yloxy)-indole-1-carboxylic acid [5-(1-trifluoromethyl-cyclopropyl)-isoxazol-3-yl]-amide | (DMSO-d$_6$) δ ppm 8.40 (s, 1H), 8.30 (d, J = 8.8 Hz, 1H), 8.15 (d, J = 3.8 Hz, 1H), 7.43 (d, J = 2.3 Hz, 1H), 7.12 (dd, J = 9.0, 2.4 Hz, 1H), 7.04 (s, 1H), 6.75 (d, J = 3.8 Hz, 1H), 3.84 (s, 2H), 3.05 (t, J = 5.8 Hz, 2H), 2.73 (t, J = 5.7 Hz, 2H), 1.46-1.61 (m, 4H) | 485.1 |
| 56-Y 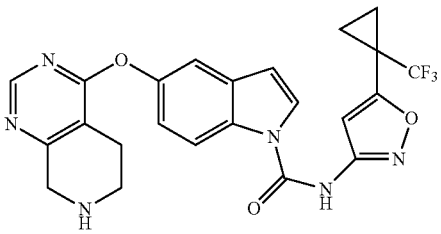<br>5-(5,6,7,8-Tetrahydro-pyrido[3,4-d]pyrimidin-4-yloxy)-indole-1-carboxylic acid [5-(1-trifluoromethyl-cyclopropyl)-isoxazol-3-yl]-amide | (DMSO-d$_6$) δ ppm 8.40 (s, 1H), 8.30 (d, J = 8.8 Hz, 1H), 8.15 (d, J = 3.8 Hz, 1H), 7.43 (d, J = 2.3 Hz, 1H), 7.12 (dd, J = 9.0, 2.4 Hz, 1H), 7.04 (s, 1H), 6.75 (d, J = 3.8 Hz, 1H), 3.84 (s, 2H), 3.05 (t, J = 5.8 Hz, 2H), 2.73 (t, J = 5.7 Hz, 2H), 1.46-1.61 (m, 4H) | 485.1 |

| | Structure/Chemical Name | ¹H NMR (400 MHz) | MS (ESI) m/z (M + 1) |
|---|---|---|---|
| 56-Z | 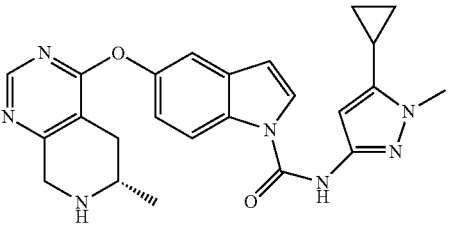 5-((S)-6-Methyl-5,6,7,8-tetrahydro-pyrido[3,4-d]pyrimidin-4-yloxy)-indole-1-carboxylic acid (5-cyclopropyl-1-methyl-1H-pyrazol-3-yl)-amide | (DMSO-d$_6$) δ ppm 10.58 (s, 1H) 8.39 (s, 1 H) 8.27 (d, J = 9.09 Hz, 1H) 8.14 (d, J = 3.79 Hz, 1H) 7.40 (d, J = 2.02 Hz, 1H) 7.07(dd, J = 8.97, 2.40 Hz, 1H) 6.70 (d, J = 3.79 Hz, 1H) 6.16 (s, 1H) 3.87 (d, J = 6.32 Hz, 2H) 3.75-3.82 (m, 3H) 2.94-2.96 (m, 1H) 2.82-2.87 (m, 1H) 2.33 (ddd, J = 3.85, 1.83, 1.64 Hz, 1H) 1.85-1.96 (m, 1H) 1.21 (d, J = 6.32 Hz, 3H) 0.92-1.02 (m, 2H) 0.62-0.70 (m, 2H) | 444.1 |
| 56-AA | 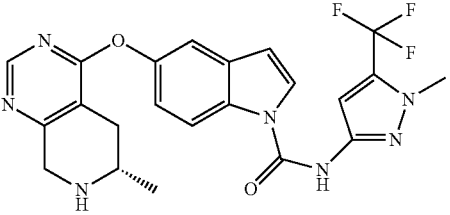 5-((S)-6-Methyl-5,6,7,8-tetrahydro-pyrido[3,4-d]pyrimidin-4-yloxy)-indole-1-carboxylic acid (1-methyl-5-trifluoromethyl-1H-pyrazol-3-yl)-amide | (DMSO-d$_6$) δ ppm 8.40 (s, 1H) 8.29 (d, J = 9.09 Hz, 1H) 8.17 (d, J = 3.79 Hz, 1H) 7.42 (d, J = 2.27 Hz, 1H) 7.07-7.12 (m, 2 H) 6.74 (d, J = 3.79 Hz, 1H) 3.95 (s, 3H) 3.87 (d, J = 6.06 Hz, 2H) 2.92-3.00 (m, 1H) 2.85 (dd, J = 16.93, 3.54 Hz, 1H) 2.33 (dd, J = 16.55, 10.48 Hz, 1H) 1.21 (d, J = 6.06 Hz, 3H) | 472.0 |

EXAMPLE 57

57-A. 5-(6,7-dihydro-5H-pyrrolo[3,4-d]pyrimidin-4-yloxy)-indole-1-carboxylic acid (5-tert-butyl-isoxazol-3-yl)-amide

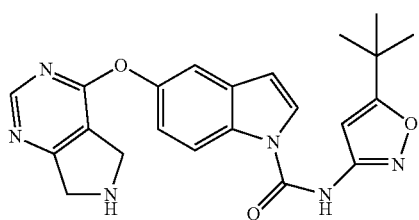

Tert-butyl 4-(1H-indol-5-yloxy)-5H-pyrrolo[3,4-d]pyrimidine-6(7H)-carboxylate (127 mg, 0.360 mmol) is dissolved in THF (8 mL), flushed with nitrogen and cooled to 0° C. Sodium hydride (23 mg, 0.575 mmol, 60% in mineral oil) is added and the mixture is stirred for 10 minutes. Phenyl 5-tert-butylisoxazol-3-ylcarbamate (140 mg, 0.538 mmol) is added neat and the reaction is allowed to stir at room temperature overnight. The reaction is cooled in an ice bath and quenched with a saturated solution of ammonium chloride (100 mL). The mixture is then diluted with ethyl acetate and the product is extracted (2×100 mL EtOAc). The organic layers are combined, dried and concentrated to a brown oil that is dissolved in 10 mL of DCM and cooled in an ice bath and 10 mL of TFA is added. Following completion of the reaction the DCM and TFA are removed and ethyl acetate is added to the residue along with ammonium hydroxide to quench the remaining TFA. The mixture is diluted with water and extracted with ethyl acetate (2×50 mL). The organic layers are removed, dried, and concentrated. The residue is absorbed onto silica and separated via FCC (0-6% Methanol/DCM) to obtain N-(5-tert-butylisoxazol-3-yl)-5-(6,7-dihydro-5H-pyrrolo[3,4-d]pyrimidin-4-yloxy)-1H-indole-1-carboxamide. MS (ESI) m/z 419.2 (M+1); ¹H NMR (400 MHz, DMSO-d$_6$) δ ppm 8.56 (s, 1 H) 8.29 (d, J=8.84 Hz, 1 H) 8.17 (d, J=3.79 Hz, 1 H) 7.47 (d, J=2.27 Hz, 1 H) 7.15 (dd, J=8.97, 2.40 Hz, 1 H) 6.76 (d, J=3.28 Hz, 1 H) 6.68 (s, 1 H) 4.07-4.14 (m, 4 H) 1.34 (s, 9 H).

The following compounds are prepared with similar method.

| | Structure/Chemical Name | ¹H NMR (400 MHz) | MS (ESI) m/z (M + 1) |
|---|---|---|---|
| 57-B | 6,7-dihydro-5H-pyrrolo[3,4-d]pyrimidin-4-yloxy)-indole-1-carboxylic acid (3-tert-butyl-isoxazol-5-yl)-amide | (DMSO-d$_6$) δ ppm 8.61 (s, 1H) 8.42 (d, J = 9.09 Hz, 1H) 8.11 (d, J = 3.79 Hz, 1H) 7.44 (d, J = 2.27 Hz, 1H) 7.11 (dd, J = 9.22, 2.40 Hz, 1H) 6.67 (d, J = 3.54 Hz, 1H) 6.22 (s, 1H) 4.25 (br. S., 4H) 1.28 (s, 9H). | 419.9 |
| 57-C | 5-(6,7-dihydro-5H-pyrrolo[3,4-d]pyrimidin-4-yloxy)-2-methyl-indole-1-carboxylic acid (5-tert-butyl-isoxazol-3-yl)-amide. | (MeOD) δ ppm 8.52 (s, 1H), 7.70 (d, J = 8.84 Hz, 1H), 7.29 (d, J = 2.27 Hz, 1H), 7.02 (dd, J = 8.84, 2.27 Hz, 1H), 6.65 (s, 1H), 6.44 (s, 1H), 4.19 (d, J = 5.56 Hz, 2H), 4.18 (s, 2H), 2.60 (s, 3H), 1.39 (s, 9H). | 433.2 |
| 57-D | 5-(6,7-dihydro-5H-pyrrolo[3,4-d]pyrimidin-4-yloxy)-indole-1-carboxylic acid 1,2-benzisoxazol-3-ylamide. | (DMSO-d$_6$) δ ppm 8.58 (s, 1H) 8.35 (d, J = 9.09 Hz, 1H) 8.19 (d, J = 3.54 Hz, 1H) 8.01 (d, J = 7.83 Hz, 1H) 7.72-7.75 (m, 1H) 7.68 (dd, J = 6.82, 1.26 Hz, 1H) 7.50 (d, J = 2.27 Hz, 1H) 7.39 (t, J = 7.58 Hz, 1H) 7.16 (dd, J = 8.97, 2.40 Hz, 1H) 6.79 (d, J = 3.79 Hz, 1H) 4.12 (d, J = 14.91 Hz, 4H). | 413.1 |
| 57-E | 5-(6,7-dihydro-5H-pyrrolo[3,4-d]pyrimidin-4-yloxy)-indole-1-carboxylic acid [3-(4-fluoro-phenyl)-isoxazol-5-yl]-amide. | (DMSO-d$_6$) δ ppm 8.68 (s, 1H) 8.58 (d, J = 8.84 Hz, 1H) 8.13 (d, J = 3.54 Hz, 1H) 7.88 (dd, J = 8.84, 5.56 Hz, 2H) 7.42 (d, J = 2.53 Hz, 1H) 7.32 (dd, J = 8.84, 4.55 Hz, 2H) 7.08 (dd, J = 8.97, 2.40 Hz, 1H) 6.60 (d, J = 3.54 Hz, 1H) 6.58 (s, 1H) 4.38 (d, J = 5.31 Hz, 4H). | 457.1 |

-continued

| | Structure/Chemical Name | $^1$H NMR (400 MHz) | MS (ESI) m/z (M + 1) |
|---|---|---|---|
| 57-F | 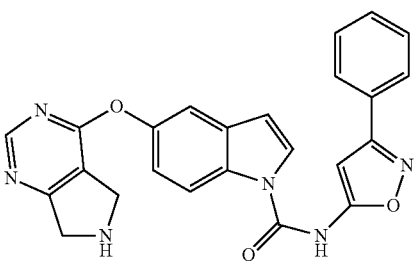<br>5-(6,7-dihydro-5H-pyrrolo[3,4-d]pyrimidin-4-yloxy)-indole-1-carboxylic acid (3-phenyl-isoxazol-5-yl)-amide. | (DMSO-d$_6$) δ ppm 8.68 (s, 1H) 8.58 (d, J = 9.35 Hz, 1H) 8.13 (d, J = 3.54 Hz, 1H) 7.83 (d, J = 8.08 Hz, 2H) 7.42-7.52 (m, 5H) 7.09 (dd, J = 8.97, 1.89 Hz, 1H) 6.61 (d, J = 3.54 Hz, 1H) 6.59 (s, 1H) 4.36 (d, J = 3.54 Hz, 4H). | 439.1 |
| 57-G | 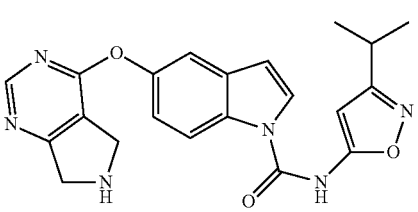<br>5-(6,7-dihydro-5H-pyrrolo[3,4-d]pyrimidin-4-yloxy)-indole-1-carboxylic acid (3-isopropyl-isoxazol-5-yl)-amide. | (DMSO-d$_6$) δ ppm 8.62 (s, 1H) 8.44 (d, J = 8.84 Hz, 1H) 8.11 (d, J = 3.54 Hz, 1H) 7.44 (d, J = 2.53 Hz, 1H) 7.11 (dd, J = 9.09, 2.53 Hz, 1H) 6.67 (d, J = 3.54 Hz, 1H) 6.17 (s, 1H) 4.26 (d, J = 5.56 Hz, 4H) 2.88-2.96 (m, 1H) 1.23 (d, J = 6.82 Hz, 6H). | 405.1 |
| 57-H | 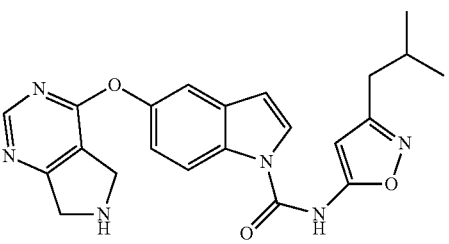<br>5-(6,7-dihydro-5H-pyrrolo[3,4-d]pyrimidin-4-yloxy)-indole-1-carboxylicacid (3-isobutyl-isoxazol-5-yl)-amide. | (DMSO-d$_6$) δ ppm 8.62 (s, 1H) 8.43 (d, J = 8.84 Hz, 1H) 8.11 (d, J = 3.79 Hz, 1H) 7.43 (d, J = 2.27 Hz, 1H) 7.10 (dd, J = 8.84, 2.53 Hz, 1H) 6.66 (d, J = 4.04 Hz, 1H) 6.11 (s, 1H) 4.25 (br. S., 3H) 4.08 (br. S., 1H) 2.41-2.45 (m, 2H) 1.96 (dd, J = 13.52, 6.69 Hz, 1H) 0.94 (d, J = 6.57 Hz, 6H). | 49.0 |
| 1£<br>57-I | 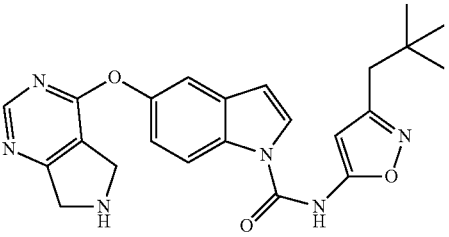<br>5-(6,7-dihydro-5H-pyrrolo[3,4-d]pyrimidin-4-yloxy)-indole-1-carboxylicacid [3-(2,2-dimethyl-propyl)-isoxazol-5-yl]-amide. | (MeOD) δ ppm 8.54 (s, 1H) 8.39 (d, J = 9.09 Hz, 1H) 7.93 (d, J = 3.79 Hz, 1H) 7.44 (d, J = 2.27 Hz, 1H) 7.15 (dd, J = 8.97, 2.40 Hz, 1H) 6.75 (d, J = 3.79 Hz, 1H) 6.32 (s, 1H) 4.26 (br. S., 4H) 2.56 (s, 2H) 0.98-1.04 (m, 9H). | 433.1 |

-continued

| Structure/Chemical Name | ¹H NMR (400 MHz) | MS (ESI) m/z (M + 1) |
|---|---|---|
| 57-J 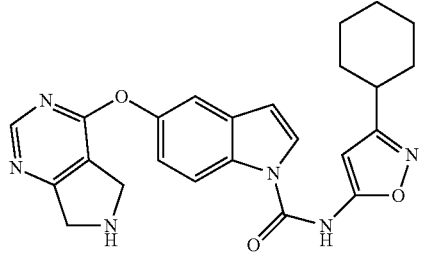 5-(6,7-dihydro-5H-pyrrolo[3,4-d]pyrimidin-4-yloxy)-indole-1-carboxylic acid (3-cyclohexyl-isoxazol-5-yl)-amide. | (DMSO-d$_6$) δ ppm 8.62 (s, 1H) 8.42 (d, J = 8.84 Hz, 1H) 8.10 (d, J = 3.79 Hz, 1H) 7.43 (d, J = 2.27 Hz, 1H) 7.11 (dd, J = 8.97, 2.40 Hz, 1H) 6.67 (d, J = 3.79 Hz, 1H) 6.14 (s, 1H) 4.22-4.29 (m, 4H) 2.63 (s, 1H) 1.89 (d, J = 12.13 Hz, 2H) 1.73-1.79 (m, 2H) 1.23-1.50 (m, 6H). | 445.0 |
| 57-K 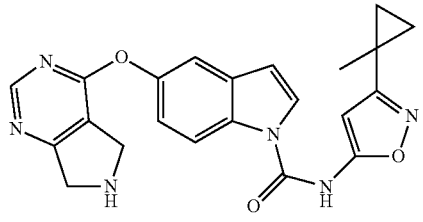 5-(6,7-dihydro-5H-pyrrolo[3,4-d]pyrimidin-4-yloxy)-indole-1-carboxylic acid [3-(1-methyl-cyclopropyl)-isoxazol-5-yl]-amide. | (DMSO-d$_6$) δ ppm 8.58 (s, 1H) 8.51 (d, J = 8.08 Hz, 1H) 8.06 (d, J = 3.54 Hz, 1H) 7.37 (d, J = 2.78 Hz, 1H) 7.04 (d, J = 9.09 Hz, 1H) 6.56 (s, 1H) 5.86 (s, 1H) 4.15 (s, 4H) 1.37 (s, 3H) 0.92 (m, 2H) 0.77 (m, 2H) | 417.1 |
| 57-L 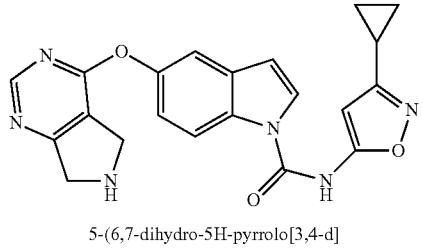 5-(6,7-dihydro-5H-pyrrolo[3,4-d]pyrimidin-4-yloxy)-indole-1-carboxylic acid (3-cyclopropyl-isoxazol-5-yl)-amide. | (TFA salt) (DMSO-d$_6$) δ ppm 8.68 (s, 1H) 8.37 (d, J = 9.09 Hz, 1H) 8.12 (d, J = 3.79 Hz, 1H) 7.48 (d, J = 2.27 Hz, 1H) 7.15 (d, J = 8.84 Hz, 1H) 6.74 (d, J = 3.54 Hz, 1H) 6.03 (s, 1H) 4.42 (d, J = 10.11 Hz, 4H) 1.96 (m, 1H) 0.97-1.03 (m, 2H) 0.77-0.80 (m, 2H) | 403.1 |
| 57-M 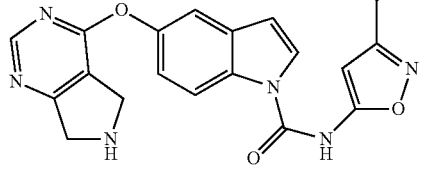 5-(6,7-dihydro-5H-pyrrolo[3,4-d]pyrimidin-4-yloxy)-indole-1-carboxylic acid (3-cyclobutyl-isoxazol-5-yl)-amide. | (DMSO-d$_6$) δ ppm 8.62 (s, 1H) 8.45 (d, J = 8.84 Hz, 1H) 8.11 (d, J = 3.79 Hz, 1H) 7.43 (d, J = 2.27 Hz, 1H) 7.11 (dd, J = 8.84 Hz, 1H) 6.66 (d, J = 3.79 Hz, 1H) 6.19 (s, 1H) 4.26 (d, J = 1.77 Hz, 4H) 2.24-2.34 (m, 4H) 1.82-2.08 (m, 3H) | 417.2 |

-continued

| Structure/Chemical Name | ¹H NMR (400 MHz) | MS (ESI) m/z (M + 1) |
|---|---|---|
| 57-N 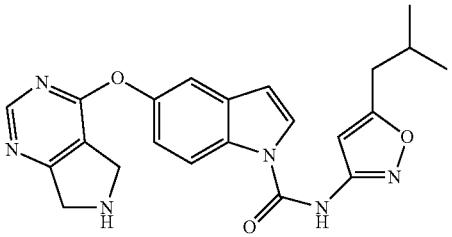 5-(6,7-dihydro-5H-pyrrolo[3,4-d]pyrimidin-4-yloxy)-indole-1-carboxylic acid (5-isobutyl-isoxazol-3-yl)-amide. | (DMSO-d₆) δ ppm 8.56 (s, 1H) 8.30 (s, 1 H) 8.17 (d, J = 3.79 Hz, 1H) 7.47 (d, J = 2.27 Hz, 1H) 7.15 (dd, J = 8.84, 2.53 Hz, 1H) 6.76 (d, J = 3.79 Hz, 1H) 6.72 (s, 1H) 4.07-4.13 (m, 4H) 2.68 (d, J = 6.82 Hz, 2H) 2.01-2.03 (m, 1H) 0.95 (d, J = 6.82 Hz, 6H) | 419.1 |
| 57-O 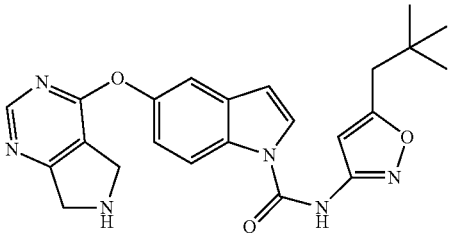 5-(6,7-dihydro-5H-pyrrolo[3,4-d]pyrimidin-4-yloxy)-indole-1-carboxylic acid [5-(2,2-dimethyl-propyl)-isoxazol-3-yl]-amide. | (DMSO-d₆) δ ppm 8.56 (s, 1H) 8.29 (d, J = 9.09 Hz, 1H) 8.17 (d, J = 3.79 Hz, 1H) 7.47 (d, J = 2.27 Hz, 1H) 7.15 (dd, J = 8.97, 2.40 Hz, 1H) 6.76 (d, J = 3.79 Hz, 1H) 6.72 (s, 1H) 4.06-4.30 (m, 4H) 2.69 (s, 2H) 0.98 (s, 9H) | 43.1 |
| 3£ 57-P 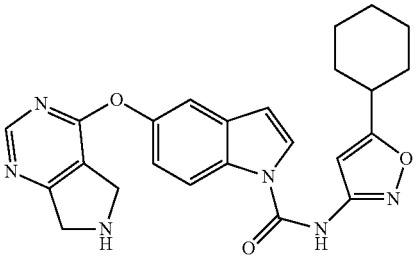 5-(6,7-dihydro-5H-pyrrolo[3,4-d]pyrimidin-4-yloxy)-indole-1-carboxylic acid (5-cyclohexyl-isoxazol-3-yl)-amide. | (DMSO-d₆) δ ppm 8.56 (s, 1H) 8.30 (s, 1H) 8.16 (d, J = 3.54 Hz, 1H) 7.47 (d, J = 2.53 Hz, 1H) 7.15 (dd, J = 8.97, 2.40 Hz, 1H) 6.76 (d, J = 3.79 Hz, 1H) 6.67 (s, 1H) 4.07-4.13 (m, 4H) 2.83 (d, J = 3.54 Hz, 1H) 1.99 (br. S., 2 H) 1.76 (d, J = 16.17 Hz, 2H) 1.34-1.51 (m, 6H). | 445.0 |
| 57-Q 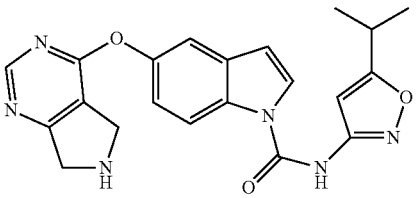 5-(6,7-dihydro-5H-pyrrolo[3,4-d]pyrimidin-4-yloxy)-indole-1-carboxylic acid (5-isopropyl-isoxazol-3-yl)-amide. | (DMSO-d₆) δ ppm 8.56 (s, 1H) 8.29 (d, J = 8.84 Hz, 1H) 8.17 (d, J = 3.79 Hz, 1H) 7.47 (d, J = 2.27 Hz, 1H) 7.15 (dd, J = 8.97, 2.40 Hz, 1H) 6.76 (d, J = 3.79 Hz, 1H) 6.69 (s, 1 H) 4.00-4.20 (m, 4H) 3.11 (m, 1H) 1.29 (d, J = 7.07 Hz, 6H). | 405.1 |

| | Structure/Chemical Name | ¹H NMR (400 MHz) | MS (ESI) m/z (M + 1) |
|---|---|---|---|
| 57-R | 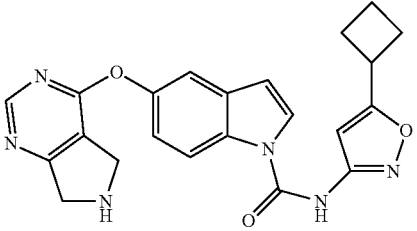<br>5-(6,7-dihydro-5H-pyrrolo[3,4-d]pyrimidin-4-yloxy)-indole-1-carboxylic acid (5-cyclobutyl-isoxazol-3-yl)-amide. | (DMSO-d₆) δ ppm 8.56 (s, 1H) 8.30 (d, J = 8.84 Hz, 1H) 8.17 (d, J = 3.54 Hz, 1H) 7.47 (d, J = 2.53 Hz, 1H) 7.15 (dd, J = 8.97, 2.40 Hz, 1H) 6.72-6.82 (m, 2H) 4.00-4.20 (m, 4H) 3.70 (m, 1H) 2.32-2.43 (m, 2H) 2.17-2.31 (m, 2H) 1.85-2.14 (m, 2H). | 417.1 |
| 57-S | 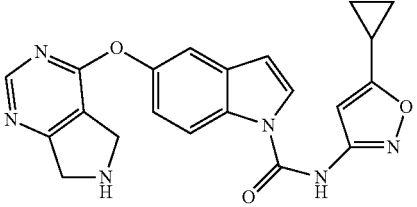<br>5-(6,7-dihydro-5H-pyrrolo[3,4-d]pyrimidin-4-yloxy)-indole-1-carboxylic acid (5-cyclopropyl-isoxazol-3-yl)-amide. | (DMSO-d₆) δ ppm 8.55 (s, 1H) 8.29 (d, J = 9.09 Hz, 1H) 8.16 (d, J = 3.79 Hz, 1H) 7.46 (d, J = 2.27 Hz, 1H) 7.14 (dd, J = 8.97, 2.40 Hz, 1H) 6.75 (d, J = 3.28 Hz, 1H) 6.65 (s, 1H) 4.04-4.16 (m, 4H) 2.07-2.26 (m, 1H) 1.01-1.15 (m, 2H) 0.87-0.98 (m, 2H). | 403.1 |
| 57-T | 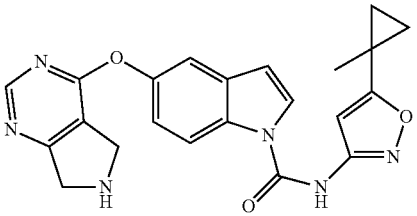<br>5-(6,7-dihydro-5H-pyrrolo[3,4-d]pyrimidin-4-yloxy)-indole-1-carboxylic acid [5-(1-methyl-cyclopropyl)-isoxazol-3-yl]-amide. | (DMSO-d₆) δ ppm 8.56 (s, 1H) 8.29 (d, J = 8.84 Hz, 1H) 8.16 (d, J = 3.79 Hz, 1H) 7.47 (d, J = 2.53 Hz, 1H) 7.15 (dd, J = 8.97, 2.40 Hz, 1H) 6.76 (d, J = 3.28 Hz, 1H) 6.67 (s, 1H) 4.01-4.19 (m, 4 H + 1 N—H) 1.46 (s, 3H) 1.07-1.21 (m, 2H) 0.86-1.02 (m, 2H). | 417.1 |
| 57-U | 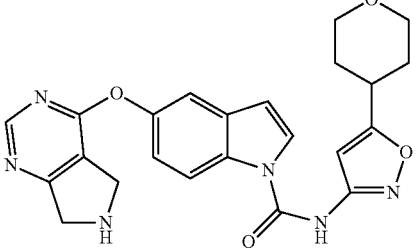<br>5-(6,7-dihydro-5H-pyrrolo[3,4-d]pyrimidin-4-yloxy)-indole-1-carboxylic acid [5-(tetrahydro-pyran-4-yl)-isoxazol-3-yl]-amide. | (DMSO-d₆) δ ppm 8.56 (s, 1H) 8.29 (d, J = 8.84 Hz, 1H) 8.17 (d, J = 3.79 Hz, 1H) 7.47 (d, J = 2.27 Hz, 1H) 7.15 (dd, J = 8.97, 2.40 Hz, 1H) 6.73-6.78 (m, 2H) 4.06-4.13 (m, 4H) 3.89-3.94 (m, 1H) 3.43-3.45 (m, 1H) 3.09-3.18 (m, 2H) 1.90-1.96 (m, 2H) 1.64-1.75 (m, 2H). | 447.1 |

| | Structure/Chemical Name | ¹H NMR (400 MHz) | MS (ESI) m/z (M + 1) |
|---|---|---|---|
| 57-V | 5-(6,7-dihydro-5H-pyrrolo[3,4-d]pyrimidin-4-yloxy)-indole-1-carboxylic acid [5-(4-methyl-tetrahydro-pyran-4-yl)-isoxazol-3-yl]-amide. | (DMSO-d₆) δ ppm 8.56 (s, 1H) 8.29 (d, J = 9.09 Hz, 1H) 8.17 (d, J = 3.79 Hz, 1H) 7.47 (d, J = 2.27 Hz, 1H) 6.78 (s, 1H) 6.76 (m, 2H) 4.08 (d, J = 2.02 Hz, 2H) 4.07-4.14 (m, 2H) 3.71-3.77 (m, 2H) 3.42-3.49 (m, 2H) 2.06 (d, J = 5.56 Hz, 1H) 2.06 (dd, J = 18.19, 3.54 Hz, 1H) 1.64-1.72 (m, 2H) 1.35 (s, 3H) | 461.1 |
| 57-W | 5-(6,7-dihydro-5H-pyrrolo[3,4-d]pyrimidin-4-yloxy)-indole-1-carboxylic acid (5-phenyl-isoxazol-3-yl)-amide. | (DMSO-d₆) δ ppm 8.56 (s, 1H) 8.21 (d, J = 3.54 Hz, 1H) 7.94 (d, J = 3.79 Hz, 1H) 7.95 (d, J = 8.08 Hz, 1H) 7.56 (d, J = 5.56 Hz, 2H) 7.55 (s, 2H) 7.45 (s, 2H) 7.48 (d, J = 2.53 Hz, 1H) 6.78 (s, 1H) 4.08 (d, J = 1.77 Hz, 4H) | 439.1 |
| 57-X | 5-(6,7-dihydro-5H-pyrrolo[3,4-d]pyrimidin-4-yloxy)-indole-1-carboxylic acid [5-(4-fluoro-phenyl)-isoxazol-3-yl]-amide. | (DMSO-d₆) δ ppm 8.55 (s, 1H) 8.30 (s, 1H) 8.20 (d, J = 3.54 Hz, 1H) 7.92 (m, 2H) 7.52 (m, 2H) 7.44 (d, J = 2.53 Hz, 2H) 7.42 (s, 2H) 7.12 (m, 1H) 6.73 (s, 1H) 4.07 (m, 4H). | 457.1 |
| 57-Y | 5-(6,7-dihydro-5H-pyrrolo[3,4-d]pyrimidin-4-yloxy)-indole-1-carboxylic acid (5-methyl-isoxazol-3-yl)-amide. | (DMSO-d₆) δ ppm 8.56 (s, 1H) 8.30 (s, 1H) 8.17 (d, J = 3.79 Hz, 1H) 7.47 (d, J = 2.02 Hz, 1H) 7.15 (dd, J = 8.97, 2.40 Hz, 1H) 6.76 (d, J = 3.79 Hz, 1H) 6.71 (s, 1H) 4.09-4.13 (m, 4H) 2.44 (s, 3H). | 337.1 |

| | Structure/Chemical Name | ¹H NMR (400 MHz) | MS (ESI) m/z (M + 1) |
|---|---|---|---|
| 57-Z | 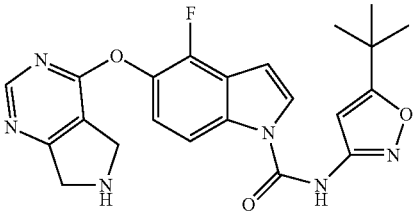<br>5-(6,7-dihydro-5H-pyrrolo[3,4-d]pyrimidin-4-yloxy)-4F-indole-1-carboxylic acid (5-tert-butyl-isoxazol-3-yl)-amide. | (DMSO-d₆) δ ppm 8.56 (s, 1H) 8.20 (d, J = 3.79 Hz, 1H) 8.12 (d, J = 9.09 Hz, 1H) 7.31 (dd, J = 7.83 Hz, 9.09 Hz, 1H) 6.89 (d, J = 3.79 Hz, 1H) 6.67 (s, 1H) 4.23 (s, 2H) 4.10-4.12 (m, 2H) 1.34 (s, 9H). | 435.2 (M − 1) |
| 57-AA | 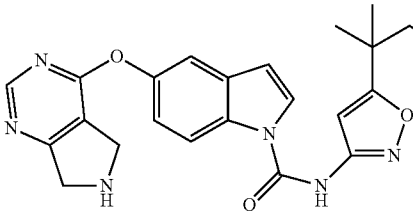 [SMILES: CC(C)(C)c1cc(NC(=O)n2ccc3cc(Oc4ncnc5c4CNC5)ccc32)no1]<br>5-(6,7-Dihydro-5H-pyrrolo[3,4-d]pyrimidin-4-yloxy)-indole-1-carboxylic acid [5-(3,3,3-trifluoro-1,1-dimethyl-propyl)-isoxazol-3-yl]-amide | (DMSO-d₆) δ ppm 8.62 (s, 1H), 8.30 (d, J = 9.1 Hz, 1H), 8.18 (d, J = 3.8 Hz, 1H), 7.49 (d, J = 2.3 Hz, 1H), 7.17 (dd, J = 9.0, 2.4 Hz, 1H), 6.81 (s, 1H), 6.78 (d, J = 3.8 Hz, 1H), 4.31 (s, 2H), 4.27 (s, 2H), 2.71-2.91 (m, 2H), 1.46 (s, 6H) | 487.0 |
| 57-AB | 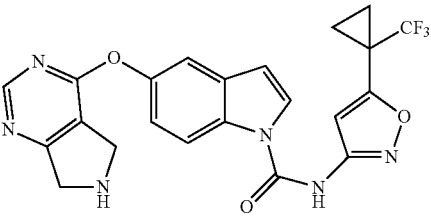<br>5-(6,7-Dihydro-5H-pyrrolo[3,4-d]pyrimidin-4-yloxy)-indole-1-carboxylic acid [5-(1 trifluoromethyl-cyclopropyl)-isoxazol-3-yl]-amide | (DMSO-d₆) δ ppm 8.56 (s, 1H) 8.30 (d, J = 8.84 Hz, 1H) 8.16 (d, J = 3.54 Hz, 1H) 7.47 (d, J = 2.27 Hz, 1H) 7.15-7.16 (m, 1H) 7.16 (d, J = 8.84 Hz, 1H) 7.04 (s, 1H) 6.76 (d, J = 3.28 Hz, 1H) 4.06-4.18 (m, 2H) 4.11 (m, 2H) 1.53-1.60 (m, 4H) | 471.1 |
| 57-AC | 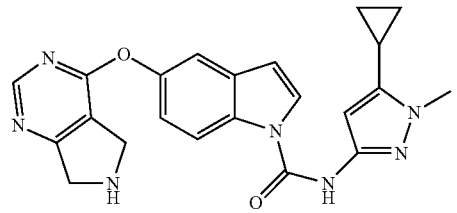<br>5-(6,7-dihydro-5H-pyrrolo[3,4-d]pyrimidin-4-yloxy)-indole-1-carboxylic acid (5-cyclopropyl-1-methyl-1H-pyrazol-3-yl)-amide | (DMSO-d₆) δ ppm 10.60 (d, J = 1.01 Hz, 1H) 8.64 (s, 1H) 8.29 (d, J = 8.84 Hz, 1H) 8.16 (d, J = 3.54 Hz, 1H) 7.46 (d, J = 2.53 Hz, 1H) 7.13 (dd, J = 9.09, 2.53 Hz, 1H) 6.72 (d, J = 3.54 Hz, 1H) 6.16 (s, 1H) 4.59 (br. S., 4H) 3.79 (s, 3H) 1.91 (s, 1H) 0.87-1.06 (m, 2H) 0.50-0.71 (m, 2H) | 416.1 |

| | Structure/Chemical Name | ¹H NMR (400 MHz) | MS (ESI) m/z (M + 1) |
|---|---|---|---|
| 57-AD | 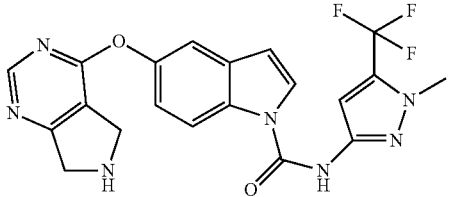<br>5-(6,7-dihydro-5H-pyrrolo[3,4-d]pyrimidin-4-yloxy)-indole-1-carboxylic acid (1-methyl-5-trifluoromethyl-1H-pyrazol-3-yl)-amide | (DMSO-d$_6$) δ ppm 8.55 (s, 1H) 8.30 (d, J = 8.84 Hz, 1H) 8.17 (d, J = 3.79 Hz, 1 H) 7.46 (d, J = 2.27 Hz, 1H) 7.14 (dd, J = 9.09, 2.53 Hz, 1H) 7.07 (s, 1H) 6.75 (d, J = 3.79 Hz, 1H) 4.03-4.16 (m, 4 H) 3.95 (s, 3H) | 444.0 |

EXAMPLE 58

58-A. 5-(6-Benzyloxymethyl-pyrimidin-4-yloxy)-indole-1-carboxylic acid 4-nitro-phenyl ester

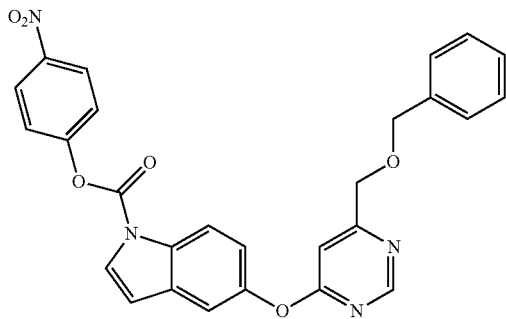 [SMILES: O=C(Oc1ccc([N+](=O)[O-])cc1)n1ccc2cc(Oc3cc(COCc4ccccc4)ncn3)ccc21]

To a solution of 5-(6-benzyloxymethyl-pyrimidin-4-yloxy)-1H-indole (943 mg, 2.85 mmol) in THF (20 mL), sodium hydride (102 mg, 4.27 mmol, 60% in mineral oil) is added under nitrogen at 0° C., the resulting mixture is stirred for 1 h. Then this reaction mixture is added to the solution of p-nitrophenyl chloromate in THF at 0° C. The mixture is stirred at 0° C. for 1 h. Then the mixture is quenched with water, the product is extracted with EtOAc (2×). Combined organic phases are washed water, brine, dried over sodium sulphate, filtered and condensed. The residue is separated by FCC (0-60% EtOAc/heptane) to provide the title compound. MS (ESI) m/z 496.9 (M+1).

58-B. 5-(6-Benzyloxymethyl-pyrimidin-4-yloxy)-indole-1-carboxylic acid (5-trifluoromethyl-2H-pyrazol-3-yl)-amide

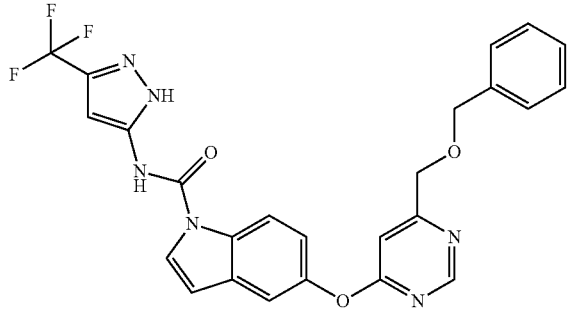 [SMILES: O=C(Nc1cc(C(F)(F)F)n[nH]1)n1ccc2cc(Oc3cc(COCc4ccccc4)ncn3)ccc21]

To a solution of 5-trifluoromethyl-2H-pyrazol-3-ylamine (876 mg, 5.80 mmol) in THF (20 mL), NaH (348 mg, 8.70 mmol, 60% in mineral oil) is added at 0° C. under nitrogen. The mixture is stirred at 0° C. for 1 h. At that point 5-(6-benzyloxymethyl-pyrimidin-4-yloxy)-indole-1-carboxylic acid 4-nitro-phenyl ester (1440 mg, 2.90 mmol) in THF (10 mL) is added. The resulting mixture is stirred overnight. Then the mixture is quenched with sat aq ammonium chloride. The product is extracted with EtOAc (2×). The combined organic layers are washed with water, brine, dried over sodium sulfate, filtered, and condensed. The residue is separated by FCC (0-70% EtOAc/heptane) to provide the title compound. MS (ESI) m/z 509.0 (M+1).

58-C. 5-(6-Hydroxymethyl-pyrimidin-4-yloxy)-indole-1-carboxylic acid (5-trifluoromethyl-1H-pyrazol-3-yl)-amide

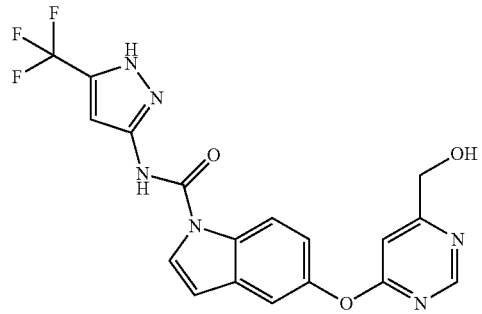 [SMILES: O=C(Nc1cc(C(F)(F)F)[nH]n1)n1ccc2cc(Oc3cc(CO)ncn3)ccc21]

A solution of 5-(6-benzyloxymethyl-pyrimidin-4-yloxy)-indole-1-carboxylic acid (5-trifluoromethyl-2H-pyrazol-3-yl)-amide (150 mg, 0.295 mmol) and TFA (1.5 mL) is stirred at 110° C. for 1.5 h. After removal of the excess TFA, the residue is quenched with saturated aqueous sodium bicarbonate solution. The mixture is then extracted with EtOAc (2×). The combined organic layers are washed with water, brine, dried over sodium sulphate, filtered, and condensed. The residue is separated by FCC (0-100% EtOAc/heptane) to provide the title compound. MS (ESI) m/z 418.9 (M+1).

58-D. 5-(6-Methylaminomethyl-pyrimidin-4-yloxy)-indole-1-carboxylic acid (5-trifluoromethyl-2H-pyrazol-3-yl)-amide

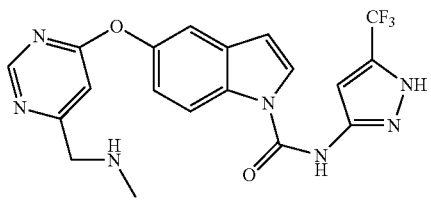 [SMILES: CNCc1cc(Oc2ccc3c(ccn3C(=O)Nc3cc(C(F)(F)F)[nH]n3)c2)ncn1]

5-(6-Hydroxymethyl-pyrimidin-4-yloxy)-indole-1-carboxylic acid (5-trifluoromethyl-1H-pyrazol-3-yl)-amide (50 mg, 0.120 mmol) is dissolved in THF (5 mL) and TEA (0.033 ml, 0.239 mmol) is added at 0° C., followed by MsCl (0.014 ml, 0.179 mmol). The mixture is stirred at 0° C. for 0.5 h. Then, the mixture is diluted with EtOAc and washed with water, brine, dried over sodium sulphate, filtered, and condensed. The residue is then used directly as is in the next step.

To a solution of methanesulfonic acid 6-[1-(5-trifluoromethyl-1H-pyrazol-3-ylcarbamoyl)-1H-indol-5-yloxy]-pyrimidin-4-ylmethyl ester (50 mg, 0.101 mmol), in THF (5 mL), methylamine in MeOH (0.5 mL, 2.0 M) is added. The mixture is stirred at rt for 3 days and then condensed. The residue is then separated by semi-prep HPLC to provide the title compound. MS (ESI) m/z 431.9 (M+1); $^1$H NMR (400 MHz, MeOD) δ ppm 8.65 (s, 1 H), 8.43 (d, J=9.09 Hz, 1 H), 7.89 (d, J=3.79 Hz, 1 H), 7.41 (d, J=2.53 Hz, 1 H), 7.11 (dd, J=8.97, 2.40 Hz, 1 H), 7.00 (s, 1 H), 6.74 (d, J=3.54 Hz, 1 H), 6.52 (s, 1 H), 3.82 (s, 2 H), 2.44 (s, 3 H).

The following compounds are prepared with similar method.

58-E. 5-(6-Methylaminomethyl-pyrimidin-4-yloxy)-indole-1-carboxylic acid (5-tert-butyl-isoxazol-3-yl)-amide

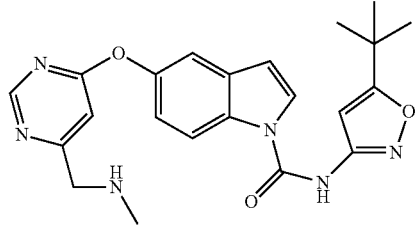 [SMILES: CNCc1cc(Oc2ccc3c(ccn3C(=O)Nc3cc(C(C)(C)C)on3)c2)ncn1]

MS (ESI) m/z 421.0 (M+1); $^1$H NMR (400 MHz, MeOD) δ ppm 8.65 (s, 1 H) 8.37 (d, J=8.84 Hz, 1H) 7.91 (d, J=3.54 Hz, 1 H) 7.41 (d, J=2.27 Hz, 1 H) 7.12 (dd, J=8.84, 2.27 Hz, 1 H) 7.00 (s, 1 H) 6.74 (d, J=3.79 Hz, 1 H) 6.65 (s, 1 H) 3.79 (s, 2 H) 2.41 (s, 3 H) 1.39 (s, 9 H).

58-F. 5-(6-Methylaminomethyl-pyrimidin-4-yloxy)-indole-1-carboxylic acid (3-tert-butyl-isoxazol-5-yl)-amide

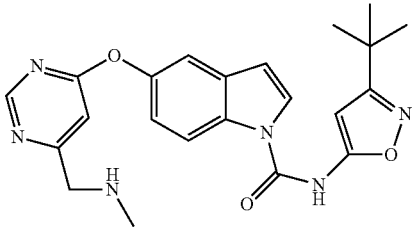 [SMILES: CNCc1cc(Oc2ccc3c(ccn3C(=O)Nc3cc(C(C)(C)C)no3)c2)ncn1]

MS (ESI) m/z 421.1 (M+1); $^1$H NMR (400 MHz, MeOD) δ ppm 8.65 (s, 1 H), 8.42 (d, J=9.1 Hz, 1 H), 7.93 (d, J=3.8 Hz, 1 H), 7.36 (d, J=2.3 Hz, 1 H), 7.05 (dd, J=8.8, 2.3 Hz, 1 H), 6.94 (s, 1 H), 6.64 (d, J=3.8 Hz, 1 H), 6.30 (s, 1 H), 3.94 (s, 2 H), 2.54 (s, 3 H), 1.34 (s, 9 H).

58-G. 4-Fluoro-5-(6-methylaminomethyl-pyrimidin-4-yloxy)-indole-1-carboxylic acid (5-tert-butyl-isoxazol-3-yl)-amide

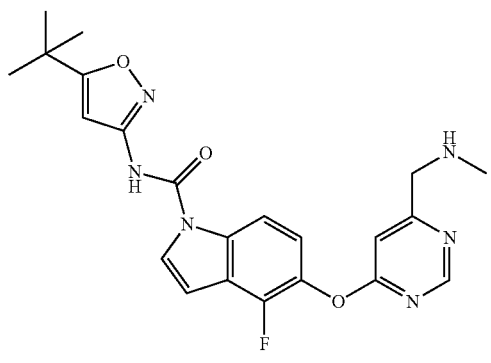 [SMILES: CNCc1cc(Oc2ccc3c(ccn3C(=O)Nc3cc(C(C)(C)C)on3)c2F)ncn1]

MS (ESI) m/z 439.1 (M+1); $^1$H NMR (400 MHz, MeOD) δ ppm 8.66 (d, J=1.01 Hz, 1 H), 8.19 (d, J=3.79 Hz, 1 H), 8.15 (d, J=9.09 Hz, 1 H), 7.28 (s, 1 H), 7.22 (d, J=1.01 Hz, 1 H), 6.87 (d, J=3.79 Hz, 1 H), 6.67 (s, 1 H), 3.79 (s, 2 H), 3.31 (s, 3 H), 1.34 (s, 9 H).

58-H. 4-Fluoro-5-(6-methylaminomethyl-pyrimidin-4-yloxy)-indole-1-carboxylic acid (5-tert-butyl-1H-pyrazol-3-yl)-amide

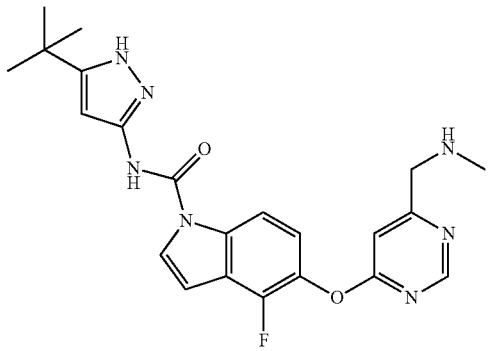 [SMILES: CNCc1cc(Oc2ccc3c(ccn3C(=O)Nc3cc(C(C)(C)C)[nH]n3)c2F)ncn1]

MS (ESI) m/z 439.1 (M+1); $^1$H NMR (400 MHz, MeOD) δ ppm 8.63 (d, J=1.01 Hz, 1 H), 8.13 (d, J=9.09 Hz, 1 H), 7.90 (d, J=3.79 Hz, 1 H), 7.17 (dd, J=8.84, 7.58 Hz, 1 H), 7.13 (s, 1 H), 6.80 (d, J=3.79 Hz, 1 H), 6.38 (s, 1 H), 3.83 (s, 2 H), 2.43 (s, 3 H), 1.36 (s, 9 H).

EXAMPLE 59

59-A. 5-(6-Benzyloxymethyl-pyrimidin-4-yloxy)-indole-1-carboxylic acid (5-tert-butyl-1H-pyrazol-3-yl)-amide

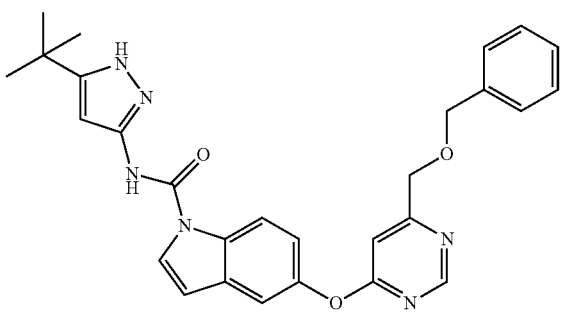 [SMILES: CC(C)(C)c1cc(NC(=O)n2ccc3cc(Oc4cc(COCc5ccccc5)ncn4)ccc32)n[nH]1]

To a solution of 5-(6-Benzyloxymethyl-pyrimidin-4-yloxy)-indole-1-carboxylic acid 4-nitro-phenyl ester, Example 58A, (100 mg, 0.201 mmol) and 5-tert-butyl-1H-pyrazol-3-ylamine (56.1 mg, 0.403 mmol) in THF (5 mL), diisopropylethylamine (0.11 mL, 0.604 mmol) is added. The resulting mixture is stirred at 65° C. overnight. After cooling to rt, the mixture is quenced with water. The product is extracted with EtOAc (2×). The combined organic layers are washed with water, brine, dried over sodium sulphate, filtered, and condensed. The residue is separated by FCC (0-60% EtOAc/heptane) to provide the title compound. MS (ESI) m/z 497.0 (M+1)

59-B. 5-(6-Methylaminomethyl-pyrimidin-4-yloxy)-indole-1-carboxylic acid (5-tert-butyl-2H-pyrazol-3-yl)-amide

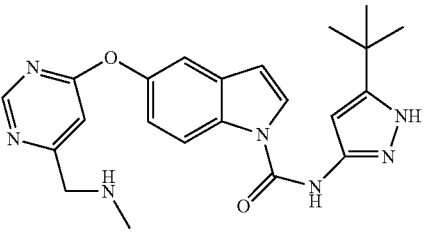 [SMILES: CNCc1cc(Oc2ccc3c(ccn3C(=O)Nc3cc(C(C)(C)C)[nH]n3)c2)ncn1]

Elaboration of 5-(6-Benzyloxymethyl-pyrimidin-4-yloxy)-indole-1-carboxylic acid (5-tert-butyl-1H-pyrazol-3-yl)-amide into 5-(6-Methylaminomethyl-pyrimidin-4-yloxy)-indole-1-carboxylic acid (5-tert-butyl-2H-pyrazol-3-yl)-amide is performed in similar fashion to that described above for Example 58D. MS (ESI) m/z 420.0 (M+1); $^1$H NMR (400 MHz, MeOD) δ ppm 8.65 (br. S., 1 H), 8.35 (d, J=9.09 Hz, 1 H), 7.90 (d, J=3.28 Hz, 1 H), 7.41 (br. S., 1 H), 7.10 (d, J=8.84 Hz, 1 H), 6.99 (br. S., 1 H), 6.72 (d, J=3.54 Hz, 1 H), 6.37 (br. S., 1 H), 3.78 (br. S., 2 H), 2.41 (br. S., 3 H), 1.36 (br. S., 9 H).

The following compounds are prepared with similar method.

59-C. 4-Fluoro-5-(6-methylaminomethyl-pyrimidin-4-yloxy)-indole-1-carboxylic acid (5-trifluoromethyl-1H-pyrazol-3-yl)-amide

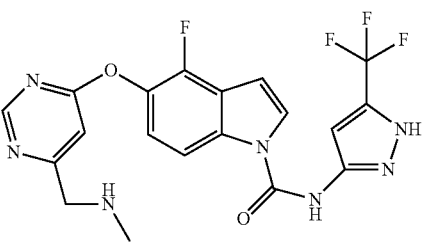 [SMILES: CNCc1cc(Oc2ccc3c(ccn3C(=O)Nc3cc(C(F)(F)F)[nH]n3)c2F)ncn1]

MS (ESI) m/z 450.0 (M+1); $^1$H NMR (400 MHz, DMSO-d$_6$) δ ppm 8.73 (s, 1 H), 8.32 (d, J=8.8 Hz, 1H), 8.09 (d, J=3.5 Hz, 1 H), 7.23 (s, 1 H), 7.20 (d, J=8.3 Hz, 1 H), 6.77 (d, J=3.5 Hz, 1 H), 6.54 (s, 1 H), 4.02-4.14 (m, 1 H), 3.98 (s, 2 H), 2.45 (s, 3 H).

EXAMPLE 60

60-A. tert-Butyl 4-(1-((4-nitrophenoxy)carbonyl)-1H-indol-5-yloxy)-5,6-dihydropyrido[3,4-d]pyrimidine-7(8H)-carboxylate

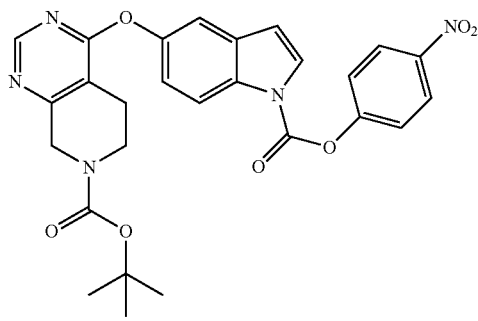 [SMILES: CC(C)(C)OC(=O)N1CCc2c(ncnc2Oc2ccc3c(ccn3C(=O)Oc3ccc([N+](=O)[O-])cc3)c2)C1]

To a solution of tert-butyl 4-(1H-indol-5-yloxy)-5,6-dihydropyrido[3,4-d]pyrimidine-7(8H)-carboxylate, Example 31-C, (1 g, 2.73 mmol) in 20 mL of THF, sodium hydride (0.164 g, 4.09 mmol, 60% in mineral oil) is added at 0° C. After 1.5 h, a solution of 4-nitrophenyl carbonochloridate (1.65 g, 8.19 mmol) in THF (10 mL) is added. The mixture is allowed to warm to rt and stir overnight before being quenched with ice water and extracted with EtOAc. The combined organic layers are washed with water and brine before being dried ($Na_2SO_4$) and concentrated. The residue is then separated by FCC (20-80% EtOAc/heptane) to give the title compound. $^1$H NMR (400 MHz, $CDCl_3$) δ ppm 8.54 (s, 1 H), 8.34-8.43 (m, 2 H), 7.79 (d, J=3.8 Hz, 1 H), 7.49-7.57 (m, 2 H), 7.41 (d, J=2.3 Hz, 1 H), 7.17 (dd, J=9.0, 2.4 Hz, 1 H), 6.75 (d, J=3.5 Hz, 1 H), 5.31 (s, 1 H), 4.65 (s, 2 H), 3.80 (t, J=5.8 Hz, 2 H), 2.95 (t, J=5.6 Hz, 2 H), 1.53 (s, 9 H).

60-B. tert-butyl 4-(1-(3-((tert-butyldimethylsilyloxy)methyl)-5-trifluoromethyl)phenylcarbamoyl)-1H-indol-5-yloxy)-5,6-dihydropyrido[3,4-d]pyrimidine-7(8H)-carboxylate

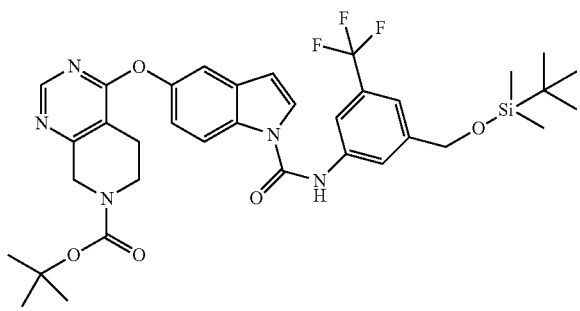 [SMILES: CC(C)(C)OC(=O)N1CCc2c(ncnc2Oc2ccc3c(ccn3C(=O)Nc3cc(CO[Si](C)(C)C(C)(C)C)cc(C(F)(F)F)c3)c2)C1]

To a solution of 2,2,6,6-tetramethylpiperidine (0.067 ml, 0.391 mmol) in THF (1.5 mL), n-BuLi (0.13 mL, 0.331 mmol) is added at −78° C. After 15 min, 3-(tert-butyl-dimethyl-silanyloxymethyl)-5-trifluoromethyl-phenylamine is added. After an additional 15 min, a solution of tert-butyl 4-(1-((4-nitrophenoxy)carbonyl)-1H-indol-5-yloxy)-5,6-dihydropyrido[3,4-d]pyrimidine-7(8H)-carboxylate in THF (3 mL) is added dropwise at −78° C. After 1 h the reaction is diluted with EtOAc, quenched with ice water and extracted with EtOAc. The combined organic layers are washed with water, brine and dried ($Na_2SO_4$), and concentrated. The residue is separated by FCC (10-60% EtOAc/heptane) to give the title compound. MS (ESI) m/z 698.3 (M+1).

60-C. 5-(5,6,7,8-Tetrahydro-pyrido[3,4-d]pyrimidin-4-yloxy)-indole-1-carboxylic acid (3-hydroxymethyl-5-trifluoromethyl-phenyl)-amide

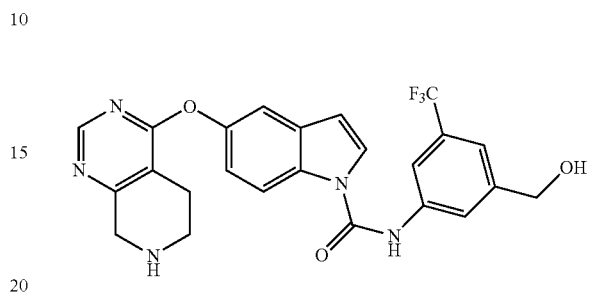

tert-Butyl 4-(1-(3-((tert-butyldimethylsilyloxy)methyl)-5-(trifluoromethyl)phenylcarbamoyl)-1H-indol-5-yloxy)-5,6-dihydropyrido[3,4-a]pyrimidine-7(8H)-carboxylate is treated with 50% TFA in DCM for 1 h. The solution is then concentrated and the residue is taken up into EtOAc, washed with saturated sodium bicarbonate and brine before being dried ($Na_2SO_4$) and concentrated. The residue is then separated by HPLC (C18; 12-42% I/$H_2O$ with 0.1% TFA) to give the title compound. MS (ESI) m/z 484.1 (M+1); $^1$H NMR (400 MHz, DMSO-$d_6$) δ ppm 10.37 (s, 1 H), 8.40 (s, 1 H), 8.27 (d, J=9.0 Hz, 1 H), 8.13 (d, J=3.7 Hz, 1 H), 7.97 (d, J=10.9 Hz, 2 H), 7.38-7.49 (m, 2 H), 7.12 (dd, J=9.0, 2.4 Hz, 1 H), 6.79 (d, J=3.7 Hz, 1 H), 5.50 (t, J=5.7 Hz, 1 H), 4.62 (d, J=5.7 Hz, 2 H), 3.82 (s, 2 H), 3.03 (t, J=5.7 Hz, 2 H), 2.72 (t, J=5.5 Hz, 2 H).

The following compounds are prepared with similar method.

60-D. (±)-5-(6-Methyl-5,6,7,8-tetrahydro-pyrido[3,4-d]pyrimidin-4-yloxy)-indole-1-carboxylic acid (3-hydroxymethyl-5-trifluoromethyl-phenyl)-amide

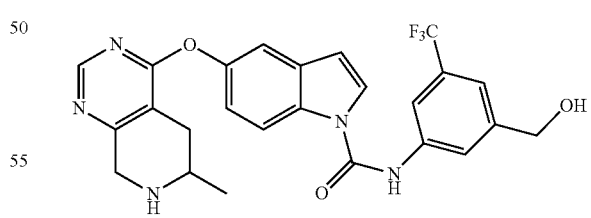

MS (ESI) m/z 498.1 (M+1); $^1$H NMR (400 MHz, DMSO-$d_6$) δ ppm 10.35 (s, 1 H), 8.40 (s, 1 H), 8.27 (d, J=9.1 Hz, 1 H), 8.13 (d, J=3.8 Hz, 1 H), 7.97 (d, J=11.1 Hz, 2 H), 7.40-7.46 (m, 2 H), 7.11 (dd, J=9.0, 2.4 Hz, 1 H), 6.78 (d, J=3.5 Hz, 1 H), 5.48 (t, J=5.7 Hz, 1 H), 4.62 (d, J=5.6 Hz, 2 H), 3.79-3.96 (m, 2 H), 2.90-3.03 (m, 1 H), 2.85 (dd, J=17.1, 3.4 Hz, 1 H), 2.29-2.38 (m, 1 H), 1.22 (d, J=6.3 Hz, 3H).

60-E. 4-Fluoro-5-(5,6,7,8-tetrahydro-pyrido[3,4-d]pyrimidin-4-yloxy)-indole-1-carboxylic acid (5-trifluoromethyl-1H-pyrazol-3-yl)-amide

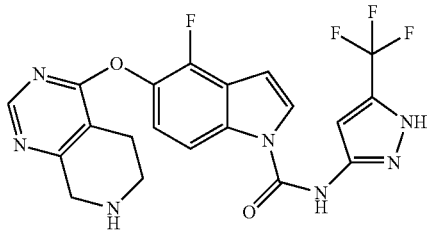 [SMILES: O=C(Nc1cc(C(F)(F)F)[nH]n1)n1ccc2c(F)c(Oc3ncnc4c3CCNC4)ccc21]

MS (ESI) m/z 462.3 (M+1); $^1$H NMR (400 MHz, MeOD) δ ppm 8.38 (br. S., 1 H), 8.13-8.24 (m, 1H), 7.83-7.96 (m, 1 H), 7.12-7.24 (m, 1 H), 6.81-6.87 (m, 1 H), 6.54 (br. S., 1 H), 3.97 (s, 2 H), 3.14-3.24 (m, 2 H), 2.92 (br. S., 2 H).

60-F. (±)-4-Fluoro-5-(6-methyl-5,6,7,8-tetrahydro-pyrido[3,4-d]pyrimidin-4-yloxy)-indole-1-carboxylic acid (5-trifluoromethyl-1H-pyrazol-3-yl)-amide

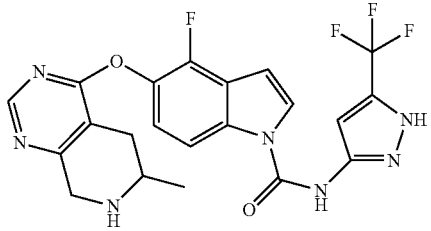 [SMILES: CC1Cc2c(ncnc2Oc2ccc3c(ccn3C(=O)Nc3cc(C(F)(F)F)[nH]n3)c2F)CN1]

MS (ESI) m/z 476.1 (M+1); $^1$H NMR (400 MHz, DMSO-d$_6$) δ ppm 8.44 (s, 1 H), 8.24 (d, J=8.84 Hz, 1H), 8.08 (d, J=3.79 Hz, 1 H), 7.22 (t, J=8.08 Hz, 1 H), 6.80 (d, J=4.04 Hz, 1 H), 6.57 (s, 1 H), 3.90-3.96 (m, 2 H), 3.07 (ddd, J=10.11, 6.06, 4.04 Hz, 1 H), 2.90-2.94 (m, 1 H), 2.38-2.45 (m, 1H), 1.24 (d, J=4.04 Hz, 3H).

EXAMPLE 61

61-A. (±)-5-Methyl-4-oxo-3,4,5,7-tetrahydro-pyrrolo[3,4-d]pyrimidine-6-carboxylic acid tert-butyl ester

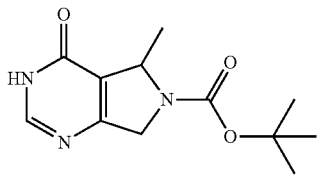 [SMILES: CC1c2c(nc[nH]c2=O)CN1C(=O)OC(C)(C)C]

To a suspension of NaH (9.72 g, 243 mmol, 60% in mineral oil) in toluene (100 mL), ethoxycarbonylamino-acetic acid ethyl ester (38 g, 187 mmol) is added at 0° C. The reaction is left stirring for 5 h at the same temperature. At that point but-2-enoic acid ethyl ester (25.6 g, 224 mmol) is added and the reaction allowed to warm up to rt and stirred for further 2 h. Ethanol (30 mL) is added and the reaction is then evaporated. The crude 1-tert-butyl 3-ethyl 2-methyl-4-oxopyrrolidine-1,3-dicarboxylate is dissolved in EtOH (1500 mL), then formamidine acetate (343 g, 1189 mmol) is added followed by sodium ethoxide (47.2 g, 694 mmol). The reaction is left stirring at 90° C. for 8 h. The solvent is then removed and to the crude material a saturated solution of NH$_4$Cl (200 mL) is added followed by DCM (1 L). The water layer is extracted two times with DCM. The organics are dried and evaporate. The crude product is separated by FCC (DCM/MeOH 100:0 to 90:10) to give the title compound. MS (ESI) m/z 252.2 (M+1).

61-B. (±)-4-(1H-Indol-5-yloxy)-5-methyl-5,7-dihydro-pyrrolo[3,4-d]pyrimidine-6-carboxylic acid tert-butyl ester

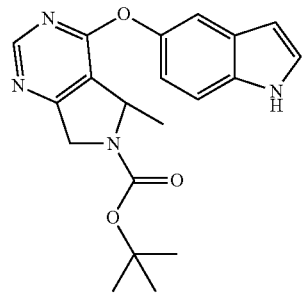 [SMILES: CC1c2c(ncnc2Oc2ccc3[nH]ccc3c2)CN1C(=O)OC(C)(C)C]

To a solution of 5-methyl-4-oxo-3,4,5,7-tetrahydro-pyrrolo[3,4-d]pyrimidine-6-carboxylic acid tert-butyl ester (1 g, 3.98 mmol) in acetonitrile (40 ml), PyBOP (2.69 g, 5.17 mmol) is added, followed by DBU (1.200 ml, 7.96 mmol). After 20 min, 5-hydroxyindole (1.060 g, 7.96 mmol) is added. The reaction is left stirring at rt overnight. The reaction mixture is then evaporated, the crude product is added to a silica gel column and is eluted with heptane/ethyl acetate (100:0 to 60:40) to give the title compound. MS (ESI) m/z 367.05 (M+1).

61-C. (±)-5-Methyl-4-[1-(3-trifluoromethyl-phenylcarbamoyl)-1H-indol-5-yloxy]-5,7-dihydro-pyrrolo[3,4-d]pyrimidine-6-carboxylic acid tert-butyl ester

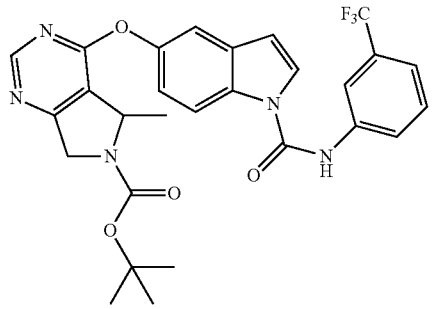 [SMILES: CC1c2c(ncnc2Oc2ccc3c(ccn3C(=O)Nc3cccc(C(F)(F)F)c3)c2)CN1C(=O)OC(C)(C)C]

To a solution of 4-(1H-Indol-5-yloxy)-5-methyl-5,7-dihydro-pyrrolo[3,4-d]pyrimidine-6-carboxylic acid tert-butyl ester (400 mg, 1.092 mmol) in THF (10 mL) at 0° C., sodium hydride (74.2 mg, 1.856 mmol, 60% in mineral oil) is added. After 10 min, 1-isocyanato-3-trifluoromethyl-benzene (0.314 ml, 2.183 mmol) is added and the reaction is allowed to reach rt. After 2 h, a saturated solution of NH$_4$Cl in water (5 mL) is added. The organics are extracted with EtOAc (×3), dried and evaporated to give the crude 5-methyl-4-[1-(3-trifluoromethyl-phenylcarbamoyl)-1H-indol-5-yloxy]-5,7-dihydro-pyrrolo[3,4-d]pyrimidine-6-carboxylic acid tert-butyl ester. MS (ESI) m/z 554.9 (M+1)

61-D. (±)-5-(5-Methyl-6,7-dihydro-5H-pyrrolo[3,4-d]pyrimidin-4-yloxy)-indole-1-carboxylic acid (3-trifluoromethyl-phenyl)-amide

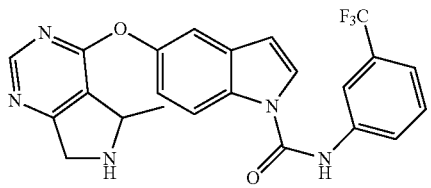 [SMILES: CC1NCc2ncnc(Oc3ccc4c(ccn4C(=O)Nc4cccc(C(F)(F)F)c4)c3)c21]

To a solution of 5-methyl-4-[1-(3-trifluoromethyl-phenylcarbamoyl)-1H-indol-5-yloxy]-5,7-dihydro-pyrrolo[3,4-d]pyrimidine-6-carboxylic acid tert-butyl ester in DCM (20 mL), TFA (20 ml, 134 mmol) is added at 0° C. After 30 min the reaction is warmed to rt. At this point, the reaction is evaporated and the crude product is dissolved in EtOAc. A Few drops of NH$_4$OH are added to freebase the amine and the whole mixture is then evaporated. The crude product is added to a silica gel column and is eluted with DCM/MeOH/NH$_4$OH (100:0:0 to 93:6:1) to give racemic 545-Methyl-6,7-dihydro-5H-pyrrolo[3,4-a]pyrimidin-4-yloxy)-indole-1-carboxylic acid (3-trifluoromethyl-phenyl)-amide. MS (ESI) m/z 454.9 (M+1); $^1$H NMR (400 MHz, MeOD) δ ppm 8.50 (s, 1 H) 8.33 (s, 1 H) 8.06 (s, 1 H) 7.94 (br. S., 2 H) 7.57 (s, 1 H) 7.42 (br. S., 2 H) 7.12 (d, J=9.09 Hz, 1 H) 6.75 (d, J=3.03 Hz, 1 H) 4.70 (br. S., 1 H) 4.10-4.22 (m, 2 H) 1.60 (d, J=6.57 Hz, 3 H). Racemate is then separated using chiral HPLC (IA column; 40% heptane, 60% Ethanol) to give the corresponding enantiomers D-1 and D-2.

61-D-1. (+)-5-(5-Methyl-6,7-dihydro-5H-pyrrolo[3,4-d]pyrimidin-4-yloxy)-indole-1-carboxylic acid (3-trifluoromethyl-phenyl)-amide R$_t$=6.09 min; MS (ESI) m/z 454.9 (M+1); $^1$H NMR (400 MHz, MeOD) δ ppm 8.48 (s, 1 H) 8.30 (d, J=9.09 Hz, 1 H) 8.03 (s, 1 H) 7.87 (d, J=3.54 Hz, 2 H) 7.52 (t, J=8.08 Hz, 1 H) 7.38 (d, J=2.27 Hz, 2 H) 7.07 (dd, J=8.84, 2.27 Hz, 1 H) 6.67 (d, J=3.79 Hz, 1 H) 4.66 (q, J=6.57 Hz, 1 H) 4.12-4.22 (m, 2 H) 1.56 (d, J=6.57 Hz, 3 H).

61-D-2. (−)-5-(5-Methyl-6,7-dihydro-5H-pyrrolo[3,4-d]pyrimidin-4-yloxy)-indole-1-carboxylic acid (3-trifluoromethyl-phenyl)-amide R$_t$=7.71 min; MS (ESI) m/z 454.9 (M+1); $^1$H NMR (400 MHz, MeOD) δ ppm 8.47 (d, J=1.77 Hz, 1H) 8.28 (dd, J=9.09, 1.77 Hz, 1 H) 8.02 (s, 1 H) 7.85 (dd, J=3.66, 2.40 Hz, 2 H) 7.49 (t, J=7.83 Hz, 1 H) 7.36 (d, J=2.02 Hz, 1 H) 7.38 (d, J=8.59 Hz, 1 H) 7.06 (dd, J=8.84, 2.27 Hz, 1 H) 6.65 (d, J=2.53 Hz, 1 H) 4.63 (d, J=6.06 Hz, 1 H) 4.15-4.23 (m, 1 H) 4.05-4.12 (m, 1 H) 1.55 (d, J=6.57 Hz, 3 H)

The following compounds are prepared with similar method.

61-K (±)-5-Methyl-6,7-dihydro-5H-pyrrolo[3,4-d]pyrimidin-4-yloxy)-indole-1-carboxylic acid (2-fluoro-5-trifluoromethyl-phenyl)-amide

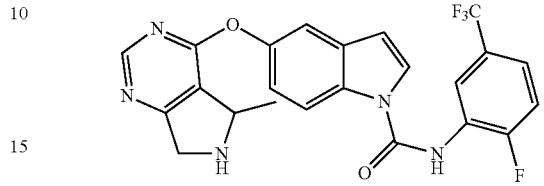

MS (ESI) m/z 472.9 (M+1); $^1$H NMR (400 MHz, MeOD) δ ppm 8.49 (s, 1 H) 8.29 (d, J=8.84 Hz, 1H) 8.17 (d, J=6.82 Hz, 1 H) 7.89 (d, J=3.79 Hz, 1 H) 7.57 (dd, J=8.72, 1.39 Hz, 1 H) 7.29-7.45 (m, 2 H) 7.10 (dd, J=8.84, 2.02 Hz, 1 H) 6.73 (d, J=3.79 Hz, 1 H) 4.68 (q, J=6.48 Hz, 1 H) 4.20 (d, J=1.77 Hz, 1 H) 4.06-4.15 (m, 1 H) 1.58 (d, J=6.82 Hz, 3 H).

EXAMPLE 62

62-A. (±)-5-Methyl-6,7-dihydro-5H-pyrrolo[3,4-d]pyrimidin-4-yloxy)-indole-1-carboxylic acid (5-tert-butyl-2H-pyrazol-3-yl)-amide

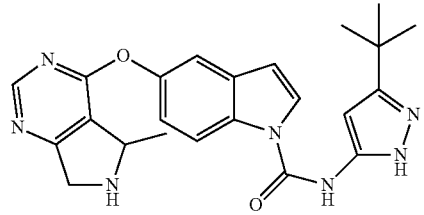 [SMILES: CC1NCc2ncnc(Oc3ccc4c(ccn4C(=O)Nc4cc(C(C)(C)C)n[nH]4)c3)c21]

To a solution of tert-butyl 4-(1H-indol-5-yloxy)-5-methyl-5H-pyrrolo[3,4-d]pyrimidine-6(7H)-carboxylate (150 mg, 0.409 mmol) in DMF (4 mL) at rt, di(1H-imidazol-1-yl)methanone (86 mg, 0.532 mmol) is added followed by TEA (0.34 mL, 2.46 mmol). After 3 h at room temperature 5-tert-butyl-1H-pyrazol-3-amine (342 mg, 2.46 mmol) is added and the reaction left stirring at rt for 48 h. At this point as 1N HCl solution in water (2 mL) is added and EtOAc (5 mL) is added. The layers are separated and the water layer extracted 3 times with EtOAc. The organics are dried and evaporated. DCM (4 mL) and TFA (10 mL, 130 mmol) are added at 0° C. and the reaction allowed to warm to rt over 1 h. At this point the reaction is complete. TFA/DCM is evaporated and then the product is taken up in EtOAc (100 mL). NH$_4$OH (20 mL) is added and then water. The organics are separated and the water layer extracted with EtOAc (2 times). The organics are dried and evaporated. The crude product is added to a silica gel column (ISCO) and eluted with DCM/MeOH/NH4OH (100:0:0 to 93:6:1) to isolate 5-methyl-6,7-dihydro-5H-pyrrolo[3,4-d]pyrimidin-4-yloxy)-indole-1-carboxylic acid (5-tert-butyl-2H-pyrazol-3-yl)-amide. MS (ESI) m/z 432.0 (M+1); $^1$H NMR (400 MHz, MeOD) δ ppm 8.50 (s, 1 H) 8.33 (d, J=9.09 Hz, 1 H) 7.89 (d, J=3.54 Hz, 1 H) 7.41 (d, J=2.27 Hz, 1 H) 7.10 (dd, J=8.97, 2.40 Hz, 1 H) 6.71 (d, J=3.54 Hz, 1 H) 6.37 (s, 1 H) 4.71 (d, J=6.57 Hz, 1 H) 4.10-4.22 (m, 2 H) 1.60 (d, J=6.82 Hz, 3 H) 1.37 (s, 9 H).

The following compounds are prepared with similar method.

62-B. (±)-5-Methyl-6,7-dihydro-5H-pyrrolo[3,4-d]pyrimidin-4-yloxy)-indole-1-carboxylic acid (5-trifluoromethyl-2H-pyrazol-3-yl)-amide

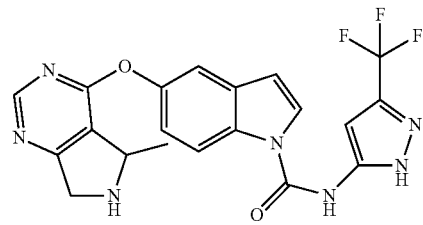 [SMILES: CC1NCc2ncnc(Oc3ccc4c(ccn4C(=O)Nc4cc(C(F)(F)F)n[nH]4)c3)c21]

MS (ESI) m/z 444.9 (M+1); $^1$H NMR (400 MHz, MeOD) δ ppm 8.50 (s, 1 H) 8.41 (d, J=9.09 Hz, 1H) 7.88 (d, J=3.79 Hz, 1 H) 7.43 (d, J=2.27 Hz, 1 H) 7.14 (dd, J=8.97, 2.40 Hz, 1 H) 6.77 (d, J=3.79 Hz, 2 H) 4.71 (d, J=6.32 Hz, 1 H) 4.22 (d, J=1.77 Hz, 1 H) 4.16 (d, J=1.26 Hz, 1 H) 1.60 (d, J=6.82 Hz, 3 H).

EXAMPLE 63

63-A. 5-(6-Methyl-6,7-dihydro-5H-pyrrolo[3,4-d]pyrimidin-4-yloxy)-indole-1-carboxylic acid (3-trifluoromethyl-phenyl)-amide

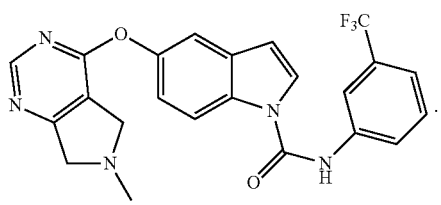 [SMILES: CN1Cc2ncnc(Oc3ccc4c(ccn4C(=O)Nc4cccc(C(F)(F)F)c4)c3)c2C1]

5-(6,7-dihydro-5H-pyrrolo[3,4-d]pyrimidin-4-yloxy)-N-(3-(trifluoromethyl)phenyl)-1H-indole-1-carboxamide (140 mg, 0.320 mmol) is suspended in 1,2-dichloroethane (5 mL), and formaldehyde (50 μl, 0.672 mmol) and acetic acid (36 μl, 0.629 mmol) and sodium triacetoxyborohydride (139 mg, 0.656 mmol) are added and the mixture heated to 60° C. overnight. The reaction is cooled to rt, diluted with water, brine and DCM. The organic phase is removed, dried, and concentrated to an oil that is purified via FCC (0-10% NH$_3$/MeOH:DCM) to obtain 5-(6-methyl-6,7-dihydro-5H-pyrrolo[3,4-d]pyrimidin-4-yloxy)-indole-1-carboxylic acid (3-trifluoromethyl-phenyl)-amide. MS (ESI) m/z 454.95 (M+1); $^1$H NMR (400 MHz, DMSO-d$_6$) δ ppm 10.38 (s, 1 H), 8.56 (s, 1 H), 8.27 (d, J=9.09 Hz, 1 H), 8.09-8.13 (m, 2 H), 7.96 (s, 1 H), 7.65 (t, J=8.08 Hz, 1 H), 7.48-7.51 (m, 2 H), 7.15 (dd, J=8.97, 2.40 Hz, 1 H), 6.80 (d, J=3.79 Hz, 1 H), 3.91 (s, 4 H), 2.52 (s, 3 H).

The following compounds are prepared with similar method.

| | Structure/Chemical Name | $^1$H NMR (400 MHz) | MS (ESI) m/z (M + 1) |
|---|---|---|---|
| 63-B | ![structure] 5-(6-Ethyl-6,7-dihydro-5H-pyrrolo[3,4-d]pyrimidin-4-yloxy)-indole-1-carboxylic acid (3-trifluoromethyl-phenyl)-amide | (DMSO-d$_6$) δ ppm 10.38 (s, 1H) 8.56 (s, 1H) 8.27 (d, J = 9.09 Hz, 1H) 8.09-8.13 (m, 2H) 7.96 (s, 1H) 7.65 (s, 1H) 7.48-7.52 (m, 2H) 7.15 (dd, J = 8.84, 2.27 Hz, 1H) 6.80 (d, J = 3.79 Hz, 1H) 3.92-3.96 (m, 4H) 2.75 (q, J = 7.33 Hz, 2H) 1.07-1.14 (t, J = 7.07 Hz, 3 H | 468.9 |

| | Structure/Chemical Name | ¹H NMR (400 MHz) | MS (ESI) m/z (M + 1) |
|---|---|---|---|
| 63-C | 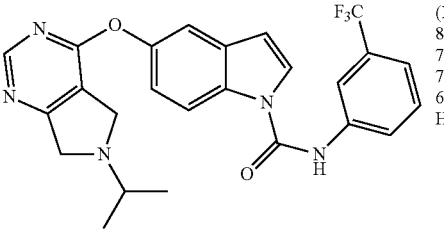<br>5-(6-Isopropyl-6,7-dihydro-5H-pyrrolo[3,4-d]pyrimidin-4-yloxy)-indole-1-carboxylic acid (3-trifluoromethyl-phenyl)-amide | (DMSO-d₆) δ ppm 10.38 (s, 1H) 8.56 (s, 1H) 8.27 (d, J = 9.09 Hz, 1H) 8.09-8.13 (m, 2H) 7.96-7.99 (m, 1H) 7.62-7.67 (m, 1H) 7.48-7.52 (m, 2H) 7.15 (dd, J = 8.84, 2.53 Hz, 1H) 6.80 (d, J = 3.79 Hz, 1H) 3.98 (d, J = 13.14 Hz, 4H) 2.83 (s, 1H) 1.07-1.14 (d, J = 6.32 Hz, 6H) | 483.0 |
| 63-D | 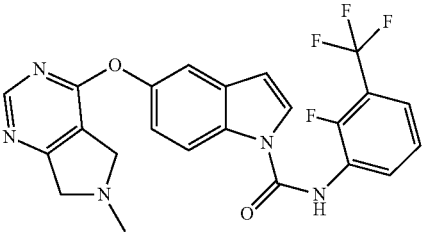<br>5-(6-Methyl-6,7-dihydro-5H-pyrrolo[3,4-d]pyrimidin-4-yloxy)-indole-1-carboxylic acid (2-fluoro-3-trifluoromethyl-phenyl)-amide | (DMSO-d₆) δ ppm 8.56 (s, 1H) 8.27 (d, J = 9.09 Hz, 1H) 8.09 (d, J = 3.79 Hz, 1H) 7.91 (s, 1H) 7.55-7.55 (m, 1H) 7.40-7.55 (m, 2H) 7.14 (dd, J = 8.97, 2.40 Hz, 1H) 6.79 (d, J = 3.79 Hz, 1H) 3.90 (s, 4H) 2.52 (s, 3H) | 472.0 |
| 63-E | 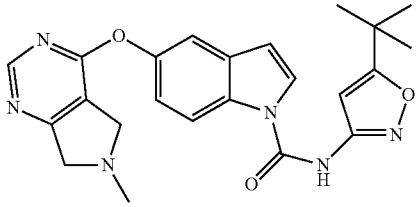<br>5-(6-Methyl-6,7-dihydro-5H-pyrrolo[3,4-d]pyrimidin-4-yloxy)-indole-1-carboxylic acid (5-tert-butyl-isoxazol-3-yl)-amide | (DMSO-d₆) δ ppm 11.28 (s, 1H) 8.56 (s, 1H) 8.30 (s, 1H) 8.17 (d, J = 3.79 Hz, 1H) 7.47 (d, J = 2.27 Hz, 1H) 7.15 (dd, J = 8.97, 2.40 Hz, 1H) 6.76 (d, J = 3.79 Hz, 1H) 6.68 (s, 1H) 3.90 (d, J = 1.52 Hz, 4H) 2.52 (s, 3H) 1.34 (s, 9H) | 433.1 |
| 63-F | 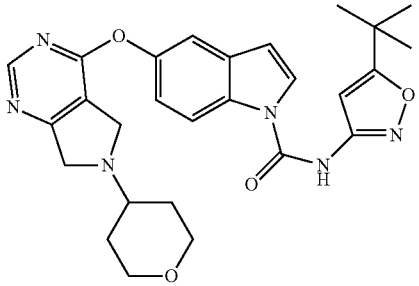<br>5-[6-(Tetrahydro-pyran-4-yl)-6,7-dihydro-5H-pyrrolo[3,4-d]pyrimidin-4-yloxy]-indole-1-carboxylic acid (5-tert-butyl-isoxazol-3-yl)-amide | (DMSO-d₆) δ ppm 11.28 (br. S., 1H) 8.56 (s, 1H) 8.29 (d, J = 9.09 Hz, 1H) 8.17 (d, J = 3.54 Hz, 1H) 7.47 (d, J = 2.27 Hz, 1H) 7.15 (dd, J = 8.97, 2.40 Hz, 1H) 6.77 (d, J = 3.79 Hz, 1H) 6.68 (s, 1H) 3.96-4.04 (m, 4H) 3.89 (dt, J = 11.56, 3.44 Hz, 2H) 3.36 (td, J = 11.31, 1.89 Hz, 2H) 2.71 (s, 1H) 1.85 (d, J = 1.26 Hz, 2H) 1.48 (d, J = 4.04 Hz, 2H) 1.34 (s, 9H) | 503.1 |

| | Structure/Chemical Name | ¹H NMR (400 MHz) | MS (ESI) m/z (M + 1) |
|---|---|---|---|
| 63-G | 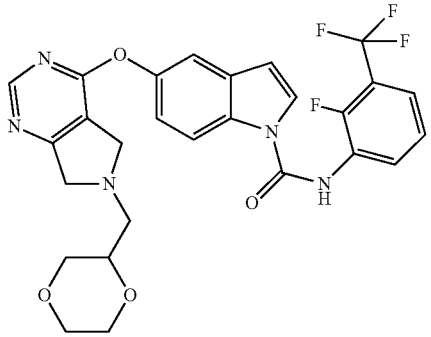<br>5-(6-1,4-dioxinan-2-ylmethyl-6,7-dihydro-5H-pyrrolo[3,4d]pyrimidin-4-yloxy)-indole-1-carboxylic acid (2-fluoro-3-trifluoromethyl-phenyl)-amide | (DMSO-d₆) δ ppm 8.52 (s, 1H) 8.31 (d, J = 8.84 Hz, 1H) 8.01 (m, 1H) 7.93 (d, J = 3.79 Hz, 1H) 7.57 (s, 1H) 7.34-7.50 (m, 2H) 7.13 (dd, J = 8.97, 2.40 Hz, 1H) 6.76 (d, J = 3.79 Hz, 1H) 4.02 (d, J = 17.43 Hz, 4H) 3.84-3.96 (m, 1H) 3.71-3.81 (m, 3H) 3.64-3.71 (m, 2H) 3.53-3.64 (m, 2H) 3.33-3.53 (m, 1H) | 558.0 |
| 63-H | 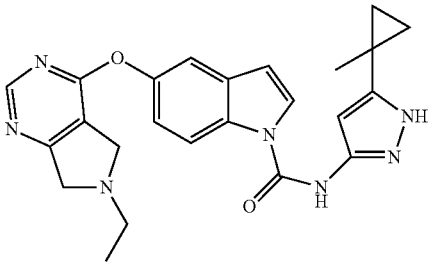<br>5-(6-Ethyl-6,7-dihydro-5H pyrrolo[3,4-d]pyrimidin-4-yloxy)-indole-1-carboxylic acid [5-(1-methyl-cyclopropyl)-1H-pyrazol-3-yl]-amide | (DMSO-d₆) δ ppm 12.13 (s, 1H) 10.57 (s, 1H) 8.56 (s, 1H) 8.30 (d, J = 8.84 Hz, 1H) 8.17 (br. S., 1H) 7.44 (d, J = 2.53 Hz, 1H) 7.11 (dd, J = 8.84, 2.27 Hz, 1H) 6.71 (d, J = 3.79 Hz, 1H) 6.29 (br. S., 1H) 3.92 (d, J = 1.52 Hz, 4H) 2.75 (q, J = 7.07 Hz, 2H) 1.41 (s, 3H) 1.11 (t, J = 7.20 Hz, 3H) 0.86-1.03 (m, 2H) 0.78 (m, 2H) | 444.1 |
| 63-I | 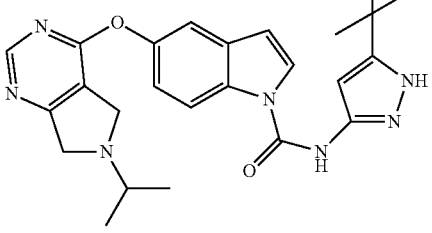<br>5-(6-Isopropyl-6,7-dihydro-5H-pyrrolo[3,4-d]pyrimidin-4-yloxy)-indole-1-carboxylic acid [5-(1-methyl-cyclopropyl)-1H-pyrazol-3-yl]-amide | (DMSO-d₆) δ ppm 12.13 (br. S., 1H) 10.57 (s, 1 H) 8.55 (s, 1H) 8.30 (d, J = 8.84 Hz, 1H) 8.17 (d, J = 3.28 Hz, 1H) 7.44 (d, J = 2.27 Hz, 1H) 7.11 (dd, J = 8.84, 2.53 Hz, 1H) 6.71 (d, J = 3.79 Hz, 1H) 6.29 (s, 1H) 3.83-4.08 (m, 4H) 2.68-2.93 (m, 1H) 1.41 (s, 3H) 1.12 (d, J = 6.32 Hz, 6H) 0.88-0.97 (m, 2H) 0.63-0.80 (m, 2H) | 458.1 |
| 63-J | 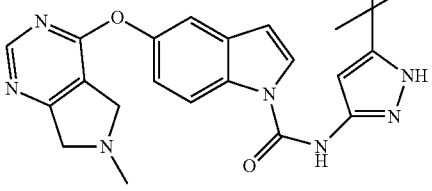<br>5-(6-Methyl-6,7-dihydro-5H-pyrrolo[3,4-d]pyrimidin-4-yloxy)-indole-1-carboxylic acid [5-(1-methyl-cyclopropyl)-1H-pyrazol-3-yl]-amide | (DMSO-d₆) δ ppm 12.13 (br. S., 1H) 10.57 (br. S., 1H) 8.56 (s, 1H) 8.30 (m, 1H) 8.16 (m, 1 H) 7.44 (m, 1H) 7.12 (m, 1H) 6.70 (m, 1H) 6.29 (s, 1H) 3.90 (s, 4H) 2.55 (s, 3H) 1.40 (s, 3 H) 0.92 (m, 2H) 0.78 (m, 2H) | 430.1 |

EXAMPLE 64

64-A. 5-[6-(2-Hydroxy-ethyl)-6,7-dihydro-5H-pyrrolo[3,4-d]pyrimidin-4-yloxy]-indole-1-carboxylic acid (3-trifluoromethyl-phenyl)-amide

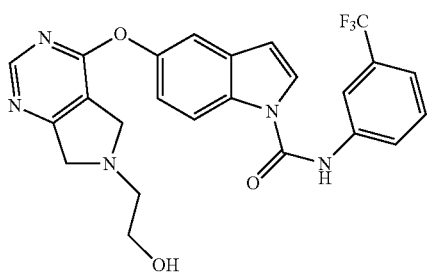 [SMILES: O=C(Nc1cccc(C(F)(F)F)c1)n1ccc2cc(Oc3ncnc4c3CN(CCO)C4)ccc21]

5-(6,7-dihydro-5H-pyrrolo[3,4-d]pyrimidin-4-yloxy)-N-(3-(trifluoromethyl)phenyl)-1H-indole-1-carboxamide (125.9 mg, 0.287 mmol) is dissolved in DMF (5 mL) and TEA (80 µL, 0.577 mmol) is added followed by 2-bromoethanol (80 µL, 1.133 mmol). The solution is stirred at rt overnight. Then the reaction is concentrated and absorbed onto silica gel and separated via FCC (0-10%, 10% $NH_4$ in MeOH:DCM) to obtain 5-(6-(2-hydroxyethyl)-6,7-dihydro-5H-pyrrolo[3,4-d]pyrimidin-4-yloxy)-N-(3-(trifluoromethyl)phenyl)-1H-indole-1-carboxamide. MS (ESI) m/z 484.0 (M+1); $^1$H NMR (400 MHz, DMSO-$d_6$) δ ppm 10.38 (s, 1 H) 8.56 (s, 1 H) 8.27 (d, J=9.09 Hz, 1 H) 8.09-8.14 (m, 2 H) 7.97 (d, J=7.58 Hz, 1 H) 7.65 (t, J=8.08 Hz, 1 H) 7.48-7.52 (m, 2 H) 7.15 (dd, J=8.84, 2.53 Hz, 1 H) 6.80 (d, J=3.54 Hz, 1 H) 4.57 (t, J=5.56 Hz, 1 H) 3.98-4.03 (m, 4 H) 3.58 (q, J=6.06 Hz, 2 H) 2.82 (t, J=6.06 Hz, 2 H).

The following compounds are prepared with similar method.

| | Structure/Chemical Name | $^1$H NMR (400 MHz) | MS (ESI) m/z (M + 1) |
|---|---|---|---|
| 64-B | 5-[6-(2-Hydroxy-ethyl)-6,7-dihydro-5H-pyrrolo[3,4-d]pyrimidin-4-yloxy]-indole-1-carboxylic acid (2-fluoro-3-trifluoromethyl-phenyl)-amide | (MeOD) δ ppm 10.27 (s, 1H) 8.56 (s, 1H) 8.24 (d, J = 8.84 Hz, 1H) 8.09 (d, J = 3.79 Hz, 1H) 7.94 (s, 1H) 7.70 (s, 1H) 7.49 (d, J = 2.02 Hz, 2H) 7.15 (dd, J = 9.09, 2.27 Hz, 1H) 6.81 (d, J = 3.79 Hz, 1H) 4.56 (t, J = 5.43 Hz, 1H) 3.90-4.08 (m, 4H) 3.58 (q, J = 5.89 Hz, 2H) 2.82 (t, J = 6.06 Hz, 2H) | 502.0 |
| 64-C | 5-[6-(2-Hydroxy-ethyl)-6,7-dihydro-5H-pyrrolo[3,4-d]pyrimidin-4-yloxy]-indole-1-carboxylic acid (5-tert-butyl-isoxazol-3-yl)-amide | (DMSO-$d_6$) δ ppm 9.95 (s, 1H) 8.36 (s, 1H) 8.27 (d, J = 8.84 Hz, 1H) 8.03 (d, J = 3.79 Hz, 1H) 7.36 (d, J = 2.53 Hz, 1H) 7.07 (dd, J = 8.97, 2.40 Hz, 1H) 6.66 (d, J = 3.79 Hz, 1 H) 6.61 (s, 1H) 3.95-3.98 (m, 2H) 3.90 (t, J = 2.27 Hz, 2H) 3.60 (q, J = 5.56 Hz, 2H) 3.42-3.46 (m, 1H) 2.82 (t, J = 5.81 Hz, 2H) 1.21-1.27 (m, 9H) | 463.4 |

| Structure/Chemical Name | $^1$H NMR (400 MHz) | MS (ESI) m/z (M + 1) |
|---|---|---|
| 64-D 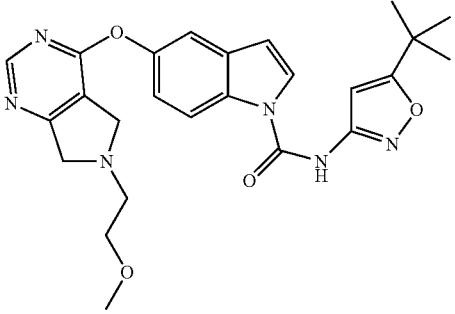<br><br>5-[6-(2-Methoxy-ethyl)-6,7-dihydro-5H-pyrrolo[3,4d]pyrimidin-4-yloxy]-indole-1-carboxylic acid (5-tert-butyl-isoxazol-3-yl)-amide | (DMSO-d$_6$) δ ppm 8.55 (s, 1H) 8.46 (d, J = 8.59 Hz, 1H) 8.11 (d, J = 3.54 Hz, 1H) 7.38 (d, J = 2.27 Hz, 1H) 7.04 (dd, J = 9.09, 2.53 Hz, 1H) 6.63 (s, 1H) 6.59 (br. S., 1H) 3.96 (s, 4H) 3.50 (t, J = 5.81 Hz, 2H) 3.26 (s, 3H) 2.89 (t, J = 5.68 Hz, 2H) 1.31-1.36 (m, 9H) | 47.1 |
| 64-E 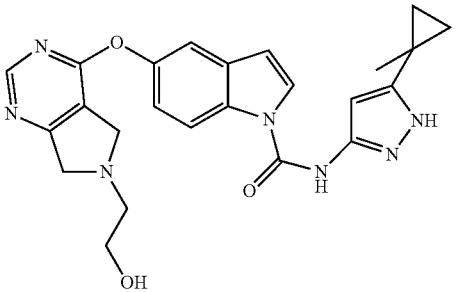<br><br>5-[6-(2-Hydroxy-ethyl)-6,7-dihydro-5H-pyrrolo[3,4-d]pyrimidin-4-yloxy]-indole-1-carboxylic acid [5-(1-methyl-cyclopropyl)-1H-pyrazol-3-yl]-amide | (DMSO-d$_6$) δ ppm 10.57 (br. S., 1H) 8.56 (s, 1H) 8.28 (d, J = 8.59 Hz, 1H) 8.15 (s, 1H) 7.44 (d, J = 2.27 Hz, 1H) 7.11 (dd, J = 9.09, 2.53 Hz, 1H) 6.68 (s, 1H) 6.29 (br. S., 1H) 4.00 (s, 4H) 3.58 (q, J = 5.56 Hz, 2H) 2.78-2.80 (m, 2H) 1.41 (s, 3H) 0.93 (m, 2H) 0.78 (m, 2H) | 460.1 |

EXAMPLE 65

65-A. {4-[1-(3-Trifluoromethyl-phenylcarbamoyl)-1H-indol-5-yloxy]-5,7-dihydro-pyrrolo[3,4-d]pyrimidin-6-yl}-acetic acid

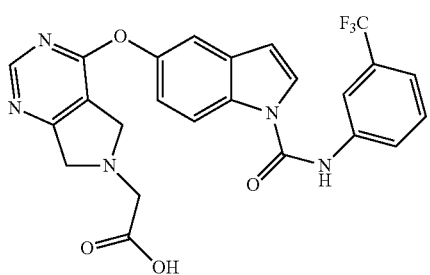 [SMILES: O=C(O)CN1Cc2ncnc(Oc3ccc4c(ccn4C(=O)Nc4cccc(C(F)(F)F)c4)c3)c2C1]

5-(6,7-dihydro-5H-pyrrolo[3,4-d]pyrimidin-4-yloxy)-N-(3-(trifluoromethyl)phenyl)-1H-indole-1-carboxamide (121.9 mg, 0.277 mmol) is dissolved in DMF (5 mL) and TEA (200 µl, 1.435 mmol) is added followed by t-butyl bromoacetate (101 µl, 0.693 mmol). The solution is stirred at rt overnight. The reaction is concentrated and then diluted with DCM (10 mL) and cooled to 0° C. TFA (5 mL) is then added and the ice bath is removed and the reaction is stirred at room temperature. The reaction is concentrated, basified with ammonium hydroxide, and diluted with ethyl acetate. The solution is then treated with 1N HCl. The ethyl acetate is removed, dried and concentrated to a residue. The residue is dissolved in DMSO and purified via HPLC (C18; 20-100% I/H$_2$O with 0.1% TFA to obtain {4-[1-(3-Trifluoromethyl-phenylcarbamoyl)-1H-indol-5-yloxy]-5,7-dihydro-pyrrolo[3,4-d]pyrimidin-6-yl}-acetic acid. MS (ESI) m/z 498.9 (M+1); $^1$H NMR (400 MHz, MeOD) δ ppm 8.50 (s, 1 H) 8.32 (d, J=8.84 Hz, 1 H) 8.06 (s, 1 H) 7.88-7.95 (m, 2 H) 7.57 (t, J=7.96 Hz, 1 H) 7.40-7.45 (m, 2 H) 7.12 (dd, J=9.09, 2.02 Hz, 1 H) 6.74 (d, J=3.79 Hz, 1 H) 4.19 (d, J=9.35 Hz, 4 H), 3.43 (s, 2H).

EXAMPLE 66

66-A. 5-(6-Carbamoylmethyl-6,7-dihydro-5H-pyrrolo[3,4-d]pyrimidin-4-yloxy)-indole-1-carboxylic acid (3-trifluoromethyl-phenyl)-amide

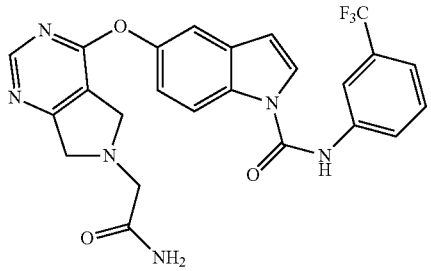 [SMILES: NC(=O)CN1Cc2ncnc(Oc3ccc4c(ccn4C(=O)Nc4cccc(C(F)(F)F)c4)c3)c2C1]

5-(6,7-dihydro-5H-pyrrolo[3,4-d]pyrimidin-4-yloxy)-N-(3-(trifluoromethyl)phenyl)-1H-indole-1-carboxamide (217 mg, 0.494 mmol) is dissolved in DMF (5 mL) and TEA (160 μl, 1.15 mmol) is added followed by 2-bromoacetamide (250 mg, 1.81 mmol). The solution is stirred at it for 1 h. The reaction is concentrated and the residue absorbed onto silica gel and separated via FCC (0-10%, 10% $NH_4$ in MeOH:DCM) to obtain 5-(6-carbamoylmethyl-6,7-dihydro-5H-pyrrolo[3,4-d]pyrimidin-4-yloxy)-indole-1-carboxylic acid (3-trifluoromethyl-phenyl)-amide. MS (ESI) m/z 497.9 (M+1); $^1$H NMR (400 MHz, MeOD) δ ppm 10.38 (br. S., 1 H) 8.58 (s, 1 H) 8.27 (d, J=8.84 Hz, 1 H) 8.09-8.13 (m, 2 H) 7.96 (s, 1 H) 7.65 (t, J=8.08 Hz, 1 H) 7.48-7.51 (m, 2 H) 7.38 (br. S., 1 H) 7.09-7.17 (m, 2 H) 6.80 (d, J=3.03 Hz, 1 H) 4.12 (dd, J=10.61, 2.02 Hz, 4 H) 3.38 (s, 2 H).

The following compounds are prepared with similar method.

| | Structure/Chemical Name | $^1$H NMR (400 MHz) | MS (ESI) m/z (M + 1) |
|---|---|---|---|
| 66-B | 5-(6-Carbamoylmethyl-6,7-dihydro-5H-pyrrolo[3,4d]pyrimidin-4-yloxy)-indole-1-carboxylic acid (2-fluoro-3-trifluoromethyl-phenyl)-amide | (DMSO-$d_6$) δ ppm 10.27 (s, 1H) 8.58 (s, 1H) 8.27 (s, 1H) 8.09 (d, J = 3.79 Hz, 1H) 7.96 (s, 1H) 7.66 (br. S., 1H) 7.44-7.52 (m, 1H) 7.14 (dd, J = 8.84, 2.53 Hz, 3H) 6.79 (d, J = 3.28 Hz, 1H) 4.11 (dd, J = 8.34, 2.02 Hz, 4H) 3.34-3.43 (m, 2H) | 515.1 |
| 66-C | 5-(6-Methylcarbamoylmethyl-6,7-dihydro-5H-pyrrolo[3,4-d]pyrimidin-4-yloxy)-indole-1-carboxylic acid (2-fluoro-3-trifluoromethyl-phenyl)-amide | (DMSO-$d_6$) δ ppm 10.27 (s, 1H) 8.58 (s, 1H) 8.26 (s, 1H) 8.09 (d, J = 3.79 Hz, 1H) 7.95 (s, 1H) 7.67 (br. S., 1H) 7.48 (overlap, m, 2H) 7.13 (dd, J = 9.09, 2.53 Hz, 1H) 6.80 (d, J = 3.79 Hz, 1H) 4.09 (dd, J = 7.45, 1.89 Hz, 4H) 3.40 (s, 2H) 2.63 (d, J = 4.55 Hz, 3H) | 529.0 |

| Structure/Chemical Name | $^1$H NMR (400 MHz) | MS (ESI) m/z (M + 1) |
|---|---|---|
| 66-D ![structure] 5-(6-Carbamoylmethyl-6,7-dihydro-5H-pyrrolo[3,4d]pyrimidin-4-yloxy)-indole-1-carboxylic acid (5-tert-butyl-isoxazol-3-yl)-amide | (DMSO-$d_6$) δ ppm 11.28 (s, 1H) 8.57 (s, 1H) 8.30 (s, 1H) 8.17 (d, J = 3.79 Hz, 1H) 7.47 (d, J = 2.53 Hz, 1H) 7.15 (dd, J = 8.97, 2.40 Hz, 1H) 6.77 (d, J = 3.79 Hz, 1H) 6.68 (s, 1H) 4.09-4.15 (m, 4H) 3.38 (s, 2H) 1.34 (s, 9H) | 476.1 |
| 66-E ![structure] 5-(6-Methylcarbamoylmethyl-6,7-dihydro-5H-pyrrolo[3,4-d]pyrimidin-4-yloxy)-indole-1-carboxylic acid (5-tert-butyl-isoxazol-3-yl)-amide | (DMSO-$d_6$) δ ppm 10.11 (s, 1H) 8.54 (s, 1H) 8.43 (d, J = 9.09 Hz, 1H) 8.19 (d, J = 3.79 Hz, 1H) 7.44-7.51 (m, 1H) 7.22 (dd, J = 8.97, 2.40 Hz, 1H) 6.81 (d, J = 3.79 Hz, 1H) 6.76 (s, 1H) 4.21 (t, J = 2.15 Hz, 2H) 4.14 (t, J = 2.27 Hz, 2H) 3.48 (s, 2H) 2.77-2.81 (m, 3H) 1.42 (s, 9H) | 490.4 |

EXAMPLE 67

67-A. 4-[4-Fluoro-1-(4-fluoro-3-trifluoromethyl-phenylcarbamoyl)-2-methyl-1H-indol-5-yloxy]-pyridine-2-carboxylic acid methyl ester

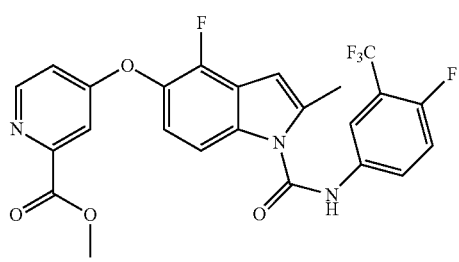 [SMILES: COC(=O)c1cc(Oc2ccc3c(cc(C)n3C(=O)Nc3ccc(F)c(C(F)(F)F)c3)c2F)ccn1]

A 1 M solution of LiHMDS in THF (4.33 mL, 4.33 mmol) is added to a solution of methyl 4-(4-fluoro-2-methyl-1H-indol-5-yloxy)picolinate (1 g, 3.33 mmol) in THF (50 mL) at −78° C. After 10 min, 1-fluoro-4-isocyanato-2-(trifluoromethyl)benzene (0.569 mL, 4.00 mmol) is added. After 40 min saturated aqueous NH$_4$Cl and EtOAc are added. The aqueous layer is extracted further with EtOAc (200 mL). The combined organic phases are washed with brine (40 mL), dried over Na$_2$SO$_4$, and concentrated in vacuo. The residue is purified via FCC (35%-90% EtOAc/heptane) to provide the title compound. MS (ESI) m/z 505.1 (M+1); $^1$H NMR (400 MHz, DMSO-$d_6$) δ ppm 11.02 (s, 1 H), 8.61 (d, J=5.56 Hz, 1 H), 8.13 (dd, J=6.32, 2.53 Hz, 1 H), 7.96 (br. S., 1 H), 7.60 (d, J=8.84 Hz, 1 H), 7.60 (t, J=9.73 Hz, 1 H), 7.43 (d, J=2.53 Hz, 1 H), 7.20-7.26 (m, 2 H), 6.67 (s, 1 H), 3.84 (s, 3 H), 2.59 (s, 3 H).

67-B. 4-Fluoro-5-(2-hydroxymethyl-pyridin-4-yloxy)-2-methyl-indole-1-carboxylic acid (4-fluoro-3-trifluoromethyl-phenyl)-amide

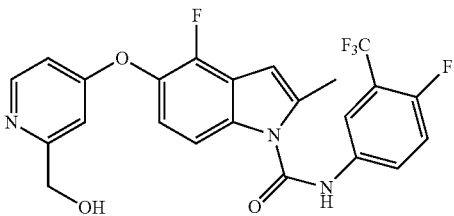 [SMILES: Cc1cc2c(F)c(Oc3ccnc(CO)c3)ccc2n1C(=O)Nc1ccc(F)c(C(F)(F)F)c1]

4-[4-Fluoro-1-(4-fluoro-3-trifluoromethyl-phenylcarbamoyl)-2-methyl-1H-indol-5-yloxy]-pyridine-2-carboxylic acid methyl ester (450 mg, 0.890 mmol) is placed in THF (10 mL) and cooled to 0° C. A 1 M solution of DIBAL-H in hexanes (2.67 mL, 2.67 mmol) is added. The reaction is stirred at 0° C. for 40 min. The reaction is then allowed to warm to rt. After an additional 45 min, LC still indicates the presence of intermediate aldehyde so an additional 1 mL of 1 M DIBAL-H in hexanes is added. After 1 h further, 3 mL MeOH and NaBH₄ (0.14 g, 3.70 mmol) are added to force the reaction to completion. The reaction is stirred for 10 min and then diluted with EtOAc and H₂O and stirred with 10 g sodium potassium tartrate for 1 h. The organic layer is washed with brine, dried over Na₂SO₄, and concentrated in vacuo. The residue is purified via FCC (50%-100% EtOAc/heptane) to provide the title compound. MS (ESI) m/z 477.9 (M+1); ¹H NMR (400 MHz, DMSO-d₆) δ ppm 11.01 (s, 1 H), 8.36 (d, J=5.56 Hz, 1 H), 8.13 (dd, J=6.57, 2.53 Hz, 1 H), 7.94-7.98 (m, 1 H), 7.56-7.62 (m, 2 H), 7.14-7.19 (m, 1 H), 6.89 (d, J=2.53 Hz, 1 H), 6.85 (dd, J=5.56, 2.53 Hz, 1 H), 6.65 (s, 1 H), 5.37 (t, J=5.68 Hz, 1 H), 4.49 (d, J=5.81 Hz, 2 H), 2.59 (s, 3 H).

67-C. Methanesulfonic acid 4-[4-fluoro-1-(4-fluoro-3-trifluoromethyl-phenylcarbamoyl)-2-methyl-1H-indol-5-yloxy]-pyridin-2-ylmethyl ester

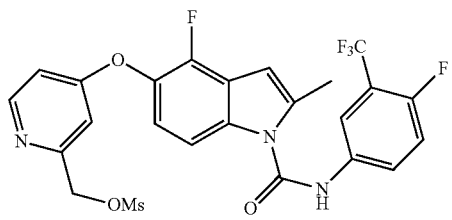 [SMILES: Cc1cc2c(F)c(Oc3ccnc(COS(C)(=O)=O)c3)ccc2n1C(=O)Nc1ccc(F)c(C(F)(F)F)c1]

4-Fluoro-5-(2-hydroxymethyl-pyridin-4-yloxy)-2-methyl-indole-1-carboxylic acid (4-fluoro-3-trifluoromethyl-phenyl)-amide (370 mg, 0.775 mmol) is placed in dichloromethane (10 mL) and methanesulfonyl chloride (0.15 mL, 1.92 mmol) and TEA (0.4 ml, 2.87 mmol) are added. The reaction is stirred at rt for 20 min before being diluted with dichloromethane and saturated aqueous NH₄Cl. The aqueous layer is extracted further with dichloromethane. The combined organic layers are washed with brine and dried over Na₂SO₄, filtered, and concentrated to give the title compound. MS (ESI) m/z 555.8 (M+1)

67-D. 5-(2-Cyclopropylaminomethyl-pyridin-4-yloxy)-4-fluoro-2-methyl-indole-1-carboxylic acid (4-fluoro-3-trifluoromethyl-phenyl)-amide

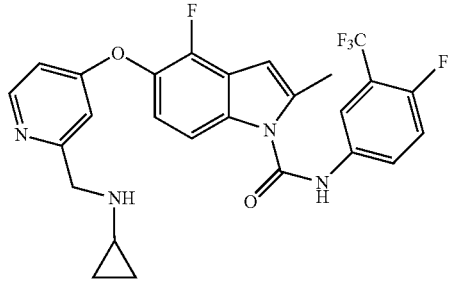 [SMILES: Cc1cc2c(F)c(Oc3ccnc(CNC4CC4)c3)ccc2n1C(=O)Nc1ccc(F)c(C(F)(F)F)c1]

Methanesulfonic acid 4-[4-fluoro-1-(4-fluoro-3-trifluoromethyl-phenylcarbamoyl)-2-methyl-1H-indol-5-yloxy]-pyridin-2-ylmethyl ester (80 mg, 0.144 mmol) is placed in THF (2 mL) and cyclopropylamine (0.030 mL, 0.432 mmol) is added and the reaction is stirred at 40° C. for 18 h. At that point DMF (0.2 mL) is added and the reaction temperature is increased to 50° C. After an additional 4 h the reaction is judged complete by LCMS analysis. The reaction is diluted with EtOAc and H₂O. The aqueous layer is washed with EtOAc (3×50 mL). The organic layers are then washed with brine and dried over Na₂SO₄, filtered, and concentrated in vacuo. The residue is purified via FCC (0-7% MeOH with 5% NH₃ in DCM) to provide the title compound. MS (ESI) m/z 516.9 (M+1); ¹H NMR (400 MHz, DMSO-d₆) δ ppm 8.34 (d, J=5.81 Hz, 1 H), 8.06 (dd, J=6.06, 2.53 Hz, 1 H), 7.85-7.98 (m, 1 H), 7.53 (d, J=8.84 Hz, 1 H), 7.38 (t, J=9.60 Hz, 1 H), 7.06 (t, J=8.21 Hz, 1 H), 6.98 (d, J=2.27 Hz, 1 H), 6.81 (dd, J=5.81, 2.27 Hz, 1 H), 6.53 (s, 1 H), 3.85 (s, 2 H), 2.61 (s, 3 H), 2.11 (ddd, J=7.01, 3.35, 3.03 Hz, 1 H), 0.34-0.49 (m, 4 H).

EXAMPLE 68

68-A. 5-(6-Benzyloxymethyl-pyrimidin-4-yloxy)-2,3-dihydro-1H-indole

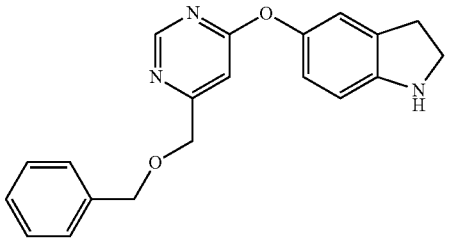 [SMILES: c1ccc(COCc2cc(Oc3ccc4c(c3)CCN4)ncn2)cc1]

Triethylsilane (4 mL, 24.7 mmol) and TFA (6 mL) are added to 5-(6-benzyloxymethyl-pyrimidin-4-yloxy)-1H-indole (0.22 g, 0.682 mmol) in 6 mL of acetonitrile and stirred at rt overnight. The reaction is concentrated to an oil that is dissolved in EtOAc and washed with a saturated aqueous sodium bicarbonate. The organic layer is removed, dried, and concentrated to an to obtain crude 5-(6-benzyloxymethyl-pyrimidin-4-yloxy)-2,3-dihydro-1H-indole. MS (ESI) m/z 334.2 (M+1).

68-B. 5-(6-Benzyloxymethyl-pyrimidin-4-yloxy)-2,3-dihydro-indole-1-carboxylic acid (3-trifluoromethyl-phenyl)-amide

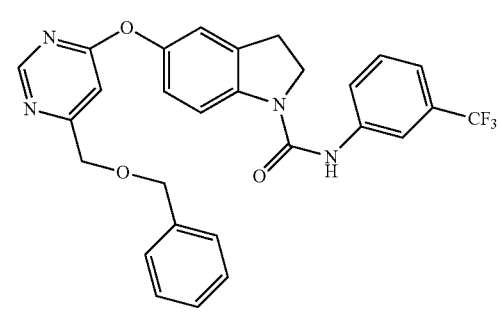 [SMILES: O=C(Nc1cccc(C(F)(F)F)c1)N1CCc2cc(Oc3cc(COCc4ccccc4)ncn3)ccc21]

5-(6-Benzyloxymethyl-pyrimidin-4-yloxy)-2,3-dihydro-1H-indole (0.17 g, 0.509 mmol) is dissolved in THF (3 mL) and cooled to 0° C. and 1-isocyanato-3-trifluoromethyl-benzene (80 μL, 0.571 mmol) is added and the reaction is warmed to rt overnight. The reaction is concentrated to an oil and absorbed onto silica gel and separated via FCC (0-50% EtOAc/heptane) to provide the title compound. MS (ESI) m/z 521.1 (M+1).

68-C. 5-(6-Hydroxymethyl-pyrimidin-4-yloxy)-indole-1-carboxylic acid (3-trifluoromethyl-phenyl)-amide

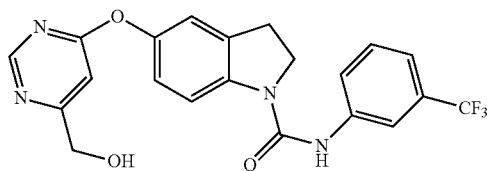 [SMILES: O=C(Nc1cccc(C(F)(F)F)c1)N1CCc2cc(Oc3cc(CO)ncn3)ccc21]

5-(6-Benzyloxymethyl-pyrimidin-4-yloxy)-2,3-dihydro-indole-1-carboxylic acid (3-trifluoromethyl-phenyl)-amide (4.11 g, 7.90 mmol) is dissolved in TFA (100 mL) and is heated at 60° C. overnight. The reaction is cooled to rt and partitioned between ethyl acetate and saturated aqueous sodium bicarbonate. The organic layer is removed, dried, and concentrated and the residue is absorbed onto silica gel and separated via FCC (0-100% ethyl acetate:heptane) to obtain the title compound. MS (ESI) m/z 431.1 (M+1).

68-D. Methanesulfonic acid 6-[1-(3-trifluoromethyl-phenylcarbamoyl)-2,3-dihydro-1H-indol-5-yloxy]-pyrimidin-4-ylmethyl ester

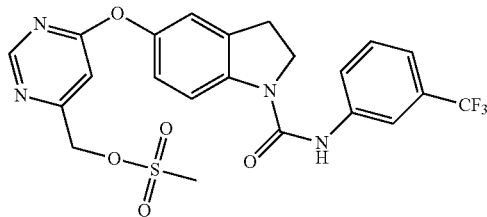 [SMILES: CS(=O)(=O)OCc1cc(Oc2ccc3c(c2)CCN3C(=O)Nc2cccc(C(F)(F)F)c2)ncn1]

5-(6-Hydroxymethyl-pyrimidin-4-yloxy)-2,3-dihydro-indole-1-carboxylic acid (3-trifluoromethyl-phenyl)-amide (0.1001, 0.232 mmol) is dissolved in THF (6 mL) and TEA (0.18 mL, 1.29 mmol) is added followed by methanesulphonyl chloride (0.028 mL, 0.361 mmol). The solution is stirred for 15 min before being partitioned between ethyl acetate and saturated aqueous sodium chloride. The layers are separated and the organic layer is washed further with water. The organic layer is then removed, dried, and concentrated to obtain the title compound. MS (ESI) m/z 510.0 (m+1).

68-E. 5-(6-Methylaminomethyl-pyrimidin-4-yloxy)-2,3-dihydro-indole-1-carboxylic acid (3-trifluoromethyl-phenyl)-amide

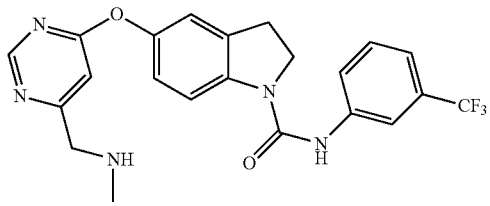

Methanesulfonic acid 6-[1-(3-trifluoromethyl-phenylcarbamoyl)-2,3-dihydro-1H-indol-5-yloxy]-pyrimidin-4-ylmethyl ester (0.1331 g, 0.261 mmol) in 10 mL of THF is added to a solution of 40% methylamine in water (0.4 mL, 4.58 mmol) and stirred at room temperature overnight. The reaction is diluted with ethyl acetate and washed with water. The organic layer is removed, dried, and concentrated to an oil that is dissolved in ether, cooled to 0° C. and treated with 0.3 mL 1 N HCl in ether to obtain 5-(6-Methylaminomethyl-pyrimidin-4-yloxy)-2,3-dihydro-indole-1-carboxylic acid (3-trifluoromethyl-phenyl)-amide HCl salt. MS (ESI) m/z 444.1 (m+1); $^1$H NMR (400 MHz, DMSO-$d_6$) δ ppm 9.26 (br. S., 1 H) 8.93 (s, 1 H) 8.85 (s, 1 H) 8.05 (s, 1 H) 7.94 (d, J=8.84 Hz, 2 H) 7.54 (t, J=8.08 Hz, 1 H) 7.36 (d, J=7.58 Hz, 1 H) 7.21 (s, 1 H) 7.11 (d, J=2.53 Hz, 1 H) 6.98 (dd, J=8.72, 2.40 Hz, 1 H) 4.31 (br. S., 2 H) 4.23 (t, J=8.59 Hz, 2 H) 3.23 (t, J=8.46 Hz, 2 H) 2.64 (br. S., 3 H).

The following compounds are prepared with similar method.

| | Structure/Chemical Name | $^1$H NMR (400 MHz) | MS (ESI) m/z (M + 1) |
|---|---|---|---|
| 68-F | 5-(6-Morpholin-4-ylmethyl-pyrimidin-4-yloxy)-2,3-dihydro-indole-1-carboxylic acid (3-trifluoromethyl-phenyl)-amide hydrochloride | (DMSO-$d_6$) δ ppm 8.93 (s, 1H) 8.85 (s, 1H) 8.05 (s, 1H) 7.88-7.96 (m, 2 H) 7.54 (t, J = 8.08 Hz, 1H) 7.31-7.38 (m, 2H) 7.11 (d, J = 1.77 Hz, 1H) 6.99 (dd, J = 8.72, 2.15 Hz, 1H) 4.47 (br. S., 2H) 4.23 (t, J = 8.59 Hz, 2H) 3.86 (br. S., 3H) 3.78 (d, J = 5.05 Hz, 1H) 3.31-3.40 (m, 2H) 3.24 (m, 4H) | 500.0 |

| | Structure/Chemical Name | $^1$H NMR (400 MHz) | MS (ESI) m/z (M + 1) |
|---|---|---|---|
| 68-G | 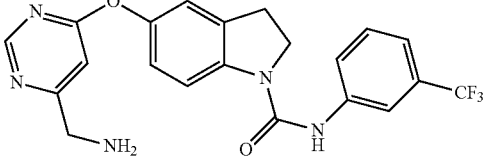<br>5-(6-Aminomethyl-pyrimidin-4-yloxy)-2,3-dihydro-indole-1-carboxylic acid (3-trifluoromethyl-phenyl)-amide hydrochloride | (DMSO-d$_6$) δ ppm 8.93 (s, 1H) 8.82 (s, 1H) 8.15 (br. S., 2H) 8.05 (s, 1H) 7.88-7.95 (m, 2H) 7.54 (t, J = 7.96 Hz, 1H) 7.36 (d, J = 8.08 Hz, 1H) 7.18 (s, 1H) 7.10 (d, J = 2.53 Hz, 1H) 6.97 (dd, J = 8.59, 2.53 Hz, 1H) 4.15-4.26 (m, 4H) 3.23 (t, J = 8.59 Hz, 2H). | 430.0 |
| 68-H | 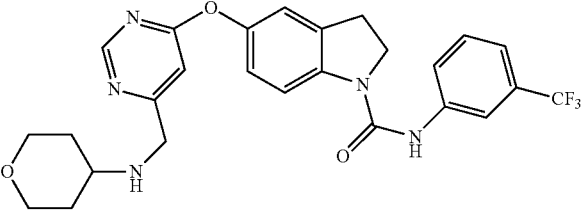<br>5-{6-[(Tetrahydro-pyran-4-ylamino)-methyl]-pyrimidin-4-yloxy}-2,3-dihydro-indole-1-carboxylic acid (3-trifluoromethyl-phenyl)-amide hydrochloride | (DMSO-d$_6$) δ ppm 9.45 (br. S., 1H) 8.93 (s, 1H) 8.86 (d, J = 1.01 Hz, 1H) 8.05 (s, 1H) 7.88-8.00 (m, 2H) 7.54 (t, J = 7.83 Hz, 1H) 7.36 (d, J = 7.83 Hz, 1H) 7.25 (s, 1H) 7.11 (d, J = 2.53 Hz, 1H) 6.98 (dd, J = 8.59, 2.53 Hz, 1H) 4.34-4.39 (m, 2H) 3.93 (d, J = 11.37 Hz, 2H) 3.19-3.32 (m, 4H) 1.99 (d, J = 1.52 Hz, 2H) 1.67 (dd, J = 12.13, 4.55 Hz, 2H) 1.04 (d, J = 6.06 Hz, 3H). | 514.1 |
| 68-I | 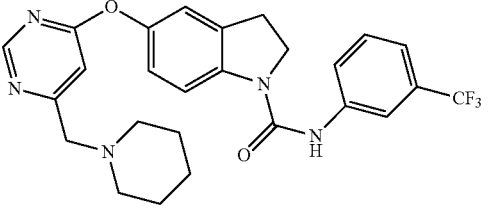<br>5-(6-Piperidin-1-ylmethyl-pyrimidin-4-yloxy)-2,3-dihydro-indole-1-carboxylic acid (3-trifluoromethyl-phenyl)-amide hydrochloride | (DMSO-d$_6$) δ ppm 10.71 (br. S., 1H) 9.00 (br. S., 1H) 8.85 (s, 1H) 8.07 (br. S., 1H) 7.93 (t, J = 7.45 Hz, 1H) 7.48-7.58 (m, 1H) 7.43 (br. S., 1H) 7.35 (d, J = 6.57 Hz, 1H) 7.11 (br. S., 1H) 6.99 (d, J = 8.08 Hz, 1H) 4.41 (br. S., 2H) 4.20-4.30 (m, 2H) 3.29-3.48 (m, 3H) 3.23 (br. S., 2H) 3.00 (br. S., 2H) 1.80 (br. S., 4H) 1.36 (br. S., 1H) | 498.0 |
| 68-J | 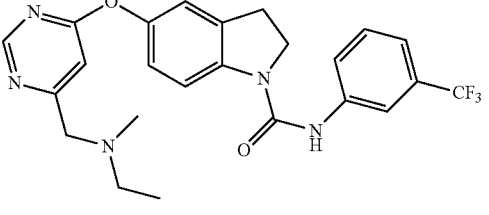<br>5-{6-[(Ethyl-methyl-amino)-methyl]-pyrimidin-4-yloxy}-2,3-dihydro-indole-1-carboxylic acid (3-trifluoromethyl-phenyl)-amide hydrochloride | (DMSO-d$_6$) δ ppm 10.35 (br. S., 1H) 8.94 (s, 1H) 8.87 (d, J = 1.01 Hz, 1H) 8.05 (s, 1H) 7.88-7.96 (m, 2H) 7.54 (t, J = 8.08 Hz, 1H) 7.32-7.37 (m, 1H) 7.12 (d, J = 2.27 Hz, 1H) 6.99 (dd, J = 8.72, 2.65 Hz, 1H) 4.42 (br. S., 4H) 4.23 (t, J = 8.72 Hz, 2H) 3.23 (t, J = 8.59 Hz, 2H) 2.78 (s, 3H) 1.27 (t, J = 7.20 Hz, 3H) | 472.0 |
| 68-K | 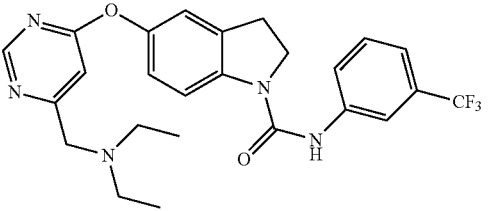<br>5-(6-diethylaminomethyl-pyrimidin-4-yloxy)-2,3-dihydro-indole-1-carboxylic acid (3-trifluoromethyl-phenyl)-amide hydrochloride | (DMSO-d$_6$) δ ppm 8.90 (d, J = 19.71 Hz, 2H) 8.05 (s, 1H) 7.88-7.96 (m, 2H) 7.54 (t, J = 7.83 Hz, 1H) 7.32-7.37 (m, 2H) 7.12 (d, J = 2.53 Hz, 1H) 6.99 (dd, J = 8.84, 2.53 Hz, 1H) 4.47 (d, J = 3.79 Hz, 2H) 4.23 (t, J = 8.59 Hz, 2H) 3.14-3.26 (m, 6H) 1.15-1.28 (m, 6H). | 486.1 |

-continued

| | Structure/Chemical Name | ¹H NMR (400 MHz) | MS (ESI) m/z (M + 1) |
|---|---|---|---|
| 68-L | 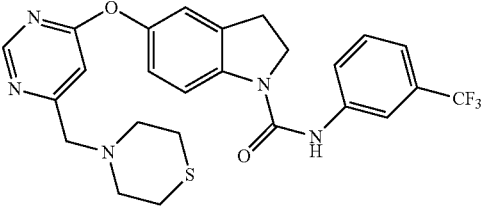<br>5-(6-Thiomorpholin-4-ylmethyl-pyrimidin-4-yloxy)-2,3-dihydro-indole-1-carboxylic acid (3-trifluoromethyl-phenyl)-amide hydrochloride | (DMSO-d₆) δ ppm 9.08 (br. S., 1H) 8.94 (s, 1H) 8.85 (s, 1H) 8.05 (s, 1H) 7.84-8.00 (m, 2H) 7.54 (t, J = 7.96 Hz, 1H) 7.29-7.42 (m, 1H) 7.11 (d, J = 2.53 Hz, 1H) 6.99 (dd, J = 8.59, 2.53 Hz, 1H) 4.48 (br. S., 2H) 4.23 (t, J = 8.59 Hz, 2H) 3.53 (br. S., 4H) 3.17-3.29 (m, 3H) 2.99 (br. S., 2H) 2.81-2.90 (m, 1H) | 516.2 |
| 68-M | 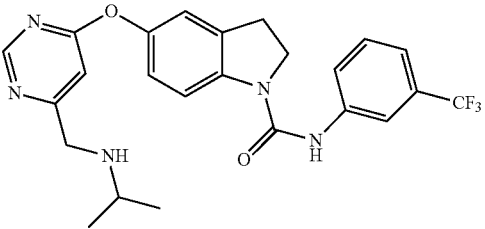<br>5-[6-(Isopropylamino-methyl)-pyrimidin-4-yloxy]-2,3-dihydro-indole-1-carboxylic acid (3-trifluoromethyl-phenyl)-amide hydrochloride | (DMSO-d₆) δ ppm 9.23 (br. S, 1H) 8.94 (s, 1H) 8.86 (d, J = 1.01 Hz, 1H) 8.05 (s, 1H) 7.88-7.96 (m, 2H) 7.54 (t, J = 7.96 Hz, 1H) 7.36 (d, J = 7.83 Hz, 1H) 7.26 (s, 1H) 7.11 (d, J = 2.53 Hz, 1H) 6.98 (dd, J = 8.84, 2.53 Hz, 1H) 4.32 (s, 2H) 4.23 (t, J = 8.59 Hz, 2H) 3.40-3.50 (m, 1H) 3.23 (t, J = 8.59 Hz, 2H) 1.29 (d, J = 6.57 Hz, 6H) | 472.0 |
| 68-N | 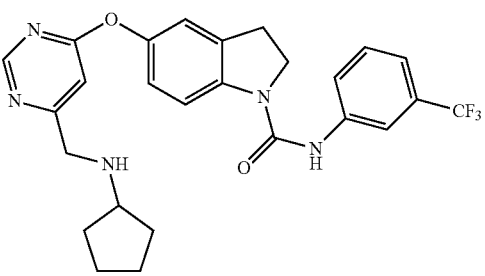<br>5-(6-Cyclopentylaminomethyl-pyrimidin-4-yloxy)-2,3-dihydro-indole-1-carboxylic acid (3-trifluoromethyl-phenyl)-amide hydrochloride | (DMSO-d₆) δ ppm 9.34 (br. S., 2H) 8.93 (s, 1H) 8.86 (d, J = 1.01 Hz, 1H) 8.05 (s, 1H) 7.88-7.96 (m, 1H) 7.54 (t, J = 7.96 Hz, 1H) 7.36 (d, J = 7.83 Hz, 1H) 7.25 (d, J = 1.01 Hz, 1H) 7.11 (d, J = 2.53 Hz, 1H) 6.98 (dd, J = 8.59, 2.53 Hz, 1H) 4.32 (t, J = 5.94 Hz, 2H) 4.23 (t, J = 8.59 Hz, 2H) 3.40-3.50 (m, 1H) 3.23 (t, J = 8.72 Hz, 2H) 1.97 (br. S., 2H) 1.64-1.76 (m, 4H) 1.49-1.58 (m, 2H) | 4980 |
| 68-O | 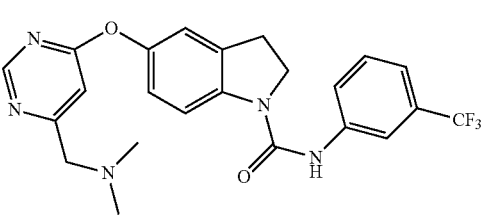<br>5-(6-dimethylaminomethyl-pyrimidin-4-yloxy)-2,3-dihydro-indole-1-carboxylic acid (3-trifluoromethyl-phenyl)-amide hydrochloride | (DMSO-d₆) δ ppm 10.50 (br. S., 1H) 8.94 (s, 1H) 8.86 (d, J = 1.01 Hz, 1H) 8.05 (s, 1H) 7.88-7.96 (m, 1H) 7.54 (t, J = 7.96 Hz, 1H) 7.36 (d, J = 7.83 Hz, 1H) 7.30 (d, J = 1.01 Hz, 1H) 7.12 (d, J = 2.53 Hz, 1H) 6.99 (dd, J = 8.72, 2.65 Hz, 1H) 4.46 (s, 2H) 4.23 (t, J = 8.72 Hz, 2H) 3.23 (t, J = 8.46 Hz, 2H) 2.83 (s, 6H). | 458.0 |

EXAMPLE 69

69-A. 5-(2-Methyl-pyridin-4-yloxy)-1H-indle

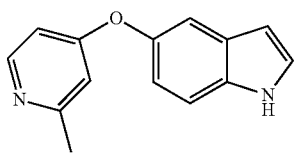 [SMILES: Cc1cc(Oc2ccc3[nH]ccc3c2)ccn1]

5-Hydroxy indole (133 mg, 3.76 mmol), 4-bromo-2-methylpyridine (711 mg, 4.13 mmol) and cesium carbonate (2.45 g, 7.52 mmol) are stirred in DMSO (3 mL) at 110° C. for 12 h. The mixture is then partitioned between DCM and water. Organic layer is removed, dried over anhydrous $Na_2SO_4$, and concentrated in vacuo. The residue is purified via FCC (EtOAc/heptanes 2:8 to EtOAc) to provide the title compound. MS (ESI) m/z 225.1 (M+1); $^1$H NMR (400 MHz, MeOD) δ ppm 8.20 (d, J=5.8 Hz, 1 H), 7.46 (d, J=8.6 Hz, 1 H), 7.33 (d, J=3.0 Hz, 1 H), 7.29 (d, J=2.3 Hz, 1 H), 6.86 (dd, J=8.8, 2.3 Hz, 1 H), 6.67-6.77 (m, 2 H), 6.48 (d, J=3.0 Hz, 1 H), 2.43 (s, 3 H).

69-B. 5-(2-Methyl-pyridin-4-yloxy)-indole-1-carboxylic acid (3-trifluoromethylphenyl)-amide

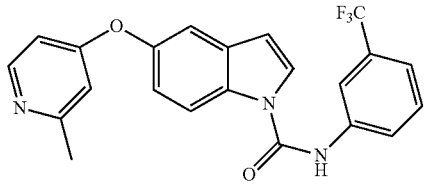 [SMILES: Cc1cc(Oc2ccc3c(ccn3C(=O)Nc3cccc(C(F)(F)F)c3)c2)ccn1]

To a solution of 2,2,6,6-Tetramethylpiperidine (0.27 mL, 1.08 mmol) in THF (5 mL) at −78° C. is added nBuLi (0.69 mL, 1.72 mmol, 2.5M in hexanes). The solution is allowed to stir for 15 min before a THF solution (2 mL) of 5-(2-methyl-pyridin-4-yloxy)-1H-indole (242 mg, 1.08 mmol) is added. This solution is then stirred for 30 min before addition of 3-trifluoromethylphenyl isocyanate (0.30 mL, 2.16 mmol) is added. The reaction is allowed to stir at room temperature for 3 h before being partitioned between EtOAc and pH 7 buffer solution. The organic layer is dried over anhydrous $Na_2SO_4$, and concentrated. The residue is purified via FCC (10-70% EtOAc/heptane) to give the title compound. MS (ESI) m/z 412.3 (M+1); $^1$H NMR (400 MHz, MeOD) δ ppm 8.38 (d, J=8.8 Hz, 1 H), 8.24 (d, J=5.8 Hz, 1 H), 8.08 (s, 1 H), 7.97 (d, J=3.8 Hz, 1 H), 7.91 (d, J=8.1 Hz, 1 H), 7.59 (t, J=8.0 Hz, 1 H), 7.46 (d, J=7.1 Hz, 1 H), 7.38 (d, J=2.3 Hz, 1 H), 7.09 (dd, J=8.8, 2.3 Hz, 1 H), 6.80 (d, J=2.3 Hz, 1 H), 6.72-6.78 (m, 2 H), 2.45 (s, 3 H).

EXAMPLE 70

70-A. 5-(benzyloxy)-N-(3-(trifluoromethyl)phenyl)-1H-indole-1-carboxamide

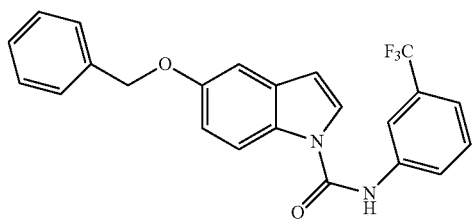 [SMILES: O=C(Nc1cccc(C(F)(F)F)c1)n1ccc2cc(OCc3ccccc3)ccc21]

To a solution of 2,2,6,6-tetramethylpiperidine (8.38 mL, 49.3 mmol) in 200 mL of THF at −78° C., 2.5 M n-butyl lithium (18 mL, 44.8 mmol) is added. After 15 min, 5-(benzyloxy)-1H-indole is added. After the other 15 min, 1-isocyanato-3-(trifluoromethyl)benzene is added dropwise at −78° C. and then stirred for 2 h at rt. The reaction is concentrated and the resulting solid is triturated with heptane and collected by filtration to give the title compound. MS (ESI) m/z 411.1 (M+1).

70-B. 70-B-1 5-hydroxy-N-(3-(trifluoromethyl)phenyl)-1H-indole-1-carboxamide and 70-B-2 5-hydroxy-N-(3-(trifluoromethyl)phenyl)indoline-1-carboxamide

70-B-1

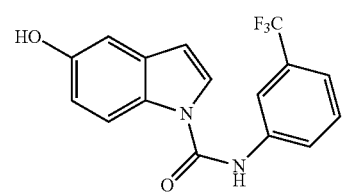

70-B-2

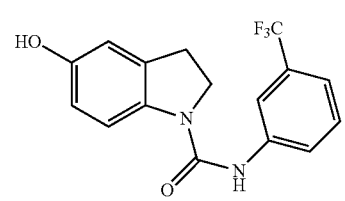

A mixture of 5-(benzyloxy)-N-(3-(trifluoromethyl)phenyl)-1H-indole-1-carboxamide (6 g, 14.6 mmol) in 60 mL of EtOH and 30 mL of EtOAc with Pd/C (0.6 g) is stirred under a hydrogen atmosphere (1 atm) at rt for 3.5 h. Additional Pd/C (0.6 g) is added and the mixture allowed to stir overnight. After filtration and concentration the solid was triturated with DCM and heptane to give a mixture of 5-hydroxy-N-(3-(trifluoromethyl)phenyl)-1H-indole-1-carboxamide and 5-hydroxy-N-(3-(trifluoromethyl)phenyl)indoline-1-carboxamide (6:4) which is carried on to next step.

70-C. 5-(2-chloropyrimidin-4-yloxy)-N-(3-(trifluoromethyl)phenyl)-1H-indole-1-carboxamide

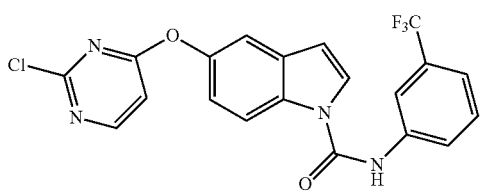 [SMILES: O=C(Nc1cccc(C(F)(F)F)c1)n1ccc2cc(Oc3ccnc(Cl)n3)ccc21]

A mixture of 5-hydroxy-N-(3-(trifluoromethyl)phenyl)-1H-indole-1-carboxamide and 5-hydroxy-N-(3-(trifluoromethyl)phenyl)indoline-1-carboxamide (6:4) (3 g) is mixed with sodium hydroxide (0.45 g, 11.2 mmol) and 2,4-dichloropyrimidine (1.68 g, 11.2 mmol) in 50 mL of acetone and 50 mL of water at 0° C. and stirred for 1.5 h. Additional sodium hydroxide (0.075 g, 1.88 mmol) and (0.279 g, 1.88 mmol) are added. After additional 30 min stirring the reaction is concentrated, diluted with EtOAc, washed with water and brine before the organic layer is dried over sodium sulfate and concentrated. The residue is separated via FCC (5-50% EtOAc in heptane) to give 5-(2-chloropyrimidin-4-yloxy)-N-(3-(trifluoromethyl)phenyl)-1H-indole-1-carboxamide. $^1$H NMR (400 MHz, CDCl$_3$) δ ppm 8.45 (d, J=5.7 Hz, 1 H), 8.24 (d, J=9.0 Hz, 1 H), 7.86 (s, 1 H), 7.78 (d, J=8.2 Hz, 1H), 7.60 (d, J=3.7 Hz, 1 H), 7.55 (t, J=8.0 Hz, 1 H), 7.45-7.50 (m, 2 H), 7.42 (d, J=2.1 Hz, 1 H), 7.15 (dd, J=8.9, 2.3 Hz, 1 H), 6.82 (d, J=5.7 Hz, 1 H), 6.73 (dd, J=3.7, 0.6 Hz, 1 H).

70-D. 5-(2-cyanopyrimidin-4-yloxy)-N-(3-(trifluoromethyl)phenyl)-1H-indole-1-carboxamide

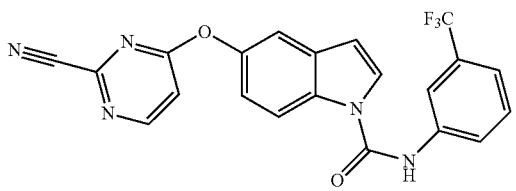 [SMILES: N#Cc1nccc(Oc2ccc3c(ccn3C(=O)Nc3cccc(C(F)(F)F)c3)c2)n1]

To a solution of 5-(2-chloropyrimidin-4-yloxy)-N-(3-(trifluoromethyl)phenyl)-1H-indole-1-carboxamide (1.76 g, 4.074 mmol) in 80 mL of a mixture of DMSO and H$_2$O (85:15), DABCO (0.92 g, 8.148 mmol) is added followed by KCN (0.53 g, 8.148 mmol). The mixture is stirred at rt for 2.5 h before being diluted with EtOAc, washed with H$_2$O and brine. The organic layer is dried over Na$_2$SO$_4$, filtered, and concentrated. The residue is purified by FCC (0-50% EtOAc/heptane) to give the title compound. MS (ESI) m/z 424.0 (M+1)

70-E. 5-(2-(aminomethyl)pyrimidin-4-yloxy)-N-(3-(trifluoromethyl)phenyl)-1H-indole-1-carboxamide

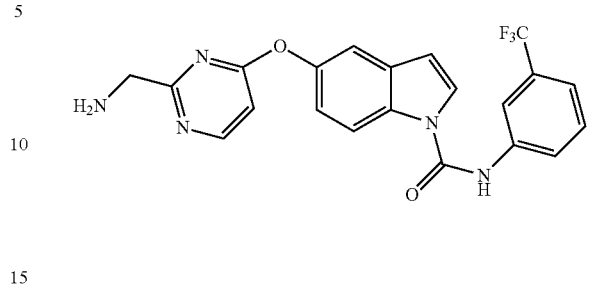

To a solution of 5-(2-cyanopyrimidin-4-yloxy)-N-(3-(trifluoromethyl)phenyl)-1H-indole-1-carboxamide (1.49 g, 3.52 mmol) in 70 mL of THF at −78° C., DIBAL (1 M in DCM, 10.6 mL) is added dropwise and stirred for 45 min at −78° C. The reaction is quenched with Roechelle's salt solution and extracted with DCM (×3). The combined organic layers are washed with brine and dried over Na$_2$SO$_4$. After concentration, the residue is purified by HPLC (5-90% I in H$_2$O with 0.1% TFA to give the title compound. MS (ESI) m/z 428.1 (M+1); $^1$H NMR (400 MHz, DMSO-d$_6$) δ ppm 10.41 (s, 1 H), 8.73 (d, J=5.8 Hz, 1 H), 8.23-8.37 (m, 3 H), 8.17 (d, J=3.8 Hz, 1 H), 8.10 (s, 1 H), 7.97 (d, J=8.3 Hz, 1 H), 7.65 (t, J=8.0 Hz, 1 H), 7.48-7.56 (m, 2 H), 7.18 (dd, J=8.8, 2.5 Hz, 1 H), 7.02 (d, J=5.8 Hz, 1 H), 6.82 (d, J=3.8 Hz, 1 H), 4.12-4.20 (m, 2 H)

EXAMPLE 71

71-A. 5-(Pyridin-4-ylmethoxy)-indole-1-carboxylic acid (3-trifluoromethyl-phenyl) Amide

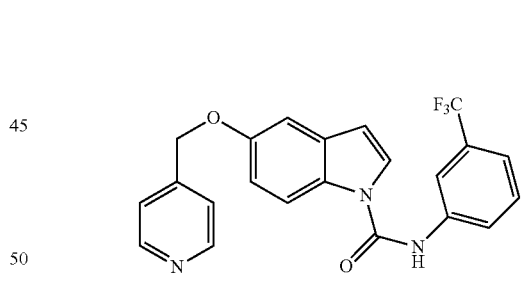

5-Hydroxy-indole-1-carboxylic acid (3-trifluoromethyl-phenyl)-amide, Example 70-B-1, (150 mg, 0.47 mmol), pyridine-4-yl-methanol (51 mg, 0.47 mmol) and cyanomethylenetri-n-butylphosphorane (0.17 mL, 0.70 mmol) are heated in a sealed tube at 100° C. for 15 h. The reaction is then concentrated in vacuo and separated directly via FCC (10-90 EtOAc/heptane) to give the title compound. MS (ESI) m/z 412.3 (M+1), $^1$H NMR (400 MHz, DMSO-d$_6$) δ ppm 10.26 (s, 1 H), 8.58 (d, J=6.1 Hz, 2 H), 8.16 (d, J=9.1 Hz, 1 H), 8.07 (s, 1 H), 8.03 (d, J=3.8 Hz, 1 H), 7.95 (d, J=8.8 Hz, 1 H), 7.63 (t, J=8.0 Hz, 1 H), 7.43-7.51 (m, 3 H), 7.23 (d, J=2.3 Hz, 1 H), 7.05 (dd, J=9.1, 2.5 Hz, 1 H), 6.71 (d, J=3.3 Hz, 1 H), 5.24 (s, 2 H).

EXAMPLE 72

72-A. (2-Isopropylamino-pyridin-4-yl)-methanol

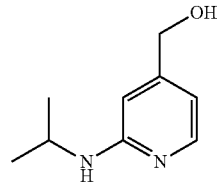

A mixture of (2-bromo-pyridin-4-yl)-methanol (500 mg, 2.66 mmol), isopropylamine (0.45 mL, 5.32 mmol), NatOBu (790 mg, 7.98 mmol) and Pd(tBu$_3$P)$_2$ (136 mg, 0.26 mmol) in 1,4-dioxane (5 mL) is heated in a microwave reactor at 110° C. for 45 min. The reaction is diluted with DCM (50 mL) and washed with saturated aqueous NH$_4$Cl. The organic layer is removed, dried over anhydrous Na$_2$SO$_4$, and concentrated in vacuo to give the title compound that is used without further purification. MS (ESI) m/z 167.1 (M+1).

72-B. 5-(2-Isopropylamino-pyridin-4-ylmethoxy)-indole-1-carboxylic acid (3-trifluoromethyl-phenyl)-amide

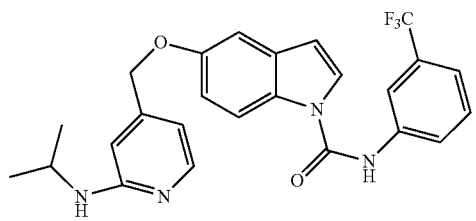 [SMILES: CC(C)Nc1cc(COc2ccc3c(ccn3C(=O)Nc3cccc(C(F)(F)F)c3)c2)ccn1]

5-Hydroxy-indole-1-carboxylic acid (3-trifluoromethyl-phenyl)-amide (100 mg, 0.31 mmol), (2-isopropylamino-pyridin-4-yl)-methanol (63 mg, 0.37 mmol) and cyanomethylenetri-n-butylphosphorane (112 mg, 0.46 mmol) are heated in a sealed tube at 90° C. for 2 h. The solution is then concentrated in vacuo and the residue separated via semi-prep HPLC (C18; 10-100% I/H$_2$O with 0.1% TFA) to give the title compound. MS (ESI) m/z 469.2 (M+1); $^1$H NMR (400 MHz, DMSO-d$_6$) δ ppm 10.26 (s, 1 H), 8.14 (d, J=9.1 Hz, 1 H), 8.07 (s, 1 H), 8.02 (d, J=3.5 Hz, 1 H), 7.90-7.98 (m, 2 H), 7.63 (t, J=8.0 Hz, 1 H), 7.48 (d, J=8.3 Hz, 1 H), 7.19 (d, J=2.5 Hz, 1 H), 7.00 (dd, J=9.0, 2.7 Hz, 1 H), 6.70 (d, J=3.8 Hz, 1 H), 6.45-6.52 (m, 2 H), 6.35 (d, J=7.6 Hz, 1 H), 5.03 (s, 2 H), 3.90-4.03 (m, 1 H), 1.12 (d, J=6.6 Hz, 6 H).

EXAMPLE 73

73-A. 5-(2-chloropyrimidin-4-yloxy)-1H-indole

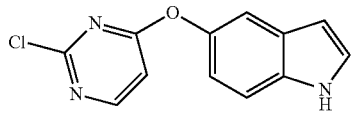 [SMILES: Clc1nccc(Oc2ccc3[nH]ccc3c2)n1]

To a solution of 1H-indol-5-ol (5.0 g, 37.6 mmol) in 40 mL of 1,2,4-dichloropyrimidine (5.6 g, 37.6 mmol) is added and the solution is cooled to 0° C. and DBU (5.71 mL, 37.6 mmol) is added dropwise. The reaction is allowed to warm to rt and stir for 2 h before being concentrated. The residue is taken up in EtOAc, washed with H$_2$O (×2), brine and the organic layer is dried over Na$_2$SO$_4$. After concentration, the resulting solid is triturated with DCM and heptane and collected by filtration to give the title compound. $^1$H NMR (400 MHz, CD$_2$Cl$_2$) δ ppm 8.29-8.50 (m, 2 H), 7.35-7.49 (m, 2 H), 7.29 (t, J=2.9 Hz, 1 H), 6.97 (dd, J=8.6, 2.3 Hz, 1 H), 6.70 (d, J=5.8 Hz, 1 H), 6.53-6.60 (m, 1 H).

73-B. 5-(2-vinylpyrimidin-4-yloxy)-1H-indole

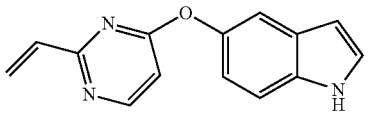 [SMILES: C=Cc1nccc(Oc2ccc3[nH]ccc3c2)n1]

A mixture of 5-(2-chloropyrimidin-4-yloxy)-1H-indole (1 g, 4.082 mmol), tri-butyl(vinyl)stannane (1.79 mL, 6.12 mmol) and Pd(PPh$_3$)$_4$ (0.377 g, 0.327 mmol) in 1,4-dioxane (10 mL) and toluene (10 mL) is heated in a microwave reactor at 140° C. for 30 min. The reaction is then diluted with EtOAc, washed with H$_2$O (×3), brine and the organic layer is dried over Na$_2$SO$_4$. After concentration, the residue is purified by FCC (0-50% EtOAc/heptane) to give the title compound. MS (ESI) m/z 238.0 (M+1).

73-C. 4-(2-(4-(1H-indol-5-yloxy)pyrimidin-2-yl)ethyl)morpholine

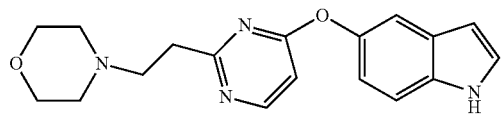 [SMILES: c1cc(Oc2ccc3[nH]ccc3c2)nc(CCN2CCOCC2)n1]

A mixture of 5-(2-vinylpyrimidin-4-yloxy)-1H-indole (0.45 g, 1.90 mmol), morpholine (0.33 mL, 3.80 mmol) and acetic acid (0.20 mL, 3.42 mmol) in 15 mL of EtOH is heated in a microwave reactor at 120° C. for 30 min. At that point the solution is concentrated and the residue is taken up in EtOAc, washed with H$_2$O (×2), sat aq NaHCO$_3$, brine and the organic layer is dried over Na$_2$SO$_4$. After concentration the title compound is obtained and carried on to next step without further purification. MS (ESI) m/z 325.1 (M+1).

73-D. 5-(2-(2-morpholinoethyl)pyrimidin-4-yloxy)-N-(3-(trifluoromethyl)phenyl)-1H-indole-1-carboxamide

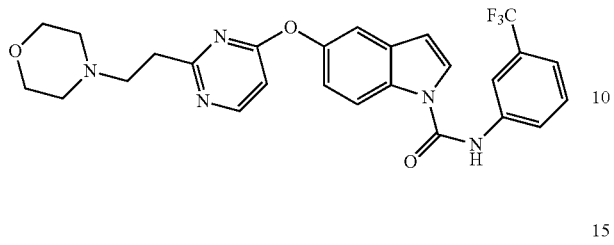

To a mixture of 2,2,6,6-tetramethylpiperidine (TMP, 0.18 mL, 1.05 mmol) and THF (12 mL) at −78° C., n-BuLi (0.42 mL, 1 M in hexane) is added. After 10 min, a solution of (4-(2-(4-(1H-indol-5-yloxy)pyrimidin-2-yl)ethyl)morpholine in 5 mL of THF is added dropwise. The solution is stirred at −78° C. for 30 min and then 1-isocyanato-3-(trifluoromethyl)benzene is added dropwise and stirring continued at −78° C. for an additional 1 h. The reaction is quenched with MeOH and then concentrated. The residue is taken up in EtOAc, washed with $H_2O$ (×2), brine and the organic layer is dried over $Na_2SO_4$. After concentration, the residue is purified by FCC (0-5% MeOH/DCM) and then by semi-prep HPLC (20-60% $CH_3CN$ in $H_2O$ with 0.1% $NH_4OH$ to give title compound. MS (ESI) m/z 512.2 (M+1); $^1$H NMR (400 MHz, DMSO-$d_6$) δ ppm 10.38 (br. S., 1 H), 8.56 (d, J=5.8 Hz, 1H), 8.29 (d, J=9.1 Hz, 1 H), 8.13 (d, J=3.8 Hz, 1 H), 8.09 (s, 1 H), 7.97 (d, J=9.1 Hz, 1 H), 7.64 (t, J=8.0 Hz, 1 H), 7.44-7.53 (m, 2 H), 7.14 (dd, J=9.0, 2.4 Hz, 1 H), 6.85 (d, J=5.8 Hz, 1 H), 6.78-6.82 (m, 1 H), 3.46-3.52 (m, 4 H), 2.85 (t, J=7.3 Hz, 2 H), 2.64 (t, J=7.3 Hz, 2 H), 2.27-2.37 (m, 4 H)

The following compounds are prepared with similar method.

73-E. 5-(2-(2-(isopropylamino)ethyl)pyrimidin-4-yloxy)-N-(3-(trifluoromethyl)phenyl)-1H-indole-1-carboxamide

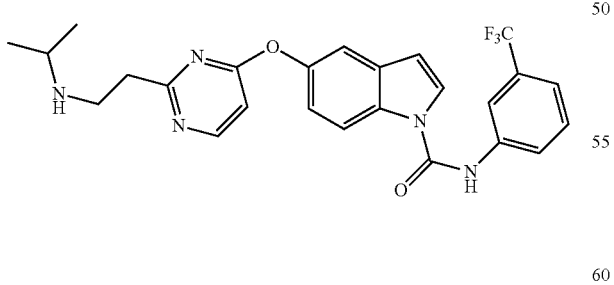

MS (ESI) m/z 484.3 (M+1); $^1$H NMR (400 MHz, DMSO-$d_6$) δ ppm 8.56 (d, J=5.8 Hz, 1 H), 8.30 (d, J=8.8 Hz, 1 H), 8.13 (d, J=3.8 Hz, 1 H), 8.09 (s, 1 H), 7.97 (d, J=8.6 Hz, 1 H), 7.64 (t, J=8.1 Hz, 1 H), 7.45-7.53 (m, 2 H), 7.15 (dd, J=8.8, 2.3 Hz, 1 H), 6.87 (d, J=5.8 Hz, 1 H), 6.79 (d, J=3.5 Hz, 1 H), 2.80 (s, 4 H), 2.55-2.68 (m, 1 H), 0.85 (d, J=6.1 Hz, 6 H)

EXAMPLE 74

74-A. 5-[2-(5-oxo-4,5-dihydro-[1,3,4]oxadiazol-2-yl)-pyridin-4-yloxy]-indole-1-carboxylic acid (3-trifluoromethyl-phenyl)-amide

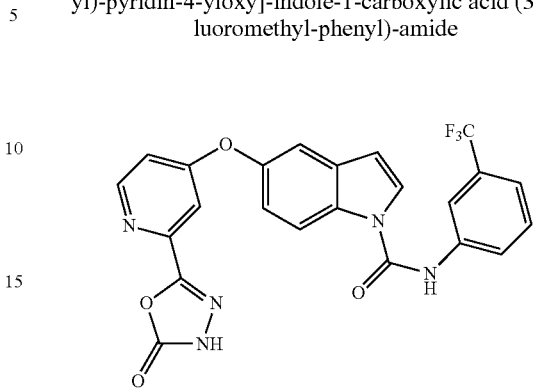

To a solution of acid 4-[1-(3-trifluoromethyl-phenylcarbamoyl)-1H-indol-5-yloxy]-pyridine-2-carboxylic acid, Example 28-A, (0.100 g, 0.226 mmol) in DCM (5 mL) is added $Et_3N$ (0.09 mL), DMF (2 drops) and oxalyl chloride (0.17 mL, 0.340 mmol, 2.0 M DCM). After 0.5 h tert-butyl carbazate is added (0.045 g, 0.340 mmol). After 1.5 h the solution is diluted with DCM (10 mL) and then washed with pH 7 buffer (15 mL). The organic layer is then dried ($Na_2SO_4$), filtered, and concentrated. The residue is separated via FCC (30-60% EtOAc/heptane) to give N'-{4-[1-(3-Trifluoromethyl-phenylcarbamoyl)-1H-indol-5-yloxy]-pyridine-2-carbonyl}-hydrazinecarboxylic acid tert-butyl ester. MS (ESI) m/z 484.3 (M+1).

The N'-{4-[1-(3-trifluoromethyl-phenylcarbamoyl)-1H-indol-5-yloxy]-pyridine-2-carbonyl}-hydrazinecarboxylic acid tert-butyl ester (0.105 g, 0.189 mmol) is then taken up in DCM (2 mL) and treated with TFA (0.5 mL). After 2 h the solution in concentrated in vacuo. The resulting residue is then taken up in THF (3 mL) and $Et_3N$ (0.079 mL) and carbonyl diimidazole is added (0.046 g, 0.283 mmol). After 0.5 h the solution is concentrated and the residue is separated via semi-prep HPLC (20-100% I/$H_2O$ with 0.1% $NH_4OH$) to give the title compound. MS (ESI) m/z 484.3 (M+1).

EXAMPLE 75

75-A. 1-{6-[1-(4-Fluoro-3-trifluoromethyl-phenylcarbamoyl)-1H-indol-5-yloxy]-pyrimidin-4-ylmethyl}-piperidine-3-carboxylic acid

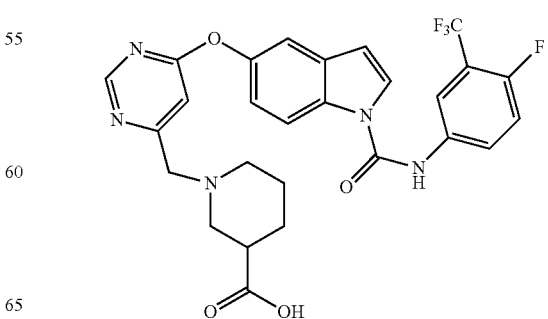

To a solution of 1-{6-[1-(4-fluoro-3-trifluoromethyl-phenylcarbamoyl)-1H-indol-5-yloxy]-pyrimidin-4-ylmethyl}-piperidine-3-carboxylic acid ethyl ester (prepared by similar method to Example 19) (0.32 g, 0.55 mmol), in THF (5.5 mL), LiOH (0.92 g, 22 mmol) in H$_2$O (8.75 mL) is added and the reaction allowed to stir overnight. The reaction is acidified to pH 4 with 1 N HCl and then extracted with EtOAc (3×). The compound is then purified by semi-prep HPLC (12-48% CH$_3$CN/H$_2$O with 0.1% TFA) to give the title compound. MS (ESI) m/z 558.9 (M+1).

EXAMPLE 76

76-A. 5-(6-(benzyloxymethyl)pyrimidin-4-yloxy)-N-(3-methoxy-5-(trifluoromethyl)phenyl)-1H-indole-1-carboxamide

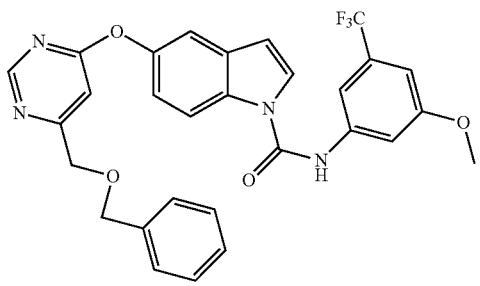 [SMILES: COc1cc(NC(=O)n2ccc3cc(Oc4cc(COCc5ccccc5)ncn4)ccc32)cc(C(F)(F)F)c1]

To a solution of TMP (1.15 ml, 6.757 mmol) in 30 ml of THF at −78° C., n-BuLi (1.15 mL, 2.88 mmol) is added. After 10 min, a solution of 5-(6-(benzyloxymethyl)pyrimidin-4-yloxy)-1H-indole (0.868 g, 2.62 mmol) in 5 mL of THF is added dropwise and stirred at −78° C. Reaction 2: To a solution of 3-methoxy-5-(trifluoromethyl)aniline (0.6 g, 3.14 mmol) in 20 mL of DCE at 0° C., triphosgene (0.931 g, 3.14 mmol) is added followed by TEA (1.74 mL, 12.6 mmol). The solution is a allowed to warm to rt and stir for 45 min. At that point reaction 2 is added to reaction 1 dropwise at −78° C. and stirred for 2 h. The reaction is then quenched with MeOH and concentrated. The residue is taken up in EtOAc, washed with H$_2$O (×2), brine and the organic layer is dried over Na$_2$SO$_4$. After concentration, the residue is purified by FCC (5-65% EtOAc/haptane) to give the title compound which is carried on to the next step as is. MS (ESI) m/z 549.1 (M+1).

76-B. 5-(6-(hydroxymethyl)pyrimidin-4-yloxy)-N-(3-methoxy-5-(trifluoromethyl)phenyl)-1H-indole-1-carboxamide

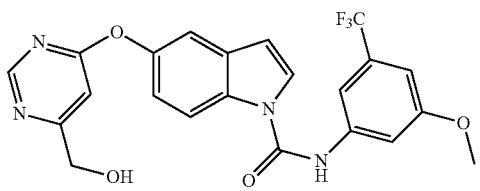 [SMILES: COc1cc(NC(=O)n2ccc3cc(Oc4cc(CO)ncn4)ccc32)cc(C(F)(F)F)c1]

5-(6-(Benzyloxymethyl)pyrimidin-4-yloxy)-N-(3-methoxy-5-(trifluoromethyl)phenyl)-1H-indole-1-carboxamide (0.94 g, 1.72 mmol) is treated with TFA (9.5 mL) at 60° C. for 24 h. After concentration, the residue is taken up in EtOAc, washed with saturated NaHCO$_3$ (×2), brine and the organic layer is dried over Na$_2$SO$_4$. After concentration, the residue is purified by FCC (20-90% EtOAc/heptane) and then semi-prep HPLC (20-60% CH$_3$CN in H$_2$O with 0.1% NH$_4$OH) to give the title compound. MS (ESI) m/z 459.0 (M+1); $^1$H NMR (400 MHz, DMSO-d$_6$) δ ppm 10.35 (br. S., 1H), 8.65 (s, 1 H), 8.31 (d, J=9.1 Hz, 1 H), 8.12 (d, J=3.5 Hz, 1 H), 7.69 (s, 1 H), 7.60 (t, J=1.9 Hz, 1 H), 7.50 (d, J=2.3 Hz, 1 H), 7.15 (dd, J=8.8, 2.3 Hz, 1 H), 6.95-7.06 (m, 2 H), 6.80 (d, J=3.5 Hz, 1 H), 5.61 (t, J=5.7 Hz, 1 H), 4.52 (d, J=5.8 Hz, 2 H), 3.86 (s, 3 H).

76-C. 5-(6-formylpyrimidin-4-yloxy)-N-(3-methoxy-5-(trifluoromethyl)phenyl)-1H-indole-1-carboxamide

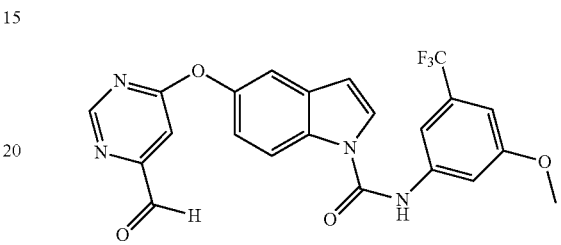

To a solution of 5-(6-(hydroxymethyl)pyrimidin-4-yloxy)-N-(3-methoxy-5-(trifluoromethyl)phenyl)-1H-indole-1-carboxamide (0.260 g, 0.568 mmol) in DCM (8 mL) is added DMP (0.265 g, 0.624 mmol) at 0° C. The mixture is then allowed to warm to it and stir for 2 h before being diluted with EtOAc and washed with aqueous NaHCO$_3$/Na$_2$S$_2$O$_4$. The organic layer is then dried and concentrated and the residue separated via FCC (10-60% EtOAc/heptane) to give the title compound. MS (ESI) m/z 457.0 (M+1).

76-D. N-(3-methoxy-5-(trifluoromethyl)phenyl)-5-(6-((methylamino)methyl)pyrimidin-4-yloxy)-1H-indole-1-carboxamide

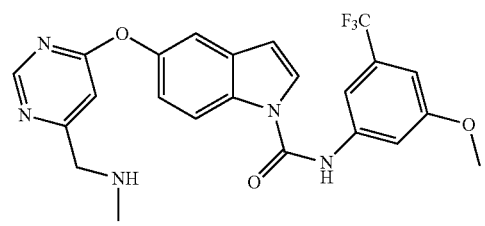 [SMILES: CNCc1cc(Oc2ccc3c(ccn3C(=O)Nc3cc(OC)cc(C(F)(F)F)c3)c2)ncn1]

To a solution of 5-(6-formylpyrimidin-4-yloxy)-N-(3-methoxy-5-(trifluoromethyl)phenyl)-1H-indole-1-carboxamide (0.219 g, 0.479 mmol) in 3 mL of DCM, 2 M methylamine in THF (0.72 mL, 1.43 mmol) is added and stirred at it for 45 min. At that point Na(Oac)$_3$BH (0.406 g, 1.92 mmol) is added followed by acetic acid (0.14 mL) and the mixture is stirred at rt for 1.5 h before being diluted with EtOAc, washed with saturated aqueous NaHCO$_3$ (×2) and brine. The organic layer is dried over Na$_2$SO$_4$. After concentration, the residue is purified by semi-prep HPLC (C-phenyl; 20-60% I/H$_2$O with 0.1% NH$_4$OH) to give the title compound. MS (ESI) m/z 472.0 (M+1); $^1$H NMR (400 MHz, DMSO-d$_6$) δ ppm 10.34 (br. S., 1 H), 8.65 (d, J=1.0 Hz, 1 H), 8.29 (d, J=9.1 Hz, 1 H), 8.12 (d, J=3.5 Hz, 1 H), 7.70 (s, 1 H), 7.60 (s, 1 H), 7.49 (d, J=2.3 Hz, 1 H), 7.15 (dd, J=8.8, 2.5 Hz, 1 H), 7.01-7.06 (m, 2 H), 6.80 (d, J=3.8 Hz, 1 H), 3.86 (s, 3 H), 3.71 (s, 2 H), 2.29 (s, 3 H).

The following compounds are prepared with similar method.

76-E. N-(4-methoxy-3-(trifluoromethyl)phenyl)-5-(6-((methylamino)methyl)pyrimidin-4-yloxy)-1H-indole-1-carboxamide

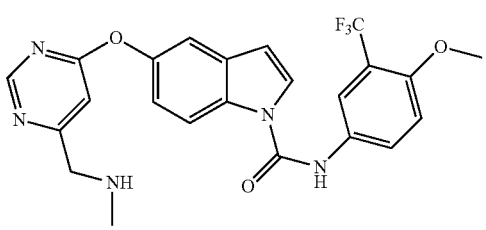 [SMILES: CNCc1cc(Oc2ccc3c(ccn3C(=O)Nc3ccc(OC)c(C(F)(F)F)c3)c2)ncn1]

MS (ESI) m/z 472.0 (M+1); $^1$H NMR (400 MHz, DMSO-$d_6$) δ ppm 10.18 (br. S., 1 H), 8.65 (d, J=1.0 Hz, 1 H), 8.28 (d, J=8.8 Hz, 1 H), 8.10 (d, J=3.5 Hz, 1 H), 7.95 (d, J=2.5 Hz, 1 H), 7.90 (dd, J=9.0, 2.7 Hz, 1 H), 7.48 (d, J=2.5 Hz, 1 H), 7.33 (d, J=9.1 Hz, 1 H), 7.13 (dd, J=9.0, 2.4 Hz, 1 H), 7.03 (d, J=0.8 Hz, 1 H), 6.79 (d, J=3.5 Hz, 1 H), 3.90 (s, 3 H), 3.70 (s, 2 H), 2.29 (s, 3 H).

76-F. 5-(6-(((1H-tetrazol-5-yl)methylamino)methyl)pyrimidin-4-yloxy)-N-(4-fluoro-3-(trifluoromethyl)phenyl)-1H-indole-1-carboxamide

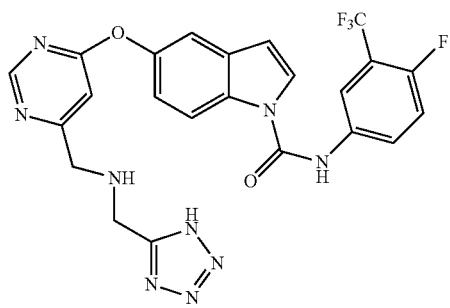 [SMILES: O=C(Nc1ccc(F)c(C(F)(F)F)c1)n1ccc2cc(Oc3cc(CNCc4nnn[nH]4)ncn3)ccc21]

MS (ESI) m/z 528.1 (M+1); $^1$H NMR (400 MHz, DMSO-$d_6$) δ ppm 10.41 (s, 1 H), 8.84 (s, 1 H), 8.31 (d, J=9.1 Hz, 1 H), 8.09-8.15 (m, 2 H), 7.95-8.05 (m, 1 H), 7.58 (t, J=9.9 Hz, 1 H), 7.51 (d, J=2.3 Hz, 1 H), 7.23 (s, 1 H), 7.16 (dd, J=8.8, 2.3 Hz, 1 H), 6.83 (d, J=3.8 Hz, 1 H), 4.56-4.67 (m, 2 H), 4.39-4.49 (m, 2 H).

EXAMPLE 77

77-A. (±)-5-[6-(1-Hydroxy-ethyl)-pyrimidin-4-yloxy]-indole-1-carboxylic acid (3-trifluoromethyl-phenyl)-amide

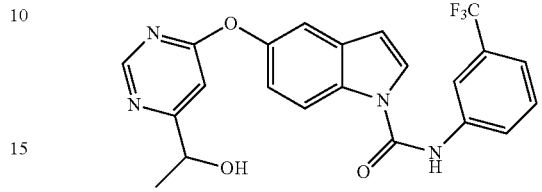

Methylmagnesium bromide solution (3 M in ether, 20 mL) is added to a solution of 5-(6-formyl-pyrimidin-4-yloxy)-indole-1-carboxylic acid (3-trifluoromethyl-phenyl)-amide (5.0 g 11.7 mmol) in THF (400 mL) at 0° C. The mixture is stirred at that temperature for 3 h before the reaction is then quenched with saturated aqueous NH$_4$Cl. The product is extracted with EtOAc (3×40 mL) and the combined organic layers are washed with brine, dried over anhydrous Na$_2$SO$_4$, filtered, and concentrated. The residue is purified semi-prep HPLC (C18; 30-100% I/H$_2$O with 0.1% TFA) to give the title compound as a racemate. MS (ESI) m/z 441.1 (M+1); $^1$H NMR (400 MHz, MeOD) δ ppm 8.62 (s, 1 H), 8.36 (d, J=8.84 Hz, 1 H), 8.06 (s, 1 H), 7.95 (d, J=3.79 Hz, 1 H), 7.90 (d, J=8.08 Hz, 1 H), 7.58 (t, J=7.83 Hz, 1 H), 7.43 (d, J=2.27 Hz, 2 H), 7.12 (dd, J=8.97, 2.40 Hz, 1 H), 7.09 (s, 1 H), 6.75 (d, J=3.79 Hz, 1 H), 4.75 (d, J=6.57 Hz, 1 H), 1.45 (d, J=6.57 Hz, 3 H).

The racemate Example 77-A is separated via chiral HPLC (Chiralpak OD-column; SFC with 20% MeOH, flow rate: 3.2 mL/min) to give the two corresponding enantiomers 77-A-1 ($R_t$ 3.33 min) and 77-A-2 ($R_t$ 4.65 min).

77-A-1. 5-[6-(1-Hydroxy-ethyl)-pyrimidin-4-yloxy]-indole-1-carboxylic acid (3-trifluoromethyl-phenyl)-amide MS (ESI) m/z 443.0 (M+1); $^1$H NMR (400 MHz, MeOD) δ ppm 8.61 (d, J=1.01 Hz, 1 H), 8.35 (d, J=9.09 Hz, 1 H), 8.06 (s, 1 H), 7.94 (d, J=3.54 Hz, 1 H), 7.89 (d, J=8.08 Hz, 1 H), 7.56 (t, J=8.08 Hz, 1 H), 7.41 (d, J=2.27 Hz, 2 H), 7.44 (d, J=7.83 Hz, 1 H), 7.11 (dd, J=8.97, 2.40 Hz, 1 H), 7.09 (s, 1 H), 6.74 (d, J=3.54 Hz, 1 H), 4.76 (q, J=6.65 Hz, 1 H), 1.45 (d, J=6.57 Hz, 3 H).

77-A-2. 5-[6-(1-Hydroxy-ethyl)-pyrimidin-4-yloxy]-indole-1-carboxylic acid (3-trifluoromethyl-phenyl)-amide MS (ESI) m/z 443.0 (M+1); $^1$H NMR (400 MHz, MeOD) δ ppm 8.62 (s, 1 H), 8.36 (d, J=9.09 Hz, 1 H), 8.06 (s, 1 H), 7.94 (d, J=3.79 Hz, 1 H), 7.89 (d, J=7.83 Hz, 1 H), 7.56 (t, J=7.96 Hz, 1 H), 7.44 (d, J=7.83 Hz, 1 H), 7.42 (d, J=2.27 Hz, 1 H), 7.11 (dd, J=8.97, 2.40 Hz, 1 H), 7.09 (s, 1 H), 6.74 (d, J=3.79 Hz, 1 H), 4.76 (d, J=6.82 Hz, 1 H), 1.45 (d, J=6.57 Hz, 3 H).

EXAMPLE 78

5-(6-Formyl-pyrimidin-4-yloxy)-indole-1-carboxylic acid (3-trifluoromethyl-phenyl)-amide

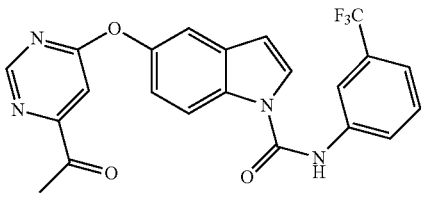 [SMILES: CC(=O)c1cc(Oc2ccc3c(ccn3C(=O)Nc3cccc(C(F)(F)F)c3)c2)ncn1]

To a suspension of 5-(6-Hydroxymethyl-pyrimidin-4-yloxy)-indole-1-carboxylic acid (3-trifluoromethyl-phenyl)-amide (310 mg, 0.724 mmol) in DCM (10 mL), DMP (337 mg, 0.795 mmol) is added. The reaction mixture is stirred at rt until complete as seen by LCMS (about 1 h). The reaction is quenched with saturated aqueous NaHCO$_3$ and extracted with EtOAc (3×10 mL). The combined organic layers are then washed by brine, dried (Na$_2$SO$_4$), filtered and concentrated. The crude residue is purified by FCC (0-40% EtOAc/Heptane) to provide the title compound. MS (ESI) m/z 443.1 (M+1); $^1$H NMR (400 MHz, MeOD) δ ppm 8.84 (d, J=1.01 Hz, 1 H), 8.36 (d, J=9.09 Hz, 1 H), 8.06 (s, 1 H), 7.96 (d, J=3.79 Hz, 1 H), 7.89 (s, 1 H), 7.55-7.60 (m, 1 H), 7.45 (s, 1 H), 7.40 (d, J=1.01 Hz, 2 H), 7.44 (d, J=2.53 Hz, 1 H), 7.13 (dd, J=8.97, 2.40 Hz, 1 H), 6.76 (d, J=3.79 Hz, 1 H), 2.66 (s, 3 H).

EXAMPLE 79

79-A. 5-[6-(1-Methylamino-ethyl)-pyrimidin-4-yloxy]-indole-1-carboxylic acid (3-trifluoromethyl-phenyl)-amide

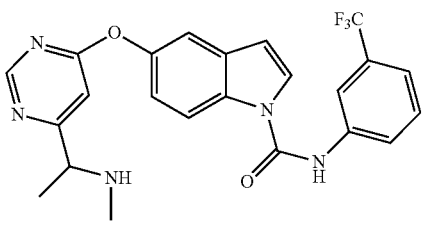 [SMILES: CNC(C)c1cc(Oc2ccc3c(ccn3C(=O)Nc3cccc(C(F)(F)F)c3)c2)ncn1]

To a solution of 5-(6-Formyl-pyrimidin-4-yloxy)-indole-1-carboxylic acid (3-trifluoromethyl-phenyl)-amide (200 mg, 0.45 mmol) in MeOH (10 mL), acetic acid (0.1 mL) is added, followed by methylamine in MeOH (0.25 mL). The mixture is stirred for 10 min before Na(CN)BH$_3$ (86 mg, 1.35 mmol) is added. The mixture is stirred overnight and then the MeOH is removed. The residue is partitioned between saturated aqueous NaHCO$_3$ and EtOAc. The aqueous layer is extracted further with EtOAc (2×30 mL) and the combined organic layers are washed with brine, dried over anhydrous Na$_2$SO$_4$, filtered and concentrated. The residue is purified with semi-prep HPLC (C18; 10-100% I/H$_2$O with 0.1% TFA) to give the title compound. MS (ESI) m/z 456.1 (M+1); $^1$H NMR (400 MHz, MeOD) δ ppm 8.66 (d, J=1.01 Hz, 1 H), 8.35 (d, J=9.09 Hz, 1 H), 8.06 (s, 1 H), 7.94 (d, J=3.54 Hz, 1 H), 7.89 (d, J=8.34 Hz, 1 H), 7.56 (t, J=7.96 Hz, 1 H), 7.44 (d, J=8.08 Hz, 1 H), 7.42 (d, J=2.53 Hz, 1 H), 7.11 (dd, J=8.97, 2.40 Hz, 1 H), 7.00 (s, 1 H), 6.74 (d, J=3.79 Hz, 1 H), 3.71 (d, J=6.82 Hz, 1 H), 2.28 (s, 3 H), 1.36 (d, J=6.82 Hz, 3 H).

The following compounds are prepared with similar method.

79-A B

5-[6-(1-Cyclopropylamino-ethyl)-pyrimidin-4-yloxy]-indole-1-carboxylic acid (3-trifluoromethyl-phenyl)-amide

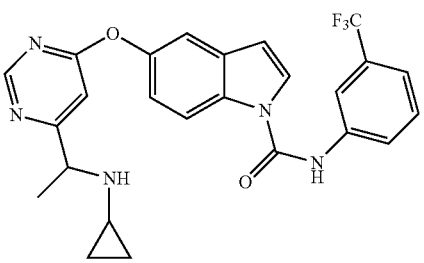 [SMILES: CC(NC1CC1)c1cc(Oc2ccc3c(ccn3C(=O)Nc3cccc(C(F)(F)F)c3)c2)ncn1]

MS (ESI) m/z 482.1 (M+1); $^1$H NUR (400 MHz, MeOD) δ ppm 8.66 (s, 1 H), 8.34 (d, J=9.09 Hz, 1H), 8.05 (s, 1 H), 7.93 (d, J=3.79 Hz, 1 H), 7.89 (d, J=8.08 Hz, 1 H), 7.55 (t, J=8.08 Hz, 1 H), 7.40 (d, J=2.27 Hz, 1 H), 7.43 (d, J=7.83 Hz, 1 H), 7.09 (dd, J=8.97, 2.40 Hz, 1 H), 7.02 (s, 1 H), 6.73 (d, J=3.79 Hz, 1 H), 3.89 (d, J=6.82 Hz, 1 H), 1.98 (dd, J=10.48, 2.91 Hz, 1 H), 1.35 (d, J=6.82 Hz, 3 H), 0.34 (tt, J=4.01, 1.93 Hz, 4 H).

The racemate is separated via chiral HPLC (Chiralpak AD-column; heptane/EtOH 1:1), flow rate: 14 mL/min) to give the two corresponding enantiomers 79-A B-1 (R$_t$ 7.10 min) and 79-A B-2 (R$_t$ 7.80 min).

79-A B-1

(−)-5-[6-(1-Cyclopropylamino-ethyl)-pyrimidin-4-yloxy]-indole-1-carboxylic acid (3-trifluoromethyl-phenyl)-amide MS (ESI) m/z 482.1 (M+1); $^1$H NMR (400 MHz, MeOD) δ ppm 8.66 (s, 1 H) 8.35 (d, J=8.84 Hz, 1 H) 8.06 (s, 1 H) 7.94 (d, J=3.54 Hz, 1 H) 7.89 (d, J=8.34 Hz, 1 H) 7.56 (t, J=7.96 Hz, 1 H) 7.41 (d, J=2.27 Hz, 1 H) 7.44 (d, J=7.83 Hz, 1 H) 7.11 (dd, J=9.09, 2.27 Hz, 1 H) 7.02 (s, 1 H) 6.74 (d, J=3.79 Hz, 1 H) 3.89 (d, J=6.82 Hz, 1 H) 1.98 (dd, J=10.48, 2.91 Hz, 1 H) 1.35 (d, J=6.82 Hz, 3 H) 0.31-0.43 (m, 4 H).

79-A B-2

(+)-5-[6-((S)-1-Cyclopropylamino-ethyl)-pyrimidin-4-yloxy]-indole-1-carboxylic acid (3-trifluoromethyl-phenyl)-amide MS (ESI) m/z 482.1 (M+1); $^1$H NMR (400 MHz, MeOD) δ ppm 8.66 (d, J=1.01 Hz, 1 H) 8.35 (d, J=9.09 Hz, 1 H) 8.06 (s, 1 H) 7.94 (d, J=3.54 Hz, 1 H) 7.90 (d, J=8.08 Hz, 1 H) 7.57 (t, J=8.08 Hz, 1 H) 7.42 (d, J=2.27 Hz, 1 H) 7.44 (d, J=7.83 Hz, 1 H) 7.11 (dd, J=8.84, 2.27 Hz, 1 H) 7.02 (s, 1 H) 6.74 (d, J=3.79 Hz, 1 H) 3.89 (q, J=6.82 Hz, 1 H) 1.98 (dd, J=10.48, 2.91 Hz, 1 H) 1.35 (d, J=6.82 Hz, 3 H) 0.31-0.43 (m, 4 H).

EXAMPLE 80

5-(2-Cyano-pyridin-4-yloxy)-indole-1-carboxylic acid (3-trifluoromethyl-phenyl)-amide

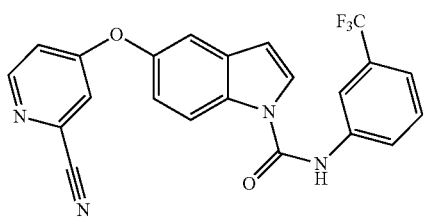 [SMILES: N#Cc1cc(Oc2ccc3c(ccn3C(=O)Nc3cccc(C(F)(F)F)c3)c2)ccn1]

DIBAL-H (0.75 mL, 1.0 M) is added to a solution of 4-[1-(3-trifluoromethyl-phenylcarbamoyl)-1H-indol-5-yloxy]-pyridine-2-carboxylic acid tert-butyl ester (0.250 g, 0.502 mmol) at 0° C. in DCM (5 mL). After 1 h the solution is allowed to warm to rt. After an additional 1 h the reaction is quenched with saturated aqueous Rochelle's salt solution. Workup is done with DCM and saturated aqueous Rochelle's salt solution. After drying the crude aldehyde is concentrated and taken to next step as is.

The aldehyde prepared above is taken up in DCM (2 mL) and Et$_3$N (0.08 mL) and hydroxylamine hydrochloride (0.021 g, 0.300 mmol) is added. After 1.5 h, Et$_3$N (0.9 mL) is added followed by methanesulfonyl chloride (0.025 mL, 0.300 mmol). After stirring overnight the reaction is diluted with DCM and washed with brine. The residue is the separated via semi-prep HPLC (10-90% I/H$_2$O with 0.1% NH$_4$OH) to give the title compound. MS (ESI) m/z 423.1 (M+1).

EXAMPLE 81

5-[2-(1-Hydroxy-1-methyl-ethyl)-pyridin-4-yloxy]-indole-1-carboxylic acid (3-trifluoromethyl-phenyl)-amide

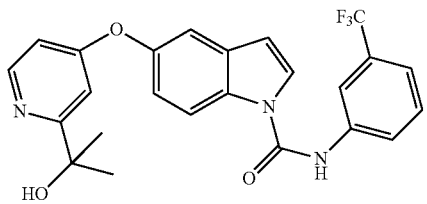 [SMILES: CC(C)(O)c1cc(Oc2ccc3c(ccn3C(=O)Nc3cccc(C(F)(F)F)c3)c2)ccn1]

Methyl magnesium iodide (0.30 mL, 3.0 M) is added to a solution of 4-[1-(3-Trifluoromethyl-phenylcarbamoyl)-1H-indol-5-yloxy]-pyridine-2-carboxylic acid tert-butyl ester (0.150 g, 0.302 mmol) in THF (5 mL) at rt. After stirring overnight the reaction is diluted with MeOH (5 mL) and workup done with DCM and pH 7 buffer. Following concentration the residue is separated by FCC (80-100% EtOAc/heptane) to give the title compound. MS (ESI) m/z 456.1 (M+1).

EXAMPLE 82

82-A. 5-(6-Chloro-pyrimidin-4-yloxy)-1H-indole

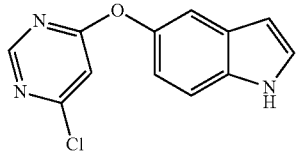 [SMILES: Clc1cc(Oc2ccc3[nH]ccc3c2)ncn1]

To a solution of 1H-Indol-5-ol (3.0 g, 22.54 mmol) and 4,6-dichloro-pyrimidine (3.7 g, 24.8 mmol) in acetonitrile (40 ml), DBU (3.52 ml, 24.8 mmol) is added. The mixture is stirred overnight. After removal of acetonitrile, the residue is partitioned between EtOAc and water. The aqueous phase is then extracted further with EtOAc. The combined organic layers are washed with brine, dried over anhydrous Na$_2$SO$_4$, filtered and concentrated. The residue is then purified by FCC (0-30% EtOAc/Heptane) to provide the title compound. MS (ESI) m/z 246.1 (M+1).

82-B. 82-B-1 4-[6-(1H-Indol-5-yloxy)-pyrimidin-4-yl]-3,6-dihydro-2H-pyridine-1-carboxylic acid tert-butyl ester and 82-B-2 4-[6-(1H-Indol-5-yloxy)-pyrimidin-4-yl]-3,4-dihydro-2H-pyridine-1-carboxylic acid tert-butyl ester

82-B-1

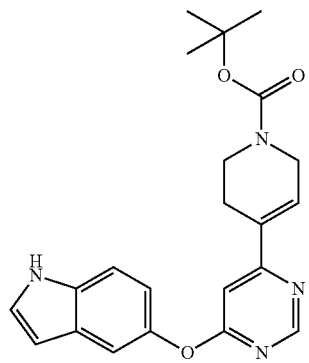

82-B-2

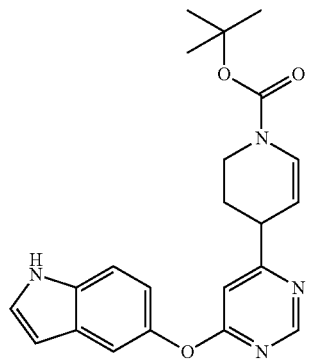

A mixture of 4-(4,4,5,5-tetramethyl-[1,3,2]dioxaborolan-2-yl)-3,6-dihydro-2H-pyridine-1-carboxylic acid tert-butyl ester (1.24 g, 4.0 mmol), 5-(6-chloro-pyrimidin-4-yloxy)-1H-indole (750 mg, 3.05 mmol), tetrakis(triphenylphosphine) palladium (106 mg, 0.03 mmol) and potassium carbonate (1.26 g, 9.15 mmol) in DMF (15 ml) is degassed and back-filled with nitrogen in a sealed microwave vial. This mixture is then stirred at 150° C. in microwave reactor for 40 min. After the mixture has cooled to rt, it is diluted with EtOAc/Heptane (8:2) and washed with water (3x) and brine, and the organic layer is dried over anhydrous $Na_2SO_4$, filtered and concentrated. The residue is then purified by FCC (0-50% EtOAc/Heptane) to provide both title compounds (B-1 and B-2). MS (ESI) m/z 393.1 (M+1).

82-C. 4-[6-(1H-Indol-5-yloxy)-pyrimidin-4-yl]-piperidine-1-carboxylic acid tert-butyl ester

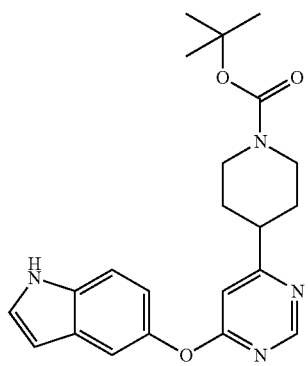 [SMILES: CC(C)(C)OC(=O)N1CCC(c2cc(Oc3ccc4[nH]ccc4c3)ncn2)CC1]

10% Pd/C (20 mg) is added to a solution of the 4-[6-(1H-Indol-5-yloxy)-pyrimidin-4-yl]-3,6-dihydro-2H-pyridine-1-carboxylic acid tert-butyl ester and 4-[6-(1H-Indol-5-yloxy)-pyrimidin-4-yl]-3,4-dihydro-2H-pyridine-1-carboxylic acid tert-butyl ester (200 mg) in EtOAc (5 mL). The mixture is stirred under a hydrogen atmosphere (1 atm) overnight before being filtered over Celite® and concentrated in vacuo to give the title compound. MS (ESI) m/z 395.0 (M+1).

EXAMPLE 83

83-A. 4-{6-[1-(3-Trifluoromethyl-phenylcarbamoyl)-1H-indol-5-yloxy]-pyrimidin-4-yl}-3,6-dihydro-2H-pyridine-1-carboxylic acid tert-butyl ester

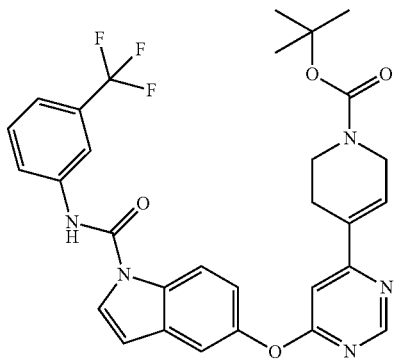 [SMILES: CC(C)(C)OC(=O)N1CC=C(c2cc(Oc3ccc4c(ccn4C(=O)Nc4cccc(C(F)(F)F)c4)c3)ncn2)CC1]

To a solution of 2,2,6,6-Tetramethyl-piperidine (46.8 mg, 0.33 mmol) in 10 mL THF at −78° C. is added n-butyllithium (1.6 M in hexane, 0.22 mL) followed by 4-[6-(1H-indol-5-yloxy)-pyrimidin-4-yl]-3,6-dihydro-2H-pyridine-1-carboxylic acid tert-butyl ester (130 mg, 0.33 mmol) while keep the temperature below −70° C. The reaction mixture is stirred for 10 min, then 1-isocyanato-3-trifluoromethyl-benzene (61.7 mg, 0.33 mmol) is added. The reaction mixture is slowly warmed to room temperature and stirred at rt overnight. Concentration under reduced pressure is followed by partitioning the residue between EtOAc and water. The aqueous layer is extracted further with EtOAc. The combined organic layers are washed with brine, dried over anhydrous $Na_2SO_4$, filtered, and concentrated. The residue is then purified by FCC (0-50% EtOAc/heptane) to provide the title compound. MS (ESI) m/z 579.9 (M+1).

The following compounds are prepared with similar method.

83-B. 4-{6-[1-(3-Trifluoromethyl-phenylcarbamoyl)-1H-indol-5-yloxy]-pyrimidin-4-yl}-3,4-dihydro-2H-pyridine-1-carboxylic acid tert-butyl ester

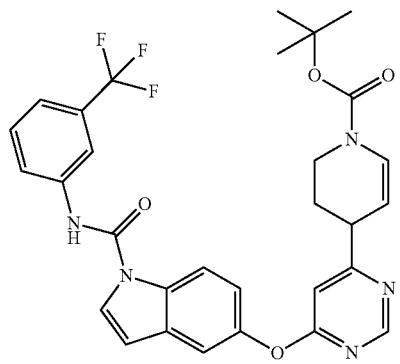 [SMILES: CC(C)(C)OC(=O)N1C=CC(c2cc(Oc3ccc4c(ccn4C(=O)Nc4cccc(C(F)(F)F)c4)c3)ncn2)CC1]

MS (ESI) m/z 579.9 (M+1).

83-C. 4-{6-[1-(3-Trifluoromethyl-phenylcarbamoyl)-1H-indol-5-yloxy]-pyrimidin-4-yl}-piperidine-1-carboxylic acid tert-butyl ester

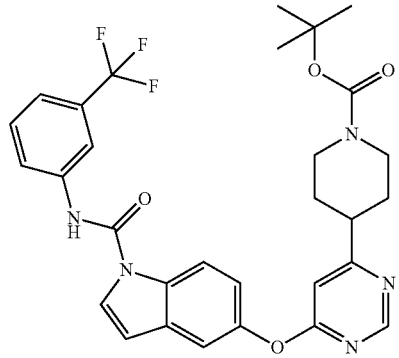 [SMILES: CC(C)(C)OC(=O)N1CCC(c2cc(Oc3ccc4c(ccn4C(=O)Nc4cccc(C(F)(F)F)c4)c3)ncn2)CC1]

MS (ESI) m/z 581.9 (M+1).

EXAMPLE 84

84-A. 5-[6-(1,2,3,6-Tetrahydro-pyridin-4-yl)-pyrimidin-4-yloxy]-indole-1-carboxylic acid (3-trifluoromethyl-phenyl)-amide

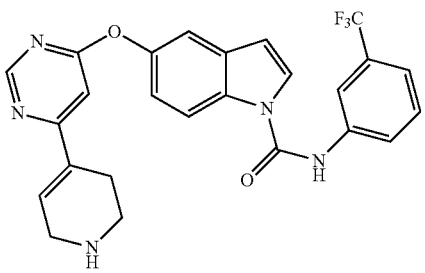 [SMILES: O=C(Nc1cccc(C(F)(F)F)c1)n1ccc2cc(Oc3cc(C4=CCNCC4)ncn3)ccc21]

TFA (0.5 ml) is added to a solution of 4-{6-[1-(3-Trifluoromethyl-phenylcarbamoyl)-1H-indol-5-yloxy]-pyrimidin-4-yl}-3,6-dihydro-2H-pyridine-1-carboxylic acid tert-butyl ester (160 mg, 0.276 mmol) in DCM (5 mL). The solution is stirred overnight and then the solvent is removed. The residue is dissolved DCM and washed with saturated aqueous NaHCO₃. The product is extracted further with EtOAc (2×25 mL) and the combined organic layers are washed brine, dried over anhydrous Na₂SO₄, filtered, and concentrated. The residue is then purified by FCC (0-10% 2 M NH₃ in MeOH/DCM) to provide the title compound. MS (ESI) m/z 480.1 (M+1); ¹H NMR (400 MHz, MeOD) δ ppm 8.60 (s, 1 H), 8.36 (d, J=8.84 Hz, 1 H), 8.06 (s, 1 H), 7.95 (d, J=3.79 Hz, 1 H), 7.91 (s, 1 H), 7.58 (t, J=8.21 Hz, 1 H), 7.45 (s, 1 H), 7.42 (d, J=2.27 Hz, 1 H), 7.12 (dd, J=8.97, 2.40 Hz, 1 H), 7.00 (dt, J=3.35, 1.74 Hz, 1 H), 6.98 (s, 1 H), 6.75 (d, J=3.79 Hz, 1 H), 3.70-3.75 (m, 2 H), 3.07 (t, J=5.81 Hz, 2 H), 1.87 (ddd, J=6.44, 3.41, 3.28 Hz, 2 H).

The following compounds are prepared with similar method.

84-B. 5-[6-(1,2,3,4-Tetrahydro-pyridin-4-yl)-pyrimidin-4-yloxy]-indole-1-carboxylic acid (3-trifluoromethyl-phenyl)-amide

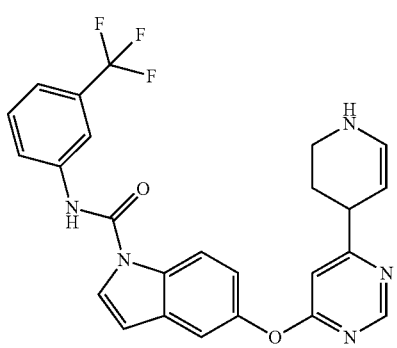 [SMILES: O=C(Nc1cccc(C(F)(F)F)c1)n1ccc2cc(Oc3cc(C4C=CNCC4)ncn3)ccc21]

MS (ESI) m/z 480.1 (M+1); ¹H NMR (400 MHz, MeOD) δ ppm 8.59 (d, J=1.01 Hz, 1 H), 8.63 (d, J=1.01 Hz, 1 H), 8.35 (d, J=8.34 Hz, 1 H), 8.06 (s, 1 H), 7.94 (d, J=2.78 Hz, 1 H), 7.54-7.60 (m, 2 H), 7.41 (d, J=1.77 Hz, 2 H), 7.44 (d, J=7.83 Hz, 1 H), 7.11 (dd, J=9.09, 1.52 Hz, 1 H), 6.84 (s, 1 H), 6.74 (d, J=3.79 Hz, 1 H), 4.33-4.35 (m, 1 H), 3.03-3.21 (m, 2 H), 2.76 (dt, J=11.37, 2.15 Hz, 2 H).

84-C. 5-(6-Piperidin-4-yl-pyrimidin-4-yloxy)-indole-1-carboxylic acid (3-trifluoromethyl-phenyl)-amide

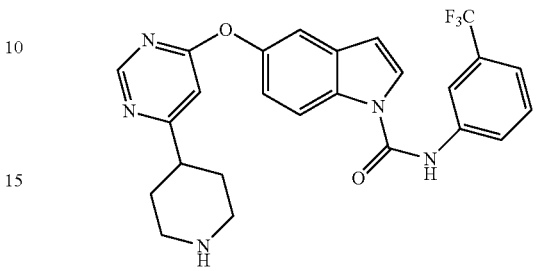

MS (ESI) m/z 482.1 (M+1); ¹H NMR (400 MHz, MeOD) δ ppm 8.60 (s, 1 H), 8.35 (d, J=8.84 Hz, 1H), 8.06 (s, 1 H), 7.94 (d, J=3.79 Hz, 1 H), 7.89 (d, J=8.08 Hz, 1 H), 7.57 (t, J=8.08 Hz, 1 H), 7.40 (d, J=2.27 Hz, 1 H), 7.44 (d, J=7.83 Hz, 1 H), 7.10 (dd, J=8.97, 2.40 Hz, 1 H), 6.85 (s, 1 H), 6.74 (d, J=3.79 Hz, 1 H), 3.13 (d, J=12.63 Hz, 2 H), 2.70 (td, J=12.44, 2.40 Hz, 2 H), 2.66-2.83 (m, 1H), 1.89 (d, J=12.13 Hz, 2 H), 1.69 (dd, J=12.63, 3.79 Hz, 2 H).

EXAMPLE 85

(±)-5-{6-[Hydroxy-(1-methyl-1H-imidazol-2-yl)-methyl]-pyrimidin-4-yloxy}indole-1-carboxylic acid (3-trifluoromethyl-phenyl)-amide

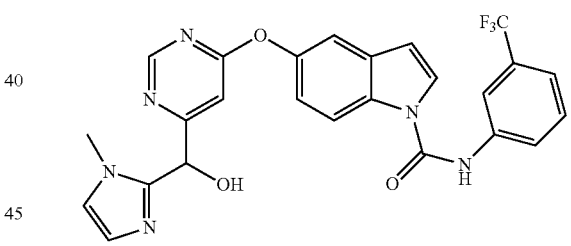

To a solution of 1-methyl-1H-imidazole (77 mg, 0.94 mmol) in 5 mL THF at −78° C. is added n-butyllithium (1.6 M in hexane, 0.44 mL). The solution is stirred at −78° C. for 1 h. Then, a solution of 5-(6-formyl-pyrimidin-4-yloxy)-indole-1-carboxylic acid (3-trifluoromethyl-phenyl)-amide (200 mg, 0.47 mmol) in THF (5 mL) is added. The reaction is allowed to warm up to rt and stir overnight. At that time the reaction is quenched with water and then extracted with EtOAc (3×25 mL). The combined organic layers are washed with brine, dried over anhydrous Na₂SO₄, filtered, and concentrated. The residue is then purified with semi-prep HPLC (C18; 30-100% I/H₂O with 0.1% TFA) to give the title compound. The fractions are pooled and the pH is adjusted to 9 with sodium bicarbonate. The product is extracted with EtOAc. The organic layer is washed with brine, dried over anhydrous sodium sulfate, and filtered. The filtrate is concentrated to give the title compound. MS (ESI) m/z 509.0 (M+1); ¹H NMR (400 MHz, MeOD) δ ppm 8.59 (d, J=1.01 Hz, 1 H), 8.36 (d, J=9.09 Hz, 1 H), 8.06 (s, 1 H), 7.94 (d, J=3.79 Hz, 1

H), 7.90 (d, J=7.83 Hz, 1 H), 7.57 (m, 2 H), 7.46 (d, J=2.02 Hz, 1 H), 7.29 (s, 1 H), 7.16 (dd, J=8.97, 2.40 Hz, 1 H), 7.05 (d, J=1.26 Hz, 1 H), 6.85 (d, J=1.26 Hz, 1 H), 6.75 (d, J=3.54 Hz, 1 H), 5.91 (s, 1 H), 3.72 (s, 3 H).

EXAMPLE 86

86-A. N-(4-fluoro-3-(trifluoromethyl)phenyl)-5-(6-(methylsulfonylmethyl)pyrimidin-4-yloxy)-1H-indole-1-carboxamide

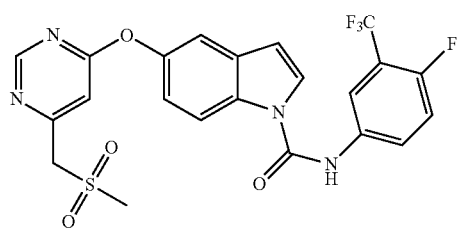 [SMILES: CS(=O)(=O)Cc1cc(Oc2ccc3c(ccn3C(=O)Nc3ccc(F)c(C(F)(F)F)c3)c2)ncn1]

To a solution of (6-(1-(4-fluoro-3-(trifluoromethyl)phenylcarbamoyl)-1H-indol-5-yloxy)pyrimidin-4-yl)methyl methanesulfonate (0.22 g, 0.42 mmol) in 5 mL of THF and 3 mL of DMF, NaI (0.095 g, 0.63 mmol) is added followed by DIEA (0.11 mL, 0.63 mmol) and sodium methanesulfinate (0.129 g, 1.26 mmol). The mixture is stirred at rt for 2 h and then diluted with EtOAc, washed with saturated NaHCO$_3$ (×2), brine and the organic layer is dried over Na$_2$SO$_4$. After concentration the residue is purified by FCC (20-90% EtOAc/heptane) and then semi-prep HPLC (22-65% I/H$_2$O with 0.1% NH$_4$OH) to give the title compound. MS (ESI) m/z 509.0 (M+1); $^1$H NMR (400 MHz, DMSO-d$_6$) δ ppm 10.38 (br. S., 1 H), 8.78 (d, J=1.0 Hz, 1 H), 8.30 (d, J=8.8 Hz, 1 H), 8.06-8.17 (m, 2 H), 7.97-8.05 (m, 1 H), 7.58 (t, J=9.7 Hz, 1 H), 7.52-7.54 (m, 1 H), 7.21 (d, J=1.0 Hz, 1 H), 7.18 (dd, J=9.0, 2.4 Hz, 1 H), 6.82 (dd, J=3.7, 0.6 Hz, 1 H), 4.70 (s, 2 H), 3.11 (s, 3 H).

The following compounds are prepared with similar method.

86-B. 4-Fluoro-5-(6-methanesulfonylmethyl-pyrimidin-4-yloxy)-indole-1-carboxylic acid (5-tert-butyl-isoxazol-3-yl)-amide

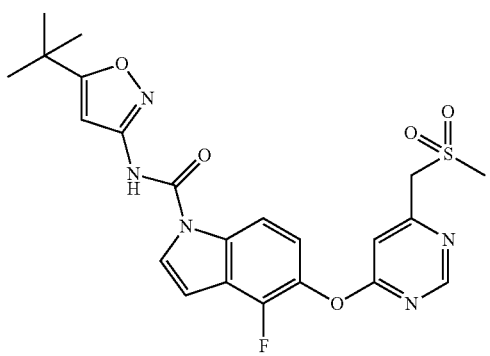 [SMILES: CC(C)(C)c1cc(NC(=O)n2ccc3c(F)c(Oc4cc(CS(C)(=O)=O)ncn4)ccc32)no1]

MS (ESI) m/z 488.1 (M+1); $^1$H NMR (400 MHz, MeOD) δ ppm 8.78 (d, J=1.01 Hz, 1 H), 8.21 (d, J=4.04 Hz, 1 H), 8.13 (d, J=9.09 Hz, 1 H), 7.38 (d, J=1.01 Hz, 1 H), 7.34 (s, 1 H), 6.91 (d, J=3.79 Hz, 1 H), 6.68 (s, 1 H), 4.74 (s, 2 H), 3.14 (s, 3 H), 1.35 (s, 9 H).

EXAMPLE 87

87-A. [6-(4-Fluoro-2-methyl-1H-indol-5-yloxy)-pyrimidin-4-yl]-methanol

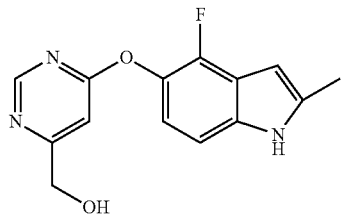 [SMILES: Cc1cc2c(F)c(Oc3cc(CO)ncn3)ccc2[nH]1]

In a 20 mL microwave vial is placed 5-(6-benzyloxymethyl-pyrimidin-4-yloxy)-4-fluoro-2-methyl-1H-indole (2.59 g, 7.13 mmol) in methane sulfonic acid (15 ml) and the solution is heated in a microwave reactor at 100° C. for 5 min. The reaction is then diluted with 250 mL EtOAc and saturated aqueous NaHCO$_3$. The aqueous layer is washed with EtOAc (4×100 mL). The organic phases are combined, washed with (2×150 mL) water, followed by (1×60 mL brine), dried over Na$_2$SO$_4$, and concentrated in vacuo. The residue is purified via FCC (0-20% MeOH/DCM) to give the title compound. MS (ESI) m/z 274.1 (M+1).

87-B. 4-Fluoro-5-(6-methanesulfonylmethyl-pyrimidin-4-yloxy)-2-methyl-1H-indole

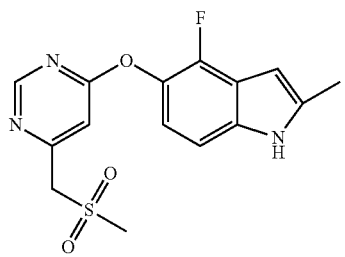 [SMILES: Cc1cc2c(F)c(Oc3cc(CS(C)(=O)=O)ncn3)ccc2[nH]1]

[6-(4-Fluoro-2-methyl-1H-indol-5-yloxy)-pyrimidin-4-yl]-methanol (1 g, 3.66 mmol) is placed in DCM (40 mL). Methanesulfonyl chloride (0.34 mL, 4.39 mmol) and DIPEA (0.89 mL, 5.12 mmol) are added and then after 15 min the reaction is diluted with water and extracted with DCM. The organic phase is washed with brine, dried over Na$_2$SO$_4$, and concentrated in vacuo. The resulting methanesulfonic acid 6-(4-fluoro-2-methyl-1H-indol-5-yloxy)-pyrimidin-4-ylmethyl ester is dissolved in DMF (10 mL) and sodium methanesulfinate (1.12 g, 11.0 mmol) is added and the reaction is stirred at rt for 18 h. The reaction is partitioned between H$_2$O and ethyl acetate. The organic phase is washed with brine, dried over Na$_2$SO$_4$, and concentrated in vacuo. The residue is purified via FCC (0-10% MeOH/DCM) to give the title compound. MS (ESI) m/z 336.0 (M+1)

87-C. 4-Fluoro-5-(6-methanesulfonylmethyl-pyrimidin-4-yloxy)-2-methyl-indole-1-carboxylic acid (3-trifluoromethyl-phenyl)-amide

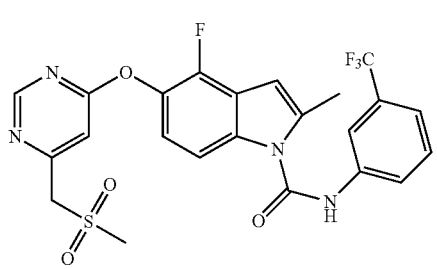 [SMILES: Cc1cc2c(F)c(Oc3cc(CS(C)(=O)=O)ncn3)ccc2n1C(=O)Nc1cccc(C(F)(F)F)c1]

4-Fluoro-5-(6-methanesulfonylmethyl-pyrimidin-4-yloxy)-2-methyl-1H-indole (250 mg, 0.745 mmol) in THF (10 mL) is cooled to −78° C. and a 1 M solution of LiHMDS in THF (1.86 mL, 1.86 mmol) is added. After 12 min 1-isocyanato-3-(trifluoromethyl)-benzene (0.12 mL, 0.895 mmol) is added and the reaction is allowed to stir at −78° C. After 1 h the reaction is quenched with saturated aqueous NH$_4$Cl and then extracted with (3×100 mL) EtOAc. The organic phases are combined and washed with brine, dried over Na$_2$SO$_4$, and concentrated in vacuo. The residue is purified FCC (0-3% MeOH/DCM) to provide 4-fluoro-5-(6-methanesulfonylmethyl-pyrimidin-4-yloxy)-2-methyl-indole-1-carboxylic acid (3-trifluoromethyl-phenyl)-amide. MS (ESI) m/z 523.1 (M+1); $^1$H NMR (400 MHz, DMSO-d$_6$) δ ppm 10.99 (s, 1 H), 8.77 (d, J=1.01 Hz, 1 H), 8.12 (s, 1 H), 7.91 (s, 1 H), 7.66 (s, 1 H), 7.53 (d, J=9.35 Hz, 2 H), 7.36 (d, J=1.01 Hz, 1 H), 7.20 (d, J=7.33 Hz, 1 H), 6.64 (s, 1 H), 4.73 (s, 2 H), 3.13 (s, 3 H), 2.59 (s, 3 H).

The following compounds are prepared with similar method.

87-D. 5-(6-Methanesulfonylmethyl-pyrimidin-4-yloxy)-indole-1-carboxylic acid (2-fluoro-3-trifluoromethyl-phenyl)-amide

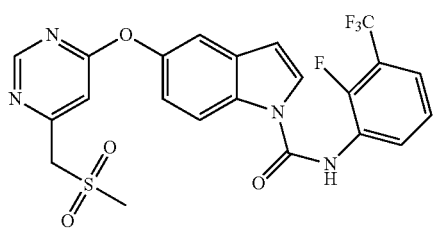 [SMILES: CS(=O)(=O)Cc1cc(Oc2ccc3c(ccn3C(=O)Nc3cccc(C(F)(F)F)c3F)c2)ncn1]

MS (ESI) m/z 509.0 (M+1); $^1$H NMR (400 MHz, DMSO-d$_6$) δ ppm 8.78 (d, J=1.01 Hz, 1 H), 8.27 (d, J=8.84 Hz, 1 H), 8.11 (d, J=3.54 Hz, 1 H), 7.94 (s, 1 H), 7.71 (s, 1 H), 7.47-7.54 (m, 2 H), 7.16-7.21 (m, 2 H), 6.83 (d, J=3.79 Hz, 1 H), 4.69 (s, 2 H), 3.11 (s, 3 H).

87-E. 4-Fluoro-5-(6-methanesulfonylmethyl-pyrimidin-4-yloxy)-indole-1-carboxylic acid (3-trifluoromethyl-phenyl)-amide

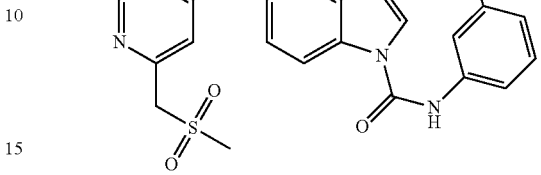

MS (ESI) m/z 509.0 (M+1); $^1$H NMR (400 MHz, DMSO-d$_6$) δ ppm 10.50 (br. S., 1 H), 8.79 (s, 1 H), 8.09-8.24 (m, 3 H), 7.97 (d, J=8.08 Hz, 1 H), 7.66 (t, J=7.96 Hz, 1 H), 7.51 (d, J=7.83 Hz, 1 H), 7.38 (s, 1 H), 7.33 (t, J=8.34 Hz, 1 H), 6.94 (d, J=3.79 Hz, 1 H), 4.74 (s, 2 H), 3.14 (s, 3 H).

EXAMPLE 88

5-(6-Hydroxymethyl-pyrimidin-4-yloxy)-indole-1-carboxylic acid (5-methyl-pyridin-3-yl)-amide

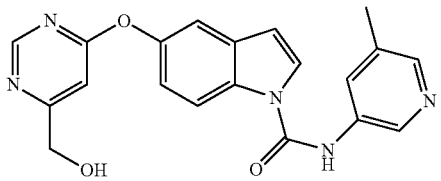 [SMILES: Cc1cncc(NC(=O)n2ccc3cc(Oc4cc(CO)ncn4)ccc32)c1]

Urea prepared by analogy to Example 51-A by coupling Example 14-A with 3-amino-5-methylpyridine followed by removal of the benzyl protecting group as described in Example 16-A. MS (ESI) m/z 376.0 (M+1).

EXAMPLE 89

1-((6-(1-(4-fluoro-3-(trifluoromethyl)phenylcarbamoyl)-1H-indol-5-yloxy)pyrimidin-4-yl)methyl)piperidine-4-carboxylic acid

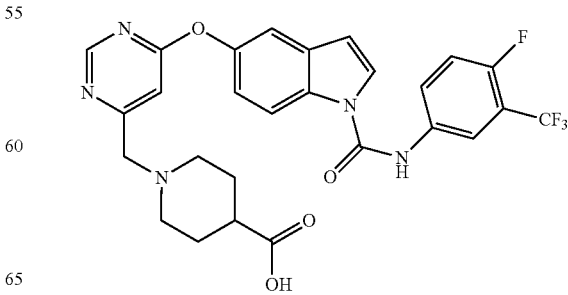

To a solution of methyl 1-((6-(1-(4-fluoro-3-(trifluoromethyl)phenylcarbamoyl)-1H-indol-5-yloxy)pyrimidin-4-yl)methyl)piperidine-4-carboxylate (0.13 g, 0.228 mmol) in 40 mL of THF/H₂O (3:1), 2 M aq LiOH solution (0.23 mL) is added. The mixture is stirred at rt for 3.5 h before being concentrated and purified by semi-prep HPLC (12-48% CAN/H₂O with 0.1% TFA) to give the title compound. MS (ESI) m/z 558.1 (M+1); ¹H NMR (400 MHz, DMSO-d₅) δ ppm 10.43 (s, 1 H), 9.93-10.12 (m, 1 H), 8.88 (s, 1 H), 8.32 (d, J=9.1 Hz, 1 H), 8.08-8.17 (m, 2 H), 7.96-8.06 (m, 1 H), 7.58 (t, J=9.9 Hz, 1 H), 7.52 (d, J=2.5 Hz, 1 H), 7.25 (br. S., 1 H), 7.17 (dd, J=9.0, 2.4 Hz, 1 H), 6.83 (d, J=3.5 Hz, 1 H), 4.39-4.60 (m, 2 H), 3.45-3.57 (m, 2 H), 2.98-3.17 (m, 2 H), 1.95-2.14 (m, 3 H), 1.73-1.91 (m, 2 H)

EXAMPLE 90

90-A. (±)-5-(6-(benzyloxymethyl)pyrimidin-4-yloxy)-N-(4-methoxy-3-(trifluoromethyl)phenyl)-1H-indole-1-carboxamide

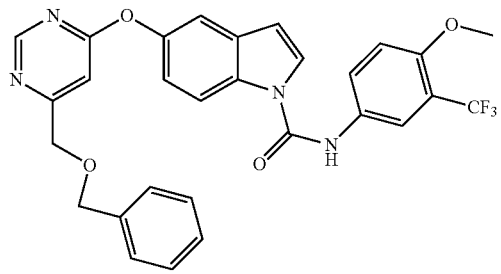 [SMILES: COc1ccc(NC(=O)n2ccc3cc(Oc4cc(COCc5ccccc5)ncn4)ccc32)cc1C(F)(F)F]

To a solution of 5-(6-(benzyloxymethyl)pyrimidin-4-yloxy)-1H-indole (0.8 g, 2.41 mmol) in 35 mL of DCE, CDI (1.17 g, 7.24 mmol) is added followed by TEA (1 mL, 7.24 mmol). Mixture is stirred at rt overnight and then 4-methoxy-3-(trifluoromethyl)aniline (1.38 g, 7.24 mmol) is added followed by stirring for 4 days. The reaction is diluted with DCM, washed with saturated aqueous NaHCO₃ (×2), brine, and the organic layer is dried over Na₂SO₄. After concentration, the residue is purified by FCC (5-60% EtOAc/heptane) to give the title compound. MS (ESI) m/z 549.1 (M+1).

90-B. 5-(6-((2-Hydroxyethylamino)methyl)pyrimidin-4-yloxy)-N-(4-methoxy-3-(trifluoromethyl)phenyl)-1H-indole-1-carboxamide

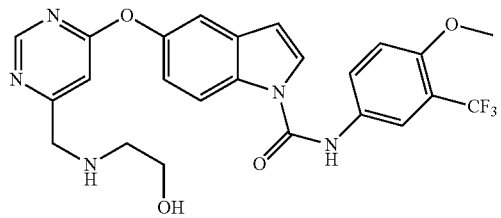 [SMILES: COc1ccc(NC(=O)n2ccc3cc(Oc4cc(CNCCO)ncn4)ccc32)cc1C(F)(F)F]

Prepared in similar manner to that described Example 19. MS (ESI) m/z 502.1 (M+1); ¹H NMR (400 MHz, DMSO-d₆) δ ppm 10.15 (br. S., 1 H), 8.65 (d, J=1.0 Hz, 1 H), 8.28 (d, J=9.1 Hz, 1 H), 8.10 (d, J=3.8 Hz, 1 H), 7.95 (d, J=2.8 Hz, 1 H), 7.91 (dd, J=8.8, 2.5 Hz, 1 H), 7.48 (d, J=2.3 Hz, 1 H), 7.33 (d, J=9.1 Hz, 1 H), 7.13 (dd, J=8.8, 2.3 Hz, 1 H), 7.09 (s, 1 H), 6.79 (d, J=3.8 Hz, 1 H), 3.90 (s, 3 H), 3.78 (s, 2 H), 3.45 (t, J=5.7 Hz, 2 H), 2.59 (t, J=5.8 Hz, 2H).

EXAMPLE 91

91-A. 5-[6-(Cyano-trimethylsilanyloxy-methyl)-pyrimidin-4-yloxy]-indole-1-carboxylic acid (3-trifluoromethyl-phenyl)-amide

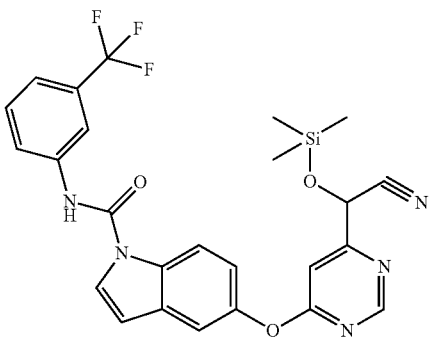 [SMILES: C[Si](C)(C)OC(C#N)c1cc(Oc2ccc3c(ccn3C(=O)Nc3cccc(C(F)(F)F)c3)c2)ncn1]

To a solution of 5-(6-formyl-pyrimidin-4-yloxy)-indole-1-carboxylic acid (3-trifluoromethyl-phenyl)-amide (200 mg, 0.471 mmol) and methyl-triphenyl-phosphonium iodide (19 mg, 0.05 mmol) in DCM (5 mL), TMSCN (0.063 mL, 0.471 mmol) is added via syringe. The mixture is stirred for 3 h, then it is diluted with DCM (20 mL), washed with water, brine, and the organic layer is dried over Na₂SO₄, filtered, and condensed to obtain the title compound that is used in the next step without further purification. MS (ESI) m/z 525.9 (M+1).

91-B. (±)-5-[6-(2-Amino-1-hydroxy-ethyl)-pyrimidin-4-yloxy]-indole-1-carboxylic acid (3-trifluoromethyl-phenyl)-amide

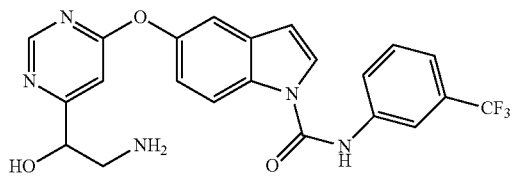 [SMILES: NCC(O)c1cc(Oc2ccc3c(ccn3C(=O)Nc3cccc(C(F)(F)F)c3)c2)ncn1]

Ranney-Ni (20 mg) is washed with MeOH (3×5 mL) before a solution of (±)-5-[6-(cyano-trimethylsilanyloxy-methyl)-pyrimidin-4-yloxy]-indole-1-carboxylic acid (3-trifluoromethyl-phenyl)-amide (100 mg, 0.19 mmol) in MeOH (5 mL) and THF (3 mL) is added. The mixture is stirred under H₂ atmosphere (ballon) overnight. The mixture is filtered through Celite® and the filtrate is concentrated. The residue is then separated by FCC (0-10% MeOH/EtOAc) to provide the title compound. MS (ESI) m/z 458.1 (M+1); ¹H NMR (400 MHz, DMSO-d₆) δ ppm 8.60-8.70 (m, 1 H), 8.36 (d, J=8.59 Hz, 1 H), 8.06 (br. S., 1 H), 7.90 (d, J=7.58 Hz, 1 H), 7.95 (d, J=3.28 Hz, 2 H), 7.73 (d, J=4.55 Hz, 1 H), 7.57 (t, J=7.83 Hz, 1 H), 7.37-7.47 (m, 3 H), 7.12 (d, J=8.59 Hz, 2 H), 7.04 (s, 1 H), 6.75 (br. S., 1 H), 4.89 (d, J=5.05 Hz, 1 H), 3.67 (dd, J=12.25, 7.71 Hz, 2 H).

EXAMPLE 92

92-A. 5-[6-((S)-2-Carbamoyl-pyrrolidin-1-ylmethyl)-pyrimidin-4-yloxy]-indole-1-carboxylic acid (3-trifluoromethyl-phenyl)-amide

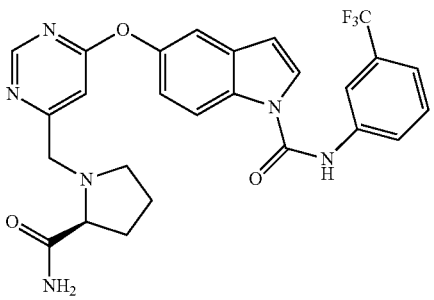 [SMILES: NC(=O)[C@@H]1CCCN1Cc1cc(Oc2ccc3c(ccn3C(=O)Nc3cccc(C(F)(F)F)c3)c2)ncn1]

To a solution of 5-(6-formyl-pyrimidin-4-yloxy)-indole-1-carboxylic acid (3-trifluoromethyl-phenyl)-amide (60 mg, 0.141 mmol) in MeOH (5 mL), AcOH (0.1 mL) is added followed by (S)-pyrrolidine-2-carboxylic acid amide (19 mg, 0.169 mmol). The mixture is stirred for 10 min before NaBH$_3$(CN) is added. The resulting mixture is stirred overnight. At that point the mixture is quenched with sat aqueous sodium bicarbonate. The product is extracted with EtOAc (3×). The combined organic layers are washed with water, and brine, and then dried over Na$_2$SO$_4$, filtered, and condensed. The residue is then separated by FCC (0-10%, 2M ammonia in MeOH/DCM) to provide the title compound. MS (ESI) m/z 524.9 (M+1); $^1$H NMR (400 MHz, MeOD) δ ppm 8.63 (s, 1 H), 8.34 (d, J=9.09 Hz, 1 H), 8.06 (s, 1 H), 7.94 (d, J=3.79 Hz, 1 H), 7.89 (d, J=7.83 Hz, 1 H), 7.57 (t, J=8.08 Hz, 1 H), 7.41 (d, J=2.53 Hz, 1 H), 7.44 (d, J=8.59 Hz, 1 H), 7.07-7.14 (m, 1 H), 7.12 (d, J=2.27 Hz, 1 H), 6.74 (d, J=3.54 Hz, 1 H), 3.94 (d, J=14.65 Hz, 1 H), 3.66 (d, J=14.65 Hz, 1 H), 3.23 (dd, J=9.73, 5.18 Hz, 1 H), 3.12 (dd, J=8.72, 4.67 Hz, 1 H), 2.46 (t, J=8.21 Hz, 1 H), 2.23 (td, J=9.09, 4.29 Hz, 1 H), 1.79-1.91 (m, 3 H).

The following compounds are prepared with similar method.

92-B. 5-[6-(I-2-Carbamoyl-pyrrolidin-1-ylmethyl)-pyrimidin-4-yloxy]-indole-1-carboxylic acid (3-trifluoromethyl-phenyl)-amide

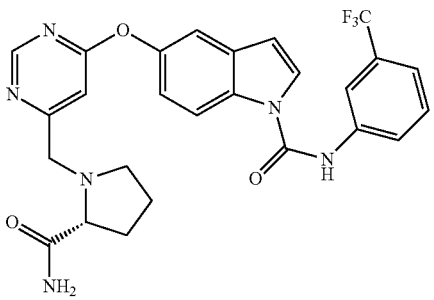 [SMILES: NC(=O)[C@H]1CCCN1Cc1cc(Oc2ccc3c(ccn3C(=O)Nc3cccc(C(F)(F)F)c3)c2)ncn1]

MS (ESI) m/z 524.9 (M+1); $^1$H NMR (400 MHz, MeOD) δ ppm 8.63 (s, 1 H), 8.34 (d, J=9.09 Hz, 1 H), 8.05 (s, 1 H), 7.93 (d, J=3.79 Hz, 1 H), 7.89 (d, J=8.08 Hz, 1 H), 7.56 (t, J=7.96 Hz, 1 H), 7.40 (d, J=2.27 Hz, 1 H), 7.43 (d, J=7.83 Hz, 1 H), 7.06-7.13 (m, 1 H), 7.11 (d, J=2.53 Hz, 1 H), 6.73 (d, J=3.54 Hz, 1 H), 3.93 (d, J=14.65 Hz, 1 H), 3.65 (d, J=14.65 Hz, 1 H), 3.22 (dd, J=9.73, 5.18 Hz, 1 H), 3.10 (d, J=4.55 Hz, 1 H), 2.44 (t, J=8.08 Hz, 1 H), 2.21 (dd, J=7.83, 2.78 Hz, 1 H), 2.15-2.36 (m, 1 H), 1.78-1.92 (m, 3 H).

92-C. 5-[6-((S)-2-Ethylcarbamoyl-pyrrolidin-1-ylmethyl)-pyrimidin-4-yloxy]-indole-1-carboxylic acid (3-trifluoromethyl-phenyl)-amide

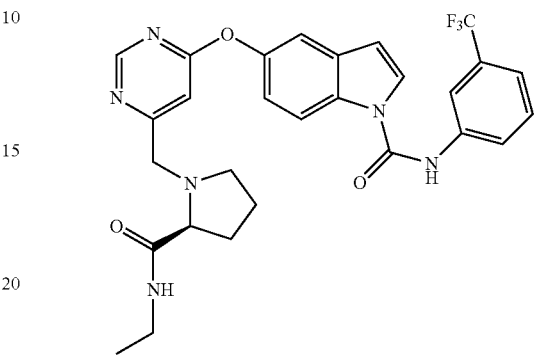

MS (ESI) m/z 552.9 (M+1); $^1$H NMR (400 MHz, MeOD) δ ppm 8.66 (s, 1 H), 8.36 (d, J=8.84 Hz, 1 H), 8.06 (s, 1 H), 7.95 (d, J=3.79 Hz, 1 H), 7.90 (d, J=6.57 Hz, 1 H), 7.57 (t, J=7.96 Hz, 1 H), 7.42 (d, J=2.27 Hz, 2 H), 7.11 (dd, J=8.97, 2.40 Hz, 1 H), 7.07 (s, 1 H), 6.75 (d, J=3.79 Hz, 1 H), 3.88 (d, J=14.40 Hz, 1 H), 3.69 (d, J=14.40 Hz, 1 H), 3.18 (qd, J=7.28, 1.14 Hz, 2 H), 3.09-3.27 (m, 2 H), 2.44-2.52 (m, 1 H), 2.21 (td, J=9.09, 4.04 Hz, 1 H), 1.74-1.87 (m, 3 H), 1.07 (t, J=7.33 Hz, 3 H).

EXAMPLE 93

93-A. (±)-3-({6-[1-(3-Trifluoromethyl-phenylcarbamoyl)-1H-indol-5-yloxy]-pyrimidin-4-ylmethyl}-amino)-pyrrolidine-1-carboxylic acid tert-butyl ester

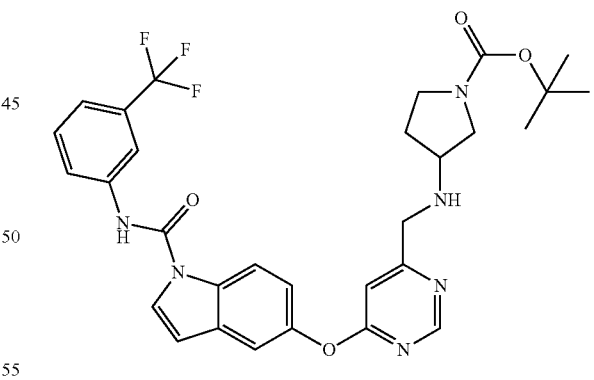

To the solution of methanesulfonic acid (±)-6-[1-(3-trifluoromethyl-phenylcarbamoyl)-1H-indol-5-yloxy]-pyrimidin-4-ylmethyl ester (80 mg, 0.158 mmol) in THF (5 mL), 3-amino-pyrrolidine-1-carboxylic acid tert-butyl ester (88 mg, 0.474 mmol) and diisopropylethylamine (61 mg, 0.474 mmol) are added. The resulting solution is stirred at 60° C. overnight. After cooling to rt, the reaction mixture is diluted with EtOAc and washed with water and then brine. The organic layer is dried with anhydrous Na$_2$SO$_4$, filtered, and condensed. The residue is purified by FCC (0-10% MeOH/DCM) to provide the title compound. MS (ESI) m/z 597.2 (M+1).

The following compounds are prepared with similar method.

| | Structure/Chemical Name | ¹H NMR (400 MHz) | MS (ESI) m/z (M + 1) |
|---|---|---|---|
| 93-B | 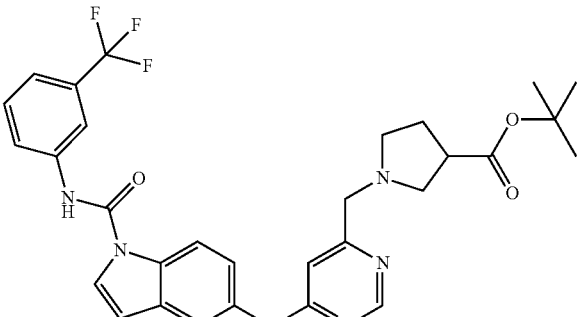<br>(±)-1-{6-[1-(3-Trifluoromethyl-phenylcarbamoyl)-1H-indol-5-yloxy]-pyrimidin-4-ylmethyl}-pyrrolidine-3-carboxylic acid tert-butyl ester | (MeOD) δ ppm 8.59 (s, 1H), 8.39 (br. S., 1H), 8.14 (d, J = 8.84 Hz, 1H), 7.72 (s, 1H), 7.67 (d, J = 8.08 Hz, 1H), 7.52 (d, J = 3.79 Hz, 1H), 7.28-7.39 (m, 1 H), 7.23 (br. S., 1H), 6.95-7.01 (m, 2 H), 6.47 (d, J = 2.78 Hz, 1H), 3.63 (d, J = 8.34 Hz, 2H), 2.79-2.91 (m, 3H), 2.65 (d, J = 6.06 Hz, 1H), 2.53 (q, J = 7.75 Hz, 1H), 1.99 (t, J = 6.95 Hz, 2H), 1.35 (s, 9H). | 582.2 |
| 93-C | 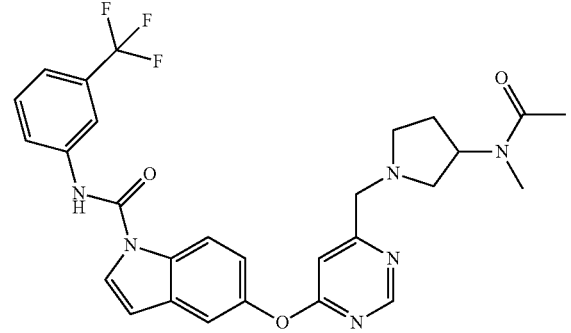<br>(±)-5-{6-[3-(Acetyl-methyl-amino)-pyrrolidin-1-ylmethyl]-pyrimidin-4-yloxy}-indole-1-carboxylic acid (3-trifluoromethyl-phenyl)-amide | (MeOD) δ ppm 8.63 (s, 1H) 8.34 (d, J = 9.09 Hz, 1H) 8.06 (s, 1H) 7.94 (d, J = 3.79 Hz, 1H) 7.89 (d, J = 7.83 Hz, 1H) 7.57 (t, J = 8.08 Hz, 1H) 7.44 (d, J = 8.59 Hz, 1H) 7.07-7.14 (m, 3H) 6.74 (d, J = 3.54 Hz, 1H) 4.85 (s, 2H) 3.94 (m, , 1H) 3.66 (m, 1H) 3.23 (m, 1H) 3.12 (m, 1H) 2.45 (m, 2H) 2.23 (m, 1H) 2.02 (s, 3H) 1.79-1.91 (m, 4H) | 553.2 |
| 93-D | 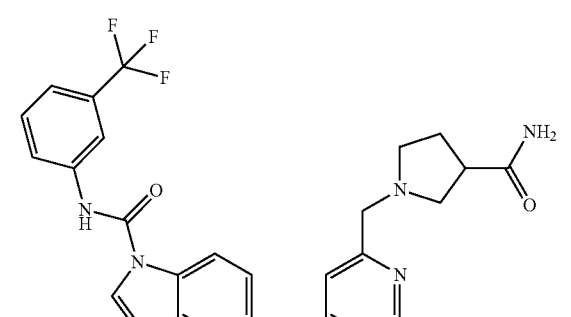<br>(±)-5-[6-(3-Carbamoyl-pyrrolidin-1-ylmethyl)-pyrimidin-4-yloxy]-indole-1-carboxylic acid (3-trifluoromethyl-phenyl)-amide | (MeOD) δ ppm 8.64 (d, J = 1.01 Hz, 1 H) 8.35 (d, J = 9.09 Hz, 1H) 8.06 (s, 1 H) 7.95 (d, J = 3.79 Hz, 1H) 7.90 (d, J = 7.83 Hz, 1H) 7.57 (t, J = 7.96 Hz, 1H) 7.42 (d, J = 2.02 Hz, 1H) 7.44 (d, J = 7.83 Hz, 1H) 7.12 (dd, J = 8.97, 2.40 Hz, 1H) 7.07 (d, J = 1.01 Hz, 1H) 6.75 (d, 7 = 3.79 Hz, 1H) 3.77 (d, J = 4.55 Hz, 2H) 2.98 (m, 1H) 2.89 (m, 1H) 2.68-2.79 (m, 3H) 2.04 (m, 2H) | 524.9 |

| | Structure/Chemical Name | ¹H NMR (400 MHz) | MS (ESI) m/z (M + 1) |
|---|---|---|---|
| 93-E | 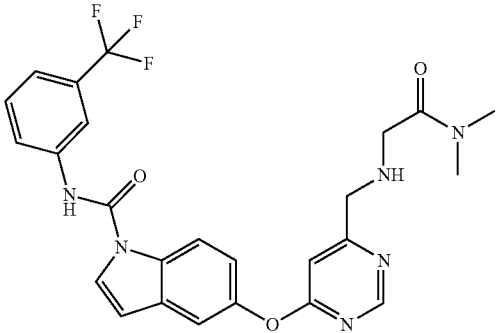<br>5-{6-[(Dimethylcarbamoylmethyl-amino)-methyl]-pyrimidin-4-yloxy}-indole-1-carboxylic acid (3-trifluoromethyl-phenyl)-amide | (MeOD) δ ppm 8.63 (d, J = 1.01 Hz, 1H) 8.35 (d, J = 9.09 Hz, 1H) 8.06 (s, 1H) 7.94 (d, J = 3.79 Hz, 1H) 7.90 (d, J = 8.08 Hz, 1H) 7.57 (t, J = 7.96 Hz 1H) 7.42 (d, J = 2.53 Hz, 1H) 7.44 (d, J = 7.83 Hz, 1H) 7.11 (dd, J = 8.97, 2.40 Hz, 1H) 7.04 (d, J = 1.01 Hz, 1H) 6.74 (d, J = 3.79 Hz, 1H) 3.86 (s, 2H) 3.51 (s, 2H) 2.95 (d, J = 15.41 Hz, 6H) | 512.9 |
| 93-F | 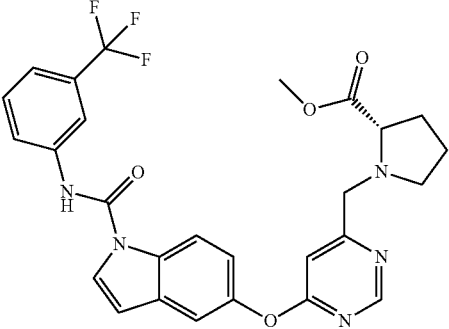<br>(S)-1-{6-[1-(3-Trifluoromethyl-phenylcarbamoyl)-1H-indol-5-yloxy]-pyrimidin-4-ylmethyl}-pyrrolidine-2-carboxylic acid methyl ester | (MeOD) δ ppm 8.60 (d, J = 1.01 Hz, 1H) 8.35 (d, J = 9.09 Hz, 1H) 8.06 (s, 1H) 7.88=7.95 (m, 1H) 7.94 (d, J = 3.54 Hz, 1H) 7.57 (t, J = 8.08 Hz, 1H) 7.42 (d, J = 2.53 Hz, 1H) 7.44 (d, J = 7.83 Hz, 1H) 7.11 (t, J = 4.42 Hz, 1H) 7.12 (d, J = 8.84 Hz, 1H) 6.74 (d, J = 3.79 Hz, 1H) 3.96 (s, 1H) 3.74 (d, J = 15.16 Hz, 1H) 3.63 (s, 3H) 3.44 (dd, J = 8.84, 5.56 Hz, 1H) 3.08 (ddd, J = 8.97, 6.69, 4.29 Hz, 1H) 2.54 (d, J = 8.84 Hz, 1H) 2.15 (dd, J = 11.37, 2.78 Hz, 1H) 1.81-1.96 (m, 3H). | 539.8 |
| 93-G | 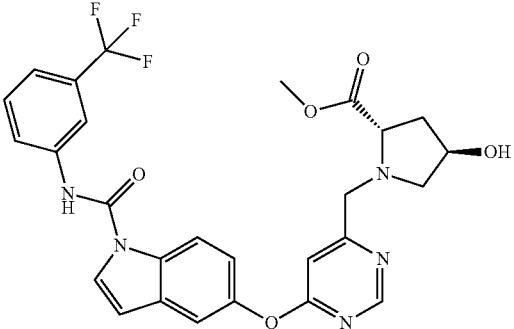<br>(2S,4R)-4-Hydroxy-1-{6-[1-(3-trifluoromethyl-phenylcarbamoyl)-1H-indol-5-yloxy]-pyrimidin-4-ylmethyl}-pyrrolidine-2-carboxylic acid methyl ester | (MeOD) δ ppm 8.60 (d, J = 1.01 Hz, 1H) 8.35 (d, J = 8.84 Hz, 1H) 8.05 (s, 1H) 7.93 (d, J = 3.79 Hz, 1H) 7.89 (d, J = 8.08 Hz, 1H) 7.56 (t, J = 8.08 Hz, 1H) 7.41 (d, J = 2.27 Hz, 1H) 7.43 (d, J = 7.83 Hz, 1H) 7.13 (s, 1H) 7.11 (dd, J = 8.97, 2.40 Hz, 1H) 6.73 (d, J = 3.79 Hz, 1H) 4.35 (dd, J = 8.97, 2.65 Hz, 1H) 4.02 (d, J = 15.66 Hz, 1H) 3.83 (s, 1H) 3.73 (t, J = 7.83 Hz, 1H) 3.64 (s, 3H) 3.34 (d, J = 4.80 Hz, 1H) 2.53 (dd, J = 10.11, 3.54 Hz, 1H) 2.04-2.18 (m, 2H). | 55 |

-continued

| Structure/Chemical Name | ¹H NMR (400 MHz) | MS (ESI) m/z (M + 1) |
|---|---|---|
| 93-H 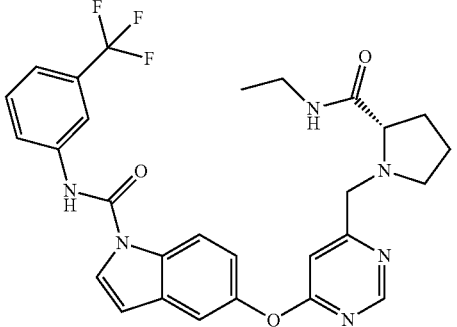 5-[6-((S)-2-Ethylcarbamoyl-pyrrolidin-1-ylmethyl)-pyrimidin-4-yloxy]-indole-1-carboxylic acid (3-trifluoromethyl-phenyl)-amide | (MeOD) δ ppm 8.66 (s, 1H) 8.36 (d, J = 8.84 Hz, 1H) 8.06 (s, 1H) 7.95 (d, J = 3.79 Hz, 1H) 7.90 (d, J = 6.57 Hz, 1H) 7.57 (t, J = 7.96 Hz, 1H) 7.42 (d, J = 2.27 Hz, 2H) 7.11 (dd, J = 8.97, 2.40 Hz, 1H) 7.07 (s, 1H) 6.75 (d, J = 3.79 Hz, 1H) 3.88 (d, J = 14.40 Hz, 1H) 3.69 (d, J = 14.40 Hz, 1H) 3.18 (qd, J = 7.28, 1.14 Hz, 2H) 3.09-3.27 (m, 2H) 2.44-2.52 (m, 1H) 2.21 (td, J = 9.09, 4.04 Hz, 1H) 1.74-1.87 (m, 3H) 1.07 (t, J = 7.33 Hz, 3H) | 552.9 |

EXAMPLE 94

94-A. (±)-5-[6-(Pyrrolidin-3-ylaminomethyl)-pyrimidin-4-yloxy]-indole-1-carboxylic acid (3-trifluoromethyl-phenyl)-amide

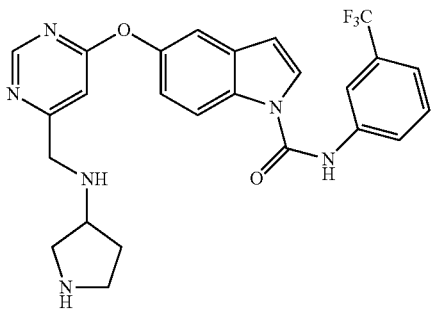 [SMILES: O=C(Nc1cccc(C(F)(F)F)c1)n1ccc2cc(Oc3cc(CNC4CCNC4)ncn3)ccc21]

(±)-3-({6-[1-(3-Trifluoromethyl-phenylcarbamoyl)-1H-indol-5-yloxy]-pyrimidin-4-ylmethyl}-amino)-pyrrolidine-1-carboxylic acid tert-butyl ester (20 mg, 3.30 mmol) is stirred in a solution of DCM (2 mL) and TFA (0.5 mL) overnight. After removal of solvents, the residue is quenched with saturated aqueous sodium bicarbonate. The mixture is then extracted with EtOAc (3×) and the combined organic layers are washed with water, brine, dried with Na₂SO₄, filtered, and condensed. The residue is purified by FCC (0-10% 2 M NH₃ in MeOH/DCM) to provide the title compound. MS (ESI) m/z 496.8 (M+1); ¹H NMR (400 MHz, MeOD) δ ppm 8.65 (s, 1 H), 8.36 (d, J=8.84 Hz, 1 H), 8.06 (s, 1H), 7.95 (d, J=3.54 Hz, 1 H), 7.88 (s, 1 H), 7.57 (t, J=7.83 Hz, 1 H), 7.44 (d, J=7.83 Hz, 1 H), 7.42 (d, J=2.27 Hz, 1 H), 7.03-7.13 (m, 2 H), 6.75 (d, J=3.79 Hz, 1 H), 3.80-3.85 (m, 2 H), 2.81-3.02 (m, 3 H), 2.52-2.75 (m, 2 H), 2.19-2.35 (m, 2 H).

The following compounds are prepared with similar method.

94-B. 5-{6-[(1S, 4S)-1-(2,5-Diaza-bicyclo[2.2.1]hept-2-yl)methyl]-pyrimidin-4-yloxy}-indole-1-carboxylic acid (3-trifluoromethyl-phenyl)-amide

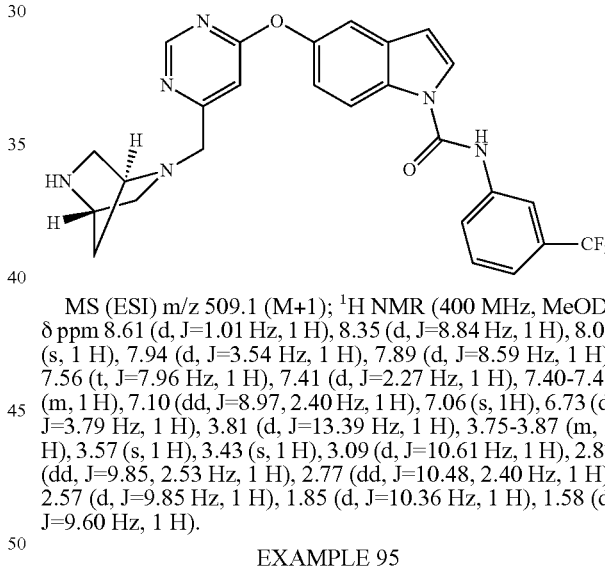

MS (ESI) m/z 509.1 (M+1); ¹H NMR (400 MHz, MeOD) δ ppm 8.61 (d, J=1.01 Hz, 1 H), 8.35 (d, J=8.84 Hz, 1 H), 8.06 (s, 1 H), 7.94 (d, J=3.54 Hz, 1 H), 7.89 (d, J=8.59 Hz, 1 H), 7.56 (t, J=7.96 Hz, 1 H), 7.41 (d, J=2.27 Hz, 1 H), 7.40-7.45 (m, 1 H), 7.10 (dd, J=8.97, 2.40 Hz, 1 H), 7.06 (s, 1H), 6.73 (d, J=3.79 Hz, 1 H), 3.81 (d, J=13.39 Hz, 1 H), 3.75-3.87 (m, 1 H), 3.57 (s, 1 H), 3.43 (s, 1 H), 3.09 (d, J=10.61 Hz, 1 H), 2.87 (dd, J=9.85, 2.53 Hz, 1 H), 2.77 (dd, J=10.48, 2.40 Hz, 1 H), 2.57 (d, J=9.85 Hz, 1 H), 1.85 (d, J=10.36 Hz, 1 H), 1.58 (d, J=9.60 Hz, 1 H).

EXAMPLE 95

(±)-5-[6-(3-Carbamoyl-pyrrolidin-1-ylmethyl)-pyrimidin-4-yloxy]-indole-1-carboxylic acid (3-trifluoromethyl-phenyl)-amide

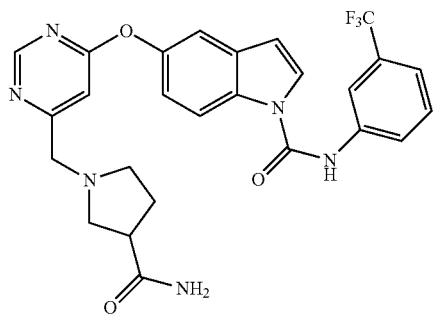 [SMILES: NC(=O)C1CCN(Cc2cc(Oc3ccc4c(ccn4C(=O)Nc4cccc(C(F)(F)F)c4)c3)ncn2)C1]

3-Carbamoyl-pyrrolidine-1-carboxylic acid tert-butyl ester (0.22 g, 1.03 mmol) is dissolved in DCM (5 mL). TFA (2 mL, 26.0 mmol) is added and the reaction is allowed to stir at rt overnight. The solvent is removed in vacuo and THF (5.0 mL) is added followed by methanesulfonic acid 6-[1-(3-trifluoromethyl-phenylcarbamoyl)-1H-indol-5-yloxy]-pyrimidin-4-ylmethyl ester (0.347 g, 0.685 mmol) and DIEA (0.60 mL, 3.42 mmol). The reaction is heated at 60° C. for 19 h. The solvent is removed in vacuo and the residue separated by FCC (0-15%, 10% NH₃MeOH/DCM) to provide (±)-5-[6-(3-carbamoyl-pyrrolidin-1-ylmethyl)-pyrimidin-4-yloxy]-indole-1-carboxylic acid (3-trifluoromethyl-phenyl)-amide. MS (ESI) m/z 524.9 (M+1); ¹H NMR (400 MHz, DMSO-d₆) δ ppm 10.41 (s, 1 H), 8.72 (s, 1 H), 8.30 (d, J=8.84 Hz, 1 H), 8.14 (d, J=3.79 Hz, 1 H), 8.10 (s, 1 H), 7.97 (s, 1 H), 7.65 (t, J=8.08 Hz, 1 H), 7.51 (d, J=2.53 Hz, 2 H), 7.16 (dd, J=8.84, 2.27 Hz, 1 H), 7.12 (s, 1 H), 6.81 (d, J=3.54 Hz, 1 H), 3.63 (br. S., 1 H), 3.14 (d, J=7.33 Hz, 1 H), 2.94 (br. S., 1 H), 1.99 (br. S., 1 H), 1.25 (d, J=6.06 Hz, 6 H).

EXAMPLE 96

96-A. 5-[7-(2-Hydroxy-ethyl)-5,6,7,8-tetrahydro-pyrido[3,4-d]pyrimidin-4-yloxy]-indole-1-carboxylic acid (3-trifluoromethyl-phenyl)-amide

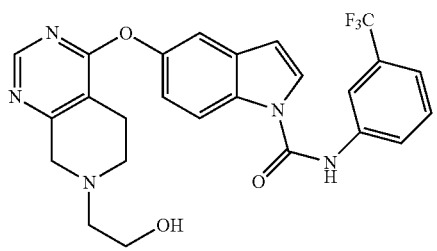 [SMILES: O=C(Nc1cccc(C(F)(F)F)c1)n1ccc2cc(Oc3ncnc4c3CCN(CCO)C4)ccc21]

A solution of 5-(5,6,7,8-tetrahydro-pyrido[3,4-d]pyrimidin-4-yloxy)-indole-1-carboxylic acid (3-trifluoromethyl-phenyl)-amide, Example 33-C, (150 mg, 0.33 mmol), 2-bromoethanol (28 uL, 0.40 mmol) and TEA (0.1 mL, 0.66 mL) in I (3 mL) is heated at 85° C. for 24 h. The reaction is then concentrated in vacuo and the residue separated via semi-prep HPLC (C18; 10-100% I/H₂O with 0.1% NH₄OH) to give the title compound. MS (ESI) m/z 498.1 (M+1); ¹H NMR (400 MHz, MeOD) δ ppm 8.38 (s, 1 H), 8.33 (d, J=8.8 Hz, 1 H), 8.06 (s, 1 H), 7.93 (d, J=3.8 Hz, 1 H), 7.90 (d, J=8.3 Hz, 1 H), 7.58 (t, J=8.1 Hz, 1 H), 7.44 (d, J=7.8 Hz, 1 H), 7.41 (d, J=2.3 Hz, 1 H), 7.11 (dd, J=9.0, 2.4 Hz, 1 H), 6.74 (d, J=3.5 Hz, 1 H), 3.81 (t, J=5.8 Hz, 2 H), 3.75 (s, 2 H), 2.96 (s, 4 H), 2.79 (t, J=5.8 Hz, 2 H).

The following compounds are prepared with similar method.

96-B. 4-Fluoro-5-[7-(3-methoxy-propyl)-5,6,7,8-tetrahydro-pyrido[3,4-d]pyrimidin-4-yloxy]-2-methyl-indole-1-carboxylic acid (3-trifluoromethyl-phenyl)-amide

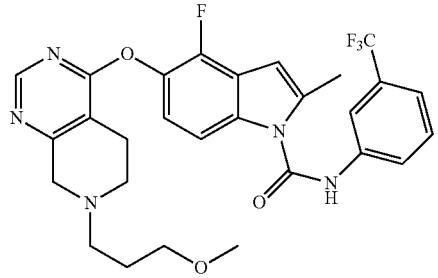 [SMILES: COCCCN1CCc2c(ncnc2Oc2ccc3c(cc(C)n3C(=O)Nc3cccc(C(F)(F)F)c3)c2F)C1]

4-Fluoro-2-methyl-5-(5,6,7,8-tetrahydro-pyrido[3,4-d]pyrimidin-4-yloxy)-indole-1-carboxylic acid (3-trifluoromethyl-phenyl)-amide (250 mg, 0.515 mmol) is dissolved in DMF (5 mL) and 1-Bromo-3-methoxypropane (79 mg, 0.515 mmol) and DIEA (0.11 mL, 0.618 mmol) are added. The reaction is stirred at rt for 72 h. At that point the reaction is diluted with EtOAc and H₂O. The organic layer is washed with water and brine before being dried over Na₂SO₄, filtered, concentrated. The residue is separated by FCC (20-100% EtOAc/heptane) to give the title compound. MS (ESI) m/z 557.9 (M+1).

EXAMPLE 97

97-A. (±)-3-(Methanesulfonyl-{6-[1-(3-trifluoromethyl-phenylcarbamoyl)-1H-indol-5-yloxy]-pyrimidin-4-ylmethyl}-amino)-pyrrolidine-1-carboxylic acid tert-butyl ester

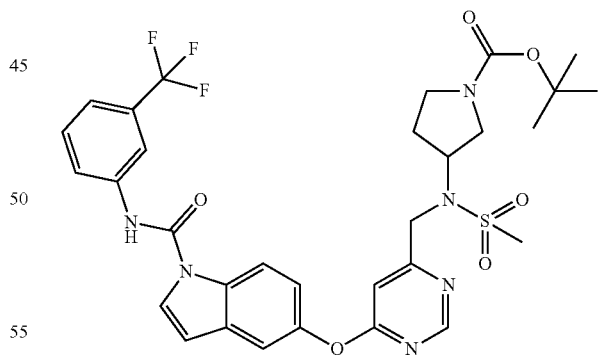

To a solution of (±)-3-({6-[1-(3-Trifluoromethyl-phenylcarbamoyl)-1H-indol-5-yloxy]-pyrimidin-4-ylmethyl}-amino)-pyrrolidine-1-carboxylic acid tert-butyl ester (20 mg, 0.033 mmol) in THF (5 mL) methanesulfonyl chloride (6.0 mg, 0.05 mmol) and TEA (7 mg, 0.066 mmol) are added at 0° C. After 30 min, the mixture is diluted with EtOAc, washed with water, brine, and then the organic layer is dried over Na₂SO₄, filtered, and, condensed. The residue is separated by FCC (0-10%, 2 M NH₃ in MeOH/DCM) to provide the title compound. MS (ESI) m/z 674.1 (M+1).

The following compounds are prepared with similar method.

97-B. 5-[6-((1R, 4S)-5-Methanesulfonyl-2,5-diaza-bicyclo[2.2.1]hept-2-ylmethyl)-pyrimidin-4-yloxy]-indole-1-carboxylic acid (3-trifluoromethyl-phenyl)-amide

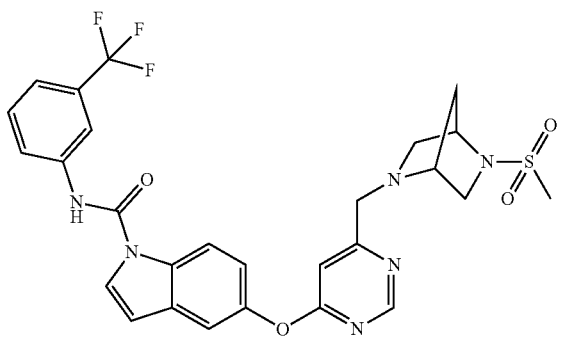 [SMILES: CS(=O)(=O)N1CC2CC1CN2Cc1cc(Oc2ccc3c(ccn3C(=O)Nc3cccc(C(F)(F)F)c3)c2)ncn1]

MS (ESI) m/z 587.1 (M+1); $^1$H NMR (400 MHz, MeOD) δ ppm 8.61 (d, J=5.05 Hz, 1 H), 8.35 (d, J=8.84 Hz, 1 H), 8.06 (s, 1 H), 7.94 (d, J=3.79 Hz, 1 H), 7.89 (d, J=8.08 Hz, 1 H), 7.57 (t, J=8.08 Hz, 1 H), 7.42 (d, J=1.77 Hz, 1 H), 7.41-7.46 (m, 1 H), 7.04-7.14 (m, 2 H), 6.74 (d, J=3.79 Hz, 1 H), 4.63 (s, 1 H), 4.26 (s, 1 H), 3.87 (d, J=5.31 Hz, 1 H), 3.61 (s, 1 H), 3.45 (d, J=9.60 Hz, 1 H), 3.24 (dd, J=9.35, 2.27 Hz, 1 H), 2.88 (s, 3 H), 2.82-2.91 (m, 3 H), 1.93 (d, J=10.61 Hz, 1 H).

EXAMPLE 98

98-A. (±)-3-(Acetyl-{6-[1-(3-trifluoromethyl-phenylcarbamoyl)-1H-indol-5-yloxy]-pyrimidin-4-ylmethyl}-amino)-pyrrolidine-1-carboxylic acid tert-butyl ester

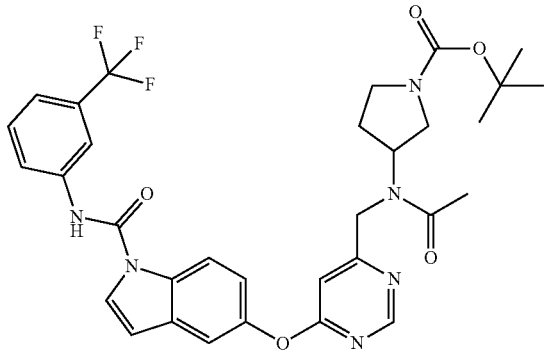 [SMILES: CC(=O)N(Cc1cc(Oc2ccc3c(ccn3C(=O)Nc3cccc(C(F)(F)F)c3)c2)ncn1)C1CCN(C(=O)OC(C)(C)C)C1]

To a solution of (±)-3-({6-[1-(3-trifluoromethyl-phenylcarbamoyl)-1H-indol-5-yloxy]-pyrimidin-4-ylmethyl}-amino)-pyrrolidine-1-carboxylic acid tert-butyl ester (60 mg, 0.10 mmol) in THF (5 mL) acetyl chloride (12 mg, 0.15 mmol) and TEA (20 mg, 0.2 mmol) are added at 0° C. After 30 min, the mixture is diluted with EtOAc, washed with water, brine, and the organic layer is dried over Na$_2$SO$_4$, filtered, and condensed. The residue is separated by FCC (0-10%, 2 M NH$_3$ in MeOH/DCM) to provide the title compound. MS (ESI) m/z 638.1 (M+1).

The following compounds are prepared with similar method.

98-B. 5-[6-((1R, 4S)-5-Acetyl-2,5-diaza-bicyclo[2.2.1]hept-2-ylmethyl)-pyrimidin-4-yloxy]-indole-1-carboxylic acid (3-trifluoromethyl-phenyl)-amide

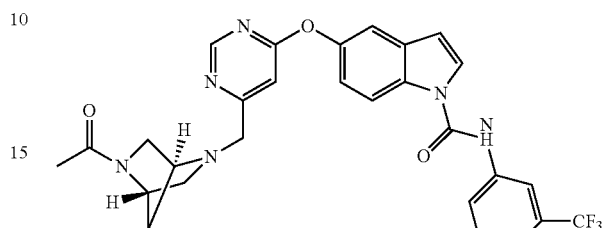

MS (ESI) m/z 551.1 (M+1); $^1$H NMR (400 MHz, MeOD) δ ppm 8.62 (d, J=4.55 Hz, 1 H), 8.37 (dd, J=8.97, 4.93 Hz, 1 H), 8.07 (s, 1 H), 7.96 (dd, J=3.79, 2.27 Hz, 1 H), 7.90 (d, J=8.84 Hz, 1 H), 7.58 (t, J=8.08 Hz, 1 H), 7.43 (s, 1 H), 7.44 (t, J=6.06 Hz, 1 H), 7.12 (ddd, J=8.97, 3.79, 2.40 Hz, 1 H), 7.07 (d, J=4.55 Hz, 1 H), 6.76 (t, J=3.41 Hz, 1 H), 4.66 (s, 1 H), 3.86 (s, 2 H), 3.62 (s, 1 H), 3.56 (dd, J=10.74, 6.95 Hz, 1 H), 3.24 (dd, J=11.49, 1.89 Hz, 1 H), 2.71 (dd, J=13.89, 9.85 Hz, 1 H), 2.08 (s, 3 H), 1.91-2.01 (m, 3 H).

EXAMPLE 99

99-A. 5-(6-((1H-tetrazol-1-yl)methyl)pyrimidin-4-yloxy)-N-(3-methoxy-5-(trifluoromethyl)phenyl)-1H-indole-1-carboxamide

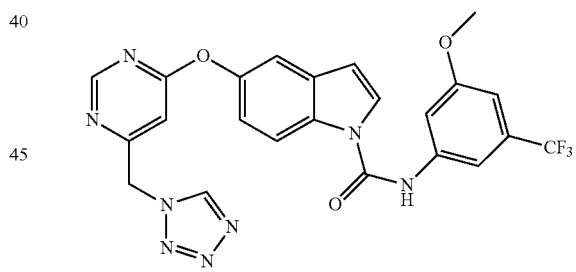

To a solution of (6-(1-(3-methoxy-5-(trifluoromethyl)phenylcarbamoyl)-1H-indol-5-yloxy)pyrimidin-4-yl)methyl methanesulfonate (1.05 mmol) in 4 mL of THF, a solution of 1H-tetrazole (0.221 g, 3.14 mmol) in 3 mL of DMF is added followed by Cs$_2$CO$_3$ (1.02 g, 3.14 mmol) and NaI (0.472 g, 3.14 mmol). The mixture is stirred at rt for 1 h and then diluted with EtOAc, washed with saturated NaHCO$_3$ (×2), brine and the organic layer is dried over Na$_2$SO$_4$. After concentration, the residue is purified by FCC (5-90% EtOAc/heptane) to provide two regioisomeric tetrazoles Example 99A and 99B.

MS (ESI) m/z 511.0 (M+1), $^1$H NMR (400 MHz, DMSO-d$_6$) δ ppm 10.35 (s, 1 H), 9.53 (s, 1 H), 8.68 (d, J=0.8 Hz, 1 H), 8.29 (d, J=8.8 Hz, 1 H), 8.12 (d, J=3.8 Hz, 1 H), 7.70 (s, 1 H), 7.60 (t, J=2.0 Hz, 1 H), 7.51 (d, J=2.5 Hz, 1 H), 7.14 (s, 2 H), 6.99-7.04 (m, 1 H), 6.81 (d, J=3.5 Hz, 1 H), 5.89 (s, 2 H), 3.86 (s, 3 H)

99-B. 5-(6-((2H-Tetrazol-2-yl)methyl-pyrimidin-4-yloxy)-indole-1-carboxylic acid (3-methoxy-5-trifluoromethyl-phenyl)-amide

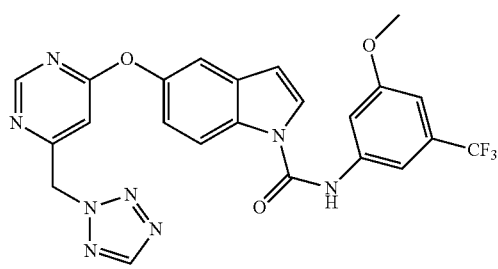 [SMILES: COc1cc(NC(=O)n2ccc3cc(Oc4cc(Cn5ncnn5)ncn4)ccc32)cc(C(F)(F)F)c1]

MS (ESI) m/z 511.4 (M+1), $^1$H NMR (400 MHz, DMSO-$d_6$) δ ppm 10.35 (s, 1 H), 9.04 (s, 1 H), 8.67 (d, J=1.0 Hz, 1 H), 8.24-8.35 (m, 1 H), 8.08-8.17 (m, 1 H), 7.67-7.74 (m, 1 H), 7.57-7.63 (m, 1 H), 7.52 (d, J=2.5 Hz, 1 H), 7.15-7.19 (m, 1 H), 7.11 (s, 1 H), 7.01-7.05 (m, 1 H), 6.79-6.83 (m, 1 H), 6.13 (s, 2 H), 3.86 (s, 3 H).

EXAMPLE 100

(±)-5-{6-[(Acetyl-pyrrolidin-3-yl-amino)-methyl]-pyrimidin-4-yloxy}-indole-1-carboxylic acid (3-trifluoromethyl-phenyl)-amide

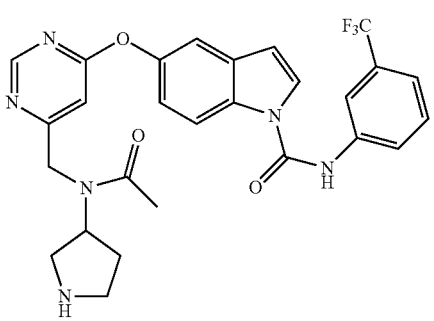 [SMILES: CC(=O)N(Cc1cc(Oc2ccc3c(ccn3C(=O)Nc3cccc(C(F)(F)F)c3)c2)ncn1)C1CCNC1]

(±)-3-(Acetyl-{6-[1-(3-trifluoromethyl-phenylcarbamoyl)-1H-indol-5-yloxy]-pyrimidin-4-ylmethyl}-amino)-pyrrolidine-1-carboxylic acid tert-butyl ester (30 mg, 0.056 mmol) is stirred in a solution of DCM (2 mL) and TFA (0.5 mL) overnight. After removal of the solvents, the residue is quenched with saturated aqueous sodium bicarbonate. The mixture is extracted with EtOAc (3×). The combined organic layers are washed with water and brine and the organic layer is dried with Na$_2$SO$_4$, filtered, and condensed. The residue is then separated by FCC (0-10%, 2 mol NH$_3$ in MeOH/DCM) to provide the title compound. MS (ESI) m/z 538.9 (M+1).

EXAMPLE 101

101-A. (±)-5-{6-[(Methanesulfonyl-pyrrolidin-3-yl-amino)-methyl]-pyrimidin-4-yloxy}-indole-1-carboxylic acid (3-trifluoromethyl-phenyl)-amide

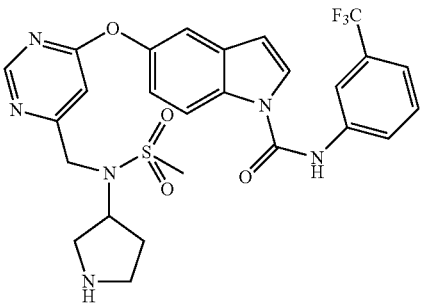 [SMILES: CS(=O)(=O)N(Cc1cc(Oc2ccc3c(ccn3C(=O)Nc3cccc(C(F)(F)F)c3)c2)ncn1)C1CCNC1]

(±)-3-(Methanesulfonyl-{6-[1-(3-trifluoromethyl-phenylcarbamoyl)-1H-indol-5-yloxy]-pyrimidin-4-ylmethyl}-amino)-pyrrolidine-1-carboxylic acid tert-butyl ester (12 mg, 0.018 mmol) is stirred in a solution of DCM (2 mL) and TFA (0.5 mL) overnight. After removal of solvents, the residue is quenched with saturated aqueous sodium bicarbonate. The mixture is extracted with EtOAc (3×). The combined organic layers are washed with water and brine and the organic layer is dried with Na$_2$SO$_4$, filtered, and condensed. The residue is then separated by FCC (0-10%, 2 M NH$_3$ in MeOH/DCM) to provide the title compound. MS (ESI) m/z 574.8 (M+1).

EXAMPLE 102

102-A. (±)-5-(Methyl-6,7-dihydro-5H-pyrrolo[3,4-d]pyrimidin-4-yloxy)-indole-1-carboxylic acid (5-tert-butyl-isoxazol-3-yl)-amide

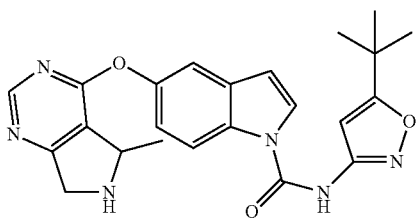

Prepared with similar method to Example 57. MS (ESI) m/z 433.0 (M+1); $^1$H NMR (400 MHz, MeOD) δ ppm 8.50 (s, 1 H) 8.35 (d, J=8.84 Hz, 1 H) 7.90 (d, J=3.79 Hz, 1 H) 7.41 (d, J=2.27 Hz, 1H) 7.12 (dd, J=8.97, 2.40 Hz, 1 H) 6.73 (d, J=3.79 Hz, 1 H) 6.66 (s, 1 H) 4.70 (q, J=6.48 Hz, 1 H) 4.10-4.16 (m, 2 H) 1.59 (d, J=6.57 Hz, 3 H) 1.38 (s, 9 H).

Chiral HPLC (Column IA, 40% acetonitrile, 60% isopropanol) provides the two enantiomers 102-A-1 and 102-A-2:

102-A-1: (−)-5-(Methyl-6,7-dihydro-5H-pyrrolo[3,4-d]pyrimidin-4-yloxy)-indole-1-carboxylic acid (5-tert-butyl-isoxazol-3-yl)-amide R$_t$=5.44 min; MS (ESI) mz 433.0 (M+1); 1H NMR (400 MHz, DMSO-$d_6$) δ ppm 8.54 (s, 1 H) 8.30 (d, J=9.09 Hz, 1 H)

8.16 (d, J=3.79 Hz, 1 H) 7.46 (d, J=2.27 Hz, 1 H) 7.14 (dd, J=8.97, 2.40 Hz, 1H) 6.76 (d, J=3.79 Hz, 1 H) 6.68 (s, 1 H) 4.62 (d, J=6.57 Hz, 1 H) 4.12 (d, J=2.27 Hz, 1 H) 4.08 (d, J=1.52 Hz, 1 H) 1.44 (d, J=6.57 Hz, 3 H) 1.34 (s, 9 H).

102-A-2: (+)-5-Methyl-6,7-dihydro-5H-pyrrolo[3,4-d]pyrimidin-4-yloxy)-indole-1-carboxylic acid (5-tert-butyl-isoxazol-3-yl)-amide R$_t$=6.54 min; MS (ESI) m/z 433.0 (M+1); 1H NMR (400 MHz, DMSO-d$_6$) δ ppm 8.54 (s, 1 H) 8.30 (d, J=8.84 Hz, 1 H) 8.17 (d, J=3.79 Hz, 1 H) 7.46 (d, J=2.27 Hz, 1 H) 7.14 (dd, J=8.97, 2.40 Hz, 1H) 6.76 (d, J=3.79 Hz, 1 H) 6.68 (s, 1 H) 4.62 (q, J=6.65 Hz, 1 H) 4.12 (d, J=2.02 Hz, 1 H) 4.08 (d, J=1.52 Hz, 1 H) 1.44 (d, J=6.57 Hz, 3 H) 1.34 (s, 9 H)

EXAMPLE 103

103-A. N-(3-(isopropylcarbamoyl)-5-(trifluoromethyl)phenyl)-5-(5,6,7,8-tetrahydropyrido[3,4-d]pyrimidin-4-yloxy)-1H-indole-1-carboxamide

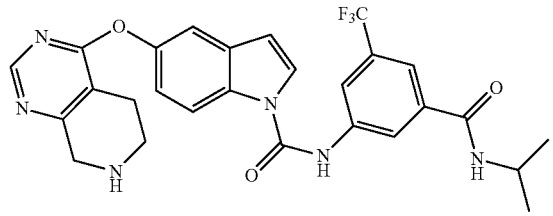 [SMILES: CC(C)NC(=O)c1cc(NC(=O)n2ccc3cc(Oc4ncnc5c4CCNC5)ccc32)cc(C(F)(F)F)c1]

To a solution of 4-(1H-Indol-5-yloxy)-5,8-dihydro-6H-pyrido[3,4-a]pyrimidine-7-carboxylic acid tert-butyl ester (0.16 g, 0.437 mmol) in 4 mL of THF at 0° C., NaH (0.105 g, 2.62 mmol) is added. After stirring for 45 min a solution of phenyl 3-(isopropylcarbamoyl)-5-(trifluoromethyl)phenyl-carbamate, Example 13-B, (0.224 g, 0.611 mmol) in 2 mL of THF and 1 mL of DMF is added dropwise. The resulting mixture is stirred for 4 h before being partitioned between EtOAc and cold H$_2$O. The aq layer is extracted further with EtOAc and the combined organic layers are washed with saturated aqueous NaHCO$_3$, brine and dried over Na$_2$SO$_4$. Following concentration the residue is separated by FCC (heptane/EtOAc). The resulting product (0.23 g, 0.360 mmol) is then treated with 70 mL of 50% TFA in DCM at rt for 1 h. After concentration the residue is separated by semi-prep HPLC (10-100% CAN/H$_2$O with 0.1% NH$_4$OH) to provide the title compound. MS (ESI) m/z 539.2 (M+1); $^1$H NMR (400 MHz, DMSO-d$_6$) δ ppm 10.49 (br. S., 1 H), 8.54 (d, J=7.8 Hz, 1 H), 8.38-8.46 (m, 2 H), 8.25-8.32 (m, 2 H), 8.15 (d, J=3.8 Hz, 1 H), 7.98 (s, 1 H), 7.46 (d, J=2.3 Hz, 1 H), 7.13 (dd, J=9.0, 2.4 Hz, 1 H), 4.07-4.21 (m, J=13.9, 6.9, 6.7, 6.7 Hz, 2 H), 3.85 (s, 2 H), 3.07 (t, J=5.8 Hz, 2 H), 2.75 (t, J=5.7 Hz, 2 H), 1.20 (d, J=6.6 Hz, 6H).

The following compounds are prepared with similar method.

103-B. N-(3-(methylcarbamoyl)-5-(trifluoromethyl)phenyl)-5-(5,6,7,8-tetrahydropyrido[3,4-d]pyrimidin-4-yloxy)-1H-indole-1-carboxamide

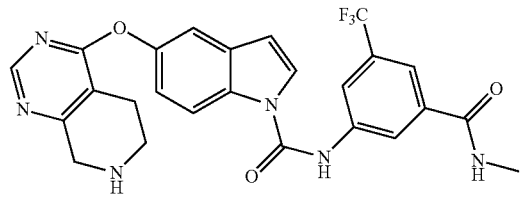 [SMILES: CNC(=O)c1cc(NC(=O)n2ccc3cc(Oc4ncnc5c4CCNC5)ccc32)cc(C(F)(F)F)c1]

MS (ESI) m/z 511.1 (M+1); $^1$H NMR (400 MHz, DMSO-d$_6$) δ ppm 10.50 (br. S., 1 H), 8.73 (q, J=4.0 Hz, 1 H), 8.45 (s, 1 H), 8.40 (s, 1 H), 8.24-8.32 (m, 2 H), 8.14 (d, J=3.8 Hz, 1 H), 7.95 (s, 1 H), 7.46 (d, J=2.5 Hz, 1 H), 7.13 (dd, J=9.0, 2.4 Hz, 1 H), 6.80 (d, J=3.5 Hz, 1 H), 3.82 (s, 2 H), 3.03 (t, J=5.8 Hz, 2 H), 2.83 (d, J=4.3 Hz, 3 H), 2.72 (t, J=5.6 Hz, 2 H).

103-C. (±)-5-(6-Methyl-5,6,7,8-tetrahydro-pyrido[3,4-d]pyrimidin-4-yloxy)-indole-1-carboxylic acid (3-isopropylcarbamoyl-5-trifluoromethyl-phenyl)-amide

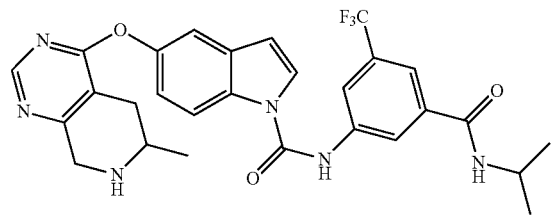 [SMILES: CC(C)NC(=O)c1cc(NC(=O)n2ccc3cc(Oc4ncnc5c4CC(C)NC5)ccc32)cc(C(F)(F)F)c1]

MS (ESI) m/z 533.2 (M+1); $^1$H NMR (400 MHz, DMSO-d$_6$) δ ppm 10.49 (br. S., 1 H), 8.53 (d, J=7.6 Hz, 1 H), 8.39-8.44 (m, 2 H), 8.25-8.33 (m, 2 H), 8.14 (d, J=3.8 Hz, 1 H), 7.97 (s, 1 H), 7.45 (d, J=2.3 Hz, 1 H), 7.12 (dd, J=9.0, 2.4 Hz, 1 H), 6.79 (d, J=3.5 Hz, 1 H), 4.06-4.21 (m, 1 H), 3.81-3.97 (m, 2 H), 2.91-3.03 (m, 1 H), 2.85 (dd, J=16.9, 3.5 Hz, 1 H), 2.29-2.39 (m, 1 H), 1.17-1.24 (m, 9 H).

103-D. (±)-5-(6-Methyl-5,6,7,8-tetrahydro-pyrido[3,4-d]pyrimidin-4-yloxy)-indole-1-carboxylic acid (3-methylcarbamoyl-5-trifluoromethyl-phenyl)-amide

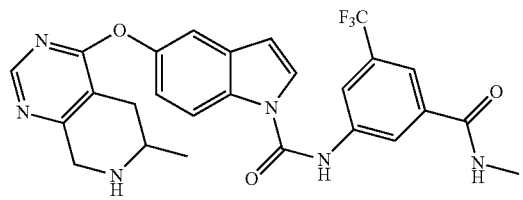 [SMILES: CNC(=O)c1cc(NC(=O)n2ccc3cc(Oc4ncnc5c4CC(C)NC5)ccc32)cc(C(F)(F)F)c1]

MS (ESI) m/z 525.2 (M+1); $^1$H NMR (400 MHz, DMSO-d$_6$) δ ppm 10.49 (br. S., 1 H), 8.70-8.77 (m, 1 H), 8.42-8.47

(m, 1 H), 8.44 (br. S., 1 H), 8.40 (s, 1 H), 8.30 (d, J=9.1 Hz, 1 H), 8.25-8.28 (m, 1 H), 8.14 (d, J=3.8 Hz, 1 H), 7.93 (br. S., 1 H), 7.45 (d, J=2.3 Hz, 1 H), 7.12 (dd, J=8.8, 2.3 Hz, 1 H), 6.79 (d, J=3.8 Hz, 1 H), 3.80-3.95 (m, 2 H), 2.90-3.03 (m, 1 H), 2.80-2.89 (m, 4 H), 2.34 (dd, J=16.3, 10.5 Hz, 1 H), 1.22 (d, J=6.3 Hz, 3 H).

EXAMPLE 104

104-A. Acetic acid 4-[4-fluoro-2-methyl-1-(3-trifluoromethyl-phenylcarbamoyl)-1H-indol-5-yloxy]-pyrimidin-2-ylmethyl ester

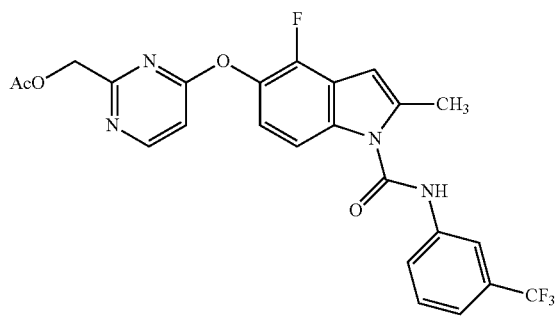 [SMILES: CC(=O)OCc1nccc(Oc2ccc3c(cc(C)n3C(=O)Nc3cccc(C(F)(F)F)c3)c2F)n1]

DBU (5.48 mL, 36.3 mmol) is added dropwise to a suspension of 4-fluoro-2-methyl-1H-indol-5-ol (5.00 g, 30.3 mmol) and 2,4-dichloropyrimidine (4.60 g, 30.9 mmol) in CH$_3$CN (60 mL) at 0° C. The resulting mixture is warmed to and stirred at 23° C. for 15 h. The reaction mixture is concentrated and the residue is partitioned between 1:1 EtOAc—CH$_2$Cl$_2$ (300 mL) and water (150 mL). The aqueous layer is extracted with EtOAc (2×100 mL). The combined organic layers are washed with brine (100 mL), dried (Na$_2$SO$_4$), and concentrated. The residue is purified by silica gel chromatography (0-100% EtOAc/heptane) to provide 5-(2-chloropyrimidin-4-yloxy)-4-fluoro-2-methyl-1H-indole.

1,2-Dibromoethane (425 µL, 5.0 mmol) is added to a suspension of zinc powder (2.83 g, 43.2 mmol) in dry DMF (8 mL). The reaction mixture is heated at 60° C. for 10 min, then cooled to room temperature. TMSCl (500 µL, 4.0 mmol) is added (caution: exothermic!) and the resulting mixture is sonicated for 30 min. Zinc powder is allowed to settle and the supernatant is removed by syringe. DMF (8 mL) is added, followed by bromomethyl acetate (2.12 mL, 21.61 mmol). The mixture is stirred at 23° C. for 2.5 h. Zinc is allowed to settle and the solution of acetoxymethylzinc bromide is then transferred to a solution of 5-(2-chloropyrimidin-4-yloxy)-4-fluoro-2-methyl-1H-indole (2.00 g, 7.20 mmol), palladium acetate (0.081 g, 0.360 mmol), and S-phos (0.355 g, 0.864 mmol) in DMF (10 mL) at 23° C. The resulting mixture is stirred at 23° C. for 15 h. Saturated aqueous NH$_4$Cl (100 mL) is added and the mixture is then partitioned between EtOAc (150 mL) and water (150 mL). The aqueous layer is extracted with EtOAc (2×100 mL). The combined organic layers are washed with brine (60 mL), dried (Na$_2$SO$_4$), and concentrated. The residue is purified by silica gel chromatography (0-100% EtOAc/heptane) to give (4-(4-fluoro-2-methyl-1H-indol-5-yloxy)pyrimidin-2-yl)methyl acetate.

LHMDS (1.0 M in THF, 7.68 mL, 7.68 mmol) is added over 1 min to a solution of (4-(4-fluoro-2-methyl-1H-indol-5-yloxy)pyrimidin-2-yl)methyl acetate (1.21 g, 3.84 mmol) and 1-isocyanato-3-(trifluoromethyl)benzene (0.70 mL, 5.08 mmol) in THF (40 mL) at −78° C. for 40 min. Saturated aqueous NH$_4$Cl (100 mL) and water (20 mL) are added and the mixture is extracted with EtOAc (3×60 mL). The combined organic layers are washed with brine (30 mL), dried (Na$_2$SO$_4$), and concentrated. The residue is purified by silica gel chromatography (0-100% EtOAc/heptane) to give acetic acid 4-[4-fluoro-2-methyl-1-(3-trifluoromethyl-phenylcarbamoyl)-1H-indol-5-yloxy]-pyrimidin-2-ylmethyl ester. MS (ESI) m/z 503.0 (M+1); $^1$H NMR (400 MHz, DMSO-d$_6$) δ ppm 10.99 (s, 1 H) 8.68 (d, J=5.81 Hz, 1 H) 8.12 (s, 1 H) 7.92 (d, J=7.83 Hz, 1 H) 7.66 (t, J=8.08 Hz, 1H) 7.51-7.55 (m, 2 H) 7.11-7.18 (m, 2 H) 6.64 (s, 1 H) 5.02 (s, 2 H) 2.59 (s, 3 H) 1.88 (s, 3 H).

104-B. 4-Fluoro-5-(2-hydroxymethyl-pyrimidin-4-yloxy)-2-methyl-indole-1-carboxylic acid (3-trifluoromethyl-phenyl)-amide

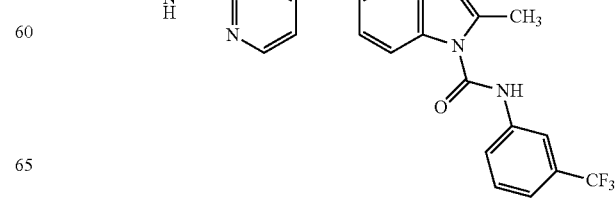

Potassium carbonate (289 mg, 2.09 mmol) is added to a solution of acetic acid 4-[4-fluoro-2-methyl-1-(3-trifluoromethyl-phenylcarbamoyl)-1H-indol-5-yloxy]-pyrimidin-2-ylmethyl ester (1.05 g, 2.09 mmol) in MeOH (40 mL) at 23° C. The resulting mixture is stirred at 23° C. for 1 h. Saturated aqueous NH$_4$Cl (50 mL) and water (20 mL) are added and the mixture is extracted with EtOAc (3×50 mL). The organic layers are combined, washed with brine (30 mL), dried (Na$_2$SO$_4$), and concentrated. The residue is purified by silica gel chromatography (10-100% EtOAc/heptane) to provide 4-fluoro-5-(2-hydroxymethyl-pyrimidin-4-yloxy)-2-methyl-indole-1-carboxylic acid (3-trifluoromethyl-phenyl)-amide. MS (ESI) m/z 461.0 (M+1); $^1$H NMR (400 MHz, DMSO-d$_6$) δ ppm 11.02 (s, 1 H) 8.69 (d, J=5.56 Hz, 1 H) 8.12 (s, 1 H) 7.91 (s, 1 H) 7.66 (t, J=7.96 Hz, 1 H) 7.52 (t, J=8.34 Hz, 2 H) 7.17 (dd, J=8.84, 7.83 Hz, 1 H) 7.05 (d, J=5.56 Hz, 1 H) 6.63 (s, 1 H) 5.14 (t, J=6.19 Hz, 1 H) 4.38 (d, J=6.32 Hz, 2 H) 2.59 (s, 3 H).

EXAMPLE 105

105-A. 4-Fluoro-5-{2-[(2-hydroxy-ethylamino)-methyl]-pyrimidin-4-yloxy}-2-methyl-indole-1-carboxylic acid (3-trifluoromethyl-phenyl)-amide Methanesulfonyl chloride (0.046 mL, 0.586 mmol) is added to a solution of 4-fluoro-5-(2-hydroxymethyl-pyrimidin-4-yloxy)-2-methyl-indole-1-carboxylic acid (3-trifluoromethyl-phenyl)-amide (180 mg, 0.391 mmol) and Et$_3$N (0.109 mL, 0.782 mmol) in CH$_2$Cl$_2$ (5 mL) at 0° C. After 10 min, ethanolamine (0.236 mL, 3.91 mmol) is added and the resulting mixture is warmed to and stirred at 23° C. for 4 h. MeOH (2 mL) is added and the reaction is stirred for another 15 h. The reaction mixture is partitioned between EtOAc (40 mL) and water (40 mL). The aqueous layer is extracted with EtOAc (2×40 mL). The combined organic layers are washed with brine (30 mL), dried (Na$_2$SO$_4$), and concentrated. The residue is purified by silica gel chromatography (0-10% MeOH/CH$_2$Cl$_2$) to give 4-fluoro-5-{2-[(2-hydroxy-ethylamino)-methyl]-pyrimidin-4-yloxy}-2-methyl-indole-1-carboxylic acid (3-trifluoromethyl-phenyl)-amide. MS (ESI) m/z 504.2 (M+1); $^1$H NMR (400 MHz, MeOD) δ ppm 8.60 (d, J=5.81 Hz, 1H) 8.07 (s, 1 H) 7.86 (s, 1 H) 7.57-7.62 (m, 1 H) 7.46-7.51 (m, 2 H) 7.09 (dd, J=8.84, 7.33 Hz, 1 H) 6.98 (d, J=5.81 Hz, 1 H) 6.54 (s, 1 H) 3.82 (s, 2 H) 3.55-3.58 (m, 2 H) 2.65-2.71 (m, 2 H) 2.62 (s, 3 H).

The following compounds are prepared with similar method.

105-B. 4-Fluoro-2-methyl-5-(2-methylaminomethyl-pyrimidin-4-yloxy)-indole-1-carboxylic acid (3-trifluoromethyl-phenyl)-amide

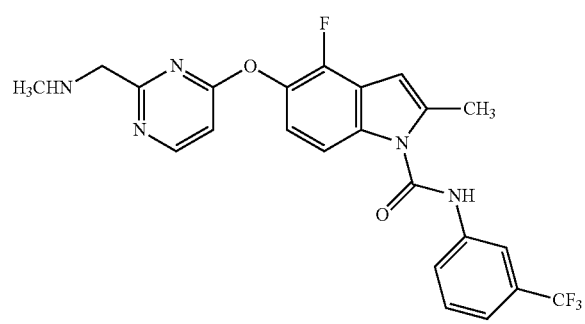

MS (ESI) m/z 474.0 (M+1); $^1$H NMR (400 MHz, MeOD) δ ppm 8.67 (d, J=5.81 Hz, 1 H) 8.08 (s, 1H) 7.87 (d, J=8.34 Hz, 1 H) 7.58-7.62 (m, 1 H) 7.47-7.53 (m, 2 H) 7.05-7.11 (m, 2 H) 6.53 (s, 1 H) 4.09 (s, 2 H) 2.63 (s, 3 H) 2.62 (s, 3 H).

EXAMPLE 106

106-A. 4-Fluoro-5-(2-methanesulfonylmethyl-pyrimidin-4-yloxy)-2-methyl-indole-1-carboxylic acid (3-trifluoromethyl-phenyl)-amide

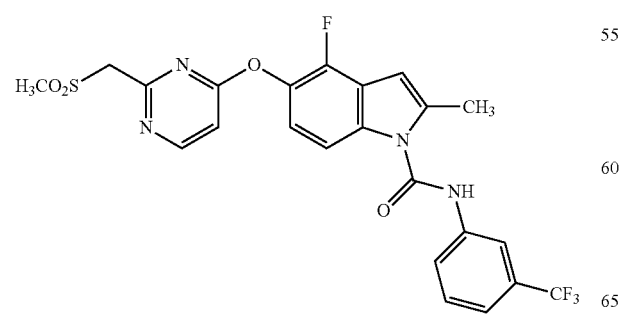

Methanesulfonyl chloride (0.046 mL, 0.586 mmol) is added to a solution of 4-fluoro-5-(2-hydroxymethyl-pyrimidin-4-yloxy)-2-methyl-indole-1-carboxylic acid (3-trifluoromethyl-phenyl)-amide (180 mg, 0.391 mmol) and Et$_3$N (0.109 mL, 0.782 mmol) in CH$_2$Cl$_2$ (5 mL) at 0° C. After 10 min, methanol is added, followed by sodium methanesulfinate (798 mg, 7.82 mmol). The resulting mixture is warmed to and stirred at 23° C. for 14 h. The mixture is concentrated and the residue is taken up in DMF (5 mL). The resulting mixture is stirred at 23° C. for 24 h, then partitioned between EtOAc (40 mL) and water (40 mL). The aqueous layer is extracted with EtOAc (2×40 mL). The combined organic layers are washed with brine (20 mL), dried (Na$_2$SO$_4$), and concentrated. The residue is purified by silica gel chromatography (0-100% EtOAc/heptane) to give 4-fluoro-5-(2-methanesulfonylmethyl-pyrimidin-4-yloxy)-2-methyl-indole-1-carboxylic acid (3-trifluoromethyl-phenyl)-amide. MS (ESI) m/z 474.0 (M+1); $^1$H NMR (400 MHz, DMSO-d$_6$) δ ppm 10.98 (s, 1 H) 8.76 (d, J=5.81 Hz, 1 H) 8.12 (s, 1 H) 7.91 (d, J=8.34 Hz, 1 H) 7.64-7.69 (m, 1 H) 7.53 (d, J=8.84 Hz, 2 H) 7.18-7.25 (m, 2 H) 6.63 (s, 1 H) 4.55 (s, 2 H) 2.97 (s, 3 H) 2.59 (s, 3 H)

EXAMPLE 107

107-A. Tert-butyl 4-(1-(3-(hydroxymethyl)-5-(trifluoromethyl)phenylcarbamoyl)-1H-indol-5-yloxy)-5,6-dihydropyrido[3,4-d]pyrimidine-7(8H)-carboxylate

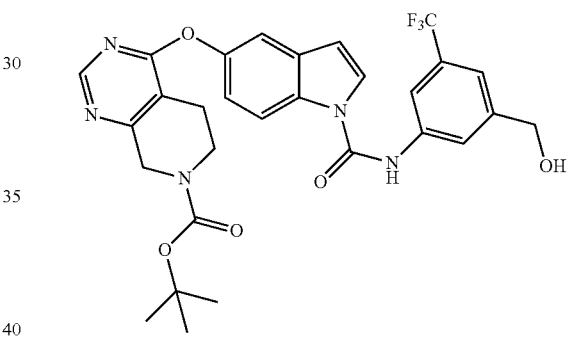

To a solution of tert-butyl 4-O-(3-((tert-butyldimethylsilyloxy)methyl)-5-(trifluoromethyl)phenylcarbamoyl)-1H-indol-5-yloxy)-5,6-dihydropyrido[3,4-a]pyrimidine-7(8H)-carboxylate (0.252 g, 0.361 mmol) in 6 mL of THF and 14 mL of water, 26 mL of acetic acid is added. The mixture is heated to 32° C. for 5 h at which point the reaction is diluted with EtOAc, washed with water/pyridine, saturated sodium bicarbonate, brine and dried over sodium sulfate, concentrated to give the title compound. MS (ESI) m/z 584.2 (M+1).

107-B. tert-Butyl 4-(1-(3-((methylsulfonyloxy)methyl)-5-(trifluoromethyl)phenylcarbamoyl)-1H-indol-5-yloxy)-5,6-dihydropyrido[3,4-d]pyrimidine-7(8H)-carboxylate

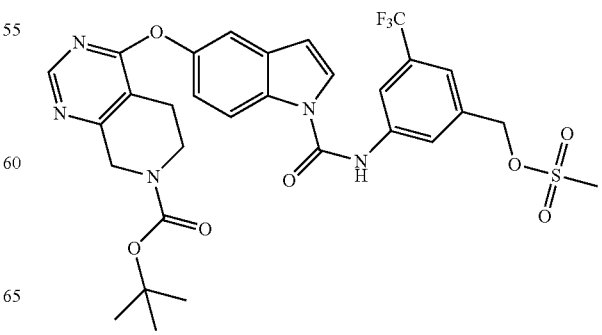

To a solution of tert-butyl 4-(1-(3-(hydroxymethyl)-5-(trifluoromethyl)phenylcarbamoyl)-1H-indol-5-yloxy)-5,6-dihydropyrido[3,4-d]pyrimidine-7(8H)-carboxylate (0.211 g, 0.361 mmol) in 6 mL of DCM with DIEA (0.19 mL, 1.08 mmol) at 0° C., methanesulfonyl chloride (0.037 mL, 0.469 mmol) is added and the reaction stirred for 3 h. At that point the reaction is diluted with EtOAc, washed with saturated sodium bicarbonate, brine and the organic layer is dried over sodium sulfate. Concentration provides a mixture of the title compound and tert-butyl 4-(1-(3-(chloromethyl)-5-(trifluoromethyl)phenylcarbamoyl)-1H-indol--yloxy)-5,6-dihydropyrido[3,4-a]pyrimidine-7(8H)-carboxylate (3:7), which is carried on to next step.

107-C. N-(3-((isopropylamino)methyl)-5-(trifluoromethyl)phenyl)-5-(5,6,7,8-tetrahydropyrido[3,4-c]pyrimidin-4-yloxy)-1H-indole-1-carboxamide

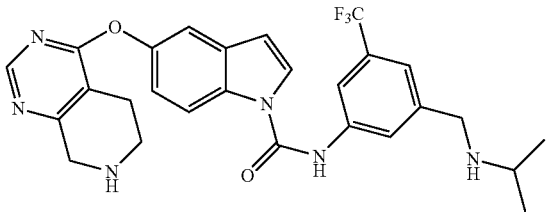 [SMILES: CC(C)NCc1cc(NC(=O)n2ccc3cc(Oc4ncnc5c4CCNC5)ccc32)cc(C(F)(F)F)c1]

To a solution of the above mixture (0.15 g, 0.227 mmol) in 3 mL of DCM, isopropyl amine (0.06 mL, 0.680 mmol) is added followed by sodium iodide (0.1 g, 0.68 mmol). After 45 min, LC-MS shows that tert-butyl 4-(1-(3-((methylsulfonyloxy)methyl)-5-(trifluoromethyl)phenylcarbamoyl)-1H-indol-5-yloxy)-5,6-dihydropyrido[3,4-d]pyrimidine-7(8H)-carboxylate is converted to desired product and the tert-butyl 4-(1-(3-(chloromethyl)-5-(trifluoromethyl)phenylcarbamoyl)-1H-indol-5-yloxy)-5,6-dihydropyrido[3,4-d]pyrimidine-7(8H)-carboxylate left over. To the reaction 3 mL (0.227 mmol) of isopropyl amine is added followed by NaI (0.1 g, 0.68 mmol) and the mixture is heated to 45° C. for 2 h. The solvent is then removed and the residue diluted with EtOAc, washed with H$_2$O, brine and the organic layer dried over Na$_2$SO$_4$. Following concentration the residue is separated by FCC (25-100% EtOAc/heptane). This product is then treated with 60 mL of 50% TFA/DCM at rt for 1.5 h. After concentration the residue is separated by semi-prep HPLC (C-18; 10-100% I/H$_2$O with 0.1% NH$_4$OH) to provide the title compound. MS (ESI) m/z 525.2 (M+1); $^1$H NMR (400 MHz, DMSO-d$_6$) δ ppm 10.33 (s, 1 H), 8.40 (s, 1 H), 8.27 (d, J=8.8 Hz, 1 H), 8.13 (d, J=3.8 Hz, 1 H), 7.95 (d, J=15.2 Hz, 2 H), 7.38-7.52 (m, 2 H), 7.11 (dd, J=9.0, 2.4 Hz, 1 H), 6.78 (d, J=3.8 Hz, 1 H), 3.81 (d, J=7.6 Hz, 4 H), 3.03 (t, J=5.8 Hz, 2 H), 2.68-2.79 (m, 3 H), 1.03 (d, J=6.1 Hz, 6 H).

EXAMPLE 108

108-A. 5-(2-Azidomethyl-pyridin-4-yloxy)-indole-1-carboxylic acid (3-trifluoromethyl-phenyl)-amide

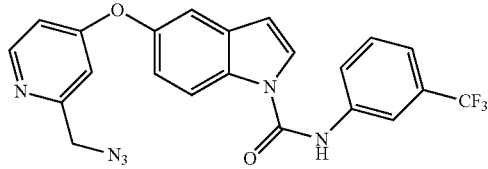 [SMILES: [N-]=[N+]=NCc1cc(Oc2ccc3c(ccn3C(=O)Nc3cccc(C(F)(F)F)c3)c2)ccn1]

A mixture of methanesulfonic acid 4-[1-(3-trifluoromethyl-phenylcarbamoyl)-1H-indol-5-yloxy]pyridine-2-ylmethyl ester (505 mg, 1.03 mmol) and sodium azide (201 mg, 3.12 mmol) in DMSO (5 mL) is heated at 80° C. for 2 h. The mixture is then diluted with DCM (100 mL) and water. The organic layer is washed further with brine and then dried over anhydrous Na$_2$SO$_4$. Following concentration the residue is separated via FCC (20-90% EtOAc/heptane) to give the title compound. MS (ESI) m/z 453.1 (M+1).

108-B. 5-(2-Aminomethyl-pyridin-4-yloxy)-indole-1-carboxylic acid (3-trifluoromethyl-phenyl)-amide

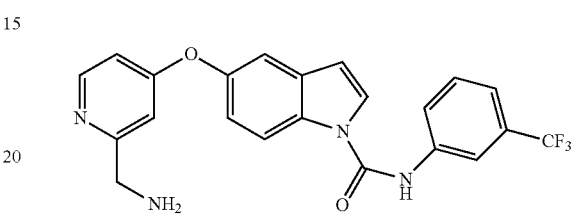

5-(2-Azidomethyl-pyridin-4-yloxy)-indole-1-carboxylic acid (3-trifluoromethyl-phenyl)-amide (165 mg, 0.36 mmol) is dissolved in THF (5 mL) at 0° C. and lithium aluminum hydride (0.55 mL, 0.55 mmol, 1.0M THF solution) is added. After 2 h, the mixture is quenched with water before extraction with EtOAc. The organic layer is washed with saturated aqueous NH$_4$Cl and then dried over anhydrous Na$_2$SO$_4$. Following concentration the residue is separated via semi-prep HPLC (C18; 10-100% I/H$_2$O with 0.1% NH$_4$OH) to give the title compound. MS (ESI) m/z 427.1 (M+1); $^1$H NMR (400 MHz, DMSO-d$_6$) δ ppm 8.29-8.39 (m, 2 H), 8.15 (d, J=3.8 Hz, 1 H), 8.09 (s, 1 H), 7.97 (d, J=8.1 Hz, 1 H), 7.64 (t, J=8.0 Hz, 1 H), 7.50 (d, J=7.6 Hz, 1 H), 7.45 (d, J=2.5 Hz, 1 H), 7.12 (dd, J=8.8, 2.5 Hz, 1 H), 7.00 (s, 1 H), 6.81 (d, J=3.3 Hz, 1 H), 6.76 (d, J=3.5 Hz, 1 H), 3.76 (s, 2 H).

EXAMPLE 109

109-A. 4-[1-(3-Cyano-5-trifluoromethyl-phenylcarbamoyl)-1H-indol-5-yloxy]-5,8-dihydro-6H-pyrido[3,4-d]pyrimidine-7-carboxylic acid tert-butyl ester

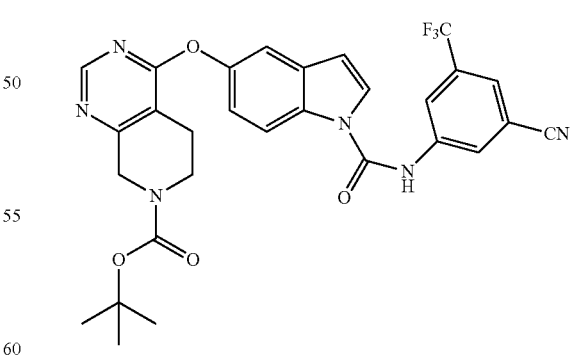

4-(1H-Indol-5-yloxy)-5,8-dihydro-6H-pyrido[3,4-d]pyrimidine-7-carboxylic acid tert-butyl ester, Example 31-F (140 mg, 0.38 mmol) is dissolved in THF (5 mL) and NaH (31 mg, 0.76 mmol, 60% in mineral oil) is added followed by (3-cyano-5-trifluoromethyl-phenyl)-carbamic acid phenyl ester (428 mg, 1.15 mmol). After 24 h, the reaction is concentrated and then partitioned between DCM and water. The crude residue is purified via FCC (5-90% EtOAc/heptane) to give the title compound. MS (ESI) m/z 579.2 (M+1).

109-D. 5-(5,6,7,8-Tetrahydro-pyrido[3,4-d]pyrimidin-4-yloxy)-indole-1-carboxylic acid (3-cyano-5-trifluoromethyl-phenyl)-amide

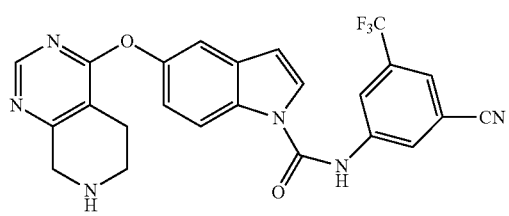 [SMILES: N#Cc1cc(NC(=O)n2ccc3cc(Oc4ncnc5c4CCNC5)ccc32)cc(C(F)(F)F)c1]

A solution of 4-[1-(3-cyano-5-trifluoromethyl-phenylcarbamoyl)-1H-indol-5-yloxy]-5,8-dihydro-6H-pyrido[3,4-d]pyrimidine-7-carboxylic acid tert-butyl ester (132 mg, 0.28 mmol) in DCM (2 mL) and TFA (2 mL) is stirred at room temperature for 2 h. The reaction is concentrated in vacuo and purified via semi-prep HPLC (C18; 10-100% I/H$_2$O with 0.1% NH$_4$OH) to give the title compound. MS (ESI) m/z 479.0 (M+1); $^1$H NMR (400 MHz, DMSO-d$_6$) δ ppm 8.38-8.42 (m, 2 H), 8.35 (s, 1 H), 8.28 (d, J=8.8 Hz, 1 H), 8.07-8.12 (m, 2 H), 7.47 (d, J=2.3 Hz, 1 H), 7.14 (dd, J=8.8, 2.3 Hz, 1 H), 6.83 (d, J=3.3 Hz, 1 H), 3.85 (s, 2 H), 3.06 (t, J=5.8 Hz, 2 H), 2.74 (t, J=5.7 Hz, 2 H).

The following compounds are prepared with similar method.

109-E. 5-(5,6,7,8-Tetrahydro-pyrido[3,4-d]pyrimidin-4-yloxy)-indole-1-carboxylic acid (3-methoxy-5-trifluoromethyl-phenyl)-amide

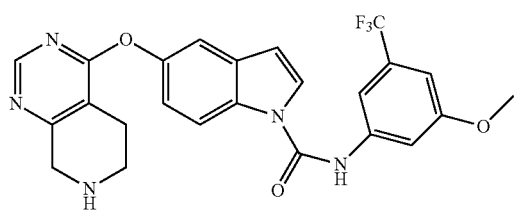 [SMILES: COc1cc(NC(=O)n2ccc3cc(Oc4ncnc5c4CCNC5)ccc32)cc(C(F)(F)F)c1]

MS (ESI) m/z 484.3 (M+1); $^1$H NMR (400 MHz, DMSO-d$_6$) δ ppm 10.33 (br. S., 1 H), 8.40 (s, 1 H), 8.26 (d, J=9.1 Hz, 1 H), 8.10 (d, J=3.5 Hz, 1 H), 7.60 (s, 1 H), 7.45 (s, 1 H), 7.12 (d, J=8.8 Hz, 1 H), 7.02 (s, 1 H), 6.79 (d, J=3.5 Hz, 1 H), 3.86 (s, 3 H), 3.82 (s, 2 H), 3.03 (t, J=5.8 Hz, 2 H), 2.67-2.76 (m, 2 H).

EXAMPLE 110

110-A. 5-{6-[(4-Bromo-butyrylamino)-methyl]-pyrimidin-4-yloxy}-indole-1-carboxylic acid (4-fluoro-3-trifluoromethyl-phenyl)-amide

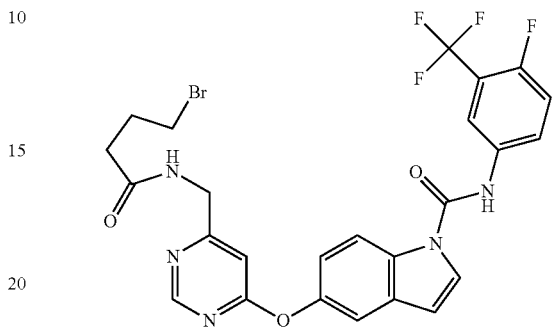

5-(6-Aminomethyl-pyrimidin-4-yloxy)-indole-1-carboxylic acid (4-fluoro-3-trifluoromethyl-phenyl)-amide (52.5 mg, 0.117 mmol) is dissolved in DCM (5 mL) at 0° C. DIEA (0.025 mL, 0.143 mmol) is added followed by 4-bromo-butyryl chloride (0.020 mL, 0.172 mmol). The reaction is stirred for 30 min before being diluted with ethyl acetate and washed with water. The organic layer is removed, dried, and concentrated to provide the title compound. MS (ESI) m/z 595.6 (M+1).

110-B. 5-[6-(2-Oxo-pyrrolidin-1-ylmethyl)-pyrimidin-4-yloxy]-indole-1-carboxylic acid (4-fluoro-3-trifluoromethyl-phenyl)-amide

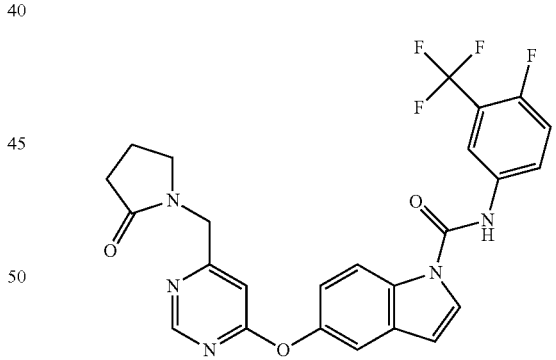

5-{6-[(4-Bromo-butyrylamino)-methyl]-pyrimidin-4-yloxy}-indole-1-carboxylic acid (4-fluoro-3-trifluoromethyl-phenyl)-amide (0.353 g, 0.595 mmol) is dissolved in 10 mL THF and cooled to 0° C. Sodium hydride (63 mg, 1.5 mmol, 60% in mineral oil) is added and the reaction is allowed to warm to room temperature overnight. The reaction is quenched with water and diluted with ethyl acetate. The organic layer is removed, dried, and concentrated and the residue is separated via semi-prep HPLC (C18; 20-100% I/H$_2$O with 0.1% TFA) to provide the title compound. MS (ESI) m/z 514.9 (M+1); $^1$H NMR (400 MHz, DMSO-d$_6$) δ ppm 10.40 (s, 1H), 8.68 (d, J=1.01 Hz, 1 H), 8.28 (d, J=9.09

Hz, 1 H), 8.09-8.12 (m, 2 H), 7.99-8.03 (m, 1 H), 7.57 (t, J=9.85 Hz, 1 H), 7.49 (d, J=2.27 Hz, 1 H), 7.15 (dd, J=8.97, 2.40 Hz, 1 H), 6.94 (d, J=1.01 Hz, 1 H), 6.81 (d, J=3.79 Hz, 1H), 4.45 (s, 2 H), 3.42 (t, J=6.95 Hz, 2 H), 2.29-2.34 (m, 3 H), 2.00 (t, J=7.58 Hz, 2 H).

EXAMPLE 111

111-A. 5-(6,7-dihydro-5H-pyrrolo[3,4-d]pyrimidin-4-yloxy)-indole-1-carboxylic acid (2-methyl-benzofuran-5-yl)-amide

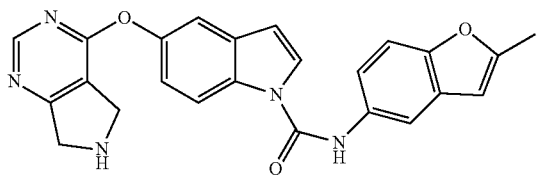 [SMILES: Cc1cc2cc(NC(=O)n3ccc4cc(Oc5ncnc6c5CNC6)ccc43)ccc2o1]

tert-Butyl 4-(1H-indol-5-yloxy)-5H-pyrrolo[3,4-d]pyrimidine-6(7H)-carboxylate (152.2 mg, 0.432 mmol) is suspended in THF (5 mL), flushed with nitrogen and cooled to 0° C. NaH (33 mg, 0.825 mmol, 60% in mineral oil) is added and mixture is stirred for 10 minutes. Phenyl 2-methylbenzofuran-5-ylcarbamate (280 mg, 1.048 mmol) is added neat and the reaction is allowed to stir to room temperature overnight. The reaction is cooled in an ice bath and quenched with a saturated solution of ammonium chloride (100 mL). The solution is then diluted with ethyl acetate and the product is extracted (2×100 mL ethyl acetate). The organic layers are combined, dried and concentrated to a brown oil that is dissolved in 10 mL of DCM and cooled in an ice bath upon which 10 mL of TFA is added. The TFA is removed and ethyl acetate is added to the residue and ammonium hydroxide is added to quench the remaining TFA. The solution is concentrated and dissolved in DMSO and is purified via semi-prep HPLC (C18; 20-100% I/H$_2$O with 0.1% TFA) to give 5-(6,7-dihydro-5H-pyrrolo[3,4-a]pyrimidin-4-yloxy)-indole-1-carboxylic acid (2-methyl-benzofuran-5-yl)-amide. MS (ESI) m/z 426.0 (M+1); $^1$H NMR (400 MHz, MeOD) δ ppm 8.53 (s, 1 H) 8.30 (d, J=8.84 Hz, 1 H) 8.15-8.20 (m, 1 H) 7.88-7.92 (m, 1 H) 7.58 (ddd, J=6.13, 3.98, 2.27 Hz, 1 H) 7.39-7.46 (m, 2 H) 7.12 (dd, J=9.09, 2.02 Hz, 1 H) 6.74 (d, J=3.79 Hz, 1 H) 6.46 (s, 1 H) 4.19 (d, J=9.35 Hz, 4 H) 2.45 (s, 3 H).

The following compounds are prepared with similar method.

111-B. 5-(6,7-dihydro-5H-pyrrolo[3,4-d]pyrimidin-4-yloxy)-indole-1-carboxylic acid (1-methyl-1H-indol-4-yl)-amide

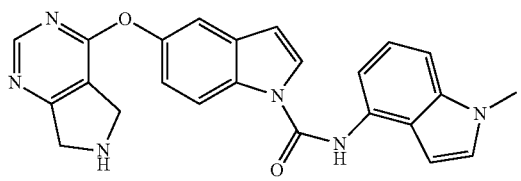 [SMILES: Cn1ccc2c(NC(=O)n3ccc4cc(Oc5ncnc6c5CNC6)ccc43)cccc21]

MS (ESI) m/z 425.0 (M+1); $^1$H NMR (400 MHz, MeOD) δ ppm 8.54 (s, 1 H) 8.30 (d, J=9.09 Hz, 1 H) 8.00 (d, J=3.54 Hz, 1 H) 7.44 (d, J=2.53 Hz, 1 H) 7.19-7.33 (m, 4 H) 7.11 (dd, J=9.09, 2.27 Hz, 1 H) 6.75 (d, J=3.79 Hz, 1 H) 6.55 (d, J=3.28 Hz, 1 H) 4.19 (d, J=1.52 Hz, 4 H) 3.84 (s, 3 H).

EXAMPLE 112

112-A. [6-(4-Fluoro-2-methyl-1H-indol-5-yloxy)-pyrimidin-4-ylmethyl]-methyl-amine

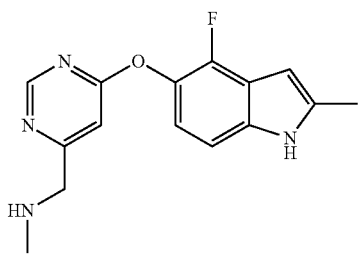 [SMILES: CNCc1cc(Oc2ccc3[nH]c(C)cc3c2F)ncn1]

Methanesulfonic acid 6-(4-fluoro-2-methyl-1H-indol-5-yloxy)-pyrimidin-4-ylmethyl ester (2.5 g, 8.78 mmol) is stirred in DCM (40.0 mL) with 1 M methylamine in THF (4.39 mL, 8.78 mmol) at rt for 24 h. The reaction is diluted with H$_2$O and EtOAc. The organic layer is washed with brine, dried over Na$_2$SO$_4$, filtered, and purified by FCC eluting with first 10-100% EtOAc in heptanes, then washing with 0-25% MeOH with NH$_3$ in EtOAc to provide the title compound. MS (ESI) m/z 287.2 (M+1); $^1$H NMR (400 MHz, MeOD) δ ppm 8.63 (d, J=1.01 Hz, 1 H) 7.11 (d, J=8.59 Hz, 1 H) 7.02 (s, 1 H) 6.85 (dd, J=8.59, 7.33 Hz, 1 H) 6.23 (s, 1 H) 3.81 (s, 2 H) 2.41 (s, 3 H) 2.44 (s, 3 H).

112-B. [6-(4-Fluoro-2-methyl-1H-indol-5-yloxy)-pyrimidin-4-ylmethyl]-methyl-carbamic acid tert-butyl ester

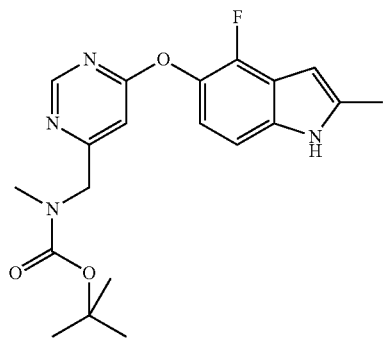

To a solution of [6-(4-Fluoro-2-methyl-1H-indol-5-yloxy)-pyrimidin-4-ylmethyl]-methyl-amine (0.68 g, 2.37 mmol) in THF (20 mL) is added BOC$_2$O (0.551 ml, 2.37 mmol) and TEA (0.33 mL, 2.37 mmol). The mixture is stirred at rt for 18 h before saturated aqueous NaHCO$_3$, water, and 150 mL EtOAc are added. The aqueous phase is extracted further with 50 mL EtOAc. The organic layers are combined, washed with brine, and dried over Na$_2$SO$_4$. Following concentration the residue is purified by FCC (0-5% MeOH in DCM) to give the title compound. MS (ESI) m/z 385.1 (M+1).

112-C. {6-[1-(5-tert-Butyl-isoxazol-3-ylcarbamoyl)-4-fluoro-2-methyl-1H-indol-5-yloxy]-pyrimidin-4-ylmethyl}-methyl-carbamic acid tert-butyl ester

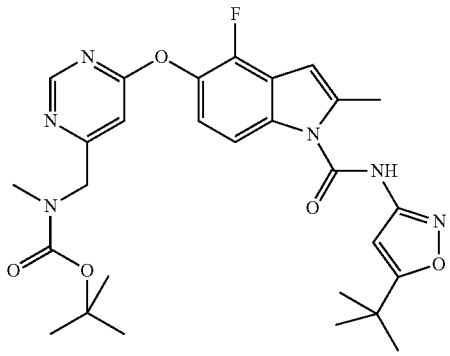 [SMILES: Cc1cc2c(F)c(Oc3cc(CN(C)C(=O)OC(C)(C)C)ncn3)ccc2n1C(=O)Nc1cc(C(C)(C)C)on1]

To a solution of [6-(4-fluoro-2-methyl-1H-indol-5-yloxy)-pyrimidin-4-ylmethyl]-methyl-carbamic acid tert-butyl ester (275 mg, 0.712 mmol) in THF (7 mL), NaH (85 mg, 2.13 mmol) is added under nitrogen at 0° C. The resulting mixture is stirred for 2 h. Then (5-tert-butyl-isoxazol-3-yl)-carbamic acid phenyl ester (370 mg, 1.42 mmol) is added to this mixture. The resulting mixture is allowed to warm to rt and stir for 18 h. The mixture is then quenched with saturated aqueous ammonium chloride. The aqueous phase is extracted with EtOAc (2×). The combined organic layers are washed with brine, dried over anhydrous sodium sulphate, concentrated and purified by FCC (0-70% EtOAc/heptane) to provide the title compound. MS (ESI) m/z 553.1 (M+1).

112-D. 4-Fluoro-2-methyl-5-(6-methylaminomethyl-pyrimidin-4-yloxy)-indole-1-carboxylic acid (5-tert-butyl-isoxazol-3-yl)-amide

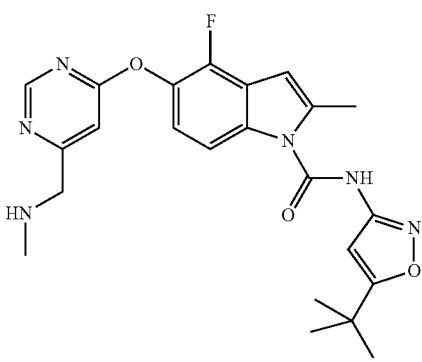 [SMILES: CNCc1cc(Oc2ccc3c(cc(C)n3C(=O)Nc3cc(C(C)(C)C)on3)c2F)ncn1]

To a solution of {6-[1-(5-tert-Butyl-isoxazol-3-ylcarbamoyl)-4-fluoro-2-methyl-1H-indol-5-yloxy]-pyrimidin-4-ylmethyl}-methyl-carbamic acid tert-butyl ester (0.25 g, 0.452 mmol) in DCM (10 mL) is added TFA (1.5 mL). After 3 h the solvent is removed by rotary evaporation and the residue is diluted with DCM and water. Concentrated NH$_4$OH is added to neutralize and the aqueous phase is extracted twice with DCM. The organic layers are washed with brine, dried over Na$_2$SO$_4$, and concentrated to give the title compound. MS (ESI) m/z 453.1 (M+1); $^1$H NMR (400 MHz, DMSO-d$_6$) δ ppm 8.64 (d, J=1.01 Hz, 1 H) 7.52 (d, J=8.59 Hz, 1 H) 7.19 (s, 1 H) 7.15 (dd, J=8.72, 7.71 Hz, 1H) 6.65 (s, 1 H) 6.58 (s, 1 H) 3.76 (s, 2 H) 2.56 (s, 3 H) 2.33 (s, 3 H) 1.34 (s, 9 H).

EXAMPLE 113

5-(7-Methyl-5,6,7,8-tetrahydro-pyrido[3,4-d]pyrimidin-4-yloxy)-indole-1-carboxylic acid [5-(1-methyl-cyclopropyl)-1H-pyrazol-3-yl]-amide

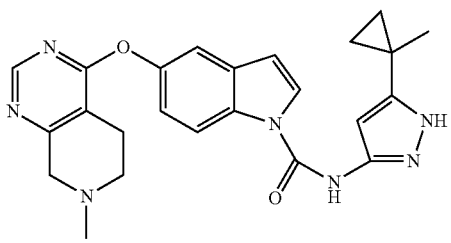 [SMILES: CN1CCc2c(ncnc2Oc2ccc3c(ccn3C(=O)Nc3cc(C4(C)CC4)[nH]n3)c2)C1]

Prepared from Example 54-Q with similar method as described for Example 63-A. MS (ESI) m/z 444.3 (M+1); $^1$H NMR (400 MHz, DMSO-d$_6$) δ ppm 12.13 (br. S., 1 H), 10.56 (s, 1 H), 8.42 (s, 1 H), 8.29 (d, J=9.1 Hz, 1 H), 8.16 (d, J=3.5 Hz, 1 H), 7.42 (d, J=2.3 Hz, 1 H), 7.09 (dd, J=9.0, 2.4 Hz, 1 H), 6.70 (d, J=3.5 Hz, 1 H), 6.29 (s, 1 H), 3.51 (s, 2 H), 2.84 (t, J=5.7 Hz, 2 H), 2.66-2.76 (m, 2 H), 2.40 (s, 3 H), 1.41 (s, 3 H), 0.89-0.97 (m, 2 H), 0.74-0.83 (m, 2 H).

EXAMPLE 114

5-(7-Ethyl-5,6,7,8-tetrahydro-pyrido[3,4-d]pyrimidin-4-yloxy)-indole-1-carboxylic acid [5-(1-methyl-cyclopropyl)-1H-pyrazol-3-yl]-amide

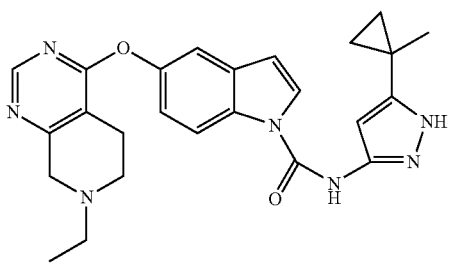 [SMILES: CCN1CCc2c(ncnc2Oc2ccc3c(ccn3C(=O)Nc3cc(C4(C)CC4)[nH]n3)c2)C1]

Prepared from Example 54-Q with similar method as Example 37-A. MS (ESI) m/z 458.4 (M+1); $^1$H NMR (400 MHz, DMSO-d$_6$) δ ppm 12.13 (s, 1 H), 10.55 (s, 1 H), 8.42 (s, 1 H), 8.29 (d, J=8.8 Hz, 1H), 8.16 (d, J=3.5 Hz, 1 H), 7.42 (d, J=2.3 Hz, 1 H), 7.09 (dd, J=8.8, 2.3 Hz, 1 H), 6.70 (d, J=3.5 Hz, 1H), 6.30 (d, J=1.8 Hz, 1 H), 3.56 (s, 2 H), 2.80-2.88 (m, 2 H), 2.73-2.80 (m, 2 H), 2.58 (q, J=7.3 Hz, 2 H), 1.41 (s, 3 H), 1.12 (t, J=7.2 Hz, 3 H), 0.89-0.96 (m, 2 H), 0.75-0.81 (m, 2 H).

EXAMPLE 115

115-A. (±)-5-[7-(2-Hydroxy-ethyl)-6-methyl-5,6,7,8-tetrahydro-pyrido[3,4-d]pyrimidin-4-yloxy]-indole-1-carboxylic acid (3-trifluoromethyl-phenyl)-amide

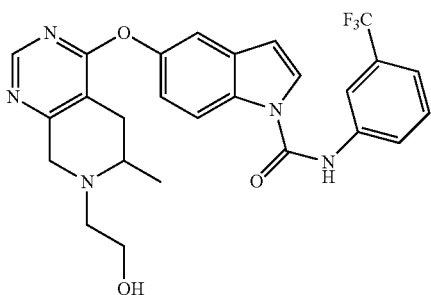 [SMILES: CC1Cc2c(ncnc2Oc2ccc3c(ccn3C(=O)Nc3cccc(C(F)(F)F)c3)c2)CN1CCO]

Methyl bromoacetate (0.15 mL, 1.58 mmol) is added to a solution of 5-(6-methyl-5,6,7,8-tetrahydro-pyrido[3,4-d]pyrimidin-4-yloxy)-indole-1-carboxylic acid (3-trifluoromethyl-phenyl)-amide, Example 52-B, (0.370 g, 0.792 mmol) and TEA (0.44 mL, 3.17 mmol) in ACN (10 mL). The solution is allowed to stir overnight. The solution is then concentrated and the residue separated directly via FCC (30-100% EtOAc/heptane) to give {6-methyl-4-[1-(3-trifluoromethyl-phenylcarbamoyl)-1H-indol-5-yloxy]-5,8-dihydro-6H-pyrido[3,4-d]pyrimidin-7-yl}-acetic acid methyl ester.

LiAlH$_4$ (0.46 mL, 1.0 M THF) is added to a solution of {6-methyl-4-[1-(3-trifluoromethyl-phenylcarbamoyl)-1H-indol-5-yloxy]-5,8-dihydro-6H-pyrido[3,4-d]pyrimidin-7-yl}-acetic acid methyl ester (0.125 g, 0.232 mmol) in THF (5 mL). After 0.5 h the excess LiAlH$_4$ is quenched by the addition of saturated aqueous NH$_4$Cl. Workup is done with saturated aqueous NH$_4$Cl and DCM (25 mL each). The residue is then separated via semi-prep HPLC to give 5-[7-(2-hydroxy-ethyl)-6-methyl-5,6,7,8-tetrahydro-pyrido[3,4-a]pyrimidin-4-yloxy]-indole-1-carboxylic acid (3-trifluoromethyl-phenyl)-amide. MS (ESI) m/z 512.3 (M+1); $^1$H NMR (400 MHz, DMSO-d$_6$) δ ppm 8.42 (s, 1 H), 8.30 (d, J=8.6 Hz, 1 H), 8.11 (d, J=3.5 Hz, 1 H), 8.09 (s, 1 H), 7.94 (d, J=8.3 Hz, 1 H), 7.57-7.65 (m, 1 H), 7.41-7.46 (m, 2 H), 7.11 (dd, J=9.0, 2.4 Hz, 1 H), 6.72-6.78 (m, 1 H), 4.47 (t, J=5.4 Hz, 1 H), 3.75 (s, 2 H), 3.57 (q, J=6.1 Hz, 2 H), 3.12-3.22 (m, 1 H), 2.88-3.00 (m, 1 H), 2.54-2.76 (m, 3 H), 1.10 (d, J=6.6 Hz, 3 H). The following compounds are prepared with similar method.

115-B. 5-[(S)-7-(2-Hydroxy-ethyl)-6-methyl-5,6,7,8-tetrahydro-pyrido[3,4-d]pyrimidin-4-yloxy]-indole-1-carboxylic acid (5-cyclopropyl-isoxazol-3-yl)-amide

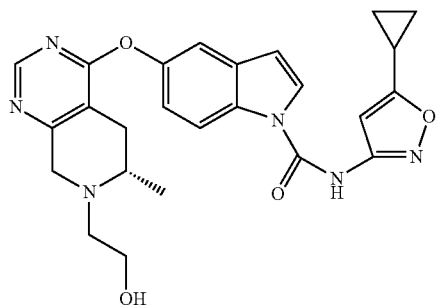 [SMILES: C[C@H]1Cc2c(ncnc2Oc2ccc3c(ccn3C(=O)Nc3cc(C4CC4)on3)c2)CN1CCO]

MS (ESI) m/z 475.1 (M+1); $^1$H NMR (400 MHz, DMSO-d$_6$) δ ppm 11.21 (s, 1 H) 8.42 (s, 1 H) 8.27 (d, J=8.84 Hz, 1 H) 8.15 (d, J=3.79 Hz, 1 H) 7.44 (d, J=2.27 Hz, 1 H) 7.13 (dd, J=8.97, 2.40 Hz, 1 H) 6.74 (d, J=3.79 Hz, 1 H) 6.65 (s, 1 H) 4.47 (t, J=5.43 Hz, 1 H) 3.74 (s, 2 H) 3.57 (q, J=6.06 Hz, 2 H) 3.13-3.19 (m, 1 H) 2.93 (dd, J=16.67, 5.05 Hz, 1 H) 2.60-2.73 (m, 2 H) 2.56 (dd, J=17.31, 5.68 Hz, 1 H) 2.17 (tt, J=8.49, 5.02 Hz, 1 H) 1.05-1.11 (m, 5 H) 0.92-0.97 (m, 2 H).

EXAMPLE 116

116-A. Diethyl-carbamic acid 1H-indol-5-yl ester

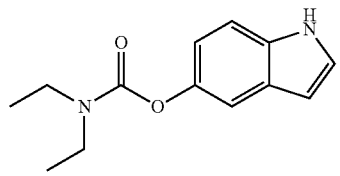 [SMILES: CCN(CC)C(=O)Oc1ccc2[nH]ccc2c1]

5-Hydroxy indole (4.4 g, 33.0 mmol) is placed in pyridine (31 mL) and TEA (5.8 mL, 41.6 mmol) is added. Diethylcarbamoyl chloride (7 mL, 55.2 mmol) is added neat and the resulting solution is stirred at room temperature for 4 hours. The reaction is then quenched with ice water and diluted with ethyl acetate. The layers are separated and the aqueous layer is further extracted with EtOAc (2×250 mL) and the organic layers are combined, dried (sodium sulfate) and concentrated to an orange oil that is absorbed onto silica and separated via FCC (0-50% ethyl acetate:heptanes) to obtain the title compound. MS (ESI) m/z 233.28 (M+1).

116-B. Diethyl-carbamic acid 1-(tert-butyl-dimethyl-silanyl)-1H-indol-5-yl ester

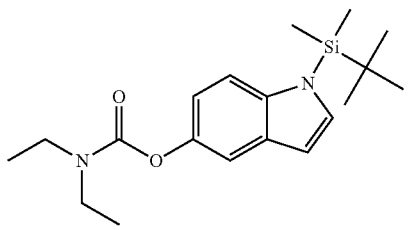 [SMILES: CCN(CC)C(=O)Oc1ccc2c(ccn2[Si](C)(C)C(C)(C)C)c1]

Diethyl-carbamic acid 1H-indol-5-yl ester (5.72 g, 24.6 mmol) is dissolved in THF (200 mL) and cooled to 0° C. The flask is purged with nitrogen and then 60% NaH (1.1 g, 27.5 mmol) is added and the mixture stirred in aen ice bath for 30 minutes. At that point TBDMSCl (0.210 g, 1.39 mmol) is added and the reaction is allowed to stir overnight (14 hours). The reaction is quenched with a saturated solution of ammonium chloride and the mixture is diluted with ethyl acetate and water. The organic layer is removed, dried (sodium sulfate) and concentrated to obtain the title compound as an oil that is used without further purification. MS (ESI) m/z 347.21 (M+1).

116-C. Diethyl-carbamic acid 1-(tert-butyl-dimethyl-silanyl)-4-chloro-1H-indol-5-yl ester

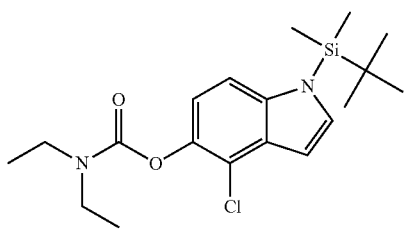 [SMILES: CCN(CC)C(=O)Oc1ccc2c(ccn2[Si](C)(C)C(C)(C)C)c1Cl]

Diethyl-carbamic acid 1-(tert-butyl-dimethyl-silanyl)-1H-indol-5-yl ester (9.26 g, 26.7 mmol) is dissolved in THF (250 mL), flushed with nitrogen and cooled to −78° C. TMEDA (5 mL, 33.1 mmol) is then added followed by sec-butyllithium (24.8 mL, 34.7 mmol) and the reaction is stirred for 30 minutes. Hexachloroethane (12.73 g, 53.8 mmol) in 50 mL of THF is added over 10 minutes to the reaction. The reaction is allowed to warm to room temperature overnight (15 hours). The reaction is cooled using an ice bath and a saturated ammonium chloride (aq) solution is added (150 mL). The mixture is then extracted with ethyl acetate, dried (sodium sulfate) and concentrated to obtain the title compound as an oil that is used without further purification. MS (ESI) m/z 381.1 (M+1).

116-D. 4-Chloro-1H-indol-5-ol

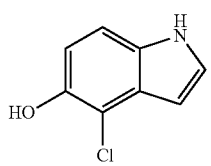

Diethyl-carbamic acid 1-(tert-butyl-dimethyl-silanyl)-4-chloro-1H-indol-5-yl ester (12.2 g, 31.9 mmol) is dissolved in diethyl ether (250 mL) and LAH (1.21 g, 31.9 mmol) is added and heated at 40° C. for 5 hours. The reaction is cooled to room temperature, placed in an ice bath and quenched with 0.5 N NaOH (aq). The reaction is diluted with ethyl acetate and the organic layer is removed, dried (sodium sulfate) and concentrated and the crude product is used without further purification. MS (ESI) m/z 282.19 (M+1).

1-(tert-Butyl-dimethyl-silanyl)-4-chloro-1H-indol-5-ol (5.35 g, 18.98 mmol) is dissolved in THF (90 mL) and cooled to 0° C. TBAF (4.96 g, 18.98 mmol) is added over 5 minutes to the brown solution. After 1 hour the reaction is quenched with ammonium chloride. The reaction is diluted with ethyl acetate and washed with water and then brine. The organic phase is removed, dried (sodium sulfate) and concentrated. The mixture is absorbed onto silica and purified via FCC (0-40% ethyl acetate:heptanes) to obtain the title compound as a solid. MS (ESI) m/z 168.15 (M+1).

116-E. 4-(4-Chloro-1H-indol-5-yloxy)-5,7-dihydro-pyrrolo[3,4-d]pyrimidine-6-carboxylic acid tert-butyl ester

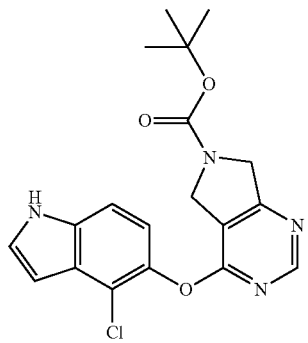 [SMILES: CC(C)(C)OC(=O)N1Cc2ncnc(Oc3ccc4[nH]ccc4c3Cl)c2C1]

Prepared with similar method to that described in Example 44-B. MS (ESI) m/z 388.96 (M+2).

EXAMPLE 117

117-A. 4-Methyl-1H-indol-5-ol

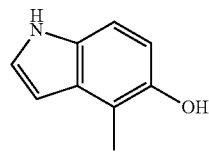

5-Methoxy-4-methyl-1H-indole (10 g, 62.0 mmol) is dissolved in DCM (400 mL) and cooled to 0° C. BBr$_3$ (155 mL, 155 mmol) is added dropwise over 1 hour and the black mixture is allowed to warm to room temperature overnight (17 hours). The reaction is poured over a mixture of ice and sodium bicarbonate (aq) solution and extracted with ethyl acetate (1.5 L) and concentrated to a black oil. The oil is absorbed onto silica and separated via FCC (0-50% ethyl acetate:heptanes) to obtain the title compound as a solid. MS (ESI) m/z 148.23 (M+1).

117-B. 4-(4-Methyl-1H-indol-5-yloxy)-5,7-dihydro-pyrrolo[3,4-d]pyrimidine-6-carboxylic acid tert-butyl ester

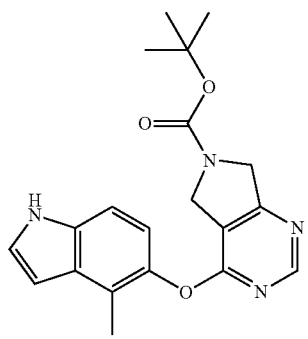 [SMILES: Cc1c(Oc2ncnc3c2CN(C(=O)OC(C)(C)C)C3)ccc2[nH]ccc12]

Prepared with similar method to that described in Example 44B. MS (ESI) m/z 367.01 (M+1).

117-C. (S)-6-Methyl-4-(4-methyl-1H-indol-5-yloxy)-5,8-dihydro-6H-pyrido[3,4-d]pyrimidine-7-carboxylic acid tert-butyl ester

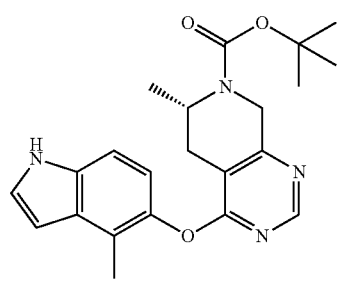 [SMILES: Cc1c(Oc2ncnc3c2C[C@H](C)N(C(=O)OC(C)(C)C)C3)ccc2[nH]ccc12]

Prepared with similar method to that described for Example 31-C. MS (ESI) m/z 395.2 (M+1).

EXAMPLE 118

118-A. 4-Chloro-5,6,7,9-tetrahydro-pyrimido[4,5-c]azepine-8-carboxylic acid tert-butyl ester & 118-B. 4-Chloro-5,7,8,9-tetrahydro-1,3,6-triaza-benzocycloheptene-6-carboxylic acid tert-butyl ester

118-A

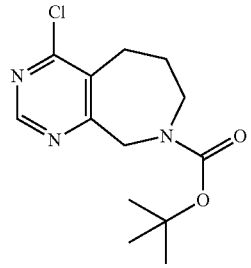

118-B

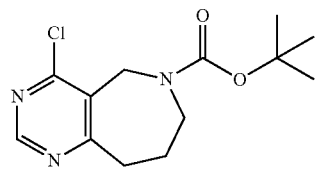

A mixture of 3-oxo-azepane-1,4-dicarboxylic acid 1-tert-butyl ester 4-ethyl ester & 4-oxo-azepane-1,3-dicarboxylic acid 1-tert-butyl ester 3-ethyl ester is prepared as described in J Med Chem 1986, 29, 224 and then is converted, with similar method to that described in Example 47D, into a mixture of 4-oxo-3,4,5,7,8,9-hexahydro-1,3,6-triaza-benzocycloheptene-6-carboxylic acid tert-butyl ester and 4-oxo-3,4,5,6,7,9-hexahydro-pyrimido[4,5-c]azepine-8-carboxylic acid tert-butyl ester which is then converted to the title compounds with similar method to that described in Example 47F, and subsequent separation of the isomers 118-A & 118-B by FCC (15-45% EtOAc/heptane. MS (ESI) m/z 284.0 (M+1) for each.

The following compounds are prepared with similar method.

118-C. 4-Chloro-5,6,8,9-tetrahydro-pyrimido[4,5-d]azepine-7-carboxylic acid tert-butyl ester

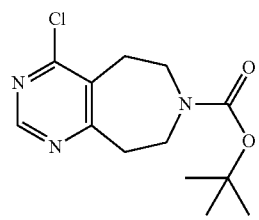 [SMILES: CC(C)(C)OC(=O)N1CCc2ncnc(Cl)c2CC1]

MS (ESI) m/z 284.0 (M+1)

EXAMPLE 119

The following compounds are prepared with similar method to Example 47-G.

119-A. 4-(1H-Indol-5-yloxy)-5,6,7,9-tetrahydro-pyrido[2,3-c]azepine-8-carboxylic acid tert-butyl ester

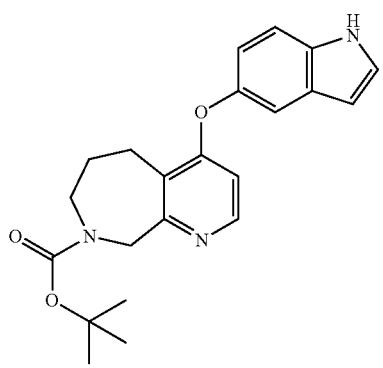 [SMILES: CC(C)(C)OC(=O)N1CCCc2c(Oc3ccc4[nH]ccc4c3)ccnc2C1]

MS (ESI) m/z 381.1 (M+1)

119-B. 4-(1H-Indol-5-yloxy)-5,7,8,9-tetrahydro-1,3,6-triaza-benzocycloheptene-6-carboxylic acid tert-butyl ester

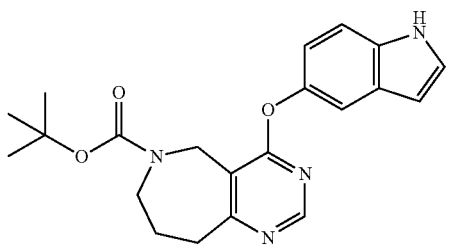 [SMILES: CC(C)(C)OC(=O)N1CCCc2ncnc(Oc3ccc4[nH]ccc4c3)c2C1]

MS (ESI) m/z 381.1 (M+1)

119-C. 4-(1H-Indol-5-yloxy)-5,6,8,9-tetrahydro-pyrimido[4,5-d]azepine-7-carboxylic acid tert-butyl ester

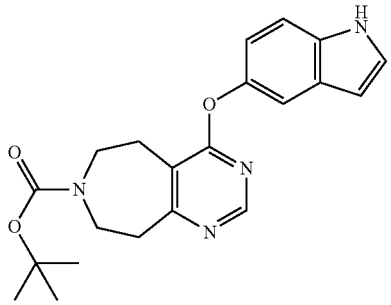 [SMILES: CC(C)(C)OC(=O)N1CCc2ncnc(Oc3ccc4[nH]ccc4c3)c2CC1]

MS (ESI) m/z 381.0 (M+1)

EXAMPLE 120

120-A. 5,7-Dihydro-3H-thieno[3,4-d]pyrimidin-4-one

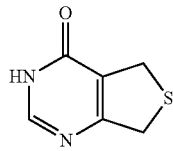

Commercially available 4-carbomethoxytetrahydro-3-thiophenone (5 g, 31.2 mmol) is dissolved in EtOH (284 mL). Formamidine acetate (22 g, 211 mmol) is then added followed by sodium ethoxide (45 mL, 121 mmol, 21% w/w) and the mixture is heated at 90° C. for 14 hours. Reaction is cooled to room temperature and concentrated to a residue which is absorbed onto silica and separated via FCC (0-10% Methanol:CH$_2$Cl$_2$) to give the title compound as a solid. MS (ESI) m/z 155.14 (M+1).

120-B. 4-(1H-Indol-5-yloxy)-5,7-dihydro-thieno[3,4-d]pyrimidine

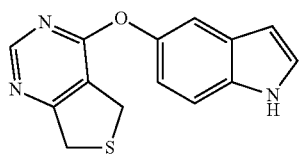 [SMILES: c1nc2c(c(Oc3ccc4[nH]ccc4c3)n1)CSC2]

Prepared with similar method to that described for Example 31-C. MS (ESI) m/z 270.07 (M+1).

120-C. 5-(5,7-Dihydro-thieno[3,4-d]pyrimidin-4-yloxy)-indole-1-carboxylic acid (2-fluoro-3-trifluoromethyl-phenyl)-amide

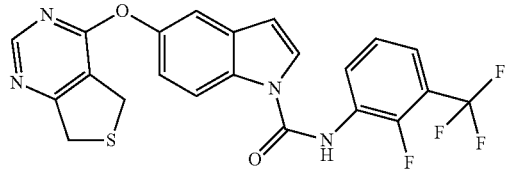 [SMILES: O=C(Nc1cccc(C(F)(F)F)c1F)n1ccc2cc(Oc3ncnc4c3CSC4)ccc21]

Prepared with similar method to that described for Example 45-A. MS (ESI) m/z 475.4 (M+1). $^1$H NMR (400 MHz, DMSO-d$_6$) δ ppm 10.27 (s, 1 H) 8.56 (s, 1 H) 8.25 (d, J=9.09 Hz, 1 H) 8.09 (d, J=3.79 Hz, 1 H) 7.91-7.95 (m, 1 H) 7.68-7.72 (m, 1 H) 7.47-7.51 (m, 2 H) 7.17 (d, J=9.09 Hz, 1 H) 6.82 (d, J=3.79 Hz, 1 H) 4.33 (d, J=1.77 Hz, 4 H).

The following compounds are prepared with similar method.

120-D. 5-(5,7-Dihydro-thieno[3,4-d]pyrimidin-4-yloxy)-indole-1-carboxylic acid [5-(1 trifluoromethyl-cyclopropyl)-isoxazol-3-yl]-amide

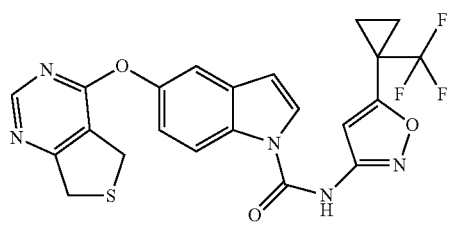 [SMILES: O=C(Nc1cc(C2(C(F)(F)F)CC2)on1)n1ccc2cc(Oc3ncnc4c3CSC4)ccc21]

MS (ESI) m/z 488.9 (M+1). $^1$H NMR (400 MHz, DMSO-d$_6$) δ ppm 11.44 (s, 1 H) 8.56 (s, 1 H) 8.30 (d, J=9.09 Hz, 1 H) 8.16 (d, J=3.79 Hz, 1 H) 7.49 (d, J=2.53 Hz, 1 H) 7.18 (d, J=8.84 Hz, 1 H) 7.04 (s, 1 H) 6.78 (d, J=3.79 Hz, 1 H) 4.33 (d, J=1.77 Hz, 4 H) 1.57 (d, J=1.52 Hz, 2 H) 1.57 (d, J=9.60 Hz, 2 H).

120-E. 5-(5,7-Dihydro-thieno[3,4-d]pyrimidin-4-yloxy)-indole-1-carboxylic acid [5-(1-methyl-cyclopropyl)-1H-pyrazol-3-yl]-amide

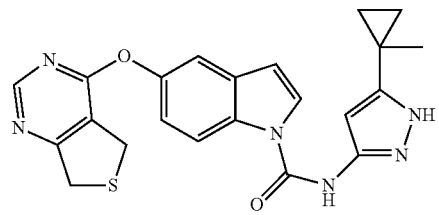 [SMILES: CC1(c2cc(NC(=O)n3ccc4cc(Oc5ncnc6c5CSC6)ccc43)n[nH]2)CC1]

MS (ESI) m/z 433.0 (M+1). $^1$H NMR (400 MHz, DMSO-d$_6$) δ ppm 8.55 (s, 1 H) 8.30 (d, J=9.09 Hz, 1 H) 8.17 (d, J=3.79 Hz, 1 H) 7.46 (d, J=2.78 Hz, 1 H) 7.13 (d, J=9.09 Hz, 1 H) 6.72 (d, J=3.79 Hz, 1 H) 6.28 (s, 1 H) 4.33 (d, J=2.02 Hz, 4 H) 1.41 (s, 3 H) 0.93 (d, J=2.02 Hz, 2 H) 0.78 (d, J=2.02 Hz, 2 H).

120-F. 5-(5,7-Dihydro-thieno[3,4-d]pyrimidin-4-yloxy)-indole-1-carboxylic acid (5-isopropyl-isoxazol-3-yl)-amide

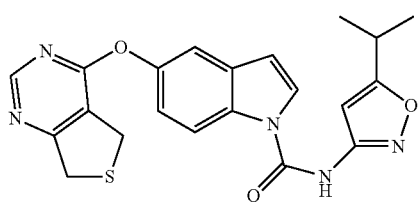 [SMILES: CC(C)c1cc(NC(=O)n2ccc3cc(Oc4ncnc5c4CSC5)ccc32)no1]

MS (ESI) m/z 422.12 (M+1). ¹H NMR (400 MHz, DMSO-d₆) δ ppm 11.27 (s, 1 H) 8.56 (s, 1 H) 8.30 (d, J=8.84 Hz, 1 H) 8.17 (d, J=3.79 Hz, 1 H) 7.49 (d, J=2.53 Hz, 1 H) 7.17 (dd, J=8.97, 2.40 Hz, 1 H) 6.77 (d, J=3.79 Hz, 1 H) 6.70 (s, 1 H) 4.33 (d, J=1.77 Hz, 4 H) 3.11 (quin, J=6.82 Hz, 1H) 1.29 (d, J=6.82 Hz, 6 H).

120-G. 5-(5,7-Dihydro-thieno[3,4-d]pyrimidin-4-yloxy)-indole-1-carboxylic acid (5-cyclopropyl-isoxazol-3-yl)-amide

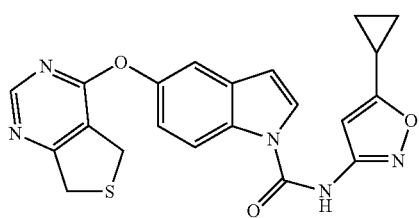 [SMILES: O=C(Nc1cc(C2CC2)on1)n1ccc2cc(Oc3ncnc4c3CSC4)ccc21]

MS (ESI) m/z 420.11 (M+1). ¹H NMR (400 MHz, DMSO-d₆) δ ppm 11.23 (s, 1 H) 8.56 (s, 1 H) 8.29 (d, J=8.84 Hz, 1 H) 8.16 (d, J=3.79 Hz, 1 H) 7.48 (d, J=2.27 Hz, 1 H) 7.17 (dd, J=8.97, 2.40 Hz, 1 H) 6.77 (d, J=3.54 Hz, 1 H) 6.65 (s, 1 H) 4.33 (d, J=1.52 Hz, 4 H) 2.14-2.21 (m, 1 H) 1.06-1.11 (m, 2 H) 0.92-0.97 (m, 2 H).

120-H. 5-(5,7-Dihydro-thieno[3,4-d]pyrimidin-4-yloxy)-indole-1-carboxylic acid (5-tert-butyl-isoxazol-3-yl)-amide

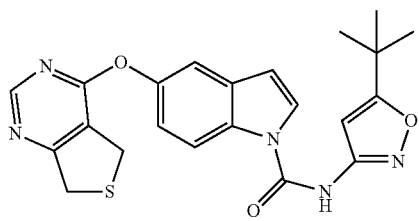 [SMILES: CC(C)(C)c1cc(NC(=O)n2ccc3cc(Oc4ncnc5c4CSC5)ccc32)no1]

MS (ESI) m/z 436.14 (M+1). ¹H NMR (400 MHz, DMSO-d₆) δ ppm 11.28 (s, 1 H) 8.56 (s, 1 H) 8.30 (d, J=8.84 Hz, 1 H) 8.17 (d, J=3.79 Hz, 1 H) 7.49 (d, J=2.53 Hz, 1 H) 7.17 (dd, J=8.97, 2.40 Hz, 1 H) 6.77 (d, J=3.79 Hz, 1 H) 6.68 (s, 1 H) 4.33 (d, J=1.52 Hz, 4 H) 1.34 (s, 9 H).

120-I. 5-(5,7-Dihydro-thieno[3,4-d]pyrimidin-4-yloxy)-indole-1-carboxylic acid (3-trifluoromethyl-phenyl)-amide

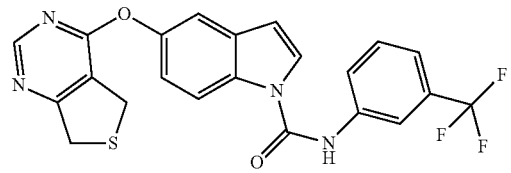 [SMILES: O=C(Nc1cccc(C(F)(F)F)c1)n1ccc2cc(Oc3ncnc4c3CSC4)ccc21]

MS (ESI) m/z 457.09 (M+1). ¹H NMR (400 MHz, DMSO-d₆) δ ppm 10.39 (s, 1 H) 8.56 (s, 1 H) 8.28 (d, J=8.84 Hz, 1 H) 8.08-8.15 (m, 2 H) 7.98 (d, J=8.34 Hz, 1 H) 7.61-7.69 (m, 1 H) 7.47-7.54 (m, 2 H) 7.17 (dd, J=8.97, 2.40 Hz, 1 H) 6.81 (d, J=3.54 Hz, 1 H) 4.33 (d, J=2.53 Hz, 4 H).

120-J. 5-(5,7-Dihydro-thieno[3,4-d]pyrimidin-4-yloxy)-indole-1-carboxylic acid [5-(1-methyl-cyclopropyl)-isoxazol-3-yl]-amide

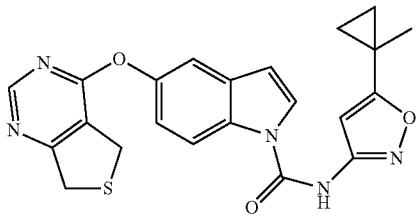 [SMILES: CC1(c2cc(NC(=O)n3ccc4cc(Oc5ncnc6c5CSC6)ccc43)no2)CC1]

MS (ESI) m/z 434.12 (M+1). ¹H NMR, (400 MHz, DMSO-d₆) δ ppm 11.24 (s, 1 H) 8.56 (s, 1 H) 8.30 (d, J=9.09 Hz, 1 H) 8.17 (d, J=3.79 Hz, 1 H) 7.48 (d, J=2.27 Hz, 1 H) 7.17 (dd, J=8.97, 2.40 Hz, 1 H) 6.77 (d, J=3.54 Hz, 1 H) 6.67 (s, 1 H) 4.33 (d, J=1.26 Hz, 4 H) 1.46 (s, 3 H) 1.13-1.17 (m, 2 H) 0.91-0.96 (m, 2 H).

EXAMPLE 121

121-A. 5-(6,6-Dioxo-6,7-di hydro-5H-6lambda*6*-thieno[3,4-d]pyrimidin-4-yloxy)-indole-1-carboxylic acid [5-(1-trifluoromethyl-cyclopropyl)-isoxazol-3-yl]-amide

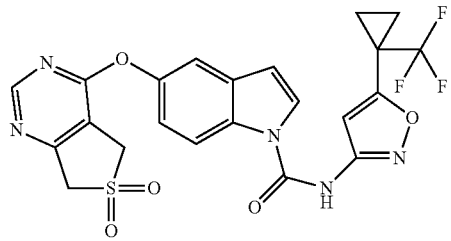 [SMILES: O=C(Nc1cc(C2(C(F)(F)F)CC2)on1)n1ccc2cc(Oc3ncnc4c3CS(=O)(=O)C4)ccc21]

A stock solution of ammonium molybdate tetrahydrate (240 mg, 0.19 mmol) in 50% w/v aqueous peroxide (0.6 mL)

is prepared at 0° C. and 0.13 mL of the stock solution is added to a solution of 5-(5,7-dihydro-thieno[3,4-d]pyrimidin-4-yloxy)-indole-1-carboxylic acid [5-(1 trifluoromethyl-cyclopropyl)-isoxazol-3-yl]-amide (55 mg, 0.113 mmol) in EtOH (8 mL) at 0° C. After stirring overnight the reaction is quenched with water and extracted with EtOAc. The title compound is the separated using FCC eluting with DCM:MeOH 100:0 to 95:5. MS (ESI) m/z 520.8 (M+1). $^1$H NMR (400 MHz, DMSO-d$_6$) δ ppm 11.45 (s, 1 H) 8.68 (s, 1 H) 8.31 (d, J=9.09 Hz, 1 H) 8.17 (d, J=3.79 Hz, 1 H) 7.52 (d, J=2.27 Hz, 1 H) 7.20 (dd, J=8.84, 2.53 Hz, 1 H) 7.04 (s, 1 H) 6.79 (d, J=4.29 Hz, 1 H) 4.72 (d, J=12.88 Hz, 4 H) 1.52-1.64 (m, 4 H).

The following compounds are prepared with similar method.

121-B. 5-(6,6-Dioxo-6,7-dihydro-5H-6lambda*6*-thieno[3,4-d]pyrimidin-4-yloxy)-indole-1-carboxylic acid (2-fluoro-3-trifluoromethyl-phenyl)-amide

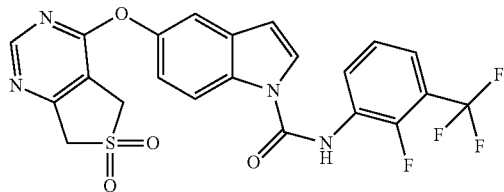 [SMILES: O=C(Nc1cccc(C(F)(F)F)c1F)n1ccc2cc(Oc3ncnc4c3CS(=O)(=O)C4)ccc21]

MS (ESI) m/z 507.8 (M+1).

121-C. 5-(6,6-Dioxo-6,7-dihydro-5H-6lambda*6*-thieno[3,4-d]pyrimidin-4-yloxy)-indole-1-carboxylic acid [5-(1-methyl-cyclopropyl)-1H-pyrazol-3-yl]-amide

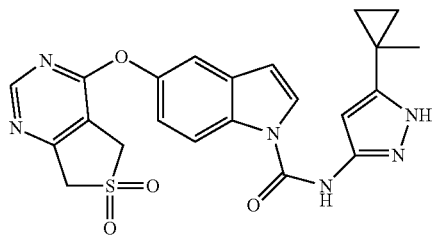 [SMILES: CC1(c2cc(NC(=O)n3ccc4cc(Oc5ncnc6c5CS(=O)(=O)C6)ccc43)n[nH]2)CC1]

MS (ESI) m/z 465.9 (M+1).

EXAMPLE 122

The following compounds are prepared with similar method to that described for Example 16-A.

122-A. 5-(6-Hydroxymethyl-pyrimidin-4-yloxy)-indole-1-carboxylic acid [5-(1-methyl-cyclopropyl)-isoxazol-3-yl]-amide

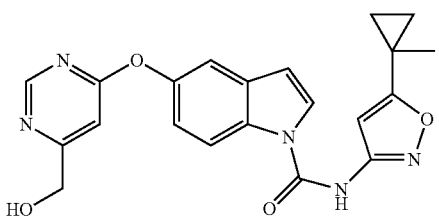 [SMILES: CC1(c2cc(NC(=O)n3ccc4cc(Oc5cc(CO)ncn5)ccc43)no2)CC1]

MS (ESI) m/z 406.1 (M+1)

122-B. 5-(6-Hydroxymethyl-pyrimidin-4-yloxy)-indole-1-carboxylic acid (5-cyclopropyl-isoxazol-3-yl)-amide

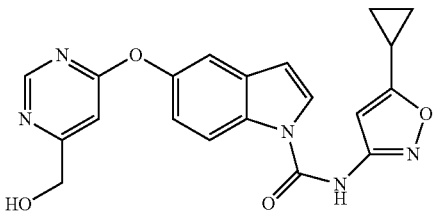 [SMILES: O=C(Nc1cc(C2CC2)on1)n1ccc2cc(Oc3cc(CO)ncn3)ccc21]

MS (ESI) m/z 392.1 (M+1)

122-C. 5-(6-Hydroxymethyl-pyrimidin-4-yloxy)-indole-1-carboxylic acid (5-isopropyl-1H-pyrazol-3-yl)-amide

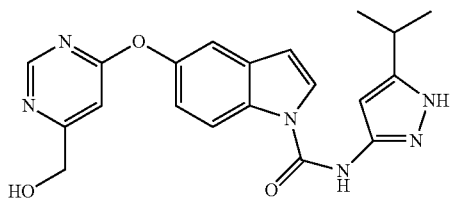 [SMILES: CC(C)c1cc(NC(=O)n2ccc3cc(Oc4cc(CO)ncn4)ccc32)n[nH]1]

MS (ESI) m/z 393.1 (M+1). $^1$H NMR (400 MHz, DMSO-d$_6$) δ ppm 12.22 (br. S., 1 H) 10.59 (s, 1H) 8.65 (d, J=1.01 Hz, 1 H) 8.32 (s, 1 H) 8.18 (br. S., 1 H) 7.46 (d, J=2.02 Hz, 1 H) 7.11-7.13 (m, 1 H) 6.98 (s, 1 H) 6.72 (d, J=3.28 Hz, 1 H) 6.34 (s, 1 H) 5.58-5.61 (m, 1 H) 4.51 (d, J=5.81 Hz, 2 H) 2.97 (d, J=6.82 Hz, 1 H) 1.25 (d, J=7.07 Hz, 6 H).

122-D. 5-(6-Hydroxymethyl-pyrimidin-4-yloxy)-4-methyl-indole-1-carboxylic acid (5-isopropyl-1H-pyrazol-3-yl)-amide

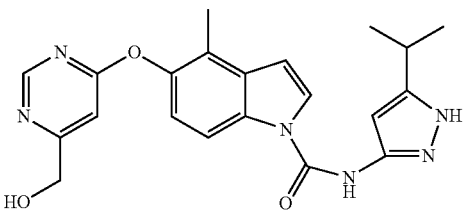 [SMILES: Cc1c(Oc2cc(CO)ncn2)ccc2c1ccn2C(=O)Nc1cc(C(C)C)[nH]n1]

MS (ESI) m/z 407.1 (M+1). $^1$H NMR (400 MHz, DMSO-d$_6$) δ ppm 12.21 (s, 1 H) 10.57 (s, 1 H) 8.62 (d, J=1.01 Hz, 1 H) 8.15-8.17 (m, 2 H) 7.05 (d, J=8.84 Hz, 1 H) 6.96 (s, 1 H) 6.83 (d, J=3.28 Hz, 1 H) 6.34 (s, 1 H) 4.50-4.53 (m, 2 H) 2.94-2.97 (m, 1 H) 2.24 (s, 3 H) 1.25 (d, J=6.82 Hz, 6 H).

122-E. 5-(6-Hydroxymethyl-pyrimidin-4-yloxy)-indole-1-carboxylic acid (5-isopropyl-isoxazol-3-yl)-amide

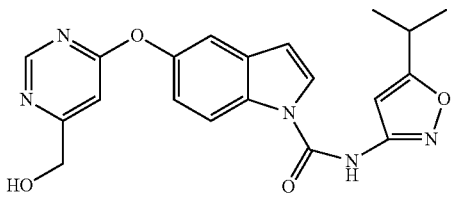 [SMILES: CC(C)c1cc(NC(=O)n2ccc3cc(Oc4cc(CO)ncn4)ccc32)no1]

MS (ESI) m/z 394.05 (M+1). $^1$H NMR (400 MHz, DMSO-d$_6$) δ ppm 11.28 (s, 1 H) 8.65 (d, J=1.01 Hz, 1 H) 8.32 (d, J=8.84 Hz, 1 H) 8.18 (d, J=3.54 Hz, 1 H) 7.49 (d, J=2.27 Hz, 1 H) 7.16 (dd, J=8.97, 2.40 Hz, 1 H) 6.99 (d, J=1.01 Hz, 1 H) 6.78 (d, J=3.79 Hz, 1 H) 6.70 (s, 1 H) 5.61 (t, J=5.81 Hz, 1 H) 4.52 (d, J=5.81 Hz, 2 H) 3.08-3.15 (m, 1 H) 1.29 (d, J=6.82 Hz, 6 H).

122-F. 5-(6-Hydroxymethyl-pyrimidin-4-yloxy)-indole-1-carboxylic acid [5-(1-trifluoromethyl-cyclopropyl)-isoxazol-3-yl]-ami

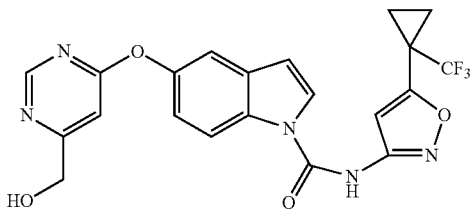 [SMILES: O=C(Nc1cc(C2(C(F)(F)F)CC2)on1)n1ccc2cc(Oc3cc(CO)ncn3)ccc21]

MS (ESI) m/z 460.12 (M+1). $^1$H NMR (400 MHz, DMSO-d$_6$) δ ppm 11.45 (s, 1 H) 8.65 (d, J=1.01 Hz, 1 H) 8.32 (d, J=9.09 Hz, 1 H) 8.18 (d, J=3.79 Hz, 1 H) 7.49 (d, J=2.27 Hz, 1 H) 7.17 (dd, J=8.97, 2.40 Hz, 1 H) 7.04 (s, 1 H) 6.99 (d, J=1.01 Hz, 1 H) 6.79 (d, J=3.79 Hz, 1 H) 5.59-5.63 (m, 1 H) 4.51-4.54 (m, 2 H) 1.54-1.60 (m, 4 H).

EXAMPLE 123

The following compounds are prepared with similar method to that described in Example 27-A.

123-A. 5-(6-Tetrazol-1-ylmethyl-pyrimidin-4-yloxy)-indole-1-carboxylic acid [5-(1-methyl-cyclopropyl)-isoxazol-3-yl]-amide

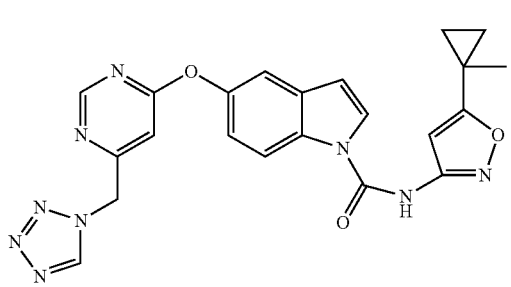 [SMILES: CC1(c2cc(NC(=O)n3ccc4cc(Oc5cc(Cn6cnnn6)ncn5)ccc43)no2)CC1]

MS (ESI) m/z 458.0 (M+1).

123-B. 5-(6-Tetrazol-2-ylmethyl-pyrimidin-4-yloxy)-indole-1-carboxylic acid [5-(1-methyl-cyclopropyl)-isoxazol-3-yl]-amide

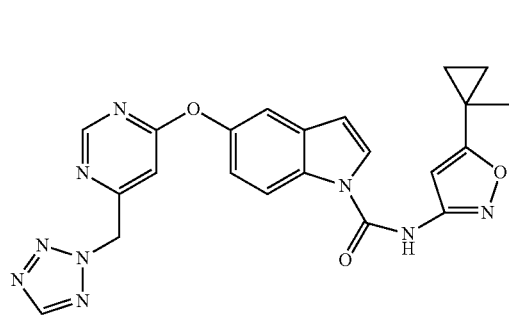 [SMILES: CC1(c2cc(NC(=O)n3ccc4cc(Oc5cc(Cn6ncnn6)ncn5)ccc43)no2)CC1]

MS (ESI) m/z 458.9 (M+1)

123-C. 5-(6-Tetrazol-2-ylmethyl-pyrimidin-4-yloxy)-indole-1-carboxylic acid (5-cyclopropyl-isoxazol-3-yl)-amide

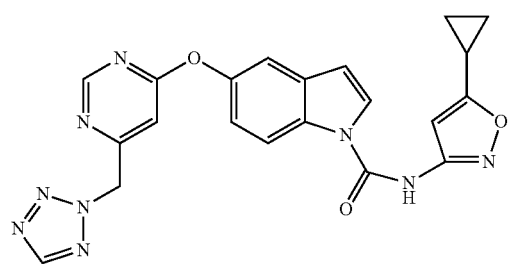 [SMILES: O=C(Nc1cc(C2CC2)on1)n1ccc2cc(Oc3cc(Cn4ncnn4)ncn3)ccc21]

MS (ESI) m/z 444.01 (M+1). NMR (400 MHz, DMSO-d$_6$) δ ppm 11.24 (s, 1 H) 9.04 (s, 1 H) 8.67 (s, 1 H) 8.30 (d, J=8.84 Hz, 1 H) 8.17 (d, J=3.79 Hz, 1 H) 7.50 (d, J=2.53 Hz, 1 H) 7.17 (dd, J=8.97, 2.40 Hz, 1 H) 7.10 (s, 1 H) 6.77 (d, J=3.79 Hz, 1 H) 6.65 (s, 1 H) 6.13 (s, 2 H) 2.14-2.21 (m, 1 H) 1.06-1.11 (m, 2 H) 0.93-0.97 (m, 2 H).

123-D. 5-(6-Tetrazol-2-ylmethyl-pyrimidin-4-yloxy)-indole-1-carboxylic acid (5-isopropyl-isoxazol-3-yl)-amide

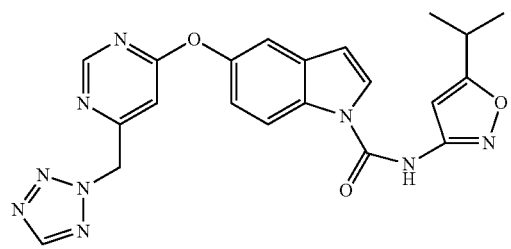 [SMILES: CC(C)c1cc(NC(=O)n2ccc3cc(Oc4cc(Cn5ncnn5)ncn4)ccc32)no1]

MS (ESI) m/z 446.99 (M+1). $^1$H NMR (400 MHz, DMSO-d$_6$) δ ppm 11.29 (s, 1 H) 9.04 (s, 1 H) 8.67 (d, J=1.01 Hz, 1 H) 8.31 (d, J=9.09 Hz, 1 H) 8.18 (d, J=3.79 Hz, 1 H) 7.51 (d, J=2.27 Hz, 1 H) 7.18 (dd, J=8.97, 2.40 Hz, 1 H) 7.11 (s, 1 H 6.78 (d, J=3.79 Hz, 1 H) 6.69 (d, J=1.01 Hz, 1 H) 6.13 (s, 2 H) 3.11 (t, J=6.95 Hz, 1 H) 1.29 (d, 6 H).

123-E. 5-(6-Tetrazol-1-ylmethyl-pyrimidin-4-yloxy)-indole-1-carboxylic acid (5-isopropyl-isoxazol-3-yl)-amide

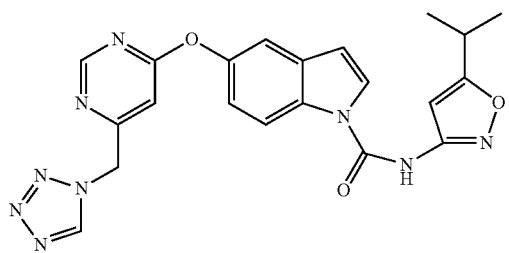 [SMILES: CC(C)c1cc(NC(=O)n2ccc3cc(Oc4cc(Cn5cnnn5)ncn4)ccc32)no1]

MS (ESI) m/z 446.98 (M+1). ¹H NMR (400 MHz, DMSO-d₆) δ ppm 11.29 (s, 1 H) 9.52 (s, 1 H) 8.68 (d, J=1.01 Hz, 1 H) 8.31 (d, J=8.84 Hz, 1 H) 8.18 (d, J=3.79 Hz, 1 H) 7.50 (d, J=2.53 Hz, 1 H) 7.13-7.19 (m, 2 H) 6.78 (d, J=3.79 Hz, 1 H) 6.69 (s, 1 H) 5.89 (s, 2 H) 3.11 (t, J=6.57 Hz, 1 H) 1.29 (d, J=6.82 Hz, 6 H).

123-F. 5-(6-Tetrazol-1-ylmethyl-pyrimidin-4-yloxy)-indole-1-carboxylic acid (5-cyclopropyl-isoxazol-3-yl)-amide

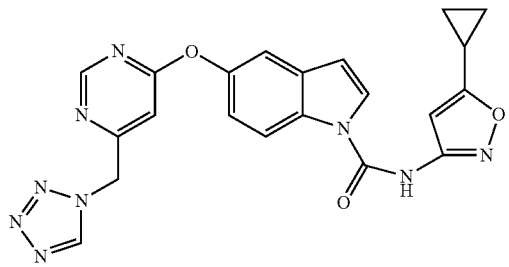 [SMILES: O=C(Nc1cc(C2CC2)on1)n1ccc2cc(Oc3cc(Cn4cnnn4)ncn3)ccc21]

MS (ESI) m/z 444.99 (M+1). ¹H NMR (400 MHz, DMSO-d₆) δ ppm 11.24 (s, 1 H) 9.52 (s, 1 H) 8.68 (d, J=1.01 Hz, 1 H) 8.31 (d, J=9.09 Hz, 1 H) 8.17 (d, J=3.54 Hz, 1 H) 7.49 (d, J=2.27 Hz, 1 H) 7.13-7.18 (m, 2 H) 6.77 (d, J=3.79 Hz, 1 H) 6.65 (s, 1 H) 5.88 (s, 2 H) 2.14-2.21 (m, 1 H) 1.09 (dd, J=8.59, 2.53 Hz, 2 H) 0.95 (dd, J=4.93, 2.40 Hz, 2 H).

EXAMPLE 124

124-A. 1-Methyl-3-(1-Methyl-cyclopropyl)-1H-pyrazol-5-ylamine

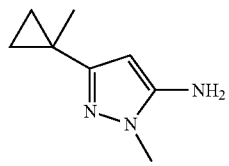

A solution of 3-(1-methyl-cyclopropyl)-3-oxo-propionitrile (1.0 g, 8.1 mmol), methylhydrazine (0.56 g, 12.2 mmol) and MeOH (40 mL) is heated at 80° C. for 16 h. The solution is then concentrated in vacuo and the residue is suspended in 5 mL DCM and 20 mL heptane, filtered to give product. MS (ESI) m/z 152.3 (M+1).

124-B. [2-Methyl-5-(1-methyl-cyclopropyl)-2H-pyrazol-3-yl]-carbamic acid phenyl ester

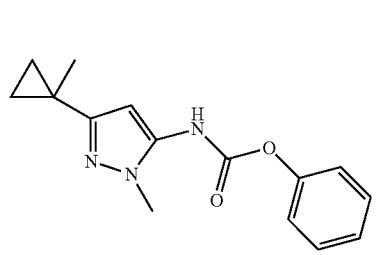 [SMILES: Cn1nc(C2(C)CC2)cc1NC(=O)Oc1ccccc1]

Prepared with similar method as described in Example 5-D. MS (ESI) m/z 272.2 (M+1).

EXAMPLE 125

1-Methyl-5-(1-Methyl-cyclopropyl)-1H-pyrazol-3-ylamine

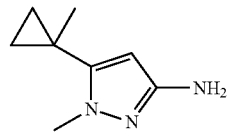

To a solution of 3-(1-methyl-cyclopropyl)-3-oxo-propionitrile (1.0 g, 8.1 mmol) in EtOH (10 mL) is added 4N HCl in Dioxane (10 mL). The mixture is stirred at room temperature for 16 hour. Concentrated under reduced pressure, the residue is dissolved in MeOH (40 mL) and treated with methylhydrazine (0.56 g, 12.2 mmol). The mixture is heated at 80° C. for 16 h. The solution is then concentrated in vacuo and the residue is purified by HPLC give product. MS (ESI) m/z 152.3 (M+1).

EXAMPLE 126

[1-Methyl-5-(1-methyl-cyclopropyl)-1H-pyrazol-3-yl]-carbamic acid phenyl ester

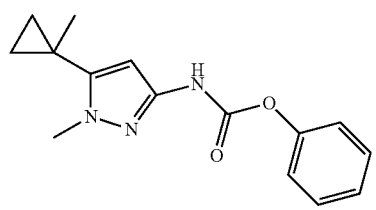 [SMILES: Cn1nc(NC(=O)Oc2ccccc2)cc1C1(C)CC1]

Prepared from Example 125 with similar method as described in Example 5-D. MS (ESI) m/z 272.2 (M+1).

EXAMPLE 127

127-A. 3-(2,5-Dimethyl-pyrrol-1-yl)-1-methyl-1H-pyrazole

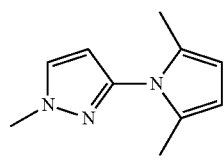

To a solution of 1-methyl-1H-pyrazol-3-amine (9.5 g, 98 mmol) and acetonylacetone (11.2 g, 98 mmol) in toluene (150 mL), AcOH (1.5 mL) is added, heated to reflux with a water separator until the formation of water ceased. Concentrated to dry. The residue is purified by flash column to give product. MS (ESI) m/z 176.3 (M+1).

127-B. 5-(2,5-Dimethyl-pyrrol-1-yl)-2-methyl-2H-pyrazole-3-carboxylic acid dimethylamide

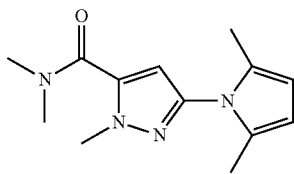 [SMILES: Cc1ccc(C)n1-c1cc(C(=O)N(C)C)n(C)n1]

To a solution of 3-(2,5-dimethyl-pyrrol-1-yl)-1-methyl-1H-pyrazole (2.0 g, 11.4 mmol) in THF (100 mL) at −78° C., 2.5M nBuLi in Hexane (5.5 mL, 13.7 mmol) is added. After stirring for 1.5 hour dimethylcarbamyl chloride (1.26 mL, 13.7 mmol) is added. After 10 min the ice bath is removed and the reaction allowed to reach room temperature and stir at room temperature for 2 hour before being poured into water, separated, and the water layer extracted with DCM. The organic layers are combined and concentrated. The residue is purified by FCC to give the title compound. MS (ESI) m/z 247.2 (M+1).

127-C. 5-Amino-2-methyl-2H-pyrazole-3-carboxylic acid dimethylamide

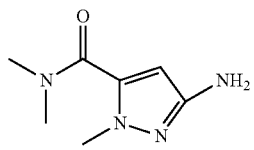

A solution of potassium hydroxide (1.1 g, 19.5 mmol) in water (30 mL) and ethanol (30 mL) is added to a slurry of hydroxylamine hydrochloride (2.7 g, 39 mmol) in ethanol (50 mL). 5-(2,5-dimethyl-pyrrol-1-yl)-2-methyl-2H-pyrazole-3-carboxylic acid dimethylamide (1.6 g, 6.5 mmol) is added and the mixture is refluxed for 48 hours. The contents of the flask are then concentrated under reduced pressure and the residue is suspended in DCM. The suspension is heated to reflux and then cooled down to room temperature, filtered and the filtrate is concentrated to give crude product. MS (ESI) m/z 169.3 (M+1).

127-D. (5-Dimethylcarbamoyl-1-methyl-1H-pyrazol-3-yl)carbamic acid phenyl ester

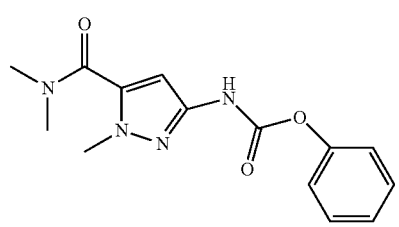 [SMILES: CN(C)C(=O)c1cc(NC(=O)Oc2ccccc2)nn1C]

Prepared with similar method as described in Example 5-D. MS (ESI) m/z 289.1 (M+1).

127-E. (1-tert-Butyl-5-methyl-1H-pyrazol-3-yl)-carbamic acid phenyl ester

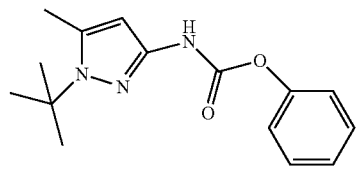 [SMILES: Cc1cc(NC(=O)Oc2ccccc2)nn1C(C)(C)C]

Prepared with similar method as described in Examples 127-A to 127-D, starting with 1-tert-butyl-1H-pyrazol-3-ylamine. In the alkylation step iodomethane is used in place of dimethylcarbamyl chloride. MS (ESI) m/z 274.3 (M+1).

EXAMPLE 128

128-A. 3-(2,5-Dimethyl-pyrrol-1-yl)-5-isopropyl-1H-pyrazole

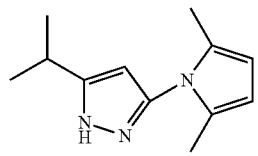

Prepared with similar method as described in Example 127-A starting from 5-Isopropyl-1H-pyrazol-3-ylamine. MS (ESI) m/z 204.3 (M+1).

128-B. 3-(2,5-Dimethyl-pyrrol-1-yl)-5-isopropyl-1-methyl-1H-pyrazole

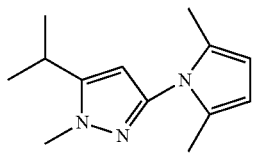 [SMILES: Cc1ccc(C)n1-c1cc(C(C)C)n(C)n1]

To a solution of 3-(2,5-dimethyl-pyrrol-1-yl)-5-isopropyl-1H-pyrazole (7.7 g, 37.9 mmol) in THF (400 mL) that is purged with nitrogen is added NaH (2.272 g, 56.8 mmol) at 0° C. The mixture is stirred for 10 min in the ice bath then for 10 min at room temperature. MeI (4.74 mL, 76 mmol) is added and the mixture is stirred at room temperature for 1 h. At that point the reaction is diluted with DCM and treated with saturated solution of ammonium chloride (10 mL). The mixture is concentrated to dryness and the residue is partitioned in water and DCM. The organic layer is combined, dried over sodium sulfate, concentrated and absorbed onto silica to purify by FCC (0-30% EtOAC/Heptane) to give 5-(2,5-Dimethyl-pyrrol-1-yl)-3-isopropyl-1-methyl-1H-pyrazole (2.4 g, 29%) as the first peak and 3-(2,5-Dimethyl-pyrrol-1-yl)-5-isopropyl-1-methyl-1H-pyrazole (5.24 g, 63%) as the second peak. MS (ESI) m/z 218.3 (m+1).

128-C. 5-Isopropyl-1-methyl-1H-pyrazol-3-ylamine

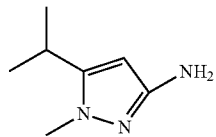

Prepared with similar method as described in Example 127-C starting with 3-(2,5-Dimethyl-pyrrol-1-yl)-5-isopropyl-1-methyl-1H-pyrazole. MS (ESI) m/z 140.3 (M+1).

128-D. (5-Isopropyl-1-methyl-1H-pyrazol-3-yl)-carbamic acid phenyl ester

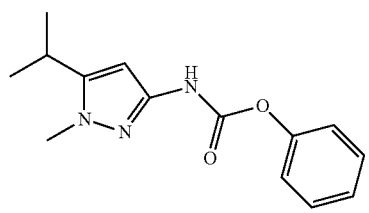 [SMILES: CC(C)c1cc(NC(=O)Oc2ccccc2)nn1C]

Prepared with similar method as described in Example 5-D starting with 5-Isopropyl-1-methyl-1H-pyrazol-3-ylamine. MS (ESI) m/z 260.2 (M+1).

The following compounds are prepared with similar method.

| | Structure/Chemical Name | MS (ESI) m/z (M − 1) |
|---|---|---|
| 128-E | 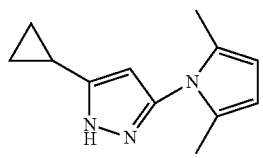<br>(5-Cyclopropyl-1-isopropyl-1H-pyrazol-3-yl)-carbamic acid phenyl ester | 286.2 |
| 128-F | 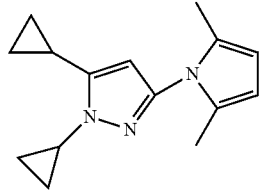 [SMILES: Cc1ccc(C)n1-c1cc(C2CC2)n(C2CC2)n1]<br>[1-Methyl-5-(1-trifluoromethyl-cyclopropyl)-1H-pyrazol-3-yl]-carbamic acid phenyl ester | 326.2 |

EXAMPLE 129

129-A. 5-Cyclopropyl-3-(2,5-dimethyl-pyrrol-1-yl)-1H-pyrazole

Prepared with similar method as described in Example 127-A starting from 5-cyclopropyl-1H-pyrazol-3-ylamine. MS (ESI) m/z 202.4 (M+1).

129-B. 1,5-Dicyclopropyl-3-(2,5-dimethyl-pyrrol-1-yl)-1H-pyrazole

A suspension of copper (II) acetate (0.902 g, 4.97 mmol) and 2,2'-bipyridine (0.776 g, 4.97 mmol) in DCE (20 mL) is stirred at 70° C. for 15 min, then transferred to a suspension of cyclopropyl trifluoroborate potassium salt (1.47 g, 9.94 mmol) and 5-Cyclopropyl-3-(2,5-dimethyl-pyrrol-1-yl)-1H-pyrazole (1 g, 4.97 mmol), and sodium carbonate (1.053 g, 9.94 mmol) in DCE (40 mL). The resulting dark-green mixture is stirred at 70° C. for 24 h. The reaction mixture is partitioned between EtOAc and 1N HCl. The aqueous layer is extracted with EtOAc. The combined organic layers are washed with brine, dried (Na$_2$SO$_4$) and concentrated. The residue (1.64 g) is purified by ISCO (EtOAc-heptane 0-30%) to provide the desired product (1.25 g) as a colorless oil. MS (ESI) m/z 242.3 (M+1).

129-C. 1,5-Dicyclopropyl-1H-pyrazol-3-ylamine

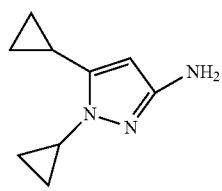 [SMILES: Nc1cc(C2CC2)n(C2CC2)n1]

Prepared with similar method as described in Example 127-C starting from 1,5-Dicyclopropyl-3-(2,5-dimethyl-pyrrol-1-yl)-1H-pyrazole. MS (ESI) m/z 164.4 (M+1).

129-D. (1,5-Dicyclopropyl-1H-pyrazol-3-yl)-carbamic acid phenyl ester

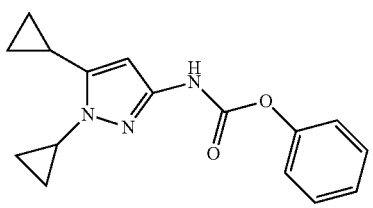 [SMILES: O=C(Nc1cc(C2CC2)n(C2CC2)n1)Oc1ccccc1]

Prepared with similar method as described in Example 5-D starting with 1,5-Dicyclopropyl-1H-pyrazol-3-ylamine. MS (ESI) m/z 284.2 (M+1).

EXAMPLE 130

130-A. 2-[5-(2,5-Dimethyl-pyrrol-1-yl)-2-methyl-2H-pyrazol-3-yl]-1,1,1-trifluoro-propan-2-ol

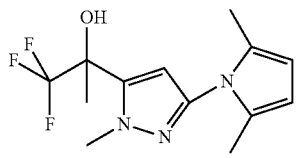 [SMILES: Cc1ccc(C)n1-c1cc(C(C)(O)C(F)(F)F)n(C)n1]

To a solution of 3-(2,5-dimethyl-pyrrol-1-yl)-1-methyl-1H-pyrazole (1.5 g, 8.6 mmol) in THF (100 mL) at −78° C., 2.5M nBuLi in Hexane (4.1 mL, 10.3 mmol) is added and stirred for 1.5 hours followed by the addition of trifluoroacetic acid ethyl ester (1.5 g, 10.3 mmol). After 10 min the ice bath is removed and the reaction is allowed to reach room temperature. Then the reaction is cooled down to −78° C. again and methylmagnesium bromide (1.0 M solution in hexane, 8.6 mL) is added. After 5 min the ice bath is removed and the mixture is stirred at room temperature for 3 hour, poured into water, separated, and the water layer is extracted with DCM. The organic layers are combined and concentrated. The residue is purified by FCC to give the title compound. MS (ESI) m/z 288.1 (M+1).

130-B. 3-(2,5-Dimethyl-pyrrol-1-yl)-1-methyl-5-(2,2,2-trifluoro-1-methoxy-1-methyl-ethyl)-1H-pyrazole

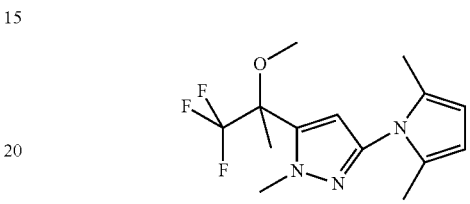

To a solution of 2-[5-(2,5-dimethyl-pyrrol-1-yl)-2-methyl-2H-pyrazol-3-yl]-1,1,1-trifluoro-propan-2-ol (0.5 g, 1.7 mmol) in THF (10 mL) at 0° C., sodium hydride (0.21 g, 60%, 5.2 mmol) is added, and the mixture is stirred for 10 min followed by the addition of methyl iodide (0.22 mL, 3.5 mmol). The ice bath is removed and the reaction mixture is stirred at room temperature for 5 hour, poured into water, separated, and the water layer is extracted with DCM. The organic layers are combined and concentrated. The residue is purified by FCC to give the title compound. MS (ESI) m/z 302.0 (M+1).

130-C. 1-Methyl-5-(2,2,2-trifluoro-1-methoxy-1-methyl-ethyl)-1H-pyrazol-3-ylamine

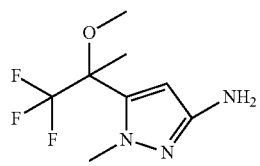

A solution of potassium hydroxide (280 mg, 5 mmol) in water (6 mL) and ethanol (6 mL) is added to a slurry of hydroxylamine hydrochloride (700 mg, 10 mmol) in ethanol (9 mL). Then 3-(2,5-dimethyl-pyrrol-1-yl)-1-methyl-5-(2,2,2-trifluoro-1-methoxy-1-methyl-ethyl)-1H-pyrazole (500 mg, 1.7 mmol) is added and the mixture is refluxed for 24 hours. At this point the contents of the flask are concentrated under reduced pressure and the residue is partitioned in water and DCM and separated. The water layer is extracted with DCM and the organic layers are combined and concentrated to give the crude title compound. MS (ESI) m/z 224.2 (M+1).

130-D. [1-Methyl-5-(2,2,2-trifluoro-1-methoxy-1-methyl-ethyl)-1H-pyrazol-3-yl]-carbamic

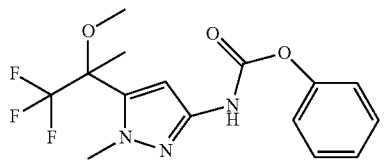 [SMILES: COC(C)(c1cc(NC(=O)Oc2ccccc2)nn1C)C(F)(F)F]

Prepared with similar method as described in Example 5-D. MS (ESI) m/z 344.0 (M+1).

EXAMPLE 131

131-A. 3-(5-Amino-2H-pyrazol-3-yl)-3-methyl-butan-1-ol

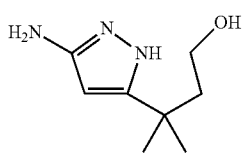

Prepared by similar method to that described above for Example 5-B starting from α,α-dimethyl-γ-butyrolactone. MS (ESI) m/z 170.1 (M+1).

131-B. 4,4-Dimethyl-5,6-dihydro-4H-pyrrolo[1,2-b]pyrazol-2-ylamine

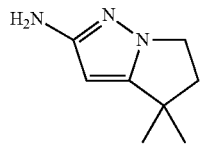

To a solution of the above pyrazole (3.35 g, 19.8 mmol) in THF (100 mL) at rt is added thionyl chloride (7.22 mL, 99 mmol). Stirring is continued for 2 h before the mixture is added slowly to 200 mL of 28% NH$_4$OH and 100 g ice. The aqueous slurry is then extracted with DCM (2×200 mL) and the combined organic layers are dried (Na$_2$SO$_4$) filtered and concentrated. The residue is then separated via FCC (1-10% MeOH/DCM) to give the title compound. MS (ESI) m/z 152.1 (M+1).

131-C. (4,4-Dimethyl-5,6-dihydro-4H-pyrrolo[1,2-b]pyrazol-2-yl)-carbamic acid phenyl ester

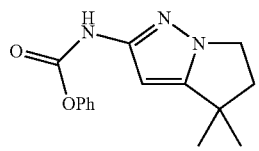 [SMILES: CC1(C)CCn2nc(NC(=O)Oc3ccccc3)cc21]

To a solution of Example 131-B (1.43 g, 9.46 mmol) and DCM (50 mL) at 0° C. is added lutidine (3.30 mL, 28.4 mmol) followed by phenyl chloroformate (1.31 mL, 10.4 mmol). The solution is left to stir at rt for 4 h. At that point the solution is washed with 2 M HCl and then the organic layer is dried (Na$_2$SO$_4$), filtered, and concentrated. The residue is then separated by FCC (30-100% EtOAc/heptane) to provide the title compound. MS (ESI) m/z 272.1 (M+1).

The following compounds are prepared with similar method.

131-D. (3-Chloro-4,4-dimethyl-5,6-dihydro-4H-pyrrolo[1,2-b]pyrazol-2-yl)-carbamic acid phenyl ester

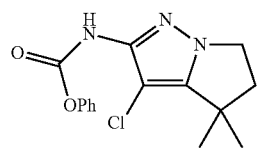 [SMILES: CC1(C)CCn2nc(NC(=O)Oc3ccccc3)c(Cl)c21]

Prepared from 3-Chloro-4,4-dimethyl-5,6-dihydro-4H-pyrrolo[1,2-b]pyrazol-2-ylamine which is isolated as a side product in the preparation of Example 131-B above. MS (ESI) m/z 306.0, 308.0 (M+1).

131-E. (5,6-Dihydro-4H-pyrrolo[1,2-b]pyrazol-2-yl)-carbamic acid phenyl ester

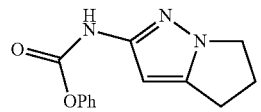 [SMILES: O=C(Nc1cc2n(n1)CCC2)Oc1ccccc1]

MS (ESI) m/z 244.086.1 (M+1).

131-F. (4,4-Dimethyl-4,5,6,7-tetrahydro-pyrazolo[1,5-a]pyridine-2-yl)-carbamic acid phenyl ester

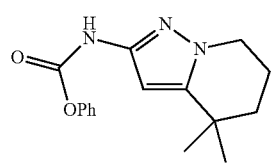 [SMILES: CC1(C)CCCn2nc(NC(=O)Oc3ccccc3)cc21]

MS (ESI) m/z 286.1 (M+1).

EXAMPLE 132

132-A. (4-Chloro-5-cyclopropyl-isoxazol-3-yl)-carbamic acid phenyl ester

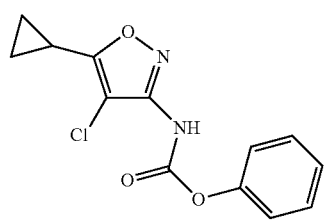 [SMILES: O=C(Nc1noc(C2CC2)c1Cl)Oc1ccccc1]

(5-Cyclopropyl-isoxazol-3-yl)-carbamic acid phenyl ester (0.25 g, 1.024 mmol) is dissolved in AcOH (7.31 mL) and NCS (0.205 g, 1.53 mmol) is added and the reaction is heated to 79° C. for 2 hours. The reaction is cooled to room temperature and diluted with water and ethyl acetate. The organic layer is washed with 500 mL of water to remove the acid. The organic layer is dried (sodium sulfate) and concentrated to an oil (352 mg) to obtain the title compound that is used without further purification. MS (ESI) m/z 279.00 (M+1).

The following are prepared with similar method.

132-B. (5-tert-Butyl-4-chloro-isoxazol-3-yl)-carbamic acid phenyl ester

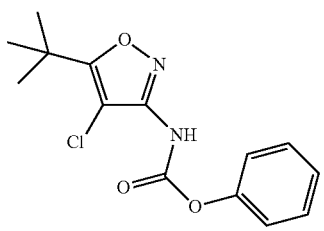 [SMILES: CC(C)(C)c1onc(NC(=O)Oc2ccccc2)c1Cl]

MS (ESI) m/z 295.02 (M+1).

132-C. [4-Chloro-5-(1-methyl-cyclopropyl)-isoxazol-3-yl]-carbamic acid phenyl ester

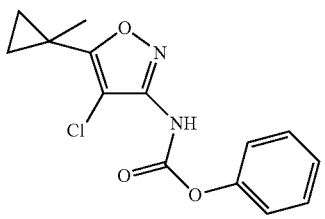 [SMILES: CC1(c2onc(NC(=O)Oc3ccccc3)c2Cl)CC1]

MS (ESI) m/z 293.01 (M+1).

EXAMPLE 133

133-A. (5-Cyclopropyl-4-methyl-isoxazol-3-yl)-carbamic acid phenyl ester

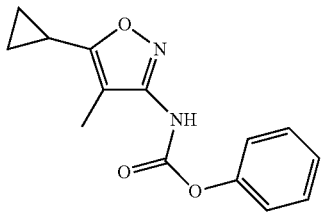 [SMILES: Cc1c(NC(=O)Oc2ccccc2)noc1C1CC1]

(5-Cyclopropyl-isoxazol-3-yl)-carbamic acid phenyl ester (0.368 g, 1.51 mmol) is dissolved in THF (10 mL) and cooled to −78° C. and flushed with nitrogen. N-butyllithium (2.17 mL, 3.47 mmol) is then added. The mixture is stirred in the dry ice/acetone bath for 30 minutes. Methyl iodide (0.10 mL, 1.66 mmol) is added neat and the reaction is stirred for 2 hours at −78° C. The reaction is quenched (0° C.) with 20 mL of a saturated solution of ammonium chloride, diluted with ethyl acetate and the organic layer is removed, dried (sodium sulfate) and concentrated to an oil that is purified via FCC (0-40% ethyl acetate:heptanes) to give the title compound as an oil. MS (ESI) m/z 259.20 (M+1).

The following are prepared with similar method.

133-B. (5-tert-Butyl-4-methyl-isoxazol-3-yl)-carbamic acid phenyl ester

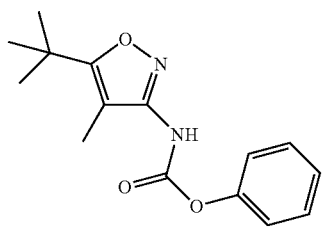 [SMILES: Cc1c(NC(=O)Oc2ccccc2)noc1C(C)(C)C]

MS (ESI) m/z 275.24 (M+1)

133-C. [4-Methyl-5-(1-methyl-cyclopropyl)-isoxazol-3-yl]-carbamic acid phenyl ester

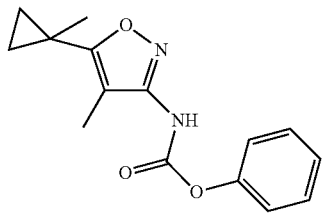 [SMILES: Cc1c(NC(=O)Oc2ccccc2)noc1C1(C)CC1]

MS (ESI) m/z 273.17 (M+1).

133-D. (5-tert-Butyl-4-methoxymethyl-isoxazol-3-yl)-carbamic acid phenyl ester

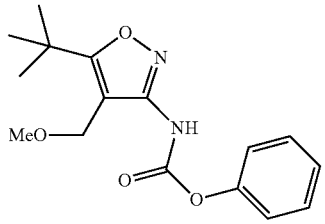 [SMILES: COCc1c(NC(=O)Oc2ccccc2)noc1C(C)(C)C]

MS (ESI) m/z 305.00 (M+1).

EXAMPLE 134

The following compounds are prepared with similar methods to those described for Examples 54 and 56.

| | Structure/Chemical Name | ¹H NMR (400 MHz) | MS (ESI) m/z (M + 1) |
|---|---|---|---|
| 134-A | 5-(6,7,8,9-Tetrahydro-5H-pyrimido[4,5-c]azepin-4-yloxy)-indole-1-carboxylic acid [5-(1-trifluoromethyl-cyclopropyl)-isoxazol-3-yl]-amide | (DMSO-$d_6$) δ ppm 8.36 (s, 1H), 8.30 (d, J = 9.1 Hz, 1H), 8.14 (d, J = 3.8 Hz, 1H), 7.40 (d, J = 2.5 Hz, 1H), 7.08 (dd, J = 9.0, 2.4 Hz, 1H), 7.04 (s, 1H), 6.74 (d, J = 3.5 Hz, 1H), 3.96 (s, 2H), 3.00-3.12 (m, 4H), 1.70-1.81 (m, 2H), 1.49-1.60 (m, 4H) | 499.1 |
| 134-B | 5-(6,7,8,9-Tetrahydro-5H-pyrimido[4,5-c]azepin-4-yloxy)-indole-1-carboxylic acid (5-cyclopropyl)-isoxazol-3-yl)-amide | (DMSO-$d_6$) δ ppm 8.35 (s, 1H), 8.30 (d, J = 9.1 Hz, 1H), 8.13 (d, J = 3.8 Hz 1H), 7.38 (d, J = 2.5 Hz, 1H), 7.06 (dd, J = 9.0, 2.1 Hz, 1H), 6.70 (d, J = 2.8 Hz, 1H), 6.64 (s, 1H), 3.93 (s, 2H), 2.96-3.13 (m, 4H), 2.09-2.22 (m, 1H), 1.68-1.82 (m, 2H), 1.03-1.15 (m, 2 H), 0.88-0.97 (m, 2H) | 431.1 |
| 134-C | 5-(6,7,8,9-Tetrahydro-5H-1,3,6-triaza-benzocyclohepten-4-yloxy)-indole-1-carboxylic acid (5-tert-butyl-isoxazol-3-yl)-amide | (DMSO-$d_6$) δ ppm 8.37 (s, 1H), 8.29 (d, J = 9.1 Hz, 1H), 8.15 (d, J = 3.5 Hz, 1H), 7.40 (d, J = 2.3 Hz, 1H), 7.09 (dd, J = 9.0, 2.4 Hz, 1H), 6.74 (d, J = 3.5 Hz, 1H), 6.68 (s, 1H), 4.03 (s, 2H), 3.02-3.13 (m, 4H), 1.63-1.75 (m, 2H), 1.34 (s, 9H) | 447.1 |
| 134-D | 5-(6,7,8,9-Tetrahydro-5H-pyrimido[4,5-c]azepin-4-yloxy)-indole-1-carboxylic acid (5-tert-butyl-isoxazol-3-yl)-amide | (DMSO-$d_6$) δ ppm 8.36 (s, 1H) 8.28 (d, J = 8.84 Hz, 1H) 8.15 (d, J = 3.79 Hz, 1H) 7.40 (d, J = 2.53 Hz, 1H) 7.09 (dd, J = 8.97, 2.40 Hz, 1H) 6.74 (d, J = 3.54 Hz, 1H) 6.68 (s, 1H) 3.94 (s, 2H) 3.01-3.10 (m, 4H) 1.69-1.81 (m, 2H) 1.34 (s, 9H) | 447.1 |

| Structure/Chemical Name | $^1$H NMR (400 MHz) | MS (ESI) m/z (M + 1) |
|---|---|---|
| 134-E 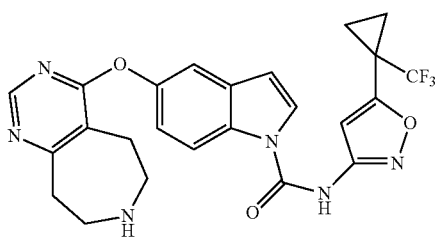<br>5-(6,7,8,9-Tetrahydro-5H-pyrimido[4,5-d]azepin-4-yloxy)-indole-1-carboxylic acid [5-(1-trifluoromethyl-cyclopropyl)-isoxazol-3-yl]-amide | (DMSO-d$_6$) δ ppm 8.32-8.38 (m, 2 H) 8.12 (d, J = 3.79 Hz, 1H) 7.37 (d, J = 2.27 Hz, 1H) 7.06 (dd, J = 8.84, 2.27 Hz, 1H) 7.03 (s, 1H) 6.68 (d, J = 3.54 Hz, 1H) 3.06 (t, J = 9.22 Hz, 4H) 2.89-2.98 (m, 4H) 1.49-1.57 (m, 4H) | 499.0 |
| 134-F 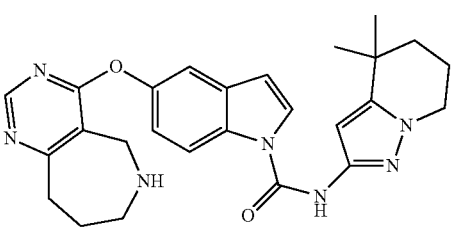<br>5-(6,7,8,9-Tetrahydro-5H-1,3,6-triaza-benzocyclohepten-4-yloxy)-indole-1-carboxylic acid (4,4-dimethyl-4,5,6,7-tetrahydro-pyrazolo[1,5-a]pyridine-2-yl)-amide | (DMSO-d$_6$) δ ppm 10.62 (s, 1H) 8.37 (s, 1H) 8.28 (d, J = 8.84 Hz, 1H) 8.14 (d, J = 3.79 Hz, 1H) 7.37 (d, J = 2.27 Hz, 1H) 7.06 (dd, J = 8.97, 2.40 Hz, 1H) 6.69 (d, J = 3.28 Hz, 1H) 6.40 (s, 1H) 4.02 (s, 2H) 3.96 (t, J = 6.19 Hz, 2H) 3.02-3.11 (m, 4H) 1.95-2.06 (m, 2 H) 1.64-1.74 (m, 4H) 1.30 (s, 6H) | 472.2 |
| 134-G 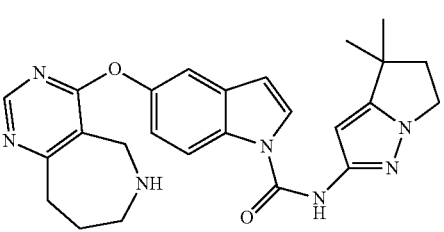<br>5-(6,7,8,9-Tetrahydro-5H-1,3,6-triaza-benzocyclohepten-4-yloxy)-indole-1-carboxylic acid (4,4-dimethyl-5,6,-dihydro-4H-pyrrolo[1,2-b]pyrazol-2-yl)-amide | (DMSO-d$_6$) δ ppm 10.61 (br. S., 1H) 8.37 (s, 1H) 8.27 (d, J = 8.84 Hz, 1H) 8.13 (d, J = 3.79 Hz, 1H) 7.38 (d, J = 2.53 Hz, 1H) 7.06 (dd, J = 8.84, 2.27 Hz, 1H) 6.70 (d, J = 3.28 Hz, 1H) 6.27 (s, 1H) 4.09 (t, J = 6.95 Hz, 2H) 4.04 (s, 2H) 3.08 (ddd, J = 10.80, 5.68, 5.49 Hz, 4H) 2.31-2.36 (m, 2H) 1.67-1.77 (m, 2H) 1.32 (s, 6H) | 458.2 |
| 134-H 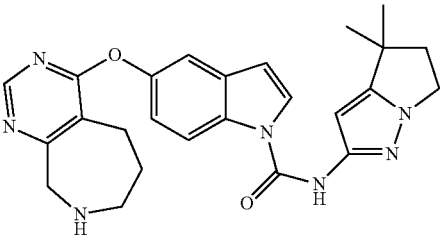<br>5-(6,7,8,9-Tetrahydro-5H-pyrimido[4,5-c]azepin-4-yloxy)-indole-1-carboxylic acid (4,4-dimethyl-5,6,-dihydro-4H-pyrrolo[1,2-b]pyrazol-2-yl)-amide | (DMSO-d$_6$) δ ppm 10.61 (s, 1H) 8.35 (s, 1H) 8.27 (d, J = 8.84 Hz, 1H) 8.13 (d, J = 3.79 Hz, 1H) 7.38 (d, J = 2.53 Hz, 1H) 7.06 (dd, J = 8.97, 2.40 Hz, 1H) 6.70 (d, J = 3.79 Hz, 1H) 6.27 (s, 1H) 4.09 (t, J = 6.82 Hz, 2H) 3.94 (s, 2H) 3.00-3.10 (m, 4H) 2.34 (t, J = 6.95 Hz, 2H) 1.70-1.79 (m, 2H) 1.32 (s, 6H) | 458.2 |

| | Structure/Chemical Name | ¹H NMR (400 MHz) | MS (ESI) m/z (M + 1) |
|---|---|---|---|
| 134-I | 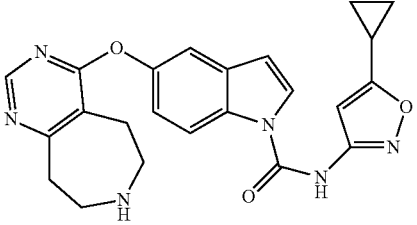<br>5-(6,7,8,9-Tetrahydro-5H-pyrimido[4,5-d]azepin-4-yloxy)-indole-1-carboxylic acid (5-cyclopropyl-isoxazol-3-yl)-amide | (DMSO-d₆) δ ppm 8.36 (s, 1H) 8.28 (d, J = 8.84 Hz, 1H) 8.14 (d, J = 3.54 Hz, 1H) 7.39 (d, J = 2.53 Hz, 1H) 7.08 (dd, J = 8.97, 2.40 Hz, 1H) 6.71 (d, J = 3.54 Hz, 1H) 6.64 (s, 1H) 3.04 (dt, J = 10.04, 4.96 Hz, 4H) 2.85-2.93 (m, 4H) 2.16 (tt, J = 8.37, 5.02 Hz, 1H) 1.03-1.10 (m, 2H) 0.89-0.96 (m, 2H) | 41.1 |
| 134-J | 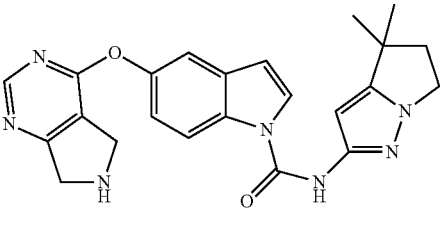<br>5-(6,7-Dihydro-5H-pyrrolo[3,4-d]pyrimidin-4-yloxy)-indole-1-carboxylic acid (4,4-dimethyl-5,6,-dihydro-4H-pyrrolo[1,2-b]pyrazol-2-yl)-amide | (DMSO-d₆) δ ppm 10.63 (br. S., 1H), 8.55 (s, 1H), 8.28 (d, J = 9.1 Hz, 1H), 8 15 (d, J = 3.5 Hz, 1H), 7.45 (d, J = 2.5 Hz, 1H), 7.12 (dd, J = 8.8, 2.5 Hz, 1H), 6.71 (d, J = 3.5 Hz, 1H), 6.27 (s, 1H), 4.05-4.13 (m, 6H), 2.34 (app t, J = 6.9 Hz, 2H), 1.32 (s, 6H) | 430.1 |
| 134-K | 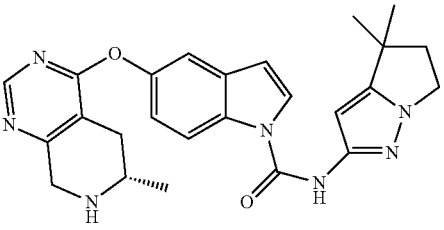<br>5-((S)-6-Methyl-5,6,7,8-tetrahydro-pyrido[3,4-d]pyrimidin-4-yloxy)-indole-1-carboxylic acid (4,4-dimethyl-5,6-dihydro-4H-pyrrolo[1,2-b]pyrazol-2-yl)-amide | (DMSO-d₆) δ ppm 10.62 (s, 1H), 8.40 (s, 1H), 8.27 (d, J = 9.1 Hz, 1H), 8.14 (d, J = 3.81 Hz, 1H), 7.41 (s, 1H), 7.08 (dd, J = 9.0, 2.4 Hz, 1H), 6.70 (d, J = 3.5 Hz, 1H), 6.27 (s, 1H), 4.09 (app t, J = 6.9 Hz, 2H), 3.75-3.98 (m, 2H), 2.89-3.05 (m, 1H), 2.85 (dd, J = 16.8, 3.4 Hz, 1H), 2.24-2.40 (m, 3H), 1.32 (s, 6H), 1.21 (d, J = 6.3 Hz, 3H) | 458.1 |
| 134-L | 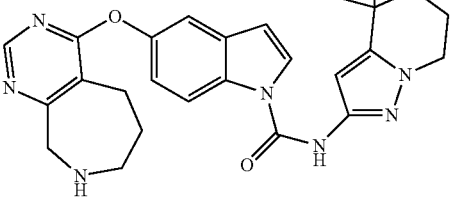<br>5-(6,7,8,9-Tetrahydro-5H-pyrimido[4,5-c]azepin-4-yloxy)-indole-1-carboxylic acid (4,4-dimethyl-4,5,6,7-tetrahydro-pyrazolo[1,5-a]pyridine-2-yl)-amide | (DMSO-d₆) δ ppm 10.62 (s, 1H) 8.37 (s, 1H) 8.28 (d, J = 9.09 Hz, 1H) 8.15 (d, J = 3.79 Hz, 1H) 7.38 (d, J = 2.27 Hz, 1H) 7.06 (dd, J = 8.84, 2.27 Hz, 1H) 6.69 (d, J = 3.54 Hz, 1H) 6.40 (s, 1H) 3.93-4.01 (m, 4H) 3.03-3.13 (m, 4H) 1.98-2.06 (m, 2H) 1.73-1.81 (m, 2H) 1.64-1.70 (m, 2H) 1.30 (s, 6H) | 47 |

| | Structure/Chemical Name | ¹H NMR (400 MHz) | MS (ESI) m/z (M + 1) |
|---|---|---|---|
| 134-M | 5-((S)-6-Methyl-5,6,7,8-tetrahydro-pyrido[3,4-d]pyrimidin-4-yloxy)-indole-1-carboxylic acid (4,4-dimethyl-4,5,6,7-tetrahydro-pyrazolo[1,5-a]pyridine-2-yl)-amide | (DMSO-d$_6$) δ ppm 10.64 (s, 1H), 8.53 (s, 1H), 8.31 (d, J = 8.8 Hz, 1H), 8.17 (d, J = 3.8 Hz, 1H), 7.43 (d, J = 2.3 Hz, 1H), 7.10 (dd, J = 9.0, 2.4 Hz, 1H), 6.72 (d, J = 3.8 Hz, 1H), 6.40 (s, 1H), 4.18-4.41 (m, 2H), 3.90-4.02 (m, 2H), 3.44-3.64 (m, 1H), 3.13 (dd, J = 17.6, 4.2 Hz, 1H), 2.66 (dd, J = 16.8, 10.7 Hz, 1H), 1.94-2.08 (m, 2H), 1.60-1.75 (m, 2H), 1.39 (d, J = 6.6 Hz, 3H), 1.30 (s, 6H) | 472.2 |
| 134-N | 5-((S)-6-Methyl-5,6,7,8-tetrahydro-pyrido[3,4-d]pyrimidin-4-yloxy)-indole-1-carboxylic acid (5,6-dihydro-4H-pyrrolo[1,2-b]pyrazol-2-yl)-amide | (DMSO-d$_6$) δ ppm 10.59 (s, 1H), 8.40 (s, 1H), 8.28 (d, J = 8.8 Hz, 1H), 8.15 (d, J = 3.8 Hz, 1H), 7.41 (d, J = 2.3 Hz, 1H), 7.08 (dd, J = 8.8, 2.3 Hz, 1H), 6.71 (d, J = 3.5 Hz, 1H), 6.28 (s, 1H), 4.04 (t, J = 7.2 Hz, 2H), 3.76-3.94 (m, 2H), 2.91-3.03 (m, 1H), 2.78-2.92 (m, 3 H), 2.54-2.62 (m, 1H), 2.33 (dd, J = 16.7, 10.4 Hz, 1H), 1.21 (d, J = 6.3 Hz, 3H) | 430.0 |
| 134-O | 5-(6,7,8,9-Tetrahydro-5H-1,3,6-triaza-benzocyclo-hepten-4-yloxy)-indole-1-carboxylic acid [5-(1-trifluoromethyl-cyclopropyl)-isoxazol-3-yl]-amide | (DMSO-d$_6$) δ ppm 8.39 (s, 1H) 8.32 (d, J = 9.09 Hz, 1H) 8.14 (d, J = 3.79 Hz, 1 H) 7.39 (d, J = 2.53 Hz, 1H) 7.08 (dd, J = 8.97, 2.40 Hz, 1H) 7.03 (s, 1H) 6.73 (d, J = 3.54 Hz, 1H) 4.07 (s, 2H) 3.10 (dt, J = 17.75, 5.40 Hz, 4H) 1.67-1.79 (m, 2H) 1.48-1.60 (m, 4H) | 499.0 |
| 134-P | 5-((S)-6-Methyl-5,6,7,8-tetrahydro-pyrido[3,4-d]pyrimidin-4-yloxy)-indole-1-carboxylic acid (3-chloro-4,4-dimethyl-5,6-dihydro-4H-pyrrolo[1,2-b]pyrazol-2-yl)-amide | (DMSO-d$_6$) δ ppm 10.10 (br. S., 1H), 8.39 (s, 1H), 8.23 (d, J = 9.1 Hz, 1H), 8.04 (d, J = 3.8 Hz, 1H), 7.43 (d, J = 2.5 Hz, 1H), 7.10 (dd, J = 9.0, 2.4 Hz, 1H), 6.77 (d, J = 3.8 Hz, 1H), 4.18 (t, J = 7.1 Hz, 2H), 3.78-3.97 (m, 2H), 2.90-3.04 (m, 1H), 2.85 (dd, J = 16.8, 3.9 Hz, 1H), 2.35-2.43 (m, 2H), 2.25-2.35 (m, 1H), 1.39 (s, 6H), 1.21 (d, J = 6.3 Hz, 3H) | 492.1, 494.0 |
| 134-Q | 5-(6,7,8,9-Tetrahydro-5H-1,3,6-triaza-benzocyclo-hepten-4-yloxy)-indole-1-carboxylic acid (5-cyclopropyl-isoxazol-3-yl)-amide | (DMSO-d$_6$) δ ppm 8.37 (s, 1H), 8.27 (d, J = 8.8 Hz, 1H), 8.14 (d, J = 3.8 Hz, 1H), 7.39 (d, J = 2.5 Hz, 1H), 7.09 (dd, J = 9.0, 2.4 Hz, 1H), 6.73 (d, J = 3.8 Hz, 1H), 6.65 (s, 1H), 4.04 (s, 2H), 3.03-3.14 (m, 4H), 2.12-2.22 (m, 1H), 1.67-1.76 (m, 2H), 1.04-1.12 (m, 2H), 0.91-0.97 (m, 2H) | 431.1 |

| | Structure/Chemical Name | ¹H NMR (400 MHz) | MS (ESI) m/z (M + 1) |
|---|---|---|---|
| 134-R | 5-(6,7-Dihydro-5H-pyrrolo[3,4-d]pyrimidin-4-yloxy)-indole-1-carboxylic acid (5-dimethylcarbamoyl-1-methyl-1H-pyrazol-3-yl)-amide | (MeOD) δ ppm 8.53 (s, 1H) 8.34 (d, J = 9.09 Hz, 1H) 7.90 (d, J = 3.79 Hz, 1H) 7.42 (d, J = 2.53 Hz, 1H) 7.12 (dd, J = 8.84, 2.27 Hz, 1H) 6.79 (s, 1H) 6.72 (d, J = 3.54 Hz, 1H) 4.20 (d, J = 8.08 Hz, 4H) 3.86 (s, 3H) 3.19 (s, 3H) 3.13 (s, 3H) | 447.0 |
| 134-S | 5-((S)-6-Methyl-5,6,7,8-tetrahydro-pyrido[3,4-d]pyrimidin-4-yloxy)-indole-1-carboxylic acid [1-methyl-5-(1-methyl-cyclopropyl)-1H-pyrazol-3-yl]-amide | (MeOD) δ ppm 8.37 (s, 1H) 8.31 (d, J = 9.09 Hz, 1H) 7.86 (d, J = 3.54 Hz 1H) 7.38 (d, J = 2.27 Hz, 1H) 7.08 (dd, J = 8.97, 2.15 Hz, 1H) 6.70 (d, J = 3.03 Hz, 1H) 6.32 (d, J = 1.26 Hz, 1H) 4.00 (d, J = 5.05 Hz, 2H) 3.86 (s, 3H) 3.12 (ddd, J = 3.35, 1.58, 1.39 Hz, 1H) 3.00 (ddd, J = 17.05, 2.02, 1.89 Hz, 1H) 2.51 (s, 1H) 1.38 (s, 3H) 1.34 (d, J = 6.32 Hz, 3H) 0.89 (br. S., 2H) 0.77-0.84 (m, 2H) | 458.0 |
| 134-T | 5-(5,6,7,8-Tetrahydro-pyrido[3,4-d]pyrimidin-4-yloxy)-indole-1-carboxylic acid [2-methyl-5-(1-methyl-cyclopropyl)-2H-pyrazol-3-yl]-amide | (DMSO-d₆) δ ppm 8.40 (s, 1H) 8.25 (d, J = 9.09 Hz, 1H) 8.04 (d, J = 3.54 Hz, 1H) 7.44 (d, J = 2.27 Hz, 1H) 7.10 (dd, J = 8.97, 2.40 Hz, 1H) 6.77 (d, J = 3.54 Hz, 1H) 6.05 (s, 1H) 3.83 (s, 2H) 3.65 (s, 3H) 3.04 (t, J = 5.81 Hz, 2H) 2.73 (t, J = 5.68 Hz, 2H) 1.38 (s, 3H) 0.85-0.88 (m, 2H) 0.67-0.70 (m, 2H) | 444.0 |
| 134-U | 5-(5,6,7,8-Tetrahydro-pyrido[3,4-d]pyrimidin-4-yloxy)-indole-1-carboxylic acid [1-methyl-5-(2,2,2-trifluoro-1-methoxy-1-methyl-ethyl)-1H-pyrazol-3-yl]-amide | (DMSO-d₆) δ ppm 8.37 (s, 1H) 8.32 (d, J = 9.09 Hz, 1H) 7.88 (d, J = 3.79 Hz, 1H) 7.39 (d, J = 1.77 Hz, 1H) 7.09 (dd, J = 9.09, 2.27 Hz, 1H) 6.74 (s, 1H) 6.71 (d, J = 3.79 Hz, 1H) 3.93 – 3.98 (m, 5H) 3.35 (s, 3H) 3.18 (t, J = 5.94 Hz, 2H) 2.88 (t, J = 5.68 Hz, 2H) 1.84 (s, 3H) | 51 |

-continued

| | Structure/Chemical Name | $^1$H NMR (400 MHz) | MS (ESI) m/z (M + 1) |
|---|---|---|---|
| 134-V | 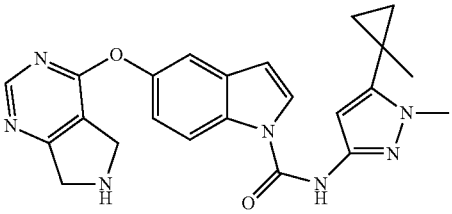<br>5-(6,7-Dihydro-5H-pyrrolo[3,4-d]pyrimidin-4-yloxy)-indole-1-carboxylic acid [1-methyl-5-(1-methyl-cyclopropyl)-1H-pyrazol-3-yl]-amide | (MeOD) δ ppm 8.53 (s, 1H) 8.31 (d, J = 9.09 Hz, 1H) 7.87 (d, J = 3.79 Hz, 1H) 7.42 (d, J = 2.27 Hz, 1H) 7.11 (dd, J = 8.97, 2.40 Hz, 1H) 6.71 (d, J = 3.79 Hz, 1H) 6.33 (s, 1H) 4.19 (d, J = 6.57 Hz, 4H) 3.86 (s, 3H) 1.38 (s, 3H) 0.88-0.91 (m, 2H) 0.79-0.83 (m, 2H) | 430.0 |
| 134-W | 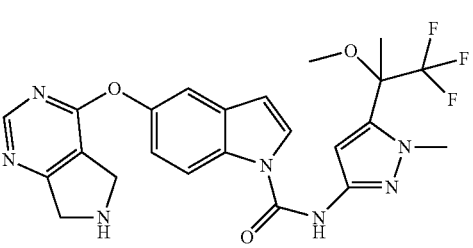<br>5-(6,7-Dihydro-5H-pyrrolo[3,4-d]pyrimidin-4-yloxy)-indole-1-carboxylic acid [1-methyl-5-(2,2,2-trifluoro-1-methoxy-1-methyl-ethyl)-1H-pyrazol-3-yl]-amide | (DMSO-d$_6$) δ ppm 8.55 (s, 1H) 8.30 (d, J = 9.09 Hz, 1H) 8.17 (d, J = 3.79 Hz, 1H) 7.45 (d, J = 2.78 Hz, 1H) 7.12 (dd, J = 9.09, 2.27 Hz, 1H) 6.75 (s, 1H) 6.73 (d, J = 3.79 Hz, 1H) 4.06-4.12 (m, 4H) 3.91 (s, 3H) 3.17 (s, 3H) 1.81 (s, 3H) | 501.9 |
| 134-X | 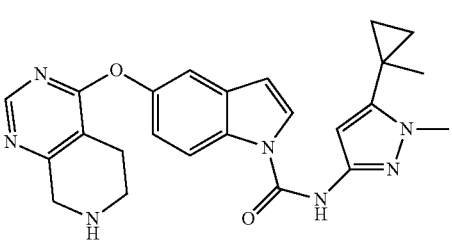<br>5-(5,6,7,8-Tetrahydro-pyrido[3,4-d]pyrimidin-4-yloxy)-indole-1-carboxylic acid [1-methyl-5-(1-methyl-cyclopropyl)-1H-pyrazol-3-yl]-amide | (MeOD) δ ppm 8.36 (s, 1H) 8.30 (d, J = 8.84 Hz, 1H) 7.85 (d, J = 3.79 Hz, 1H) 7.37 (d, J = 2.27 Hz, 1H) 7.07 (dd, J = 8.84, 2.27 Hz, 1H) 6.69 (d, J = 3.79 Hz, 1H) 6.32 (s, 1H) 3.93 (s, 2H) 3.85 (s, 3H) 3.16 (t, J = 5.94 Hz, 2H) 2.86 (t, J = 5.81 Hz, 2H) 1.37 (s, 3H) 0.87-0.90 (m, 2H) 0.78-0.81 (m, 2H) | 444.1 |
| 134-Y | 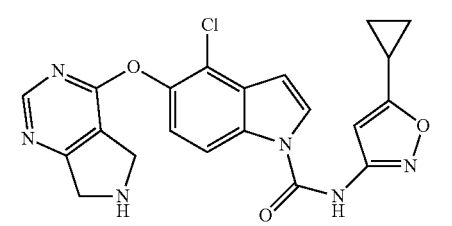<br>4-Chloro-5-(6,7-dihydro-5H-pyrrolo[3,4-d]pyrimidin-4-yloxy)-indole-1-carboxylic acid (5-cyclopropyl-isoxazol-3-yl)-amide | (DMSO-d$_6$) 8.55 (s, 1H) 8.26 (dd, J = 6.32, 2.53 Hz, 2H) 7.33 (d, J = 8.84 Hz, 1H) 6.83 (d, J = 3.79 Hz, 1H) 6.65 (s, 1H) 4.21 (s, 2H) 4.12 (s, 2H) 2.10-2.25 (m, 1H) 0.84-1.21 (m, 4H) | 437.11 |
| 134-Z | 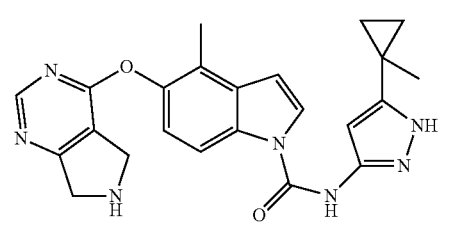<br>5-(6,7-Dihydro-5H-pyrrolo[3,4-d]pyrimidin-4-yloxy)-4-methyl-indole-1-carboxylic acid [5-(1-methyl-cyclopropyl)-1H-pyrazol-3-yl]-amide | (DMSO-d$_6$) ppm 12.13 (br. S., 1H) 10.56 (br. S., 1H) 8.52 (s, 1H) 8.12-8.17 (m, 2H) 7.05 (d, J = 8.84 Hz, 1H) 6.81 (d, J = 3.79 Hz, 1H) 6.29 (br. S., 1H) 4.07-4.14 (m, 4H) 2.22-2.25 (m, 3H) 1.41 (s, 3H) 0.91-0.94 (m, 2H) 0.76-0.79 (m, 2H) | 430.19 |

-continued

| | Structure/Chemical Name | $^1$H NMR (400 MHz) | MS (ESI) m/z (M + 1) |
|---|---|---|---|
| 134-AA | 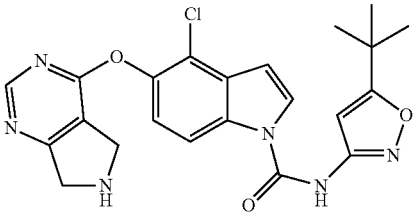<br>4-Chloro-5-(6,7-dihydro-5H-pyrrolo[3,4-d]pyrimidin-4-yloxy)-indole-1-carboxylic acid (5-tert-butyl-isoxazol-3-yl)-amide | (DMSO-d$_6$) ppm 8.55 (s, 1H) 8.23-8.32 (m, 2H) 7.33 (d, J = 8.84 Hz, 1H) 6.83 (d, J = 3.54 Hz, 1H) 6.67 (s, 1H) 4.21 (s, 2H) 4.12 (s, 2H) 1.34 (s, 9H) | 453.14 |
| 134-AB | 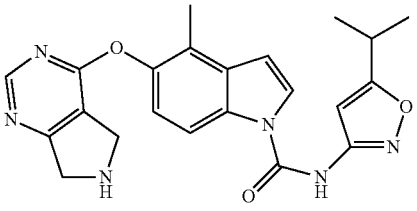<br>5-(6,7-Dihydro-5H-pyrrolo[3,4-d]pyrimidin-4-yloxy)-4-methyl-indole-1-carboxylic acid (5-isopropyl-isoxazol-3-yl)-amide | (DMSO-d$_6$) ppm 8.52 (s, 1H) 8.11-8.16 (m, 2H) 7.09 (d, J = 9.09 Hz, 1H) 6.88 (d, J = 3.79 Hz, 1H) 6.69 (s, 1H) 4.14 (s, 2H) 4.08-4.10 (m, 2H) 3.11 (t, J = 6.57 Hz, 1H) 2.24 (s, 3H) 1.29 (d, J = 7.07 Hz, 6H) | 419.18 |
| 134-AC | 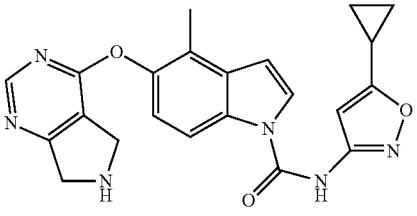<br>5-(6,7-Dihydro-5H-pyrrolo[3,4-d]pyrimidin-4-yloxy)-4-methyl-indole-1-carboxylic acid (5-cyclopropyl-isoxazol-3-yl)-amide | (DMSO-d$_6$) ppm 8.52 (s, 1H) 8.10-8.15 (m, 2H) 7.09 (d, J = 8.84 Hz, 1H) 6.87 (d, J = 3.79 Hz, 1H) 6.65 (s, 1H) 4.14 (s, 2H) 4.06-4.10 (m, 2H) 2.24 (s, 3H) 2.17 (s, 1H) 1.06-1.11 (m, 2H) 0.92-0.96 (m, 2H) | 417.16 |
| 134-AD | 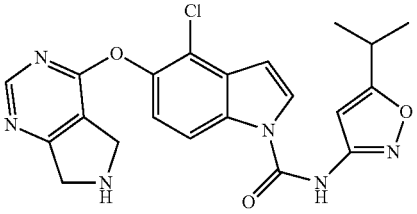<br>4-Chloro-5-(6,7-dihydro-5H-pyrrolo[3,4-d]pyrimidin-4-yloxy)-indole-1-carboxylic acid (5-cyclopropyl-isoxazol-3-yl)-amide | (DMSO-d$_6$) ppm 8.55 (s, 1H) 8.27 (dd, J = 6.06, 2.27 Hz, 2H) 7.33 (d, J = 9.09 Hz, 1H) 6.83 (d, J = 3.79 Hz, 1H) 6.69 (s, 1H) 4.22 (s, 2H) 4.13 (s, 2H) 3.11 (quin, J = 6.88 Hz, 1H) 1.29 (d, J = 6.82 Hz, 6H) | 439.12 |
| 134-AE | 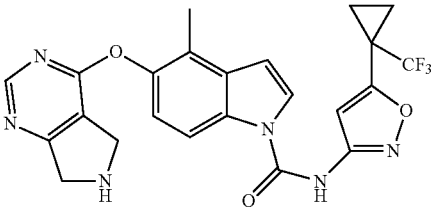<br>5-(6,7-Dihydro-5H-pyrrolo[3,4-d]pyrimidin-4-yloxy)-4-methyl-indole-1-carboxylic acid [5-(1-trifluoro-methyl-cyclopropyl)-isoxazol-3-yl]-amide | (DMSO-d$_6$) ppm 8.53 (s, 1H) 8.11-8.16 (m, 2H) 7.10 (d, J = 9.09 Hz, 1H) 7.05 (s, 1H) 6.89 (d, J = 3.79 Hz, 1H) 4.17 (s, 2H) 4.11 (s, 2H) 2.24 (s, 3H) 1.53-1.60 (m, 4H) | 485.15 |

| | Structure/Chemical Name | ¹H NMR (400 MHz) | MS (ESI) m/z (M + 1) |
|---|---|---|---|
| 134-AF | 4-Methyl-5-((S)-6-methyl-5,6,7,8-tetrahydro-pyrido[3,4-d]pyrimidin-4-yloxy)-indole-1-carboxylic acid [5-(1-trifluoromethyl-cyclopropyl)-isoxazol-3-yl]-amide | (DMSO-$d_6$) ppm 8.37 (s, 1H) 8.13 (dd, J = 6.32, 2.53 Hz, 2H) 7.04-7.07 (m, 2 H) 6.87 (d, J = 3.79 Hz, 1H) 3.89 (d, J = 10.36 Hz, 2H) 3.00 (ddd, J = 10.11, 6.32, 4.04 Hz, 1H) 2.90 (dd, J = 16.80, 3.41 Hz, 1H) 2.32-2.45 (m, 1H) 2.22 (s, 3H) 1.52-1.60 (m, 4H) 1.23 (d, J = 6.32 Hz, 3H) | 513.18 |
| 134-AG | 4-Methyl-5-((S)-6-methyl-5,6,7,8-tetrahydro-pyrido[3,4-d]pyrimidin-4-yloxy)-indole-1-carboxylic acid (5-cyclopropyl-isoxazol-3-yl)-amide | (DMSO-$d_6$) ppm 8.36 (s, 1H) 8.10-8.14 (m, 2H) 7.05 (d, J = 9.09 Hz, 1H) 6.86 (d, J = 3.79 Hz, 1H) 6.65 (s, 1H) 3.88 (d, J = 9.60 Hz, 2H) 2.94-3.02 (m, 1H) 2.88 (dd, J = 16.93, 3.79 Hz, 1H) 2.37 (dd, J = 16.93, 10.61 Hz, 1H) 2.14-2.23 (m, 4H) 1.22 (d, J = 6.06 Hz, 3H) 1.06-1.11 (m, 2H) 0.92-0.96 (m, 2H) | 445.19 |
| 134-AH | 4-Methyl-5-((S)-6-methyl-5,6,7,8-tetrahydro-pyrido[3,4-d]pyrimidin-4-yloxy)-indole-1-carboxylic acid [5-(1-methyl-cyclopropyl)-isoxazol-3-yl]-amide | (DMSO-$d_6$) ppm 8.36 (s, 1H) 8.09-8.16 (m, 2H) 7.05 (d, J = 8.84 Hz, 1H) 6.86 (d, J = 3.79 Hz, 1H) 6.67 (s, 1H) 3.80-3.96 (m, 2H) 2.87 (s, 1H) 2.67 (t, J = 1.89 Hz, 1H) 2.30-2.40 (m, 1H) 2.22 (s, 3H) 1.46 (s, 3H) 1.23 (d, J = 6.32 Hz, 3H) 1.11-1.18 (m, 2H) 0.90-0.97 (m, 2H) | 459.21 |
| 134-AI | 4-Methyl-5-((S)-6-methyl-5,6,7,8-tetrahydro-pyrido[3,4-d]pyrimidin-4-yloxy)-indole-1-carboxylic acid (5-isopropyl-isoxazol-3-yl)-amide | (DMSO-$d_6$) ppm 8.36 (s, 1H) 8.09-8.16 (m, 2H) 7.05 (d, J = 8.84 Hz, 1H) 6.86 (d, J = 3.79 Hz, 1H) 6.69 (s, 1H) 3.81-3.95 (m, 2H) 3.10 (d, J = 7.07 Hz, 1H) 2.99 (br. S., 1H) 2.89 (d, J = 14.65 Hz, 1H) 2.31-2.43 (m, 1H) 2.22 (s, 3 H) 1.29 (d, J = 6.82 Hz, 6H) 1.23 (d, J = 6.32 Hz, 3H) | 447 |

| | Structure/Chemical Name | ¹H NMR (400 MHz) | MS (ESI) m/z (M + 1) |
|---|---|---|---|
| 134-AJ | 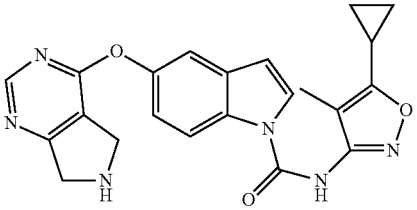<br>5-(6,7-Dihydro-5H-pyrrolo[3,4-d]pyrimidin-4-yloxy)-indole-1-carboxylic acid (5-cyclopropyl-4-methyl-isoxazol-3-yl)-amide | (DMSO-d₆) ppm 8.55 (s, 1H) 8.25 (d, J = 9.09 Hz, 1H) 8.07 (d, J = 3.54 Hz, 1H) 7.48 (d, J = 2.27 Hz, 1H) 7.15 (dd, J = 8.97, 2.40 Hz, 1H) 6.78 (d, J = 3.54 Hz, 1H) 4.10 (d, J = 14.91 Hz, 4H) 2.12-2.19 (m, 1H) 1.95 (s, 3H) 0.94-1.10 (m, 4H) | 417.03 |
| 134-AK | 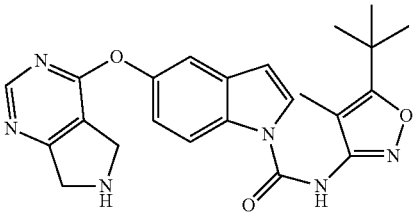<br>5-(6,7-Dihydro-5H-pyrrolo[3,4-d]pyrimidin-4-yloxy)-indole-1-carboxylic acid (5-tert-butyl-4-methyl-isoxazol-3-yl)-amide | (DMSO-d₆) ppm 8.55 (s, 1H) 8.24 (d, J = 8.84, 1H) 8.23 (s, 1H) 8.07 (d, J = 3.79 Hz, 1H) 7.48 (d, J = 2.27 Hz, 1 H) 7.14 (dd, J = 8.97, 2.40 Hz, 1H) 6.79 (d, J = 3.79 Hz, 1H) 4.11 (d, J = 15.16 Hz, 4H) 1.98 (s, 3H) 1.38 (s, 9H) | 433.19 |
| 134-AL | 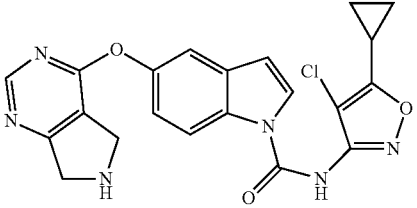<br>5-(6,7-Dihydro-5H-pyrrolo[3,4-d]pyrimidin-4-yloxy)-indole-1-carboxylic acid (4-chloro-5-cyclopropyl-isoxazol-3-yl)-amide | (DMSO-d₆) ppm 8.58 (s, 1H) 8.29 (d, J = 9.09 Hz, 1H) 8.04 (d, J = 3.79 Hz, 1 H) 7.48 (d, J = 2.27 Hz, 1H) 7.14 (dd, J = 8.97, 2.40 Hz, 1H) 6.77 (d, J = 3.54 Hz, 1H) 4.15 (d, J = 13.89 Hz, 4H) 2.17-2.24 (m, 1H) 1.07-1.20 (m, 4H) | 437.11 |
| 134-AM | 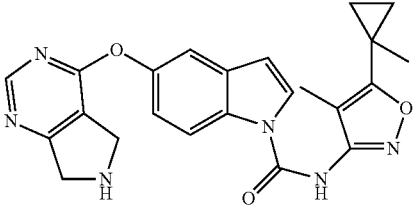<br>5-(6,7-Dihydro-5H-pyrrolo[3,4-d]pyrimidin-4-yloxy)-indole-1-carboxylic acid [4-methyl-5-(1-methyl-cyclopropyl)-isoxazol-3-yl]-amide | (DMSO-d₆) ppm 8.55 (s, 1H) 8.24 (d, J = 9.09 Hz, 1H) 8.06 (d, J = 3.79 Hz, 1 H) 7.48 (d, J = 2.27 Hz, 1H) 7.14 (dd, J = 8.97, 2.40 Hz, 1H) 6.79 (d, J = 3.54 Hz, 1H) 4.08-4.14 (m, 4H) 1.96 (s, 3 H) 1.41 (s, 3H) 1.03 (d, J = 2.27 Hz, 2 H) 0.83-0.87 (m, 2H). | 431.18 |
| 134-AN | 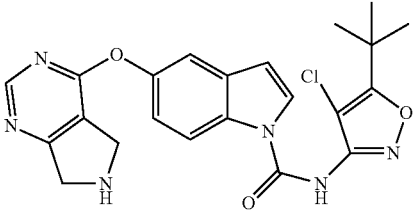<br>5-(6,7-Dihydro-5H-pyrrolo[3,4-d]pyrimidin-4-yloxy)-indole-1-carboxylic acid (5-tert-butyl-4-chloro-isoxazol-3-yl)-amide | (DMSO-d₆) ppm 8.56 (s, 1H) 8.28 (s, 1 H) 8.03 (d, J = 3.79 Hz, 1H) 7.47 (d, J = 2.53 Hz, 1H) 7.13 (dd, J = 9.09, 2.27 Hz, 1H) 6.77 (d, J = 3.79 Hz, 1H) 4.10-4.15 (m, 4H) 1.43 (s, 9H) | 453.14 |

| | Structure/Chemical Name | $^1$H NMR (400 MHz) | MS (ESI) m/z (M + 1) |
|---|---|---|---|
| 134-AO | 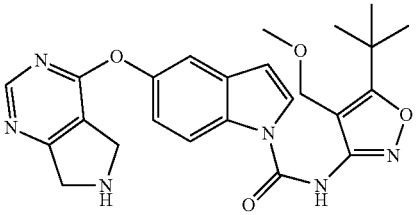<br>5-(6,7-Dihydro-5H-pyrrolo[3,4-d]pyrimidin-4-yloxy)-indole-1-carboxylic acid (5-tert-butyl-4-methoxymethyl-isoxazol-3-yl)-amide | (DMSO-$d_6$) ppm 8.55 (s, 1H) 8.25 (s, 1 H) 8.22 (s, 1H) 8.05 (d, J = 3.54 Hz, 1 H) 7.48 (d, J = 2.27 Hz, 1H) 7.15 (dd, J = 8.84, 2.53 Hz, 1H) 6.79 (d, J = 3.79 Hz, 1H) 4.32 (s, 2H) 4.13 (s, 2H) 4.09 (d, J = 1.77 Hz, 2H) 3.19 (s, 3H) 1.40 (s, 9H) | 463.20 |
| 134-AP | 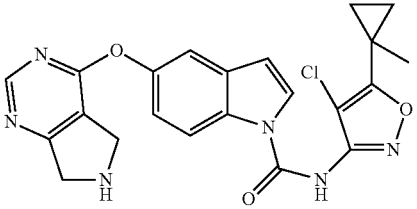<br>5-(6,7-Dihydro-5H-pyrrolo[3,4-d]pyrimidin-4-yloxy)-indole-1-carboxylic acid [4-chloro-5-(1-methyl-cyclopropyl)-isoxazol-3-yl]-amide | (DMSO-$d_6$) ppm 8.57 (s, 1H) 8.28 (d, J = 9.09 Hz, 1H) 8.02 (d, J = 3.79 Hz, 1 H) 7.48 (d, J = 2.27 Hz, 1H) 7.14 (dd, J = 8.84, 2.27 Hz, 1H) 6.77 (d, J = 3.54 Hz, 1H) 4.14 (d, J = 12.88 Hz, 4H) 1.48 (s, 3H) 1.21-1.25 (m, 2H) 0.93-0.96 (m, 2H). | 451.12 |
| 134-AQ | 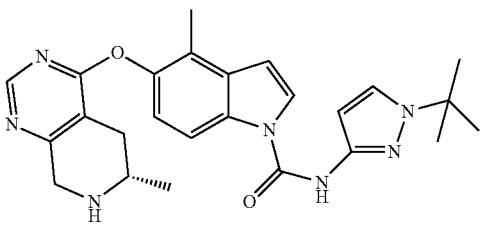<br>4-Methyl-5-((S)-6-methyl-5,6,7,8-tetrahydro-pyrido[3,4-d]pyrimidin-4-yloxy)-indole-1-carboxylic acid (1-tert-butyl-1H-pyrazol-3-yl)-amide | (DMSO-$d_6$) ppm 10.69 (s, 1H) 8.35 (s, 1H) 8.18 (d, J = 3.79 Hz, 1H) 8.13 (d, J = 9.09 Hz, 1H) 7.78 (d, J = 2.53 Hz, 1H) 7.01 (d, J = 8.84 Hz, 1H) 6.80 (d, J = 3.79 Hz, 1H) 6.52 (d, J = 2.53 Hz, 1H) 3.82-3.93 (m, 2H) 2.82-2.95 (m, 2H) 2.31-2.42 (m, 1H) 2.21 (s, 3H) 1.54 (s, 9H) 1.22 (d, J = 6.32 Hz, 3H) | 460.2 |
| 134-AR | 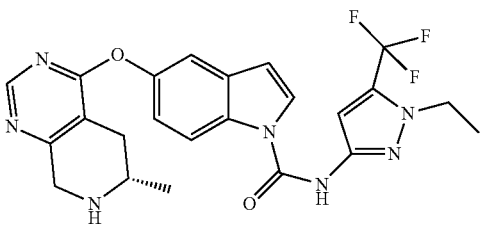<br>((S)-6-Methyl-5,6,7,8-tetrahydro-pyrido[3,4-d]pyrimidin-4-yloxy)-indole-1-carboxylic acid (1-ethyl-5-trifluoro-methyl-1H-pyrazol-3-yl)-amide | (DMSO-$d_6$) ppm 8.40 (s, 1H) 8.29 (d, J = 8.84 Hz, 1H) 8.18 (d, J = 3.54 Hz, 1 H) 7.42 (d, J = 2.02 Hz, 1H) 7.06-7.24 (m, 2H) 6.74 (d, J = 3.79 Hz, 1H) 4.18-4.37 (m, 2H) 3.84-3.93 (m, 2H) 2.95-2.97 (m, 1H) 2.85 (d, J = 16.67 Hz, 1 H) 2.29-2.35 (m, 1H) 1.38-1.42 (m, 3H) 1.21 (d, J = 6.32 Hz, 3H) | 486.1 |

| | Structure/Chemical Name | $^1$H NMR (400 MHz) | MS (ESI) m/z (M + 1) |
|---|---|---|---|
| 134-AS | 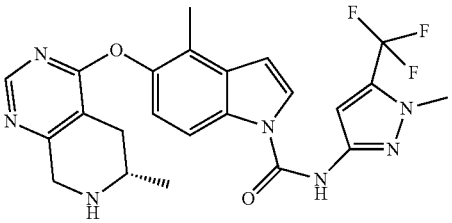<br>4-Methyl-5-((S)-6-methyl-5,6,7,8-tetrahydro-pyrido[3,4-d]pyrimidin-4-yloxy)-indole-1-carboxylic acid (1-methyl-5-trifluoromethyl-1H-pyrazol-3-yl)-amide | (DMSO-d$_6$) ppm 11.02 (br. s., 1H) 8.36 (s, 1H) 8.02-8.21 (m, 2H) 6.96-7.14 (m, 2H) 6.85 (d, J = 3.79 Hz, 1H) 3.5 (s, 3H) 3.88 (d, J = 9.60 Hz, 2H) 2.93-3.04 (m, 1H) 2.89-2.93 (m, 1H) 2.36-2.40 (m, 1H) 2.22 (s, 3H) 1.22 (d, J = 6.32 Hz, 3H) | 486.0 |
| 134-AT | 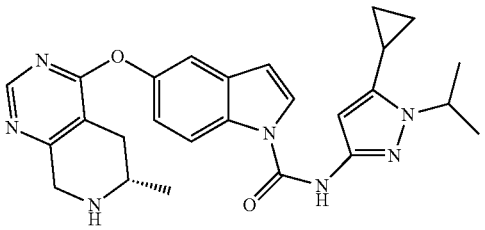<br>5-((S)-6-Methyl-5,6,7,8-tetrahydro-pyrido[3,4-d]pyrimidin-4-yloxy)-indole-1-carboxylic acid (5-cyclopropyl-1-isopropyl-1H-pyrazol-3-yl)-amide | (DMSO-d$_6$) ppm 10.63 (s, 1H) 8.39 (s, 1H) 8.28 (d, J = 8.84 Hz, 1H) 8.18 (d, J = 3.79 Hz, 1H) 7.39 (d, J = 2.27 Hz, 1H) 7.07 (dd, J = 8.97, 2.40 Hz, 1H) 6.68 (d, J = 3.54 Hz, 1H) 6.16 (s, 1H) 4.76 (quin, J = 6.57 Hz, 1H) 3.77-3.96 (m, 2H) 2.90-3.03 (m, 1H) 2.84 (dd, J = 16.80, 3.66 Hz, 1H) 2.33 (dd, J = 16.04, 10.23 Hz, 1H) 1.86-1.98 (m, 1H) 1.42 (d, J = 6.57 Hz, 6H) 1.21 (d, J = 6.32 Hz, 3H) 0.87-1.03 (m, 2H) 0.59-0.76 (m, 2H) | 472.0 |
| 134-AU | 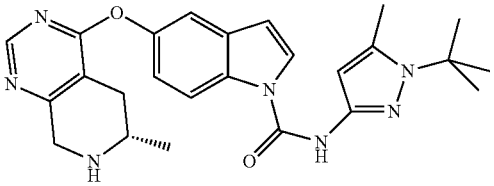<br>5-((S)-6-Methyl-5,6,7,8-tetrahydro-pyrido[3,4-d]pyrimidin-4-yloxy)-indole-1-carboxylic acid (1-tert-butyl-5-methyl-1H-pyrazol-3-yl)-amide | (DMSO-d$_6$) ppm 8.36 (s, 1H) 8.30 (d, J = 8.84 Hz, 1H) 7.85 (d, J = 3.54 Hz, 1H) 7.37 (d, J = 2.27 Hz, 1H) 7.07 (dd, J = 8.97, 2.15 Hz, 1H) 6.68 (d, J = 3.28 Hz, 1H) 6.37 (s, 1H) 3.98 (d, J = 4.55 Hz, 2H) 2.94-3.11 (m, 2H) 2.41-2.49 (m, 4H) 1.63 (s, 9H) 1.32 (d, J = 6.32 Hz, 3H). | 460.2 |

EXAMPLE 135

135-A. (−)-5-((S)-7-Acetyl-6-methyl-5,6,7,8-tetrahydro-pyrido[3,4-d]pyrimidin-4-yloxy)-indole-1-carboxylic acid (5-cyclopropyl-isoxazol-3-yl)-amide

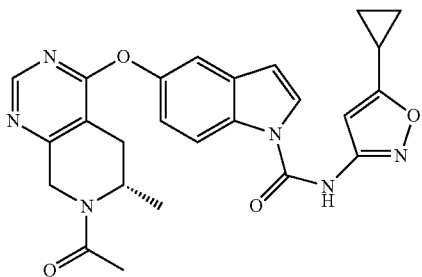 [SMILES: CC(=O)N1Cc2ncnc(Oc3ccc4c(ccn4C(=O)Nc4cc(C5CC5)on4)c3)c2C[C@@H]1C]

To a solution of Example 56-S (0.350 g, 0.813 mmol), Et$_3$N (0.57 mL, 4.07 mmol) and DCM (5 mL) is added acetic anhydride (0.084 mL, 0.894 mmol). After 0.5 h the solution is concentrated and the residue partitioned between DCM and saturated NaHCO$_3$. The organic layer is washed with brine. Following drying the organic layer is concentrated and the residue separated via FCC (1-10% MeOH/DCM) to give the title compound. MS (ESI) m/z 473.2 (M+1); At 27° C. in DMSO-d$_6$ solution Example 135-A exists as a mixture of amide rotamers. While not wishing to be bound by theory, hindered rotation about the nitrogen carbonyl bond results in two magnetically distinct environments for some protons. $^1$H NMR is acquired at 80° C. which is above the temperature at which the separate rotamer $^1$H peaks coalesce. (400 MHz, DMSO-d$_6$) δ ppm 10.95 (br. S., 1 H) 8.50 (s, 1 H) 8.28 (d, J=8.97 Hz, 1 H) 8.13 (d, J=3.66 Hz, 1 H) 7.45 (d, J=2.27 Hz, 1 H) 7.14 (dd, J=9.03, 2.34 Hz, 1 H) 6.73 (d, J=3.66 Hz, 1 H) 6.59 (s, 1 H) 4.61-5.43 (m, 2 H) 4.22 (br. S., 1 H) 2.99 (br. S., 1 H) 2.79-2.89 (m, 1 H) 2.11-2.19 (m, 4 H) 1.17 (d, J=7.33 Hz, 3 H) 1.06-1.13 (m, 2 H) 0.91-0.96 (m, 2 H).

The following compounds are prepared with similar method. Such compounds are also prepared from the corresponding carboxylic acid and amine using peptide coupling reagents (e.g. HATU see Example 40) or using the corresponding carboxylic acid chloride. Example 135-BN is prepared with similar method using ethyl chloroformate. For Examples 135-I, J, L, P, AC, AD, AE, AF, AG, AH removal of a BOC group from the nitrogen following amide formation is accomplished via treatment of the parent compound with TFA in DCM as described in previous examples.

| Structure/Chemical Name | ¹H NMR (400 MHz) | MS (ESI) m/z (M + 1) |
|---|---|---|
| 135-B[a]<br><br>(+)-5-(1-7-Acetyl-6-methyl-5,6,7,8-tetrahydro-pyrido[3,4-d]pyrimidin-4-yloxy)-indole-1-carboxylic acid (5-cyclopropyl-isoxazol-3-yl)-amide | (DMSO-d₆) δ ppm 11.22 (s, 1H), 8.52 (br. S.), 8.28 (d, J = 8.8 Hz, 1H), 8.16 (d, J = 3.5 Hz, 1H), 7.46 (d, J = 2.5 Hz, 1H), 7.15 (dd, J = 9.0, 2.4 Hz, 1H), 6.76 (d, J = 3.3 Hz, 1H), 6.65 (s, 1H), 5.16-5.22 (m), 5.13 (d), 4.73-4.79 (m), 4.48-4.63 (m), 4.04 (d), 3.04-3.15 (m), 2.78-2.88 (m), 2.09-2.23 (m), 1.21 (d, J = 6.6 Hz, 2H), 1.03-1.13 (m, 3H), 0.89-0.98 (m, 2H) | 473.0 |
| 135-C[b]<br><br>5-((S)-7-Acetyl-6-methyl-5,6,7,8-tetrahydro-pyrido[3,4-d]pyrimidin-4-yloxy)-indole-1-carboxylic acid [5-(1-trifluoromethyl-cyclopropyl)-isoxazol-3-yl]-amide | (110° C.; DMSO-d₆) δ ppm 10.33 (br. S., 1H) 8.50 (s, 1H) 8.29 (d, J = 8.97 Hz, 1H) 8.11 (d, J = 3.79 Hz, 1H) 7.45 (d, J = 2.27 Hz, 1H) 7.14 (dd, J = 8.97, 2.40 Hz, 1H) 6.96 (s, 1H) 6.73 (d, J = 3.66 Hz, 1H) 4.98 (d, J = 19.71 Hz, 1H) 4.87 (br. S., 1H) 4.26 (d, J = 17.68 Hz, 1H) 2.97-3.07 (m, 1H) 2.88 (br. S., 1H) 2.15 (s, 3H) 1.49-1.60 (m, 4H) 1.19 (d, J = 6.82 Hz, 3H) | 541.1 |
| 135-D[a]<br><br>5-((S)-7-Cyclopropanecarbonyl-6-methyl-5,6,7,8-tetrahydro-pyrido[3,4-d]pyrimidin-4-yloxy)-indole-1-carboxylic acid (5-cyclopropyl-isoxazol-3-yl)-amide | (DMSO-d₆) δ ppm 11.22 (s, 1H), 8.51 (s, 1H), 8.28 (d, J = 9.1 Hz, 1H), 8.16 (d, J = 3.5 Hz, 1H), 7.47 (d, J = 2.3 Hz, 1H), 7.16 (dd, J = 9.0, 2.4 Hz, 1H), 6.76 (d, J = 3.5 Hz, 1H), 6.65 (s, 1H), 4.97-5.24 (m), 4.52-4.74 (m), 4.03-4.23 (m), 2.99-3.17 (m), 2.76-2.96 (m), 2.14-2.23 (m), 2.02-2.16 (m), 1.19-1.32 (m), 1.05-1.13 (m), 0.91-0.98 (m), 0.81-0.89 (m), 0.71-0.81 (m) | 499.1 |

| Structure/Chemical Name | ¹H NMR (400 MHz) | MS (ESI) m/z (M + 1) |
|---|---|---|
| 135-E[b]<br><br>5-[(S)-6-Methyl-7-(3-methyl-butyryl)-5,6,7,8-tetrahydro-pyrido[3,4-d]pyrimidin-4-yloxy]-indole-1-carboxylic acid [5-(1-trifluoromethyl-cyclopropyl)-isoxazol-3-yl]-amide | (110° C.; DMSO-d₆) δ ppm 10.98 (br. S., 1H) 8.50 (s, 1H) 8.28 (d, J = 8.84 Hz, 1H) 8.11 (d, J = 3.54 Hz, 1H) 7.46 (d, J = 1.77 Hz, 1H) 7.15 (dd, J = 8.84, 1.77 Hz, 1H) 6.96 (s, 1H) 6.74 (d, J = 3.54 Hz, 1H) 5.02 (d, J = 18.69 Hz, 1H) 4.92 (br. S., 1H) 4.25 (d, J = 18.95 Hz, 1H) 2.95-3.05 (m, 1H) 2.83 (br. S., 1H) 2.35 (d, J = 5.68 Hz, 2H) 2.07-2.17 (m, 1H) 1.48-1.62 (m, 4H) 1.19 (d, J = 6.69 Hz, 3H) 0.98 (d, J = 5.05 Hz, 6H) | 583.2 |
| 135-F<br><br>5-[(S)-7-(2,2-Dimethyl-propionyl)-6-methyl-5,6,7,8-tetrahydro-pyrido[3,4-d]pyrimidin-4-yloxy]-indole-1-carboxylic acid [5-(1-trifluoromethyl-cyclopropyl)-isoxazol-3-yl]-amide | (DMSO-d₆) δ ppm 11.43 (s, 1H) 8.49 (s, 1H) 8.29 (d, J = 9.09 Hz, 1H) 8.16 (d, J = 3.54 Hz, 1H) 7.48 (d, J = 2.27 Hz, 1H) 7.16 (dd, J = 8.97, 2.40 Hz, 1H) 7.04 (s, 1H) 6.77 (d, J = 3.79 Hz, 1H) 5.10 (d, J = 19.20 Hz, 1H) 4.94-5.06 (m, 1H) 4.17 (d, J = 19.20 Hz, 1H) 2.93-3.04 (m, 1H) 2.81 (d, J = 16.93 Hz, 1H) 1.53-1.60 (m, 4H) 1.27 (s, 9H) 1.21 (d, J = 6.82 Hz, 3H) | 583.2 |
| 135-G<br><br>5-(7-Acetyl-5,6,7,8-tetrahydro-pyrido[3,4-d]pyrimidin-4-yloxy)-indole-1-carboxylic acid (5-cyclopropyl-isoxazol-3-yl)-amide | (DMSO-d₆) δ ppm 11.22 (s, 1H), 8.50 (s, 1H), 8.28 (d, J = 8.8 Hz, 1H), 8.16 (d, J = 3.8 Hz, 1H), 7.45 (d, J = 2.3 Hz, 1H), 7.14 (dd, J = 9.0, 2.4 Hz, 1H), 6.76 (d, J = 3.5 Hz, 1H), 6.65 (s, 1H), 4.59-4.71 (m, 2H), 3.81 (t, J = 5.8 Hz, 2H), 2.76-2.98 (m, 2H), 2.08-2.26 (m, 4H), 1.05-1.15 (m, 2H), 0.89-0.98 (m, 2H) | 459.2 |

| Structure/Chemical Name | ¹H NMR (400 MHz) | MS (ESI) m/z (M + 1) |
|---|---|---|
| 135-H 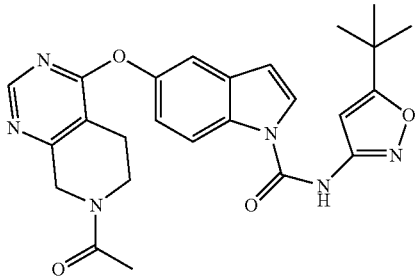<br>5-(7-Acetyl-5,6,7,8-tetrahydro-pyrido[3,4-d]pyrimidin-4-yloxy)-indole-1-carboxylic acid (5-tert-butyl-isoxazol-3-yl)-amide | (DMSO-d₆) δ ppm 11.27 (s, 1H), 8.48 (s, 1H), 8.29 (d, J = 8.8 Hz, 1H), 8.16 (d, J = 3.8 Hz, 1H), 7.45 (d, J = 2.5 Hz, 1H), 7.14 (dd, J = 8.8, 2.3 Hz, 1H), 6.76 (d, J = 3.8 Hz, 1H), 6.68 (s, 1H), 4.62 (s, 1 H), 3.75-3.85 (m, 2H), 2.89-2.97 (m, 2 H), 2.15 (s, 3H), 1.34 (s, 9H) | 475.2 |
| 135-I 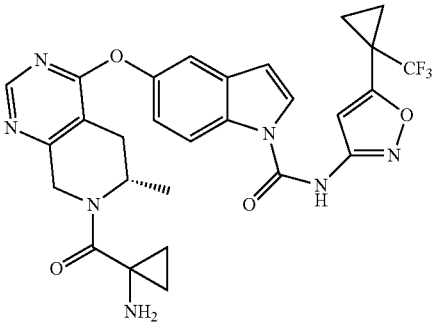<br>5-[(S)-7-(1-Amino-cyclopropanecarbonyl)-6-methyl-5,6,7,8-tetrahydro-pyrido[3,4-d]pyrimidin-4-yloxy]-indole-1-carboxylic acid [5-(1-trifluoromethyl-cyclopropyl)-isoxazol-3-yl]-amide | (DMSO-d₆) δ ppm 8.50 (s, 1H) 8.35 (d, J = 8.84 Hz, 1H) 8.14 (d, J = 3.54 Hz, 1 H) 7.44 (d, J = 2.27 Hz, 1H) 7.12 (dd, J = 8.84, 2.27 Hz, 1H) 7.03 (s, 1H) 6.70 (d, J = 3.54 Hz, 1H) 5.18 (br. S., 2H) 4.25 (br. S., 1H) 2.93-3.20 (m, 1H) 2.80 (d, J = 16.67 Hz, 1H) 1.45-1.60 (m, 5H) 1.20 (d, J = 6.57 Hz, 3H) 0.94-1.04 (m, 1H) 0.81-0.90 (m, 1H) 0.65-0.79 (m, 2H) | 581.9 |
| 135-J 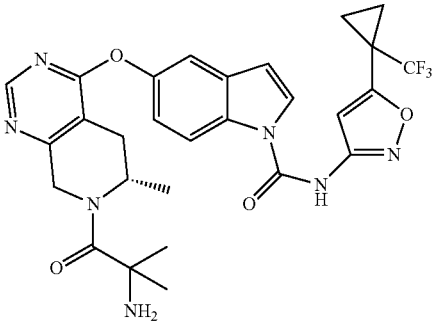<br>5-[(S)-7-(2-Amino-2-methyl-propionyl)-6-methyl-5,6,7,8-tetrahydro-pyrido[3,4-d]pyrimidin-4-yloxy]-indole-1-carboxylic acid [5-(1-trifluoromethyl-cyclopropyl)-isoxazol-3-yl]-amide | (DMSO-d₆) δ ppm 8.50 (s, 1H) 8.33 (d, J = 8.84 Hz, 1H) 8.15 (d, J = 3.79 Hz, 1 H) 7.45 (d, J = 2.27 Hz, 1H) 7.13 (dd, J = 8.97, 2.40 Hz, 1H) 7.03 (s, 1H) 6.73 (d, J = 3.54 Hz, 1H) 5.48 (br. S., 2H) 4.21 (br. S., 1H) 3.00 (br. S., 1H) 2.78 (d, J = 17.18 Hz, 1H) 1.50-1.59 (m, 4 H) 1.42 (s, 6H) 1.20 (d, J = 6.82 Hz, 3H) | 583.9 |

| Structure/Chemical Name | $^1$H NMR (400 MHz) | MS (ESI) m/z (M + 1) |
|---|---|---|
| 135-K[a] 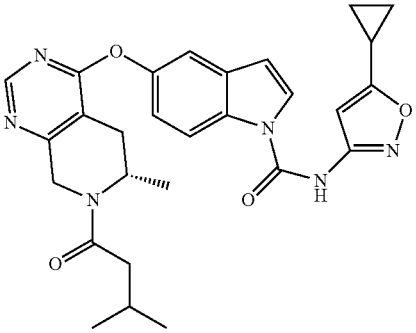 5-[(S)-6-Methyl-7-(3-methyl-butyryl)-5,6,7,8-tetrahydro-pyrido[3,4-d]pyrimidin-4-yloxy]-indole-1-carboxylic acid (5-cyclopropyl)-isoxazol-3-yl)-amide | (DMSO-$d_6$) δ ppm 11.22 (s, 1H), 8.50 (br. S., 1H), 8.29 (d, J = 9.1 Hz, 1H), 8.15 (d, J = 3.5 Hz, 1H), 7.46 (d, J = 2.3 Hz, 1H), 7.14 (dd, J = 9.0, 2.4 Hz, 1H), 6.75 (d, J = 3.5 Hz, 1H), 6.65 (s, 1H), 5.20-5.29 (m, 1H), 5.16 (d, J = 18.9 Hz), 4.81 (d, J = 18.4 Hz), 4.61-4.72 (m), 4.49 (d, J = 19.2 Hz), 4.05 (d, J = 19.2 Hz), 2.97-3.09 (m), 2.75-2.88 (m), 2.29-2.40 (m), 2.12-2.22 (m, 1H), 1.98-2.11 (m, 1H), 1.20 (d, J = 6.1 Hz, 2H), 1.02-1.13 (m, 4H), 0.89-0.99 (m, 9H) | 499.1 |
| 135-L[a] 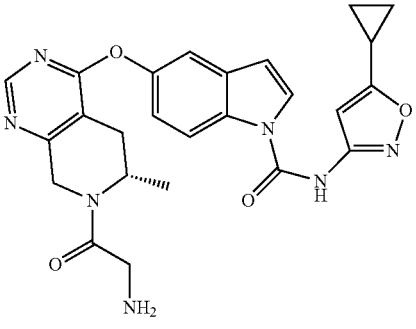 5-[(S)-7-(2-Amino-acetyl)-6-methyl-5,6,7,8-tetrahydro-pyrido[3,4-d]pyrimidin-4-yloxy]-indole-1-carboxylic acid (5-cyclopropyl-isoxazol-3-yl)-amide | (DMSO-$d_6$) δ ppm 8.51 (s, 1H), 8.34 (d, J = 9.1 Hz, 1H), 8.13 (d, J = 3.5 Hz, 1H), 7.43 (d, J = 2.3 Hz, 1H), 7.10 (dd, J = 9.0, 2.4 Hz, 1H), 6.69 (d, J = 3.5 Hz, 1H), 6.63 (s, 1H), 5.07-5.53 (m), 4.65-4.81 (m), 4.37-4.61 (m), 4.04-4.19 (m) 3.43-3.69 (m), 2.99-3.18 (m), 2.76-2.91 (m), 2.07-2.20 (m), 1.09-1.26 (m), 1.02-1.09 (m, 2H), 0.86-0.94 (m, 2H) | 488.1 |
| 135-M[a] 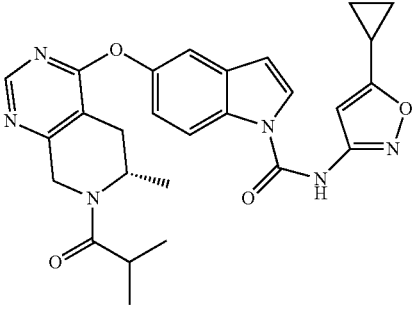 5-((S)-7-Isobutyryl-6-methyl-5,6,7,8-tetrahydro-pyrido[3,4-d]pyrimidin-4-yloxy)-indole-1-carboxylic acid (5-cyclopropyl-isoxazol-3-yl)-amide | (DMSO-$d_6$) δ ppm 11.22 (s, 1H), 8.50 (br. S., 1H), 8.28 (d, J = 9.1 Hz, 1H), 8.16 (d, J = 3.8 Hz, 1H), 7.46 (d, J = 2.3 Hz, 1H), 7.15 (dd, J = 9.0, 2.4 Hz, 1H), 6.75 (d, J = 3.5 Hz, 1H), 6.65 (s, 1H), 5.10-5.31 (m), 4.87 (d), 4.66-4.78 (m), 4.54 (d), 4.06 (d), 2.94-3.13 (m), 2.76-2.92 (m), 2.10-2.24 (m), 1.23 (d, J = 6.6 Hz, 2H), 1.04-1.13 (m), 0.97-1.03 (m), 0.88-0.97 (m, 2H) | 501.1 |

| | Structure/Chemical Name | ¹H NMR (400 MHz) | MS (ESI) m/z (M + 1) |
|---|---|---|---|
| 135-N | 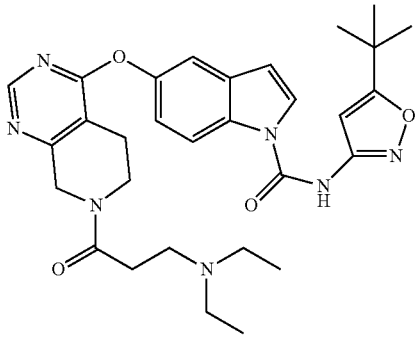<br>5-[7-(3-Diethylamino-propionyl)-5,6,7,8-tetrahydro-pyrido[3,4-d]pyrimidin-4-yloxy]-indole-1-carboxylic acid (5-tert-butyl-isoxazol-3-yl)-amide | (DMSO-d$_6$) δ ppm 11.04 (br. S., 1H), 8.48 (s, 1H), 8.30 (d, J = 9.1 Hz, 1H), 8.17 (d, J = 3.8 Hz, 1H), 7.45 (d, J = 2.3 Hz, 1H), 7.13 (d, J = 9.1 Hz, 1H), 6.76 (d, J = 3.5 Hz, 1H), 6.68 (s, 1H), 4.64 (s, 2H), 3.84 (q, J = 6.0 Hz, 2H), 2.93 (t, J = 4.9 Hz, 1H), 2.71-2.84 (m, 3H), 2.52-2.66 (m, 6H), 1.34 (s, 9H), 0.90-1.03 (m, 6H) | 560.3 |
| 135-O | 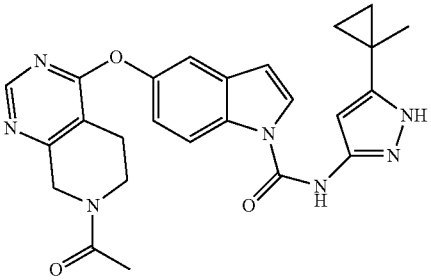<br>5-(7-Acetyl-5,6,7,8-tetrahydro-pyrido[3,4-d]pyrimidin-4-yloxy)-indole-1-carboxylic acid [5-(1-methyl-cyclopropyl)-1H-pyrazol-3-yl]-amide | (DMSO-d$_6$) δ ppm 10.55 (br. S., 1H), 8.47 (s, 1H), 8.30 (d, J = 8.8 Hz, 1H), 8.17 (d, J = 3.3 Hz, 2H), 7.42 (s, 1H), 7.10 (d, J = 7.8 Hz, 1H), 6.65-6.73 (m, 1H), 6.30 (s, 1H), 4.61 (s, 2H), 3.74-3.85 (m, 2H), 2.88-2.97 (m, 1H), 2.76-2.84 (m, 1H), 2.15 (s, 3H), 1.41 (s, 3H), 0.89-0.97 (m, 2H), 0.73-0.80 (m, 2H) | 472.3 |
| 135-P[b] | 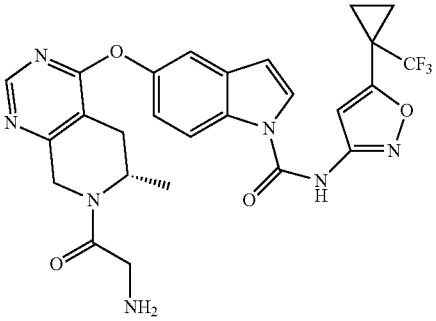<br>5-[(S)-7-(2-Amino-acetyl)-6-methyl-5,6,7,8-tetrahydro-pyrido[3,4-d]pyrimidin-4-yloxy]-indole-1-carboxylic acid [5-(1-trifluoromethyl-cyclopropyl)-isoxazol-3-yl]-amide | (80° C. DMSO-d$_6$) δ ppm 8.51 (s, 1H) 8.35 (d, J = 8.84 Hz, 1H) 8.12 (d, J = 3.66 Hz, 1H) 7.42 (d, J = 2.27 Hz, 1H) 7.10 (dd, J = 8.91, 2.34 Hz, 1H) 6.98 (s, 1H) 6.68 (d, J = 3.66 Hz, 1H) 5.28 (br. S., 2H) 4.94 (br. S., 2H) 4.16-4.41 (m, 1H) 2.96-3.01 (m, 1H) 2.79-2.92 (m, 1H) 1.47-1.57 (m, 4H) 1.19 (d, J = 7.07 Hz, 3H) | 556.1 |

| Structure/Chemical Name | ¹H NMR (400 MHz) | MS (ESI) m/z (M + 1) |
|---|---|---|
| 135-Q[b] 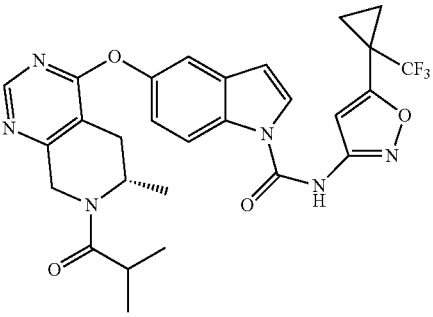 5-((S)-7-Isobutyryl-6-methyl-5,6,7,8-tetrahydro-pyrido[3,4-d]pyrimidin-4-yloxy)-indole-1-carboxylic acid [5-(1-trifluoromethyl-cyclopropyl)-isoxazol-3-yl]-amide | (100° C. DMSO-$d_6$) δ ppm 11.04 (br. S., 1H) 8.50 (s, 1H) 8.28 (d, J = 8.84 Hz, 1 H) 8.12 (d, J = 3.79 Hz, 1H) 7.46 (d, J = 2.15 Hz, 1H) 7.15 (dd, J = 8.84, 2.27 Hz, 1H) 6.97 (s, 1H) 6.75 (d, J = 3.66 Hz, 1H) 5.05 (d, J = 18.95 Hz, 1H) 4.94 (br. S., 1H) 4.26 (d, J = 18.95 Hz, 1H) 2.97-3.05 (m, 2H) 2.81-2.91 (m, 1 H) 1.47-1.61 (m, 4H) 1.20 (d, J = 6.69 Hz, 3H) 1.10 (t, J = 7.14 Hz, 6H) | 569.2 |
| 135-R[b] 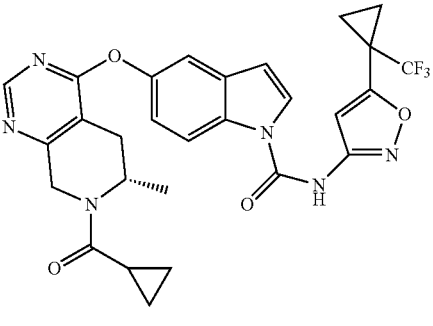 5-((S)-7-Cyclopropanecarbonyl-6-methyl-5,6,7,8-tetrahydro-pyrido[3,4-d]pyrimidin-4-yloxy)-indole-1-carboxylic acid [5-(1-trifluoromethyl-cyclopropyl)-isoxazol-3-yl]-amide | (80° C. DMSO-$d_6$) δ ppm 11.17 (br. S., 1H) 8.51 (s, 1H) 8.30 (d, J = 8.97 Hz, 1 H) 8.13 (d, J = 3.79 Hz, 1H) 7.46 (d, J = 2.15 Hz, 1H) 7.15 (dd, J = 8.97, 2.40 Hz, 1H) 6.99 (s, 1H) 6.74 (d, J = 3.16 Hz, 1H) 5.11 (d, J = 18.95 Hz, 2H) 4.33 (d, J = 18.57 Hz, 1H) 2.99-3.04 (m, 1H) 2.85-2.92 (m, 1H) 2.03-2.12 (m, 1H) 1.50-1.59 (m, 4H) 1.20 (d, J = 6.82 Hz, 3H) 0.78-0.89 (m, 4H) | 567.2 |
| 135-S[a] 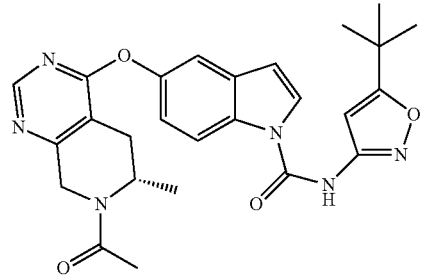 5-((S)-7-Acetyl-6-methyl-5,6,7,8-tetrahydro-pyrido[3,4-d]pyrimidin-4-yloxy)-indole-1-carboxylic acid (5-tert-butyl-isoxazol-3-yl)-amide | (DMSO-$d_6$) δ ppm 11.27 (s, 1H), 8.52 (br. S.), 8.50 (s), 8.29 (d, J = 9.1 Hz, 1 H), 8.17 (d, J = 3.5 Hz, 1H), 7.47 (d, J = 2.5 Hz, 1H), 7.15 (dd, J = 8.8, 2.5 Hz, 1H), 6.76 (d, J = 3.8 Hz, 1H), 6.68 (s, 1H), 5.16-5.24 (m), 5.13 (d, J = 19.5 Hz), 4.70-4.82 (m), 4.47-4.64 (m), 4.05 (d, J = 19.7 Hz), 3.02-3.16 (m), 2.77-2.89 (m), 2.17 (s), 2.12 (s), 1.34 (s), 1.21 (d, J = 6.6 Hz), 1.07 (d, J = 6.8 Hz) | 489.1 |

| Structure/Chemical Name | ¹H NMR (400 MHz) | MS (ESI) m/z (M + 1) |
|---|---|---|
| 135-Tᵃ<br>5-((S)-7-Acetyl-6-methyl-5,6,7,8-tetrahydro-pyrido[3,4-d]pyrimidin-4-yloxy)-indole-1-carboxylic acid (5-isopropyl-isoxazol-3-yl)-amide | (DMSO-$d_6$) δ ppm 11.26 (s, 1H), 8.52 (br. S.), 8.50 (s), 8.29 (d, J = 8.8 Hz, 1 H), 8.17 (d, J = 3.8 Hz, 1H), 7.47 (d, J = 2.3 Hz, 1H), 7.15 (dd, J = 9.0, 2.4 Hz, 1H), 6.76 (d, J = 3.8 Hz, 1H), 6.70 (s, 1H), 5.16-5.22 (m), 5.13 (d, J = 19.7 Hz), 4.76 (d, J = 18.7 Hz), 4.56-4.64 (m), 4.43-4.55 (m), 4.05 (d, J = 20.0 Hz), 3.03-3.17 (m, 2H), 2.77-2.87 (m), 2.17 (s), 2.12 (s), 1.29 (d, J = 6.8 Hz, 6H), 1.21 (d, J = 6.8 Hz), 1.07 (d, J = 6.8 Hz) | 475.1 |
| 135-Uᵃ<br>5-((S)-7-Cyclobutanecarbonyl-6-methyl-5,6,7,8-tetrahydro-pyrido[3,4-d]pyrimidin-4-yloxy)-indole-1-carboxylic acid (5-cyclopropyl-isoxazol-3-yl)-amide | (DMSO-$d_6$) δ ppm 11.19 (br. S., 1H), 8.49 (s, 1H), 8.29 (d, J = 8.8 Hz, 1H), 8.15 (d, J = 3.8 Hz, 1H), 7.45 (d, J = 2.3 Hz, 1H), 7.13 (dd, J = 9.0, 2.4 Hz, 1H), 6.74 (d, J = 3.5 Hz, 1H), 6.65 (s, 1H), 5.18 (br. S.), 5.14 (d, J = 19.5 Hz), 4.59 (d, J = 18.7 Hz), 4.33-4.50 (m), 4.06 (d, J = 19.5 Hz), 3.40-3.59 (m, 1H), 2.92-3.04 (m), 2.71-2.90 (m), 2.04-2.36 (m), 1.86-2.02 (m), 1.67-1.83 (m, 1H), 1.18 (d, J = 6.8 Hz), 1.01-1.11 (m), 0.89-0.98 (m) | 513.2 |
| 135-Vᵃ<br>5-((S)-7-Acetyl-6-methyl-5,6,7,8-tetrahydro-pyrido[3,4-d]pyrimidin-4-yloxy)-indole-1-carboxylic acid (3-trifluoromethyl-phenyl)-amide | (DMSO-$d_6$) δ ppm 10.38 (s, 1H), 8.52 (br. S.), 8.50 (s), 8.27 (d, J = 9.1 Hz, 1H), 8.12 (d, J = 3.5 Hz, 1H), 8.10 (s, 1H), 7.97 (d, J = 10.1 Hz, 1H), 7.65 (app t, J = 8.0 Hz, 1H), 7.48-7.54 (m, 1H), 7.43-7.52 (m, 2H), 7.15 (dd, J = 8.8, 2.3 Hz, 1H), 6.80 (d, J = 3.5 Hz, 1H), 5.17-5.23 (m), 5.13 (d, J = 18.7 Hz), 4.69-4.81 (m), 4.43-4.65 (m), 4.05 (d, J = 19.5 Hz), 3.02-3.14 (m), 2.78-2.89 (m), 2.17 (br. S.), 2.12 (br. S.), 1.21 (d, J = 6.6 Hz), 1.08 (d, J = 6.8 Hz) | 510.1 |
| 135-Wᵃ<br>5-[(S)-6-Methyl-7-((S)-2-methyl-butyryl)-5,6,7,8-tetrahydro-pyrido[3,4-d]pyrimidin-4-yloxy]-indole-1-carboxylic acid (5-cyclopropyl-isoxazol-3-yl)-amide | (DMSO-$d_6$) δ ppm 11.22 (s, 1H), 8.52 (br. S), 8.50 (s), 8.28 (d, J = 9.1 Hz, 1H), 8.16 (d, J = 3.8 Hz, 1H), 7.47 (d, J = 2.3 Hz, 1H), 7.15 (dd, J = 9.0, 2.4 Hz, 1H), 6.76 (d, J = 3.5 Hz, 1H), 6.65 (s, 1H), 5.24-5.30 (m), 5.20 (d, J = 19.5 Hz), 4.85-4.98 (m), 4.70-4.84 (m), 4.52 (d, J = 16.4 Hz), 4.07 (d, J = 18.7 Hz), 2.98-3.10 (m), 2.74-2.92 (m), 2.08-2.24 (m, 1H), 1.46-1.73 (m), 1.26-1.46 (m), 1.22 (d, J = 6.6 Hz), 1.01-1.13 (m), 0.91-0.99 (m), 0.87 (t, J = 7.3 Hz), 0.73-0.83 (m) | 515.3 |

-continued

| | Structure/Chemical Name | ¹H NMR (400 MHz) | MS (ESI) m/z (M + 1) |
|---|---|---|---|
| 135-X[a] | 5-((S)-7-Acetyl-6-methyl-5,6,7,8-tetrahydro-pyrido[3,4-d]pyrimidin-4-yloxy)-indole-1-carboxylic acid (4,4-dimethyl-4,5,6,7-tetrahydro-pyrazolo[1,5-a]pyridine-2-yl)-amide | (DMSO-d₆) δ ppm 10.63 (s, 1H), 8.52 (br. S.), 8.49 (s), 8.30 (d, J = 9.1 Hz, 1 H), 8.16 (d, J = 3.5 Hz, 1H), 7.44 (d, J = 2.5 Hz, 1H), 7.11 (dd, J = 9.0, 2.4 Hz, 1H), 6.71 (d, J = 3.8 Hz, 1H), 6.40 (s, 1H), 5.16-5.23 (m), 5.12 (d, J = 19.7 Hz), 4.76 (d, J = 17.4 Hz), 4.55-4.64 (m), 4.43-4.55 (m), 4.04 (d, J = 19.7 Hz), 3.96 (t, J = 6.2 Hz, 2H), 3.00-3.14 (m), 2.75-2.87 (m), 2.17 (s), 2.12 (s), 1.96-2.06 (m, 2H), 1.61-1.72 (m, 2 H), 1.30 (s, 6H), 1.21 (d, J = 6.8 Hz), 1.07 (d, J = 6.6 Hz) | 514.1 |
| 135-Y[a] | 5-((S)-7-Acetyl-6-methyl-5,6,7,8-tetrahydro-pyrido[3,4-d]pyrimidin-4-yloxy)-indole-1-carboxylic acid (4,4-dimethyl-5,6-dihydro-4H-pyrrolo[1,2-b]pyrazole-2-yl)-amide | (DMSO-d₆) δ ppm 10.63 (s, 1H), 8.52 (br. S.), 8.49 (s), 8.28 (d, J = 9.1 Hz, 1 H), 8.15 (d, J = 3.5 Hz, 1H), 7.44 (d, J = 2.5 Hz, 1H), 7.11 (dd, J = 9.0, 2.4 Hz, 1H), 6.71 (d, J = 3.8 Hz, 1H), 6.28 (s, 1H), 5.15-5.24 (m), 5.12 (d, J = 19.7 Hz), 4.76 (d, J = 18.9 Hz), 4.55-4.62 (m), 4.46-4.56 (m), 4.09 (t, J = 6.9 Hz, 2H), 3.04-3.14 (m), 2.77-2.89 (m), 2.34 (t, J = 6.8 Hz, 2H), 2.17 (s), 2.12 (s), 1.32 (s, 6H), 1.21 (d, J = 6.8 Hz), 1.07 (d, J = 6.8 Hz) | 500.1 |
| 135-Z[a] | 5-((S)-7-Cyclopropanecarbonyl-6-methyl-5,6,7,8-tetrahydro-pyrido[3,4-d]pyrimidin-4-yloxy)-indole-1-carboxylic acid (4,4-dimethyl-5,6-dihydro-4H-pyrrolo[1,2-b]pyrazole-2-yl)-amide | (DMSO-d₆) δ ppm 10.63 (s, 1H), 8.51 (s, 1H), 8.28 (d, J = 9.1 Hz, 1H), 8.15 (d, J = 3.5 Hz, 1H), 7.45 (d, J = 2.5 Hz, 1 H), 7.12 (dd, J = 9.0, 2.4 Hz, 1H), 6.71 (d, J = 3.5 Hz, 1H), 6.27 (s, 1H), 4.96-5.27 (m), 4.42-4.73 (m), 4.09 (app t, J = 6.9 Hz, 2H), 2.99-3.17 (m), 2.76-2.95 (m), 2.28-2.39 (m), 2.07-2.21 (m), 1.24 (br. S.), 1.03-1.15 (m), 0.81-0.91 (m), 0.70-0.81 (m) | 526.2 |
| 135-AA[a] | 5-((S)-7-Acetyl-6-methyl-5,6,7,8-tetrahydro-pyrido[3,4-d]pyrimidin-4-yloxy)-indole-1-carboxylic acid (1-tert-butyl-1H-pyrazol-3-yl)-amide | (DMSO-d₆) δ ppm 10.71 (s, 1H) 8.42-8.59 (m, 1H) 8.31 (d, J = 9.09 Hz, 1H) 8.21 (d, J = 3.54 Hz, 1H) 7.78 (d, J = 2.27 Hz, 1H) 7.44 (d, J = 2.27 Hz, 1H) 7.11 (dd, J = 8.97, 2.40 Hz, 1H) 6.70 (d, J = 3.54 Hz, 1H) 6.52 (d, J = 2.53 Hz, 1 H) 5.02-2.77 [2 sets of signals are observed at about 3/2 ratio, totally 5 H; 5.02-5.27 (m) 4.76 (d, J = 18.44 Hz) 4.43-4.64 (m) 4.05 (d, J = 19.20 Hz) 3.01-3.13 (m,) 2.77-2.91 (m)] [2.17 (s) 2.12 (s) totally 3H] 1.54 (s, 9H) [1.21 (d, J = 6.57 Hz) 1.07 (d, J = 6.57 Hz) totally 3H] | 488.1 |

| | Structure/Chemical Name | ¹H NMR (400 MHz) | MS (ESI) m/z (M + 1) |
|---|---|---|---|
| 135-AB | 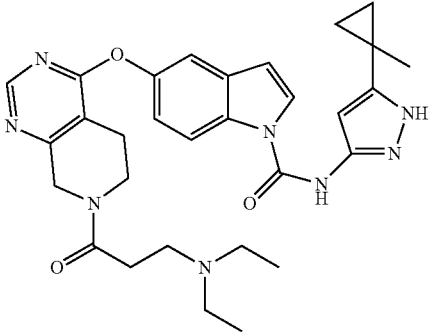<br>5-[7-(3-Diethylamino-propionyl)-5,6,7,8-tetrahydro-pyrido[3,4-d]pyrimidin-4-yloxy]-indole-1-carboxylic acid [5-(1-methyl-cyclopropyl)-1H-pyrazol-3-yl]-amide | (DMSO-$d_6$) δ ppm 12.13 (br. S., 1H), 10.56 (br. S., 1H), 8.48 (s, 1H), 8.30 (d, J = 8.8 Hz, 1H), 8.17 (d, J = 3.3 Hz, 1H), 7.42 (d, J = 2.0 Hz, 1H), 7.09 (d, J = 9.1 Hz, 1H), 6.71 (d, J = 3.5 Hz, 1H), 6.29 (br. S., 1H), 4.63 (s, 2H), 3.77-3.89 (m, 2H), 2.89-2.96 (m, 1H), 2.76-2.83 (m, 1H), 2.64-2.74 (m, 2 H), 2.51-2.61 (m, 6H), 1.41 (s, 3H), 0.87-1.01 (m, 8H), 0.74-0.82 (m, 2H) | 557.3 |
| 135-AC | 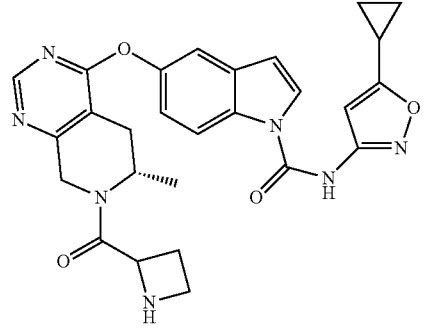<br>5-[(S)-7-(Azetidine-2-carbonyl)-6-methyl-5,6,7,8-tetrahydro-pyrido[3,4-d]pyrimidin-4-yloxy]-indole-1-carboxylic acid (5-cyclopropyl-isoxazol-3-yl)-amide | Complex NMR due to the existanc of both rotamers and diastereomers. | 514.1 |
| 135-AD | 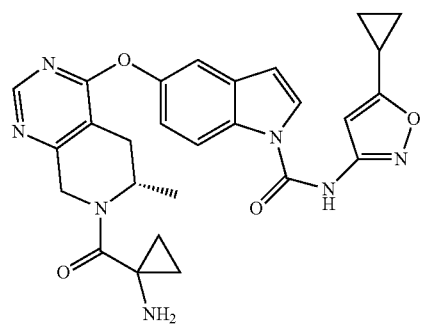<br>5-[(S)-7-(1-Amino-cyclopropanecarbonyl)-6-methyl-5,6,7,8-tetrahydro-pyrido[3,4-d]pyrimidin-4-yloxy]-indole-1-carboxylic acid (5-cyclopropyl-isoxazol-3-yl)-amide | (DMSO-$d_6$) δ ppm 11.20 (br. S., 1H) 8.50 (s, 1H) 8.28 (d, J = 9.09 Hz, 1H) 8.16 (d, J = 3.54 Hz, 1H) 7.46 (d, J = 2.53 Hz, 1H) 7.15 (dd, J = 8.97, 2.40 Hz, 1H) 6.75 (d, J = 3.54 Hz, 1H) 6.65 (s, 1H) 5.18 (br. S., 2H) 4.26 (br. S., 1H) 3.06 (br. S., 1H) 2.80 (d, J = 16.93 Hz, 1H) 2.35 (br. S., 1H) 2.09-2.24 (m, 1H) 1.16-1.27 (m, 3 H) 1.05-1.14 (m, 2H) 0.91-1.03 (m, 3 H) 0.81-0.90 (m, 1H) 0.65-0.79 (m, 2H) | 514.1 |

| Structure/Chemical Name | ¹H NMR (400 MHz) | MS (ESI) m/z (M + 1) |
|---|---|---|
| 135-AE 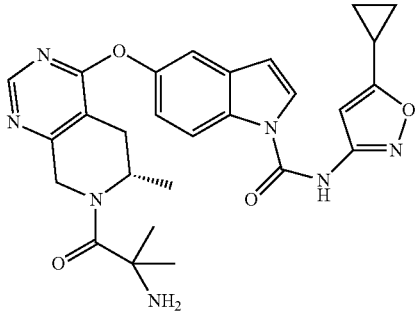 5-[(S)-7-(2-Amino-2-methyl-propionyl)-6-methyl-5,6,7,8-tetrahydro-pyrido[3,4-d]pyrimidin-4-yloxy]-indole-1-carboxylic acid (5-cyclopropyl-isoxazol-3-yl)-amide | (DMSO-d$_6$) δ ppm 8.49 (s, 1H) 8.29 (d, J = 8.84 Hz, 1H) 8.15 (d, J = 3.79 Hz, 1H) 7.45 (d, J = 2.53 Hz, 1H) 7.13 (dd, J = 8.97, 2.40 Hz, 1H) 6.74 (d, J = 3.79 Hz, 1H) 6.65 (s, 1H) 4.09-4.32 (m, 2H) 2.93-3.13 (m, 2H) 2.76 (d, J = 17.18 Hz, 2H) 2.64-2.69 (m, 1H) 2.10-2.22 (m, 1H) 1.36 (d, J = 4.80 Hz, 6H) 1.19 (d, J = 6.82 Hz, 3H) 1.03-1.12 (m, 2H) 0.90-0.98 (m, 2H) | 516.1 |
| 135-AF$^a$ 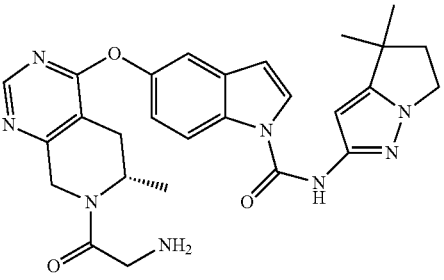 5-[(S)-7-(2-Amino-acetyl)-6-methyl-5,6,7,8-tetrahydro-pyrido[3,4-d]pyrimidin-4-yloxy]-indole-1-carboxylic acid (4,4-dimethyl-5,6-dihydro-4H-pyrrolo[1,2-b]pyrazol-2-yl)-amide | (DMSO-d$_6$) δ ppm 8.50 (s, 1H), 8.28 (d, J = 8.8 Hz, 1H), 8.14 (d, J = 3.8 Hz, 1 H), 7.44 (d, J = 2.3 Hz, 1H), 7.11 (dd, J = 9.0, 2.4 Hz, 1H), 6.71 (d, J = 3.5 Hz, 1 H), 6.27 (s, 1H), 5.06-5.25 (m), 4.64-4.83 (m), 4.39-4.61 (m), 4.11-4.15 (m), 4.09 (t, J = 6.8 Hz, 2H), 3.37-3.61 (m), 2.97-3.14 (m), 2.84 (br. S.), 2.79 (br. S.), 2.30-2.38 (m, 2H), 1.32 (s, 6 H), 1.15-1.25 (m), 1.02-1.13 (m). | 515.2 |
| 135-AG$^a$ 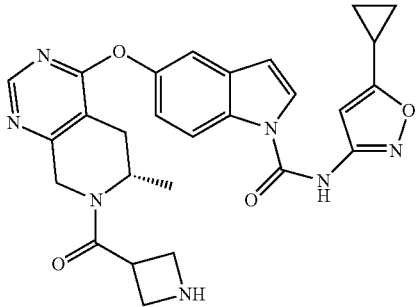 5-[(S)-7-(Azetidine-3-carbonyl)-6-methyl-5,6,7,8-tetrahydro-pyrido[3,4-d]pyrimidin-4-yloxy]-indole-1-carboxylic acid (5-cyclopropyl-isoxazol-3-yl)-amide | (DMSO-d$_6$) δ ppm 8.53 (s), 8.46 (s) 8.33 (d, J = 9.09 Hz, 1H) 8.14 (d, J = 3.79 Hz, 1H) 7.43 (d, J = 2.27 Hz, 1H) 7.10 (dd, J = 8.97, 2.40 Hz, 1H) 6.70 (d, J = 3.54 Hz, 1H) 6.63 (s, 1H) 5.17 (m) 5.15 (d, J = 19.20 Hz) 4.43 (m) 4.24-4.31 (m) 4.10 (d, J = 19.45 Hz) 3.82-3.96 (m) 3.63-3.81 (m) 2.94-3.06 (m) 2.72-2.89 (m) 2.08-2.19 (m, 1H) 1.18 (d, J = 6.82 Hz) 1.02-1.13 (m) 0.84-0.96 (m) | 514.1 |

| Structure/Chemical Name | ¹H NMR (400 MHz) | MS (ESI) m/z (M + 1) |
|---|---|---|
| 135-AH 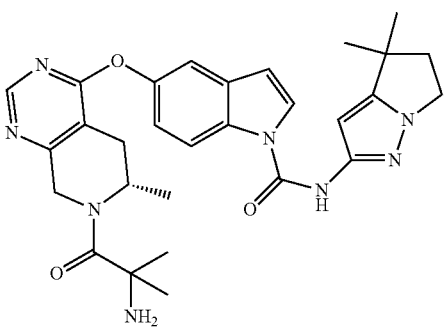 5-[(S)-7-(2-Amino-2-methyl-propionyl)-6-methyl-5,6,7,8-tetrahydro-pyrido[3,4-d]pyrimidin-4-yloxy]-indole-1-carboxylic acid (4,4-dimethyl-5,6-dihydro-4H-pyrrolo[1,2-b]pyrazole-2-yl)-amide | (DMSO-d₆) δ ppm 10.63 (s, 1H), 8.51 (s, 1H), 8.29 (d, J = 8.8 Hz, 1H), 8.15 (d, J = 3.8 Hz, 1H), 7.44 (d, J = 2.5 Hz, 1H), 7.12 (dd, J = 9.0, 2.4 Hz, 1H), 6.71 (d, J = 3.3 Hz, 1H), 6.27 (s, 1H), 5.28 (br. S., 1H), 4.27 (br. S., 1H), 4.09 (t, J = 6.8 Hz, 2H), 2.95-3.12 (m, 1H), 2.81 (d, J = 16.7 Hz, 1H), 2.27-2.37 (m, 2H), 1.50 (br. S., 6H), 1.32 (s, 6H), 1.22 (d, J = 6.6 Hz, 3H) | 543.2 |
| 135-AI<sup>a</sup> 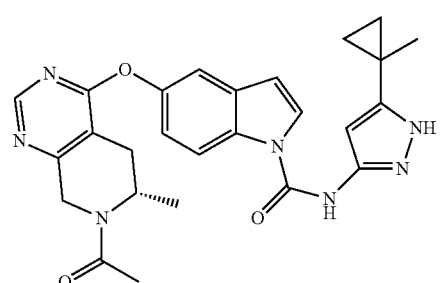 5-((S)-7-Acetyl-6-methyl-5,6,7,8-tetrahydro-pyrido[3,4-d]pyrimidin-4-yloxy]-indole-1-carboxylic acid [5-(1-methyl-cyclopropyl)-1H-pyrazole-3-yl]-amide | (DMSO-d₆) δ ppm 10.56 (s, 1H), 8.52 (br. S.), 8.50 (s), 8.30 (d, J = 8.8 Hz, 1H), 8.17 (d, J = 3.3 Hz, 1H), 7.44 (d, J = 2.5 Hz, 1H), 7.11 (dd, J = 9.1, 2.3 Hz, 1H), 6.70 (d, J = 3.8 Hz, 1H), 6.29 (s, 1H), 5.16-5.25 (m), 5.12 (d, J = 19.7 Hz), 4.76 (d, J = 18.7 Hz), 4.55-4.63 (m), 4.48-4.54 (m), 4.04 (d, J = 19.5 Hz), 3.03-3.15 (m), 2.74-2.88 (m), 2.17 (s), 2.12 (s), 1.41 (s, 3H), 1.21 (d, J = 6.6 Hz), 1.07 (d, J = 6.8 Hz), 0.89-0.97 (m, 2H), 0.74-0.80 (m, 2H) | 486.2 |
| 135-AJ<sup>a</sup> 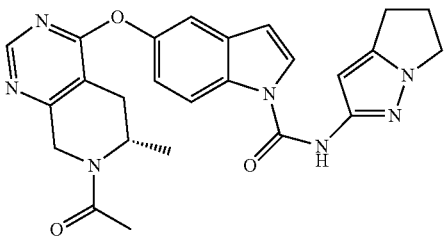 5-((S)-7-Acetyl-6-methyl-5,6,7,8-tetrahydro-pyrido[3,4-d]pyrimidin-4-yloxy)-indole-1-carboxylic acid (5,6-dihydro-4H-pyrrolo[1,2-b]pyrazole-2-yl)-amide | (DMSO-d₆) δ ppm 10.60 (s, 1H), 8.50-8.55 (m), 8.49 (s), 8.29 (d, J = 9.0 Hz, 1H), 8.16 (d, J = 3.5 Hz, 1H), 7.44 (d, J = 2.4 Hz, 1H), 7.11 (dd, J = 9.0, 2.4 Hz, 1H), 6.71 (d, J = 3.7 Hz, 1H), 6.28 (s, 1H), 5.06-5.23 (m), 4.70-4.82 (m), 4.40-4.66 (m), 3.94-4.11 (m), 3.03-3.14 (m), 2.78-2.91 (m), 2.17 (s), 2.12 (s), 1.21 (d, J = 6.3 Hz), 1.00-1.10 (m) | 472.2 |

| | Structure/Chemical Name | ¹H NMR (400 MHz) | MS (ESI) m/z (M + 1) |
|---|---|---|---|
| 135-AK[a] | 5-[(S)-6-Methyl-7-(2,2,3,3-tetramethyl-cyclo-propanecarbonyl)-5,6,7,8-tetrahydro-pyrido[3,4-d]pyrimidin-4-yloxy]-indole-1-carboxylic acid (5-cyclopropyl-isoxazol-3-yl)-amide | Due to the existance of rotamers about the amide bond the ¹H NMR is complex when taken at 27° C., thus only a partial listing of NMR signals are reported. (DMSO-d₆) δ ppm 11.22 (s, 1 H), 8.51 (s, 1H), 8.28 (d, J = 9.1 Hz, 1 H), 8.16 (d, J = 3.8 Hz, 1H), 7.47 (d, J = 2.3 Hz, 1H), 7.15 (dd, J = 9.0, 2.4 Hz, 1H), 6.76 (d, J = 3.3 Hz, 1H), 6.65 (s, 1 H), 2.11-2.25 (m, 1H), 1.20 (s, 6H), 1.13 (s, 6H) | 555.3 |
| 135-AL[a] | 5-((S)-7-Acetyl-6-methyl-5,6,7,8-tetrahydro-pyrido[3,4-d]pyrimidin-4-yloxy)-indole-1-carboxylic acid (5-methyl-isoxazol-3-yl)-amide | (DMSO-d₆) δ ppm 11.23 (s, 1H), 8.52 (br. S.), 8.50 (s), 8.28 (d, J = 8.8 Hz, 1 H), 8.16 (d, J = 3.8 Hz, 1H), 7.47 (d, J = 2.3 Hz, 1H), 7.15 (dd, J = 9.0, 2.4 Hz, 1H), 6.76 (d, J = 3.8 Hz, 1H), 6.71 (s, 1 H), 5.17-5.25 (m), 5.06-5.17 (m), 4.76 (d, J = 18.9 Hz), 4.42-4.64 (m), 4.05 (d, J = 19.2 Hz), 3.02-3.16 (m), 2.73-2.89 (m), 2.44 (s, 3H), 2.17 (s), 2.12 (s), 1.21 (d, J = 6.8 Hz), 1.07 (d, J = 6.8 Hz) | 447.0 |
| 135-AM | 5-(6-Cyclopropanecarbonyl-6,7-dihydro-5H-pyrrolo[3,4-d]pyrimidin-4-yloxy)-indole-1-carboxylic acid (5-cyclopropyl-isoxazol-3-yl)-amide | (DMSO-d₆) δ ppm 11.24 (s, 1H) 8.66 (d, J = 8.34 Hz, 1H) 8.30 (d, J = 9.09 Hz, 1H) 8.17 (d, J = 3.79 Hz, 1H) 7.50 (d, J = 2.27 Hz, 1H) 7.18 (dd, J = 8.84, 2.27 Hz, 1H) 6.78 (d, J = 3.28 Hz, 1H) 6.65 (s, 1H) 5.15 (s, 1H) 5.07 (s, 1H) 4.67 (br. S., 2H) 2.10-2.25 (m, 1H) 1.85-2.08 (m, 1H) 1.09 (dd, J = 8.59, 2.53 Hz, 1H) 1.02-1.18 (m, 1H) 0.88-1.00 (m, 2H) 0.83 (dd, J = 6.32, 2.53 Hz, 4H) | 471.0 |
| 135-AN | 5-(6-Isobutyryl-6,7-dihydro-5H-pyrrolo[3,4-d]pyrimidin-4-yloxy)-indole-1-carboxylic acid (5-cyclopropyl-isoxazol-3-yl)-amide | (DMSO-d₆) δ ppm 11.24 (s, 1H) 8.66 (d, J = 7.33 Hz, 1H) 8.30 (d, J = 8.59 Hz, 1H) 8.17 (d, J = 4.04 Hz, 1H) 7.50 (t, J = 2.27 Hz, 1H) 7.16-7.20 (m, 1H) 6.78 (dd, J = 3.54, 2.02 Hz, 1H) 6.65 (s, 1H) 5.03 (s, 1H) 4.95 (s, 1H) 4.65 (d, J = 7.07 Hz, 2H) 3.36-3.38 (m, 1H) 2.12-2.15 (m, 1H) 1.09 (dd, J = 6.57, 5.56 Hz, 8H) 0.92-0.97 (m, 2H) | 473.0 |

| | Structure/Chemical Name | ¹H NMR (400 MHz) | MS (ESI) m/z (M + 1) |
|---|---|---|---|
| 135-AO | 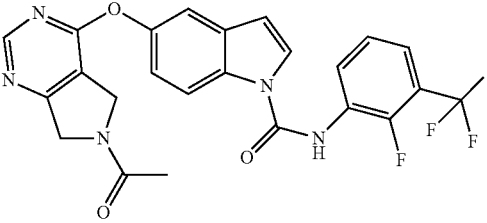<br>5-(6-Acetyl-6,7-dihydro-5H-pyrrolo[3,4-d]pyrimidin-4-yloxy)-indole-1-carboxylic acid (2-fluoro-3-trifluoromethyl-phenyl)-amide | (DMSO-$d_6$) δ ppm 10.27 (s, 1H) 8.66 (d, J = 5.56 Hz, 1H) 8.27 (dd, J = 8.84, 2.78 Hz, 1H) 8.10 (d, J = 3.79 Hz, 1H) 7.92-8.05 (m, 1H) 7.69 (t, J = 6.82 Hz, 1H) 7.46-7.55 (m, 1H) 7.16 (dd, J = 4.80, 2.27 Hz, 1H) 7.18 (dd, J = 4.80, 2.53 Hz, 1H) 6.82 (d, J = 1.26 Hz, 1H) 4.97 (s, 1H) 4.90 (s, 1H) 4.63 (d, J = 3.79 Hz, 2H) 2.11 (d, J = 6.57 Hz, 3H) | 500.9 |
| 135-AP | 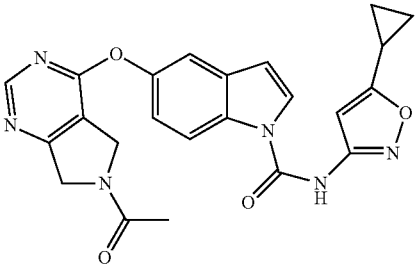<br>5-(6-Acetyl-6,7-dihydro-5H-pyrrolo[3,4-d]pyrimidin-4-yloxy)-indole-1-carboxylic acid (5-cyclopropyl-isoxazol-3-yl)-amide | (DMSO-$d_6$) δ ppm 11.13 (br. S., 1H) 8.59 (d, J = 5.05 Hz, 1H) 8.22 (d, J = 2.02 Hz, 1H) 8.10 (d, J = 3.54 Hz, 1H) 7.42 (br. S., 1H) 7.10 (td, J = 4.29, 2.78 Hz, 1 H) 6.69 (br. S., 1H) 6.58 (s, 1H) 4.90 (s, 1H) 4.83 (s, 1H) 4.56 (br. S., 2H) 2.04 (d, J = 5.81 Hz, 3H) 2.01-2.14 (m, 1H) 1.02 (dd, J = 8.34, 2.27 Hz, 2H) 0.87 (dd, J = 4.55, 2.27 Hz, 2H) | 4459 |
| .£<br>135-AQ | 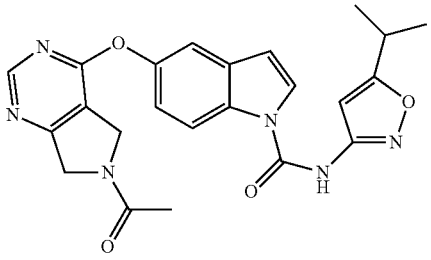<br>5-(6-Acetyl-6,7-dihydro-5H-pyrrolo[3,4-d]pyrimidin-4-yloxy)-indole-1-carboxylic acid (5-isopropyl-isoxazol-3-yl)-amide | (DMSO-$d_6$) δ ppm 11.26 (br. S., 1H) 8.66 (d, J = 5.05 Hz, 1H) 8.31 (dd, J = 9.09, 2.53 Hz, 1H) 8.18 (d, J = 3.79 Hz, 1H) 7.50 (d, J = 2.78 Hz, 1H) 7.15-7.23 (m, 1H) 6.77 (d, J = 2.53 Hz, 1H) 6.69 (s, 1H) 4.97 (s, 1H) 4.90 (s, 1H) 4.64 (s, 2H) 3.10 (d, J = 7.33 Hz, 1H) 2.11 (d, J = 6.32 Hz, 3H) 1.29 (d, J = 7.07 Hz, 6H) | 447.9 |
| 135-AR | 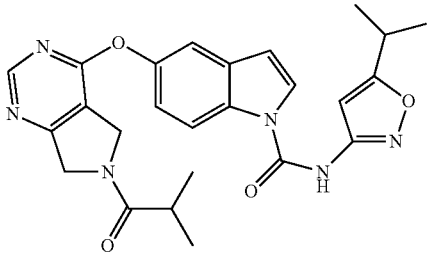<br>5-(6-Isobutyryl-6,7-dihydro-5H-pyrrolo[3,4-d]pyrimidin-4-yloxy)-indole-1-carboxylic acid (5-isopropyl-isoxazol-3-yl)-amide | (DMSO-$d_6$) δ ppm 11.28 (s, 1H) 8.66 (d, J = 7.07 Hz, 1H) 8.31-8.33 (m, 1H) 8.18 (d, J = 4.04 Hz, 1H) 7.50 (t, J = 2.27 Hz, 1H) 7.16-7.20 (m, 1H) 6.79 (d, J = 1.77 Hz, 1H) 6.70 (s, 1H) 5.03 (s, 1 H) 4.95 (d, J = 1.26 Hz, 1H) 4.65 (s, 2 H) 3.08-3.15 (m, 1H) 2.79-2.85 (m, 1H) 1.29 (d, J = 6.82 Hz, 6H) 1.09 (d, J = 5.31 Hz, 2H) 1.08 (d, J = 5.56 Hz, 4H) | 475.9 |

-continued

| | Structure/Chemical Name | ¹H NMR (400 MHz) | MS (ESI) m/z (M + 1) |
|---|---|---|---|
| 135-AS | 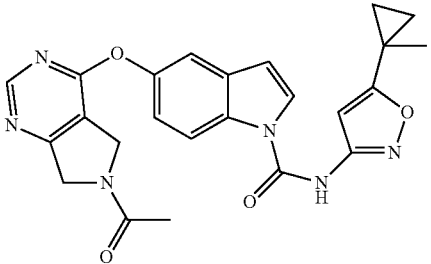<br>5-(6-Acetyl-6,7-dihydro-5H-pyrrolo[3,4-d]pyrimidin-4-yloxy)-indole-1-carboxylic acid [5-(1-methyl-cyclopropyl)-isoxazol-3-yl]-amide | (DMSO-$d_6$) δ ppm 11.25 (br. S., 1H) 8.66 (d, J = 4.80 Hz, 1H) 8.24-8.42 (m, 1H) 8.17 (d, J = 3.54 Hz, 1H) 7.49 (d, J = 3.28 Hz, 1H) 7.17 (d, J = 6.06 Hz, 1H) 6.77 (br. S., 1H) 6.67 (s, 1H) 4.97 (s, 1H) 4.90 (br. S., 1H) 4.64 (br. S., 2H) 2.10-2.11 (m, 3H) 1.46 (s, 3H) 1.15 (d, J = 2.27 Hz, 2H) 0.93 (d, J = 2.53 Hz, 2H) | 459.9 |
| 135-AT | 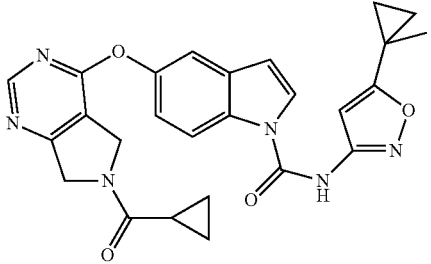<br>5-(6-Cyclopropanecarbonyl-6,7-dihydro-5H-pyrrolo[3,4-d]pyrimidin-4-yloxy)-indole-1-carboxylic acid [5-(1-methyl-cyclopropyl)-isoxazol-3-yl]-amide | (DMSO-$d_6$) δ ppm 11.25 (s, 1H) 8.66 (d, J = 8.34 Hz, 1H) 8.28-8.31 (m, 1H) 8.18 (d, J = 3.79 Hz, 1H) 7.50 (d, J = 2.27 Hz, 1H) 7.17-7.18 (m, 1H) 6.78 (d, J = 3.28 Hz, 1H) 6.67 (s, 1H) 5.15 (s, 1H) 5.07 (s, 1H) 4.67 (br. S., 2H) 1.92-1.99 (m, 1H) 1.46 (s, 3H) 1.16 (d, J = 2.53 Hz, 2H) 1.16 (d, J = 10.86 Hz, 1H) 0.94 (d, J = 2.27 Hz, 1H) 0.89-0.99 (m, 1H) 0.83 (d, J = 3.03 Hz, 1H) 0.83 (d, J = 8.84 Hz, 2H) | 485.9 |
| 135-AU | 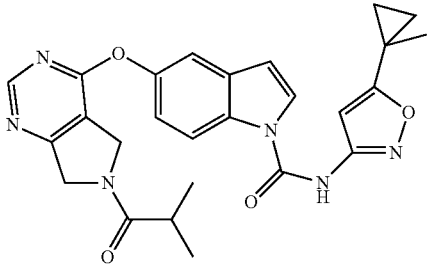<br>5-(6-Isobutyryl-6,7-dihydro-5H-pyrrolo[3,4-d]pyrimidin-4-yloxy)-indole-1-carboxylic acid [5-(1-methyl-cyclopropyl)-isoxazol-3-yl]-amide | (DMSO-$d_6$) δ ppm 11.25 (s, 1H) 8.66 (d, J = 7.07 Hz, 1H) 8.30-8.31 (m, 1H) 8.18 (d, J = 3.79 Hz, 1H) 7.41-7.59 (m, 1H) 7.10-7.29 (m, 1H) 6.79 (d, J = 2.02 Hz, 1H) 6.67 (s, 1H) 5.03 (s, 1H) 4.96 (s, 1H) 4.65 (s, 2H) 2.84 (dd, J = 16.17, 6.82 Hz, 1H) 1.46 (s, 3H) 1.15-1.17 (m, 2H) 1.07-1.10 (m, 6H) 0.93-0.95 (m, 2H) | 487.9 |
| 135-AV | 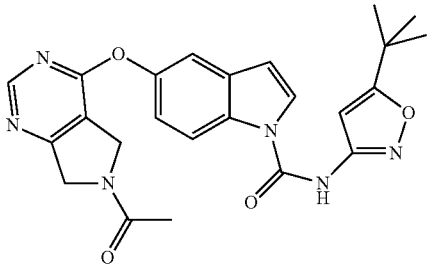<br>5-(6-Acetyl-6,7-dihydro-5H-pyrrolo[3,4-d]pyrimidin-4-yloxy)-indole-1-carboxylic acid (5-tert-butyl-isoxazol-3-yl)-amide | (DMSO-$d_6$) δ ppm 11.19 (br. S., 1H) 8.59 (d, J = 5.05 Hz, 1H) 8.23-8.25 (m, 1H) 8.11 (d, J = 3.79 Hz, 1H) 7.43 (br. S., 1H) 7.43 (d, J = 5.56 Hz, 1H) 7.08-7.18 (m, 1H) 6.70 (br. S., 1H) 6.71 (d, J = 1.52 Hz, 1H) 6.61 (s, 1H) 4.90 (s, 2H) 4.83 (s, 2H) 4.57 (s, 3H) 2.04 (d, J = 6.32 Hz, 5H) 1.28 (s, 9H) | 461.9 |

| Structure/Chemical Name | ¹H NMR (400 MHz) | MS (ESI) m/z (M + 1) |
|---|---|---|
| 135-AW 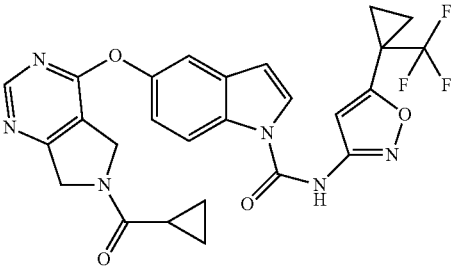<br>5-(6-Cyclopropanecarbonyl-6,7-dihydro-5H-pyrrolo[3,4-d]pyrimidin-4-yloxy)-indole-1-carboxylic acid [5-(1-trifluoromethyl-cyclopropyl)-isoxazole-3-yl]-amide | (DMSO-$d_6$) δ ppm 11.45 (s, 1H) 8.66 (d, J = 8.34 Hz, 1H) 8.31 (dd, J = 9.09, 3.03 Hz, 1H) 8.18 (d, J = 3.79 Hz, 1H) 7.51 (d, J = 2.53 Hz, 1H) 7.19 (dd, J = 8.97, 2.40 Hz, 1H) 7.04 (s, 1H) 6.79 (t, J = 3.28 Hz, 1H) 5.15 (s, 1H) 5.07 (s, 1H) 4.66 (d, J = 3.28 Hz, 2H) 1.80-2.10 (m, 1H) 1.44-1.70 (m, 4H) 0.71-0.95 (m, 4H) | 539.9 |
| 135-AX 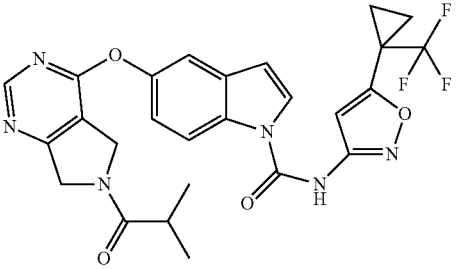<br>5-(6-Isobutyryl-6,7-dihydro-5H-pyrrolo[3,4-d]pyrimidin-4-yloxy)-indole-1-carboxylic acid [5-(1-trifluoromethyl-cyclopropyl)-isoxazole-3-yl]-amide | (DMSO-$d_6$) δ ppm 11.46 (s, 1H) 8.66 (d, J = 6.82 Hz, 1H) 8.31 (dd, J = 8.97, 1.89 Hz, 1H) 8.18 (d, J = 3.79 Hz, 1H) 7.50 (t, J = 2.27 Hz, 1H) 7.19 (dt, J = 9.09, 2.27 Hz, 1H) 7.05 (s, 1H) 6.79 (dd, J = 3.28, 1.77 Hz, 1H) 5.03 (s, 1H) 4.95 (s, 1H) 4.65 (d, J = 6.32 Hz, 2H) 2.75-2.92 (m, 1H) 1.46-1.68 (m, 4 H) 1.01-1.22 (m, 6H) | 541.9 |
| 135-AY 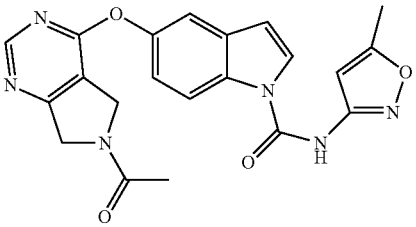<br>5-(6-Acetyl-6,7-dihydro-5H-pyrrolo[3,4-d]pyrimidin-4-yloxy)-indole-1-carboxylic acid (5-methyl-isoxazol-3-yl)-amide | (DMSO-$d_6$) δ ppm 11.24 (s, 1H) 8.66 (d, J = 5.05 Hz, 1H) 8.30 (d, J = 8.84 Hz, 1H) 8.31 (d, J = 9.09 Hz, 1H) 8.18 (d, J = 3.79 Hz, 1H) 7.50 (d, J = 5.81 Hz, 1 H) 7.16-7.20 (m, 1H) 6.78 (d, J = 5.56 Hz, 1H) 6.71 (d, J = 1.26 Hz, 1H) 4.97 (s, 1H) 4.90 (s, 1H) 4.64 (d, J = 1.52 Hz, 2H) 2.11 (d, J = 6.57 Hz, 3H) | 419.1 |
| 135-AZ[a] 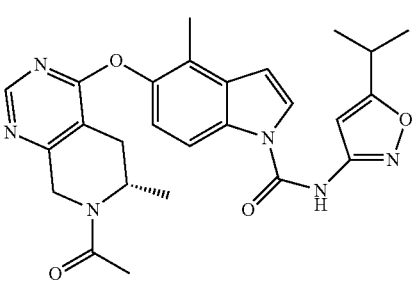<br>5-((S)-7-Acetyl-6-methyl-5,6,7,8-tetrahydro-pyrido[3,4-d]pyrimidin-4-yloxy)-4-methyl-indole-1-carboxylic acid (5-isopropyl-isoxazol-3-yl)-amide | (DMSO-$d_6$) δ ppm 11.28 (s, 1H) 8.49 (br. S.) 8.46 (br. S.) 8.13-8.17 (m) 8.12 (br. S.) 7.10 (d, J = 8.84 Hz, 1H) 6.88 (d, J = 3.79 Hz, 1H) 6.70 (s, 1H) 5.20 (br. S.) 5.16 (br. S.) 5.11 (br. S.) 4.80 (br. S.) 4.75 (br. S.) 4.57-4.63 (m) 4.55 (br. S.) 4.50 (br. S.) 4.05 (d, J = 19.45 Hz, 1H) 3.05-3.18 (m) 2.82-2.91 (m) 2.21 (s, 3H) 2.18 (s, 2H) 2.13 (s, 1H) 1.29 (d, J = 7.07 Hz, 6H) 1.21 (d, J = 6.82 Hz, 2H) 1.08 (d, J = 6.82 Hz, 1H) | 4 |

| | Structure/Chemical Name | ¹H NMR (400 MHz) | MS (ESI) m/z (M + 1) |
|---|---|---|---|
| 135-BA[b] | 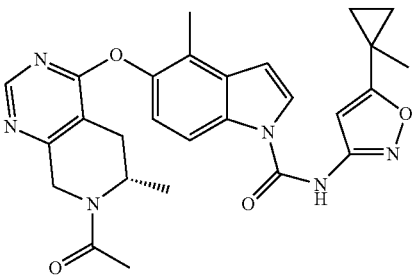<br>5-((S)-7-Acetyl-6-methyl-5,6,7,8-tetrahydro-pyrido[3,4-d]pyrimidin-4-yloxy)-4-methyl-indole-1-carboxylic acid [5-(1-methyl-cyclopropyl)-isoxazol-3-yl]-amide | (DMSO-$d_6$) δ ppm 11.25 (s, 1H) 8.49 (br. S.) 8.46 (br. S.) 8.13-8.16 (m) 8.12 (s, 1H) 7.10 (d, J = 9.09 Hz, 1H) 6.87 (d, J = 3.79 Hz, 1H) 6.68 (s, 1H) 5.17-5.24 (m) 5.16 (br. S.) 5.11 (br. S.) 4.80 (br. S.) 4.75 (br. S.) 4.56-4.64 (m) 4.54 (br. S.) 4.50 (br. S.) 4.08 (br. S.) 4.03 (br. S.) 3.13-3.18 (m) 3.07-3.13 (m) 2.85-2.91 (m) 2.84 (br. S.) 2.21 (s, 3H) 2.18 (s, 2H) 2.13 (s, 1H) 1.21 (d, J = 6.82 Hz, 2H) 1.13-1.18 (m, 2H) 1.08 (d, J = 6.82 Hz, 1H) 0.91-0.97 (m, 2H) | 501.2 |
| 135-BB | 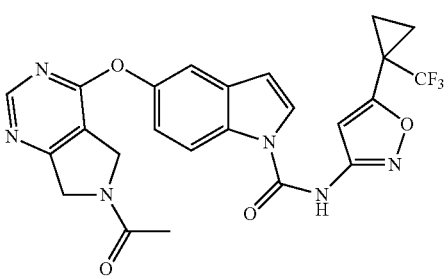<br>5-(6-Acetyl-6,7-dihydro-5H-pyrrolo[3,4-d]pyrimidin-4-yloxy)-indole-1-carboxylic acid [5-(1-trifluoromethyl-cyclopropyl)-isoxazole-3-yl]-amide | (DMSO-$d_6$) δ ppm 11.45 (s, 1H) 8.66 (d, J = 5.05 Hz, 1H) 8.31 (dd, J = 8.97, 2.15 Hz, 1H) 8.17 (d, J = 3.79 Hz, 1H) 7.51 (t, J = 2.91 Hz, 1H) 7.19 (ddd, J = 8.97, 4.55, 2.40 Hz, 1H) 7.04 (s, 1H) 6.79 (dd, J = 4.04, 1.52 Hz, 1H) 4.97 (s, 1H) 4.90 (s, 1H) 4.64 (s, 2H) 2.11 (d, J = 6.57 Hz, 3H) 1.54-1.60 (m, 4H) | 513.1 |
| 135-BC[a] | 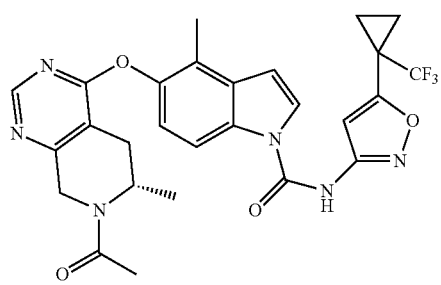<br>5-((S)-7-Acetyl-6-methyl-5,6,7,8-tetrahydro-pyrido[3,4-d]pyrimidin-4-yloxy)-4-methyl-indole-1-carboxylic acid [5-(1-trifluoromethyl-cyclopropyl)-isoxazole-3-yl]-amide | (DMSO-$d_6$) δ ppm 11.42 (s, 1H) 8.48 (br. S.) 8.46 (br. S.) 8.13-8.16 (m) 8.12 (br. S.) 7.10 (d, J = 8.84 Hz, 1H) 7.04 (s, 1H) 6.88 (d, J = 3.79 Hz, 1H) 5.17-5.23 (m) 5.16 (br. S.) 5.11 (br. S.) 4.80 (br. S.) 4.75 (br. S.) 4.57-4.64 (m) 4.54 (br. S.) 4.50 (br. S.) 4.07 (br. S.) 4.02 (br. S.) 3.15 (br. S.) 3.12 (m) 2.82-2.91 (m) 2.21 (s, 1H) 2.17 (s, 1 H) 2.12 (s, 1H) 1.52-1.59 (m, 2H) 1.21 (d, J = 7.07 Hz, 1H) 1.08 (d, J = 7.33 Hz, 1H) | 555.1 |
| 135-BD | 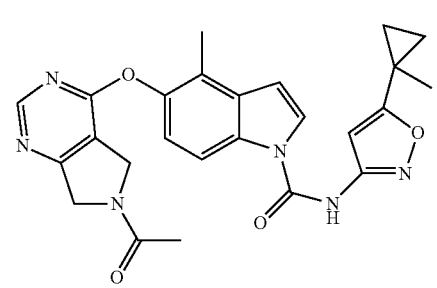<br>5-(6-Acetyl-6,7-dihydro-5H-pyrrolo[3,4-d]pyrimidin-4-yloxy)-4-methyl-indole-1-carboxylic acid [5-(1-methyl-cyclopropyl)-isoxazole-3-yl]-amide | (DMSO-$d_6$) δ ppm 11.23 (br. S., 1H) 8.62 (d, J = 6.06 Hz, 1H) 8.03-8.25 (m, 2H) 7.12 (dd, J = 8.97, 6.19 Hz, 1H) 6.88 (d, J = 3.79 Hz, 1H) 6.67 (s, 1H) 4.82-5.09 (m, 2H) 4.64 (s, 2H) 2.26 (d, J = 4.04 Hz, 3H) 2.11 (d, J = 8.59 Hz, 3H) 1.46 (s, 3H) 1.08-1.24 (m, 2H) 0.87-1.01 (m, 2H) | 473.2 |

| Structure/Chemical Name | ¹H NMR (400 MHz) | MS (ESI) m/z (M + 1) |
|---|---|---|
| 135-BE<sup>a</sup> 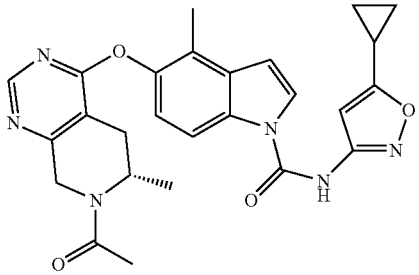 5-((S)-7-Acetyl-6-methyl-5,6,7,8-tetrahydro-pyrido[3,4-d]pyrimidin-4-yloxy)-4-methyl-indole-1-carboxylic acid (5-cyclopropyl-isoxazole-3-yl)-amide | (DMSO-d$_6$) ppm 11.24 (s, 1H) 8.48 (br. S.) 8.46 (br. S.) 8.12-8.17 (m) 8.11 (s, 1H) 7.09 (d, J = 8.84 Hz, 1H) 6.87 (d, J = 3.79 Hz, 1H) 6.66 (s, 1H) 5.16-5.24 (m) 5.15 (br. S.) 5.11 (br. S.) 4.80 (br. S.) 4.75 (br. S.) 4.58 (d, 1 H) 4.54 (br. S.) 4.50 (br. S.) 3.99-4.10 (m) 3.16 (br. S.) 3.12 (br. S.) 2.19-2.24 (m, 3H) 2.15-2.19 (m, 2H) 2.12 (br. S.) 1.18-1.25 (m, 2H) 1.05-1.11 (m, 3H) 0.92-0.97 (m, 2H) | 487.2 |
| 135-BF 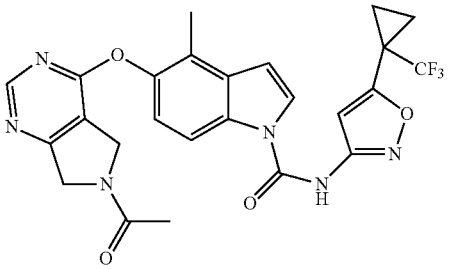 5-(6-Acetyl-6,7-dihydro-5H-pyrrolo[3,4-d]pyrimidin-4-yloxy)-4-methyl-indole-1-carboxylic acid [5-(1-trifluoromethyl-cyclopropyl)-isoxazole-3-yl]-amide | (DMSO-d$_6$) ppm 11.44 (s, 1H) 8.62 (d, J = 6.06 Hz, 1H) 8.04-8.26 (m, 2H) 7.12 (dd, J = 8.84, 5.81 Hz, 1H) 7.04 (s, 1H) 6.90 (d, J = 3.79 Hz, 1H) 4.84-5.07 (m, 2H) 4.64 (s, 2H) 2.26 (d, J = 3.79 Hz, 3H) 2.11 (d, J = 8.59 Hz, 3 H) 1.44-1.63 (m, 4H) | 527.2 |
| 135-BG 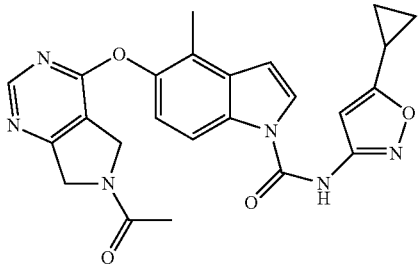 5-(6-Acetyl-6,7-dihydro-5H-pyrrolo[3,4-d]pyrimidin-4-yloxy)-4-methyl-indole-1-carboxylic acid (5-cyclopropyl-isoxazole-3-yl)-amide | (DMSO-d$_6$) ppm 11.22 (s, 1H) 8.62 (d, J = 6.06 Hz, 1H) 8.02-8.25 (m, 2H) 7.11 (dd, J = 8.72, 5.94 Hz, 1H) 6.88 (d, J = 3.79 Hz, 1H) 6.65 (s, 1H) 4.84-5.08 (m, 2H) 4.64 (s, 2H) 2.26 (d, J = 3.79 Hz, 3H) 2.15-2.20 (m, 1H) 2.11 (d, J = 8.59 Hz, 3H) 1.06-1.12 (m, 2H) 0.92-0.97 (m, 2H) | 459.2 |
| 135-BH<sup>a</sup> 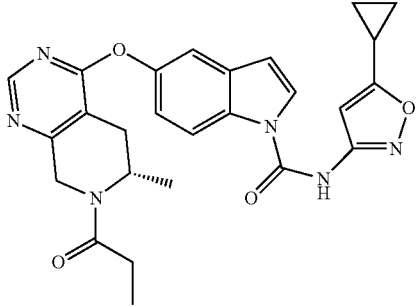 5-((S)-6-Methyl-7-propionyl-5,6,7,8-tetrahydro-pyrido[3,4-d]pyrimidin-4-yloxy)-indole-1-carboxylic acid (5-cyclopropyl-isoxazole-3-yl)-amide | (DMSO-d$_6$) δ ppm 11.22 (s, 1H), 8.50 (br. S., 1H), 8.28 (d, J = 9.6 Hz, 1H), 8.15 (d, J = 3.8 Hz, 1H), 7.46 (d, J = 2.5 Hz, 1H), 7.14 (dd, J = 9.0, 2.5 Hz, 1H), 6.75 (d, J = 4.4 Hz, 1H), 6.65 (s, 1H), 5.07-5.30 (m, 0H), 4.78 (d, J = 22.1 Hz, 0H), 4.64 (br. S., 0H), 4.49 (d, J = 18.9 Hz, 0H), 4.06 (d, J = 18.6 Hz, 0 H), 2.99-3.14 (m, 0H), 2.78-2.89 (m, 0H), 2.10-2.25 (m, 1H), 1.16-1.26 (m, 0H), 0.99-1.12 (m, 0H), 0.90-0.98 (m, 0H) | 487.1 |

| | Structure/Chemical Name | ¹H NMR (400 MHz) | MS (ESI) m/z (M + 1) |
|---|---|---|---|
| 135-BI[a] | 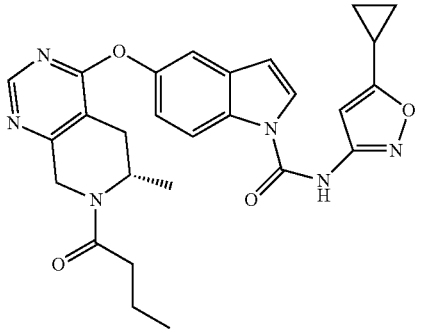<br>5-((S)-7-Butyryl-6-methyl-5,6,7,8-tetrahydro-pyrido[3,4-d]pyrimidin-4-yloxy)-indole-1-carboxylic acid (5-cyclopropyl-isoxazole-3-yl)-amide | (DMSO-$d_6$) δ ppm 11.13 (br. S., 1H), 8.50 (br. S., 1H), 8.30 (d, J = 9.0 Hz, 1 H), 8.15 (d, J = 3.8 Hz, 1H), 7.45 (d, J = 2.4 Hz, 1H), 7.13 (dd, J = 8.9, 2.3 Hz, 1H), 6.73 (d, J = 3.8 Hz, 1H), 6.65 (s, 1 H), 5.19-5.25 (m), 5.11-5.18 (m), 4.79 (d, J = 18.6 Hz), 4.59-4.70 (m), 4.44-4.53 (m), 4.01-4.09 (m), 3.00-3.12 (m), 2.78-2.88 (m), 2.36-2.48 (m), 2.12-2.21 (m, 1H), 1.47-1.64 (m, 2H), 1.20 (d, J = 5.6 Hz, 2H), 1.03-1.11 (m), 0.90-0.97 (m) | 501.1 |
| 135-BJ[a] | 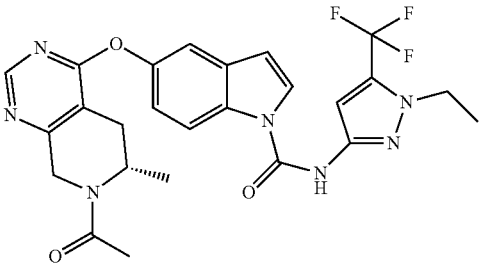<br>5-((S)-7-Acetyl-6-methyl-5,6,7,8-tetrahydro-pyrido[3,4-d]pyrimidin-4-yloxy)-indole-1-carboxylic acid (1-ethyl-5-trifluoromethyl-1H-pyrazol-3-yl)-amide | (DMSO-$d_6$) δ ppm 11.08 (s, 1H) 8.48-8.55 (m, 1H) 8.30 (d, J = 9.09 Hz, 1H) 8.18 (d, J = 3.79 Hz, 1H) 7.46 (d, J = 2.27 Hz, 1H) 7.13 (d, J = 9.09 Hz, 1H) 7.06 (s, 1 H) 6.75 (d, J = 3.79 Hz, 1H) 5.10-5.12 (m) 4.74 (br. s.) 4.52-4.54 (m) 4.24 (d, J = 7.07 Hz) 4.01-4.10 (m) 3.10 (br. s.) 2.85 (br. s.) 2.11-2.18 (m) 1.42 (t, J = 7.33 Hz) 1.20-1.22 (m) 1.08-1.10 (m) | 528.1 |
| 135-BK[a] | 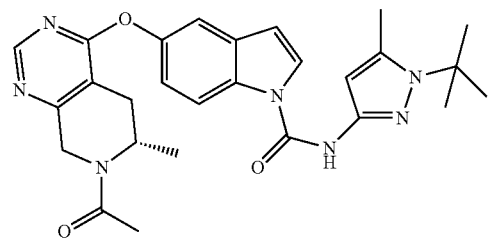<br>5-((S)-7-Acetyl-6-methyl-5,6,7,8-tetrahydro-pyrido[3,4-d]pyrimidin-4-yloxy)-indole-1-carboxylic acid (1-tert-butyl-5-methyl-1H-pyrazol-3-yl)-amide | (DMSO-$d_6$) δ ppm 10.54 (s, 1H) 8.49-8.53 (m, 1H) 8.29 (d, J = 9.09 Hz, 1H) 8.18 (d, J = 3.54 Hz, 1H) 7.43 (d, J = 2.53 Hz, 1H) 7.10 (dd, J = 8.97, 2.40 Hz, 1H) 6.69 (d, J = 3.03 Hz, 1H) 6.37 (s, 1H) 5.15-5.35 (m, 1H) 4.05-4.58 (m, 2H) 3.05-3.20 (m, 1H) 2.79-2.86 (m, 1H) 2.45 (s, 3H) 2.12-2.17 (m, 3H) 1.59 (s, 9H) 1.07-1.23 (m, 3H) | 502.1 |
| 135-BL[a] | 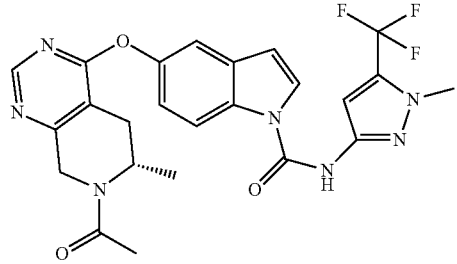<br>5-((S)-7-Acetyl-6-methyl-5,6,7,8-tetrahydro-pyrido[3,4-d]pyrimidin-4-yloxy)-indole-1-carboxylic acid (1-methyl-5-trifluoromethyl-1H-pyrazol-3-yl)-amide | (DMSO-$d_6$) δ ppm 11.04 (s, 1H) 8.46-8.56 (m, 1H) 8.30 (d, J = 8.84 Hz, 1H) 8.17 (d, J = 3.79 Hz, 1H) 7.46 (d, J = 2.27 Hz, 1H) 7.14 (dd, J = 9.09, 2.53 Hz, 1H) 7.07 (s, 1H) 6.75 (d, J = 3.79 Hz, 1H) 5.13 (m) 4.76 (m) 4.47-4.62 (m,) 4.06 (s) 3.99-4.04 (m) 3.95 (s, 3H) 3.11 (br. S.) 3.05-3.09 (m) 2.85 (br. S.) 2.17 (br. S.) 2.12 (br. S.) 1.23-1.28 (m) 1.17-1.23 (m) 1.10 (s) | 514.2 |

| Structure/Chemical Name | ¹H NMR (400 MHz) | MS (ESI) m/z (M + 1) |
|---|---|---|
| 135-BM[a] 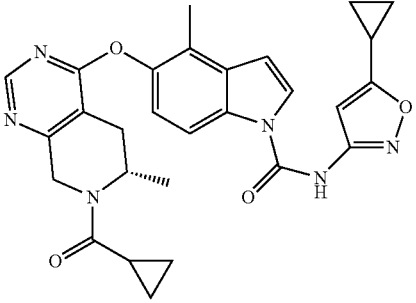  5-((S)-7-Cyclopropanecarbonyl-6-methyl-5,6,7,8-tetrahydro-pyrido[3,4d]pyrimidin-4-yloxy)-4-methyl-indole-1-carboxylic acid (5-cyclopropyl-isoxazol-3-yl)-amide | (DMSO-$d_6$) δ ppm 11.21 (s, 1H) 8.47 (s, 1H) 8.07-8.19 (m, 2H) 7.10 (d, J = 9.09 Hz, 1H) 6.87 (d, J = 3.03 Hz, 1 H) 6.65 (s, 1H) 4.98-5.28 (m) 4.49-4.73 (m) 4.02-4.19 (m) 3.12 (br. s.) 2.90 (br. s.) 2.22 (s, 3H) 2.14-2.20 (m, 1H) 1.23 (br. s.) 1.05-1.13 (m) 0.91-0.98 (m) 0.82-0.89 (m) 0.73-0.82 (m) | 513.2 |
| 135-BN[a] 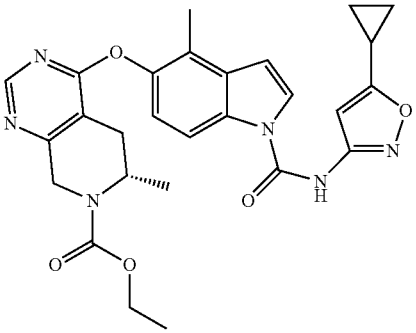  (S)-4-[1-(5-Cyclopropyl-isoxazol-3-ylcarbamoyl)-4-methyl-1H-indol-5yloxy]-6-methyl-5,8-dihydro-6Hpyrido[3,4-d]pyrimidine-7-carboxylic acidethyl ester | (DMSO-$d_6$) δ 11.21 (s, 1H) 8.46 (s, 1 H) 8.01-8.20 (m, 2H) 7.09 (d, J = 8.84 Hz, 1H) 6.86 (d, J = 3.79 Hz, 1H) 6.65 (s, 1H) 4.67-4.88 (m) 4.22-4.34 (m) 4.13 (qd, J = 7.07, 1.26 Hz, 2H) 2.95-3.07 (m) 2.78-2.92 (m) 2.21 (s, 3H) 1.24 (t, J = 7.07 Hz, 3H) 1.15 (d, J = 7.07 Hz, 3H) 1.05-1.11 (m, 2H) 0.92-0.97 (m, 2H). | 517.1 |
| 135-BO[a] 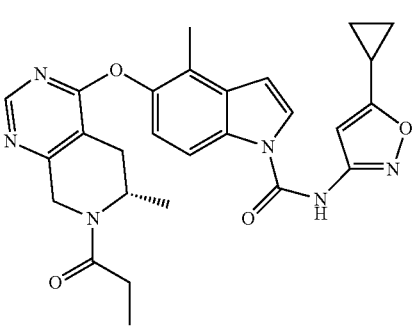  4-Methyl-5-((S)-6-methyl-7-propionyl-5,6,7,8-tetrahydropyrido[3,4d]pyrimidin-4-yloxy)-indole-1-carboxylic acid (5-cyclopropyl-isoxazol-3-yl)-amide | (DMSO-$d_6$) δ 11.21 (s, 1H) 8.46 (br. s., 1H) 8.03-8.21 (m, 2H) 7.09 (d, J = 8.84 Hz, 1H) 6.86 (d, J = 3.79 Hz, 1 H) 6.65 (s, 1H) 5.08-5.27 (m, 1H) 4.80 (br. s.) 4.62 (br. s.) 4.42-4.53 (m) 3.99-4.14 (m) 3.05-3.18 (m) 2.88 (br. s.) 2.21 (s, 3H) 2.14-2.19 (m) 1.21 (br. s.) 1.01-1.12 (m) 0.91-0.97 (m, 2H) | 501.2 |

| Structure/Chemical Name | ¹H NMR (400 MHz) | MS (ESI) m/z (M + 1) |
|---|---|---|
| 135-BP[a] 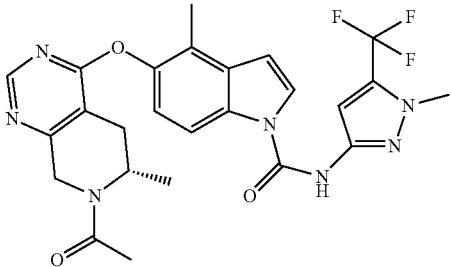<br>5-((S)-7-Acetyl-6-methyl-5,6,7,8-tetrahydro-pyrido[3,4-d]pyrimidin-4-yloxy)-4-methyl-indole-1-carboxylic acid (1-methyl-5-trifluoromethyl-1H-pyrazol-3-yl)-amide | (DMSO-$d_6$) δ 11.03 (s, 1H) 8.43-8.51 (m, 1H) 8.08-8.19 (m, 2H) 7.03-7.12 (m, 2H) 6.85 (d, J = 3.79 Hz, 1H) 5.13 (m) 4.71-4.82 (m) 4.59 (br. s.) 4.46-4.56 (m) 4.00-4.11 (m) 3.95 (s, 3H) 3.07-3.18 (m) 2.81-2.92 (m) 2.21 (s, 3H) 2.17 (s, 2H) 2.12 (s, 1H) 1.21 (d, J = 6.57 Hz, 2H) 1.08 (d, J = 6.57 Hz, 1H) | 528.2 |
| 135-BQ[a] 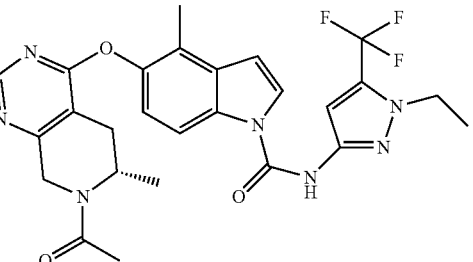<br>5-((S)-7-Acetyl-6-methyl-5,6,7,8-tetrahydro-pyrido[3,4-d]pyrimidin-4-yloxy)-4-methyl-indole-1-carboxylic acid (1-ethyl-5-trifluoromethyl-1H-pyrazol-3-yl)-amide | (DMSO-$d_6$) δ 11.07 (s, 1H) 8.42-8.51 (m, 1H) 8.10-8.18 (m, 2H) 7.04-7.11 (m, 2H) 6.85 (d, J = 3.54 Hz, 1H) 5.13 (m) 4.75 (br. s.) 4.54 (br. s) 4.24 (q, J = 7.07 Hz, 2H) 4.05 (m) 2.81-2.92 (m) 2.21 (s, 3H) 2.17 (s) 2.12 (s) 1.42 (t, J = 7.20 Hz, 3H) 1.22 (m) 1.08 (m) | 542.21 |

[a]¹H NMR spectra collected at 27° C. in DMSO-$d_6$ solution. At this temperature, the identified compounds exist as a mixture of amide rotamers (presumably due to hindered rotation around the nitrogen carbonyl bond). This does not permit for unequivocal assignment of each proton NMR signal. For signals that include both rotamers, assignment of shift, coupling, and proton number are noted. Other peaks corresponding to individual rotamers are noted by shift and coupling.
[b]¹H NMR spectra collected at the temperature listed with the Table for samples in DMSO-$d_6$ solution. At the specified temperature, the rate of rotation about the amide bond is sufficiently fast such that the ¹H NMR signals for the separate rotamers have collasced to a single signal thereby permiting assignment of each signal the proton NMR spectrum.

EXAMPLE 136

136-A. 5-((S)-7-Ethyl-6-methyl-5,6,7,8-tetrahydro-pyrido[3,4-d]pyrimidin-4-yloxy)-indole-1-carboxylic acid (5-cyclopropyl-isoxazol-3-yl)-amide

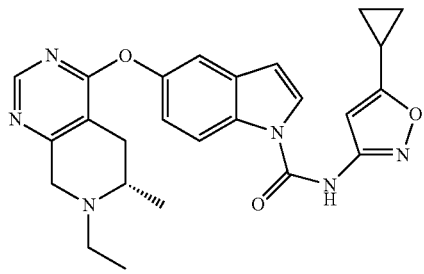 [SMILES: CCN1Cc2ncnc(Oc3ccc4c(ccn4C(=O)Nc4cc(C5CC5)on4)c3)c2C[C@@H]1C]

Prepared with similar method to that described for Example 37. MS (ESI) m/z 459.2 (M+1); ¹H NMR (400 MHz, DMSO-$d_6$) δ ppm 11.21 (s, 1 H), 8.42 (s, 1 H), 8.27 (d, J=9.1 Hz, 1 H), 8.15 (d, J=3.5 Hz, 1 H), 7.44 (d, J=2.3 Hz, 1 H), 7.13 (dd, J=8.8, 2.3 Hz, 1 H), 6.75 (d, J=3.8 Hz, 1 H), 6.65 (s, 1 H), 3.59-3.75 (m, 2 H), 3.05-3.17 (m, 1 H), 2.93 (dd, J=16.7, 5.3 Hz, 1 H), 2.67-2.77 (m, 1 H), 2.53-2.64 (m, 2 H), 2.11-2.23 (m, 1 H), 1.04-1.12 (m, 8 H), 0.91-0.98 (m, 2 H).

The following compounds are prepared with similar method.

| | Structure/Chemical Name | ¹H NMR (400 MHz) | MS (ESI) m/z (M + 1) |
|---|---|---|---|
| 136-B | 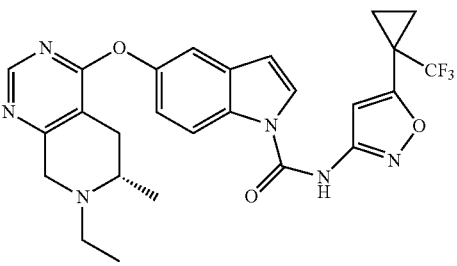 [SMILES: CCN1Cc2ncnc(Oc3ccc4c(ccn4C(=O)Nc4cc(C5(C(F)(F)F)CC5)on4)c3)c2C[C@@H]1C]<br>5-((S)-7-Ethyl-6-methyl-5,6,7,8-tetrahydro-pyrido[3,4-d]pyrimidin-4-yloxy)-indole-1-carboxylic acid [5-(1-trifluoromethyl-cyclopropyl)-isoxazol-3-yl]-amide | (DMSO-$d_6$) δ ppm 11.45 (br. S., 1H), 8.42 (s, 1H), 8.29 (d, J = 9.0 Hz, 1H), 8.15 (d, J = 3.8 Hz, 1H), 7.45 (d, J = 2.3 Hz, 1H), 7.14 (dd, J = 9.0, 2.4 Hz, 1H), 7.05 (s, 1H), 6.76 (d, J = 3.7 Hz, 1H), 3.66 (s, 2H), 3.06-3.16 (m, 1H), 2.93 (dd, J = 17.0, 4.7 Hz, 1H), 2.65-2.77 (m, 1H), 2.53-2.63 (m, 2H), 1.52-1.59 (m, 5H), 1.03-1.12 (m, 5H) | 527.2 |
| 136-C | 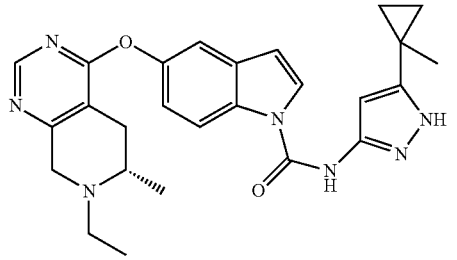 [SMILES: CCN1Cc2ncnc(Oc3ccc4c(ccn4C(=O)Nc4cc(C5(C)CC5)[nH]n4)c3)c2C[C@@H]1C]<br>5-((S)-7-Ethyl-6-methyl-5,6,7,8-tetrahydro-pyrido[3,4-d]pyrimidin-4-yloxy)-indole-1-carboxylic acid [5-(1-methyl-cyclopropyl)-1H-pyrazol-3-yl]-amide | (DMSO-$d_6$) δ ppm 12.12 (s, 1H), 10.55 (s, 1H), 8.42 (s, 1H), 8.29 (d, J = 8.8 Hz, 1H), 8.16 (d, J = 3.8 Hz, 1H), 7.42 (d, J = 2.3 Hz, 1H), 7.09 (dd, J = 9.0, 2.4 Hz, 1H), 6.70 (d, J = 3.8 Hz, 1H), 6.30 (d, J = 2.3 Hz, 1H), 3.66 (s, 2H), 3.03-3.19 (m, 1H), 2.86-2.98 (m, 1H), 2.65-2.78 (m, 1H), 2.52-2.65 (m, 2H), 1.41 (s, 3H), 1.02-1.13 (m, 6H), 0.89-0.96 (m, 2H), 0.74-0.81 (m, 2H) | 472.2 |
| 136-D | 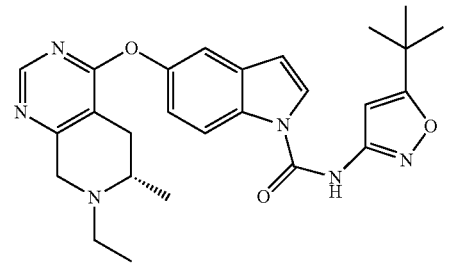 [SMILES: CCN1Cc2ncnc(Oc3ccc4c(ccn4C(=O)Nc4cc(C(C)(C)C)on4)c3)c2C[C@@H]1C]<br>5-((S)-7-Ethyl-6-methyl-5,6,7,8-tetrahydro-pyrido[3,4-d]pyrimidin-4-yloxy)-indole-1-carboxylic acid (5-tert-butyl-isoxazol-3-yl)-amide | (DMSO-$d_6$) δ ppm 11.26 (br. S., 1H), 8.42 (s, 1H), 8.35 (d, J = 8.8 Hz, 1H), 8.13 (d, J = 3.8 Hz, 1H), 7.41 (d, J = 2.3 Hz, 1H), 7.08 (dd, J = 9.0, 2.1 Hz, 1H), 6.67-6.71 (m, 1H), 6.66 (s, 1H), 3.56 (s, 2H), 2.81-2.87 (m, 2H), 2.72-2.79 (m, 2H), 2.58 (q, J = 7.1 Hz, 2H), 1.33 (s, 9H), 1.12 (t, J = 7.2 Hz, 3H). | 461.2 |
| 136-E | 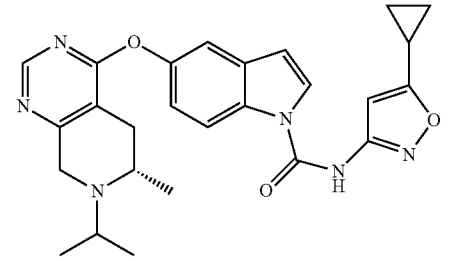 [SMILES: CC(C)N1Cc2ncnc(Oc3ccc4c(ccn4C(=O)Nc4cc(C5CC5)on4)c3)c2C[C@@H]1C]<br>5-((S)-7-Isopropyl-6-methyl-5,6,7,8-tetrahydro-pyrido[3,4-d]pyrimidin-4-yloxy)-indole-1-carboxylic acid (5-cyclopropyl-isoxazol-3-yl)-amide | (DMSO-$d_6$) δ ppm 11.21 (br. S, 1H) 8.41 (s, 1H) 8.27 (d, J = 9.09 Hz, 1H) 8.15 (d, J = 3.79 Hz, 1H) 7.44 (d, J = 2.27 Hz, 1H) 7.13 (dd, J = 8.97, 2.40 Hz, 1H) 6.75 (d, J = 3.28 Hz, 1H) 6.65 (s, 1H) 3.60-3.81 (m, 2H) 3.07-3.25 (m, 2H) 2.91 (dd, J = 17.94, 2.53 Hz, 1H) 2.09-2.24 (m, 1H) 1.11-1.18 (m, 6H) 1.05-1.11 (m, 3H) 1.02 (d, J = 6.06 Hz, 3H) 0.90-0.97 (m, 2H) | 473.1 |

-continued

| | Structure/Chemical Name | ¹H NMR (400 MHz) | MS (ESI) m/z (M + 1) |
|---|---|---|---|
| 136-F | 5-((S)-7-Ethyl-6-methyl-5,6,7,8-tetrahydro-pyrido[3,4-d]pyrimidin-4-yloxy)-indole-1-carboxylic acid (4,4-dimethyl-4,5,6,7-tetrahydro-pyrazolo[1,5-a]pyridine-2-yl)-amide | (DMSO-d₆) δ ppm 10.62 (s, 1H), 8.42 (s, 1H), 8.29 (d, J = 9.1 Hz, 1H), 8.15 (d, J = 3.8 Hz, 1H), 7.42 (d, J = 2.3 Hz, 1H), 7.09 (dd, J = 9.0, 2.4 Hz, 1H), 6.70 (d, J = 3.5 Hz, 1H), 6.40 (s, 1H), 3.96 (t, J = 6.2 Hz, 2H), 3.57-3.71 (m, 2H), 3.05-3.17 (m, 1H), 2.92 (dd, J = 17.1, 4.7 Hz, 1H), 2.65-2.78 (m, 1H), 2.51-2.65 (m, 2H), 1.92-2.09 (m, 1H), 1.57-1.74 (m, 1H), 1.30 (s, 6H), 1.10 (d, 3H), 1.08 (t, 3H) | 500.1 |
| 136-G | 5-(7-Methyl-5,6,7,8-tetrahydro-pyrido[3,4-d]pyrimidin-4-yloxy)-indole-1-carboxylic acid (5-tert-butyl-isoxazol-3-yl)-amide | (DMSO-d₆) δ ppm 11.25 (br. S., 1H), 8.42 (s, 1H), 8.30 (d, J = 9.1 Hz, 1H), 8.16 (d, J = 3.8 Hz, 1H), 7.44 (d, J = 2.0 Hz, 1H), 7.13 (dd, J = 8.8, 2.3 Hz, 1H), 6.74 (d, J = 3.5 Hz, 1H), 6.68 (s, 1H), 3.51 (s, 2H), 2.84 (t, J = 5.4 Hz, 2H), 2.71 (t, J = 5.7 Hz, 2H), 2.41 (s, 3H), 1.34 (s, 9H) | 447.2 |
| 136-H | 5-((S)-6-Methyl-7-propyl-5,6,7,8-tetrahydro-pyrido[3,4-d]pyrimidin-4-yloxy)-indole-1-carboxylic acid (5-cyclopropyl-isoxazol-3-yl)-amide | (DMSO-d₆) δ ppm 11.21 (s, 1H) 8.42 (s, 1H) 8.28 (d, J = 9.09 Hz, 1H) 8.15 (d, J = 3.79 Hz, 1H) 7.44 (d, J = 2.53 Hz, 1H) 7.12 (dd, J = 8.97, 2.40 Hz, 1H) 6.74 (d, J = 3.54 Hz, 1H) 6.65 (s, 1H) 3.66 (d, J = 5.05 Hz, 2H) 3.06-3.17 (m, 1H) 2.92 (dd, J = 17.05, 4.67 Hz, 1H) 2.53-2.62 (m, 2H) 2.11-2.23 (m, 1H) 1.43-1.61 (m, 2H) 1.01-1.13 (m, 5H) 0.82-0.98 (m, 6H) (d, J = 6.06 Hz, 3H) 0.90-0.97 (m, 2H) | 473.1 |
| 136-I | 5-((S)-7-Ethyl-6-methyl-5,6,7,8-tetrahydro-pyrido[3,4-d]pyrimidin-4-yloxy)-indole-1-carboxylic acid (4,4-dimethyl-5,6-dihydro-4H-pyrrolo[1,2-b]pyrazol-2-yl)-amide | (DMSO-d₆) δ ppm 10.62 (s, 1H), 8.42 (s, 1H), 8.27 (d, J = 9.1 Hz, 1H), 8.14 (d, J = 3.8 Hz, 1H), 7.42 (d, J = 2.3 Hz, 1H), 7.10 (dd, J = 9.0, 2.4 Hz, 1H), 6.70 (d, J = 3.5 Hz, 1H), 6.27 (s, 1H), 4.09 (t, J = 6.9 Hz, 1H), 3.66 (br. S., 2H), 3.06-3.17 (m, 1H), 2.92 (dd, J = 17.2, 4.8 Hz, 1H), 2.65-2.77 (m, 1H), 2.52-2.64 (m, 2H), 2.29-2.38 (m, 3H), 1.32 (s, 6H), 1.09 (overlapping d, J = 6.8 Hz, 3H), 1.06 (overlapping t, J = 6.8 Hz, 3H). | 486.1 |

-continued

| | Structure/Chemical Name | ¹H NMR (400 MHz) | MS (ESI) m/z (M + 1) |
|---|---|---|---|
| 136-J | 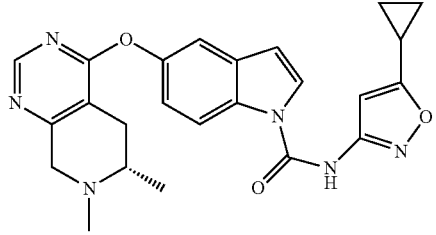 [SMILES: C[C@H]1Cc2c(ncnc2Oc2ccc3c(ccn3C(=O)Nc3cc(C4CC4)on3)c2)CN1C]<br>5-((S)-6,7-Dimethyl-5,6,7,8-tetrahydro-pyrido[3,4-d]pyrimidin-4-yloxy)-indole-1-carboxylic acid (5-cyclopropyl-isoxazol-3-yl)-amide | (DMSO-$d_6$) δ ppm 11.24 (s, 1H), 8.42 (s, 1H), 8.27 (d, J = 9.0 Hz, 1H), 8.15 (d, J = 3.7 Hz, 1H), 7.45 (d, J = 2.3 Hz, 1 H), 7.13 (dd, J = 9.0, 2.4 Hz, 1H), 6.75 (d, J = 3.8 Hz, 1H), 6.66 (s, 1H), 3.75 (d, J = 17.6 Hz, 1H), 3.48 (d, J = 17.6 Hz, 1H), 2.91 (dd, J = 16.9, 4.0 Hz, 1H), 2.72 (dq, J = 12.5, 6.4 Hz, 1H), 2.55 (d, J = 8.0 Hz, 1H), 2.36 (s, 3H), 2.11-2.24 (m, 1H), 1.16 (d, J = 6.3 Hz, 3H), 1.03-1.12 (m, 2H), 0.91-0.99 (m, 2H) | 445.1 |
| 136-K | 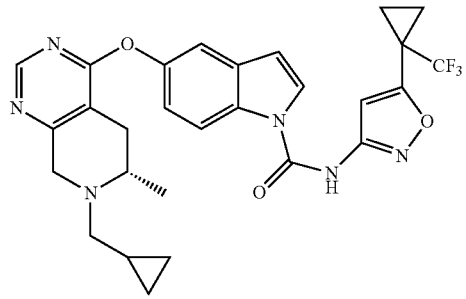 [SMILES: C[C@H]1Cc2c(ncnc2Oc2ccc3c(ccn3C(=O)Nc3cc(C4(C(F)(F)F)CC4)on3)c2)CN1CC1CC1]<br>5-((S)-7-Cyclopropylmethyl-6-methyl-5,6,7,8-tetrahydro-pyrido[3,4-d]pyrimidin-4-yloxy)-indole-1-carboxylic acid [5-(1-trifluoromethyl-cyclopropyl)-isoxazol-3-yl]-amide | (DMSO-$d_6$) δ ppm 11.43 (s, 1H) 8.42 (s, 1H) 8.28 (d, J = 9.09 Hz, 1H) 8.15 (d, J = 3.79 Hz, 1H) 7.45 (d, J = 2.53 Hz, 1H) 7.14 (dd, J = 8.84, 2.27 Hz, 1H) 7.04 (s, 1H) 6.77 (d, J = 3.54 Hz, 1H) 3.73-3.84 (m, 2H) 3.17-3.23 (m, 1 H) 2.94 (dd, J = 17.43, 5.31 Hz, 1H) 2.54-2.63 (m, 1H) 2.43-2.47 (m, 2 H) 1.54-1.59 (m, 4H) 1.07 (d, J = 6.57 Hz, 3H) 0.86-0.93 (m, 1H) 0.51 (d, J = 8.34 Hz, 2H) 0.13-0.17 (m, 2H) | 553.2 |
| 136-L | 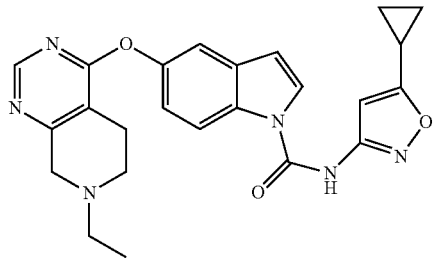 [SMILES: CCN1CCc2c(ncnc2Oc2ccc3c(ccn3C(=O)Nc3cc(C4CC4)on3)c2)C1]<br>5-(7-Ethyl-5,6,7,8-tetrahydro-pyrido[3,4-d]pyrimidin-4-yloxy)-indole-1-carboxylic acid (5-cyclopropyl-isoxazol-3-yl)-amide | (DMSO-$d_6$) δ ppm 11.21 (s, 1H), 8.42 (s, 1H), 8.27 (d, J = 8.8 Hz, 1H), 8.15 (d, J = 3.8 Hz, 1H), 7.44 (d, J = 2.3 Hz, 1H), 7.13 (dd, J = 9.0, 2.4 Hz, 1H), 6.75 (d, J = 3.8 Hz, 1H), 6.65 (s, 1H), 3.57 (s, 2 H), 2.71-2.90 (m, 4H), 2.59 (q, J = 7.1 Hz, 2H), 2.10-2.22 (m, 1H), 1.02-1.19 (m, 5H), 0.86-0.98 (m, 2H), | 445.2 |

EXAMPLE 137

137-A. 1-[5-(6-Hydroxymethyl-pyrimidin-4-yloxy)-indol-1-yl]-ethanone

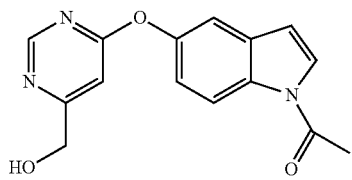 [SMILES: CC(=O)n1ccc2cc(Oc3cc(CO)ncn3)ccc21]

To a solution of 5-(6-benzyloxymethyl-pyrimidin-4-yloxy)-1H-indole (12 g, 36.2 mmol) in THF (300 mL), NaH (1.74 g, 43.5 mmol) and acetic anhydride (5.13 mL, 54.3 mmol) are added. After 1 h the reaction is quenched with aqueous ammonium chloride and extracted with EtOAc. Most of the impurities are removed passing it through a silica gel column eluting with 50:50 heptane:EtOAc to give crude 1-[5-(6-benzyloxymethyl-pyrimidin-4-yloxy)-indol-1-yl]-ethanone. This is then dissolved in TFA (300 mL) and heated to 100° C. for 6 hours. At this point the solvent is removed and 1-[5-(6-hydroxymethyl-pyrimidin-4-yloxy)-indol-1-yl]-ethanone isolated via FCC eluting with EtOAc. MS (ESI) m/z 284.0 (M+1).

137-B. [6-(1H-Indol-5-yloxy)-pyrimidin-4-ylmethyl]-methyl-carbamic acid tert-butyl ester

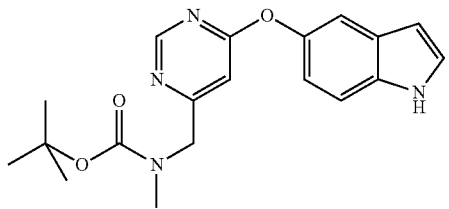 [SMILES: CN(Cc1cc(Oc2ccc3[nH]ccc3c2)ncn1)C(=O)OC(C)(C)C]

To a solution of 1-[5-(6-hydroxymethyl-pyrimidin-4-yloxy)-indol-1-yl]-ethanone (7.92 g, 28.0 mmol) in DCM (300 mL), MsCl (3.27 mL, 41.9 mmol) and triethylamine (7.79 mL, 55.9 mmol) are added followed by DMAP (0.342 g, 2.80 mmol). At this point the reaction is stirred for 1 h at 0° C. Water is then added and the reaction extracted with EtOAc. To a solution of the concentrated product (11.2 g, 31.0 mmol) in THF (1000 mL), methylamine (2 M in THF) (465 mL, 930 mmol) is added and the reaction stirred for 24 h. At this point the solvent is removed and the residue is then re-dissolved in DCM (300 mL) and Boc-anhydride (8.64 mL, 37.2 mmol) is added. After 10 h the solvent is evaporated and the residue separated using FCC eluting with Heptane:EtOAc 100:0 to 50:50 to give the title compound. MS (ESI) m/z 355.1 (M+1).

137-C. 5-(6-Methylaminomethyl-pyrimidin-4-yloxy)-indole-1-carboxylic acid (5-isopropyl-1H-pyrazol-3-yl)-amide

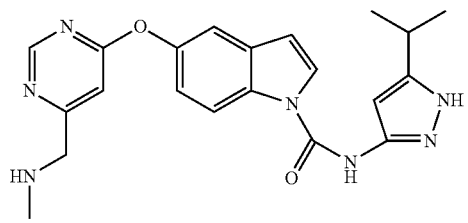 [SMILES: CNCc1cc(Oc2ccc3c(ccn3C(=O)Nc3cc(C(C)C)[nH]n3)c2)ncn1]

[6-(1H-Indol-5-yloxy)-pyrimidin-4-ylmethyl]-methyl-carbamic acid tert-butyl ester (300 mg, 0.846 mmol) is dissolved in DMF (8.46 mL), cooled to 0° C. and flushed with nitrogen. NaH (102 mg, 2.54 mmol) is added. The reaction is stirred in the ice bath for 30 minutes before Example 5-F (439 mg, 1.270 mmol) is added in 6 mL of DMF. After 2 h the reaction is cooled in an ice bath and diluted with 15 mL of ethyl acetate and quenched with 2 mL of a saturated solution of ammonium chloride. The mixture is diluted with ethyl acetate and placed in a separatory funnel. The organic layer is removed and the water layer is extracted with another 50 mL ethyl acetate. The combined organics are dried, and concentrated. The solid is dissolved in 10 mL of DCM, cooled to 0° C., and treated with 2 mL of TFA. The ice bath is removed after 30 minutes and after an additional 1 h the reaction is concentrated and then diluted with 10 mL of ethyl acetate. The solution is treated with 3 mL of ammonium hydroxide. The solution is concentrated again to a white solid. The solid absorbed onto silica and separated via flash chromatography (0-10% NH$_3$/MeOH:DCM) to obtain the title compound. MS (ESI) m/z 406.0 (M+1). $^1$H NMR (400 MHz, DMSO-d$_6$) δ ppm 12.22 (br. S., 1 H) 10.59 (br. S., 1 H) 8.65 (d, J=1.01 Hz, 1 H) 8.32 (d, J=9.09 Hz, 1 H) 8.18 (d, J=3.79 Hz, 1 H) 7.45 (d, J=2.53 Hz, 1 H) 7.11 (dd, J=8.84, 2.53 Hz, 1 H) 7.03 (d, J=1.01 Hz, 1 H) 6.72 (d, J=3.28 Hz, 1 H) 6.34 (s, 1 H) 3.71 (s, 2 H) 2.96 (t, J=7.07 Hz, 1 H) 2.29 (s, 3 H) 1.25 (d, J=6.82 Hz, 6 H).

The following compounds are prepared with similar method or by similar method to those described for Example 19, Example 112-D, and/or Example 76-D.

| 137-D | | |
|---|---|---|
| 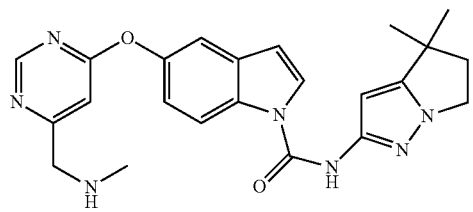 [SMILES: CNCc1cc(Oc2ccc3c(ccn3C(=O)Nc3cc4n(n3)CCC4(C)C)c2)ncn1] 5-(6-Methylaminomethyl-pyrimidin-4-yloxy)-indole-1-carboxylic acid (4,4-dimethyl-5,6-dihydro-4H-pyrrolo[1,2-b]pyrazol-2-yl)-amide | (DMSO-d$_6$) δ ppm 10.64 (br. S., 1H), 8.65 (s, 1H), 8.30 (d, J = 8.8 Hz, 1H), 8.16 (d, J = 3.5 Hz, 1H), 7.45 (d, J = 2.3 Hz, 1 H), 7.12 (dd, J = 8.8, 2.5 Hz, 1H), 7.03 (s, 1H), 6.72 (d, J = 3.5 Hz, 1H), 6.27 (s, 1 H), 4.04-4.14 (m, 2H), 3.70 (s, 2H), 2.31-2.38 (m, 2H), 2.29 (s, 3H), 1.32 (s, 6H) | 432.1 |

| | | | |
|---|---|---|---|
| 137-E | 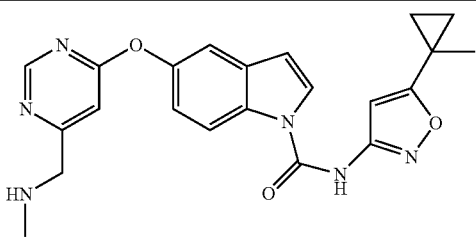<br>5-(6-Methylaminomethyl-pyrimidin-4-yloxy)-indole-1-carboxylic acid [5-(1-methyl cyclopropyl)-isoxazol-3-yl]-amide | (DMSO-d$_6$) δ ppm 8.66 (d, J = 1.01 Hz, 1H) 8.32 (d, J = 9.09 Hz, 1H) 8.17 (d, J = 3.79 Hz, 1H) 7.47 (d, J = 2.53 Hz, 1H) 7.14 (dd, J = 8.84, 2.27 Hz, 1H) 7.04 (d, J = 1.01 Hz, 1H) 6.76 (d, J = 3.79 Hz, 1H) 6.67 (s, 1H) 3.73 (s, 2H) 2.29 (s, 3H) 1.46 (s, 3H) 1.12-1.14 (m, 2H) 0.84-1.00 (m, 2H) | 419.0 |
| 137-F | 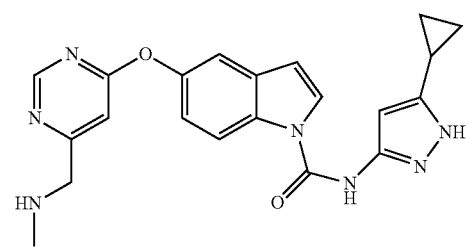<br>5-(6-Methylaminomethyl-pyrimidin-4-yloxy)-indole-1-carboxylic acid (5-cyclopropyl-1H-pyrazol-3-yl)-amide | (DMSO-d$_6$) δ ppm 12.24 (br. S., 1H) 10.56 (br. S., 1H) 8.65 (d, J = 1.01 Hz, 1H) 8.31 (d, J = 9.09 Hz, 1H) 8.17 (d, J = 3.79 Hz, 1H) 7.44 (d, J = 2.02 Hz, 1H) 7.11 (d, J = 9.09 Hz, 1H) 7.03 (d, J = 1.01 Hz, 1H) 6.71 (d, J = 3.54 Hz, 1H) 6.22 (s, 1H) 3.71 (s, 2H) 2.29 (s, 3H) 1.88-1.95 (m, 1H) 0.84-0.99 (m, 2H) 0.72 (dd, J = 4.80, 2.02 Hz, 2H) | 404.1 |
| 137-G | 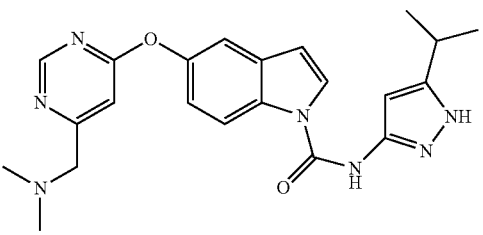 [SMILES: CC(C)c1cc(NC(=O)n2ccc3cc(Oc4cc(CN(C)C)ncn4)ccc32)n[nH]1]<br>5-(6-Dimethylaminomethyl-pyrimidin-4-yloxy)-indole-1-carboxylic acid (5-isopropyl-1H-pyrazol-3-yl)-amide | (DMSO-d$_6$) δ ppm 12.22 (br. S., 1H) 10.59 (s, 1H) 8.67 (d, J = 1.01 Hz, 1H) 8.32 (d, J = 9.09 Hz, 1H) 8.19 (d, J = 3.54 Hz, 1H) 7.46 (d, J = 2.53 Hz, 1H) 7.11-7.14 (m, 1H) 6.97 (d, J = 1.01 Hz, 1H) 6.72 (d, J = 3.54 Hz, 1H) 6.34 (s, 1H) 3.51 (s, 2H) 2.21 (s, 6H) 2.19 (d, J = 4.04 Hz, 1H) 1.25 (d, J = 6.82 Hz, 6H) | 420.1 |
| 137-H | 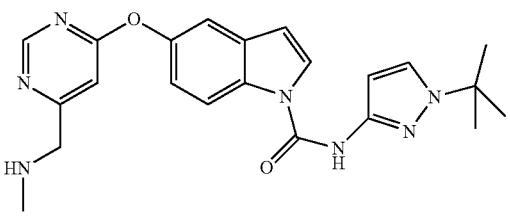 [SMILES: CNCc1cc(Oc2ccc3c(ccn3C(=O)Nc3ccn(C(C)(C)C)n3)c2)ncn1]<br>5-(6-Methylaminomethyl-pyrimidin-4-yloxy)-indole-1-carboxylic acid (1-tert-butyl-1H-pyrazol-3-yl)-amide | (DMSO-d$_6$) δ ppm 10.73 (br. S., 1H) 8.65 (d, J = 1.01 Hz, 1H) 8.32 (d, J = 8.84 Hz, 1H) 8.22 (d, J = 3.54 Hz, 1H) 7.78 (d, J = 2.53 Hz, 1H) 7.44 (d, J = 2.53 Hz, 1H) 7.10-7.12 (m, 1H) 7.03 (d, J = 1.01 Hz, 1H) 6.71 (d, J = 3.03 Hz, 1H) 6.52 (d, J = 2.27 Hz, 1H) 3.70 (s, 2H) 2.28 (s, 3H) 1.54 (s, 9H) | 420.1 |
| 137-I | 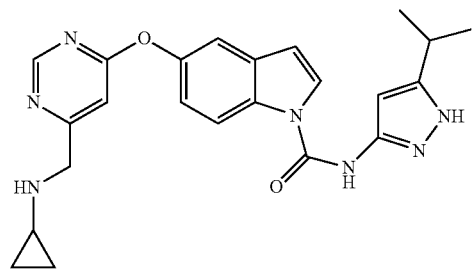 [SMILES: CC(C)c1cc(NC(=O)n2ccc3cc(Oc4cc(CNC5CC5)ncn4)ccc32)n[nH]1]<br>5-(6-Cyclopropylaminomethyl-pyrimidin-4-yloxy)-indole-1-carboxylic acid (5-isopropyl-1H-pyrazol-3-yl)-amide | (DMSO-d$_6$) δ ppm 12.22 (br. S., 1H), 10.59 (br. S., 1H), 8.65 (d, J = 1.0 Hz, 1H), 8.26-8.41 (m, 1H), 8.17 (br. S., 1H), 7.42 (br. S., 1H), 7.06-7.13 (m, 1H), 7.04 (s, 1H), 6.70 (br. S., 1H), 6.26-6.41 (m, 1H), 3.79 (s, 2H), 2.86-3.04 (m, 1H), 2.04-2.16 (m, 1H), 1.24 (d, J = 6.6 Hz, 6H), 0.30-0.40 (m, 2H), 0.21-0.27 (m, 2H) | 432.1 |

| | | | |
|---|---|---|---|
| 137-J | 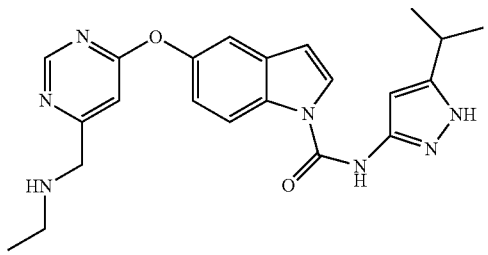 [SMILES: CCNCc1cc(Oc2ccc3c(ccn3C(=O)Nc3cc(C(C)C)[nH]n3)c2)ncn1]<br>5-(6-Ethylaminomethyl-pyrimidin-4-yloxy)-indole-1-carboxylic acid (5-isopropyl-1H-pyrazol-3-yl)-amide | (DMSO-d$_6$) δ ppm 12.22 (br. S., 1H) 10.58 (s, 1H) 8.66 (d, J = 1.01 Hz, 1H) 8.32 (d, J = 9.09 Hz, 1H) 8.18 (d, J = 3.79 Hz, 1H) 7.45 (d, J = 2.53 Hz, 1H) 7.07 (d, J = 1.01 Hz, 1H) 7.11 (dd, J = 8.84, 2.53 Hz, 1H) 6.72 (d, J = 3.54 Hz, 1H) 6.34 (s, 1H) 3.79 (s, 2H) 2.97 (d, J = 6.57 Hz, 1H) 2.57-2.59 (m, 2H) 1.25 (d, J = 7.07 Hz, 6H) 1.03 (t, J = 7.07 Hz, 3H) | 420.1 |
| 137-K | 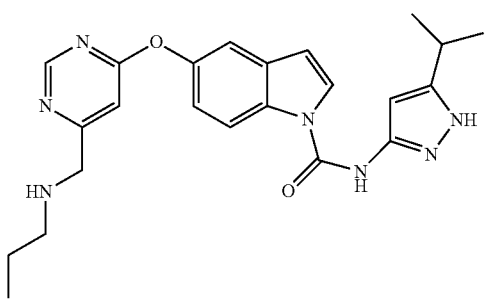 [SMILES: CCCNCc1cc(Oc2ccc3c(ccn3C(=O)Nc3cc(C(C)C)[nH]n3)c2)ncn1]<br>5-(6-Propylaminomethyl-pyrimidin-4-yloxy)-indole-1-carboxylic acid (5-isopropyl-1H-pyrazol-3-yl)-amide | (DMSO-d$_6$) δ ppm 12.22 (br. S., 1H) 10.58 (s, 1H) 8.64 (d, J = 1.01 Hz, 1H) 8.32 (d, J = 8.84 Hz, 1H) 8.18 (d, J = 3.79 Hz, 1H) 7.44 (d, J = 2.53 Hz, 1H) 7.11-7.12 (m, 1H) 7.06 (d, J = 1.01 Hz, 1H) 6.71 (d, J = 3.28 Hz, 1H) 6.34 (d, J = 1.26 Hz, 1H) 3.74 (s, 2H) 2.95 (d, J = 7.07 Hz, 1H) 1.40-1.43 (m, 2H) 1.25 (d, J = 7.07 Hz, 6H) 1.22 (br. S., 1H) 0.81-0.88 (m, 4H) | 434.2 |
| 137-L | 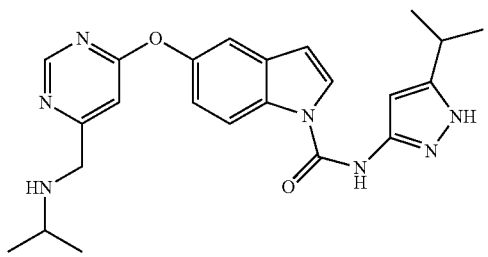 [SMILES: CC(C)NCc1cc(Oc2ccc3c(ccn3C(=O)Nc3cc(C(C)C)[nH]n3)c2)ncn1]<br>5-[6-(Isopropylamino-methyl)-pyrimidin-4-yloxy]-indole-1-carboxylic acid (5-isopropyl-1H-pyrazol-3-yl)-amide | (DMSO-d$_6$) δ ppm 12.21 (br. S., 1H) 10.58 (s, 1H) 8.65 (s, 1H) 8.32 (d, J = 8.84 Hz, 1H) 8.18 (d, J = 3.79 Hz, 1 H) 7.44 (d, J = 2.53 Hz, 1H) 7.04-7.12 (m, 1H) 7.11 (d, J = 8.84 Hz, 1H) 6.72 (d, J = 3.54 Hz, 1H) 6.34 (s, 1H) 3.79 (s, 2H) 2.94-2.99 (m, 1H) 2.73-2.76 (m, 1H) 1.25 (d, J = 6.82 Hz, 6H) 1.00 (d, J = 6.32 Hz, 6H) | 434.2 |
| 137-M | 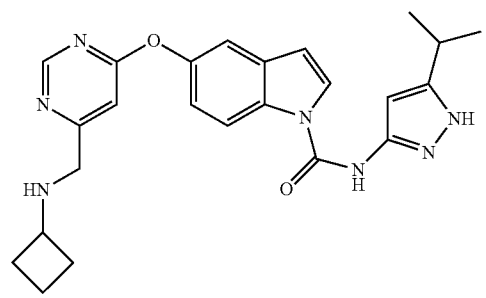 [SMILES: CC(C)c1cc(NC(=O)n2ccc3cc(Oc4cc(CNC5CCC5)ncn4)ccc32)n[nH]1]<br>5-(6-Cyclobutylaminomethyl-pyrimidin-4-yloxy)-indole-1-carboxylic acid (5-isopropyl-1H-pyrazol-3-yl)-amide | (DMSO-d$_6$) δ ppm 12.21 (br. S., 1H) 10.58 (s, 1H) 8.64 (d, J = 1.01 Hz, 1H) 8.32 (d, J = 8.84 Hz, 1H) 8.18 (d, J = 3.54 Hz, 1H) 7.44 (d, J = 2.53 Hz, 1H) 7.09-7.12 (m, 1H) 7.05 (d, J = 1.01 Hz, 1H) 6.72 (d, J = 3.54 Hz, 1H) 6.34 (s, 1H) 3.68 (s, 2H) 3.17 (d, J = 5.31 Hz, 1H) 2.95 (d, J = 6.57 Hz, 1H) 2.02-2.09 (m, 2H) 1.51-1.72 (m, 4H) 1.25 (d, J = 7.07 Hz, 6H) | 446.2 |

| | | | |
|---|---|---|---|
| 137-N | 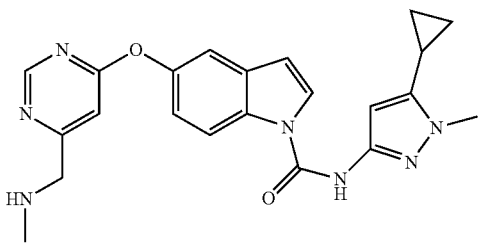 [SMILES: CNCc1cc(Oc2ccc3c(ccn3C(=O)Nc3cc(C4CC4)n(C)n3)c2)ncn1] 5-(6-Methylaminomethyl-pyrimidin-4-yloxy)-indole-1-carboxylic acid (5-cyclopropyl-1-methyl-1H-pyrazol-3-yl)-amide | (DMSO-$d_6$) δ ppm 8.65 (d, J = 1.01 Hz, 1H) 8.30 (d, J = 9.09 Hz 1H) 8.16 (d, J = 3.79 Hz, 1H) 7.44 (d, J = 2.02 Hz, 1H) 7.11 (dd, J = 8.84, 2.27 Hz, 1H) 7.02 (d, J = 1.01 Hz, 1H) 6.71 (d, J = 3.03 Hz, 1H) 6.16 (s, 1H) 3.79 (s, 3H) 3.70 (s, 2H) 2.28 (s, 3H) 1.81-1.99 (m, 1H) 0.96-0.99 (m, 2H) 0.59-0.73 (m, 2H) | 418.1 |
| 137-O | 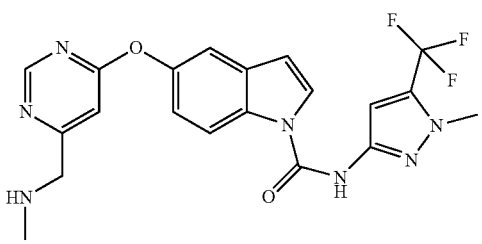 [SMILES: CNCc1cc(Oc2ccc3c(ccn3C(=O)Nc3cc(C(F)(F)F)n(C)n3)c2)ncn1] 5-(6-Methylaminomethyl-pyrimidin-4-yloxy)-indole-1-carboxylic acid (1-methyl-5-trifluoromethyl-1H-pyrazol-3-yl)-amide | (DMSO-$d_6$) δ ppm 8.66 (d, J = 1.01 Hz, 1H) 8.32 (d, J = 9.09 Hz, 1H) 8.18 (d, J = 3.79 Hz, 1H) 7.47 (d, J = 2.53 Hz, 1H) 7.13 (d, J = 2.53 Hz, 1H) 7.04 (d, J = 1.01 Hz, 1H) 7.07 (s, 1H) 6.76 (d, J = 3.79 Hz, 1H) 3.95 (s, 3H) 3.72 (s, 2H) 2.29 (s, 3H) | 446.1 |
| 137-P | 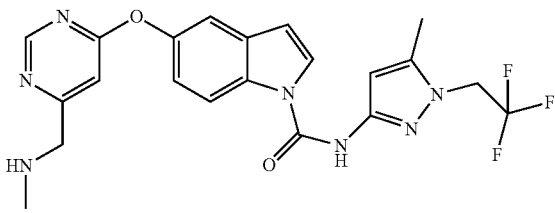 [SMILES: CNCc1cc(Oc2ccc3c(ccn3C(=O)Nc3cc(C)n(CC(F)(F)F)n3)c2)ncn1] 5-(6-Methylaminomethyl-pyrimidin-4-yloxy)-indole-1-carboxylic acid [5-methyl-1-(2,2,2-trifluoro-ethyl)-1H-pyrazol-3-yl]-amide | (DMSO-$d_6$) δ ppm 8.65 (d, J = 1.01 Hz, 1H) 8.31 (d, J = 8.84 Hz, 1H) 8.20 (d, J = 3.79 Hz, 1H) 7.45 (d, J = 2.53 Hz, 1H) 7.11-7.13 (m, 1H) 7.03 (d, J = 1.01 Hz, 1H) 6.72 (d, J = 4.29 Hz, 1H) 6.51 (s, 1H) 4.97-5.05 (m, 2H) 3.71 (s, 2H) 2.26-2.35 (m, 6H) | 460.1 |
| 137-Q | 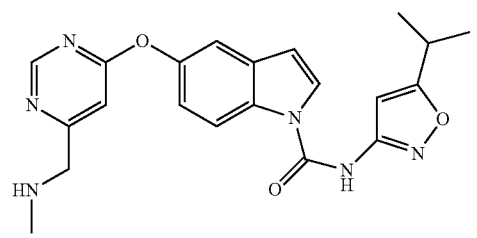 [SMILES: CNCc1cc(Oc2ccc3c(ccn3C(=O)Nc3cc(C(C)C)on3)c2)ncn1] 5-(6-Methylaminomethyl-pyrimidin-4-yloxy)-indole-1-carboxylic acid (5-isopropyl-isoxazol-3-yl)-amide | (DMSO-$d_6$) δ ppm 8.66 (d, J = 1.01 Hz, 1H) 8.32 (d, J = 9.09 Hz, 1H) 8.17 (d, J = 3.79 Hz, 1H) 7.47 (d, J = 2.53 Hz, 1H) 7.14 (dd, J = 8.97, 2.40 Hz, 1H) 7.04 (s, 1H) 6.76 (d, J = 3.79 Hz, 1H) 6.69 (s, 1H) 3.73 (s, 2H) 3.07-3.14 (m, 1H) 2.30 (s, 3H) 1.28-1.31 (m, 6H) | 407.1 |
| 137-R | 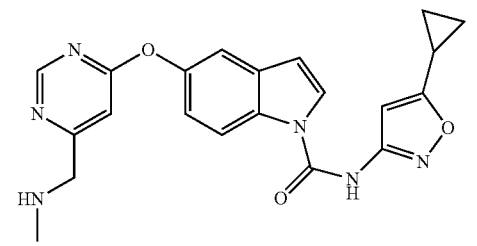 [SMILES: CNCc1cc(Oc2ccc3c(ccn3C(=O)Nc3cc(C4CC4)on3)c2)ncn1] 5-(6-Methylaminomethyl-pyrimidin-4-yloxy)-indole-1-carboxylic acid (5-cyclopropyl-isoxazol-3-yl)-amide | (DMSO-$d_6$) δ ppm 8.66 (s, 1H) 8.32 (d, J = 9.09 Hz, 1H) 8.16 (d, J = 3.79 Hz, 1H) 7.46 (d, J = 2.53 Hz, 1H) 7.13 (dd, J = 8.97, 2.40 Hz, 1H) 7.04 (s, 1H) 6.74 (d, J = 3.79 Hz, 1H) 6.65 (s, 1H) 3.71 (s, 2H) 2.29 (s, 3H) 2.13-2.20 (m, 1H) 1.08 (dd, J = 8.46, 2.65 Hz, 2H) 0.94 (dd, J = 4.80, 2.53 Hz, 2H) | 405.1 |

| | | | |
|---|---|---|---|
| 137-S | 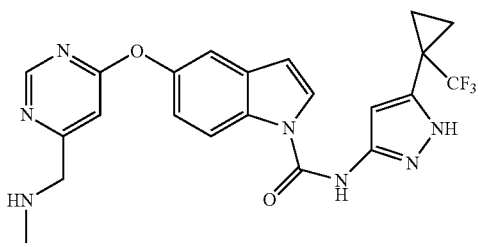 [SMILES: CNCc1cc(Oc2ccc3c(ccn3C(=O)Nc3cc(C4(C(F)(F)F)CC4)[nH]n3)c2)ncn1]<br><br>5-(6-Methylaminomethyl-pyrimidin-4-yloxy)-indole-1-carboxylic acid [5-(1-trifluoromethyl-cyclopropyl)-1H-pyrazol-3-yl]-amide | (DMSO-$d_6$) δ ppm 12.79 (br. S., 1H) 8.66 (s, 1H) 8.32 (d, J = 8.84 Hz, 1H) 8.18 (br. S., 1H) 7.46 (d, J = 2.27 Hz, 1H) 7.12 (dd, J = 8.97, 2.40 Hz, 1H) 7.04 (s, 1H) 6.73 (d, J = 3.28 Hz, 1H) 6.67 (br. S., 1H) 3.72 (s, 2H) 2.30 (s, 3H) 1.40 (br. S., 2H) 1.29 (br. S., 2H) | 472.2 |
| 137-T | 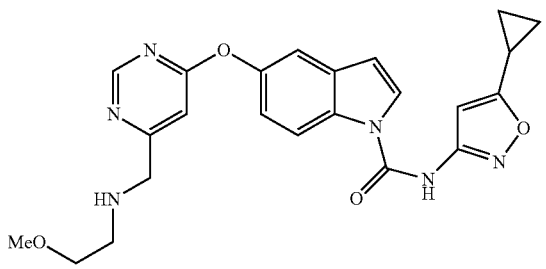 [SMILES: COCCNCc1cc(Oc2ccc3c(ccn3C(=O)Nc3cc(C4CC4)on3)c2)ncn1]<br><br>5-{6-[(2-Methoxy-ethylamino)-methyl]-pyrimidin-4-yloxy}-indole-1-carboxylic acid (5-cyclopropyl-isoxazol-3-yl)-amide | (DMSO-$d_6$) δ ppm 8.65 (d, J = 1.01 Hz, 1H) 8.30 (d, J = 9.09 Hz, 1H) 8.17 (d, J = 3.54 Hz, 1H) 7.47 (d, J = 2.27 Hz, 1H) 7.14 (dd, J = 8.97, 2.40 Hz, 1H) 7.07 (s, 1H) 6.76 (d, J = 3.79 Hz, 1H) 6.65 (s, 1H) 3.78 (s, 2H) 3.38 (t, J = 5.56 Hz, 2H) 3.22 (s, 3H) 2.68 (t, J = 5.68 Hz, 2H) 2.14-2.21 (m, 1H) 1.06-1.11 (m, 2H) 0.92-0.97 (m, 2H) | 449.0 |
| 137-U | 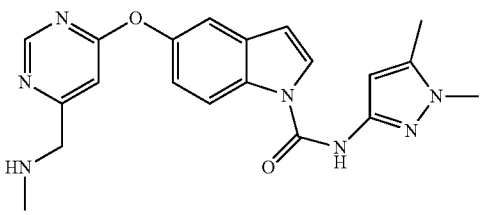 [SMILES: CNCc1cc(Oc2ccc3c(ccn3C(=O)Nc3cc(C)n(C)n3)c2)ncn1]<br><br>5-(6-Methylaminomethyl-pyrimidin-4-yloxy)-indole-1-carboxylic acid (1,5-dimethyl-1H-pyrazol-3-yl)-amide | (DMSO-$d_6$) δ ppm 8.65 (d, J = 1.01 Hz, 1H) 8.31 (d, J = 9.09 Hz, 1H) 8.17 (d, J = 3.79 Hz, 1H) 7.44 (d, J = 2.02 Hz, 1H) 7.11 (dd, J = 8.97, 2.40 Hz, 1H) 7.02 (d, J = 1.01 Hz, 1H) 6.72 (d, J = 3.03 Hz, 1H) 6.34 (s, 1H) 3.67-3.71 (m, 5H) 2.27-2.30 (m, 6H) | 392 |
| 137-V | 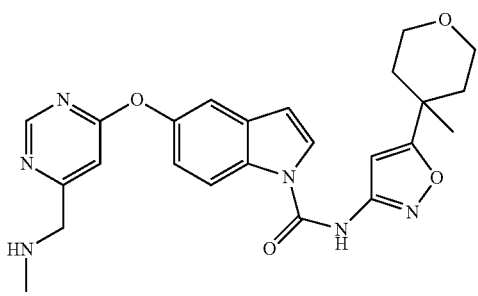 [SMILES: CNCc1cc(Oc2ccc3c(ccn3C(=O)Nc3cc(C4(C)CCOCC4)on3)c2)ncn1]<br><br>5-(6-Methylaminomethyl-pyrimidin-4-yloxy)-indole-1-carboxylic acid [5-(4-methyl-tetrahydro-pyran-4-yl)-isoxazol-3-yl]-amide | (DMSO-$d_6$) δ ppm 8.66 (d, J = 1.01 Hz, 1H) 8.33 (d, J = 9.09 Hz, 1H) 8.18 (d, J = 3.79 Hz, 1H) 7.47 (d, J = 2.53 Hz, 1H) 7.14 (dd, J = 8.97, 2.40 Hz, 1H) 7.05 (s, 1H) 6.75-6.78 (m, 2H) 6.30-6.31 (m, 1H) 3.71-3.77 (m, 4H) 3.46 (ddd, J = 11.75, 8.59, 2.91 Hz, 2H) 2.30 (s, 3H) 2.05 (d, J = 9.85 Hz, 2H) 1.64-1.71 (m, 2H) 1.34 (s, 3H) | 463.2 |

| | | | |
|---|---|---|---|
| 137-W | 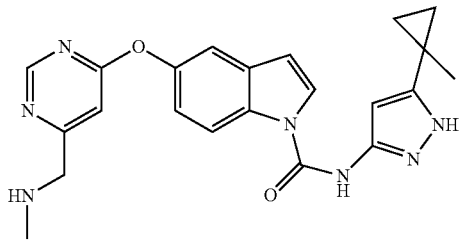 [SMILES: CNCc1cc(Oc2ccc3c(ccn3C(=O)Nc3cc(C4(C)CC4)[nH]n3)c2)ncn1]<br>5-(6-Methylaminomethyl-pyrimidin-4-yloxy)-indole-1-carboxylic acid [5-(1-methyl-cyclopropyl)-1H-pyrazol-3-yl]-amide | (DMSO-d$_6$) δ ppm 12.13 (s, 1H) 10.57 (br. S., 1H) 8.65 (d, J = 1.01 Hz, 1H) 8.32 (d, J = 9.09 Hz, 1H) 8.18 (d, J = 3.54 Hz, 1H) 7.44 (d, J = 2.53 Hz, 1H) 7.11 (dd, J = 8.97, 2.40 Hz, 1H) 7.03 (d, J = 1.01 Hz, 1H) 6.71 (d, J = 3.79 Hz, 1 H) 6.30 (d, J = 2.02 Hz, 1H) 3.71 (s, 2 H) 2.29 (s, 3H) 1.41 (s, 3H) 0.91-0.95 (m, 2H) 0.76-0.80 (m, 2H). | 418.2 |
| 137-X | 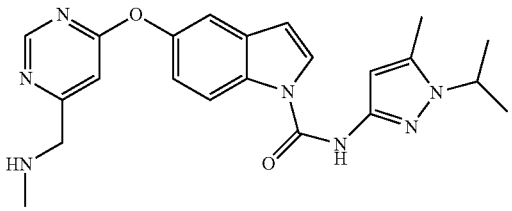 [SMILES: CNCc1cc(Oc2ccc3c(ccn3C(=O)Nc3cc(C)n(C(C)C)n3)c2)ncn1]<br>5-(6-Methylaminomethyl-pyrimidin-4-yloxy)-indole-1-carboxylic acid (1-isopropyl-5-methyl-1H-pyrazol-3-yl)-amide | (DMSO-d$_6$) δ ppm 10.64 (s, 1H) 8.65 (d, J = 1.01 Hz, 1H) 8.31 (d, J = 8.84 Hz, 1H) 8.20 (d, J = 3.79 Hz, 1H) 7.44 (d, J = 2.53 Hz, 1H) 7.11 (dd, J = 8.97, 2.40 Hz, 1H) 7.02 (s, 1H) 6.70 (d, J = 3.79 Hz, 1H) 6.33 (s, 1H) 4.37-4.58 (m, 1 H) 3.70 (s, 2H) 2.29 (d, J = 3.54 Hz, 6 H) 1.38 (d, J = 6.57 Hz, 6H) | 420.2 |
| 137-Y | 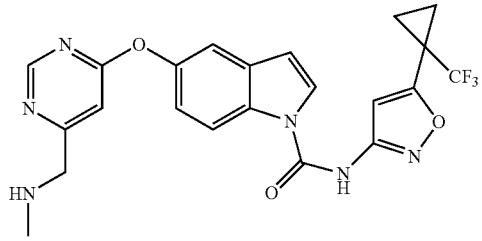 [SMILES: CNCc1cc(Oc2ccc3c(ccn3C(=O)Nc3cc(C4(C(F)(F)F)CC4)on3)c2)ncn1]<br>5-(6-Methylaminomethyl-pyrimidin-4-yloxy)-indole-1-carboxylic acid [5-(1-trifluoromethyl-cyclopropyl)-isoxazol-3-yl]-amide | (DMSO-d$_6$) δ ppm 8.67 (s, 1H) 8.35 (d, J = 9.09 Hz, 1H) 8.16 (d, J = 3.54 Hz, 1 H) 7.46 (d, J = 2.27 Hz, 1H) 7.13 (dd, J = 8.97, 2.40 Hz, 1H) 7.04 (d, J = 5.31 Hz, 2H) 6.74 (d, J = 3.79 Hz, 1H) 3.77 (s, 2H) 2.30-2.34 (m, 3H) 1.50-1.59 (m, 4H) | 473.2 |
| 137-Z | 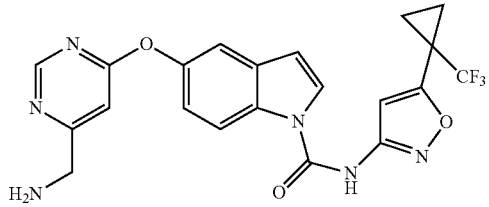 [SMILES: NCc1cc(Oc2ccc3c(ccn3C(=O)Nc3cc(C4(C(F)(F)F)CC4)on3)c2)ncn1]<br>5-(6-Aminomethyl-pyrimidin-4-yloxy)-indole-1-carboxylic acid [5-(1-tri fluoromethyl-cyclopropyl)-isoxazol-3-yl]-amide | (DMSO-d$_6$) δ ppm 8.67 (s, 1H) 8.39 (d, J = 8.84 Hz, 1H) 8.15 (d, J = 3.54 Hz, 1 H) 7.43 (d, J = 2.53 Hz, 1H) 7.07-7.13 (m, 2H) 7.03 (s, 1H) 6.71 (d, J = 3.79 Hz, 1H) 3.85 (s, 2H) 1.49-1.57 (m, 4H) | 459 |

| | | | |
|---|---|---|---|
| 137-AA | 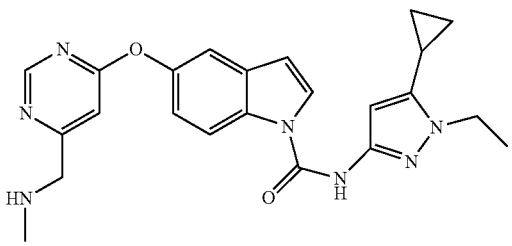 [SMILES: CCn1nc(NC(=O)n2ccc3cc(Oc4cc(CNC)ncn4)ccc32)cc1C1CC1]<br>5-(6-Methylaminomethyl-pyrimidin-4 yloxy)-indole-1-carboxylic acid (5-cyclopropyl-1-ethyl-1H-pyrazol-3-yl)-amide | (DMSO-$d_6$) δ ppm 10.64 (br. s., 1H) 8.65 (s, 1H) 8.30 (d, J = 9.09 Hz, 1H) 8.17 (d, J = 3.79 Hz, 1H) 7.44 (d, J = 2.53 Hz, 1H) 7.11 (dd, J = 8.97, 2.40 Hz, 1H) 7.03 (d, J = 1.01 Hz, 1H) 6.71 (d, J = 4.29 Hz, 1H) 6.16 (s, 1H) 4.15 (q, J = 7.24 Hz, 2H) 3.72 (s, 2H) 2.30 (s, 3H) 1.83-1.98 (m, 1H) 1.32-1.43 (m, 3H) 0.93-1.04 (m, 2H) 0.60-0.73 (m, 2H) | 432.2 |
| 137-AB | 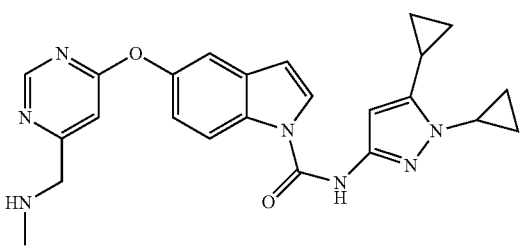 [SMILES: CNCc1cc(Oc2ccc3c(ccn3C(=O)Nc3cc(C4CC4)n(C4CC4)n3)c2)ncn1]<br>5-(6-Methylaminomethyl-pyrimidin-4-yloxy)-indole-1-carboxylic acid (1,5-dicyclopropyl-1H-pyrazol-3-yl)-amide | (DMSO-$d_6$) δ ppm 10.64 (br. s., 1H) 8.65 (d, J = 1.01 Hz, 1H) 8.30 (d, J = 8.84 Hz, 1H) 8.16 (d, J = 3.79 Hz, 1H) 7.44 (d, J = 2.53 Hz, 1H) 7.10 (dd, J = 8.84, 2.53 Hz, 1H) 7.02 (s, 1H) 6.70 (d, J = 3.79 Hz, 1H) 6.16 (s, 1H) 3.70 (s, 2 H) 3.57-3.63 (m, 1H) 2.28 (s, 3H) 2.03-2.10 (m, 1H) 0.99-1.12 (m, 6H) 0.69-0.74 (m, 2H) | 444.2 |
| 137-AC | 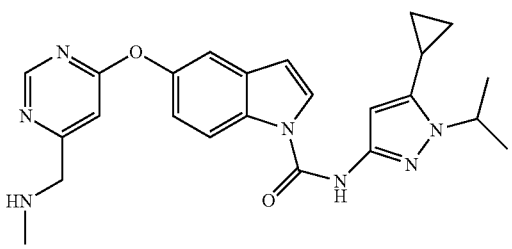 [SMILES: CNCc1cc(Oc2ccc3c(ccn3C(=O)Nc3cc(C4CC4)n(C(C)C)n3)c2)ncn1]<br>5-(6-Methylaminomethyl-pyrimidin-4-yloxy)-indole-1-carboxylic acid (5-cyclopropyl-1-isopropyl-1H-pyrazol-3-yl)-amide | (DMSO-$d_6$) δ ppm 10.66 (br. s., 1H) 8.66 (s, 1H) 8.31 (d, J = 8.84 Hz, 1H) 8.19 (d, J = 3.54 Hz, 1H) 7.44 (d, J = 2.27 Hz, 1H) 7.10 (dd, J = 8.97, 2.40 Hz, 1H) 7.03 (s, 1H) 6.70 (d, J = 3.03 Hz, 1H) 6.17 (s, 1H) 4.76 (quin, J = 6.57 Hz, 1 H) 3.73 (s, 2H) 2.30 (s, 3H) 1.86-2.00 (m, 1H) 1.42 (d, J = 6.57 Hz, 6H) 0.91-1.04 (m, 2H) 0.60-0.72 (m, 2H) | 446.2 |
| 137-AD | 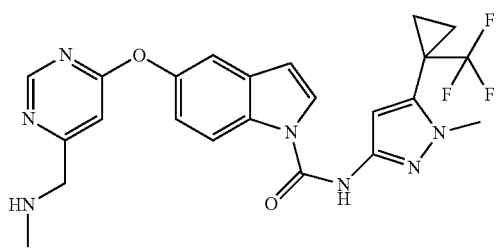 [SMILES: CNCc1cc(Oc2ccc3c(ccn3C(=O)Nc3cc(C4(C(F)(F)F)CC4)n(C)n3)c2)ncn1]<br>5-(6-Methylaminomethyl-pyrimidin-4-yloxy)-indole-1-carboxylic acid [1-methyl-5-(1-trifluoromethyl-cyclopropyl)-1H-pyrazol-3-yl]-amide | (DMSO-$d_6$) δ ppm 8.65 (d, J = 1.26 Hz, 1H) 8.31 (d, J = 8.84 Hz, 1H) 8.17 (d, J = 3.54 Hz, 1H) 7.45 (d, J = 2.27 Hz, 1 H) 7.12 (dd, J = 8.97, 2.40 Hz, 1H) 7.03 (d, J = 1.01 Hz, 1H) 6.73 (d, J = 3.03 Hz, 1H) 6.66 (s, 1H) 3.83 (s, 3H) 3.70 (s, 2H) 2.29 (s, 3H) 1.49-1.52 (m, 2H) 1.30-1.34 (m, 2H) | 486.2 |

| | | |
|---|---|---|
| 137-AE | 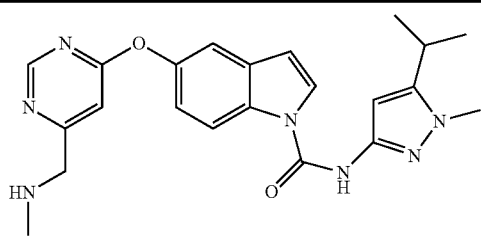<br>5-(6-Methylaminomethyl-pyrimidin-4-yloxy)-indole-1-carboxylic acid (5-isopropyl-1-methyl-1H-pyrazol-3-yl)-amide | (DMSO-d$_6$) δ ppm 10.62 (br. s., 1H) 8.66 (d, J = 1.01 Hz, 1H) 8.32 (d, J = 8.84 Hz, 1H) 8.17 (d, J = 3.54 Hz, 1H) 7.45 (d, J = 2.02 Hz, 1H) 7.11 (dd, J = 8.97, 2.40 Hz, 1H) 7.03 (d, J = 1.01 Hz, 1H) 6.72 (d, J = 3.03 Hz, 1H) 6.36 (s, 1H) 3.72 (s, 5H) 3.04 (dt, J = 13.64, 6.82 Hz, 1H) 2.22-2.38 (m, 3H) 1.23 (d, J = 6.82 Hz, 6H)   420.2 |

EXAMPLE 138

138-A. 5-(6-Methanesulfonylmethyl-pyrimidin-4-yloxy)-indole-1-carboxylic acid (4,4-dimethyl-5,6-dihydro-4H-pyrrolo[1,2-b]pyrazol-2-yl)-amide

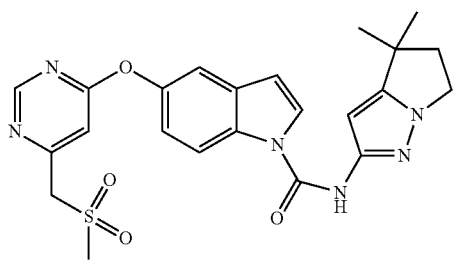 [SMILES: CC1(C)CCn2nc(NC(=O)n3ccc4cc(Oc5cc(CS(C)(=O)=O)ncn5)ccc43)cc21]

Prepared by similar method to that described in Example 86A. MS (ESI) m/z 481.0 (M+1); $^1$H NMR (400 MHz, DMSO-d$_6$) δ ppm 10.65 (s, 1 H), 8.77 (s, 1 H), 8.31 (d, J=8.8 Hz, 1 H), 8.16 (d, J=3.5 Hz, 1 H), 7.49 (d, J=2.3 Hz, 1 H), 7.19 (s, 1 H), 7.15 (dd, J=9.0, 2.4 Hz, 1 H), 6.73 (d, J=3.8 Hz, 1 H), 6.28 (s, 1 H), 4.69 (s, 2 H), 4.09 (t, J=6.9 Hz, 2 H), 3.11 (s, 3 H), 2.29-2.38 (m, 2 H), 1.32 (s, 6 H).

The following compounds are prepared by similar method.

138-B. 5-(6-Methanesulfonylmethyl-pyrimidin-4-yloxy)-indole-1-carboxylic acid (5,6-dihydro-4H-pyrrolo[1,2-b]pyrazol-2-yl)-amide

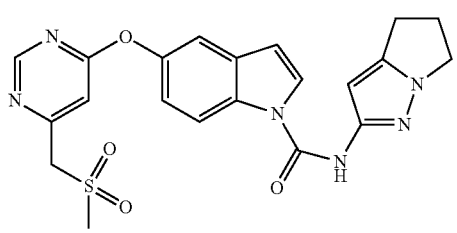 [SMILES: CS(=O)(=O)Cc1cc(Oc2ccc3c(ccn3C(=O)Nc3cc4n(n3)CCC4)c2)ncn1]

MS (ESI) m/z 453.0 (M+1); $^1$H NMR (400 MHz, DMSO-d$_6$) δ ppm 10.62 (s, 1 H), 8.78 (d, J=1.0 Hz, 1 H), 8.32 (d, J=9.1 Hz, 1 H), 8.17 (d, J=3.8 Hz, 1 H), 7.48 (d, J=2.5 Hz, 1 H), 7.18 (d, J=1.0 Hz, 1 H), 7.14 (dd, J=9.0, 2.4 Hz, 1 H), 6.73 (d, J=3.8 Hz, 1 H), 6.28 (s, 1 H), 4.69 (s, 2 H), 4.04 (t, J=7.1 Hz, 2 H), 3.11 (s, 3 H), 2.88 (t, J=7.2 Hz, 2 H).

EXAMPLE 139

139-A. 5-(7-Methanesulfonyl-5,6,7,8-tetrahydro-pyrido[3,4-d]pyrimidin-4-yloxy)-indole-1-carboxylic acid (5-cyclopropyl-isoxazol-3-yl)-amide

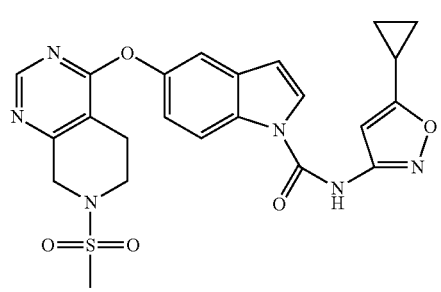 [SMILES: CS(=O)(=O)N1CCc2c(ncnc2Oc2ccc3c(ccn3C(=O)Nc3cc(C4CC4)on3)c2)C1]

Prepared by similar method to that described in Example 35. MS (ESI) m/z 495.1 (M+1); 1H NMR (400 MHz, DMSO-d$_6$) δ ppm 11.22 (s, 1 H), 8.50 (s, 1 H), 8.28 (d, J=9.1 Hz, 1 H), 8.16 (d, J=3.8 Hz, 1 H), 7.47 (d, J=2.3 Hz, 1 H), 7.15 (dd, J=8.8, 2.3 Hz, 1 H), 6.76 (d, J=3.8 Hz, 1 H), 6.65 (s, 1 H), 4.39 (s, 2 H), 3.57 (t, J=5.8 Hz, 2 H), 3.06 (s, 3 H), 2.96 (t, J=5.7 Hz, 2 H), 2.12-2.25 (m, 1 H), 1.04-1.13 (m, 2 H), 0.89-0.99 (m, 2 H).

The following compounds are prepared by similar method.

139-B. 5-(7-Methanesulfonyl-5,6,7,8-tetrahydro-pyrido[3,4-d]pyrimidin-4-yloxy)-indole-1-carboxylic acid (5-tert-butyl-isoxazol-3-yl)-amide

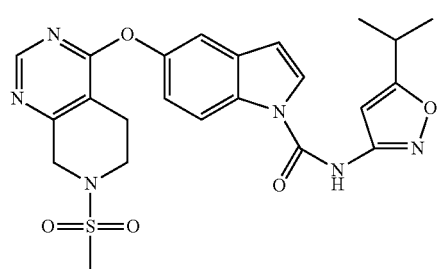 [SMILES: CC(C)c1cc(NC(=O)n2ccc3cc(Oc4ncnc5c4CCN(S(C)(=O)=O)C5)ccc32)no1]

MS (ESI) m/z 511.2 (M+1); $^1$H NMR (400 MHz, DMSO-$d_6$) δ ppm 11.27 (s, 1 H), 8.51 (s, 1 H), 8.29 (d, J=9.0 Hz, 1 H), 8.17 (d, J=3.7 Hz, 1 H), 7.47 (d, J=2.4 Hz, 1 H), 7.16 (dd, J=9.0, 2.3 Hz, 1 H), 6.77 (d, J=3.7 Hz, 1 H), 6.68 (s, 1 H), 4.39 (s, 2 H), 3.57 (t, J=5.9 Hz, 2 H), 3.06 (s, 3 H), 2.96 (t, 2 H), 1.34 (s, 9 H).

139-C. 5-((S)-7-Methanesulfonyl-6-methyl-5,6,7,8-tetrahydro-pyrido[3,4-d]pyrimidin-4-yloxy)-indole-1-carboxylic acid (5-cyclopropyl-isoxazol-3-yl)-amide

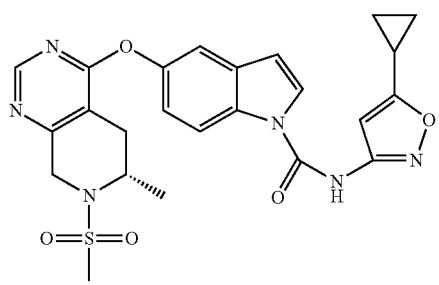 [SMILES: C[C@H]1Cc2c(ncnc2Oc2ccc3c(ccn3C(=O)Nc3cc(C4CC4)on3)c2)CN1S(C)(=O)=O]

MS (ESI) m/z 509.1 (M+1); 1H NMR (400 MHz, DMSO-$d_6$) δ ppm 11.22 (s, 1 H), 8.51 (s, 1 H), 8.28 (d, J=9.1 Hz, 1 H), 8.16 (d, J=3.8 Hz, 1 H), 7.47 (d, J=2.3 Hz, 1 H), 7.16 (dd, J=9.0, 2.4 Hz, 1 H), 6.76 (d, J=3.8 Hz, 1 H), 6.65 (s, 1 H), 4.29-4.63 (m, 3 H), 3.06 (s, 4 H), 2.80 (d, J=16.9 Hz, 1 H), 2.10-2.27 (m, 1 H), 1.23 (d, J=6.8 Hz, 3 H), 1.03-1.14 (m, 2 H), 0.89-0.99 (m, 2 H).

139-D. 5-(6-Methanesulfonyl-6,7-dihydro-5H-pyrrolo[3,4-d]pyrimidin-4-yloxy)-indole-1-carboxylic acid [5-(1-trifluoromethyl-cyclopropyl)-isoxazol-3-yl]-amide

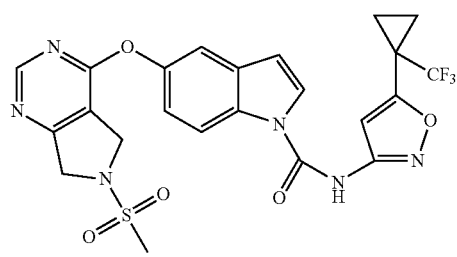 [SMILES: CS(=O)(=O)N1Cc2ncnc(Oc3ccc4c(ccn4C(=O)Nc4cc(C5(C(F)(F)F)CC5)on4)c3)c2C1]

MS (ESI) m/z 549.15 (M+1); $^1$H NMR (400 MHz, DMSO-$d_6$) δ ppm 11.45 (s, 1 H) 8.67 (s, 1 H) 8.31 (d, J=8.84 Hz, 1 H) 8.17 (d, J=4.04 Hz, 1 H) 7.50 (d, J=2.78 Hz, 1 H) 7.18 (dd, J=8.97, 2.40 Hz, 1 H) 7.04 (s, 1 H) 6.79 (d, J=4.04 Hz, 1 H) 4.71-4.77 (m, 4 H) 3.10 (s, 3 H) 1.54-1.60 (m, 4 H).

EXAMPLE 140

140-A. 5-0)-6-Methyl-7-methylcarbamoylmethyl-5,6,7,8-tetrahydro-pyrido[3,4-d]pyrimidin-4-yloxy)-indole-1-carboxylic acid (5-cyclopropyl-isoxazol-3-yl)-amide

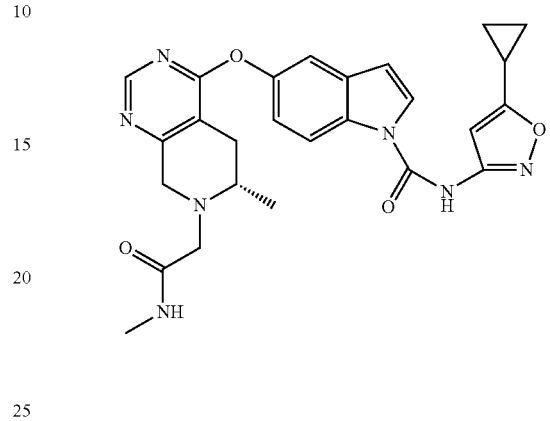

Prepared by similar method to that described in Example 41-C. MS (ESI) m/z 502.1 (M+1); $^1$H NMR (400 MHz, DMSO-$d_6$) δ ppm 11.22 (s, 1 H) 8.43 (s, 1 H) 8.28 (d, J=8.84 Hz, 1 H) 8.15 (d, J=3.79 Hz, 1 H) 7.82 (d, J=4.55 Hz, 1 H) 7.44 (d, J=2.27 Hz, 1 H) 7.12 (dd, J=8.84, 2.27 Hz, 1 H) 6.75 (d, J=3.79 Hz, 1 H) 6.65 (s, 1 H) 3.74 (d, J=4.55 Hz, 2 H) 3.08-3.22 (m, 3 H) 3.00 (dd, J=17.05, 4.67 Hz, 1 H) 2.59-2.66 (m, 4 H) 2.09-2.24 (m, 1 H) 1.03-1.15 (m, 5 H) 0.89-1.00 (m, 2 H).

The following compounds are prepared by similar method.

140-B. 5-((S)-6-Methyl-7-methylcarbamoylmethyl-5,6,7,8-tetrahydro-pyrido[3,4-d]pyrimidin-4-yloxy)-indole-1-carboxylic acid [5-(1-methyl-cyclopropyl)-1H-pyrazol-3-yl]amide

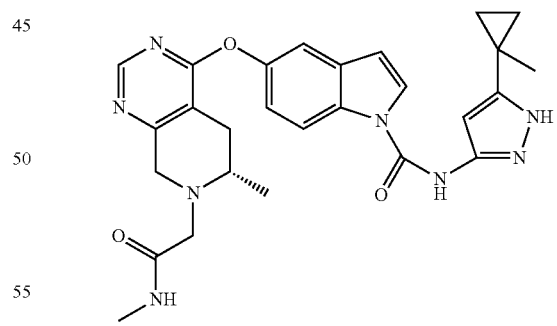

MS (ESI) m/z 501.3 (M+1); $^1$H NMR (400 MHz, DMSO-$d_6$) δ ppm 12.13 (s, 1 H), 10.56 (s, 1 H), 8.43 (s, 1 H), 8.30 (d, J=9.1 Hz, 1 H), 8.17 (d, J=3.5 Hz, 1 H), 7.83 (d, J=4.3 Hz, 1 H), 7.41 (d, J=2.5 Hz, 1 H), 7.08 (dd, J=9.0, 2.4 Hz, 1 H), 6.71 (d, J=3.5 Hz, 1 H), 6.29 (s, 1 H), 3.68 (s, 2 H), 3.19 (s, 2 H), 2.87 (dd, J=15.8, 4.7 Hz, 1 H), 2.64 (d, J=4.5 Hz, 3 H), 1.41 (s, 3 H), 0.89-0.96 (m, 2 H), 0.72-0.82 (m, 2 H).

EXAMPLE 141

(S)-4-[1-(5-Cyclopropyl-isoxazol-3-ylcarbamoyl)-1H-indol-5-yloxy]-6-methyl-5,8-dihydro-6H-pyrido[3,4-d]pyrimidine-7-carboxylic acid ethylamide

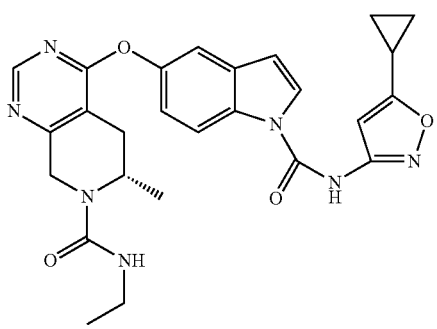 [SMILES: CCNC(=O)N1Cc2ncnc(Oc3ccc4c(ccn4C(=O)Nc4cc(C5CC5)on4)c3)c2C[C@@H]1C]

Prepared with similar method to that described for Example 36 using ethyl isocyanate. MS (ESI) m/z 502.1 (M+1); rotamers exist at 27° C. in DMSO-d₆, 1H NMR (400 MHz, DMSO-d₆) δ ppm 11.22 (s, 1 H) 8.49 (s, 1 H) 8.28 (d, J=9.09 Hz, 1 H) 8.15 (d, J=3.79 Hz, 1 H) 7.46 (d, J=2.27 Hz, 1 H) 7.15 (dd, J=8.97, 2.40 Hz, 1 H) 6.75 (d, J=3.28 Hz, 1 H) 6.69 (t, J=5.18 Hz, 1 H) 6.65 (s, 1 H) 4.68-4.85 (m, 2 H) 4.14 (d, J=18.95 Hz, 1 H) 3.11 (ddd, J=7.26, 5.12, 2.53 Hz, 2 H) 2.88-2.99 (m, 1 H) 2.72-2.82 (m, 1 H) 2.12-2.23 (m, 1 H) 1.02-1.13 (m, 8 H) 0.89-0.99 (m, 2 H).

EXAMPLE 142

142-A. 1-Hydroxymethyl-cyclopropanecarboxylic acid methyl ester

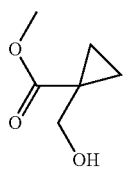

A solution of cyclopropane-1,1-dicarboxylic acid methyl ester (9 g, 62.4 mmol) in THF (180 mL), is cooled to 0° C. and triethylamine (9.7 mL, 69.6 mmol) and 3-methyl-butyryl chloride (9.1 mL, 9.6 mmol) are added and the reaction stirred for 1 h. In a separate flask, sodium borohydride (7.1 g, 188 mmol) is dissolved in THF (100 mL)/H₂O (25 mL) and cooled to 0° C. The mixed anhydride is filtered through a sintered funnel to remove salts from previous reaction and added to the flask containing sodium borohydride and the reaction stirred for 1 h at 0° C. 1 N HCl is added and the product is extracted with EtOAc and then with CCl₃H/iPrOH. It is then purified via FCC eluting with Heptane/EtOAc (100:0 to 20:80) to give 1-hydroxymethyl-cyclopropanecarboxylic acid methyl ester. ¹H NMR (400 MHz, DMSO-d₆) δ ppm 4.61 (t, J=5.81 Hz, 1 H) 3.59 (s, 3 H) 3.55 (d, J=6.06 Hz, 2 H) 1.01 (d, J=3.03 Hz, 2 H) 1.01 (d, J=10.36 Hz, 1 H) 0.87 (d, J=3.03 Hz, 1 H) 0.85-0.88 (m, 1 H).

142-B. 3-(1-Hydroxymethyl-cyclopropyl)-3-oxo-propionitrile

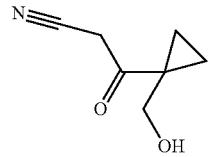

To a solution of LDA (115 mmol) in THF (300 mL), at −78° C., a solution of 1-hydroxymethyl-cyclopropanecarboxylic acid methyl ester (5 g, 28.4 mmol) in CH3CN (5.91 mL, 115 mmol) is added. The reaction is allowed to reach rt. At this point it is quenched with 1N HCl (200 mL) and extracted with EtOAc (200 mL, ×3). It is then dried and evaporated to give 3-(1-hydroxymethyl-cyclopropyl)-3-oxo-propionitrile. ¹H NMR (400 MHz, DMSO-d₆) δ ppm 4.26 (s, 2 H) 4.03 (s, 1 H) 3.58 (br. s., 2 H) 1.15-1.16 (m, 2 H) 0.92-0.95 (m, 2 H).

142-C. [1-(3-Amino-isoxazol-5-yl)-cyclopropyl]-methanol

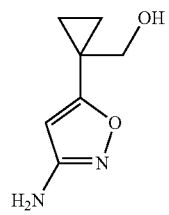

Prepared with similar method to that described above in Example 7-A. MS (ESI) m/z 155.2 (M+1).

142-D. {5-[1-(tert-Butyl-dimethyl-silanyloxymethyl)-cyclopropyl]-isoxazol-3-yl}-carbamic acid phenyl ester

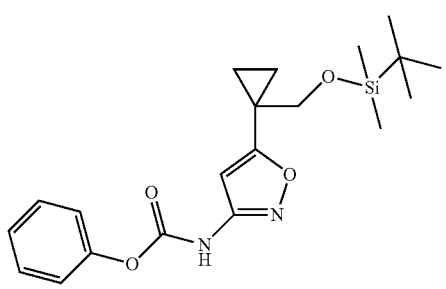 [SMILES: CC(C)(C)[Si](C)(C)OCC1(c2cc(NC(=O)Oc3ccccc3)no2)CC1]

To a solution of [1-(3-amino-isoxazol-5-yl)-cyclopropyl]-methanol (3.6 g, 23.35 mmol) in DCM (200 mL) at 0° C., imidazole (2.385 g, 35.0 mmol) and tert-butylchlorodimethylsilane (4.22 g, 28.0 mmol) are added. After 1 h the reaction is complete. After washing the organics with 1N HCl the organics are concentrated and then dissolved in THF (200 mL) at 0° C., and pyridine (3.62 ml, 44.7 mmol) and phenyl chloroformate (5.63 mL, 44.7 mmol) are added. After 1 h the reaction is complete and it is quenched with water. The organics are then extracted with EtOAc, dried and evaporated. The title compound is then isolated using FCC and elution with heptane:EtOAc 100:0 to 90:10. MS (ESI) m/z 389.0 (M+1).

142-E. 5-(6,7-Dihydro-5H-pyrrolo[3,4-d]pyrimidin-4-yloxy)-indole-1-carboxylic acid [5-(1-hydroxymethyl-cyclopropyl)-isoxazol-3-yl]-amide

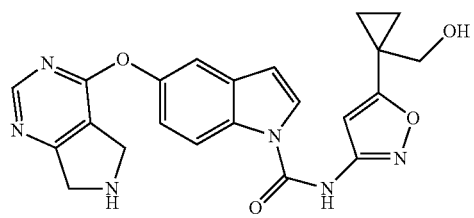 [SMILES: O=C(Nc1cc(C2(CO)CC2)on1)n1ccc2cc(Oc3ncnc4c3CNC4)ccc21]

To a solution of tert-butyl 4-(1H-indol-5-yloxy)-5H-pyrrolo[3,4-d]pyrimidine-6(7H)-carboxylate (2 g, 5.68 mmol) in DMF (50 mL), at 0° C., NaH (0.681 g, 17.0 mmol) and {5-[1-(tert-Butyl-dimethyl-silanyloxymethyl)-cyclopropyl]-isoxazol-3-yl}-carbamic acid phenyl ester (3.09 g, 7.95 mmol) are added. After 1 h the reaction is complete. After quenching with water, the organics are extracted with EtOAc and the fractions combined, dried and evaporated. The crude product is dissolved in THF (10 mL) at 0° C. and TBAF (17.0 ml, 17.03 mmol) is added. After 2 h at it the reaction is complete and is quenched with NH$_4$Cl and extracted with EtOAc. The product is separated with FCC eluting with 50:50 heptane:EtOAc to give 4-{1-[5-(1-hydroxymethyl-cyclopropyl)-isoxazol-3-ylcarbamoyl]-1H-indol-5-yloxy}-5,7-dihydro-pyrrolo[3,4-d]pyrimidine-6-carboxylic acid tert-butyl ester which is then dissolved in DCM (10 mL) and TFA (10 mL) is added. The reaction is stirred for 20 minutes. The organics are then evaporated and the crude product is taken up in EtOAc and NH$_4$OH (37% in water) is added to free-base the amine. Then the flask is again subjected to vacuum to remove the excess EtOAc. The crude product is then loaded onto a silica gel column and eluted with DCM:MeOH:NH$_4$OH 100:0:0 to 90:9.5:0.5 to give the title compound. MS (ESI) m/z 433.9 (M+1). $^1$H NMR (400 MHz, DMSO-d$_6$) δ ppm 11.25 (s, 1 H) 8.65 (d, J=2.02 Hz, 1 H) 8.31 (d, J=8.84 Hz, 1 H) 8.18 (d, J=3.79 Hz, 1 H) 7.50 (d, J=2.53 Hz, 1 H) 7.18 (dd, J=9.09, 2.27 Hz, 1 H) 6.80-6.82 (m, 2 H) 4.99 (s, 1 H) 4.58-4.67 (m, 4 H) 3.66 (d, J=5.81 Hz, 2 H) 1.10-1.11 (m, 2 H) 1.03-1.04 (m, 2 H).

EXAMPLE 143

143-A. 5-(6,7-Dihydro-5H-pyrrolo[3,4-d]pyrimidin-4-yloxy)-indole-1-carboxylic acid [5-(1-aminomethyl-cyclopropyl)-isoxazol-3-yl]-amide

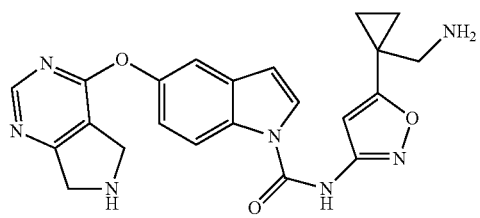 [SMILES: NCC1(c2cc(NC(=O)n3ccc4cc(Oc5ncnc6c5CNC6)ccc43)no2)CC1]

To a solution of 4-{1-[5-(1-hydroxymethyl-cyclopropyl)-isoxazol-3-ylcarbamoyl]-1H-indol-5-yloxy}-5,7-dihydro-pyrrolo[3,4-a]pyrimidine-6-carboxylic acid tert-butyl ester (500 mg, 0.939 mmol) in THF (10 mL), at 0° C., triethylamine (0.262 mL, 1.88 mmol) methanesulfonyl chloride (0.110 mL, 1.41 mmol) and DMAP (11.5 mg, 0.094 mmol) are added. After 2 h the reaction is complete and is quenched with water and the organics extracted with EtOAc. The crude product following concentration is then dissolved in THF (30 mL), and NH$_3$ in MeOH (1.82 mL, 12.8 mmol) is added. The reaction is stirred for 36 h. At this point the volatiles are removed and the crude product is dissolved in DCM (10 mL) and then TFA (10 mL, 130 mmol) is added. After 10 minutes the volatiles are removed in vacuo. The product is dissolved in EtOAc and then NH$_4$OH is added. The organics are removed and the crude product separated via FCC eluting with DCM:MeOH:NH$_4$OH (100:0:0 to 92:7:1) to give the title compound. MS (ESI) m/z 432.0 (M+1). $^1$H NMR (400 MHz, DMSO-d$_6$) δ ppm 8.55 (s, 1 H) 8.35 (d, J=8.84 Hz, 1 H) 8.15 (d, J=3.54 Hz, 1 H) 7.44 (d, J=2.53 Hz, 1 H) 7.11 (dd, J=9.09, 2.53 Hz, 1 H) 6.77 (s, 1 H) 6.70 (d, J=4.04 Hz, 1 H) 4.09 (d, J=11.87 Hz, 4 H) 2.94 (s, 2 H) 1.05 (d, J=3.03 Hz, 4 H).

EXAMPLE 144

144-A. 4-{1-[5-(1-Formyl-cyclopropyl)-isoxazol-3-ylcarbamoyl]-1H-indol-5-yloxy}-5,7-dihydro-pyrrolo[3,4-d]pyrimidine-6-carboxylic acid tert-butyl ester

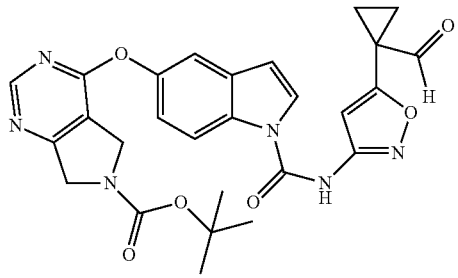 [SMILES: CC(C)(C)OC(=O)N1Cc2ncnc(Oc3ccc4c(ccn4C(=O)Nc4cc(C5(C=O)CC5)on4)c3)c2C1]

To a solution of SO3 pyridine (0.992 g, 6.23 mmol), triethylamine (1.086 mL, 7.79 mmol) and DMSO (1.11 mL, 15.6 mmol) at 0° C., 4-{1-[5-(1-hydroxymethyl-cyclopropyl)-isoxazol-3-ylcarbamoyl]-1H-indol-5-yloxy}-5,7-dihydro-pyrrolo[3,4-d]pyrimidine-6-carboxylic acid tert-butyl ester (0.83 g, 1.559 mmol) in DCM (5 mL) and DMSO (1 mL) is added. The reaction is stirred at 0° C. for 2 h. After the reaction is complete, it is quenched with NH$_4$CL, extracted, and evaporated. 4-{1-[5-(1-Formyl-cyclopropyl)-isoxazol-3-ylcarbamoyl]-1H-indol-5-yloxy}-5,7-dihydro-pyrrolo[3,4-d]pyrimidine-6-carboxylic acid tert-butyl ester is then obtained using FCC and eluting with 100:0 heptane:EtOAc to 0:100 Heptane:EtOAc. MS (ESI) m/z 531.0 (M+1).

144-B. 5-(6,7-Dihydro-5H-pyrrolo[3,4-d]pyrimidin-4-yloxy)-indole-1-carboxylic acid [5-(1-dimethylaminomethyl-cyclopropyl)-isoxazol-3-yl]-amide

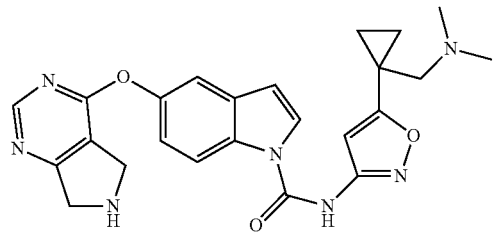 [SMILES: CN(C)CC1(c2cc(NC(=O)n3ccc4cc(Oc5ncnc6c5CNC6)ccc43)no2)CC1]

To a solution of 4-{1-[5-(1-formyl-cyclopropyl)-isoxazol-3-ylcarbamoyl]-1H-indol-5-yloxy}-5,7-dihydro-pyrrolo[3,4-a]pyrimidine-6-carboxylic acid tert-butyl ester (120 mg, 0.226 mmol) in DCE (2 ml), dimethylamine (0.34 mL, 0.679 mmol) and sodium triacetoxyborohydride (192 mg, 0.905 mmol) are added. After 2 h the reaction is complete, brine is added and the product is extracted with EtOAc. The organics are dried and evaporated to give the crude product. The mixture is diluted with DCM (10 mL) and then TFA (10 ml, 130 mmol) is added. After 10 minutes the volatiles are removed in vacuo. The product is dissolved in EtOAc and then NH$_4$OH is added. The organics are removed and the crude product separated via FCC eluting with DCM:MeOH:NH$_4$OH (100:0:0 to 92:7:1) to give 5-(6,7-dihydro-5H-pyrrolo[3,4-d]pyrimidin-4-yloxy)-indole-1-carboxylic acid [5-(1-dimethylaminomethyl-cyclopropyl)-isoxazol-3-yl]-amide. MS (ESI) m/z 460.9 (M+1). $^1$H NMR (400 MHz, DMSO-d$_6$) δ ppm 8.55 (s, 1 H) 8.29 (d, J=8.84 Hz, 1 H) 8.16 (d, J=3.79 Hz, 1 H) 7.47 (d, J=2.27 Hz, 1 H) 7.16 (s, 1 H) 6.82 (s, 1 H) 6.75 (d, J=4.04 Hz, 1 H) 4.06-4.15 (m, 1 H) 2.57 (s, 2 H) 2.20 (s, 6 H) 1.17 (d, J=2.27 Hz, 2 H) 0.93 (d, J=2.27 Hz, 2 H).

The following compounds are prepared with similar method.

144-C. 5-(6,7-Dihydro-5H-pyrrolo[3,4-d]pyrimidin-4-yloxy)-indole-1-carboxylic acid [5-(1-methylaminomethyl-cyclopropyl)-isoxazol-3-yl]-amide

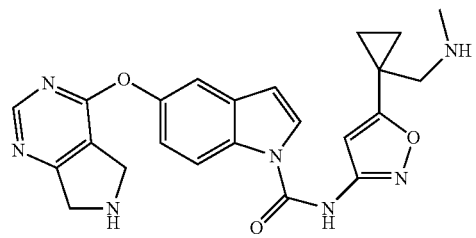 [SMILES: CNCC1(c2cc(NC(=O)n3ccc4cc(Oc5ncnc6c5CNC6)ccc43)no2)CC1]

MS (ESI) m/z 446.1 (M+1). $^1$H NMR (400 MHz, DMSO-d$_6$) δ ppm 8.55 (s, 1 H) 8.32 (d, J=9.09 Hz, 1 H) 8.16 (d, J=3.79 Hz, 1 H) 7.46 (d, J=2.53 Hz, 1 H) 7.13-7.14 (m, 1 H) 6.78 (s, 1 H) 6.73 (d, J=3.79 Hz, 1 H) 4.08-4.10 (m, 4 H) 2.84 (s, 2 H) 2.33 (s, 3 H) 1.05-1.18 (m, 2 H) 1.00-1.01 (m, 2 H).

144-D. 5-(6,7-Dihydro-5H-pyrrolo[3,4-d]pyrimidin-4-yloxy)-indole-1-carboxylic acid (5-{1-[(2-methoxy-ethylamino)-methyl]-cyclopropyl}-isoxazol-3-yl)-amide

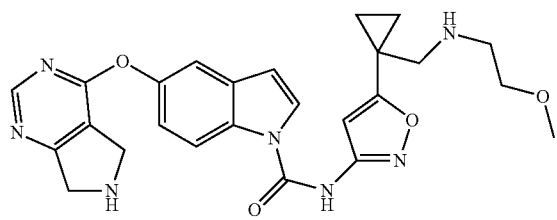 [SMILES: COCCNCC1(c2cc(NC(=O)n3ccc4cc(Oc5ncnc6c5CNC6)ccc43)no2)CC1]

MS (ESI) m/z 490.0 (M+1). $^1$H NMR (400 MHz, DMSO-d$_6$) δ ppm 8.55 (s, 1 H) 8.30 (d, J=9.09 Hz, 1 H) 8.16 (d, J=3.79 Hz, 1 H) 7.46 (d, J=2.27 Hz, 1 H) 7.13-7.16 (m, 1 H) 6.75 (d, J=3.79 Hz, 1 H) 6.78 (s, 1 H) 4.10 (d, J=15.16 Hz, 4 H) 3.37-3.39 (m, 2 H) 3.25 (s, 3 H) 2.88 (s, 2 H) 2.70-2.72 (m, 2 H) 1.07-1.10 (m, 2 H) 0.98-1.00 (m, 2 H).

EXAMPLE 145

145-A. 5-[6-(2-Methylamino-ethyl)-pyrimidin-4-yloxy]-indole-1-carboxylic acid [5-(1-methyl-cyclopropyl)-isoxazol-3-yl]-amide

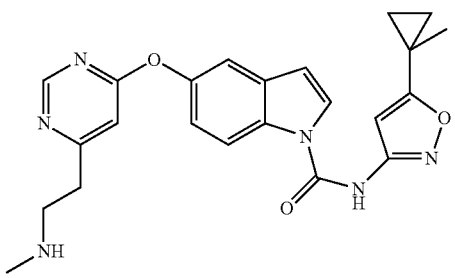

Prepared with similar method to that described for Example 73-D MS (ESI) m/z 432.2 (M+1). $^1$H NMR (400 MHz, DMSO-d$_6$) δ ppm 8.64 (d, J=1.01 Hz, 1 H) 8.36 (d, J=8.84 Hz, 1 H) 8.15 (d, J=3.79 Hz, 1 H) 7.43 (d, J=2.53 Hz, 1 H) 7.09-7.11 (m, 1 H) 6.97 (s, 1 H) 6.66 (s, 1 H) 6.71 (d, J=3.79 Hz, 1 H) 2.84-2.89 (m, 4 H) 2.32 (s, 3 H) 1.45 (s, 3 H) 1.13-1.15 (m, 2 H) 0.90-0.92 (m, 2 H).

The following compounds are prepared with similar method.

145-B. 5-[6-(2-Dimethylamino-ethyl)-pyrimidin-4-yloxy]-indole-1-carboxylic acid (5-isopropyl-1H-pyrazol-3-yl)-amide

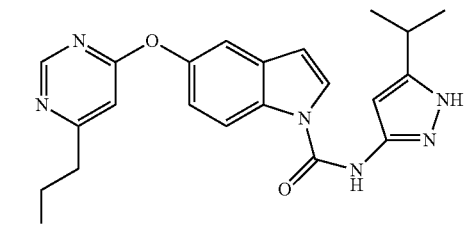

MS (ESI) m/z 434.2 (M+1). $^1$H NMR (400 MHz, DMSO-d$_6$) δ ppm 12.24 (s, 1 H) 10.61 (s, 1 H) 8.63 (d, J=1.01 Hz, 1 H) 8.31 (d, J=8.84 Hz, 1 H) 8.18 (d, J=3.79 Hz, 1 H) 7.44 (d, J=2.27 Hz, 1 H) 7.10 (dd, J=8.84, 2.53 Hz, 1 H) 7.02 (s, 1 H) 6.71 (d, J=3.54 Hz, 1 H) 6.34 (d, J=1.26 Hz, 1 H) 2.90-3.01 (m, 1 H) 2.84 (t, J=7.07 Hz, 2 H) 2.60-2.70 (m, 2 H) 2.19 (s, 6 H) 1.25 (d, J=7.07 Hz, 6 H).

145-C. 5-[6-(2-Methylamino-ethyl)-pyrimidin-4-yloxy]-indole-1-carboxylic acid (5-isopropyl-1H-pyrazol-3-yl)-amide

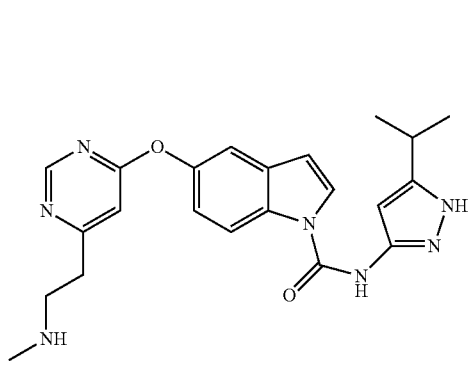 [SMILES: CNCCc1cc(Oc2ccc3c(ccn3C(=O)Nc3cc(C(C)C)[nH]n3)c2)ncn1]

MS (ESI) m/z 420.1 (M+1). ¹H NMR (400 MHz, DMSO-d₆) δ ppm 12.24 (br. s., 1 H) 8.63 (d, J=1.26 Hz, 1 H) 8.31 (d, J=9.09 Hz, 1 H) 8.18 (d, J=3.79 Hz, 1 H) 7.43 (d, J=2.27 Hz, 1 H) 7.10 (dd, J=8.97, 2.40 Hz, 1 H) 6.97 (d, J=1.01 Hz, 1 H) 6.71 (d, J=3.03 Hz, 1 H) 6.34 (s, 1 H) 2.89-3.01 (m, 1 H) 2.76-2.86 (m, 4 H) 2.28 (s, 3 H) 1.25 (d, J=7.07 Hz, 6 H)

EXAMPLE 146

146-A. 5-{6-[(Acetyl-methyl-amino)-methyl]-pyrimidin-4-yloxy}-indole-1-carboxylic acid [5-(1-trifluoromethyl-cyclopropyl)-isoxazol-3-yl]-amide

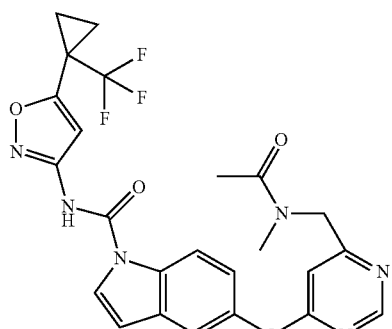

Prepared with similar method to that described for Example 21 MS (ESI) m/z 515.2 (M+1). ¹H NMR (400 MHz, DMSO-d₆) δ ppm 11.44 (s, 1 H) 8.59-8.74 (m, 1 H) 8.30 (d, J=9.09 Hz, 1 H) 8.17 (d, J=3.79 Hz, 1 H) 7.43-7.53 (m, 1 H) 7.10-7.21 (m, 1 H) 7.04 (s, 1 H) 6.92 (s, 1 H) 6.78 (d, J=3.54 Hz, 1 H) 4.63 (s, 1 H) 4.54 (s, 1 H) 3.09 (s, 2 H) 2.84 (s, 1 H) 2.10 (s, 2 H) 2.03 (s, 1 H) 1.48-1.65 (m, 4 H).

146-B. 5-{6-[(Acetyl-methyl-amino)-methyl]-pyrimidin-4-yloxy}-indole-1-carboxylic acid (5-isopropyl-isoxazol-3-yl)-amide

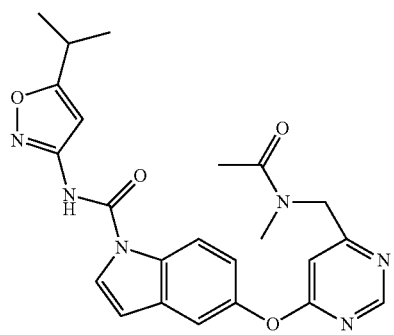 [SMILES: CC(=O)N(C)Cc1cc(Oc2ccc3c(ccn3C(=O)Nc3cc(C(C)C)on3)c2)ncn1]

MS (ESI) m/z 449.19 (M+1). ¹H NMR (400 MHz, DMSO-d₆) δ ppm 11.27 (s, 1 H) 8.60-8.78 (m, 1 H) 8.27-8.35 (m, 1 H) 8.14-8.21 (m, 1 H) 7.44-7.51 (m, 1 H) 7.14 (dd, J=8.84, 2.53 Hz, 1 H) 6.90-6.97 (m, 1 H) 6.77 (t, J=2.91 Hz, 1 H) 4.59-4.61 (m, 1 H) 4.63 (s, 1 H) 4.54 (s, 1 H) 3.10-3.15 (m, 1 H) 3.09 (s, 2 H) 2.84 (s, 1 H) 2.10 (s, 2 H) 2.03 (s, 1 H) 1.26-1.33 (m, 6 H).

146-C. 5-{6-[2-(Acetyl-methyl-amino)-ethyl]-pyrimidin-4-yloxy}-indole-1-carboxylic acid (5-isopropyl-1H-pyrazol-3-yl)-amide

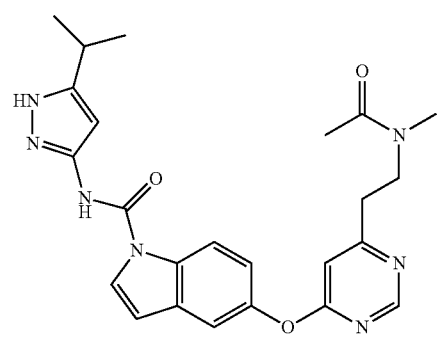 [SMILES: CC(=O)N(C)CCc1cc(Oc2ccc3c(ccn3C(=O)Nc3cc(C(C)C)[nH]n3)c2)ncn1]

MS (ESI) m/z 462.1 (M+1). ¹H NMR (400 MHz, DMSO-d₆) δ ppm 12.22 (s, 1 H) 10.58 (s, 1 H) 8.67 (dd, J=14.91, 1.01 Hz, 1 H) 8.32 (d, J=8.84 Hz, 1 H) 8.18 (d, J=3.54 Hz, 1 H) 7.43 (d, J=2.02 Hz, 1 H) 7.03-7.16 (m, 1 H) 6.96 (s, 1 H) 6.72 (d, J=3.54 Hz, 1 H) 6.34 (s, 1 H) 3.57-3.69 (m, 2 H) 2.93-3.01 (m, 2 H) 2.93 (s, 2 H-rotamer) 2.83-2.89 (m, 1 H) 2.78 (s, 1 H-rotamer) 1.93 (d, J=7.33 Hz, 3 H) 1.25 (d, J=7.07 Hz, 6 H)

EXAMPLE 147

5-[6-(2-Methoxy-ethoxymethyl)-pyrimidin-4-yloxy]-indole-1-carboxylic acid [5-(1-methyl-cyclopropyl)-isoxazol-3-yl]-amide

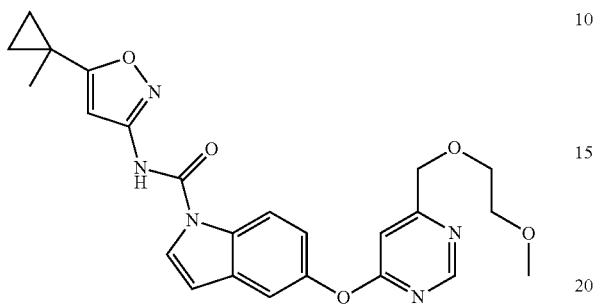

Prepared with similar method to that described for Example 20-A MS (ESI) m/z 464.0 (M+1). $^1$H NMR (400 MHz, DMSO-d$_6$) δ ppm 11.25 (s, 1 H) 8.68 (d, J=1.01 Hz, 1 H) 8.31 (d, J=9.09 Hz, 1 H) 8.18 (d, J=3.79 Hz, 1 H) 7.49 (d, J=2.53 Hz, 1 H) 7.16 (dd, J=8.97, 2.40 Hz, 1 H) 7.00 (d, J=1.01 Hz, 1 H) 6.77 (d, J=3.79 Hz, 1 H) 6.67 (s, 1 H) 4.57 (s, 2 H) 3.63-3.69 (m, 2 H) 3.46-3.52 (m, 2 H) 3.21 (s, 3 H) 1.46 (s, 3 H) 1.13-1.17 (m, 2 H) 0.90-0.97 (m, 2 H).

EXAMPLE 148

148-A. 4-Oxo-pyrrolidine-1,2-dicarboxyc acid 1-tert-butyl ester 2-methyl ester

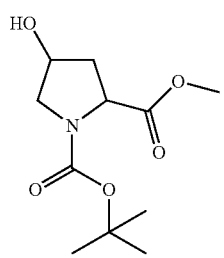 [SMILES: COC(=O)C1CC(O)CN1C(=O)OC(C)(C)C]

To a solution of 4-hydroxy-pyrrolidine-1,2-dicarboxylic acid 1-tert-butyl ester 2-methyl ester (5 g, 20.4 mmol) in DCM (100 mL), Dess-Martin periodinane (12.97 g, 30.6 mmol) is added. After completion of the reaction as judged by TLC the reaction is quenched with sat NaHCO$_3$, washed with sat sodium thiosulfate and extracted with DCM. The organics are dried and evaporated and used crude in the next step.

148-B. B-1. 5-Oxo-piperidine-1,2,4-tricarboxylic acid 1-tert-butyl ester 4-ethyl ester 2-methyl ester and B-2 4-Oxo-piperidine-1,2,5-tricarboxylic acid 1-tert-butyl ester 5-ethyl ester 2-methyl ester

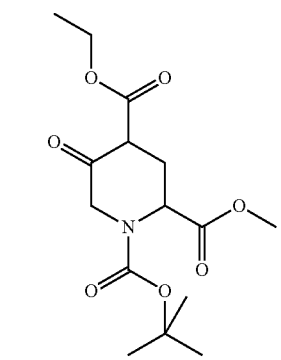

B-1

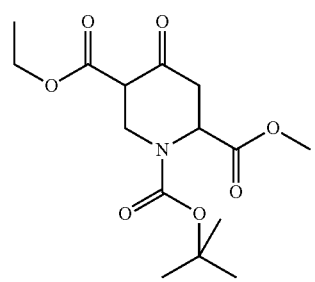

B-2

To a solution of 4-oxo-pyrrolidine-1,2-dicarboxylic acid 1-tert-butyl ester 2-methyl ester (3.73 g, 15.3 mmol) in diethyl ether (50 mL), at 0° C., boron trifluoride etherate (2.14 ml, 16.9 mmol) followed by ethyl diazoacetate (2.39 mL, 23.0 mmol) are added. After stirring overnight the reaction is quenched with water and extracted with EtOAc. The two products are isolated (as inseparable mixtures) using FCC eluting with heptane:EtOAc 1:1. MS (ESI) m/z 328.1 (M−1).

148-C. (±)-C-1. 4-Oxo-4,5,6,8-tetrahydro-3H-pyrido[3,4-d]pyrimidine-6,7-dicarboxylic acid 7-tert-butyl ester 6-ethyl ester and (±)-C-2. 4-Oxo-3,5,7,8-tetrahydro-4H-pyrido[4,3-d]pyrimidine-6,7-dicarboxylic acid 6-tert-butyl ester 7-ethyl ester

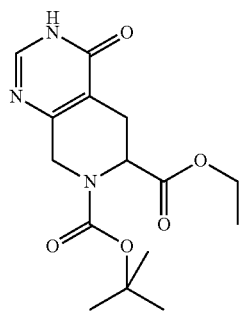

C-1

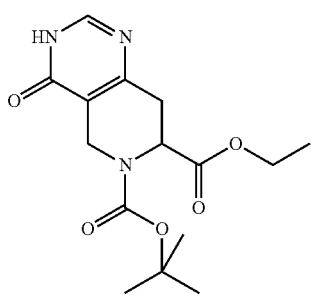
C-2

To a solution of 5-oxo-piperidine-1,2,4-tricarboxylic acid 1-tert-butyl ester 4-ethyl ester 2-methyl ester and 4-oxo-piperidine-1,2,5-tricarboxylic acid 1-tert-butyl ester 5-ethyl ester 2-methyl ester (2.84 g, 8.62 mmol) in EtOH (20 mL), formamidine acetate (1.347 g, 12.93 mmol) and sodium ethoxide (6.99 g, 21.6 mmol) are added and the reaction heated at 90° C. After 3 h, 0.75 eq of formamidine acetate is added added. After completion of reaction as judged by LCMS the reaction is evaporated, quenched with NH$_4$Cl and extracted with DCM. The products are purified using FCC eluting with heptane:EtOAc 1:2 and isolated as an inseperable mixture. MS (ESI) m/z 324.1 (M+1)

148-D. (±)-D-1. 4-Chloro-5,8-dihydro-6H-pyrido[3,4-d]pyrimidine-6,7-dicarboxylic acid 7-tert-butyl ester 6-ethyl ester and (±)-D-2. 4-chloro-7,8-dihydro-5H-pyrido[4,3-d]pyrimidine-6,7-dicarboxylic acid 6-tert-butyl ester 7-ethyl ester

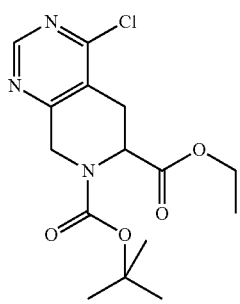
D-1

D-2

To a solution of the mixture of 4-oxo-4,5,6,8-tetrahydro-3H-pyrido[3,4-d]pyrimidine-6,7-dicarboxylic acid 7-tert-butyl ester 6-ethyl ester and 4-Oxo-3,5,7,8-tetrahydro-4H-pyrido[4,3-d]pyrimidine-6,7-dicarboxylic acid 6-tert-butyl ester 7-ethyl ester (1.5 g, 4.64 mmol) in DCE (25 mL), carbon tetrachloride (1.34 mL, 13.9 mmol) and triphenylphosphine (2.43 g, 9.28 mmol) are added. The reaction is heated at reflux and after completion of reaction as judged by LCMS. The solvents are removed and the products are isolated using FCC eluting with heptane:EtOAc 80:20. At this point the two products are separated. 4-Chloro-5,8-dihydro-6H-pyrido[3,4-d]pyrimidine-6,7-dicarboxylic acid 7-tert-butyl ester 6-ethyl ester MS (ESI) m/z 342.1 (M+1) and 4-chloro-7,8-dihydro-5H-pyrido[4,3-a]pyrimidine-6,7-dicarboxylic acid 6-tert-butyl ester 7-ethyl ester MS (ESI) m/z 342.1 (M+1) are isolated as an almost 4:1 ratio.

148-E. (±)-4-(1H-Indol-5-yloxy)-5,8-dihydro-6H-pyrido[3,4-d]pyrimidine-6,7-dicarboxylic acid 7-tert-butyl ester 6-ethyl ester

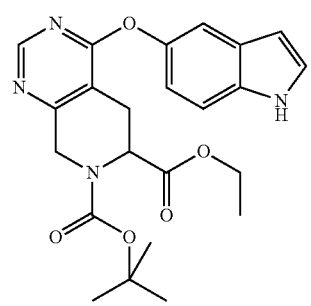 [SMILES: CCOC(=O)C1Cc2c(ncnc2Oc2ccc3[nH]ccc3c2)CN1C(=O)OC(C)(C)C]

To a solution of 4-chloro-5,8-dihydro-6H-pyrido[3,4-d]pyrimidine-6,7-dicarboxylic acid 7-tert-butyl ester 6-ethyl ester (1 g, 2.93 mmol) in CH$_3$CN (30 mL), 5-hydroxy-indole (0.779 g, 5.85 mmol) and DBU (0.88 mL, 5.85 mmol) are added. After heating at 60° C. for 5 h the reaction is evaporated and the product isolated using FCC eluting with heptane:EtOAc 1:1. MS (ESI) m/z 439.1 (M+1).

148-F. (±)-4-[1-(5-Cyclopropyl-isoxazol-3-ylcarbamoyl)-1H-indol-5-yloxy]-5,8-dihydro-6H-pyrido[3,4-d]pyrimidine-6,7-dicarboxylic acid 7-tert-butyl ester 6-ethyl ester

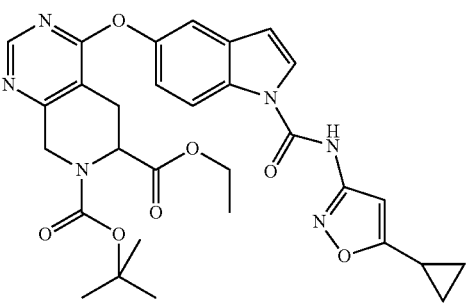 [SMILES: CCOC(=O)C1Cc2c(ncnc2Oc2ccc3c(ccn3C(=O)Nc3cc(C4CC4)on3)c2)CN1C(=O)OC(C)(C)C]

Prepared by similar method to that described in Example 56-A. MS (ESI) m/z 589.1 (M+1)

148-G. (±)-4-[1-(5-Cyclopropyl-isoxazol-3-ylcarbamoyl)-1H-indol-5-yloxy]-5,6,7,8-tetrahydro-pyrido[3,4-d]pyrimidine-6-carboxylic acid methylamide

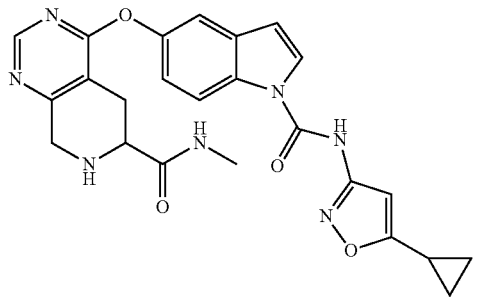 [SMILES: CNC(=O)C1Cc2c(ncnc2Oc2ccc3c(ccn3C(=O)Nc3cc(C4CC4)on3)c2)CN1]

To a solution of 4-[1-(5-cyclopropyl-isoxazol-3-ylcarbamoyl)-1H-indol-5-yloxy]-5,8-dihydro-6H-pyrido[3,4-d]pyrimidine-6,7-dicarboxylic acid 7-tert-butyl ester 6-ethyl ester (110 mg, 0.196 mmol) in THF/EtOH/H$_2$O (3:1:1 mL) LiOH (0.016 g, 0.392 mmol) is added and the reaction stirred until starting material is consumed. At this point the reaction is quenched with 1 HCl (2 mL) and extracted with EtOAc. After drying and evaporation, the crude product is dissolved in DCM (3 mL) at 0° C., oxalyl chloride (0.026 mL, 0.294 mmol) and DMF (2 drops) are added. At this point Methylamine (2 M in THF) (0.49 mL, 0.981 mmol) is added and the reaction stirred for 1 h at rt. After work up with water and extraction with EtOAc the crude product is dissolved in DCM (2 mL) and TFA (1 mL) is added. After removing the solvent in vacuo, and basifying with NH$_4$OH, the product is separated using FCC eluting with DCM:MeOH:NH$_4$OH 100:0:0 to 90:8:2. MS (ESI) m/z 474.1 (M+1). $^1$H NMR (400 MHz, DMSO-d$_6$) δ ppm 11.21 (s, 1 H) 8.43 (s, 1 H) 8.21-8.33 (m, 1 H) 8.15 (d, J=3.79 Hz, 1 H) 7.94 (d, J=5.81 Hz, 1 H) 7.44 (d, J=2.27 Hz, 1 H) 7.12 (d, J=9.09 Hz, 1 H) 6.75 (d, J=3.03 Hz, 1 H) 6.65 (s, 1 H) 3.91-4.15 (m, 2 H) 3.61 (br. s, 1 H) 2.83-2.95 (m, 2 H) 2.66 (d, J=4.80 Hz, 3 H) 2.12-2.24 (m, 1 H) 1.03-1.17 (m, 2 H) 0.94 (dd, J=4.80, 2.53 Hz, 2 H).

EXAMPLE 149

149-A. (4-(1H-indol-5-yloxy)pyridin-2-yl)methanol

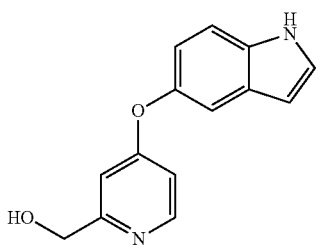 [SMILES: OCc1cc(Oc2ccc3[nH]ccc3c2)ccn1]

To a solution of (4-chloropyridin-2-yl)methanol (384 mg, 2.67 mmol) in DMF (12 mL) is added 1H-indol-5-ol (534 mg, 4.01 mmol), and cesium carbonate (1307 mg, 4.01 mmol). The reaction is sealed and heated to 160° C. via microwave irradiation for 30 min. The reaction mixture is then cooled to room temperature and diluted brine and DCM. The resulting layers are separated and the aqueous layer is extracted three additional times with DCM. The organic layers are combined dried over anhydrous Na$_2$SO$_4$, filtered, and concentrated. The resulting residue is purified via FCC (0-100% EtOAc/heptane) to give the title compound. MS (ESI) m/z 241.2 (M+1).

149-B. tert-butyl (4-(1H-indol-5-yloxy)pyridin-2-yl)methyl(methyl)carbamate

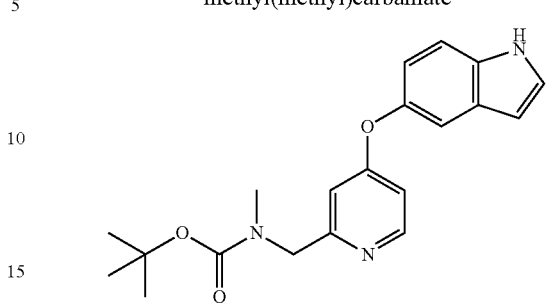

To a solution of (4-(1H-indol-5-yloxy)pyridin-2-yl)methanol (2 g, 8.32 mmol) in THF (40 mL) is added triethylamine (3.48 ml, 24.97 mmol). The reaction mixture is cooled to 0° C., and methanesulfonyl chloride (0.973 mL, 12.49 mmol) is added dropwise. The reaction is stirred at 0° C. for 45 min at which time the reaction is placed at room temperature and a 40% solution of methylamine in water (7.21 mL, 83 mmol) is added. The reaction is stirred for 30 min and then diluted with brine. The resulting mixture is extracted twice with ethyl acetate. The combined organic layers are dried over anhydrous Na$_2$SO$_4$, filtered, and concentrated. The resulting residue is then dissolved in DCM (50 mL) and di-tert-butyl dicarbonate (2.0 g, 9.15 mmol) is added. The reaction is permitted to stir for approximately 30 minutes at room temperature at which time it is diluted with saturated aqueous NaHCO$_3$. The resulting mixture is extracted twice with DCM. The organic layers are combined dried over anhydrous Na$_2$SO$_4$, filtered, and concentrated. The resulting residue is purified via FCC (0-100% EtOAc/heptane) to give the title compound. MS (ESI) m/z 354.3 (M+1).

149-C. tert-butyl (4-(1-(5-cyclopropyl-1-methyl-1H-pyrazol-3-ylcarbamoyl)-1H-indol-5-yloxy)pyridin-2-yl)methyl(methyl)carbamate

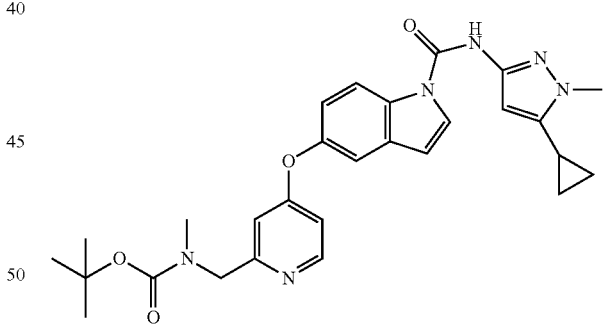

To a solution of tert-butyl (4-(1H-indol-5-yloxy)pyridin-2-yl)methyl(methyl)carbamate (115 mg, 0.325 mmol), in DMF (5 ml) is added phenyl 5-cyclopropyl-1-methyl-1H-pyrazol-3-ylcarbamate (126 mg, 0.488 mmol), prepared as described in Example 5-N. The resulting mixture is placed at 0° C. and sodium hydride (60% dispersion in oil; 39.0 mg, 0.98 mmol) is added. The reaction is permitted to stir at 0° C. for 30 min at which time the reaction is quenched with saturated aqueous NH$_4$Cl. The resulting mixture is diluted with brine and DCM. The resulting layers are separated and the aqueous layer is extracted twice with DCM. The organic layers are combined, dried over anhydrous Na$_2$SO$_4$, filtered, and concentrated. The resulting residue is purified via FCC (0-100% EtOAc/heptane) to give the title compound. MS (ESI) m/z 517.6 (M+1).

149-D. N-(5-cyclopropyl-1-methyl-1H-pyrazol-3-yl)-5-(2-((methylamino)methyl)pyridin-4-yloxy)-1H-indole-1-carboxamide

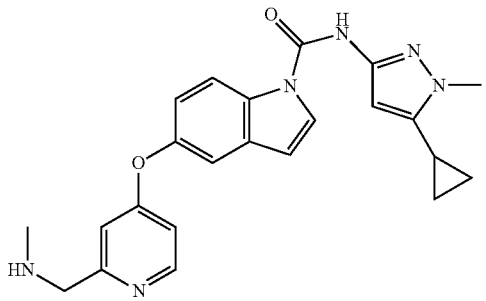 [SMILES: CNCc1cc(Oc2ccc3c(ccn3C(=O)Nc3cc(C4CC4)n(C)n3)c2)ccn1]

To a solution of tert-butyl (4-(1-(5-cyclopropyl-1-methyl-1H-pyrazol-3-ylcarbamoyl)-1H-indol-5-yloxy)pyridin-2-yl)methyl(methyl)carbamate (0.124 g, 0.240 mmol) in DCM (5 ml) is added TFA (2 ml, 0.240 mmol). The reaction is stirred for approximately 30 minutes and then concentrated in vacuo to near dryness. The residue is dissolved in DCM, diluted with water and neutralized via the addition of saturated aqueous NaHCO$_3$. The resulting layers are then separated and the aqueous layer is extracted twice with DCM. The organic layers are combined dried over anhydrous Na$_2$SO$_4$, filtered, and concentrated. The resulting residue is purified via FCC (0-15% MeOH/DCM) to provide the title compound. MS (ESI) m/z 417.2 (M+1). $^1$H NMR (400 MHz, DMSO-d$_6$) δ ppm 0.64-0.70 (m, 2 H) 0.96-1.02 (m, 2 H) 1.87-1.96 (m, 1 H) 2.27 (s, 3 H) 3.71 (s, 2 H) 3.80 (s, 3 H) 6.16 (d, J=0.51 Hz, 1 H) 6.73 (dd, J=3.79, 0.51 Hz, 1 H) 6.80 (dd, J=5.56, 2.53 Hz, 1 H) 6.93 (d, J=2.02 Hz, 1 H) 7.09 (dd, J=8.97, 2.40 Hz, 1 H) 7.42 (d, J=2.27 Hz, 1 H) 8.17 (d, J=3.54 Hz, 1 H) 8.33 (d, J=8.84 Hz, 1 H) 8.36 (d, J=5.81 Hz, 1 H).

The following compounds are prepared with similar method.

| | Structure/Chemical Name | $^1$H NMR (400 MHz) | MS (ESI) m/z (M + 1) |
|---|---|---|---|
| 149-E | N-(5-cyclopropyl-1H-pyrazol-3-yl)-5-(2-((methylamino)methyl)pyridin-4-yloxy)-1H-indole-1-carboxamide | (DMSO-d$_6$ with ~1% d-TFA) δ ppm 0.73-0.83 (m, 2H) 0.92-1.07 (m, 2H) 1.88-2.02 (m, 1 H) 2.61 (s, 3H) 4.31 (s, 2H) 6.21 (s, 1H) 6.78 (d, J = 3.03 Hz, 1H) 7.16 (dd, J = 8.97, 2.40 Hz, 1 H) 7.20-7.27 (m, 2H) 7.50 (d, J = 2.53 Hz, 1H) 8.18 (d, J = 3.79 Hz, 1H) 8.40 (d, J = 9.09 Hz, 1 H) 8.58-8.75 (m, 1H) | 403.3 |
| 149-F | N-(1-methyl-5-(trifluoromethyl)-1H-pyrazol-3-yl)-5-(2-((methylamino)methyl)pyridin-4-yloxy)-1H-indole-1-carboxamide | (DMSO-d$_6$) δ ppm 2.26 (s, 3H) 3.70 (s, 2H) 3.94 (s, 3H) 6.75 (d, J = 3.79 Hz, 1H) 6.79 (dd, J = 5.56, 2.53 Hz, 1H) 6.92 (d, J = 2.27 Hz, 1H) 7.06 (s, 1H) 7.11 (dd, J = 8.84, 2.53 Hz, 1H) 7.42 (d, J = 2.27 Hz, 1H) 8.18 (d, J = 3.79 Hz, 1 H) 8.34 (d, J = 5.56 Hz, 1H) 8.35 (d, J = 2.53 Hz, 1H) | 445.2 |

| Structure/Chemical Name | $^1$H NMR (400 MHz) | MS (ESI) m/z (M + 1) |
|---|---|---|
| 149-G 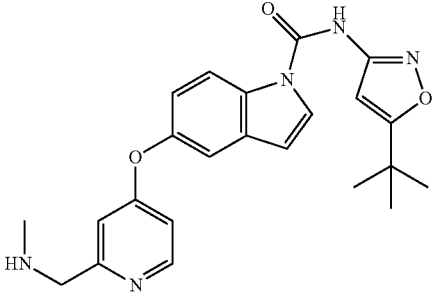 [SMILES: CNCc1cc(Oc2ccc3c(ccn3C(=O)Nc3cc(C(C)(C)C)on3)c2)ccn1]<br>N-(5-tert-butylisoxazol-3-yl)-5-(2-((methylamino)methyl)pyridin-4-yloxy)-1H-indole-1-carboxamide | (DMSO-d$_6$) δ ppm 1.34 (s, 9H), 2.29 (s, 3H), 3.74 (s, 2H), 6.67 (s, 1H), 6.74 (d, J = 3.3 Hz, 1 H), 6.81 (dd, J = 5.7, 2.4 Hz, 1H), 6.94 (d, J = 2.3 Hz, 1H), 7.10 (dd, J = 9.0, 2.4 Hz, 1H), 7.42 (d, J = 2.5 Hz, 1H), 8.17 (d, J = 3.5 Hz, 1H), 8.33-8.39 (m, 2H) | 420.2 |
| 149-H 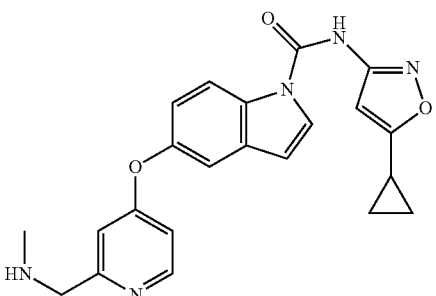<br>N-(5-cyclopropylisoxazol-3-yl)-5-(2-((methylamino)methyl)pyridin-4-yloxy)-1H-indole-1-carboxamide | (DMSO-d$_6$) δ ppm 0.88-0.98 (m, 2H) 1.03-1.13 (m, 2H) 2.11-2.22 (m, J = 8.53, 8.53, 5.05, 4.93 Hz, 1H) 2.30 (s, 3H) 3.75 (s, 2H) 6.65 (s, 1H) 6.75 (d, J = 3.54 Hz, 1H) 6.82 (dd, J = 5.56, 2.53 Hz, 1H) 6.94 (d, J = 2.53 Hz, 1H) 7.11 (dd, J = 8.97, 2.40 Hz, 1H) 7.43 (d, J = 2.27 Hz, 1H) 8.17 (d, J = 3.79 Hz, 1H) 8.33-8.40 (m, 2H) | 404.2 |

EXAMPLE 150

150-A. (4-(1H-indol-5-yloxy)pyrimidin-2-yl)methyl acetate

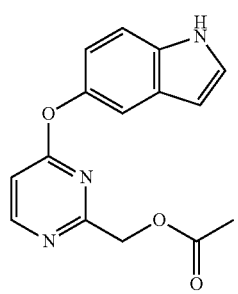 [SMILES: CC(=O)OCc1nccc(Oc2ccc3[nH]ccc3c2)n1]

To a suspension of nano zinc metallic powder (Strem Chemicals; average particle size 75-125 nm) (1.34 g, 20.52 mmol) in DMF (8 ml) is added 1,2-dibromoethane (0.19 mL, 2.2 mmol). The heterogeneous mixture is heated to 60° C. and then stirred for 10 min. The mixture is cooled to room temperature and charged with chlorotrimethylsilane (0.24 mL, 1.8 mmol). The reaction vessel is then sonicated in a room temperature water bath for 30 min. The suspension is then left standing for ca. 30 min to permit the solid to settle and the supernatant is then removed via syringe. DMF (8 ml) is then added, followed by bromomethyl acetate (1.00 mL, 10.3 mmol). The reaction mixture is then stirred for 2 hr at room temperature. The suspension is then left standing for 1 hour to permit the solid to settle. Next a separate flask is charged with 5-(2-chloropyrimidin-4-yloxy)-1H-indole (450 mg, 1.83 mmol), prepared as described in Example 73-A, DMF (3 mL) is then added to the 5-(2-chloropyrimidin-4-yloxy)-1H-indole followed by Pd(dppf)Cl$_2$.CH$_2$Cl$_2$ (230 mg, 0.28 mmol). To this solution is added a portion of the supernatant (6 mL), from the flask containing the organozincate, via syringe. The reaction is heated at 50° C. for 16 h then cooled to room temperature and diluted with DCM and saturated aqueous NH$_4$Cl. The layers are separated and the aqueous layer is extracted 2 additional times with DCM. The organic layers are combined dried over anhydrous Na$_2$SO$_4$, filtered, and concentrated. The resulting residue is purified via FCC (0-60% EtOAc/DCM) to provide the title compound. MS (ESI) m/z 284.0 (M+1).

150-B. (4-(1H-indol-5-yloxy)pyrimidin-2-yl)methanol

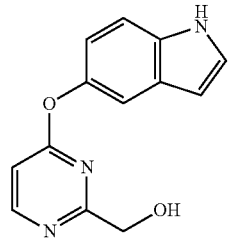 [SMILES: OCc1nccc(Oc2ccc3[nH]ccc3c2)n1]

To a solution of (4-(1H-indol-5-yloxy)pyrimidin-2-yl)methyl acetate (0.51 g, 1.8 mmol) in MeOH (18 mL) at 0° C. is added solid $K_2CO_3$ (0.6 g, 4.5 mmol). The reaction is stirred for 30 minutes at 0° C. and then warmed to room temperature and stirred for an additional 30 minutes. The reaction mixture is then diluted with DCM and water and the layers are separated. The aqueous layer is extracted 2 additional times with DCM. The organic layers are combined dried over anhydrous $Na_2SO_4$, filtered, and concentrated to afford the title compound. MS (ESI) m/z 242.1 (M+1).

150-C. tert-butyl (4-(1H-indol-5-yloxy)pyrimidin-2-yl)methyl(methyl)carbamate

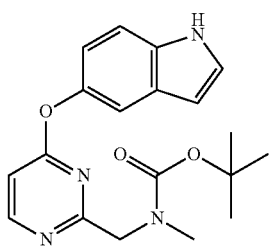 [SMILES: CN(Cc1nccc(Oc2ccc3[nH]ccc3c2)n1)C(=O)OC(C)(C)C]

To a solution of (4-(1H-indol-5-yloxy)pyrimidin-2-yl) methanol (0.47 g, 1.95 mmol) and triethylamine (0.815 ml, 5.84 mmol) in THF at 0° C. is added methanesulfonyl chloride (0.228 mL, 2.92 mmol). The reaction is allowed to stir at 0° C. for 45 min at which time a 40% solution of methylamine in water (3.37 ml, 39.0 mmol) is added. The reaction is placed at room temperature and stirred for 30 min. The reaction is then diluted with brine and ethyl acetate. The layers are separated and the aqueous layer is extracted two additional times with ethyl acetate. The organic layers are combined, dried over anhydrous $Na_2SO_4$, filtered, and concentrated. The resulting residue is then diluted with DCM (15 mL), to the resulting solution is added di-tert-butyl dicarbonate (0.42 g, 1.9 mmol). The reaction is permitted to stir for approximately 30 minutes at room temperature, at which time it is diluted with saturated aqueous $NaHCO_3$. The resulting mixture is extracted twice with DCM. The organic layers are combined dried over anhydrous $Na_2SO_4$, filtered, and concentrated. The resulting residue is purified via FCC (30-80% EtOAc (2.5% EtOH)/heptane) to give the title compound. MS (ESI) m/z 355.2 (M+1).

150-D. tert-butyl (4-(1-(5-cyclopropyl-1-ethyl-1H-pyrazol-3-ylcarbamoyl)-1H-indol-5-yloxy)pyrimidin-2-yl)methyl(methyl)carbamate

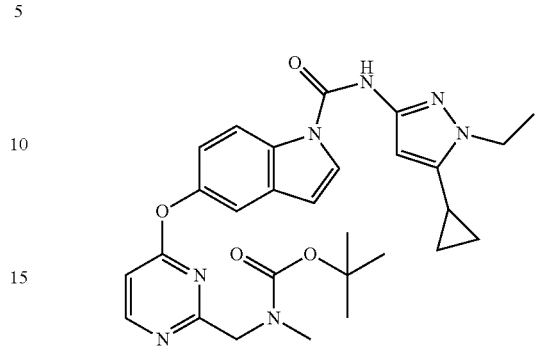

To a solution of tert-butyl (4-(1H-indol-5-yloxy)pyrimidin-2-yl) methyl(methyl)carbamate (35 mg, 0.099 mmol) in THF (2 ml) is added phenyl 5-cyclopropyl-1-ethyl-1H-pyrazol-3-ylcarbamate (29.5 mg, 0.109 mmol), which is prepared as described in Example 5-S. The mixture is put at 0° C. and NaH (60% dispersion in oil; 11.85 mg, 0.296 mmol) is then added and the reaction is then stirred for 30 minutes. The reaction is then quenched with 10% AcOH/MeOH (0.3 mL) and further diluted with DCM and saturated aqueous $NaHCO_3$. The resulting layers are then separated and the aqueous layer is extracted two additional times with DCM. The organic layers are combined, dried over anhydrous $Na_2SO_4$, filtered, and concentrated. The resulting residue is purified via FCC (10-100% EtOAc (2.5% EtOH)/DCM) to give the title compound. MS (ESI) m/z 532.3 (M+1).

150-E. N-(5-cyclopropyl-1-ethyl-1H-pyrazol-3-yl)-5-(2-((methylamino)methyl)pyrimidin-4-yloxy)-1H-indole-1-carboxamide

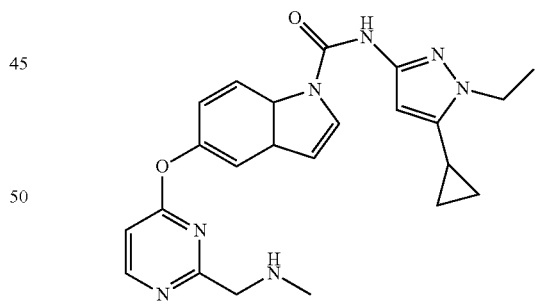

To a solution of tert-butyl (4-(1-(5-cyclopropyl-1-ethyl-1H-pyrazol-3-ylcarbamoyl)-1H-indol-5-yloxy)pyrimidin-2-yl)methyl(methyl)carbamate (33 mg, 0.062 mmol) in DCM (2 mL) at 0° C. is added TFA (0.7 mL, 9.1 mmol). The reaction is stirred for 30 minutes at 0° C. and is then placed at room temperature for an additional 20 minutes. The reaction mixture is then concentrated in vacuo to near dryness and then diluted with DCM and water. The mixture is neutralized by the addition of saturated aqueous $NaHCO_3$ and the resulting layers are separated. The aqueous layer is extracted two additional times with DCM. The organic layers are combined, dried over anhydrous $Na_2SO_4$, filtered, and concentrated. The resulting residue is purified via FCC (0-20% MeOH)/DCM) to give the title compound. MS (ESI) m/z 432.2 (M+1). (DMSO-$d_6$) δ ppm 0.62-0.71 (m, 2 H) 0.93-1.02 (m, 2 H) 1.37 (t, J=7.20 Hz, 3 H) 1.86-1.99 (m, 1 H) 2.30 (s, 3 H) 3.71 (s, 2 H) 4.15 (q, J=7.24 Hz, 2 H) 6.16 (s, 1 H) 6.71 (d, J=4.29 Hz, 1 H) 6.87 (d, J=5.56 Hz, 1 H) 7.12 (dd, J=9.09, 2.27 Hz, 1 H) 7.46 (d, J=2.27 Hz, 1 H) 8.17 (d, J=3.79 Hz, 1 H) 8.31 (d, J=9.09 Hz, 1 H) 8.61 (d, J=5.56 Hz, 1 H) 10.64 (s, 1 H).

EXAMPLE 151

Ba/F3-Tel-KDR Cell Viability Inhibition Assay

This assay is a cell-based assay to measure the compound-mediated suppression of Ba/F3 cell proliferation and viability using the Luciferase bioluminescent assay commercially known as CellTiter-Glo™. In this case, a specifically modified cell line, Ba/F3-Tel-KDR is used. These cells are engineered such that intact signaling through the tyrosine kinase domain of KDR is critical for their survival. Inhibition of KDR signaling results in cell death which is quantitated using a cell viability assay. This is a homogeneous bioluminescent assay that yields a rapid, simple and sensitive determination of the number of viable cells in culture by generation of a luminescent signal proportional to the amount of ATP present in cells. KDR inhibitor compound dilutions are incubated with Ba/F3-Tel-KDR cells over a 48 hour period and the resulting cell viability is measured with a suitable luminometer.

This assay is performed in Ba/F3-Tel-KDR cells. Cells are cultured at 37° C. (5% $CO_2$) in medium containing RPMI-1640, 10% Fetal Bovine Serum, 2 mM Glutamax, 100 units/ml Pen/Strep, and 0.8 mg/ml G418. Medium is changed the day before the experiment. On Day 1, cells are plated into white solid bottom 384-well plates at 5000 cells/well in 25 μl culture medium. A ten-point dose response curve is prepared as follows: compounds are first serially diluted 3-fold in 100% DMSO, starting from 10 mM. Then the compounds are further diluted 166.67-fold in culture medium. 5 μl of diluted compound is added to cell plates with 25 μl culture medium. The final concentrations of the compounds are: 10, 3.33, 1.11, 0.37, 0.123, 0.041, 0.0137, 0.0046, 0.0015, and 0.0005 μM. The final concentration of DMSO is 0.1%. Wells without or with cells plus 0.1% DMSO serve as controls. On Day 3, Lyophilized CellTiter-Glo buffer and substrate and the cell plates are first equilibrated to room temperature. Substrate is reconstituted in buffer and 30 μl reconstituted substrate is added to each well. After incubation for 10 minutes at room temperature, plates are read in a luminometer. Compounds are tested in a 10-point dose response and each concentration is run in triplicate on a given plate. Each plate is run in duplicate. Data analysis and 1050 generation are performed using Excel and Prism software.

| Example number | $IC_{50}$ (nM) | Example number | $IC_{50}$ (nM) |
|---|---|---|---|
| 37-A | 10 | 57-B | 167 |
| 19-A | 76 | 102-A-1 | 2 |
| 33-D | 189 | 102-A-2 | 12 |
| 27-A | 5 | 19-AP | 430 |
| 19-Y | 23 | 54-Q | 3 |
| 33-C | 10 | 59-C | 114 |
| 86-A | <1 | 56-F | 8 |

-continued

| Example number | $IC_{50}$ (nM) | Example number | $IC_{50}$ (nM) |
|---|---|---|---|
| 76-E | <1 | 56-G | 2 |
| 35 | 13 | 54-O | <1 |
| 57-A | 4 | 73-D | 9 |
| 64-A | 8 | 54-Q | 7 |
| 45-B | <1 | 42-E | 81 |
| 56-B | <1 | 98-B | <1 |
| 52-B-1 | 58 | 87-E | 7 |
| 52-B-2 | 78 | 74-A | 162 |
| 33-E | 9 | 40 | 13 |
| 59-B | 4 | 24-F | 2 |
| 45-G | 3 | 27-I | <1 |
| 57-S | 49 | 54-B | 1 |
| 57-N | 91 | 54-C | 19 |
| 57-T | 6 | 39 | 2 |
| 51-C | 1 | 24-F | 24 |
| 63-A | 8 | 51-D | 11 |
| 33-H | 330 | 33-L | 87 |
| 96-A | 1 | 54-H | 1 |
| 28-B | 11 | 54-I | <1 |
| 49-B | 22 | 19-K | 222 |
| 55-B | 107 | 20-C | 6 |
| 111-B | 10 | 137-O | 10 |
| 136-B | 2 | 136-J | 36 |
| 135-E | <1 | 56-S | 89 |
| 134-A | 3 | 135-BE | <1 |
| 134-AG | 95 | 134-AM | 6 |
| 57-AB | <1 | 56-U | 2 |
| 54-V | 63 | 135-D | <1 |
| 134-AC | 4 | 137-E | 9 |
| 135-C | <1 | 137-F | 19 |
| 135-A | 2 | 137-P | 11 |
| 136-I | 1 | 135-BI | 3 |
| 136-K | 91 | 57-C | <1 |
| 137-C | 3 | 25-D | 3 |
| 149-F | 6 | 137-N | 14 |
| 137-AA | 2 | 135-AS | 10 |
| 137-AB | 1 | | |
| 148-G | 88 | | |
| 135-AA | <1 | | |
| 135-BH | 2 | | |
| 137-I | 100 | | |
| 68-F | 8 | | |

The invention claimed is:

1. A compound, or pharmaceutically acceptable salt thereof, according to the formula:

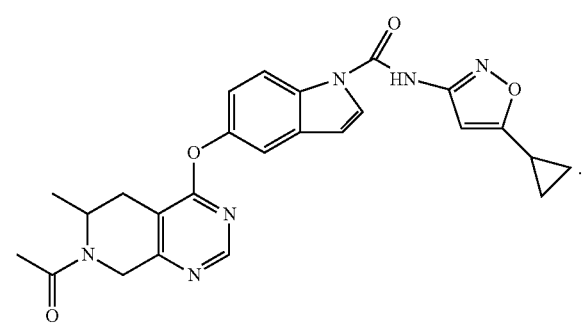 [SMILES: CC(=O)N1Cc2ncnc(Oc3ccc4c(ccn4C(=O)Nc4cc(C5CC5)on4)c3)c2CC1C]

2. A compound, or pharmaceutically acceptable salt thereof, according to claim 1, which compound is

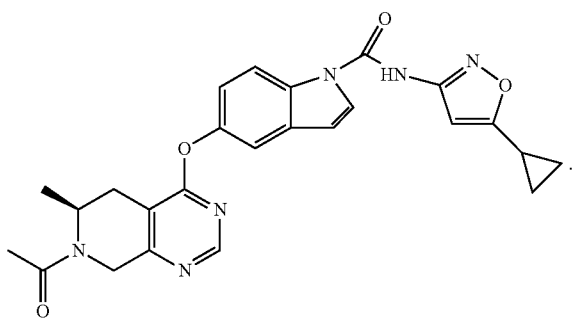 [SMILES: CC(=O)N1Cc2ncnc(Oc3ccc4c(ccn4C(=O)Nc4cc(C5CC5)on4)c3)c2C[C@@H]1C]

3. A pharmaceutical composition comprising at least one compound of claim 1 and at least one pharmaceutically acceptable carrier.

4. A method of treating a disorder or a disease in a subject mediated by VEGF-R, wherein the method comprises administering to the subject a therapeutically effective amount of the compound according to claim 1 and the disease or disorder is selected from age related macular degeneration, diabetic retinopathy, retinitis pigmentosa and retinopathy, geographic atrophy.

5. A pharmaceutical composition comprising at least one compound of claim 2 and at least one pharmaceutically acceptable carrier.

6. A method of treating a disorder or a disease in a subject mediated by VEGF-R, wherein the method comprises administering to the subject a therapeutically effective amount of the compound according to claim 2 and the disease or disorder is selected from age related macular degeneration, diabetic retinopathy, retinitis pigmentosa and retinopathy, geographic atrophy.

* * * * *